(12) United States Patent
Bellenie et al.

(10) Patent No.: US 11,161,839 B2
(45) Date of Patent: Nov. 2, 2021

(54) 2-QUINOLONE DERIVED INHIBITORS OF BCL6

(71) Applicants: Cancer Research Technology Limited, London (GB); The Institute of Cancer Research: Royal Cancer Hospital, London (GB)

(72) Inventors: Benjamin Richard Bellenie, London (GB); Kwai Ming Jack Cheung, London (GB); Owen Alexander Davis, London (GB); Swen Hoelder, London (GB); Rosemary Huckvale, London (GB); Matthew Garth Lloyd, London (GB)

(73) Assignees: The Institute of Cancer Research: Royal Cancer Hospital, London (GB); Cancer Research Technology Limited, London (GB)

( * ) Notice: Subject to any disclaimer, the term of this patent is extended or adjusted under 35 U.S.C. 154(b) by 134 days.

(21) Appl. No.: 16/616,906

(22) PCT Filed: May 25, 2018

(86) PCT No.: PCT/GB2018/051444
§ 371 (c)(1),
(2) Date: Nov. 25, 2019

(87) PCT Pub. No.: WO2018/215798
PCT Pub. Date: Nov. 29, 2018

(65) Prior Publication Data
US 2021/0206756 A1      Jul. 8, 2021

(30) Foreign Application Priority Data

May 26, 2017   (GB) ...................................... 1708510
Apr. 13, 2018   (GB) ...................................... 1806131

(51) Int. Cl.
| | | |
|---|---|---|
| *C07D 413/14* | (2006.01) |
| *C07D 401/14* | (2006.01) |
| *C07D 471/04* | (2006.01) |
| *C07D 471/10* | (2006.01) |
| *C07D 491/10* | (2006.01) |
| *C07D 405/14* | (2006.01) |
| *C07D 401/12* | (2006.01) |
| *A61P 35/00* | (2006.01) |

(52) U.S. Cl.
CPC ......... *C07D 413/14* (2013.01); *C07D 401/12* (2013.01); *C07D 401/14* (2013.01); *C07D 405/14* (2013.01); *C07D 471/04* (2013.01); *C07D 471/10* (2013.01); *C07D 491/10* (2013.01); *A61P 35/00* (2018.01)

(58) Field of Classification Search
CPC combination set(s) only.
See application file for complete search history.

(56) References Cited

U.S. PATENT DOCUMENTS 8,338,464 B2 *   12/2012   Melnick .................. A61P 35/00
                                                                  514/365
2005/0256157 A1   11/2005   Gesner et al.

FOREIGN PATENT DOCUMENTS

| WO | WO-2008/066887 A2 | 6/2008 |
| WO | WO-2018/108704 A1 | 6/2018 |

OTHER PUBLICATIONS

International Search Report for International Application No. PCT/GB2018/051444 dated Aug. 13, 2018.

* cited by examiner

*Primary Examiner* — Heidi Reese
(74) *Attorney, Agent, or Firm* — David P. Halstead; Foley Hoag LLP

(57) ABSTRACT

The present invention relates to compounds of formula I that function as inhibitors of BCL6 (B-cell lymphoma 6) activity: Formula I wherein $X_1$, $X_2$, $X_3$, $R^1$, $R^2$, $R^3$, $R^4$ and $R^5$ are each as defined herein. The present invention also relates to processes for the preparation of these compounds, to pharmaceutical compositions comprising them, and to their use in the treatment of proliferative disorders, such as cancer, as well as other diseases or conditions in which BCL6 activity is implicated.

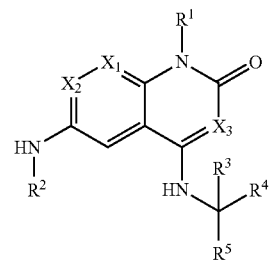

Formula I

19 Claims, No Drawings

2-QUINOLONE DERIVED INHIBITORS OF BCL6

RELATED APPLICATIONS

This application is a U.S. National Stage application of International Application No. PCT/GB2018/051444 filed May 25, 2018, which claims priority from Great Britain Application No. 1806131.7 filed Apr. 13, 2018 and Great Britain Application No. 1708510.1 filed May 26, 2017.

INTRODUCTION

The present invention relates to certain compounds that function as inhibitors of BCL6 (B-cell lymphoma 6) activity. The present invention also relates to processes for the preparation of these compounds, to pharmaceutical compositions comprising them, and to their use in the treatment of proliferative disorders, such as cancer, as well as other diseases or conditions in which BCL6 activity is implicated.

BACKGROUND OF THE INVENTION

BCL6 is a zinc finger transcription repressor that plays a key role in the formation and development of germinal centres, in which B cells undergo somatic hypermutation and recombination of the immunoglobulin genes, in order to generate diversity in antibodies against a variety of foreign antigens (Dent et al., *Science*, 1997, 276, 589-592). BCL6 allows the proliferation of antibody producing B cells by repressing genes involved in DNA damage response, cell cycle arrest and apoptosis. BCL6 mediates this repression by recruiting the corepressor proteins SMRT, NCoR and BCoR to an extended groove motif that forms along the dimer interface of the BCL6 BTB (BR-C, Ttk and Bab) domain (Ahmad et al., *Mol Cell*, 2003, 12, 1551-1564; Ghetu et al., *Mol Cell*, 2008, 29, 384-391). Genetic upregulation of the BCL6 gene, as seen in many lymphomas, leads to malignant B cell proliferation (Hatzi & Melnick, *Trends Mol Med*, 2014, 20, 343-352). Therefore, there exists a need to develop agents that inhibit the tumourigenic effects of BCL6, either by selectively binding to the BTB domain and preventing corepressor recruitment, or by binding to the BTB domain and inducing protein degradation (Kerres et al. *Cell Rep.*, 2017, 20, 2860-2875).

SUMMARY OF THE INVENTION

According to a first aspect of the present invention, there is provided a compound, or a pharmaceutically acceptable salt, hydrate or solvate thereof, as defined herein.

According to a further aspect of the present invention, there is provided a pharmaceutical composition comprising a compound as defined herein, or a pharmaceutically acceptable salt, hydrate or solvate thereof, in admixture with a pharmaceutically acceptable diluent or carrier.

According to a further aspect of the present invention, there is provided a method of inhibiting BCL6 activity, in vitro or in vivo, said method comprising contacting a cell with an effective amount of a compound or a pharmaceutically acceptable salt, hydrate or solvate thereof as defined herein.

According to a further aspect of the present invention, there is provided a method of inhibiting cell proliferation, in vitro or in vivo, said method comprising contacting a cell with an effective amount of a compound or a pharmaceutically acceptable salt, hydrate or solvate thereof as defined herein, or a pharmaceutical composition as defined herein.

According to a further aspect of the present invention, there is provided a method of treating a disease or disorder in which BCL6 activity is implicated in a patient in need of such treatment, said method comprising administering to said patient a therapeutically effective amount of a compound or a pharmaceutically acceptable salt, hydrate or solvate thereof as defined herein, or a pharmaceutical composition as defined herein.

According to a further aspect of the present invention, there is provided a method of treating a proliferative disorder in a patient in need of such treatment, said method comprising administering to said patient a therapeutically effective amount of a compound or a pharmaceutically acceptable salt, hydrate or solvate thereof as defined herein, or a pharmaceutical composition as defined herein.

According to a further aspect of the present invention, there is provided a method of treating cancer in a patient in need of such treatment, said method comprising administering to said patient a therapeutically effective amount of a compound or a pharmaceutically acceptable salt, hydrate or solvate thereof as defined herein, or a pharmaceutical composition as defined herein.

According to a further aspect of the present invention, there is provided a compound, or a pharmaceutically acceptable salt, hydrate or solvate thereof, or a pharmaceutical composition as defined herein for use in therapy.

According to a further aspect of the present invention, there is provided a compound or a pharmaceutically acceptable salt, hydrate or solvate thereof as defined herein, or a pharmaceutical composition as defined herein, for use in the treatment of a proliferative condition.

According to a further aspect of the present invention, there is provided a compound, or a pharmaceutically acceptable salt, hydrate or solvate thereof, or a pharmaceutical composition as defined herein for use in the treatment of cancer. In a particular embodiment, the cancer is human cancer.

According to a further aspect of the present invention, there is provided a compound, or a pharmaceutically acceptable salt, hydrate or solvate thereof, as defined herein for use in the inhibition of BCL6 activity.

According to a further aspect of the present invention, there is provided a compound, or a pharmaceutically acceptable salt, hydrate or solvate thereof, as defined herein for use in the treatment of a disease or disorder in which BCL6 activity is implicated.

According to a further aspect of the present invention, there is provided the use of a compound, or a pharmaceutically acceptable salt, hydrate or solvate thereof, as defined herein in the manufacture of a medicament for the treatment of a proliferative condition.

Suitably, the proliferative disorder is cancer, suitably a human cancer (for example haematological cancers such as lymphomas (including diffuse large B-cell lymphoma (DLBCL), follicular lymphoma (FL), Burkitt lymphoma (BL) and angioimmunoblastic T-cell lymphoma (AITL)), leukaemias (including acute lymphoblastic leukaemia (ALL) and chronic myeloid leukaemia (CML)) and multiple myeloma, and solid tumours (including glioma, breast cancer, non-small cell lung cancer (NSCLC) and squamous cell carcinomas (SCC) (including SCC of the head and neck, oesophagus, lung and ovary)).

According to a further aspect of the present invention, there is provided the use of a compound, or a pharmaceutically acceptable salt, hydrate or solvate thereof, as defined herein in the manufacture of a medicament for the treatment of cancer.

According to a further aspect of the present invention, there is provided a use of a compound, or a pharmaceutically acceptable salt, hydrate or solvate thereof, as defined herein in the manufacture of a medicament for the inhibition of BCL6 activity.

According to a further aspect of the present invention, there is provided a use of a compound, or a pharmaceutically acceptable salt, hydrate or solvate thereof, as defined herein in the manufacture of a medicament for the treatment of a disease or disorder in which BCL6 activity is implicated.

According to a further aspect of the present invention, there is provided a process for preparing a compound, or a pharmaceutically acceptable salt, hydrate or solvate thereof, as defined herein.

According to a further aspect of the present invention, there is provided a compound, or a pharmaceutically acceptable salt, hydrate or solvate thereof, obtainable by, or obtained by, or directly obtained by a process of preparing a compound as defined herein.

According to a further aspect of the present invention, there are provided novel intermediates as defined herein which are suitable for use in any one of the synthetic methods set out herein.

Features, including optional, suitable, and preferred features in relation to one aspect of the invention may also be features, including optional, suitable and preferred features in relation to any other aspect of the invention.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl.

The term "(m-nC)" or "(m-nC) group" used alone or as a prefix, refers to any group having m to n carbon atoms.

An "alkylene" group is an alkyl group that is positioned between and serves to connect two other chemical groups. Thus, "(1-6C)alkylene" means a linear saturated divalent hydrocarbon radical of one to six carbon atoms or a branched saturated divalent hydrocarbon radical of three to six carbon atoms, for example, methylene (—$CH_2$—), ethylene (—$CH_2CH_2$—), propylene (—$CH_2CH_2CH_2$—), 2-methylpropylene (—$CH_2CH(CH_3)CH_2$—), pentylene (—$CH_2CH_2CH_2CH_2CH_2$—), and the like.

"(3-10C)cycloalkyl" means a hydrocarbon ring containing from 3 to 10 carbon atoms, for example, cyclopropyl, cyclobutyl, cyclopentyl, cyclohexyl, cycloheptyl and bicyclo[2.2.1]heptyl.

"(3-10C)cycloalkenyl" means a hydrocarbon ring containing from 3 to 10 carbon atoms and at least one double bond, for example, cyclobutenyl, cyclopentenyl, cyclohexenyl or cycloheptenyl, such as 3-cyclohexen-1-yl, or cyclooctenyl.

The term "halo" or "halogeno" refers to fluoro, chloro, bromo and iodo, suitably fluoro, chloro and bromo, more suitably, fluoro and chloro.

The term "heterocyclyl", "heterocyclic" or "heterocycle" means a non-aromatic saturated or partially saturated monocyclic, fused, bridged, or spiro bicyclic heterocyclic ring system(s). Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example *Advanced Organic Chemistry*, by Jerry March, 4th Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane and quinuclidine.

By "spiro bi-cyclic ring systems" we mean that the two ring systems share one common spiro carbon atom, i.e. the heterocyclic ring is linked to a further carbocyclic or heterocyclic ring through a single common spiro carbon atom. Examples of spiro ring systems include 6-azaspiro[3.4]octane, 2-oxa-6-azaspiro[3.4]octane, 2-azaspiro[3.3]heptanes, 2-oxa-6-azaspiro[3.3]heptanes, 7-oxa-2-azaspiro[3.5]nonane, 6-oxa-2-azaspiro[3.4]octane, 2-oxa-7-azaspiro[3.5]nonane and 2-oxa-6-azaspiro[3.5]nonane.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. The term heteroaryl includes both monovalent species and divalent species. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:
a benzene ring fused to a 5- or 6-membered ring containing 1, 2 or 3 ring heteroatoms;
a pyridine ring fused to a 5- or 6-membered ring containing 1, 2 or 3 ring heteroatoms;
a pyrimidine ring fused to a 5- or 6-membered ring containing 1 or 2 ring heteroatoms;
a pyrrole ring fused to a 5- or 6-membered ring containing 1, 2 or 3 ring heteroatoms;
a pyrazole ring fused to a 5- or 6-membered ring containing 1 or 2 ring heteroatoms;
a pyrazine ring fused to a 5- or 6-membered ring containing 1 or 2 ring heteroatoms;
an imidazole ring fused to a 5- or 6-membered ring containing 1 or 2 ring heteroatoms;
an oxazole ring fused to a 5- or 6-membered ring containing 1 or 2 ring heteroatoms;
an isoxazole ring fused to a 5- or 6-membered ring containing 1 or 2 ring heteroatoms;
a thiazole ring fused to a 5- or 6-membered ring containing 1 or 2 ring heteroatoms;
an isothiazole ring fused to a 5- or 6-membered ring containing 1 or 2 ring heteroatoms;
a thiophene ring fused to a 5- or 6-membered ring containing 1, 2 or 3 ring heteroatoms;
a furan ring fused to a 5- or 6-membered ring containing 1, 2 or 3 ring heteroatoms;
a cyclohexyl ring fused to a 5- or 6-membered heteroaromatic ring containing 1, 2 or 3 ring heteroatoms; and
a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzfuranyl, benzthiophenyl, benzimidazolyl, benzoxazolyl, benzisoxazolyl, benzthiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In a particular embodiment, an aryl is phenyl.

The term "optionally substituted" refers to either groups, structures, or molecules that are substituted and those that are not substituted. The term "wherein a/any CH, $CH_2$, $CH_3$ group or heteroatom (i.e. NH) within a $R^1$ group is optionally substituted" suitably means that (any) one of the hydrogen radicals of the $R^1$ group is substituted by a relevant stipulated group.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

Compounds of the Invention

In one aspect, the present invention relates to compounds, or pharmaceutically acceptable salts, hydrates or solvates thereof, having the structural formula (I), shown below:

Formula (I)

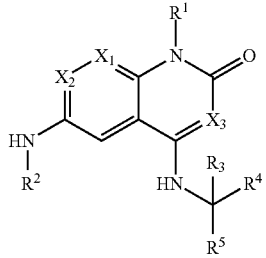

wherein:
$X_1$ is selected from N or $CR^a$, wherein $R^a$ is selected from hydrogen, (1-2C)alkyl, halogen, hydroxy, (1-2C)alkoxy, (1-2C)haloalkyl, (1-2C)haloalkoxy, (2-4C)alkenyl, (2-4C)alkynyl, nitro, cyano or $NR^bR^c$, wherein $R^b$ and $R^c$ are each independently selected from hydrogen or (1-2C)alkyl;
$X_2$ is selected from N, CH, CF, CCl or C—$CH_3$;
$X_3$ is selected from N or $CR^d$, wherein $R^d$ is selected from hydrogen, fluoro, chloro or methyl;
$R^1$ is selected from hydrogen or a group of the formula:

-L-Y—Z 

wherein:
L is absent or (1-5C)alkylene optionally substituted by one or more substituents selected from (1-2C)alkyl or oxo;
Y is absent or O, S, SO, $SO_2$, $N(R^e)$, C(O), C(O)O, OC(O), $C(O)N(R^e)$, $N(R^e)C(O)$, $N(R^e)C(O)N(R^f)$, $N(R^e)C(O)O$, $OC(O)N(R^e)$, $S(O)_2N(R^e)$, or $N(R^e)SO_2$, wherein $R^e$ and $R^f$ are each independently selected from hydrogen or (1-4C)alkyl; and
Z is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein
Z is optionally further substituted by one or more substituent groups independently selected from oxo, (1-4C)alkyl, halo, (1-4C)haloalkyl, (1-4C)haloalkoxy, amino, (1-4C)aminoalkyl, cyano, hydroxy, carboxy, carbamoyl, sulphamoyl, mercapto, ureido, $NR^gR^h$, $OR^g$, $C(O)R^g$, $C(O)OR^g$, $OC(O)R^g$, $C(O)N(R^g)R^h$, $N(R^g)C(O)R^h$, $S(O)_yR^g$ (where y is 0, 1 or 2), $SO_2N(R^g)R^h$, $N(R^g)SO_2R^g$, $Si(R^g)(R^h)R^i$ or $(CH_2)_zNR^gR^h$ (where z is 1, 2 or 3); wherein $R^g$, $R^h$ and $R^i$ are each independently selected from hydrogen, (1-6C)alkyl or (3-6C)cycloalkyl; or $R^g$ and $R^h$ can be linked such that, together with the nitrogen atom to which they are attached, they form a 4-9 membered heterocyclic ring which is optionally substituted by one or more substituents selected from (1-4C)alkyl, halo, (1-4C)haloalkyl, (1-4C)haloalkoxy, (1-4C)alkoxy, (1-4C)alkylamino, amino, cyano or hydroxy;

$R^2$ is selected from:
i) a group of Formula A shown below:

Formula A

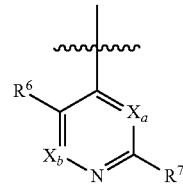

wherein:
 denotes the point of attachment;
$X_a$ and $X_b$ are each independently selected from N or $CR^{x1}$, wherein $R^{x1}$ is selected from hydrogen, fluoro, chloro, bromo, (1-2C)alkyl, (1-2C)alkoxy, cyano, nitro, acetylenyl, $CH_2F$, $CF_2H$ or $CF_3$;
$R^6$ is selected from hydrogen, fluoro, chloro, bromo, (1-2C)alkyl, (1-2C)alkoxy, cyano, nitro, acetylenyl, $CH_2F$, $CF_2H$ or $CF_3$;
$R^7$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_3$—$Z_3$ wherein:
$Y_3$ is absent or O, S, SO, $SO_2$, $N(R^j)(CR^jR^k)_{q1}$ (where $q_1$ is 0, 1 or 2), C(O), C(O)O, OC(O), $C(O)N(R^j)$, $N(R^j)C(O)$, $N(R^j)C(O)N(R^k)$, $N(R^j)C(O)O$, $OC(O)N(R^j)$, $S(O)_2N(R^j)$ or $N(R^j)SO_2$, wherein $R^j$ and $R^k$ are each independently selected from hydrogen or (1-4C)alkyl; and
$Z_3$ is hydrogen, (1-6C)alkyl, aryl, (3-6C)cycloalkyl, (2-4C)alkenyl, (2-4C)alkynyl, (3-6C)cycloalkenyl, heteroaryl or a 4 to 11-membered heterocyclyl; wherein $Z_3$ is optionally further substituted by one or more substituent groups independently selected from oxo, (1-4C)alkyl, (3-6C)cycloalkyl, halo, (1-4C)haloalkyl, (1-4C) haloalkoxy, (1-4C)hydroxyalkyl, amino, cyano, hydroxy, carboxy, carbamoyl, sulphamoyl, mercapto, $C(O)NR^lR^m$, $NR^lR^m$ or $OR^l$, wherein $R^l$ and $R^m$ are each independently selected from hydrogen, (1-4C)alkyl or (3-6C)cycloalkyl; and/or $Z^3$ is optionally further substituted by a group of the formula:

-$L_Z$-$W_Z$ 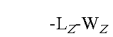

wherein:
$L_Z$ is absent or a (1-5C)alkylene optionally substituted by one or more substituents selected from (1-2C)alkyl or oxo; and
$W_Z$ is aryl, heteroaryl, 4- to 7-membered heterocyclyl, (3-6C)cycloalkyl, halo, (1-4C)haloalkyl, (1-4C)haloalkoxy, cyano, hydroxy, (1-4C)alkoxy, $CR^{xa}$, $COOR^{xa}$, $C(O)NR^{xa}R^{xb}$ or $NR^{xa}R^{xb}$, wherein $R^{xa}$ and $R^{xb}$ are each independently selected from hydrogen or (1-4C)alkyl; and wherein each aryl, heteroaryl, 4-to 7-membered heterocyclyl or (3-6C)cycloalkyl is optionally further substituted by one or more substituent groups independently selected from (1-4C)alkyl, halo, (1-4C)haloalkyl, amino, cyano or hydroxy;

ii) a group of Formula B shown below:

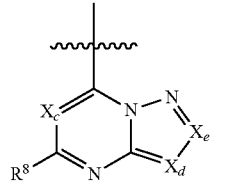

Formula B wherein:

⤴ denotes the point of attachment;

$X_c$, $X_d$ and $X_e$ are each independently selected from N, CH, CF, CCl, C—CN or $CCH_3$;

$R^8$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_5$—$Z_5$ wherein:

$Y_5$ is absent or O, N(R″), C(O), C(O)O, OC(O), C(O)N(R″), N(R″)C(O), N(R″)C(O)N(R°), N(R″)C(O)O, OC(O)N(R″), S(O)$_2$N(R″), N(R″)SO$_2$, wherein R″ and R° are each independently selected from hydrogen or (1-4C)alkyl; and $Z_5$ is hydrogen, (1-6C)alkyl, aryl, (3-8C)cycloalkyl, (3-8C)cycloalkenyl, heteroaryl or heterocyclyl; wherein $Z_5$ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, $NR^pR^q$, $OR^p$, wherein $R^p$ and $R^q$ are each independently selected from hydrogen, (1-4C)alkyl or (3-6C)cycloalkyl; and iii) a group of Formula C shown below:

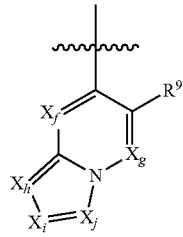

Formula C wherein:

⤴ denotes the point of attachment;

$R^9$ is selected from fluoro, chloro, bromo, (1-2C) alkyl, (1-2C)alkoxy, cyano, nitro, (2-4C)alkenyl, (2-4C)alkynyl, $CH_2F$, $CF_2H$ or $CF_3$;

$X_f$ and $X_g$ are each independently selected from N or $CR^{10}$, wherein $R^{10}$ is selected from hydrogen, fluoro, chloro, (1-2C)alkyl, (1-2C)haloalkyl or (1-2C)haloalkoxy; $X_h$, $X_i$ and $X_j$ are each independently selected from N or $CR^{11}$, wherein $R^{11}$ is selected from hydrogen, halo, (1-2C)alkyl, (1-2C)alkoxy, (1-2C)haloalkyl or (1-2C)haloalkoxy;

$R^3$ is selected from hydrogen, (1-2C)alkyl, (3-4C)cycloalkyl, (1-2C)haloalkyl, cyano, (2-4C)alkenyl or (2-4C)alkynyl;

$R^4$ is selected from (1-4C)alkyl, cyano, (1-4C)haloalkyl or a group of the formula:

$Y_5$-$L_5$-$Z_5$ wherein:

$Y_5$ is absent or selected from C(O), C(O)O, OC(O), C(O)N(R′) or S(O)$_2$N(R′), wherein R′ is selected from hydrogen or (1-2C)alkyl;

$L_5$ is absent or (1-2C)alkylene, optionally substituted by one or more substituents selected from (1-2C)alkyl or oxo; and $Z_5$ is hydrogen, (1-6C)alkyl, (2-4C)alkenyl, (2-4C)alkynyl, aryl, (3-6C)cycloalkyl, (3-6C)cycloalkenyl, heteroaryl or heterocyclyl; wherein $Z_5$ is optionally substituted by one or more substituents selected from oxo, (1-4C)alkyl, (3-6C)cycloalkyl, halo, (1-4C)haloalkyl, (1-4C)haloalkoxy, (1-4C)alkoxy, (1-4C)alkylamino, amino, cyano, nitro, hydroxy, $C(O)R^s$, $C(O)OR^s$, $OC(O)R^s$, $C(O)N(R^s)R^t$, $NR^sC(O)R^t$, wherein $R^s$ and $R^t$ are each independently selected from hydrogen, (1-4C)alkyl or (3-6C)cycloalkyl; or $Z_5$ is optionally substituted by a group of the formula:

$Q_5$-$L_5$-$W_5$ wherein:

$Q_5$ is absent or selected from O or $N(R^{x3})$, wherein $R^{x3}$ is selected from hydrogen or (1-2C)alkyl;

$L_5$ is absent or (1-2C)alkylene, optionally substituted by one or more substituents selected from (1-2C)alkyl or oxo; and $W_5$ is selected from (1-4C)alkyl, aryl, (3-6C)cycloalkyl, (3-6C)cycloalkenyl, 5- or 6-membered heteroaryl or a 5- or 6-membered heterocyclyl, and wherein $W_5$ is optionally further substituted by one or more substituents selected from (1-4C)alkyl, halo, (1-4C)haloalkyl, (1-4C) haloalkoxy, (1-4C)alkoxy, (1-4C)alkylamino, amino, cyano, nitro or hydroxy; or $R^3$ and $R^4$ are linked such that, together with the carbon atom to which they are attached, they form a 3-10 membered carbocyclic ring or a 4-10 membered heterocyclic ring, which is optionally substituted by one or more substituents selected from oxo, (1-2C)alkyl, halo, (1-2C)haloalkyl, (1-2C)haloalkoxy, (1-2C) alkoxy, (1-2C)alkylamino, amino, cyano, nitro or hydroxy; or the 3-10 membered carbocyclic or 4-10 membered heterocyclic ring is optionally fused to a 5 or 6 membered heteroaryl or phenyl ring, and the 5 or 6 membered heteroaryl or phenyl ring is optionally substituted by (1-2C)alkyl, halo, (1-2C)haloalkyl, (1-2C)haloalkoxy, (1-2C)alkoxy, (1-2C)alkylamino, amino, cyano, nitro or hydroxy; and $R^5$ is selected from hydrogen, (1-4C)alkyl, (1-2C)haloalkyl, (1-2C)alkoxy, (1-2C)haloalkoxy, cyano, nitro, acetylenyl, phenyl or 5- or 6-membered heteroaryl, wherein said (1-4C)alkyl, phenyl or 5- or 6-membered heteroaryl are independently optionally substituted by one or more substituents selected from halo, hydroxy or amino; with the proviso that:

(i) no more than one or two of $X_1$, $X_2$ and $X_3$ are nitrogen;

(ii) when $R^2$ is a group of Formula B, no more than one or two of $X_c$, $X_d$ and $X_e$ are nitrogen; and (iii) when $R^2$ is a group of Formula C, no more than three of $X_f$, $X_g$, $X_h$, $X_i$ and $X_j$ are nitrogen.

In an embodiment, the present invention relates to compounds, or pharmaceutically acceptable salts, hydrates or solvates thereof, having the structural formula (I), shown below:

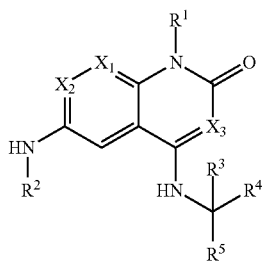

Formula (I)

wherein:
$X_1$ is selected from N or $CR^a$, wherein $R^a$ is selected from hydrogen, (1-2C)alkyl, halogen, hydroxy, (1-2C)alkoxy, (1-2C)haloalkyl, (1-2C)haloalkoxy, (2-4C)alkenyl, (2-4C)alkynyl, nitro, cyano or $NR^bR^c$, wherein $R^b$ and $R^c$ are each independently selected from hydrogen or (1-2C)alkyl;

$X_2$ is selected from N, CH, CF, CCl or C—$CH_3$;

$X_3$ is selected from N or $CR^d$, wherein $R^d$ is selected from hydrogen, fluoro, chloro or methyl;

$R^1$ is selected from hydrogen or a group of the formula:

-L-Y—Z wherein:
L is absent or (1-5C)alkylene optionally substituted by one or more substituents selected from (1-2C)alkyl or oxo;

Y is absent or O, S, SO, $SO_2$, $N(R^e)$, C(O), C(O)O, OC(O), $C(O)N(R^e)$, $N(R^e)C(O)$, $N(R^e)C(O)N(R^f)$, $N(R^e)C(O)O$, $OC(O)N(R^e)$, $S(O)_2N(R^e)$, or $N(R^e)SO_2$, wherein $R^e$ and $R^f$ are each independently selected from hydrogen or (1-4C)alkyl; and Z is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Z is optionally further substituted by one or more substituent groups independently selected from oxo, (1-4C)alkyl, halo, (1-4C)haloalkyl, (1-4C)haloalkoxy, amino, (1-4C)aminoalkyl, cyano, hydroxy, carboxy, carbamoyl, sulphamoyl, mercapto, ureido, $NR^gR^h$, $OR^g$, C(O)$R^g$, C(O)O$R^g$, OC(O)$R^g$, C(O)N($R^g$)$R^h$, N($R^g$)C(O)$R^h$, S(O)$_y$$R^g$ (where y is 0, 1 or 2), $SO_2N(R^g)R^h$, $N(R^g)SO_2R^g$, $Si(R^g)(R^h)R^i$ or $(CH_2)_zNR^gR^h$ (where z is 1, 2 or 3); wherein $R^g$, $R^h$ and $R^i$ are each independently selected from hydrogen, (1-6C)alkyl or (3-6C)cycloalkyl; or $R^g$ and $R^h$ can be linked such that, together with the nitrogen atom to which they are attached, they form a 4-9 membered heterocyclic ring which is optionally substituted by one or more substituents selected from (1-4C)alkyl, halo, (1-4C)haloalkyl, (1-4C)haloalkoxy, (1-4C)alkoxy, (1-4C)alkylamino, amino, cyano or hydroxy;

$R^2$ is selected from:
i) a group of Formula A shown below:

Formula A wherein:
 denotes the point of attachment;
$X_a$ and $X_b$ are each independently selected from N or $CR^{x1}$, wherein $R^{x1}$ is selected from hydrogen, fluoro, chloro, bromo, (1-2C)alkyl, (1-2C)alkoxy, cyano, nitro, acetylenyl, $CH_2F$, $CF_2H$ or $CF_3$;

$R^6$ is selected from hydrogen, fluoro, chloro, bromo, (1-2C)alkyl, (1-2C)alkoxy, cyano, nitro, acetylenyl, $CH_2F$, $CF_2H$ or $CF_3$;

$R^7$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_3$—$Z_3$ wherein:
$Y_3$ is absent or O, S, SO, $SO_2$, $N(R^j)(CR^jR^k)_{q1}$ (where $q_1$ is 0, 1 or 2), C(O), C(O)O, OC(O), $C(O)N(R^j)$, $N(R^j)C(O)$, $N(R^j)C(O)N(R^k)$, $N(R^j)C(O)O$, $OC(O)N(R^j)$, $S(O)_2N(R^j)$ or $N(R^j)SO_2$, wherein $R^j$ and $R^k$ are each independently selected from hydrogen or (1-4C)alkyl; and $Z_3$ is hydrogen, (1-6C)alkyl, aryl, (3-6C)cycloalkyl, (2-4C)alkenyl, (2-4C)alkynyl, (3-6C)cycloalkenyl, heteroaryl or a 4 to 11-membered heterocyclyl; wherein $Z_3$ is optionally further substituted by one or more substituent groups independently selected from oxo, (1-4C)alkyl, (3-6C)cycloalkyl, halo, (1-4C)haloalkyl, (1-4C)haloalkoxy, amino, cyano, hydroxy, carboxy, carbamoyl, sulphamoyl, mercapto, $C(O)NR^lR^m$, $NR^lR^m$ or $OR^l$, wherein $R^l$ and $R^m$ are each independently selected from hydrogen, (1-4C)alkyl or (3-6C)cycloalkyl;

or $Z^3$ is optionally further substituted by a group of the formula:

-$L_Z$-$W_Z$ wherein:
$L_Z$ is a (1-5C)alkylene optionally substituted by one or more substituents selected from (1-2C)alkyl or oxo; and $W_Z$ is halo, (1-4C)haloalkyl, (1-4C)haloalkoxy, cyano, hydroxy, (1-4C)alkoxy, $CR^{xa}$, $COOR^{xa}$, C(O)NR$^{xa}$R$^{xb}$ or NR$^{xa}$R$^{xb}$, wherein R$^{xa}$ and R$^{xb}$ are each independently selected from hydrogen or (1-4C)alkyl;

ii) a group of Formula B shown below:

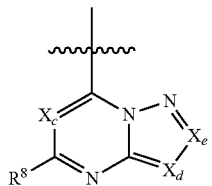

Formula B wherein:

~ denotes the point of attachment;

X$_c$, X$_d$ and X$_e$ are each independently selected from N, CH, CF, CCl, C—CN or CCH$_3$;

R$^8$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_5$—Z$_5$ wherein:

Y$_5$ is absent or O, N(R″), C(O), C(O)O, OC(O), C(O)N(R″), N(R″)C(O), N(R″)C(O)N(R$^o$), N(R″)C(O)O, OC(O)N(R″), S(O)$_2$N(R″), N(R″)SO$_2$, wherein R″ and R$^o$ are each independently selected from hydrogen or (1-4C)alkyl; and Z$_5$ is hydrogen, (1-6C)alkyl, aryl, (3-8C)cycloalkyl, (3-8C)cycloalkenyl, heteroaryl or heterocyclyl; wherein Z$_5$ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, NR$^p$R$^q$, OR$^p$, wherein R$^p$ and R$^q$ are each independently selected from hydrogen, (1-4C)alkyl or (3-6C)cycloalkyl; and iii) a group of Formula C shown below:

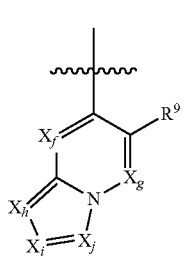

Formula C wherein:

~ denotes the point of attachment;

R$^9$ is selected from fluoro, chloro, bromo, (1-2C)alkyl, (1-2C)alkoxy, cyano, nitro, (2-4C)alkenyl, (2-4C)alkynyl, CH$_2$F, CF$_2$H or CF$_3$;

X$_f$ and X$_g$ are each independently selected from N or CR$^{10}$, wherein R$^{10}$ is selected from hydrogen, fluoro, chloro, (1-2C)alkyl, (1-2C)haloalkyl or (1-2C)haloalkoxy;

X$_h$, X$_i$ and X$_j$ are each independently selected from N or CR$^{11}$, wherein R$^{11}$ is selected from hydrogen, halo, (1-2C)alkyl, (1-2C)alkoxy, (1-2C)haloalkyl or (1-2C)haloalkoxy;

R$^3$ is selected from hydrogen, (1-2C)alkyl, (3-4C)cycloalkyl, (1-2C)haloalkyl, cyano, (2-4C)alkenyl or (2-4C)alkynyl;

R$^4$ is selected from (1-4C)alkyl, cyano, (1-4C)haloalkyl or a group of the formula:

Y$_5$-L$_5$-Z$_5$ wherein:

Y$_5$ is absent or selected from C(O), C(O)O, OC(O), C(O)N(R$^r$) or S(O)$_2$N(R$^r$), wherein R$^r$ is selected from hydrogen or (1-2C)alkyl;

L$_5$ is absent or (1-2C)alkylene, optionally substituted by one or more substituents selected from (1-2C)alkyl or oxo; and Z$_5$ is hydrogen, (1-6C)alkyl, (2-4C)alkenyl, (2-4C)alkynyl, aryl, (3-6C)cycloalkyl, (3-6C)cycloalkenyl, heteroaryl or heterocyclyl; wherein Z$_5$ is optionally substituted by one or more substituents selected from oxo, (1-4C)alkyl, (3-6C)cycloalkyl, halo, (1-4C)haloalkyl, (1-4C)haloalkoxy, (1-4C)alkoxy, (1-4C)alkylamino, amino, cyano, nitro, hydroxy, C(O)R$^s$, C(O)OR$^s$, OC(O)R$^s$, C(O)N(R$^s$)R$^t$, NR$^s$C(O)R$^t$, wherein R$^s$ and R$^t$ are each independently selected from hydrogen, (1-4C)alkyl or (3-6C)cycloalkyl; or Z$_5$ is optionally substituted by a group of the formula:

Q$_5$-L$_5$-W$_5$ wherein:

Q$_5$ is absent or selected from O or N(R$^{x3}$), wherein R$^{x3}$ is selected from hydrogen or (1-2C)alkyl;

L$_5$ is absent or (1-2C)alkylene, optionally substituted by one or more substituents selected from (1-2C)alkyl or oxo; and W$_5$ is selected from (1-4C)alkyl, aryl, (3-6C)cycloalkyl, (3-6C)cycloalkenyl, 5- or 6-membered heteroaryl or a 5- or 6-membered heterocyclyl, and wherein W$_5$ is optionally further substituted by one or more substituents selected from (1-4C)alkyl, halo, (1-4C)haloalkyl, (1-4C)haloalkoxy, (1-4C)alkoxy, (1-4C)alkylamino, amino, cyano, nitro or hydroxy; or R$^3$ and R$^4$ are linked such that, together with the carbon atom to which they are attached, they form a 3-10 membered carbocyclic ring or a 4-10 membered heterocyclic ring, which is optionally substituted by one or more substituents selected from oxo, (1-2C)alkyl, halo, (1-2C)haloalkyl, (1-2C)haloalkoxy, (1-2C)alkoxy, (1-2C)alkylamino, amino, cyano, nitro or hydroxy; or the 3-10 membered carbocyclic or 4-10 membered heterocyclic ring is optionally fused to a 5 or 6 membered heteroaryl or phenyl ring, and the 5 or 6 membered heteroaryl or phenyl ring is optionally substituted by (1-2C)alkyl, halo, (1-2C)haloalkyl, (1-2C)haloalkoxy, (1-2C)alkoxy, (1-2C)alkylamino, amino, cyano, nitro or hydroxy; and R$^5$ is selected from hydrogen, (1-4C)alkyl, (1-2C)haloalkyl, (1-2C)alkoxy, (1-2C)haloalkoxy, cyano, nitro, acetylenyl, phenyl or 5- or 6-membered heteroaryl, wherein said (1-4C)alkyl, phenyl or 5- or 6-membered heteroaryl are independently optionally substituted by one or more substituents selected from halo, hydroxy or amino; with the proviso that:
(i) no more than one or two of $X_1$, $X_2$ and $X_3$ are nitrogen;
(ii) when $R^2$ is a group of Formula B, no more than one or two of $X_c$, $X_d$ and $X_e$ are nitrogen; and
(iii) when $R^2$ is a group of Formula C, no more than three of $X_f$, $X_g$, $X_h$, $X_i$ and $X_j$ are nitrogen.

In another embodiment, the present invention provides compounds, or pharmaceutically acceptable salts, hydrates or solvates thereof, having the structural formula (I), shown below:

Formula (I)

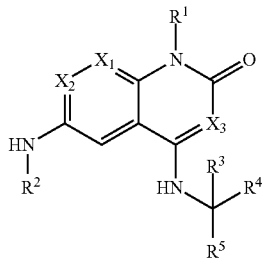

wherein:
$X_1$ is selected from N or $CR^a$, wherein $R^a$ is selected from hydrogen, (1-2C)alkyl, halogen, hydroxy, (1-2C)alkoxy, (1-2C)haloalkyl, (1-2C)haloalkoxy, (2-4C)alkenyl, (2-4C)alkynyl, nitro, cyano or $NR^bR^c$, wherein $R^b$ and $R^c$ are each independently selected from hydrogen or (1-2C)alkyl;
$X_2$ is selected from N, CH, CF, CCl or C—$CH_3$;
$X_3$ is selected from N or $CR^d$, wherein $R^d$ is selected from hydrogen, fluoro, chloro or methyl;
$R^1$ is selected from hydrogen or a group of the formula:

-L-Y—Z 

wherein:
L is absent or (1-5C)alkylene optionally substituted by one or more substituents selected from (1-2C)alkyl or oxo;
Y is absent or O, S, SO, $SO_2$, $N(R^e)$, C(O), C(O)O, OC(O), C(O)$N(R^e)$, $N(R^e)$C(O), $N(R^e)$C(O)N($R^f$), $N(R^e)$C(O)O, OC(O)$N(R^e)$, S(O)$_2$$N(R^e)$, or $N(R^e)$SO$_2$, wherein $R^e$ and $R^f$ are each independently selected from hydrogen or (1-4C)alkyl; and
Z is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Z is optionally further substituted by one or more substituent groups independently selected from oxo, (1-4C)alkyl, halo, (1-4C)haloalkyl, (1-4C)haloalkoxy, amino, (1-4C)aminoalkyl, cyano, hydroxy, carboxy, carbamoyl, sulphamoyl, mercapto, ureido, $NR^gR^h$, $OR^g$, $C(O)R^g$, $C(O)OR^g$, $OC(O)R^g$, $C(O)N(R^g)R^h$, $N(R^g)C(O)R^h$, $S(O)_yR^g$ (where y is 0, 1 or 2), $SO_2N(R^g)R^h$, $N(R^g)SO_2R^g$, $Si(R^g)(R^h)R^i$ or $(CH_2)_zNR^gR^h$ (where z is 1, 2 or 3); wherein $R^g$, $R^h$ and $R^i$ are each independently selected from hydrogen, (1-6C)alkyl or (3-6C)cycloalkyl; or $R^g$ and $R^h$ can be linked such that, together with the nitrogen atom to which they are attached, they form a 4-9 membered heterocyclic ring which is optionally substituted by one or more substituents selected from oxo, (1-4C)alkyl, halo, (1-4C)haloalkyl, (1-4C)haloalkoxy, (1-4C)alkoxy, (1-4C)alkylamino, amino, cyano or hydroxy;

$R^2$ is selected from:
i) a group of Formula A shown below:

Formula A

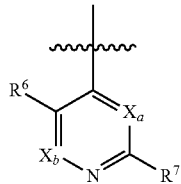

wherein:
 denotes the point of attachment;
$X_a$ and $X_b$ are each independently selected from N or $CR^{x1}$, wherein $R^{x1}$ is selected from hydrogen, fluoro, chloro, bromo, (1-2C)alkyl, (1-2C)alkoxy, cyano, nitro, acetylenyl, $CH_2F$, $CF_2H$ or $CF_3$;
$R^6$ is selected from hydrogen, fluoro, chloro, bromo, (1-2C)alkyl, (1-2C)alkoxy, cyano, nitro, acetylenyl, $CH_2F$, $CF_2H$ or $CF_3$;
$R^7$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_3$—$Z_3$ wherein:
$Y_3$ is absent or C(O), C(O)O, OC(O), C(O)N($R^j$), $N(R^j)$C(O), $N(R^j)$C(O)N($R^k$), $N(R^i)$C(O)O, OC(O)N($R^j$), S(O)$_2$N($R^j$), N($R^j$)SO$_2$, wherein $R^j$ and $R^k$ are each independently selected from hydrogen or (1-4C)alkyl; and
$Z_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or 5- or 6-membered heterocyclyl; wherein $Z_3$ is optionally further substituted by one or more substituent groups independently selected from oxo, (1-4C)alkyl, halo, (1-4C)haloalkyl, (1-4C)haloalkoxy, amino, cyano, hydroxy, amido, carboxy, carbamoyl, sulphamoyl, mercapto, $NR^lR^m$ or $OR^l$, wherein $R^l$ and $R^m$ are each independently selected from hydrogen, (1-4C)alkyl or (3-6C)cycloalkyl;

ii) a group of Formula B shown below:

Formula B

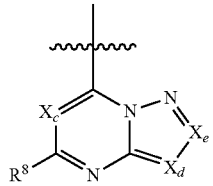

wherein:
 denotes the point of attachment;
$X_c$, $X_d$ and $X_e$ are each independently selected from N, CH, CF, CCl, C—CN or $CCH_3$;

R⁸ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y₅—Z₅ wherein:
Y₅ is absent or O, N(R″), C(O), C(O)O, OC(O), C(O)N(R″), N(R″)C(O), N(R″)C(O)N(R°), N(R″)C(O)O, OC(O)N(R″), S(O)₂N(R″), N(R″)SO₂, wherein R″ and R° are each independently selected from hydrogen or (1-4C)alkyl; and
Z₅ is hydrogen, (1-6C)alkyl, aryl, (3-8C)cycloalkyl, (3-8C)cycloalkenyl, heteroaryl or heterocyclyl; wherein Z₅ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, NRᵖR^q, ORᵖ, wherein Rᵖ and R^q are each independently selected from hydrogen, (1-4C)alkyl or (3-6C)cycloalkyl; and iii) a group of Formula C shown below:

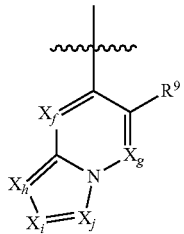

Formula C wherein:

⸺ denotes the point of attachment;
R⁹ is selected from fluoro, chloro, bromo, (1-2C)alkyl, (1-2C)alkoxy, cyano, nitro, (2-4C)alkenyl, (2-4C)alkynyl, CH₂F, CF₂H or CF₃;
X_f and X_g are each independently selected from N or CR¹⁰, wherein R¹⁰ is selected from hydrogen, fluoro, chloro, (1-2C)alkyl, (1-2C)haloalkyl or (1-2C)haloalkoxy;
X_h, X_i and X_j are each independently selected from N or CR¹¹, wherein R¹¹ is selected from hydrogen, halo, (1-2C)alkyl, (1-2C)alkoxy, (1-2C)haloalkyl or (1-2C)haloalkoxy;
R³ is selected from hydrogen, (1-2C)alkyl, (1-2C)haloalkyl, cyano, (2-4C)alkenyl or (2-4C)alkynyl;
R⁴ is selected from (1-4C)alkyl, cyano, (1-4C)haloalkyl or a group of the formula:

Y₅-L₅-Z₅ wherein:
Y₅ is absent or selected from C(O), C(O)O, OC(O), C(O)N(R^r) or S(O)₂N(R^r), wherein R^r is selected from hydrogen or (1-2C)alkyl; L₅ is absent or (1-2C)alkylene, optionally substituted by one or more substituents selected from (1-2C)alkyl or oxo; and
Z₅ is hydrogen, (1-6C)alkyl, (2-4C)alkenyl, (2-4C)alkynyl, aryl, (3-6C)cycloalkyl, (3-6C)cycloalkenyl, heteroaryl or heterocyclyl; wherein Z₅ is optionally substituted by one or more substituents selected from oxo, (1-4C)alkyl, halo, (1-4C)haloalkyl, (1-4C)haloalkoxy, (1-4C)alkoxy, (1-4C)alkylamino, amino, cyano, nitro, hydroxy, C(O)Rˢ, C(O)ORˢ, OC(O)Rˢ, C(O)N(Rˢ)Rᵗ, NRˢC(O)Rᵗ, wherein Rˢ and Rᵗ are each independently selected from hydrogen, (1-4C)alkyl or (3-6C)cycloalkyl; or R³ and R⁴ are linked such that, together with the carbon atom to which they are attached, they form a 3-10 membered carbocyclic ring or a 4-10 membered heterocyclic ring, which is optionally substituted by one or more substituents selected from oxo, (1-2C)alkyl, halo, (1-2C)haloalkyl, (1-2C)haloalkoxy, (1-2C)alkoxy, (1-2C)alkylamino, amino, cyano, nitro or hydroxy; or the 3-10 membered carbocyclic or 4-10 membered heterocyclic ring is optionally fused to a 5 or 6 membered heteroaryl or phenyl ring, and the 5 or 6 membered heteroaryl or phenyl ring is optionally substituted by (1-2C)alkyl, halo, (1-2C)haloalkyl, (1-2C)haloalkoxy, (1-2C)alkoxy, (1-2C)alkylamino, amino, cyano, nitro or hydroxy; and R⁵ is selected from hydrogen, (1-4C)alkyl, (1-2C)haloalkyl, (1-2C)alkoxy, (1-2C)haloalkoxy, cyano, nitro or acetylenyl, wherein said (1-4C)alkyl is optionally substituted by one or more substituents selected from halo, hydroxy or amino;

with the proviso that:
(i) only one or two of X₁, X₂ and X₃ are nitrogen;
(ii) when R³ is a group of Formula B, only one or two of X_c, X_d and X_e are nitrogen; and
(iii) when R³ is a group of Formula C, no more than three of X_f, X_g, X_h, X_i and X_j are nitrogen.

In a particular group of compounds of the present invention, no more than one of X₁, X₂ and X₃ is nitrogen.

In a particular group of compounds of the present invention, when R³ is a group of Formula B, no more than one of X_c, X_d and X_e is nitrogen.

In a particular group of compounds of the present invention, when R³ is a group of Formula C, no more than two of X_f, X_g, X_h, X_i and X_j are nitrogen.

In a particular group of compounds of the present invention, when R³ is a group of Formula C, no more than one of X_f, X_g, X_h, X^i and X^j is nitrogen.

Particular compounds of the invention include, for example, compounds of the Formula I, or pharmaceutically acceptable salts, hydrates and/or solvates thereof, wherein, unless otherwise stated, each of X₁, X₂, X₃, R¹, R², R³, R⁴, R⁵ and any associated substituent groups has any of the meanings defined hereinbefore or in any of paragraphs (1) to (101) hereinafter:—

(1) X₁ is selected from N or CRᵃ, wherein Rᵃ is selected from hydrogen, (1-2C)alkyl, fluoro, chloro, hydroxy, (1-2C)alkoxy, CH₂F, CHF₂, CF₃, OCF₃, acetylenyl, nitro, cyano or NR^bR^c, wherein R^b and R^c are independently selected from hydrogen or (1-2C)alkyl;

(2) X₁ is selected from N or CRᵃ, wherein Rᵃ is selected from hydrogen, methyl, fluoro, chloro, hydroxy, OCH₃, CH₂F, CHF₂, CF₃, OCF₃, acetylenyl, cyano or NH₂;

(3) X₁ is selected from N or CRᵃ, wherein Rᵃ is selected from hydrogen, methyl, fluoro, chloro, hydroxy, OCH₃, CH₂F, CHF₂, acetylenyl, cyano or NH₂;

(4) X₁ is selected from N or CRᵃ, wherein Rᵃ is selected from hydrogen, methyl, fluoro, chloro, hydroxy, OCH₃, acetylenyl or cyano;

(5) $X_1$ is selected from N or $CR^a$, wherein $R^a$ is selected from hydrogen, methyl, fluoro, chloro, $OCH_3$ or cyano;
(6) $X_1$ is selected from N or $CR^a$, wherein $R^a$ is selected from hydrogen, (1-2C)alkyl or (1-2C)alkoxy
(7) $X_1$ is selected from N or $CR^a$, wherein $R^a$ is selected from hydrogen, methyl, $OCH_3$, fluoro or chloro;
(8) $X_1$ is selected from N or CH;
(9) $X_1$ is N;
(10) $X_1$ is CH;
(11) $X_2$ is selected from N, CH, CF or C—$CH_3$;
(12) $X_2$ is selected from N or CH;
(13) $X_2$ is N;
(14) $X_2$ is selected from CH, CF or C—$CH_3$;
(15) $X_2$ is CH;
(16) $X_3$ is selected from N or $CR^d$, wherein $R^d$ is selected from hydrogen, fluoro or methyl;
(17) $X_3$ is selected from N or $CR^d$, wherein $R^d$ is selected from hydrogen or fluoro;
(18) $X_3$ is selected from N or CH;
(19) $X_3$ is N;
(20) $X_3$ is CH;
(21) $R^1$ is selected from hydrogen or a group of the formula:

-L-Y—Z wherein:
L is absent or (1-5C)alkylene optionally substituted by one or more substituents selected from (1-2C)alkyl or oxo;
Y is absent or O, S, SO, $SO_2$, $N(R^e)$, C(O), C(O)O, OC(O), $C(O)N(R^e)$, $N(R^e)C(O)$, $S(O)_2N(R^e)$, or $N(R^e)SO_2$, wherein $R^e$ is selected from hydrogen or (1-4C)alkyl; and
Z is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Z is optionally further substituted by one or more substituent groups independently selected from oxo, (1-4C)alkyl, halo, (1-4C)haloalkyl, (1-4C)haloalkoxy, amino, (1-4C)aminoalkyl, cyano, hydroxy, carboxy, carbamoyl, sulphamoyl, mercapto, ureido, $NR^gR^h$, $OR^g$, $C(O)R^g$, $C(O)OR^g$, $OC(O)R^g$, $C(O)N(R^g)R^h$, $N(R^g)C(O)R^h$, $S(O)_yR^g$ (where y is 0, 1 or 2), $SO_2N(R^g)R^h$, $N(R^g)SO_2R^g$, $Si(R^g)(R^h)R^i$ or $(CH_2)_zNR^gR^h$ (where z is 1, 2 or 3); wherein $R^g$, $R^h$ and $R^i$ are each independently selected from hydrogen, (1-6C)alkyl or (3-6C)cycloalkyl; or $R^g$ and $R^h$ can be linked such that, together with the nitrogen atom to which they are attached, they form a 4-9 membered heterocyclic ring which is optionally substituted by one or more substituents selected from oxo, (1-4C)alkyl, halo, (1-4C)haloalkyl, (1-4C)haloalkoxy, (1-4C)alkoxy, (1-4C)alkylamino, amino, cyano or hydroxy;
(22) $R^1$ is selected from hydrogen or a group of the formula:

-L-Y—Z wherein:
L is absent or (1-5C)alkylene optionally substituted by one or more substituents selected from (1-2C)alkyl;
Y is absent or O, S, SO, $SO_2$, $N(R^e)$, C(O), C(O)O, OC(O), $C(O)N(R^e)$, $N(R^e)C(O)$, $S(O)_2N(R^e)$, or $N(R^e)SO_2$, wherein $R^e$ is selected from hydrogen or (1-4C)alkyl; and
Z is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Z is optionally further substituted by one or more substituent groups independently selected from oxo, (1-4C)alkyl, halo, (1-4C)haloalkyl, (1-4C)haloalkoxy, amino, (1-4C)aminoalkyl, cyano, hydroxy, carboxy, carbamoyl, sulphamoyl, mercapto, ureido, $NR^gR^h$, $OR^g$, $C(O)R^g$, $C(O)OR^g$, $OC(O)R^g$, $C(O)N(R^g)R^h$, $N(R^g)C(O)R^h$, $S(O)_yR^g$ (where y is 0, 1 or 2), $SO_2N(R^g)R^h$, $N(R^g)SO_2R^g$, $Si(R^g)(R^h)R^i$ or $(CH_2)_zNR^gR^h$ (where z is 1, 2 or 3); wherein $R^g$, $R^h$ and $R^i$ are each independently selected from hydrogen, (1-6C)alkyl or (3-6C)cycloalkyl; or $R^g$ and $R^h$ can be linked such that, together with the nitrogen atom to which they are attached, they form a 4-9 membered heterocyclic ring;
(23) $R^1$ is selected from hydrogen or a group of the formula:

-L-Y—Z wherein:
L is absent or (1-5C)alkylene;
Y is absent or O, $SO_2$, $N(R^e)$, C(O), C(O)O, OC(O), $C(O)N(R^e)$, $N(R^e)C(O)$, $S(O)_2N(R^e)$, or $N(R^e)SO_2$, wherein $R^e$ is selected from hydrogen or (1-4C)alkyl; and
Z is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Z is optionally further substituted by one or more substituent groups independently selected from oxo, (1-4C)alkyl, halo, (1-4C)haloalkyl, (1-4C)haloalkoxy, amino, (1-4C)aminoalkyl, cyano, hydroxy, carboxy, carbamoyl, sulphamoyl, mercapto, ureido, $NR^gR^h$, $OR^g$, $C(O)R^g$, $C(O)OR^g$, $OC(O)R^g$, $C(O)N(R^g)R^h$, $N(R^g)C(O)R^h$, $S(O)_yR^g$ (where y is 0, 1 or 2), $SO_2N(R^g)R^h$, $N(R^g)SO_2R^g$, $Si(R^g)(R^h)R^i$ or $(CH_2)_zNR^gR^h$ (where z is 1, 2 or 3); wherein $R^g$, $R^h$ and $R^i$ are each independently selected from hydrogen, (1-6C)alkyl or (3-6C)cycloalkyl;
(24) $R^1$ is selected from hydrogen or a group of the formula:

-L-Y—Z wherein:
L is absent or (1-5C)alkylene;
Y is absent or O, $SO_2$, C(O), C(O)O, $C(O)N(R^e)$ or $S(O)_2N(R^e)$, wherein $R^e$ is selected from hydrogen or (1-4C)alkyl; and
Z is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Z is optionally further substituted by one or more substituent groups independently selected from oxo, (1-2C)alkyl, halo, (1-2C)haloalkyl, (1-2C)haloalkoxy, amino, (1-2C)aminoalkyl, cyano, hydroxy, carboxy, carbamoyl, sulphamoyl, mercapto, ureido, $NR^gR^h$, $OR^g$, $C(O)R^g$, $C(O)OR^g$, $OC(O)R^g$, $C(O)N(R^g)R^h$, $N(R^g)C(O)R^h$, $S(O)_yR^g$ (where y is 0, 1 or 2), $SO_2N(R^g)R^h$, $N(R^g)SO_2R^g$, $Si(R^g)(R^h)R^i$ or $(CH_2)_zNR^gR^h$ (where z is 1, 2 or 3); wherein $R^g$, $R^h$ and $R^i$ are each independently selected from hydrogen or (1-4C)alkyl;
(25) $R^1$ is selected from hydrogen or a group of the formula:

-L-Y—Z wherein:
L is absent or (1-5C)alkylene;
Y is absent or O, $SO_2$, C(O), C(O)O, $C(O)N(R^e)$ or $S(O)_2N(R^e)$, wherein $R^e$ is selected from hydrogen or (1-4C)alkyl; and
Z is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Z is optionally further substituted by one or more substituent groups independently selected from oxo, (1-2C)alkyl, halo, (1-2C)haloalkyl, (1-2C)haloalkoxy, amino, (1-2C) aminoalkyl, cyano, hydroxy, carboxy, carbamoyl, sulphamoyl, mercapto, ureido, $NR^gR^h$ or $OR^g$; wherein $R^g$ and $R^h$ are each independently selected from hydrogen or (1-4C)alkyl;

(26) $R^1$ is selected from hydrogen or a group of the formula:

-L-Y—Z wherein:
L is absent or (1-5C)alkylene;
Y is absent or O, $SO_2$, C(O), C(O)O, $C(O)N(R^e)$ or $S(O)_2N(R^e)$, wherein $R^e$ is selected from hydrogen or (1-4C)alkyl; and
Z is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Z is optionally further substituted by one or more substituent groups independently selected from oxo, (1-2C)alkyl, halo, (1-2C)haloalkyl, (1-2C)haloalkoxy, amino, (1-2C) aminoalkyl, cyano, hydroxy, $NR^gR^h$ or $OR^g$; wherein $R^g$ and $R^h$ are each independently selected from hydrogen or (1-4C)alkyl;

(27) $R^1$ is selected from hydrogen or a group of the formula:

-L-Y—Z wherein:
L is absent or (1-3C)alkylene;
Y is absent or O, C(O), C(O)O or $C(O)N(R^e)$, wherein $R^e$ is selected from hydrogen or (1-4C)alkyl; and
Z is hydrogen, (1-6C)alkyl, (2-4C)alkenyl, (2-4C)alkynyl, aryl, (3-6C)cycloalkyl, (3-6C)cycloalkenyl, 5 or 6 membered heteroaryl or 5 or 6 membered heterocyclyl; wherein Z is optionally further substituted by one or more substituent groups independently selected from oxo, (1-2C)alkyl, halo, (1-2C)haloalkyl, (1-2C)haloalkoxy, amino, (1-2C)aminoalkyl, cyano, hydroxy, $NR^gR^h$ or $OR^g$; wherein $R^g$ and $R^h$ are each independently selected from hydrogen or (1-4C)alkyl;

(28) $R^1$ is selected from hydrogen or a group of the formula:

-L-Y—Z wherein:
L is absent or (1-3C)alkylene;
Y is absent or O, C(O), C(O)O or $C(O)N(R^e)$, wherein $R^e$ is selected from hydrogen or (1-4C)alkyl; and
Z is hydrogen, (1-6C)alkyl, aryl, (3-6C)cycloalkyl, (3-6C)cycloalkenyl, 5 or 6 membered heteroaryl or 4 to 7-membered heterocyclyl; wherein Z is optionally further substituted by one or more substituent groups independently selected from oxo, (1-2C)alkyl, halo, (1-2C)haloalkyl, (1-2C)haloalkoxy, amino, (1-2C) aminoalkyl, cyano, hydroxy, $NR^gR^h$ or $OR^g$; wherein $R^g$ and $R^h$ are each independently selected from hydrogen or (1-4C)alkyl;

(29) $R^1$ is selected from hydrogen or a group of the formula:

-L-Y—Z wherein:
L is absent or (1-3C)alkylene;
Y is absent or O, C(O), C(O)O or $C(O)N(R^e)$, wherein $R^e$ is selected from hydrogen or (1-4C)alkyl; and
Z is hydrogen, (1-6C)alkyl, aryl, (3-6C)cycloalkyl, (3-6C)cycloalkenyl, 5 or 6 membered heteroaryl or 5 or 6 membered heterocyclyl; wherein Z is optionally further substituted by one or more substituent groups independently selected from oxo, (1-2C)alkyl, halo, (1-2C)haloalkyl, (1-2C)haloalkoxy, amino, (1-2C) aminoalkyl, cyano, hydroxy, $NR^gR^h$ or $OR^g$; wherein $R^g$ and $R^h$ are each independently selected from hydrogen or (1-4C)alkyl;

(30) $R^1$ is selected from hydrogen or a group of the formula:

-L-Z wherein:
L is absent or (1-3C)alkylene; and
Z is (1-6C)alkyl, aryl, (3-6C)cycloalkyl, (3-6C)cycloalkenyl, 5 or 6 membered heteroaryl or 4 to 7 membered heterocyclyl; wherein Z is optionally further substituted by one or more substituent groups independently selected from oxo, (1-2C)alkyl, halo, (1-2C)haloalkyl, (1-2C)haloalkoxy, amino, (1-2C) aminoalkyl, cyano, hydroxy, $NR^gR^h$ or $OR^g$; wherein $R^g$ and $R^h$ are each independently selected from hydrogen or (1-2C)alkyl;

(31) $R^1$ is selected from hydrogen or a group of the formula:

-L-Z wherein:
L is absent or (1-2C)alkylene; and
Z is (1-6C)alkyl, (3-6C)cycloalkyl or 4 to 7 membered heterocyclyl; wherein Z is optionally further substituted by one or more substituent groups independently selected from oxo, (1-2C)alkyl, halo, (1-2C) haloalkyl, (1-2C)haloalkoxy, amino, (1-2C) aminoalkyl, cyano, hydroxy, $NR^gR^h$ or $OR^g$; wherein $R^g$ and $R^h$ are each independently selected from hydrogen or (1-2C)alkyl;

(32) $R^1$ is selected from hydrogen, (1-6C)alkyl or a group of the formula:

-L-Z wherein:
L is (1-2C)alkylene; and
Z is (3-6C)cycloalkyl or 4 to 7 membered heterocyclyl; wherein Z is optionally further substituted by one or more substituent groups independently selected from oxo, (1-2C)alkyl, halo, (1-2C)haloalkyl, (1-2C)haloalkoxy, amino, (1-2C)aminoalkyl, cyano, hydroxy, $NR^gR^h$ or $OR^g$; wherein $R^g$ and $R^h$ are each independently selected from hydrogen or methyl;

(33) $R^1$ is selected from hydrogen, (1-6C)alkyl or (3-6C)cycloalkyl; wherein each (1-6C)alkyl or (3-6C)cycloalkyl is optionally further substituted by one or more substituent groups independently selected from oxo, (1-2C)alkyl, halo, (1-2C)haloalkyl, (1-2C)haloalkoxy, amino, (1-2C) aminoalkyl, cyano, hydroxy or $NH_2$;

(34) $R^1$ is selected from hydrogen, (1-6C)alkyl or (3-6C)cycloalkyl;

(35) $R^1$ is (1-6C)alkyl (e.g. methyl);

(36) $R^2$ is selected from:
i) a group of Formula A shown below:

Formula A

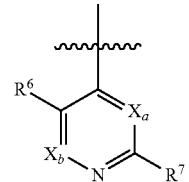

wherein:

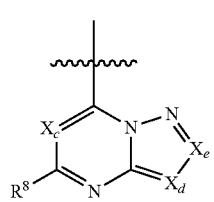 denotes the point of attachment;

$X_a$ and $X_b$ are each independently selected from N or $CR^{x1}$, wherein $R^{x1}$ is selected from hydrogen, fluoro, chloro, bromo, (1-2C)alkyl, (1-2C)alkoxy, cyano, nitro, acetylenyl, $CH_2F$, $CF_2H$ or $CF_3$;

$R^6$ is selected from hydrogen, fluoro, chloro, bromo, (1-2C)alkyl, (1-2C)alkoxy, cyano, nitro, acetylenyl, $CH_2F$, $CF_2H$ or $CF_3$;

$R^7$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_3$—$Z_3$ wherein:

$Y_3$ is absent or O, S, $N(R^j)(CR^jR^k)_{q1}$ (where $q_1$ is 0, 1 or 2), C(O), C(O)O, OC(O), C(O)N($R^j$), N($R^j$)C(O), $S(O)_2N(R^j)$, $N(R^j)SO_2$, wherein $R^j$ is selected from hydrogen or (1-4C)alkyl; and $Z_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or a 4 to 11-membered heterocyclyl; wherein $Z_3$ is optionally further substituted by one or more substituent groups independently selected from oxo, (1-4C)alkyl, cyclopropyl, halo, (1-4C)haloalkyl, (1-4C)haloalkoxy, amino, cyano, hydroxy, carboxy, carbamoyl, sulphamoyl, mercapto, $C(O)NR^lR^m$, $NR^lR^m$ or $OR^l$, wherein $R^l$ and $R^m$ are each independently selected from hydrogen, (1-4C)alkyl or (3-6C)cycloalkyl; or $Z^3$ is optionally further substituted by a group of the formula:

-$L_Z$-$W_Z$ wherein:

$L_Z$ is absent or a (1-3C)alkylene optionally substituted by one or more (1-2C)alkyl groups; and $W_Z$ is aryl, 5- or 6-membered heteroaryl, 5- or 6-membered heterocyclyl, halo, (1-4C)haloalkyl, (1-4C)haloalkoxy, cyano, hydroxy, (1-4C)alkoxy, $C(O)R^{xa}$, $COOR^{xa}$, $C(O)NR^{xa}R^{xb}$ or $NR^{xa}R^{xb}$, wherein $R^{xa}$ and $R^{xb}$ are each independently selected from hydrogen or (1-4C)alkyl; and wherein each aryl, 5- or 6-membered heteroaryl, 5- or 6-membered heterocyclyl is optionally further substituted by one or more substituent groups independently selected from (1-4C)alkyl, halo, (1-4C)haloalkyl, amino, cyano or hydroxy;

ii) a group of Formula B shown below:

Formula B wherein:

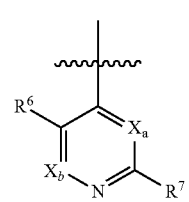 denotes the point of attachment;

$X_c$, $X_d$ and $X_e$ are each independently selected from N, CH, CF, CCl, C—CN or $CCH_3$;

$R^8$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_5$—$Z_5$ wherein:

$Y_5$ is absent or O, N($R''$), C(O), C(O)O, OC(O), C(O)N($R''$), N($R''$)C(O), $S(O)_2N(R'')$, $N(R'')SO_2$, wherein $R''$ is selected from hydrogen or (1-4C)alkyl; and $Z_5$ is hydrogen, (1-6C)alkyl, aryl, (3-8C)cycloalkyl, (3-8C)cycloalkenyl, heteroaryl or heterocyclyl; wherein $Z_5$ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, $NR^pR^q$, $OR^p$, wherein $R^p$ and $R^q$ are each independently selected from hydrogen, (1-4C)alkyl or (3-6C)cycloalkyl; and iii) a group of Formula C shown below:

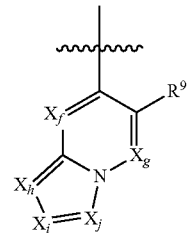

Formula C wherein:

 denotes the point of attachment;

$R^9$ is selected from fluoro, chloro, bromo, (1-2C)alkyl, (1-2C)alkoxy, cyano, nitro, (2-4C)alkynyl, $CH_2F$, $CF_2H$ or $CF_3$;

$X_f$ and $X_g$ are independently selected from N or $CR^{10}$, wherein $R^{10}$ is selected from hydrogen, fluoro, chloro, (1-2C)alkyl, (1-2C)haloalkyl or (1-2C)haloalkoxy;

$X_h$, $X_i$ and $X_j$ are independently selected from N or $CR^{11}$, wherein $R^{11}$ is selected from hydrogen, halo, (1-2C)alkyl, (1-2C)alkoxy, (1-2C)haloalkyl or (1-2C)haloalkoxy;

(37) $R^2$ is selected from:

i) a group of Formula A shown below:

Formula A wherein:

 denotes the point of attachment;

$X_a$ and $X_b$ are each independently selected from N or $CR^{x1}$, wherein $R^{x1}$ is selected from hydrogen, fluoro, chloro, bromo, (1-2C)alkyl, (1-2C)alkoxy, cyano, nitro, acetylenyl, $CH_2F$, $CF_2H$ or $CF_3$;

$R^6$ is selected from hydrogen, fluoro, chloro, bromo, (1-2C)alkyl, (1-2C)alkoxy, cyano, nitro, acetylenyl, $CH_2F$, $CF_2H$ or $CF_3$;

$R^7$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_3$—$Z_3$ wherein:

$Y_3$ is absent or O, S, $N(R^j)(CR^jR^k)_{q1}$ (where $q_1$ is 0, 1 or 2), C(O), C(O)O, OC(O), C(O)N($R^j$), N($R^j$)C(O), S(O)$_2$N($R^j$), N($R^j$)SO$_2$, wherein $R^j$ is selected from hydrogen or (1-4C)alkyl; and $Z_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or a 4 to 11-membered heterocyclyl; wherein $Z_3$ is optionally further substituted by one or more substituent groups independently selected from oxo, (1-4C)alkyl, cyclopropyl, halo, (1-4C)haloalkyl, (1-4C)haloalkoxy, amino, cyano, hydroxy, carboxy, carbamoyl, sulphamoyl, mercapto, C(O)NR$^l$R$^m$, NR$^l$R$^m$ or OR$^l$, wherein R$^l$ and R$^m$ are each independently selected from hydrogen, (1-4C)alkyl or (3-6C)cycloalkyl; or $Z^3$ is optionally further substituted by a group of the formula:

-L$_Z$-W$_Z$ wherein:

L$_Z$ is a (1-3C)alkylene optionally substituted by one or more substituents selected from (1-2C)alkyl or oxo; and W$_Z$ is halo, (1-4C)haloalkyl, (1-4C)haloalkoxy, cyano, hydroxy, (1-4C)alkoxy, CR$^{xa}$, COOR$^{xa}$, C(O)NR$^{xa}$R$^{xb}$ or NR$^{xa}$R$^{xb}$, wherein R$^{xa}$ and R$^{xb}$ are each independently selected from hydrogen or (1-4C)alkyl;

ii) a group of Formula B shown below:

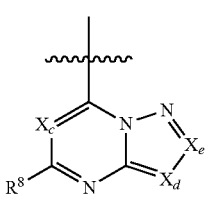

Formula B wherein:

⟿ denotes the point of attachment; X$_c$, X$_d$ and X$_e$ are each independently selected from N, CH, CF, CCl, C—CN or CCH$_3$;

$R^8$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_5$—$Z_5$ wherein:

$Y_5$ is absent or O, N(R″), C(O), C(O)O, OC(O), C(O)N(R″), N(R″)C(O), S(O)$_2$N(R″), N(R″)SO$_2$, wherein R″ is selected from hydrogen or (1-4C)alkyl; and $Z_5$ is hydrogen, (1-6C)alkyl, aryl, (3-8C)cycloalkyl, (3-8C)cycloalkenyl, heteroaryl or heterocyclyl; wherein $Z_5$ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, NR$^p$R$^q$, OR$^p$, wherein R$^p$ and R$^q$ are each independently selected from hydrogen, (1-4C)alkyl or (3-6C)cycloalkyl; and iii) a group of Formula C shown below:

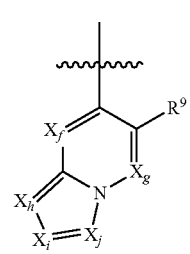

Formula C wherein:

⟿ denotes the point of attachment;

$R^9$ is selected from fluoro, chloro, bromo, (1-2C)alkyl, (1-2C)alkoxy, cyano, nitro, (2-4C)alkynyl, $CH_2F$, $CF_2H$ or $CF_3$;

X$_f$ and X$_g$ are independently selected from N or CR$^{10}$, wherein R$^{10}$ is selected from hydrogen, fluoro, chloro, (1-2C)alkyl, (1-2C)haloalkyl or (1-2C)haloalkoxy;

X$_h$, X$_i$ and X$_j$ are independently selected from N or CR$^{11}$, wherein R$^{11}$ is selected from hydrogen, halo, (1-2C)alkyl, (1-2C)alkoxy, (1-2C)haloalkyl or (1-2C)haloalkoxy;

(38) $R^2$ is selected from:

i) a group of Formula A shown below:

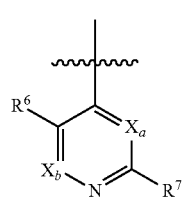

Formula A wherein:

⟿ denotes the point of attachment;

X$_a$ and X$_b$ are each independently selected from N or CR$^{x1}$, wherein R$^{x1}$ is selected from hydrogen, fluoro, chloro, bromo, (1-2C)alkyl, (1-2C)alkoxy, cyano, nitro, acetylenyl, $CH_2F$, $CF_2H$ or $CF_3$;

$R^6$ is selected from hydrogen, fluoro, chloro, bromo, methyl, OCH$_3$, cyano, nitro, acetylenyl, $CH_2F$ or $CF_2H_3$;

$R^7$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_3$—$Z_3$ wherein:
- $Y_3$ is absent or $N(R^j)(CH_2)_{q1}$ (where $q_1$ is 0 or 1), C(O), C(O)O, OC(O), C(O)N(R^j), N(R^j)C(O), S(O)_2N(R^j), N(R^j)SO_2, wherein $R^j$ is selected from hydrogen or (1-4C)alkyl; and
- $Z_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or a 4 to 11-membered heterocyclyl; wherein $Z_3$ is optionally further substituted by one or more substituent groups independently selected from oxo, (1-4C)alkyl, halo, (1-4C)haloalkyl, (1-4C)haloalkoxy, amino, cyano, hydroxy, carboxy, carbamoyl, sulphamoyl, mercapto, $C(O)NR^lR^m$, $NR^lR^m$ or $OR^l$, wherein $R^l$ and $R^m$ are each independently selected from hydrogen, (1-4C)alkyl or (3-6C)cycloalkyl; or $Z^3$ is optionally further substituted by a group of the formula:

-L_Z-W_Z wherein:
- $L_Z$ is a (1-3C)alkylene; and
- $W_Z$ is halo, (1-4C)haloalkyl, (1-4C)haloalkoxy, cyano, hydroxy, (1-4C)alkoxy, $CR^{xa}$, $COOR^{xa}$, $C(O)NR^{xa}R^{xb}$ or $NR^{xa}R^{xb}$, wherein $R^{xa}$ and $R^{xb}$ are each independently selected from hydrogen or (1-4C)alkyl;

ii) a group of Formula B shown below:

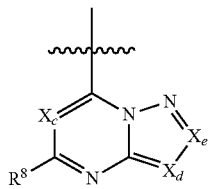

Formula B wherein:
- denotes the point of attachment;
- $X_c$, $X_d$ and $X_e$ are each independently selected from N, CH, CF, CCl, C—CN or $CCH_3$;
- $R^8$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y_5—Z_5 wherein:
- $Y_5$ is absent or O, N(R''), C(O), C(O)O, C(O)N(R'') or $S(O)_2N(R'')$, wherein $R''$ is selected from hydrogen or (1-4C)alkyl; and
- $Z_5$ is hydrogen, (1-6C)alkyl, aryl, (3-8C)cycloalkyl, (3-8C)cycloalkenyl, heteroaryl or heterocyclyl; wherein $Z_5$ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, $NR^pR^q$ or $OR^p$, wherein $R^p$ and $R^q$ are each independently selected from hydrogen, (1-4C)alkyl or (3-6C)cycloalkyl; and iii) a group of Formula C shown below:

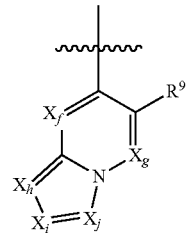

Formula C wherein:
- denotes the point of attachment;
- $R^9$ is selected from fluoro, chloro, bromo, methyl, $OCH_3$, cyano, acetylenyl, $CH_2F$, $CF_2H$ or $CF_3$;
- $X_f$ and $X_g$ are independently selected from N or $CR^{10}$, wherein $R^{10}$ is selected from hydrogen, fluoro, chloro, methyl, $CH_2F$, $CF_2H$ or $CF_3$;
- $X_h$, $X_i$ and $X_j$ are independently selected from N or $CR^{11}$, wherein $R^{11}$ is selected from hydrogen, halo, (1-2C)alkyl, (1-2C)alkoxy, (1-2C)haloalkyl or (1-2C)haloalkoxy;

(39) $R^2$ is selected from:
i) a group of Formula A shown below:

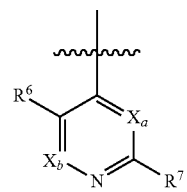

Formula A wherein:
- denotes the point of attachment;
- $X_a$ and $X_b$ are each independently selected from N or $CR^{x1}$, wherein $R^{x1}$ is selected from hydrogen, fluoro, chloro, bromo, (1-2C)alkyl, (1-2C)alkoxy, cyano, nitro, acetylenyl, $CH_2F$, $CF_2H$ or $CF_3$;
- $R^6$ is selected from hydrogen, fluoro, chloro, bromo, (1-2C)alkyl, (1-2C)alkoxy, cyano, nitro, acetylenyl, $CH_2F$, $CF_2H$ or $CF_3$;
- $R^7$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y_3—Z_3 wherein:
- $Y_3$ is absent or C(O), C(O)O, OC(O), C(O)N(R^j), N(R^j)C(O), N(R^j)C(O)N(R^k), N(R^j)C(O)O, OC(O)N(R^j), S(O)_2N(R^j), N(R^j)SO_2, wherein $R^j$ and $R^k$ are each independently selected from hydrogen or (1-4C)alkyl; and
- $Z_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or 5- or 6-membered heterocyclyl; wherein $Z_3$ is optionally further substituted by one or more substituent groups independently selected from oxo, (1-4C)alkyl, halo, (1-4C)haloalkyl, (1-4C)haloalkoxy, amino, cyano, hydroxy, amido, carboxy, carbamoyl, sulphamoyl, mercapto, NR$^l$R$^m$ or OR$^l$, wherein R$^l$ and R$^m$ are each independently selected from hydrogen, (1-4C)alkyl or (3-6C)cycloalkyl;

ii) a group of Formula B shown below:

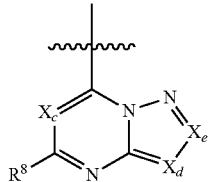

Formula B wherein:

⤳ denotes the point of attachment;

X$_c$, X$_d$ and X$_e$ are each independently selected from N, CH, CF, CCl, C—CN or CCH$_3$;

R$^8$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_5$—Z$_5$ wherein:

Y$_5$ is absent or O, N(R''), C(O), C(O)O, OC(O), C(O)N(R''), N(R'')C(O), N(R'')C(O)N(R$^o$), N(R'')C(O)O, OC(O)N(R''), S(O)$_2$N(R''), N(R'')SO$_2$, wherein R'' and R$^o$ are each independently selected from hydrogen or (1-4C)alkyl; and Z$_5$ is hydrogen, (1-6C)alkyl, aryl, (3-8C)cycloalkyl, (3-8C)cycloalkenyl, heteroaryl or heterocyclyl; wherein Z$_5$ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, NR$^p$R$^q$, OR$^p$, wherein R$^p$ and R$^q$ are each independently selected from hydrogen, (1-4C)alkyl or (3-6C)cycloalkyl; and iii) a group of Formula C shown below:

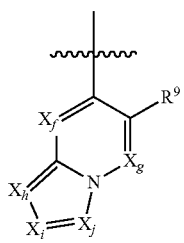

Formula C wherein:

⤳ denotes the point of attachment;

R$^9$ is selected from fluoro, chloro, bromo, (1-2C)alkyl, (1-2C)alkoxy, cyano, nitro, (2-4C)alkenyl, (2-4C)alkynyl, CH$_2$F, CF$_2$H or CF$_3$;

X$_f$ and X$_g$ are each independently selected from N or CR$^{10}$, wherein R$^{10}$ is selected from hydrogen, fluoro, chloro, (1-2C)alkyl, (1-2C)haloalkyl or (1-2C)haloalkoxy;

X$_h$, X$_i$ and X$_j$ are each independently selected from N or CR$^{11}$, wherein R$^{11}$ is selected from hydrogen, halo, (1-2C)alkyl, (1-2C)alkoxy, (1-2C)haloalkyl or (1-2C)haloalkoxy;

(40) R$^2$ is selected from:

i) a group of Formula A shown below:

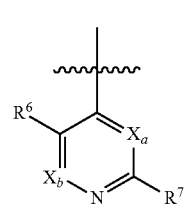

Formula A wherein:

⤳ denotes the point of attachment;

X$_a$ and X$_b$ are independently selected from N or CR$^{x1}$, wherein R$^{x1}$ is selected from hydrogen, fluoro, chloro, bromo, (1-2C)alkyl, (1-2C)alkoxy, cyano, nitro, acetylenyl, CH$_2$F, CF$_2$H or CF$_3$;

R$^6$ is selected from hydrogen, fluoro, chloro, bromo, (1-2C)alkyl, (1-2C)alkoxy, cyano, nitro, acetylenyl, CH$_2$F, CF$_2$H or CF$_3$;

R$^7$ is selected from hydrogen, halo, (1-2C)alkyl, (1-2C)alkoxy, (1-2C)haloalkyl, (1-2C)haloalkoxy, cyano, nitro, (2-4C)alkenyl, (2-4C)alkynyl or a group of the formula:

—Y$_3$—Z$_3$ wherein:

Y$_3$ is absent or C(O), C(O)O, OC(O), C(O)N(R$^j$), N(R$^j$)C(O), S(O)$_2$N(R$^j$), N(R$^j$)SO$_2$, wherein R$^j$ is selected from hydrogen or (1-4C)alkyl; and Z$_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or 5- or 6-membered heterocyclyl; wherein Z$_3$ is optionally further substituted by one or more substituent groups independently selected from oxo, (1-4C)alkyl, halo, (1-4C)haloalkyl, (1-4C)haloalkoxy, amino, cyano, hydroxy, amido, carboxy, carbamoyl, sulphamoyl, mercapto, NR$^l$R$^m$ or OR$^l$, wherein R$^l$ and R$^m$ are each independently selected from hydrogen, (1-4C)alkyl or (3-6C)cycloalkyl;

ii) a group of Formula B shown below:

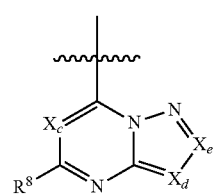

Formula B wherein:

⤳ denotes the point of attachment;

X$_c$, X$_d$ and X$_e$ are independently selected from N, CH, CF, CCl, C—CN or CCH$_3$;

R$^8$ is selected from hydrogen, halo, (1-2C)alkyl, (1-2C)alkoxy, (1-2C)haloalkyl, (1-2C)haloalkoxy, cyano, nitro, (2-4C)alkenyl, (2-4C)alkynyl or a group of the formula:

—Y$_5$—Z$_5$ wherein:
Y₅ is absent or O, N(R″), C(O), C(O)O, OC(O), C(O)N(R″), N(R″)C(O), S(O)₂N(R″), N(R″)SO₂, wherein R″ is selected from hydrogen or (1-4C)alkyl; and Z₅ is hydrogen, (1-6C)alkyl, aryl, (3-8C)cycloalkyl, (3-8C)cycloalkenyl, heteroaryl or heterocyclyl; wherein Z₅ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, NR$^p$R$^q$, OR$^p$, wherein R$^p$ and R$^q$ are each independently selected from hydrogen, (1-4C)alkyl or (3-6C)cycloalkyl; and iii) a group of Formula C shown below:

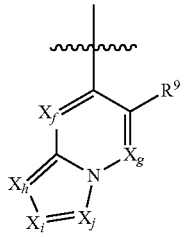

Formula C wherein:

denotes the point of attachment;

R⁹ is selected from fluoro, chloro, bromo, (1-2C)alkyl, (1-2C)alkoxy, cyano, nitro, (2-4C)alkynyl, CH₂F, CF₂H or CF₃;

$X_f$ and $X_g$ are independently selected from N or CR¹⁰, wherein R¹⁰ is selected from hydrogen, fluoro, chloro, (1-2C)alkyl, (1-2C)haloalkyl or (1-2C)haloalkoxy;

$X_h$, $X_i$ and $X_j$ are independently selected from N or CR¹¹, wherein R¹¹ is selected from hydrogen, halo, (1-2C)alkyl, (1-2C)alkoxy, (1-2C)haloalkyl or (1-2C)haloalkoxy;

(41) R² is selected from:
i) a group of Formula A shown below:

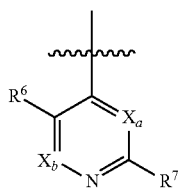

Formula A wherein:

denotes the point of attachment;

$X_a$ and $X_b$ are independently selected from N or CR$^{x1}$, wherein R$^{x1}$ is selected from hydrogen, fluoro, chloro, bromo, methyl, OCH₃, cyano, nitro, acetylenyl, CH₂F, CF₂H or CF₃;

R⁶ is selected from hydrogen, fluoro, chloro, bromo, methyl, OCH₃, cyano, nitro, acetylenyl, CH₂F or CF₂H;

R⁷ is selected from hydrogen, halo, (1-2C)alkyl, (1-2C)alkoxy, (1-2C)haloalkyl, (1-2C)haloalkoxy, cyano, nitro, (2-4C)alkenyl, (2-4C)alkynyl or a group of the formula:

—Y₃—Z₃ 

wherein:

Y₃ is absent or C(O), C(O)O, OC(O), C(O)N(R$^j$), N(R$^j$)C(O), S(O)₂N(R$^j$), N(R$^j$)SO₂, wherein R$^j$ is selected from hydrogen or (1-4C)alkyl; and Z₃ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or 5- or 6-membered heterocyclyl; wherein Z₃ is optionally further substituted by one or more substituent groups independently selected from oxo, (1-4C)alkyl, halo, (1-4C)haloalkyl, (1-4C)haloalkoxy, amino, cyano, hydroxy, amido, carboxy, NR$^l$R$^m$ or OR$^l$, wherein R$^l$ and R$^m$ are each independently selected from hydrogen or (1-4C)alkyl;

ii) a group of Formula B shown below:

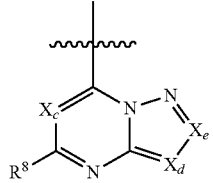

Formula B wherein:

denotes the point of attachment;

$X_c$, $X_d$ and $X_e$ are independently selected from N, CH, CF, CCl, C—CN or CCH₃;

R⁸ is selected from hydrogen, halo, (1-2C)alkyl, (1-2C)alkoxy, (1-2C)haloalkyl, (1-2C)haloalkoxy, cyano, nitro, (2-4C)alkenyl, (2-4C)alkynyl or a group of the formula:

—Y₅—Z₅ 

wherein:

Y₅ is absent or O, N(R″), C(O), C(O)O, OC(O), C(O)N(R″), N(R″)C(O), S(O)₂N(R″), N(R″)SO₂, wherein R″ is selected from hydrogen or (1-4C)alkyl; and Z₅ is hydrogen, (1-6C)alkyl, aryl, (3-6C)cycloalkyl, (3-6C)cycloalkenyl, 5 or 6 membered heteroaryl or 5 or 6 membered heterocyclyl; wherein Z₅ is optionally further substituted by one or more substituent groups independently selected from oxo, (1-4C)alkyl, halo, (1-4C)haloalkyl, (1-4C)haloalkoxy, amino, cyano, hydroxy, amido, carboxy, NR$^p$R$^q$, OR$^p$, wherein R$^p$ and R$^q$ are each independently selected from hydrogen or (1-4C)alkyl; and iii) a group of Formula C shown below:

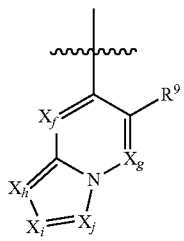

Formula C wherein:

⸺ denotes the point of attachment;
R$^9$ is selected from fluoro, chloro, bromo, methyl, OCH$_3$, cyano, nitro, acetylenyl, CH$_2$F, CF$_2$H or CF$_3$;
X$_f$ and X$_g$ are independently selected from N or CR$^{10}$, wherein R$^{10}$ is selected from hydrogen, fluoro, chloro, methyl, (1-2C)alkyl, (1-2C)haloalkyl or (1-2C)haloalkoxy;
X$_h$, X$_i$ and X$_j$ are independently selected from N or CR$^{11}$, wherein R$^{11}$ is selected from hydrogen, halo, (1-2C)alkyl, (1-2C)alkoxy, (1-2C)haloalkyl or (1-2C)haloalkoxy;
(42) R$^2$ is selected from:
i) a group of Formula A shown below:

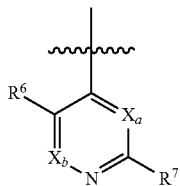

Formula A wherein:

⸺ denotes the point of attachment;
X$_a$ and X$_b$ are independently selected from N or CR$^{x1}$, wherein R$^{x1}$ is selected from hydrogen, fluoro, chloro, bromo, methyl, OCH$_3$, cyano, acetylenyl, CH$_2$F, CF$_2$H or CF$_3$;
R$^6$ is selected from fluoro, chloro, bromo, methyl, OCH$_3$, cyano, nitro or acetylenyl;
R$^7$ is selected from hydrogen, halo, (1-2C)alkyl, (1-2C)alkoxy, (1-2C)haloalkyl, (1-2C)haloalkoxy, cyano, nitro, (2-4C)alkenyl, (2-4C)alkynyl or a group of the formula:

—Y$_3$—Z$_3$ wherein:
Y$_3$ is absent or C(O), C(O)O, C(O)N(R$^i$) or S(O)$_2$N(R$^i$), wherein R$^i$ is selected from hydrogen or (1-4C)alkyl; and
Z$_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or 5- or 6-membered heterocyclyl; wherein Z$_3$ is optionally further substituted by one or more substituent groups independently selected from (1-2C)alkyl, halo, (1-2C)haloalkyl, (1-2C)haloalkoxy, amino, cyano, hydroxy, amido, carboxy, NR$^l$R$^m$ or OR$^l$, wherein R$^l$ and R$^m$ are each independently selected from hydrogen or (1-2C)alkyl;
ii) a group of Formula B shown below:

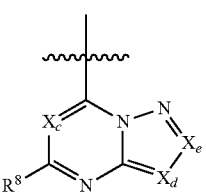

Formula B wherein:

⸺ denotes the point of attachment;
X$_c$, X$_d$ and X$_e$ are independently selected from N, CH, CF, CCl, C—CN or CCH$_3$;
R$^8$ is selected from hydrogen, halo, (1-2C)alkyl, (1-2C)alkoxy, (1-2C)haloalkyl, (1-2C)haloalkoxy, cyano, nitro, (2-4C)alkenyl, (2-4C)alkynyl or a group of the formula:

—Y$_5$—Z$_5$ wherein:
Y$_5$ is absent or O, N(R$''$), C(O), C(O)O, C(O)N(R$''$) or S(O)$_2$N(R$''$), wherein R$''$ is selected from hydrogen or (1-4C)alkyl; and
Z$_5$ is hydrogen, (1-6C)alkyl, aryl, (3-6C)cycloalkyl, (3-6C)cycloalkenyl, 5 or 6 membered heteroaryl or 5 or 6 membered heterocyclyl; wherein Z$_5$ is optionally further substituted by one or more substituent groups independently selected from (1-2C)alkyl, halo, (1-2C)haloalkyl, (1-2C)haloalkoxy, amino, cyano, hydroxy, amido, carboxy, NR$^p$R$^q$, OR$^p$, wherein R$^p$ and R$^q$ are each independently selected from hydrogen or (1-2C)alkyl; and
iii) a group of Formula C shown below:

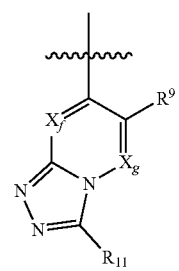

Formula C wherein:

⸺ denotes the point of attachment;
R$^9$ is selected from fluoro, chloro, bromo, methyl, OCH$_3$, cyano, acetylenyl, CH$_2$F, CF$_2$H or CF$_3$;
X$_f$ and X$_g$ are independently selected from N or CR$^{10}$, wherein R$^{10}$ is selected from hydrogen, fluoro, chloro, methyl, CH$_2$F, CF$_2$H or CF$_3$;
R$^{11}$ is selected from hydrogen, halo, (1-2C)alkyl, (1-2C)alkoxy, (1-2C)haloalkyl or (1-2C)haloalkoxy;

(43) R² is selected from:
i) a group of Formula A shown below:

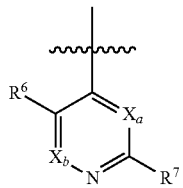

Formula A wherein:

⤳ denotes the point of attachment;

$X_a$ and $X_b$ are independently selected from N or $CR^{x1}$, wherein $R^{x1}$ is selected from hydrogen, fluoro, chloro, bromo, methyl, $OCH_3$, cyano, acetylenyl, $CH_2F$, $CF_2H$ or $CF_3$;

$R^6$ is selected from fluoro, chloro, bromo, methyl, $OCH_3$, cyano, nitro or acetylenyl;

$R^7$ is selected from hydrogen, halo, (1-2C)alkyl, (1-2C)alkoxy, (1-2C)haloalkyl, (1-2C)haloalkoxy, cyano, nitro, (2-4C)alkenyl, (2-4C)alkynyl or a group of the formula:

—$Y_3$—$Z_3$ wherein:

$Y_3$ is absent or C(O), C(O)O, C(O)N($R^j$) or S(O)₂N($R^i$), wherein $R^j$ is selected from hydrogen or (1-4C)alkyl; and $Z_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or 5- or 6-membered heterocyclyl; wherein $Z_3$ is optionally further substituted by one or more substituent groups independently selected from (1-2C)alkyl, halo, (1-2C)haloalkyl, (1-2C)haloalkoxy, amino, cyano, hydroxy, amido, carboxy, $NR^lR^m$ or $OR^l$, wherein $R^l$ and $R^m$ are each independently selected from hydrogen or (1-2C)alkyl;

ii) a group of Formula B shown below:

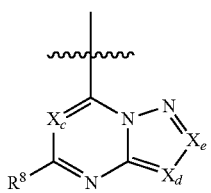

Formula B wherein:

⤳ denotes the point of attachment;

$X_c$, $X_d$ and $X_e$ are independently selected from N, CH, CF, CCl or CCH₃;

$R^8$ is selected from hydrogen, halo, (1-2C)alkyl, (1-2C)alkoxy, (1-2C)haloalkyl, (1-2C)haloalkoxy, cyano, nitro, (2-4C)alkenyl, (2-4C)alkynyl or a group of the formula:

—$Y_5$—$Z_5$ wherein:

$Y_5$ is absent or O, N($R''$), C(O), C(O)O, C(O)N($R''$) or S(O)₂N($R''$), wherein $R''$ is selected from hydrogen or (1-4C)alkyl; and $Z_5$ is hydrogen, (1-6C)alkyl, aryl, (3-6C)cycloalkyl, (3-6C)cycloalkenyl, 5 or 6 membered heteroaryl or 5 or 6 membered heterocyclyl; wherein $Z_5$ is optionally further substituted by one or more substituent groups independently selected from (1-2C)alkyl, halo, (1-2C)haloalkyl, (1-2C)haloalkoxy, amino, cyano, hydroxy, amido, carboxy, $NR^pR^q$, $OR^p$, wherein $R^p$ and $R^q$ are each independently selected from hydrogen or (1-2C)alkyl; and iii) a group of Formula C shown below:

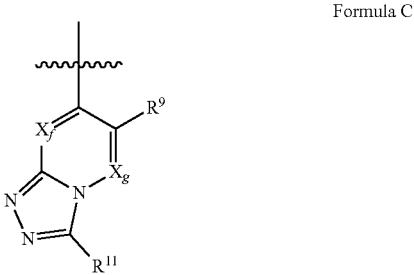

Formula C wherein:

⤳ denotes the point of attachment;

$R^9$ is selected from fluoro, chloro, bromo, methyl, $OCH_3$, cyano, acetylenyl, $CH_2F$, $CF_2H$ or $CF_3$;

$X_f$ and $X_g$ are independently selected from N or $CR^{10}$, wherein $R^{10}$ is selected from hydrogen, fluoro, chloro or methyl;

$R^{11}$ is selected from halo, methyl, $OCH_3$, $CH_2F$, $CF_2H$ or $CF_3$;

(44) R² is selected from:
i) a group of Formula A shown below:

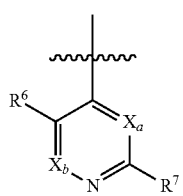

Formula A wherein:

⤳ denotes the point of attachment;

$X_a$ and $X_b$ are both $CR^{x1}$, wherein $R^{x1}$ is selected from hydrogen, fluoro, chloro, bromo, methyl, $OCH_3$, cyano or acetylenyl;

$R^6$ is selected from fluoro, chloro, bromo, methyl, $OCH_3$, cyano or acetylenyl;

$R^7$ is selected from hydrogen, halo, (1-2C)alkyl, (1-2C)alkoxy, (1-2C)haloalkyl, (1-2C)haloalkoxy, cyano, (2-4C)alkenyl, (2-4C)alkynyl or a group of the formula:

—$Y_3$—$Z_3$ wherein:

$Y_3$ is absent or C(O), C(O)O, C(O)N($R^j$) or S(O)₂N($R^i$), wherein $R^j$ is selected from hydrogen or (1-4C)alkyl; and Z₃ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or 5- or 6-membered heterocyclyl;
wherein Z₃ is optionally further substituted by one or more substituent groups independently selected from (1-2C)alkyl, halo, (1-2C)haloalkyl, (1-2C)haloalkoxy, amino, cyano, hydroxy, amido, carboxy, NR$^l$R$^m$ or OR$^l$, wherein R$^l$ and R$^m$ are each independently selected from hydrogen or (1-2C)alkyl;

ii) a group of Formula B shown below:

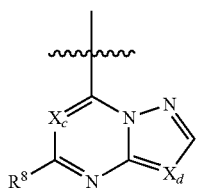

Formula B wherein:
  ⁀ denotes the point of attachment;
  X$_c$ and X$_d$ are independently selected from N, CH, CF, CCl, C—CN or CCH₃;
  R⁸ is selected from hydrogen, halo, (1-2C)alkyl, (1-2C)alkoxy, (1-2C)haloalkyl, (1-2C)haloalkoxy, cyano, (2-4C)alkenyl, (2-4C)alkynyl or a group of the formula:

—Y₅—Z₅ wherein:
    Y₅ is absent or O, N(R″), C(O), C(O)O, C(O)N(R″) or S(O)₂N(R″), wherein R″ is selected from hydrogen or (1-4C)alkyl; and
    Z₅ is hydrogen, (1-6C)alkyl, aryl, (3-6C)cycloalkyl, (3-6C)cycloalkenyl, 5 or 6 membered heteroaryl or 5 or 6 membered heterocyclyl; wherein Z₅ is optionally further substituted by one or more substituent groups independently selected from (1-2C)alkyl, halo, (1-2C)haloalkyl, (1-2C)haloalkoxy, amino, cyano, hydroxy, amido, carboxy, NR$^p$R$^q$, OR$^p$, wherein R$^p$ and R$^q$ are each independently selected from hydrogen or (1-2C)alkyl; and iii) a group of Formula C shown below:

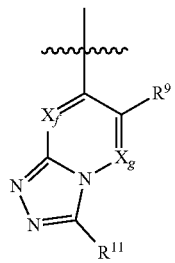

Formula C wherein:
  ⁀ denotes the point of attachment;
  R⁹ is selected from fluoro, chloro, bromo, methyl, OCH₃, cyano or acetylenyl;

X$_f$ and X$_g$ are independently selected from N or CR¹⁰, wherein R¹⁰ is selected from hydrogen, fluoro, chloro or methyl;
R¹¹ is selected from hydrogen, halo, methyl, OCH₃, CH₂F, CF₂H or CF₃;

(45) R² is selected from:
  i) a group of Formula A shown below:

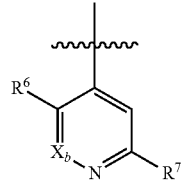

Formula A wherein:
  ⁀ denotes the point of attachment;
  X$_b$ is CR$^{x1}$, wherein R$^{x1}$ is selected from hydrogen, methyl or chloro;
  R⁶ is selected from fluoro, chloro, bromo, methyl, OCH₃, cyano or acetylenyl;
  R⁷ is selected from hydrogen, halo, (1-2C)alkyl, (1-2C)alkoxy, (1-2C)haloalkyl, (1-2C)haloalkoxy, cyano, or a group of the formula:

—Y₃—Z₃ wherein:
    Y₃ is absent or C(O), C(O)O, C(O)N(R$^j$) or S(O)₂N(R$^j$), wherein R$^j$ is selected from hydrogen or (1-4C)alkyl; and
    Z₃ is hydrogen, (1-6C)alkyl, aryl, (2-4C)alkynyl, 5- or 6-membered heteroaryl or 5- or 6-membered heterocyclyl; wherein Z₃ is optionally further substituted by one or more substituent groups independently selected from (1-2C)alkyl, halo, (1-2C)haloalkyl, (1-2C)haloalkoxy, amino, cyano, hydroxy, amido, carboxy, NR$^l$R$^m$ or OR$^l$, wherein R$^l$ and R$^m$ are each independently selected from hydrogen or (1-2C)alkyl;

ii) a group of Formula B shown below:

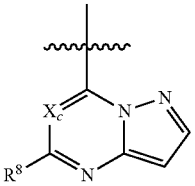

Formula B wherein:
  ⁀ denotes the point of attachment;
  X$_c$ is selected from N, CH, CF, CCl, C—CN or CCH₃;
  R¹¹ is selected from hydrogen, halo, (1-2C)alkyl, (1-2C)alkoxy, (1-2C)haloalkyl, (1-2C)haloalkoxy, cyano, (2-4C)alkenyl, (2-4C)alkynyl or a group of the formula:

—Y₅—Z₅ wherein:
    Y₅ is absent or O, N(R″), C(O), C(O)O, C(O)N(R″) or S(O)₂N(R″), wherein R″ is selected from hydrogen or (1-4C)alkyl; and
    Z₅ is hydrogen, (1-6C)alkyl, aryl, 5 or 6 membered heteroaryl or 5 or 6 membered heterocyclyl;

wherein $Z_5$ is optionally further substituted by one or more substituent groups independently selected from (1-2C)alkyl, halo, (1-2C)haloalkyl, (1-2C)haloalkoxy, amino, cyano, hydroxy, amido, carboxy, $NR^pR^q$, $OR^p$, wherein $R^p$ and $R^q$ are each independently selected from hydrogen or (1-2C)alkyl; and iii) a group of Formula C shown below:

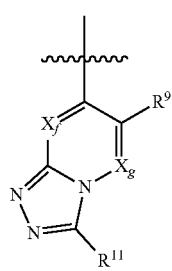

Formula C wherein:

↯ denotes the point of attachment;
$R^9$ is selected from fluoro, chloro, bromo, methyl, $OCH_3$, cyano or acetylenyl;
$X_f$ and $X_g$ are independently selected from N or $CR^{10}$, wherein $R^{10}$ is selected from hydrogen, fluoro, chloro or methyl;
$R^{11}$ is selected from hydrogen, halo, methyl, $OCH_3$, $CH_2F$, $CF_2H$ or $CF_3$;

(46) $R^2$ is selected from:

i) a group of Formula A shown below:

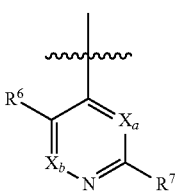

Formula A wherein:

↯ denotes the point of attachment;
$X_a$ and $X_b$ are each independently selected from N or $CR^{x1}$, wherein $R^{x1}$ is selected from hydrogen, fluoro, chloro, bromo, (1-2C)alkyl, (1-2C)alkoxy, cyano, nitro, acetylenyl, $CH_2F$, $CF_2H$ or $CF_3$;
$R^6$ is selected from hydrogen, fluoro, chloro, bromo, (1-2C)alkyl, (1-2C)alkoxy, cyano, nitro, acetylenyl, $CH_2F$, $CF_2H$ or $CF_3$;
$R^7$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_3$—$Z_3$ wherein:

$Y_3$ is absent or O, S, $N(R^j)(CR^jR^k)_{q1}$ (where $q_1$ is 0, 1 or 2), C(O), C(O)O, OC(O), C(O)N($R^j$), N($R^j$)C(O), S(O)$_2$N($R^j$), N($R^j$)SO$_2$, wherein $R^j$ is selected from hydrogen or (1-4C)alkyl; and $Z_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or a 4 to 11-membered heterocyclyl; wherein $Z_3$ is optionally further substituted by one or more substituent groups independently selected from oxo, (1-4C)alkyl, cyclopropyl, halo, (1-4C)haloalkyl, (1-4C)haloalkoxy, amino, cyano, hydroxy, carboxy, carbamoyl, sulphamoyl, mercapto, $C(O)NR^lR^m$, $NR^lR^m$ or $OR^l$, wherein $R^l$ and $R^m$ are each independently selected from hydrogen, (1-4C)alkyl or (3-6C)cycloalkyl; or $Z^3$ is optionally further substituted by a group of the formula:

-$L_Z$-$W_Z$ wherein:

$L_Z$ is absent or a (1-3C)alkylene optionally substituted by one or more (1-2C)alkyl groups; and
$W_Z$ is aryl, 5- or 6-membered heteroaryl, 5- or 6-membered heterocyclyl, halo, (1-4C)haloalkyl, (1-4C)haloalkoxy, cyano, hydroxy, (1-4C)alkoxy, $CR^{xa}$, $COOR^{xa}$, $C(O)NR^{xa}R^{xb}$ or $NR^{xa}R^{xb}$, wherein $R^{xa}$ and $R^{xb}$ are each independently selected from hydrogen or (1-4C)alkyl; and wherein each aryl, 5- or 6-membered heteroaryl, 5- or 6-membered heterocyclyl is optionally further substituted by one or more substituent groups independently selected from (1-4C)alkyl, halo, (1-4C)haloalkyl, amino, cyano or hydroxy;

ii) a group of Formula B shown below:

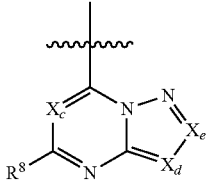

Formula B wherein:

↯ denotes the point of attachment;
$X_c$, $X_d$ and $X_e$ are each independently selected from N, CH, CF, CCl, C—CN or $CCH_3$;
$R^8$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_5$—$Z_5$ wherein:

$Y_5$ is absent or O, N($R''$), C(O), C(O)O, OC(O), C(O)N($R''$), N($R''$)C(O), S(O)$_2$N($R''$), N($R''$)SO$_2$, wherein $R''$ is selected from hydrogen or (1-4C)alkyl; and $Z_5$ is hydrogen, (1-6C)alkyl, aryl, (3-8C)cycloalkyl, (3-8C)cycloalkenyl, heteroaryl or heterocyclyl; wherein $Z_5$ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, $NR^pR^q$, OR$^p$, wherein R$^p$ and R$^q$ are each independently selected from hydrogen, (1-4C)alkyl or (3-6C)cycloalkyl;

(47) R$^2$ is selected from:

i) a group of Formula A shown below:

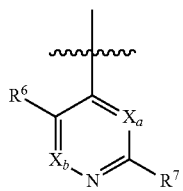

Formula A wherein:

⁂ denotes the point of attachment;

X$_a$ and X$_b$ are each independently selected from N or CR$^{x1}$, wherein R$^{x1}$ is selected from hydrogen, fluoro, chloro, bromo, (1-2C)alkyl, (1-2C)alkoxy, cyano, nitro, acetylenyl, CH$_2$F, CF$_2$H or CF$_3$;

R$^6$ is selected from hydrogen, fluoro, chloro, bromo, (1-2C)alkyl, (1-2C)alkoxy, cyano, nitro, acetylenyl, CH$_2$F, CF$_2$H or CF$_3$;

R$^7$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_3$—Z$_3$ wherein:

Y$_3$ is absent or O, S, N(R$^j$)(CR$^j$R$^k$)$_{q1}$ (where q$_1$ is 0, 1 or 2), C(O), C(O)O, OC(O), C(O)N(R$^j$), N(R$^j$)C(O), S(O)$_2$N(R$^j$), N(R$^j$)SO$_2$, wherein R$^j$ is selected from hydrogen or (1-4C)alkyl; and Z$_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or a 4 to 11-membered heterocyclyl; wherein Z$_3$ is optionally further substituted by one or more substituent groups independently selected from oxo, (1-4C)alkyl, cyclopropyl, halo, (1-4C)haloalkyl, (1-4C)haloalkoxy, amino, cyano, hydroxy, carboxy, carbamoyl, sulphamoyl, mercapto, C(O)NR$^l$R$^m$, NR$^l$R$^m$ or OR$^l$, wherein R$^l$ and R$^m$ are each independently selected from hydrogen, (1-4C)alkyl or (3-6C)cycloalkyl; or Z$^3$ is optionally further substituted by a group of the formula:

-L$_Z$-W$_Z$ wherein:

L$_Z$ is absent or a (1-3C)alkylene optionally substituted by one or more (1-2C)alkyl groups; and W$_Z$ is aryl, 5- or 6-membered heteroaryl, 5- or 6-membered heterocyclyl, halo, (1-4C)haloalkyl, (1-4C)haloalkoxy, cyano, hydroxy, (1-4C)alkoxy, C(O)R$^{xa}$, COOR$^{xa}$, C(O)NR$^{xa}$R$^{xb}$ or NR$^{xa}$R$^{xb}$, wherein R$^{xa}$ and R$^{xb}$ are each independently selected from hydrogen or (1-4C)alkyl;

ii) a group of Formula B shown below:

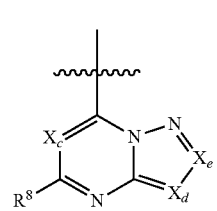

Formula B wherein:

⁂ denotes the point of attachment;

X$_c$, X$_d$ and X$_e$ are each independently selected from N, CH, CF, CCl, C—CN or CCH$_3$;

R$^8$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_5$—Z$_5$ wherein:

Y$_5$ is absent or O, N(R″), C(O), C(O)O, OC(O), C(O)N(R″), N(R″)C(O), S(O)$_2$N(R″), N(R″)SO$_2$, wherein R″ is selected from hydrogen or (1-4C)alkyl; and Z$_5$ is hydrogen, (1-6C)alkyl, aryl, (3-8C)cycloalkyl, (3-8C)cycloalkenyl, heteroaryl or heterocyclyl; wherein Z$_5$ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, NR$^p$R$^q$, OR$^p$, wherein R$^p$ and R$^q$ are each independently selected from hydrogen, (1-4C)alkyl or (3-6C)cycloalkyl;

(48) R$^2$ is selected from:

i) a group of Formula A shown below:

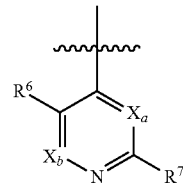

Formula A wherein:

⁂ denotes the point of attachment;

X$_a$ and X$_b$ are each independently selected from N or CR$^{x1}$, wherein R$^{x1}$ is selected from hydrogen, fluoro, chloro, bromo, (1-2C)alkyl, (1-2C)alkoxy, cyano, nitro, acetylenyl, CH$_2$F, CF$_2$H or CF$_3$;

R$^6$ is selected from hydrogen, fluoro, chloro, bromo, (1-2C)alkyl, (1-2C)alkoxy, cyano, nitro, acetylenyl, CH$_2$F, CF$_2$H or CF$_3$;

R$^7$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_3$—Z$_3$ wherein:
Y$_3$ is absent or O, S, N(R$^j$)(CR$^j$R$^k$)$_{q_1}$ (where q$_1$ is 0, 1 or 2), C(O), C(O)O, OC(O), C(O)N(R$^j$), N(R$^j$)C(O), S(O)$_2$N(R$^j$), N(R$^j$)SO$_2$, wherein R$^j$ is selected from hydrogen or (1-4C)alkyl; and
Z$_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or a 4 to 11-membered heterocyclyl; wherein Z$_3$ is optionally further substituted by one or more substituent groups independently selected from oxo, (1-4C)alkyl, cyclopropyl, halo, (1-4C)haloalkyl, (1-4C)haloalkoxy, amino, cyano, hydroxy, carboxy, carbamoyl, sulphamoyl, mercapto, C(O)NR$^l$R$^m$, NR$^l$R$^m$ or OR$^l$, wherein R$^l$ and R$^m$ are each independently selected from hydrogen, (1-4C)alkyl or (3-6C)cycloalkyl; or Z$^3$ is optionally further substituted by a group of the formula:

-L$_Z$-W$_Z$ wherein:
L$_Z$ is a (1-3C)alkylene; and
W$_Z$ is phenyl, 5- or 6-membered heteroaryl, 6-membered heterocyclyl, halo, (1-4C)haloalkyl, (1-4C)haloalkoxy, cyano, hydroxy, (1-4C)alkoxy, C(O)R$^{xa}$, COOR$^{xa}$, C(O)NR$^{xa}$R$^{xb}$ or NR$^{xa}$R$^{xb}$, wherein R$^{xa}$ and R$^{xb}$ are each independently selected from hydrogen or (1-4C)alkyl;

ii) a group of Formula B shown below:

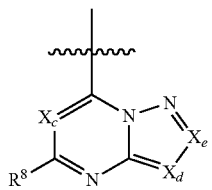

Formula B wherein:
denotes the point of attachment;
X$_c$, X$_d$ and X$_e$ are each independently selected from N, CH, CF, CCl, C—CN or CCH$_3$;
R$^8$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_5$—Z$_5$ wherein:
Y$_5$ is absent or O, N(R''), C(O), C(O)O, OC(O), C(O)N(R''), N(R'')C(O), S(O)$_2$N(R''), N(R'')SO$_2$, wherein R'' is selected from hydrogen or (1-4C)alkyl; and
Z$_5$ is hydrogen, (1-6C)alkyl, aryl, (3-8C)cycloalkyl, (3-8C)cycloalkenyl, heteroaryl or heterocyclyl; wherein Z$_5$ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, NR$^p$R$^q$, OR$^p$, wherein R$^p$ and R$^q$ are each independently selected from hydrogen, (1-4C)alkyl or (3-6C)cycloalkyl;

(49) R$^2$ is selected from:
i) a group of Formula A shown below:

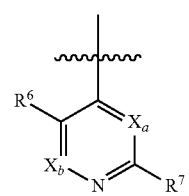

Formula A wherein:
denotes the point of attachment;
X$_a$ and X$_b$ are each independently selected from N or CR$^{x1}$, wherein R$^{x1}$ is selected from hydrogen, fluoro, chloro, bromo, (1-2C)alkyl, (1-2C)alkoxy, cyano, nitro, acetylenyl, CH$_2$F, CF$_2$H or CF$_3$;
R$^6$ is selected from hydrogen, fluoro, chloro, bromo, (1-2C)alkyl, (1-2C)alkoxy, cyano, nitro, acetylenyl, CH$_2$F, CF$_2$H or CF$_3$;
R$^7$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_3$—Z$_3$ wherein:
Y$_3$ is absent or O, S, N(R$^j$)(CR$^j$R$^k$)$_{q_1}$ (where q$_1$ is 0, 1 or 2), C(O), C(O)O, OC(O), C(O)N(R$^j$), N(R$^j$)C(O), S(O)$_2$N(R$^j$), N(R$^j$)SO$_2$, wherein R$^j$ is selected from hydrogen or (1-4C)alkyl; and
Z$_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or a 4 to 11-membered heterocyclyl; wherein Z$_3$ is optionally further substituted by one or more substituent groups independently selected from oxo, (1-4C)alkyl, cyclopropyl, halo, (1-4C)haloalkyl, (1-4C)haloalkoxy, amino, cyano, hydroxy, carboxy, carbamoyl, sulphamoyl, mercapto, C(O)NR$^l$R$^m$, NR$^l$R$^m$ or OR$^l$, wherein R$^l$ and R$^m$ are each independently selected from hydrogen, (1-4C)alkyl or (3-6C)cycloalkyl; or Z$^3$ is optionally further substituted by a group of the formula:

-L$_Z$-W$_Z$ wherein:
L$_Z$ is a (1-3C)alkylene optionally substituted by one or more substituents selected from (1-2C)alkyl or oxo; and
W$_Z$ is halo, (1-4C)haloalkyl, (1-4C)haloalkoxy, cyano, hydroxy, (1-4C)alkoxy, C(O)$^{xa}$, COOR$^{xa}$, C(O)NR$^{xa}$R$^{xb}$ or NR$^{xa}$R$^{xb}$, wherein R$^{xa}$ and R$^{xb}$ are each independently selected from hydrogen or (1-4C)alkyl;

ii) a group of Formula B shown below:

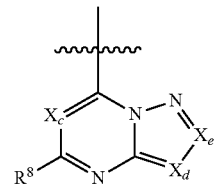

Formula B wherein:

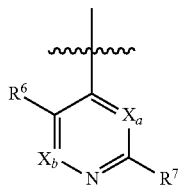 denotes the point of attachment;

$X_c$, $X_d$ and $X_e$ are each independently selected from N, CH, CF, CCl, C—CN or CCH$_3$;

R$^8$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_5$—Z$_5$ wherein:

Y$_5$ is absent or O, N(R″), C(O), C(O)O, OC(O), C(O)N(R″), N(R″)C(O), S(O)$_2$N(R″), N(R″)SO$_2$, wherein R″ is selected from hydrogen or (1-4C)alkyl; and Z$_5$ is hydrogen, (1-6C)alkyl, aryl, (3-8C)cycloalkyl, (3-8C)cycloalkenyl, heteroaryl or heterocyclyl; wherein Z$_5$ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, NR$^p$R$^q$, OR$^p$, wherein R$^p$ and R$^q$ are each independently selected from hydrogen, (1-4C)alkyl or (3-6C)cycloalkyl;

(50) R$^2$ is selected from:
i) a group of Formula A shown below:

Formula A wherein:

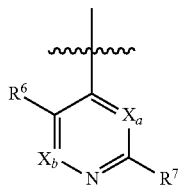 denotes the point of attachment;

$X_a$ and $X_b$ are each independently selected from N or CR$^{x1}$, wherein R$^{x1}$ is selected hydrogen, fluoro, chloro, bromo, methyl, OCH$_3$, cyano, acetylenyl, CH$_2$F, CF$_2$H or CF$_3$;

R$^6$ is selected from hydrogen, fluoro, chloro, bromo, methyl, OCH$_3$, cyano, nitro, acetylenyl, CH$_2$F or CF$_2$H$_3$;

R$^7$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_3$—Z$_3$ wherein:

Y$_3$ is absent or N(R$^j$)(CH$_2$)$_{q1}$ (where q$_1$ is 0 or 1), C(O), C(O)O, C(O)N(R$^j$) or S(O)$_2$N(R$^j$), wherein R$^j$ is selected from hydrogen or (1-4C)alkyl; and Z$_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or a 4 to 11-membered heterocyclyl; wherein Z$_3$ is optionally further substituted by one or more substituent groups independently selected from oxo, (1-4C)alkyl, halo, (1-4C)haloalkyl, (1-4C)haloalkoxy, amino, cyano, hydroxy, carboxy, carbamoyl, sulphamoyl, mercapto, C(O)NR$^l$R$^m$, NR$^l$R$^m$ or OR$^l$, wherein R$^l$ and R$^m$ are each independently selected from hydrogen, (1-4C)alkyl or (3-6C)cycloalkyl; or Z$^3$ is optionally further substituted by a group of the formula:

-L$_Z$W$_Z$ wherein:

L$_Z$ is a (1-3C)alkylene; and

W$_Z$ is halo, (1-4C)haloalkyl, (1-4C)haloalkoxy, cyano, hydroxy, (1-4C)alkoxy, CR$^{xa}$, COOR$^{xa}$, C(O)NR$^{xa}$R$^{xb}$ or NR$^{xa}$R$^{xb}$, wherein R$^{xa}$ and R$^{xb}$ are each independently selected from hydrogen or (1-4C)alkyl;

ii) a group of Formula B shown below:

Formula B wherein:

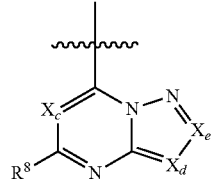 denotes the point of attachment;

$X_c$, $X_d$ and $X_e$ are each independently selected from N, CH, CF, CCl or CCH$_3$;

R$^8$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_5$—Z$_5$ wherein:

Y$_5$ is absent or O, N(R″), C(O), C(O)O, C(O)N(R″) or S(O)$_2$N(R″), wherein R″ is selected from hydrogen or (1-4C)alkyl; and Z$_5$ is hydrogen, (1-6C)alkyl, aryl, (3-6C)cycloalkyl, (3-6C)cycloalkenyl, 5 or 6 membered heteroaryl or 5 or 6 membered heterocyclyl; wherein Z$_5$ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, NR$^p$R$^q$ or OR$^p$, wherein R$^p$ and R$^q$ are each independently selected from hydrogen, (1-4C)alkyl or cyclopropyl;

(51) R$^2$ is selected from:
i) a group of Formula A shown below:

Formula A wherein:

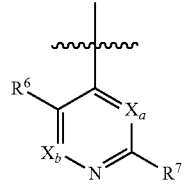 denotes the point of attachment;

$X_a$ and $X_b$ are each independently selected from N or CR$^{x1}$, wherein R$^{x1}$ is selected from hydrogen, fluoro, chloro, bromo, methyl, OCH$_3$, cyano or acetylenyl;

R⁶ is selected from fluoro, chloro, bromo, methyl, OCH₃, cyano or acetylenyl;

R⁷ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y₃—Z₃ wherein:
Y₃ is absent or N(Rʲ)(CH₂)_{q1} (where q₁ is 0 or 1), C(O), C(O)O, C(O)N(Rʲ) or S(O)₂N(Rʲ), wherein Rʲ is selected from hydrogen or (1-4C)alkyl; and
Z₃ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or a 4 to 11-membered heterocyclyl; wherein Z₃ is optionally further substituted by one or more substituent groups independently selected from (1-2C)alkyl, halo, (1-2C)haloalkyl, (1-2C)haloalkoxy, amino, cyano, hydroxy, amido, carboxy, C(O)NRʲRᵐ, NRʲRᵐ or ORʲ, wherein Rʲ and Rᵐ are each independently selected from hydrogen, (1-4C)alkyl or cyclopropyl; or Z³ is optionally further substituted by a group of the formula:

-L_Z-W_Z wherein:
L_Z is a (1-3C)alkylene; and
W_Z is halo, (1-2C)haloalkyl, (1-2C)haloalkoxy, cyano, hydroxy, (1-2C)alkoxy, CR^{xa}, COOR^{xa}, C(O)NR^{xa}R^{xb} or NR^{xa}R^{xb}, wherein R^{xa} and R^{xb} are each independently selected from hydrogen or (1-2C)alkyl;

ii) a group of Formula B shown below:

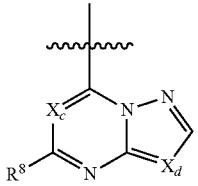

Formula B wherein:

⤳ denotes the point of attachment;
X_c is selected from CH or N;
X_d is selected from N, CH, CF, CCl or CCH₃;
R⁸ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y₅—Z₅ wherein:
Y₅ is absent or O, N(R″), C(O), C(O)O, C(O)N(R″) or S(O)₂N(R″), wherein R″ is selected from hydrogen or (1-2C)alkyl; and
Z₅ is hydrogen, (1-6C)alkyl, aryl, 5 or 6 membered heteroaryl or 5 or 6 membered heterocyclyl; wherein Z₅ is optionally further substituted by one or more substituent groups independently selected from (1-2C)alkyl, halo, (1-2C)haloalkyl, (1-2C)haloalkoxy, amino, cyano, hydroxy, amido, carboxy, NR^{p}R^{q}, OR^{p}, wherein R^{p} and R^{q} are each independently selected from hydrogen or (1-2C)alkyl;

(52) R² is selected from:
i) a group of Formula A shown below:

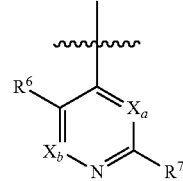

Formula A wherein:

⤳ denotes the point of attachment;
X_a and X_b are independently selected from N or CR^{x1}, wherein R^{x1} is selected from hydrogen, fluoro, chloro, bromo, (1-2C)alkyl, (1-2C)alkoxy, cyano, nitro, acetylenyl, CH₂F or CF₂H;
R⁶ is selected from fluoro, chloro, bromo, (1-2C)alkyl, (1-2C)alkoxy, cyano, nitro, acetylenyl, CH₂F, CF₂H or CF₃;
R⁷ is selected from hydrogen, halo, (1-2C)alkyl, (1-2C)alkoxy, (1-2C)haloalkyl, (1-2C)haloalkoxy, cyano, nitro, (2-4C)alkenyl, (2-4C)alkynyl or a group of the formula:

—Y₃—Z₃ wherein:
Y₃ is absent or C(O), C(O)O, OC(O), C(O)N(Rʲ), N(Rʲ)C(O), S(O)₂N(Rʲ), N(Rʲ)SO₂, wherein Rʲ is selected from hydrogen or (1-4C)alkyl; and
Z₃ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or 5- or 6-membered heterocyclyl; wherein Z₃ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, NRʲRᵐ or ORʲ, wherein Rʲ and Rᵐ are each independently selected from hydrogen, (1-4C)alkyl or (3-6C)cycloalkyl;

ii) a group of Formula B shown below:

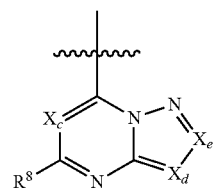

Formula B wherein:

⤳ denotes the point of attachment;
X_c, X_d and X_e are independently selected from N, CH, CF, CCl, C—CN or CCH₃;

R[8] is selected from hydrogen, halo, (1-2C)alkyl, (1-2C)alkoxy, (1-2C)haloalkyl, (1-2C)haloalkoxy, cyano, nitro, (2-4C)alkenyl, (2-4C)alkynyl or a group of the formula:

—Y$_5$—Z$_5$ wherein:
  Y$_5$ is absent or O, N(R″), C(O), C(O)O, OC(O), C(O)N(R″), N(R″)C(O), S(O)$_2$N(R″), N(R″)SO$_2$, wherein R″ is selected from hydrogen or (1-4C)alkyl; and
  Z$_5$ is hydrogen, (1-6C)alkyl, aryl, (3-8C)cycloalkyl, (3-8C)cycloalkenyl, heteroaryl or heterocyclyl; wherein Z$_5$ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, NR$^p$R$^q$, OR$^p$, wherein R$^p$ and R$^q$ are each independently selected from hydrogen, (1-4C)alkyl or (3-6C)cycloalkyl;

(53) R$^2$ is selected from:
  i) a group of Formula A shown below:

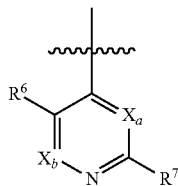

Formula A wherein:
  denotes the point of attachment;
  X$_a$ and X$_b$ are independently selected from N or CR$^{x1}$, wherein R$^{x1}$ is selected from hydrogen, fluoro, chloro, bromo, methyl, OCH$_3$, cyano or acetylenyl;
  R$^6$ is selected from fluoro, chloro, bromo, methyl, OCH$_3$, cyano, nitro or acetylenyl;
  R$^7$ is selected from hydrogen, halo, (1-2C)alkyl, (1-2C)alkoxy, (1-2C)haloalkyl, (1-2C)haloalkoxy, cyano, nitro, (2-4C)alkenyl, (2-4C)alkynyl or a group of the formula:

—Y$_3$—Z$_3$ wherein:
  Y$_3$ is absent or C(O), C(O)O, C(O)N(R$^j$) or S(O)$_2$N(R$^j$), wherein R$^j$ is selected from hydrogen or (1-4C)alkyl; and
  Z$_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or 5- or 6-membered heterocyclyl; wherein Z$_3$ is optionally further substituted by one or more substituent groups independently selected from (1-2C)alkyl, halo, (1-2C)haloalkyl, (1-2C)haloalkoxy, amino, cyano, hydroxy, amido, carboxy, NR$^l$R$^m$ or OR$^l$, wherein R$^l$ and R$^m$ are each independently selected from hydrogen or (1-2C)alkyl;

ii) a group of Formula B shown below:

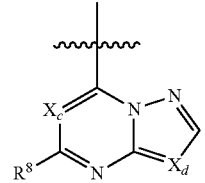

Formula B wherein:
  denotes the point of attachment;
  X$_c$ and X$_d$ are independently selected from N, CH, CF, CCl or CCH$_3$;
  R$^8$ is selected from hydrogen, halo, (1-2C)alkyl, (1-2C)alkoxy, (1-2C)haloalkyl, (1-2C)haloalkoxy, cyano, nitro, (2-4C)alkenyl, (2-4C)alkynyl or a group of the formula:

—Y$_5$—Z$_5$ wherein:
  Y$_5$ is absent or O, N(R″), C(O), C(O)O, C(O)N(R″) or S(O)$_2$N(R″), wherein R″ is selected from hydrogen or (1-4C)alkyl; and
  Z$_5$ is hydrogen, (1-6C)alkyl, aryl, (3-6C)cycloalkyl, (3-6C)cycloalkenyl, 5 or 6 membered heteroaryl or 5 or 6 membered heterocyclyl; wherein Z$_5$ is optionally further substituted by one or more substituent groups independently selected from (1-2C)alkyl, halo, (1-2C)haloalkyl, (1-2C)haloalkoxy, amino, cyano, hydroxy, amido, carboxy, NR$^p$R$^q$, OR$^p$, wherein R$^p$ and R$^q$ are each independently selected from hydrogen or (1-2C)alkyl;

(54) R$^2$ is selected from:
  i) a group of Formula A shown below:

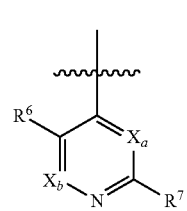

Formula A wherein:
  denotes the point of attachment;
  X$_a$ and X$_b$ are independently CR$^{x1}$, wherein R$^{x1}$ is selected from hydrogen, fluoro, chloro, bromo or methyl;
  R$^6$ is selected from fluoro, chloro, bromo, methyl, OCH$_3$, cyano or acetylenyl;
  R$^7$ is selected from hydrogen, halo, (1-2C)alkyl, (1-2C)alkoxy, (1-2C)haloalkyl, (1-2C)haloalkoxy, cyano, (2-4C)alkenyl, (2-4C)alkynyl or a group of the formula:

—Y$_3$—Z$_3$ wherein:
  Y$_3$ is absent or C(O), C(O)O, C(O)N(R$^j$) or S(O)$_2$N(R$^j$), wherein R$^j$ is selected from hydrogen or (1-4C)alkyl; and Z₃ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or 5- or 6-membered heterocyclyl; wherein Z₃ is optionally further substituted by one or more substituent groups independently selected from (1-2C)alkyl, halo, (1-2C)haloalkyl, (1-2C)haloalkoxy, amino, cyano, hydroxy, amido, carboxy, NR^l R^m or OR^l, wherein R^l and R^m are each independently selected from hydrogen or (1-2C)alkyl;

ii) a group of Formula B shown below:

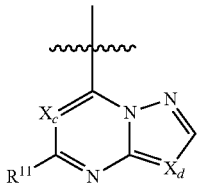

Formula B wherein:

⤳ denotes the point of attachment;

X_c and X_d are independently selected from N, CH, CF, CCl or CCH₃;

R⁸ is selected from hydrogen, halo, (1-2C)alkyl, (1-2C)alkoxy, (1-2C)haloalkyl, (1-2C)haloalkoxy, cyano, (2-4C)alkenyl, (2-4C)alkynyl or a group of the formula:

—Y₅—Z₅ wherein:

Y₅ is absent or O, N(R″), C(O), C(O)O, C(O)N(R″) or S(O)₂N(R″), wherein R″ is selected from hydrogen or (1-4C)alkyl; and Z₅ is hydrogen, (1-6C)alkyl, aryl, (3-6C)cycloalkyl, (3-6C)cycloalkenyl, 5 or 6 membered heteroaryl or 5 or 6 membered heterocyclyl; wherein Z₅ is optionally further substituted by one or more substituent groups independently selected from (1-2C)alkyl, halo, (1-2C)haloalkyl, (1-2C)haloalkoxy, amino, cyano, hydroxy, amido, carboxy, NR^p R^q, OR^p, wherein R^p and R^q are each independently selected from hydrogen or (1-2C)alkyl;

(55) R² is selected from:

i) a group of Formula A shown below:

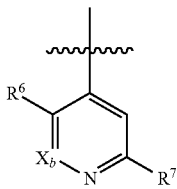

Formula A wherein:

⤳ denotes the point of attachment;

X_b is CR^x1, wherein R^x1 is selected from hydrogen, fluoro, chloro, bromo or methyl;

R⁶ is selected from fluoro, chloro, bromo, methyl, OCH₃, cyano or acetylenyl;

R⁷ is selected from hydrogen, halo, (1-2C)alkyl, (1-2C)alkoxy, (1-2C)haloalkyl, (1-2C)haloalkoxy, cyano, (2-4C)alkenyl, (2-4C)alkynyl or a group of the formula:

—Y₃—Z₃ wherein:

Y₃ is absent or C(O), C(O)O, C(O)N(R^j) or S(O)₂N(R^j), wherein R^j is selected from hydrogen or (1-4C)alkyl; and Z₃ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or 5- or 6-membered heterocyclyl; wherein Z₃ is optionally further substituted by one or more substituent groups independently selected from (1-2C)alkyl, halo, (1-2C)haloalkyl, (1-2C)haloalkoxy, amino, cyano, hydroxy, amido, carboxy, NR^l R^m or OR^l, wherein R^l and R^m are each independently selected from hydrogen or (1-2C)alkyl;

ii) a group of Formula B shown below:

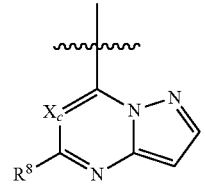

Formula B wherein:

⤳ denotes the point of attachment;

X_c is selected from N, CH, CF, CCl or CCH₃;

R⁸ is selected from hydrogen, halo, (1-2C)alkyl, (1-2C)alkoxy, (1-2C)haloalkyl, (1-2C)haloalkoxy, cyano, (2-4C)alkenyl, (2-4C)alkynyl or a group of the formula:

—Y₅—Z₅ wherein:

Y₅ is absent or O, N(R″), C(O), C(O)O, C(O)N(R″) or S(O)₂N(R″), wherein R″ is selected from hydrogen or (1-4C)alkyl; and Z₅ is hydrogen, (1-6C)alkyl, aryl, (3-6C)cycloalkyl, (3-6C)cycloalkenyl, 5 or 6 membered heteroaryl or 5 or 6 membered heterocyclyl; wherein Z₅ is optionally further substituted by one or more substituent groups independently selected from (1-2C)alkyl, halo, (1-2C)haloalkyl, (1-2C)haloalkoxy, amino, cyano, hydroxy, amido, carboxy, NR^p R^q, OR^p, wherein R^p and R^q are each independently selected from hydrogen or (1-2C)alkyl;

(56) R² is selected from:

i) a group of Formula A shown below:

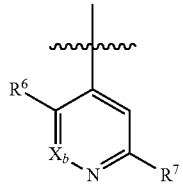

Formula A wherein:

 denotes the point of attachment;

$X_b$ is $CR^{x1}$, wherein $R^{x1}$ is selected from hydrogen or chloro;

$R^6$ is selected from fluoro, chloro, bromo, methyl, $OCH_3$, cyano or acetylenyl;

$R^7$ is selected from hydrogen, halo, (1-2C)alkyl, (1-2C)alkoxy, (1-2C)haloalkyl, (1-2C)haloalkoxy, cyano, (2-4C)alkenyl, (2-4C)alkynyl or a group of the formula:

—$Y_3$—$Z_3$ wherein:

$Y_3$ is absent or C(O), C(O)O, C(O)N($R^j$) or $S(O)_2$N($R^j$), wherein $R^j$ is selected from hydrogen or (1-4C)alkyl; and $Z_3$ is hydrogen, (1-6C)alkyl, aryl, (2-4C)alkynyl, 5- or 6-membered heteroaryl or 5- or 6-membered heterocyclyl; wherein $Z_3$ is optionally further substituted by one or more substituent groups independently selected from (1-2C)alkyl, halo, (1-2C)haloalkyl, (1-2C)haloalkoxy, amino, cyano, hydroxy, amido, carboxy, $NR^lR^m$ or $OR^l$, wherein $R^l$ and $R^m$ are each independently selected from hydrogen or (1-2C)alkyl;

ii) a group of Formula B shown below:

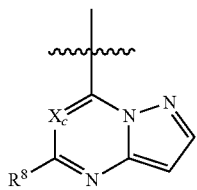

Formula B

 denotes the point of attachment;

$X_c$ is selected from N, CH, CF, CCl or $CCH_3$;

$R^8$ is selected from hydrogen, halo, (1-2C)alkyl, (1-2C)alkoxy, (1-2C)haloalkyl, (1-2C)haloalkoxy, cyano, (2-4C)alkenyl, (2-4C)alkynyl or a group of the formula:

—$Y_5$—$Z_5$ wherein:

$Y_5$ is absent or O, N(R″), C(O), C(O)O, C(O)N(R″) or $S(O)_2$N(R″), wherein R″ is selected from hydrogen or (1-4C)alkyl; and $Z_5$ is hydrogen, (1-6C)alkyl, aryl, 5 or 6 membered heteroaryl or 5 or 6 membered heterocyclyl; wherein $Z_5$ is optionally further substituted by one or more substituent groups independently selected from (1-2C)alkyl, halo, (1-2C)haloalkyl, (1-2C)haloalkoxy, amino, cyano, hydroxy, amido, carboxy, $NR^pR^q$, $OR^p$, wherein $R^p$ and $R^q$ are each independently selected from hydrogen or (1-2C)alkyl;

(57) $R^2$ is selected from a group of Formula A shown below:

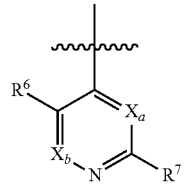

Formula A wherein:

 denotes the point of attachment;

$X_a$ and $X_b$ are each independently selected from N or $CR^{x1}$, wherein $R^{x1}$ is selected from hydrogen, fluoro, chloro, bromo, (1-2C)alkyl, (1-2C)alkoxy, cyano, nitro, acetylenyl, $CH_2F$, $CF_2H$ or $CF_3$;

$R^6$ is selected from hydrogen, fluoro, chloro, bromo, (1-2C)alkyl, (1-2C)alkoxy, cyano, nitro, acetylenyl, $CH_2F$, $CF_2H$ or $CF_3$;

$R^7$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_3$—$Z_3$ wherein:

$Y_3$ is absent or O, S, N($R^j$)($CR^jR^k$)$_{q1}$ (where $q_1$ is 0, 1 or 2), C(O), C(O)O, OC(O), C(O)N($R^j$), N($R^j$)C(O), $S(O)_2$N($R^j$), N($R^j$)$SO_2$, wherein $R^j$ is selected from hydrogen or (1-4C)alkyl; and $Z_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or a 4 to 11-membered heterocyclyl; wherein $Z_3$ is optionally further substituted by one or more substituent groups independently selected from oxo, (1-4C)alkyl, cyclopropyl, halo, (1-4C)haloalkyl, (1-4C)haloalkoxy, amino, cyano, hydroxy, carboxy, carbamoyl, sulphamoyl, mercapto, C(O)$NR^lR^m$, $NR^lR^m$ or $OR^l$, wherein $R^l$ and $R^m$ are each independently selected from hydrogen, (1-4C)alkyl or (3-6C)cycloalkyl; or $Z^3$ is optionally further substituted by a group of the formula:

-$L_Z$-$W_Z$ wherein:

$L_Z$ is absent or a (1-3C)alkylene optionally substituted by one or more substituents selected from (1-2C)alkyl or oxo; and $W_Z$ is aryl, heteroaryl, 4- to 7-membered heterocyclyl, halo, (1-4C)haloalkyl, (1-4C)haloalkoxy, cyano, hydroxy, (1-4C)alkoxy, C(O)$R^{xa}$, COO$R^{xa}$, C(O)$NR^{xa}R^{xb}$ or $NR^{xa}R^{xb}$, wherein $R^{xa}$ and $R^{xb}$ are each independently selected from hydrogen or (1-4C)alkyl; and wherein each aryl, heteroaryl or 4- to 7-membered heterocyclyl is optionally further substituted by one or more substituent groups independently selected from (1-4C)alkyl, halo, (1-4C)haloalkyl, amino, cyano or hydroxy;

(58) $R^2$ is selected from a group of Formula A shown below:

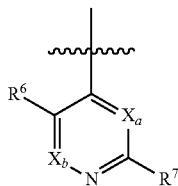

Formula A wherein:
- ⤴ denotes the point of attachment;
- $X_a$ and $X_b$ are each independently selected from N or $CR^{x1}$, wherein $R^{x1}$ is selected from hydrogen, fluoro, chloro, bromo, (1-2C)alkyl, (1-2C)alkoxy, cyano, nitro, acetylenyl, $CH_2F$, $CF_2H$ or $CF_3$;
- $R^6$ is selected from hydrogen, fluoro, chloro, bromo, (1-2C)alkyl, (1-2C)alkoxy, cyano, nitro, acetylenyl, $CH_2F$, $CF_2H$ or $CF_3$;
- $R^7$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y₃—Z₃ wherein:
- $Y_3$ is absent or O, S, $N(R^j)(CR^jR^k)_{q1}$ (where $q_1$ is 0, 1 or 2), C(O), C(O)O, OC(O), $C(O)N(R^j)$, $N(R^j)C(O)$, $S(O)_2N(R^j)$, $N(R^j)SO_2$, wherein $R^j$ is selected from hydrogen or (1-4C)alkyl; and
- $Z_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or a 4 to 11-membered heterocyclyl; wherein $Z_3$ is optionally further substituted by one or more substituent groups independently selected from oxo, (1-4C)alkyl, cyclopropyl, halo, (1-4C)haloalkyl, (1-4C)haloalkoxy, amino, cyano, hydroxy, carboxy, carbamoyl, sulphamoyl, mercapto, $C(O)NR^lR^m$, $NR^lR^m$ or $OR^l$, wherein $R^l$ and $R^m$ are each independently selected from hydrogen, (1-4C)alkyl or (3-6C)cycloalkyl; or $Z^3$ is optionally further substituted by a group of the formula:

-L_Z-W_Z wherein:
- $L_Z$ is absent or a (1-3C)alkylene optionally substituted by one or more substituents selected from (1-2C)alkyl or oxo; and
- $W_Z$ is aryl, 5- or 6-membered heteroaryl, 5- or 6-membered heterocyclyl, halo, (1-4C)haloalkyl, (1-4C)haloalkoxy, cyano, hydroxy, (1-4C)alkoxy, $C(O)R^{xa}$, $COOR^{xa}$, $C(O)NR^{xa}R^{xb}$ or $NR^{xa}R^{xb}$, wherein $R^{xa}$ and $R^{xb}$ are each independently selected from hydrogen or (1-4C)alkyl;

(59) $R^2$ is selected from a group of Formula A shown below:

Formula A

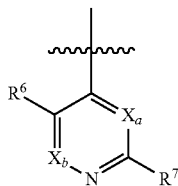

wherein:
- ⤴ denotes the point of attachment;
- $X_a$ is CH or N;
- $X_b$ is $CR^{x1}$, wherein $R^{x1}$ is selected from hydrogen, fluoro, chloro, bromo, methyl, $OCH_3$, cyano or acetylenyl;
- $R^6$ is selected from hydrogen, fluoro, chloro, bromo, (1-2C)alkyl, (1-2C)alkoxy, cyano, nitro, acetylenyl, $CH_2F$, $CF_2H$ or $CF_3$;
- $R^7$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y₃—Z₃ wherein:
- $Y_3$ is absent or O, S, $N(R^j)(CR^jR^k)_{q1}$ (where $q_1$ is 0, 1 or 2), C(O), C(O)O, OC(O), $C(O)N(R^j)$, $N(R^j)C(O)$, $S(O)_2N(R^j)$, $N(R^j)SO_2$, wherein $R^j$ is selected from hydrogen or (1-4C)alkyl; and
- $Z_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or a 4 to 11-membered heterocyclyl; wherein $Z_3$ is optionally further substituted by one or more substituent groups independently selected from oxo, (1-4C)alkyl, cyclopropyl, halo, (1-4C)haloalkyl, (1-4C)haloalkoxy, amino, cyano, hydroxy, carboxy, carbamoyl, sulphamoyl, mercapto, $C(O)NR^lR^m$, $NR^lR^m$ or $OR^l$, wherein $R^l$ and $R^m$ are each independently selected from hydrogen, (1-4C)alkyl or (3-6C)cycloalkyl; or $Z^3$ is optionally further substituted by a group of the formula:

-L_Z-W_Z wherein:
- $L_Z$ is absent or a (1-3C)alkylene optionally substituted by one or more substituents selected from (1-2C)alkyl or oxo; and
- $W_Z$ is phenyl, 5- or 6-membered heteroaryl, 6-membered heterocyclyl, halo, (1-4C)haloalkyl, (1-4C)haloalkoxy, cyano, hydroxy, (1-4C)alkoxy, $C(O)R^{xa}$, $COOR^{xa}$, $C(O)NR^{xa}R^{xb}$ or $NR^{xa}R^{xb}$, wherein $R^{xa}$ and $R^{xb}$ are each independently selected from hydrogen or (1-4C)alkyl;

(60) $R^2$ is selected from a group of Formula A shown below:

Formula A

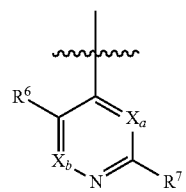

wherein:
- ⤴ denotes the point of attachment;
- $X_a$ and $X_b$ are each independently selected from N or $CR^{x1}$, wherein $R^{x1}$ is selected from hydrogen, fluoro, chloro, bromo, (1-2C)alkyl, (1-2C)alkoxy, cyano, nitro, acetylenyl, $CH_2F$, $CF_2H$ or $CF_3$;
- $R^6$ is selected from hydrogen, fluoro, chloro, bromo, (1-2C)alkyl, (1-2C)alkoxy, cyano, nitro, acetylenyl, $CH_2F$, $CF_2H$ or $CF_3$;

$R^7$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_3$—$Z_3$ wherein:
$Y_3$ is absent or O, S, N($R^j$)($CR^jR^k$)$_{q1}$ (where $q_1$ is 0, 1 or 2), C(O), C(O)O, OC(O), C(O)N($R^j$), N($R^j$)C(O), S(O)$_2$N($R^j$), N($R^j$)SO$_2$, wherein $R^j$ is selected from hydrogen or (1-4C)alkyl; and
$Z_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or a 4 to 11-membered heterocyclyl; wherein $Z_3$ is optionally further substituted by one or more substituent groups independently selected from oxo, (1-4C)alkyl, cyclopropyl, halo, (1-4C)haloalkyl, (1-4C)haloalkoxy, amino, cyano, hydroxy, carboxy, carbamoyl, sulphamoyl, mercapto, C(O)N$R^iR^m$, N$R^iR^m$ or O$R^i$, wherein $R^i$ and $R^m$ are each independently selected from hydrogen, (1-4C)alkyl or (3-6C)cycloalkyl; or $Z^3$ is optionally further substituted by a group of the formula:

-$L_Z$-$W_Z$ wherein:
$L_Z$ is a (1-3C)alkylene optionally substituted by one or more substituents selected from (1-2C)alkyl or oxo; and
$W_Z$ is halo, (1-4C)haloalkyl, (1-4C)haloalkoxy, cyano, hydroxy, (1-4C)alkoxy, C(O)$R^{xa}$, COO$R^{xa}$, C(O)N$R^{xa}R^{xb}$ or N$R^{xa}R^{xb}$, wherein $R^{xa}$ and $R^{xb}$ are each independently selected from hydrogen or (1-4C)alkyl;

(61) $R^2$ is selected from a group of Formula A shown below:

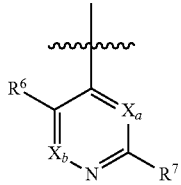

Formula A wherein:

 denotes the point of attachment;
$X_a$ and $X_b$ are each independently selected from N or $CR^{x1}$, wherein $R^{x1}$ is selected from hydrogen, fluoro, chloro, bromo, methyl, OCH$_3$, cyano or acetylenyl;
$R^6$ is selected from fluoro, chloro, bromo, methyl, OCH$_3$, cyano or acetylenyl;
$R^7$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_3$—$Z_3$ wherein:
$Y_3$ is absent or O, N($R^j$)(CH$_2$)$_{q1}$ (where $q_1$ is 0 or 1), C(O), C(O)O, C(O)N($R^j$) or S(O)$_2$N($R^j$), wherein $R^j$ is selected from hydrogen or (1-4C)alkyl; and
$Z_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or a 4 to 11-membered heterocyclyl; wherein $Z_3$ is optionally further substituted by one or more substituent groups independently selected from (1-2C)alkyl, halo, (1-2C)haloalkyl, (1-2C)haloalkoxy, amino, cyano, hydroxy, amido, carboxy, C(O)N$R^iR^m$, N$R^iR^m$ or O$R^i$, wherein $R^i$ and $R^m$ are each independently selected from hydrogen, (1-4C)alkyl or cyclopropyl; or $Z^3$ is optionally further substituted by a group of the formula:

-$L_Z$-$W_Z$ wherein:
$L_Z$ is a (1-3C)alkylene; and
$W_Z$ is halo, (1-2C)haloalkyl, (1-2C)haloalkoxy, cyano, hydroxy, (1-2C)alkoxy, $CR^{xa}$, COO$R^{xa}$, C(O)N$R^{xa}R^{xb}$ or N$R^{xa}R^{xb}$, wherein $R^{xa}$ and $R^{xb}$ are each independently selected from hydrogen or (1-2C)alkyl;

(62) $R^2$ is selected from a group of Formula A shown below:

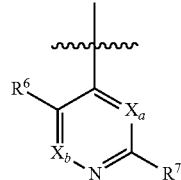

Formula A wherein:

 denotes the point of attachment;
$X_a$ and $X_b$ are each independently selected from N or $CR^{x1}$, wherein $R^{x1}$ is selected from hydrogen, fluoro, chloro, bromo, methyl, OCH$_3$, cyano or acetylenyl;
$R^6$ is selected from fluoro, chloro, bromo, methyl, OCH$_3$, cyano or acetylenyl;
$R^7$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_3$—$Z_3$ wherein:
$Y_3$ is absent or N($R^j$)(CH$_2$)$_{q1}$ (where $q_1$ is 0 or 1), C(O), C(O)O, C(O)N($R^j$) or S(O)$_2$N($R^j$), wherein $R^j$ is selected from hydrogen or (1-4C)alkyl; and
$Z_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or a 4 to 11-membered heterocyclyl; wherein $Z_3$ is optionally further substituted by one or more substituent groups independently selected from (1-2C)alkyl, halo, (1-2C)haloalkyl, (1-2C)haloalkoxy, amino, cyano, hydroxy, amido, carboxy, C(O)N$R^iR^m$, N$R^iR^m$ or O$R^i$, wherein $R^i$ and $R^m$ are each independently selected from hydrogen, (1-4C)alkyl or cyclopropyl; or $Z^3$ is optionally further substituted by a group of the formula:

-$L_Z$-$W_Z$ wherein:
$L_Z$ is a (1-3C)alkylene; and
$W_Z$ is halo, (1-2C)haloalkyl, (1-2C)haloalkoxy, cyano, hydroxy, (1-2C)alkoxy, $CR^{xa}$, COO$R^{xa}$, C(O)NR$^{xa}$R$^{xb}$ or NR$^{xa}$R$^{xb}$, wherein R$^{xa}$ and R$^{xb}$ are each independently selected from hydrogen or (1-2C)alkyl;

(63) R$^2$ is selected from a group of Formula A shown below:

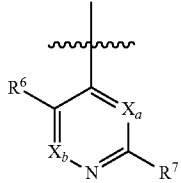

Formula A wherein:

⤳ denotes the point of attachment;
X$_a$ is CH or N;
X$_b$ is CR$^{x1}$, wherein R$^{x1}$ is selected from hydrogen, fluoro, chloro, bromo, methyl, OCH$_3$, cyano or acetylenyl;
R$^6$ is selected from fluoro, chloro, bromo, methyl, OCH$_3$, cyano or acetylenyl;
R$^7$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_3$—Z$_3$ wherein:
Y$_3$ is absent or N(R$^j$)(CH$_2$)$_{q1}$ (where q$_1$ is 0 or 1), C(O), C(O)O, C(O)N(R$^j$) or S(O)$_2$N(R$^j$), wherein R$^j$ is selected from hydrogen or methyl; and
Z$_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or a 4 to 9-membered heterocyclyl; wherein Z$_3$ is optionally further substituted by one or more substituent groups independently selected from (1-2C)alkyl, halo, (1-2C)haloalkyl, cyano, hydroxy, carboxy, C(O)NR$^l$R$^m$, NR$^l$R$^m$ or OR$^l$, wherein R$^l$ and R$^m$ are each independently selected from hydrogen or methyl; or Z$^3$ is optionally further substituted by a group of the formula:

-L$_Z$-W$_Z$ wherein:
L$_Z$ is a (1-3C)alkylene; and
W$_Z$ is halo, (1-2C)haloalkyl, (1-2C)haloalkoxy, cyano, hydroxy, (1-2C)alkoxy, CR$^{xa}$, COOR$^{xa}$, C(O)NR$^{x3}$R$^{xb}$ or NR$^{x3}$R$^{xb}$, wherein R$^{xa}$ and R$^{xb}$ are each independently selected from hydrogen or (1-2C)alkyl;

(64) R$^2$ is selected from a group of Formula A shown below:

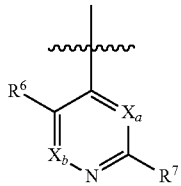

Formula A wherein:

⤳ denotes the point of attachment;
X$_a$ is CH or N;
X$_b$ is CR$^{x1}$, wherein R$^{x1}$ is selected from hydrogen, fluoro, chloro, bromo, methyl, OCH$_3$, cyano or acetylenyl;
R$^6$ is selected from fluoro, chloro, bromo, methyl, OCH$_3$, cyano or acetylenyl;
R$^7$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_3$—Z$_3$ wherein:
Y$_3$ is absent or N(R$^j$)(CH$_2$)$_{q1}$ (where q$_1$ is 0 or 1), C(O), C(O)O, C(O)N(R$^j$) or S(O)$_2$N(R$^j$), wherein R$^j$ is selected from hydrogen or methyl; and
Z$_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or a 4 to 9-membered heterocyclyl; wherein Z$_3$ is optionally further substituted by one or more substituent groups independently selected from (1-2C)alkyl, halo, (1-2C)haloalkyl, cyano, hydroxy, carboxy, C(O)NR$^l$R$^m$, NR$^l$R$^m$ or OR$^l$, wherein R$^l$ and R$^m$ are each independently selected from hydrogen or methyl; or Z$^3$ is optionally further substituted by a group of the formula:

-L$_Z$-W$_Z$ wherein:
L$_Z$ is absent or a (1-3C)alkylene optionally substituted by one or more substituents selected from (1-2C)alkyl or oxo; and
W$_Z$ is aryl, 5- or 6-membered heteroaryl, 4- to 7-membered heterocyclyl, halo, (1-4C)haloalkyl, (1-4C)haloalkoxy, cyano, hydroxy, (1-4C)alkoxy, C(O)R$^{xa}$, COOR$^{xa}$, C(O)NR$^{xa}$R$^{xb}$ or NR$^{xa}$R$^{xb}$, wherein R$^{xa}$ and R$^{xb}$ are each independently selected from hydrogen or (1-4C)alkyl; and wherein each aryl, 5- or 6-membered heteroaryl or 4- to 7-membered heterocyclyl is optionally further substituted by one or more substituent groups independently selected from (1-4C)alkyl, halo, (1-4C)haloalkyl, amino, cyano or hydroxy;

(65) R$^2$ is selected from a group of Formula A shown below:

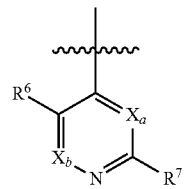

Formula A wherein:

⤳ denotes the point of attachment;
X$_a$ is CH or N;
X$_b$ is CR$^{x1}$, wherein R$^{x1}$ is selected from hydrogen, fluoro, chloro, bromo, methyl, OCH$_3$, cyano or acetylenyl;
R$^6$ is selected from fluoro, chloro, bromo, methyl, OCH$_3$, cyano or acetylenyl;
R$^7$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_3$—Z$_3$ wherein:
Y$_3$ is absent or N(R$^j$)(CH$_2$)$_{q1}$ (where q$_1$ is 0 or 1), C(O), C(O)O, C(O)N(R$^j$) or S(O)$_2$N(R$^j$), wherein R$^j$ is selected from hydrogen or methyl; and $Z_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or a 4 to 9-membered heterocyclyl; wherein $Z_3$ is optionally further substituted by one or more substituent groups independently selected from (1-2C)alkyl, halo, (1-2C)haloalkyl, cyano, hydroxy, carboxy, $C(O)NR^iR^m$, $NR^iR^m$ or $OR^i$, wherein $R^i$ and $R^m$ are each independently selected from hydrogen or methyl; or $Z^3$ is optionally further substituted by a group of the formula:

$-L_Z-W_Z$ wherein:
  $L_Z$ is absent or a (1-3C); and
  $W_Z$ is phenyl, 5- or 6-membered heteroaryl, 6-membered heterocyclyl, halo, (1-4C)haloalkyl, (1-4C)haloalkoxy, cyano, hydroxy, (1-4C)alkoxy, $C(O)R^{xa}$, $COOR^{xa}$, $C(O)NR^{xa}R^{xb}$ or $NR^{xa}R^{xb}$, wherein $R^{xa}$ and $R^{xb}$ are each independently selected from hydrogen or (1-4C)alkyl;
(66) $R^2$ is selected from a group of Formula A shown below:

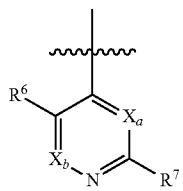

Formula A wherein:
  ⇝ denotes the point of attachment;
  $X_a$ is CH or N;
  $X_b$ is $CR^{x1}$, wherein $R^{x1}$ is selected from hydrogen, fluoro, chloro, bromo, methyl, $OCH_3$, cyano or acetylenyl;
  $R^6$ is selected from chloro or cyano;
  $R^7$ is selected from hydrogen, halo, (1-4C)alkyl, (1-4C)alkoxy, (1-4C)haloalkyl, (1-4C)haloalkoxy, cyano or a group of the formula:

$-Y_3-Z_3$ wherein:
  $Y_3$ is absent or $N(R^j)(CH_2)_{q1}$ (where $q_1$ is 0 or 1), C(O), C(O)O or $C(O)N(R^j)$, wherein $R^j$ is selected from hydrogen or methyl; and
  $Z_3$ is hydrogen, (1-6C)alkyl, (3-6C)cycloalkyl, 5- or 6-membered heteroaryl or a 4 to 9-membered heterocyclyl; wherein $Z_3$ is optionally further substituted by one or more substituent groups independently selected from (1-2C)alkyl, halo, (1-2C)haloalkyl, cyano, hydroxy, $C(O)NR^iR^m$, $NR^iR^m$ or $OR^i$, wherein $R^i$ and $R^m$ are each independently selected from hydrogen or methyl; or $Z^3$ is optionally further substituted by a group of the formula:

$-L_Z-W_Z$ wherein:
  $L_Z$ is a (1-3C)alkylene; and
  $W_Z$ is halo, (1-2C)haloalkyl, cyano, hydroxy, (1-2C)alkoxy, $CR^{xa}$, $COOR^{xa}$, $C(O)NR^{xa}R^{xb}$ or $NR^{xa}R^{xb}$ wherein $R^{xa}$ and $R^{xb}$ are each independently selected from hydrogen or methyl;

(67) $R^2$ is selected from a group of Formula A shown below:

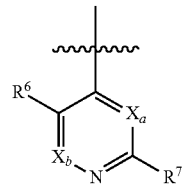

Formula A wherein:
  ⇝ denotes the point of attachment;
  $X_a$ is CH or N;
  $X_b$ is $CR^{x1}$, wherein $R^{x1}$ is selected from hydrogen, fluoro, chloro, bromo, methyl, $OCH_3$, cyano or acetylenyl;
  $R^6$ is selected from chloro or cyano;
  $R^7$ is selected from hydrogen, halo, (1-4C)alkyl, (1-4C)alkoxy, (1-4C)haloalkyl, (1-4C)haloalkoxy, cyano or a group of the formula:

$-Y_3-Z_3$ wherein:
  $Y_3$ is absent or $N(R^j)(CH_2)_{q1}$ (where $q_1$ is 0 or 1), C(O), C(O)O or $C(O)N(R^j)$, wherein $R^j$ is selected from hydrogen or methyl; and
  $Z_3$ is hydrogen, (1-6C)alkyl, (3-6C)cycloalkyl, 5- or 6-membered heteroaryl or a 4 to 9-membered heterocyclyl; wherein $Z_3$ is optionally further substituted by one or more substituent groups independently selected from (1-2C)alkyl, halo, (1-2C)haloalkyl, cyano, hydroxy, $C(O)NR^iR^m$, $NR^iR^m$ or $OR^i$, wherein $R^i$ and $R^m$ are each independently selected from hydrogen or methyl;

(68) $R^2$ is selected from a group of Formula A shown below:

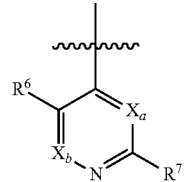

Formula A wherein:
  ⇝ denotes the point of attachment;
  $X_a$ is CH or N;
  $X_b$ is $CR^{x1}$, wherein $R^{x1}$ is selected from hydrogen, fluoro, chloro, bromo, methyl, $OCH_3$, cyano or acetylenyl;
  $R^6$ is selected from chloro or cyano;
  $R^7$ is selected from halo, (1-4C)alkyl, (1-4C)alkoxy or a group of the formula:

$-Y_3-Z_3$ wherein:
  $Y_3$ is absent or $C(O)N(R^j)$, wherein $R^j$ is selected from hydrogen or methyl; and
  $Z_3$ is (3-6C)cycloalkyl, 5- or 6-membered heteroaryl or a 4 to 9-membered heterocyclyl; wherein $Z_3$ is optionally further substituted by one or more substituent groups independently selected from (1-2C) alkyl, halo, (1-2C)haloalkyl, cyano, hydroxy, C(O)

NR$^l$R$^m$, NR$^l$R$^m$ or OR$^l$, wherein R$^l$ and R$^m$ are each independently selected from hydrogen or methyl;
(69) R$^2$ is a compound of Formula A as defined in any one of paragraphs 36 to 68 above;
(70) R$^2$ is a compound of Formula B as defined in any one of paragraphs 36 to 56 above;
(71) R$^2$ is a compound of Formula C as defined in any one of paragraphs 36 to 45 above;
(72) R$^3$ is selected from hydrogen, (1-2C)alkyl, cyclopropyl, (1-2C)haloalkyl, cyano, (2-4C)alkenyl or (2-4C)alkynyl;
(73) R$^3$ is selected from hydrogen, (1-2C)alkyl, (1-2C)haloalkyl, cyano, (2-4C)alkenyl or (2-4C)alkynyl;
(74) R$^3$ is selected from hydrogen, (1-2C)alkyl, cyclopropyl, CH$_2$F, CF$_2$H, CF$_3$, cyano or acetylenyl;
(75) R$^3$ is selected from hydrogen, (1-2C)alkyl, cyclopropyl, CH$_2$F, CF$_2$H, CF$_3$ or acetylenyl;
(76) R$^3$ is selected from hydrogen, (1-2C)alkyl, CH$_2$F, CF$_2$H, CF$_3$, cyano or acetylenyl;
(77) R$^3$ is selected from hydrogen, (1-2C)alkyl, CH$_2$F, CF$_2$H, CF$_3$ or acetylenyl;
(78) R$^3$ is selected from hydrogen, methyl, cyclopropyl, CH$_2$F, CF$_2$H, cyano or acetylenyl;
(79) R$^3$ is selected from hydrogen, methyl, cyclopropyl, CH$_2$F, CF$_2$H or acetylenyl;
(80) R$^3$ is selected from hydrogen, methyl, CH$_2$F, CF$_2$H, cyano or acetylenyl;
(81) R$^3$ is selected from hydrogen, methyl, CH$_2$F, CF$_2$H or acetylenyl;
(82) R$^3$ is selected from hydrogen or methyl;
(83) R$^4$ is selected from (1-4C)alkyl, cyano, (1-4C)haloalkyl or a group of the formula:

$$Y_5-L_5-Z_5$$

wherein:
Y$_5$ is absent or selected from C(O), C(O)O, OC(O), C(O)N(R$^r$) or S(O)$_2$N(R$^r$), wherein R$^r$ is selected from hydrogen or (1-2C)alkyl;
L$_5$ is absent or (1-2C)alkylene, optionally substituted by one or more substituents selected from (1-2C) alkyl; and
Z$_5$ is hydrogen, (1-6C)alkyl, (2-4C)alkenyl, (2-4C)alkynyl, aryl, (3-6C)cycloalkyl, (3-6C)cycloalkenyl, heteroaryl or heterocyclyl; wherein Z$_5$ is optionally substituted by one or more substituents selected from oxo, (1-4C)alkyl, (3-6C)cycloalkyl, halo, (1-4C)haloalkyl, (1-4C)haloalkoxy, (1-4C)alkoxy, (1-4C)alkylamino, amino, cyano, nitro, hydroxy, C(O)R$^s$, C(O)OR$^s$, OC(O)R$^s$, C(O)N(R$^s$)R$^t$, NR$^s$C(O)R$^t$, wherein R$^s$ and R$^t$ are each independently selected from hydrogen, (1-4C)alkyl or (3-6C)cycloalkyl; or
Z$_5$ is optionally substituted by a group of the formula:

$$Q_5-L_5-W_5$$

wherein:
Q$_5$ is absent or selected from O or N(R$^{x3}$), wherein R$^{x3}$ is selected from hydrogen or (1-2C)alkyl;
L$_5$ is absent or (1-2C)alkylene, optionally substituted by one or more substituents selected from (1-2C) alkyl or oxo; and
W$_5$ is selected from (1-4C)alkyl, aryl, (3-6C)cycloalkyl, 5- or 6-membered heteroaryl or a 5- or 6-membered heterocyclyl, and wherein W$_5$ is optionally further substituted by one or more substituents selected from (1-4C)alkyl, halo, (1-4C)haloalkyl, (1-4C)haloalkoxy, (1-4C)alkoxy, amino, cyano, nitro or hydroxy; or R$^3$ and R$^4$ are linked such that, together with the carbon atom to which they are attached, they form a 3-10 membered carbocyclic ring or a 4-10 membered heterocyclic ring, which is optionally substituted by one or more substituents selected from oxo, (1-2C) alkyl, halo, (1-2C)haloalkyl, (1-2C)haloalkoxy, (1-2C)alkoxy, (1-2C)alkylamino, amino, cyano, nitro or hydroxy; or the 3-10 membered carbocyclic or 4-10 membered heterocyclic ring is optionally fused to a 5 or 6 membered heteroaryl or phenyl ring;
(84) R$^4$ is selected from (1-4C)alkyl, cyano, (1-4C)haloalkyl or a group of the formula:

$$Y_5-L_5-Z_5$$

wherein:
Y$_5$ is absent or selected from C(O), C(O)O, C(O)N(R$^r$) or S(O)$_2$N(R$^r$), wherein R$^r$ is selected from hydrogen or (1-2C)alkyl;
L$_5$ is absent or (1-2C)alkylene, optionally substituted by one or more substituents selected from (1-2C) alkyl; and
Z$_5$ is hydrogen, (1-6C)alkyl, (2-4C)alkenyl, (2-4C)alkynyl, aryl, (3-6C)cycloalkyl, (3-6C)cycloalkenyl, 5 or 6 membered heteroaryl or 5 or 6 membered heterocyclyl; wherein Z$_5$ is optionally substituted by one or more substituents selected from oxo, (1-4C)alkyl, (3-6C)cycloalkyl, halo, (1-4C)haloalkyl, (1-4C)haloalkoxy, (1-4C)alkoxy, (1-4C)alkylamino, amino, cyano, nitro, hydroxy, C(O)R$^s$, C(O)OR$^s$, OC(O)R$^s$, C(O)N(R$^s$)R$^t$, NR$^s$C(O)R$^t$, wherein R$^s$ and R$^t$ are each independently selected from hydrogen, (1-4C)alkyl or cyclopropyl; or
Z$_5$ is optionally substituted by a group of the formula:

$$Q_5-L_5-W_5$$

wherein:
Q$_5$ is absent or selected from O or NH;
L$_5$ is absent or (1-2C)alkylene, optionally substituted by one or more substituents selected from (1-2C) alkyl; and
W$_5$ is selected from (1-4C)alkyl, phenyl, (3-6C) cycloalkyl, 5- or 6-membered heteroaryl or a 5- or 6-membered heterocyclyl, and wherein W$_5$ is optionally further substituted by one or more substituents selected from (1-4C)alkyl, halo, (1-4C)haloalkyl, (1-4C)haloalkoxy, (1-4C)alkoxy, amino, cyano, nitro or hydroxy; or
R$^3$ and R$^4$ are linked such that, together with the carbon atom to which they are attached, they form a 3-7 membered carbocyclic ring or a 4-7 membered heterocyclic ring, which is optionally substituted by one or more substituents selected from oxo, (1-2C)alkyl, halo, (1-2C)haloalkyl, (1-2C)haloalkoxy, (1-2C) alkoxy, amino or hydroxy;
(85) R$^4$ is selected from (1-4C)alkyl, cyano, (1-4C)haloalkyl or a group of the formula:

$$Y_5-L_5-Z_5$$

wherein:
Y$_5$ is absent or selected from C(O), C(O)O, C(O)N(R$^r$) or S(O)$_2$N(R$^r$), wherein R$^r$ is selected from hydrogen or (1-2C)alkyl;
L$_5$ is absent or (1-2C)alkylene, optionally substituted by one or more substituents selected from (1-2C) alkyl; and
Z$_5$ is hydrogen, (1-6C)alkyl, (2-4C)alkenyl, (2-4C)alkynyl, aryl, (3-6C)cycloalkyl, (3-6C)cycloalkenyl, heteroaryl or heterocyclyl; wherein $Z_5$ is optionally substituted by one or more substituents selected from oxo, (1-4C)alkyl, halo, (1-4C)haloalkyl, (1-4C)haloalkoxy, (1-4C)alkoxy, (1-4C)alkylamino, amino, cyano, nitro, hydroxy, $C(O)R^s$, $C(O)OR^s$, $OC(O)R^s$, $C(O)N(R^s)R^t$, $NR^sC(O)R^t$, wherein $R^s$ and $R^t$ are each independently selected from hydrogen, (1-4C)alkyl or (3-6C)cycloalkyl; or $R^3$ and $R^4$ are linked such that, together with the carbon atom to which they are attached, they form a 3-9 membered carbocyclic ring or a 4-9 membered heterocyclic ring, which is optionally substituted by one or more substituents selected from oxo, (1-2C)alkyl, halo, (1-2C)haloalkyl, (1-2C)haloalkoxy, (1-2C)alkoxy, amino or hydroxy; or the 3-9 membered carbocyclic or 4-9 membered heterocyclic ring is optionally fused to a 5 or 6 membered heteroaryl or phenyl ring;

(86) $R^4$ is selected from (1-4C)alkyl, cyano, (1-4C)haloalkyl or a group of the formula:

$Y_5$-$L_5$-$Z_5$ wherein:
$Y_5$ is absent or selected from C(O), C(O)O, C(O)N(R') or $S(O)_2N(R')$, wherein R' is selected from hydrogen or (1-2C)alkyl;
$L_5$ is absent or (1-2C)alkylene, optionally substituted by one or more substituents selected from (1-2C) alkyl; and
$Z_5$ is hydrogen, (1-6C)alkyl, (2-4C)alkenyl, (2-4C) alkynyl, aryl, (3-6C)cycloalkyl, (3-6C)cycloalkenyl, 5 or 6 membered heteroaryl or 5 or 6 membered heterocyclyl; wherein $Z_5$ is optionally substituted by one or more substituents selected from oxo, (1-4C) alkyl, halo, (1-4C)haloalkyl, (1-4C)haloalkoxy, (1-4C)alkoxy, (1-4C)alkylamino, amino, cyano, nitro, hydroxy, $C(O)OR^s$, $C(O)N(R^s)R^t$, $NR^sC(O)R^t$, wherein $R^s$ and $R^t$ are each independently selected from hydrogen or (1-4C)alkyl; or $R^3$ and $R^4$ are linked such that, together with the carbon atom to which they are attached, they form a 3-7 membered carbocyclic ring or a 4-7 membered heterocyclic ring, which is optionally substituted by one or more substituents selected from oxo, (1-2C)alkyl, halo, (1-2C)haloalkyl, (1-2C)haloalkoxy, (1-2C) alkoxy, amino or hydroxy;

(87) $R^4$ is selected from (1-4C)alkyl, cyano, (1-4C)haloalkyl or a group of the formula:

$Y_5$-$L_5$-$Z_5$ wherein:
$Y_5$ is absent or selected from C(O)O or C(O)N(R'), wherein R' is selected from hydrogen or (1-2C)alkyl;
$L_5$ is absent or (1-2C)alkylene, optionally substituted by one or more substituents selected from (1-2C) alkyl; and
$Z_5$ is hydrogen, (1-6C)alkyl, (2-4C)alkynyl, aryl, (3-6C)cycloalkyl, (3-6C)cycloalkenyl, 5 or 6 membered heteroaryl or 5 or 6 membered heterocyclyl; wherein $Z_5$ is optionally substituted by one or more substituents selected from (1-2C)alkyl, halo, (1-2C) haloalkyl, (1-2C)haloalkoxy, (1-2C)alkoxy, (1-2C) alkylamino, amino, cyano, nitro, hydroxy, $C(O)OR^s$, $C(O)N(R^s)R^t$, $NR^sC(O)R^t$, wherein $R^s$ and $R^t$ are each independently selected from hydrogen or (1-2C)alkyl; or $R^3$ and $R^4$ are linked such that, together with the carbon atom to which they are attached, they form a 3-7 membered carbocyclic ring or a 4-7 membered heterocyclic ring, which is optionally substituted by one or more substituents selected from (1-2C)alkyl, halo, (1-2C)haloalkyl, (1-2C)haloalkoxy, (1-2C)alkoxy, amino or hydroxy;

(88) $R^4$ is selected from (1-4C)alkyl, cyano, (1-4C)haloalkyl or a group of the formula:

$Y_5$-$L_5$-$Z_5$ wherein:
$Y_5$ is absent or selected from C(O)O or C(O)N(R'), wherein R' is selected from hydrogen or (1-2C)alkyl;
$L_5$ is absent or (1-2C)alkylene, optionally substituted by one or more substituents selected from (1-2C) alkyl; and
$Z_5$ is hydrogen, (1-6C)alkyl, (2-4C)alkenyl, (2-4C) alkynyl, aryl, (3-6C)cycloalkyl, (3-6C)cycloalkenyl, 5 or 6 membered heteroaryl or 5 or 6 membered heterocyclyl; wherein $Z_5$ is optionally substituted by one or more substituents selected from oxo, (1-4C) alkyl, halo, (1-4C)haloalkyl, (1-4C)haloalkoxy, (1-4C)alkoxy, (1-4C)alkylamino, amino, cyano, nitro, hydroxy, $C(O)R^s$, $C(O)OR^s$, $OC(O)R^s$, $C(O)N(R^s)R^t$, $NR^sC(O)R^t$, wherein $R^s$ and $R^t$ are each independently selected from hydrogen, (1-4C)alkyl or cyclopropyl; or $Z_5$ is optionally substituted by a group of the formula:

$Q_5$-$L_5$-$W_5$ wherein:
$Q_5$ is absent or O;
$L_5$ is absent or (1-2C)alkylene; and
$W_5$ is selected from (1-4C)alkyl, phenyl, (3-6C) cycloalkyl, 5- or 6-membered heteroaryl or a 5- or 6-membered heterocyclyl, and wherein $W_5$ is optionally further substituted by one or more substituents selected from (1-4C)alkyl, halo, (1-4C)haloalkyl, (1-4C)haloalkoxy, (1-4C)alkoxy, amino, cyano, nitro or hydroxy; or $R^3$ and $R^4$ are linked such that, together with the carbon atom to which they are attached, they form a 3-7 membered carbocyclic ring or a 4-7 membered heterocyclic ring, which is optionally substituted by one or more substituents selected from (1-2C)alkyl, halo, (1-2C)haloalkyl, (1-2C)alkoxy, amino or hydroxy;

(89) $R^4$ is selected from (1-4C)alkyl, cyano, (1-4C)haloalkyl or a group of the formula:

$Y_5$-$L_5$-$Z_5$ wherein:
$Y_5$ is absent or selected from C(O)O or C(O)N(R'), wherein R' is selected from hydrogen or (1-2C)alkyl;
$L_5$ is absent or (1-2C)alkylene, optionally substituted by one or more substituents selected from (1-2C) alkyl; and
$Z_5$ is hydrogen, (1-6C)alkyl, (2-4C)alkynyl, aryl, (3-6C)cycloalkyl, (3-6C)cycloalkenyl, 5 or 6 membered heteroaryl or 5 or 6 membered heterocyclyl; wherein $Z_5$ is optionally substituted by one or more substituents selected from (1-2C)alkyl, (3-6C)cycloalkyl, halo, (1-2C)haloalkyl, (1-2C)haloalkoxy, (1-2C)alkoxy, (1-2C)alkylamino, amino, cyano, nitro, hydroxy, $C(O)OR^s$, $C(O)N(R^s)R^t$, $NR^sC(O)R^t$, wherein $R^s$ and $R^t$ are each independently selected from hydrogen or (1-2C)alkyl; or $R^3$ and $R^4$ are linked such that, together with the carbon atom to which they are attached, they form a 3-7 membered carbocyclic ring or a 4-7 membered heterocyclic ring;

(90) $R^4$ is selected from (1-6C)alkyl, (3-6C)cycloalkyl, 5 or 6 membered heteroaryl or 5 or 6 membered heterocyclyl; wherein each of (1-6C)alkyl, (3-6C)cycloalkyl, 5 or 6 membered heteroaryl or 5 or 6 membered heterocyclyl is optionally substituted by one or more substituents selected from (1-2C)alkyl, (3-6C)cycloalkyl, halo, (1-2C)haloalkyl, (1-2C)haloalkoxy, (1-2C)alkoxy, (1-2C)alkylamino, amino, cyano, nitro, hydroxy, $C(O)OR^s$, $C(O)N(R^s)R^t$, $NR^sC(O)R^t$, wherein $R^s$ and $R^t$ are each independently selected from hydrogen or (1-2C)alkyl;

(91) $R^4$ is selected from cyclopropyl or a 5 or 6 membered heteroaryl, wherein each cyclopropyl or 5 or 6 membered heteroaryl is optionally substituted by one or more substituents selected from (1-2C)alkyl, cyclopropyl, halo, (1-2C)haloalkyl, (1-2C)haloalkoxy, (1-2C)alkoxy, (1-2C)alkylamino, amino, cyano, nitro, hydroxy, $C(O)OR^s$, $C(O)N(R^s)R^t$, $NR^sC(O)R^t$, wherein $R^s$ and $R^t$ are each independently selected from hydrogen or (1-2C)alkyl;

(92) $R^4$ is selected from cyclopropyl or pyrimidine, wherein said pyrimidine is optionally substituted by one or more substituents selected from (1-2C)alkyl, cyclopropyl, halo, (1-2C)haloalkyl, (1-2C)haloalkoxy, (1-2C)alkoxy, (1-2C)alkylamino, amino, cyano, nitro, hydroxy, $C(O)OR^s$, $C(O)N(R^s)R^t$, $NR^sC(O)R^t$, wherein $R^s$ and $R^t$ are each independently selected from hydrogen or (1-2C)alkyl;

(93) $R^5$ is selected from hydrogen, (1-4C)alkyl, (1-2C)haloalkyl, (1-2C)alkoxy, (1-2C)haloalkoxy, cyano, acetylenyl or a 5- or 6-membered heteroaryl, wherein said (1-4C)alkyl, or 5- or 6-membered heteroaryl are independently optionally substituted by one or more substituents selected from halo, hydroxy or amino;

(94) $R^5$ is selected from hydrogen, (1-4C)alkyl, (1-2C)haloalkyl, cyano, acetylenyl or a 5- or 6-membered heteroaryl, wherein said (1-4C)alkyl, or 5- or 6-membered heteroaryl are independently optionally substituted by one or more substituents selected from halo, hydroxy or amino;

(95) $R^5$ is selected from hydrogen, (1-4C)alkyl, (1-2C)haloalkyl, (1-2C)alkoxy, (1-2C)haloalkoxy, cyano or acetylenyl, wherein said (1-4C)alkyl is optionally substituted by one or more substituents selected from halo, hydroxy or amino;

(96) $R^5$ is selected from hydrogen, (1-4C)alkyl, $CH_2F$, $CF_2H$, $CF_3$, $OCH_3$, cyano, acetylenyl or -membered heteroaryl, wherein said (1-4C)alkyl or a 6-membered heteroaryl are independently optionally substituted by one or more substituents selected from fluoro, chloro, hydroxy or amino;

(97) $R^5$ is selected from hydrogen, (1-4C)alkyl, $CH_2F$, $CF_2H$, $CF_3$, $OCH_3$, cyano or acetylenyl, wherein said (1-4C)alkyl is optionally substituted by one or more substituents selected from fluoro, chloro, hydroxy or amino;

(98) $R^5$ is selected from hydrogen, (1-4C)alkyl, $CH_2F$, $CF_2H$, $CF_3$, cyano or acetylenyl, wherein said (1-4C)alkyl is optionally substituted by one or more substituents selected from fluoro, chloro, hydroxy or amino;

(99) $R^5$ is selected from hydrogen, (1-4C)alkyl, $OCH_3$, cyano or acetylenyl, wherein said (1-4C)alkyl is optionally substituted by one or more substituents selected from fluoro, chloro or hydroxy;

(100) $R^5$ is selected from hydrogen or (1-4C)alkyl, wherein said (1-4C)alkyl is optionally substituted by one or more substituents selected from fluoro, chloro, hydroxy or amino;

(101) $R^5$ is selected from hydrogen or (1-4C)alkyl (e.g. methyl).

Suitably, a heteroaryl is a 5- or 6-membered heteroaryl ring comprising one, two or three heteroatoms selected from N, O or S.

Suitably, a heterocyclyl group is a 4-, 5-, 6- or 7-membered heterocyclyl ring comprising one, two or three heteroatoms (preferably one or two heteroatoms) selected from N, O or S. Most suitably, a heterocyclyl group is a 5-, 6- or 7-membered ring comprising one, two or three heteroatoms selected from N, O or S [e.g. morpholinyl (e.g. 4-morpholinyl), pyridinyl, piperazinyl, homopiperazinyl or pyrrolidinonyl].

Suitably an aryl group is phenyl.

Suitably, $X_1$ is as described in any one of paragraphs (1) to (10) above. Most suitably, $X_1$ is as described in paragraph (10) above.

Suitably, $X_2$ is as described in any one of paragraphs (11) to (15) above. Most suitably, $X_2$ is as described in paragraph (15) above.

Suitably, $X_3$ is as described in any one of paragraphs (16) to (20) above. Most suitably, $X_3$ is as described in any one of paragraphs (18) to (20) above.

Suitably, $R^1$ is as described in any one of paragraphs (21) to (35) above. More suitably, $R^1$ is as described in any one of paragraphs (26) to (35) above Most suitably, $R^1$ is as described in paragraph (35) above.

Suitably, $R^2$ is as described in any one of paragraphs (36) to (71) above. More suitably, $R^2$ is as described in any one of paragraphs (46) to (68) above. Yet more suitably, $R^2$ is as described in any one of paragraphs (57) to (68) above Most suitably, $R^2$ is as described in paragraph (68) above.

Suitably, $R^3$ is as described in any one of paragraphs (72) to (82) above. More suitably, $R^3$ is as described in any one of paragraphs (76) to (82) above Most suitably, $R^3$ is as described in paragraph (82) above.

Suitably, $R^4$ is as described in any one of paragraphs (83) to (92) above. More suitably, $R^4$ is as described in any one of paragraphs (87) to (92) above Most suitably, $R^4$ is as described in paragraph (92) above.

Suitably, $R^5$ is as described in any one of paragraphs (93) to (101) above. Most suitably, $R^5$ is as described in paragraph (101) above.

In a particular group of compounds of the invention, $X_2$ is CH, i.e. the compounds have the structural formula Ia (a sub-definition of Formula (I)) shown below, or a pharmaceutically acceptable salt, hydrate and/or solvate thereof:

Formula Ia

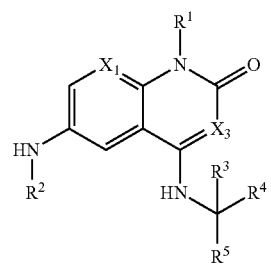

wherein each of $X_1$, $X_3$, $R^1$, $R^2$, $R^3$, $R^4$ and $R^5$ are as defined hereinabove.

In an embodiment of the compounds of Formula Ia:
X₁ is as defined in any one of paragraphs (1) to (10) above;
X₃ is as defined in any one of paragraphs (16) to (20) above;
R¹ is as defined in any one of paragraphs (21) to (35) above;
R² is as defined in any one of paragraphs (36) to (71) above;
R³ is as defined in any one of paragraphs (72) to (82) above;
R⁴ is as defined in any one of paragraphs (83) to (92) above; and
R⁵ is as defined in any one of paragraphs (93) to (101) above.

In another embodiment of the compounds of Formula Ia:
X₁ is as defined in paragraph (10) above;
X₃ is as defined in paragraph (18) above;
R¹ is as defined in paragraph (35) above;
R² is as defined in any one of paragraphs (56) or (68) above;
R³ is as defined in paragraph (82) above;
R⁴ is as defined in paragraph (92) above; and
R⁵ is as defined in paragraph (101) above.

In a particular group of compounds of the invention, X₂ is CH and R³ is hydrogen or methyl, i.e. the compounds have the structural formula Ib (a sub-definition of Formula (I)) shown below, or a pharmaceutically acceptable salt, hydrate and/or solvate thereof:

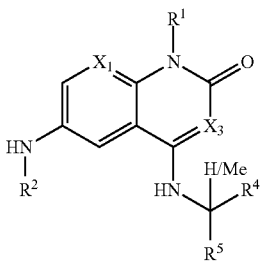

Formula Ib wherein each of X₁, X₃, R¹, R², R⁴ and R⁵ are as defined hereinabove

In an embodiment of the compounds of Formula Ib:
X₁ is as defined in any one of paragraphs (1) to (10) above;
X₃ is as defined in any one of paragraphs (16) to (20) above;
R¹ is as defined in any one of paragraphs (21) to (35) above;
R² is as defined in any one of paragraphs (36) to (71) above;
R⁴ is as defined in any one of paragraphs (83) to (92) above; and
R⁵ is as defined in any one of paragraphs (93) to (101) above.

In another embodiment of the compounds of Formula Ib:
X₁ is as defined in paragraph (10) above;
X₃ is as defined in paragraph (18) above;
R¹ is as defined in paragraph (35) above;
R² is as defined in any one of paragraphs (56) or (68) above;
R⁴ is as defined in paragraph (92) above; and
R⁵ is as defined in paragraph (101) above.

In a particular group of compounds of the invention, X₂ is CH, R³ is hydrogen or methyl and R⁵ is CH₃, i.e. the compounds have the structural formula Ic (a sub-definition of Formula (I)) shown below, or a pharmaceutically acceptable salt, hydrate and/or solvate thereof:

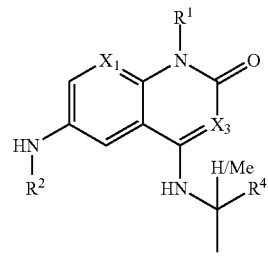

Formula Ic wherein each of X₁, X₃, R¹, R² and R⁴ are as defined hereinabove.

In an embodiment of the compounds of Formula Ic:
X₁ is as defined in any one of paragraphs (1) to (10) above;
X₃ is as defined in any one of paragraphs (16) to (20) above;
R¹ is as defined in any one of paragraphs (21) to (35) above;
R² is as defined in any one of paragraphs (36) to (71) above; and
R⁴ is as defined in any one of paragraphs (83) to (92) above.

In another embodiment of the compounds of Formula Ic:
X₁ is as defined in paragraph (10) above;
X₃ is as defined in paragraph (18) above;
R¹ is as defined in paragraph (35) above;
R² is as defined in any one of paragraphs (56) or (68) above; and
R⁴ is as defined in paragraph (92) above.

In a particular group of compounds of the invention, X₁, X₂, and X₃ are CH, R³ is hydrogen or methyl and R⁵ is CH₃, i.e. the compounds have the structural formula Id (a sub-definition of Formula (I)) shown below, or a pharmaceutically acceptable salt, hydrate and/or solvate thereof:

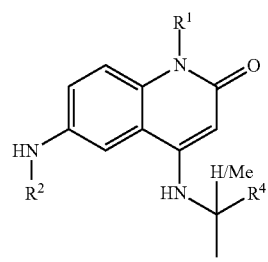

Formula Id wherein each of R¹, R² and R⁴ are as defined hereinabove.

In an embodiment of the compounds of Formula Id:
R¹ is as defined in any one of paragraphs (21) to (35) above;
R² is as defined in any one of paragraphs (36) to (71) above; and
R⁴ is as defined in any one of paragraphs (83) to (92) above.

In another embodiment of the compounds of Formula Id:

R¹ is as defined in paragraph (35) above;

R² is as defined in any one of paragraphs (56) or (68) above; and

R⁴ is as defined in paragraph (92) above.

In a particular group of compounds of the invention, R² is as shown below, i.e. the compounds have the structural formula Ie (a sub-definition of Formula (I)) shown below, or a pharmaceutically acceptable salt, hydrate and/or solvate thereof:

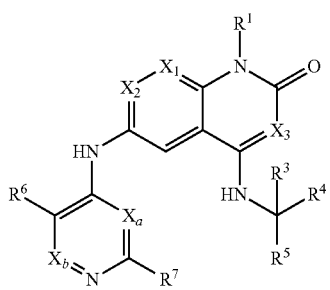

Formula Ie wherein each of $X_1$, $X_2$, $X_3$, $X_a$, $X_b$, $R^1$, $R^3$, $R^4$, $R^5$, $R^6$ and $R^7$ are as defined hereinabove.

In an embodiment of the compounds of Formula Ie:

$X_1$ is as defined in any one of paragraphs (1) to (10) above;

$X_2$ is as defined in any one of paragraphs (11) to (15) above;

$X_3$ is as defined in any one of paragraphs (16) to (20) above;

$R^1$ is as defined in any one of paragraphs (21) to (35) above;

$X_a$, $X_b$, $R^6$ and $R^7$ are each as defined in any one of paragraphs (36) to (68) above;

$R^3$ is as defined in any one of paragraphs (72) to (82) above;

$R^4$ is as defined in any one of paragraphs (83) to (92) above; and $R^5$ is as defined in any one of paragraphs (93) to (101) above.

In another embodiment of the compounds of Formula Ie:

$X_i$ is as defined in paragraph (10) above;

$X_2$ is as defined in paragraph (15) above $X_3$ is as defined in paragraph (18) above;

$R^1$ is as defined in paragraph (35) above;

$X_a$, $X_b$, $R^6$ and $R^7$ are each as defined in any one of paragraphs (56) or (68) above;

$R^3$ is as defined in paragraph (82) above;

$R^4$ is as defined in paragraph (92) above; and $R^5$ is as defined in paragraph (101) above.

In a particular group of compounds of the invention, $X_1$, $X_2$, and $X_3$ are CH and R² is as shown below, i.e. the compounds have the structural formula If (a sub-definition of Formula (I)) shown below, or a pharmaceutically acceptable salt, hydrate and/or solvate thereof:

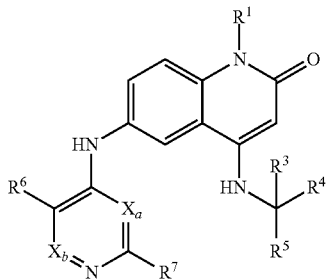

Formula If wherein each of $X_a$, $X_b$, $R^1$, $R^3$, $R^4$, $R^5$, $R^6$ and $R^7$ are as defined hereinabove In an embodiment of the compounds of Formula If:

$R^1$ is as defined in any one of paragraphs (21) to (35) above;

$X_a$, $X_b$, $R^6$ and $R^7$ are each as defined in any one of paragraphs (36) to (68) above;

$R^3$ is as defined in any one of paragraphs (72) to (82) above;

$R^4$ is as defined in any one of paragraphs (83) to (92) above; and $R^5$ is as defined in any one of paragraphs (93) to (101) above.

In another embodiment of the compounds of Formula If:

$R^1$ is as defined in paragraph (35) above;

$X_a$, $X_b$, $R^6$ and $R^7$ are each as defined in any one of paragraphs (56) or (68) above;

$R^3$ is as defined in paragraph (82) above;

$R^4$ is as defined in paragraph (92) above; and $R^5$ is as defined in paragraph (101) above.

In a particular group of compounds of the invention, $X_1$, $X_2$, and $X_3$ are CH, $R^1$ and $R^3$ are methyl and R² is as shown below, i.e. the compounds have the structural formula Ig (a sub-definition of Formula (I)) shown below, or a pharmaceutically acceptable salt, hydrate and/or solvate thereof:

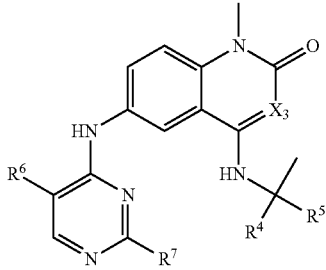

Formula Ig wherein each of $X_3$, $R^4$, $R^5$, $R^6$ and $R^7$ are as defined hereinabove.

In an embodiment of the compounds of Formula Ig:

$X_3$ is as defined in any one of paragraphs (16) to (20) above;

$R^6$ and $R^7$ are each as defined in any one of paragraphs (62) to (68) above;

$R^4$ is as defined in any one of paragraphs (87) to (92) above; and $R^5$ is as defined in any one of paragraphs (96) to (101).

In another embodiment of the compounds of Formula Ig:

$X_3$ is as defined in paragraph (19) above;

$R^6$ is chloro;

$R^7$ is as defined in paragraph (68) above;

$R^4$ is as defined in paragraph (92) above; and $R^5$ is methyl.

Particular compounds of the present invention include any of the compounds exemplified in the present application, or a pharmaceutically acceptable salt or solvate thereof, and, in particular, any of the following:

2-Chloro-4-[[1-methyl-4-[(1-methyl-1-pyrimidin-2-yl-ethyl)amino]-2-oxo-6-quinolyl]amino]pyridine-3-carbonitrile;

2-chloro-4-[[1-methyl-2-oxo-4-(1-pyrimidin-2-ylethylamino)-6-quinolyl]amino]pyridine-3-carbonitrile;

2-chloro-4-[[1-[2-(2,5-dioxopyrrolidin-1-yl)ethyl]-2-oxo-4-(1-pyrimidin-2-ylethylamino)-6-quinolyl]amino]pyridine-3-carbonitrile;

2-chloro-4-[[2-oxo-4-(1-pyrimidin-2-ylethylamino)-1-(tetrahydropyran-4-ylmethyl)-6-quinolyl]amino]pyridine-3-carbonitrile;

2-chloro-4-[[1-methyl-2-oxo-4-[1-(1H-1,2,4-triazol-3-yl)ethylamino]-6-quinolyl]amino]pyridine-3-carbonitrile;

trans-2-chloro-4-[[4-[(3-hydroxycyclobutyl)amino]-1-methyl-2-oxo-6-quinolyl]amino]pyridine-3-carbonitrile;

2-chloro-4-[[1-methyl-2-oxo-4-[[(3S)-tetrahydrofuran-3-yl]amino]-6-quinolyl]amino]pyridine-3-carbonitrile;

2-chloro-4-[[1-methyl-4-[1-(5-methyl-1,2,4-oxadiazol-3-yl)ethylamino]-2-oxo-6-quinolyl]amino]pyridine-3-carbonitrile;

2-chloro-4-[[1-methyl-4-[1-(4-methylpyrimidin-2-yl)ethylamino]-2-oxo-6-quinolyl]amino]pyridine-3-carbonitrile;

2-chloro-4-[[1-methyl-2-oxo-4-(1-pyrazin-2-ylethylamino)-6-quinolyl]amino]pyridine-3-carbonitrile;

2-chloro-4-[[4-[(3-hydroxy-1-methyl-propyl)amino]-1-methyl-2-oxo-quinazolin-6-yl]amino]pyridine-3-carbonitrile;

2-chloro-4-[[4-[(2-hydroxy-1-methyl-ethyl)amino]-1-methyl-2-oxo-quinazolin-6-yl]amino]pyridine-3-carbonitrile;

2-chloro-4-[[1-methyl-4-[1-(5-methylisoxazol-3-yl)ethylamino]-2-oxo-6-quinolyl]amino]pyridine-3-carbonitrile;

2-chloro-4-[[4-[(2-hydroxy-1-methyl-ethyl)amino]-2-oxo-1H-quinazolin-6-yl]amino]pyridine-3-carbonitrile;

2-chloro-4-[[4-(ethylamino)-1-[2-(2-methoxyethoxy)ethyl]-2-oxo-6-quinolyl]amino]pyridine-3-carbonitrile;

2-chloro-4-[[1-methyl-4-(1-oxazol-2-ylethylamino)-2-oxo-6-quinolyl]amino]pyridine-3-carbonitrile;

2-chloro-4-[[1-methyl-2-oxo-4-(1-pyrimidin-4-ylethylamino)-6-quinolyl]amino]pyridine-3-carbonitrile;

2-chloro-4-[[1-[2-(2,5-dioxopyrrolidin-1-yl)ethyl]-4-(ethylamino)-2-oxo-6-quinolyl]amino]pyridine-3-carbonitrile;

2-chloro-4-[[1-methyl-2-oxo-4-(1-thiazol-2-ylethylamino)-6-quinolyl]amino]pyridine-3-carbonitrile;

2-chloro-4-[[1-methyl-2-oxo-4-[1-(1H-pyrazol-3-yl)ethylamino]-6-quinolyl]amino]pyridine-3-carbonitrile;

6-chloro-5-cyano-N-methyl-4-[[1-methyl-4-[(1-methyl-1-pyrimidin-2-yl-ethyl)amino]-2-oxo-6-quinolyl]amino]pyridine-2-carboxamide;

6-chloro-5-cyano-N-methyl-4-[[1-methyl-2-oxo-4-(1-pyrimidin-2-ylethylamino)-6-quinolyl]amino]pyridine-2-carboxamide;

2-chloro-6-methyl-4-[[1-methyl-2-oxo-4-(1-pyrimidin-2-ylethylamino)-6-quinolyl]amino]pyridine-3-carbonitrile;

2-chloro-4-[[8-methyl-5-[(1-methyl-1-pyrimidin-2-yl-ethyl)amino]-7-oxo-1,8-naphthyridin-3-yl]amino]pyridine-3-carbonitrile;

6-Chloro-5-cyano-4-[[4-(1-cyclopropylethylamino)-1-methyl-2-oxo-6-quinolyl]amino]pyridine-2-carboxylic acid;

6-chloro-5-cyano-4-[[4-(cyclopropylamino)-1-methyl-2-oxo-6-quinolyl]amino]pyridine-2-carboxylic acid;

6-chloro-5-cyano-4-[[1-methyl-4-[(1-methylcyclopropyl)amino]-2-oxo-6-quinolyl]amino]pyridine-2-carboxylic acid;

6-chloro-5-cyano-4-[[1-methyl-4-[(1-methylcyclopentyl)amino]-2-oxo-6-quinolyl]amino]pyridine-2-carboxylic acid;

(R)-2-((6-((2-Chloro-3-cyanopyridin-4-yl)amino)-1-methyl-2-oxo-1,2-dihydroquinolin-4-yl)amino)-N-((1-methyl-1H-pyrazol-4-yl)methyl)propanamide;

(R)-2-((6-((2-chloro-3-cyanopyridin-4-yl)amino)-1-methyl-2-oxo-1,2-dihydroquinolin-4-yl)amino)-N-(2-hydroxyethyl)propanamide;

2-Chloro-4-((1-methyl-4-((1-(3-methyl-1H-1,2,4-triazol-5-yl)ethyl)amino)-2-oxo-1,2-dihydroquinolin-6-yl)amino)nicotinonitrile;

(R)-2-((6-((2-Chloro-3-cyanopyridin-4-yl)amino)-1-methyl-2-oxo-1,2-dihydroquinolin-4-yl)amino)-N-cyclopentylpropanamide;

(R)-2-((6-((2-chloro-3-cyanopyridin-4-yl)amino)-1-methyl-2-oxo-1,2-dihydroquinolin-4-yl)amino)-N-(2-methoxyethyl)propanamide;

(R)—N-(But-3-yn-1-yl)-2-((6-((2-chloro-3-cyanopyridin-4-yl)amino)-1-methyl-2-oxo-1,2-dihydroquinolin-4-yl)amino)propanamide;

(S)-2-Chloro-4-((4-((1-hydroxypropan-2-yl)amino)-1-methyl-2-oxo-1,2-dihydroquinolin-6-yl)amino)nicotinonitrile;

2-((6-((2-Chloro-3-cyanopyridin-4-yl)amino)-1-methyl-2-oxo-1,2-dihydroquinolin-4-yl)amino)-N-ethyl-2-methylpropanamide;

(R)-2-((6-((2-Chloro-3-cyanopyridin-4-yl)amino)-1-methyl-2-oxo-1,2-dihydroquinolin-4-yl)amino)-N-(4-methoxycyclohexyl)propanamide;

(R)-2-chloro-4-((4-((1-hydroxypropan-2-yl)amino)-1-methyl-2-oxo-1,2-dihydroquinolin-6-yl)amino)nicotinonitrile;

rac-2-((6-((2-Chloro-3-cyanopyridin-4-yl)amino)-1-methyl-2-oxo-1,2-dihydroquinolin-4-yl)amino)-N-ethylpropanamide;

2-Chloro-4-((1-methyl-4-((1-(5-methyl-1,3,4-oxadiazol-2-yl)ethyl)amino)-2-oxo-1,2-dihydroquinolin-6-yl)amino)nicotinonitrile;

(R)-2-((6-((2-Chloro-3-cyanopyridin-4-yl)amino)-1-methyl-2-oxo-1,2-dihydroquinolin-4-yl)amino)-N-(2-(1-methyl-1H-pyrazol-4-yl)ethyl)propanamide;

(S)-2-Chloro-4-((4-((4-hydroxybutan-2-yl)amino)-1-methyl-2-oxo-1,2-dihydroquinolin-6-yl)amino)nicotinonitrile;

(R)-2-((6-((2-chloro-3-cyanopyridin-4-yl)amino)-1-methyl-2-oxo-1,2-dihydroquinolin-4-yl)amino)-N-methylpropanamide;

(R)-2-((6-((2-chloro-3-cyanopyridin-4-yl)amino)-2-oxo-1,2-dihydroquinolin-4-yl)amino)-N-methylpropanamide;

6-Chloro-5-cyano-4-[[4-(ethylamino)-1-methyl-2-oxo-6-quinolyl]amino]pyridine-2-carboxylic acid;

6-Chloro-5-cyano-4-[[4-(ethylamino)-1-methyl-2-oxo-6-quinolyl]amino]-N-methyl-pyridine-2-carboxamide;

6-[(2,3-Dichloro-4-pyridyl)amino]-1-methyl-4-(1-pyrimidin-2-ylethylamino)quinolin-2-one;

6-((2,3-dichloropyridin-4-yl)amino)-1-methyl-4-((2-(pyrimidin-2-yl)propan-2-yl)amino)quinolin-2(1H)-one;

6-((2,3-dichloropyridin-4-yl)amino)-1-methyl-4-((1-(pyrimidin-2-yl)ethyl)amino)quinazolin-2(1H)-one;

(R)-4-((1-cyclopropylethyl)amino)-6-((2,3-dichloropyridin-4-yl)amino)-1-methylquinazolin-2(1H)-one;

6-((2,3-dichloropyridin-4-yl)amino)-1-methyl-4-((1-(pyrimidin-2-yl)ethyl)amino)-1,8-naphthyridin-2(1H)-one;

(R)-4-((1-cyclopropylethyl)amino)-6-((2,3-dichloropyridin-4-yl)amino)-1-methyl-1,8-naphthyridin-2(1H)-one;
1-(cyclopropylmethyl)-6-[(2,3-dichloro-4-pyridyl)amino]-4-(1-pyrimidin-2-ylethylamino)quinolin-2-one;
6-((5-chloro-2-((2S,6R)-2,6-dimethylmorpholino)pyridin-4-yl)amino)-4-(((R)-1-cyclopropylethyl)amino)-1-methylquinolin-2(1H)-one;
(R)-1-(5-chloro-4-((4-((1-cyclopropylethyl)amino)-1-methyl-2-oxo-1,2-dihydroquinolin-6-yl)amino)pyridin-2-yl)-N,N-dimethylpiperidine-4-carboxamide;
4-((2-(5-cyclopropylpyrimidin-2-yl)propan-2-yl)amino)-6-((2,3-dichloropyridin-4-yl)amino)-1-methylquinolin-2(1H)-one;
2-Chloro-4-((4-((2-(5-((2R,6S)-2,6-dimethylmorpholino)pyrimidin-2-yl)propan-2-yl)amino)-1-methyl-2-oxo-1,2-dihydroquinolin-6-yl)amino)nicotinonitrile;
6-chloro-5-cyano-4-((4-((1-cyclopropylethyl)amino)-1-methyl-2-oxo-1,2-dihydroquinolin-6-yl)amino)-N-methylpicolinamide;
4-((4-(tert-butylamino)-1-methyl-2-oxo-1,2-dihydroquinolin-6-yl)amino)-6-chloro-5-cyano-N-methylpicolinamide;
6-chloro-5-cyano-4-[[4-[(2-methoxy-1,1-dimethyl-ethyl)amino]-1-methyl-2-oxo-6-quinolyl]amino]-N-methyl-pyridine-2-carboxamide;
6-(Azetidine-1-carbonyl)-2-chloro-4-((1-methyl-2-oxo-4-((2-(pyrimidin-2-yl)propan-2-yl)amino)-1,2-dihydroquinolin-6-yl)amino)nicotinonitrile;
6-(azetidine-1-carbonyl)-2-chloro-4-((4-((2-(5-cyclopropylpyrimidin-2-yl)propan-2-yl)amino)-1-methyl-2-oxo-1,2-dihydroquinolin-6-yl)amino)nicotinonitrile;
(R)-6-(azetidine-1-carbonyl)-2-chloro-4-((4-((1-cyclopropylethyl)amino)-1-methyl-2-oxo-1,2-dihydroquinolin-6-yl)amino)nicotinonitrile;
2-chloro-4-((1-methyl-2-oxo-4-((2-(pyrimidin-2-yl)propan-2-yl)amino)-1,2-dihydroquinolin-6-yl)amino)-6-(3-(trifluoromethyl)azetidine-1-carbonyl)nicotinonitrile;
(S)-2-chloro-6-(2-(methoxymethyl)pyrrolidine-1-carbonyl)-4-((1-methyl-2-oxo-4-((2-(pyrimidin-2-yl)propan-2-yl)amino)-1,2-dihydroquinolin-6-yl)amino)nicotinonitrile;
2-chloro-4-((4-((1-(5-cyclopropylpyrimidin-2-yl)ethyl)amino)-1-methyl-2-oxo-1,2-dihydroquinolin-6-yl)amino)-6-(3-(trifluoromethyl)azetidine-1-carbonyl)nicotinonitrile;
6-chloro-5-cyano-4-((4-((2-(5-cyclopropylpyrimidin-2-yl)propan-2-yl)amino)-1-methyl-2-oxo-1,2-dihydroquinolin-6-yl)amino)picolinic acid;
(R)-6-chloro-5-cyano-4-((4-((1-cyclopropylethyl)amino)-1-methyl-2-oxo-1,2-dihydroquinolin-6-yl)amino)picolinic acid;
6-chloro-5-cyano-4-((4-((2-fluoroethyl)amino)-1-methyl-2-oxo-1,2-dihydroquinolin-6-yl)amino)picolinic acid;
(S)-6-chloro-5-cyano-4-((4-((1-cyclopropylethyl)amino)-1-methyl-2-oxo-1,2-dihydroquinolin-6-yl)amino)picolinic acid;
6-chloro-5-cyano-4-((1-methyl-2-oxo-4-((2-(pyrimidin-2-yl)propan-2-yl)amino)-1,2-dihydroquinolin-6-yl)amino)picolinic acid;
6-chloro-5-cyano-4-((4-((1-cyanocyclopropyl)amino)-1-methyl-2-oxo-1,2-dihydroquinolin-6-yl)amino)picolinic acid;
6-chloro-5-cyano-4-((4-((1-ethynylcyclopropyl)amino)-1-methyl-2-oxo-1,2-dihydroquinolin-6-yl)amino)picolinic acid;
rac-6-chloro-5-cyano-4-((4-(((1R,2R)-2-ethylcyclopropyl)amino)-1-methyl-2-oxo-1,2-dihydroquinolin-6-yl)amino)picolinic acid;
6-chloro-5-cyano-4-((4-((2,2-dimethylcyclopropyl)amino)-1-methyl-2-oxo-1,2-dihydroquinolin-6-yl)amino)picolinic acid;
6-chloro-5-cyano-4-((4-((1-(hydroxymethyl)cyclopropyl)amino)-1-methyl-2-oxo-1,2-dihydroquinolin-6-yl)amino)picolinic acid;
6-chloro-5-cyano-4-((4-((cyclopropylmethyl)amino)-1-methyl-2-oxo-1,2-dihydroquinolin-6-yl)amino)picolinic acid;
6-chloro-5-cyano-4-((4-((1-methoxy-2-methylpropan-2-yl)amino)-1-methyl-2-oxo-1,2-dihydroquinolin-6-yl)amino)picolinic acid;
4-((4-(tert-butylamino)-1-methyl-2-oxo-1,2-dihydroquinolin-6-yl)amino)-6-chloro-5-cyanopicolinic acid;
6-chloro-5-cyano-4-((1-methyl-2-oxo-4-(tert-pentylamino)-1,2-dihydroquinolin-6-yl)amino)picolinic acid;
6-chloro-5-cyano-4-((4-((1-(5-cyclopropylpyrimidin-2-yl)ethyl)amino)-1-methyl-2-oxo-1,2-dihydroquinolin-6-yl)amino)picolinic acid;
4-((1-benzyl-2-oxo-4-((1-(pyrimidin-2-yl)ethyl)amino)-1,2-dihydroquinolin-6-yl)amino)-6-chloro-5-cyanopicolinic acid;
2-chloro-4-((4-((2-(5-cyclopropylpyrimidin-2-yl)propan-2-yl)amino)-1-methyl-2-oxo-1,2-dihydroquinolin-6-yl)amino)nicotinonitrile;
2-chloro-4-((4-((1-(5-((2S,6R)-2,6-dimethylmorpholino)pyrimidin-2-yl)ethyl)amino)-1-methyl-2-oxo-1,2-dihydroquinolin-6-yl)amino)nicotinonitrile;
2-chloro-4-((1-methyl-4-((1-(5-(1-methyl-1H-pyrazol-4-yl)pyrimidin-2-yl)ethyl)amino)-2-oxo-1,2-dihydroquinolin-6-yl)amino)nicotinonitrile;
2-chloro-4-((1-methyl-2-oxo-4-((1-(5-(2-(trifluoromethyl)morpholino)pyrimidin-2-yl)ethyl)amino)-1,2-dihydroquinolin-6-yl)amino)nicotinonitrile;
2-chloro-4-((4-((1-(5-cyclopropylpyrimidin-2-yl)ethyl)amino)-1-methyl-2-oxo-1,2-dihydroquinolin-6-yl)amino)nicotinonitrile;
2-chloro-4-((1-methyl-4-((1-(5-methylpyrimidin-2-yl)ethyl)amino)-2-oxo-1,2-dihydroquinolin-6-yl)amino)nicotinonitrile;
(R)-2-chloro-4-((1-methyl-2-oxo-4-((1-(pyrimidin-2-yl)ethyl)amino)-1,2-dihydroquinolin-6-yl)amino)nicotinonitrile;
2-chloro-4-((1-methyl-2-oxo-4-((1-(pyrimidin-2-yl)ethyl)amino)-1,2-dihydroquinazolin-6-yl)amino)nicotinonitrile;
(R)-6-chloro-5-cyano-4-((4-((1-cyclopropylethyl)amino)-1-methyl-2-oxo-1,2-dihydroquinolin-6-yl)amino)-N-methylpicolinamide;
4-((4-((1-(5-bromopyrimidin-2-yl)ethyl)amino)-1-methyl-2-oxo-1,2-dihydroquinolin-6-yl)amino)-2-chloronicotinonitrile;
2-chloro-4-((4-((1-(5-((3R,5S)-3,5-dimethylpiperidin-1-yl)pyrimidin-2-yl)ethyl)amino)-1-methyl-2-oxo-1,2-dihydroquinolin-6-yl)amino)nicotinonitrile;
2-chloro-4-((1-methyl-4-((1-(1-methyl-1H-1,2,4-triazol-3-yl)ethyl)amino)-2-oxo-1,2-dihydroquinolin-6-yl)amino)nicotinonitrile;
(R)-2-chloro-4-((4-((1-cyclopropylethyl)amino)-1-methyl-2-oxo-1,2-dihydroquinazolin-6-yl)amino)nicotinonitrile;
(R)-2-chloro-4-((4-((1-cyclopropylethyl)amino)-1-methyl-2-oxo-1,2-dihydroquinolin-6-yl)amino)nicotinonitrile;
2-chloro-4-((1-(cyclohexylmethyl)-2-oxo-4-((2-(pyrimidin-2-yl)propan-2-yl)amino)-1,2-dihydroquinolin-6-yl)amino)nicotinonitrile;

2-chloro-4-((4-((cyclopropyl(pyrimidin-2-yl)methyl) amino)-1-methyl-2-oxo-1,2-dihydroquinolin-6-yl)amino) nicotinonitrile;
ethyl 7-((1-methyl-2-oxo-4-((1-(pyrimidin-2-yl)ethyl) amino)-1,2-dihydroquinolin-6-yl)amino)pyrazolo[1,5-a] pyrimidine-5-carboxylate;
2-chloro-4-((8-methoxy-1-methyl-2-oxo-4-((2-(pyrimidin-2-yl)propan-2-yl)amino)-1,2-dihydroquinolin-6-yl) amino)nicotinonitrile;
(S)-2-chloro-4-((1-methyl-2-oxo-4-((1-(pyrimidin-2-yl) ethyl)amino)-1,2-dihydroquinolin-6-yl)amino)nicotinonitrile;
4-chloro-6-((1-methyl-2-oxo-4-((1-(pyrimidin-2-yl)ethyl) amino)-1,2-dihydroquinolin-6-yl)amino)pyrimidine-5-carbonitrile;
2-chloro-4-((1-methyl-2-oxo-4-((1-(pyrimidin-2-yl)cyclopropyl)amino)-1,2-dihydroquinolin-6-yl)amino)nicotinonitrile;
2-chloro-4-((1-(cyclohexylmethyl)-2-oxo-4-((1-(pyrimidin-2-yl)ethyl)amino)-1,2-dihydroquinolin-6-yl)amino)nicotinonitrile;
2-chloro-4-[[1-methyl-2-oxo-4-[1-(5-tetrahydropyran-4-ylpyrimidin-2-yl)ethylamino]-6-quinolyl]amino]pyridine-3-carbonitrile;
2-chloro-4-((1-methyl-4-((1-(5-morpholinopyrimidin-2-yl) ethyl)amino)-2-oxo-1,2-dihydroquinolin-6-yl)amino) nicotinonitrile;
(S)-2-chloro-4-((4-((1-cyclopropyl-2-hydroxyethyl)amino)-1-methyl-2-oxo-1,2-dihydroquinolin-6-yl)amino)nicotinonitrile;
2-chloro-4-((1-methyl-2-oxo-4-((2-(pyridin-2-yl)propan-2-yl)amino)-1,2-dihydroquinolin-6-yl)amino)nicotinonitrile;
2-((6-((2-chloro-3-cyanopyridin-4-yl)amino)-1-methyl-2-oxo-1,2-dihydroquinolin-4-yl)amino)-2-methyl-N-((1-methyl-1H-pyrazol-4-yl)methyl)propanamide;
2-chloro-4-((1-methyl-2-oxo-4-((1-(pyridin-2-yl)ethyl) amino)-1,2-dihydroquinolin-6-yl)amino)nicotinonitrile;
(R)-6-((5-chloro-2-methoxypyrimidin-4-yl)amino)-4-((1-cyclopropylethyl)amino)-1-methylquinolin-2(1H)-one;
(S)-6-((5-chloro-2-methoxypyrimidin-4-yl)amino)-4-((1-cyclopropyl-2-hydroxyethyl)amino)-1-methylquinolin-2 (1H)-one;
2-chloro-4-((4-((1-(2-methoxyethoxy)propan-2-yl)amino)-1-methyl-2-oxo-1,2-dihydroquinolin-6-yl)amino)nicotinonitrile;
2-chloro-4-((1-(cyclopropylmethyl)-2-oxo-4-((1-(pyrimidin-2-yl)ethyl)amino)-1,2-dihydroquinolin-6-yl)amino) nicotinonitrile;
2-chloro-4-((1-(cyclobutylmethyl)-2-oxo-4-((1-(pyrimidin-2-yl)ethyl)amino)-1,2-dihydroquinolin-6-yl)amino)nicotinonitrile;
2-chloro-4-((1-(2-hydroxyethyl)-2-oxo-4-((1-(pyrimidin-2-yl)ethyl)amino)-1,2-dihydroquinolin-6-yl)amino)nicotinonitrile;
6-((5-Chloro-2-(4,4-difluoropiperidin-1-yl)pyrimidin-4-yl) amino)-1-methyl-4-((1-(pyrimidin-2-yl)ethyl)amino)quinazolin-2(1H)-one;
(R)-1-(5-chloro-4-((4-((1-cyclopropylethyl)amino)-1-methyl-2-oxo-1,2-dihydroquinolin-6-yl)amino)pyrimidin-2-yl)-N,N-dimethylpiperidine-4-carboxamide;
1-(5-chloro-4-((8-methoxy-1-methyl-2-oxo-4-((2-(pyrimidin-2-yl)propan-2-yl)amino)-1,2-dihydroquinolin-6-yl) amino)pyrimidin-2-yl)-N,N-dimethylpiperidine-4-carboxamide;

1-(5-chloro-4-((1-methyl-2-oxo-4-((1-(pyrimidin-2-yl) ethyl)amino)-1,2-dihydroquinazolin-6-yl)amino)pyrimidin-2-yl)-N,N-dimethylpiperidine-4-carboxamide;
6-((5-chloro-2-((3R,5S)-3,5-dimethylpiperidin-1-yl)pyrimidin-4-yl)amino)-1-methyl-4-((1-(pyrimidin-2-yl)ethyl) amino)quinazolin-2(1H)-one;
6-((5-chloro-2-((2S,6R)-2,6-dimethylmorpholino)pyrimidin-4-yl)amino)-1-methyl-4-((2-(pyrimidin-2-yl)propan-2-yl)amino)quinolin-2(1H)-one;
6-((5-chloro-2-(4,4-difluoropiperidin-1-yl)pyrimidin-4-yl) amino)-1-methyl-4-((2-(pyrimidin-2-yl)propan-2-yl) amino)quinolin-2(1H)-one;
rac-6-((5-chloro-2-((3R,5S)-4,4-difluoro-3,5-dimethylpiperidin-1-yl)pyrimidin-4-yl)amino)-1-methyl-4-((1-(pyrimidin-2-yl)ethyl)amino)quinazolin-2(1H)-one;
6-((5-chloro-2-(4,4-difluoro-3-(hydroxymethyl)piperidin-1-yl)pyrimidin-4-yl)amino)-1-methyl-4-((2-(pyrimidin-2-yl)propan-2-yl)amino)quinazolin-2(1H)-one;
1-methyl-4-((2-(pyrimidin-2-yl)propan-2-yl)amino)-6-((2,3,6-trichloropyridin-4-yl)amino)quinolin-2(1H)-one;
6-((5-chloro-6-methyl-2-(3-(trifluoromethyl)-1H-pyrazol-1-yl)pyrimidin-4-yl)amino)-1-methyl-4-((2-(pyrimidin-2-yl)propan-2-yl)amino)quinolin-2(1H)-one;
6-((5-chloro-2-(3,5-dimethyl-1H-pyrazol-1-yl)pyrimidin-4-yl)amino)-1-methyl-4-((1-(1-methyl-1H-1,2,4-triazol-3-yl)ethyl)amino)quinolin-2(1H)-one;
(R)-6-((5-chloro-2-(3,5-dimethyl-1H-pyrazol-1-yl)pyrimidin-4-yl)amino)-4-((1-cyclopropylethyl)amino)-1-methylquinolin-2(1H)-one;
6-((5-chloro-2-(3-(trifluoromethyl)-1H-pyrazol-1-yl)pyrimidin-4-yl)amino)-1-methyl-4-((2-(pyrimidin-2-yl)propan-2-yl)amino)quinolin-2(1H)-one;
6-((5-chloro-2-(3,5-dimethyl-1H-pyrazol-1-yl)pyrimidin-4-yl)amino)-4-((1-methoxy-2-methylpropan-2-yl)amino)-1-methylquinolin-2(1H)-one;
6-((5-chloro-2-(3,5-dimethyl-1H-pyrazol-1-yl)pyrimidin-4-yl)amino)-1-methyl-4-((1-(pyrimidin-2-yl)ethyl)amino) quinolin-2(1H)-one;
6-((5-Chloro-2-((S)-2-(methoxymethyl)pyrrolidine-1-carbonyl)pyridin-4-yl)amino)-4-(((R)-1-cyclopropylethyl) amino)-1-methylquinolin-2(1H)-one;
6-((5-chloro-2-(2-(2-methoxyethyl)pyrrolidine-1-carbonyl) pyridin-4-yl)amino)-4-(((R)-1-cyclopropylethyl)amino)-1-methylquinolin-2(1H)-one;
(S)-6-((5-chloro-2-methoxypyridin-4-yl)amino)-4-((1-cyclopropyl-2-hydroxyethyl)amino)-1-methylquinolin-2 (1H)-one;
(R)-6-((2-(azetidine-1-carbonyl)-5-chloropyridin-4-yl) amino)-4-((1-cyclopropylethyl)amino)-1-methylquinolin-2(1H)-one;
6-((5-chloro-2-((2S,6R)-2,6-dimethylmorpholino)pyridin-4-yl)amino)-1-methyl-4-((1-(pyrimidin-2-yl)ethyl) amino)quinolin-2(1H)-one;
(R)-6-((5-chloro-2-(4-(2-hydroxyethyl)-1H-pyrazol-1-yl) pyridin-4-yl)amino)-4-((1-cyclopropylethyl)amino)-1-methylquinolin-2(1H)-one;
1-(5-chloro-4-((1-methyl-2-oxo-4-((1-(pyrimidin-2-yl) ethyl)amino)-1,2-dihydroquinolin-6-yl)amino)pyridin-2-yl)-N,N-dimethylpiperidine-4-carboxamide;
6-((5-chloro-2-(4,4-difluoropiperidin-1-yl)pyridin-4-yl) amino)-1-methyl-4-((1-(pyrimidin-2-yl)ethyl)amino)quinolin-2(1H)-one;
6-((5-chloro-2-(4-(2-hydroxyethyl)-1H-pyrazol-1-yl)pyridin-4-yl)amino)-1-methyl-4-((1-(pyrimidin-2-yl)ethyl) amino)quinolin-2(1H)-one;

1-(5-chloro-4-((1-methyl-2-oxo-4-((2-(pyrimidin-2-yl)propan-2-yl)amino)-1,2-dihydroquinolin-6-yl)amino)pyrimidin-2-yl)-N,N-dimethylpiperidine-4-carboxamide;

1-(5-chloro-4-((4-((1-cyanocyclopropyl)amino)-1-methyl-2-oxo-1,2-dihydroquinolin-6-yl)amino)pyrimidin-2-yl)-N,N-dimethylpiperidine-4-carboxamide;

1-(5-chloro-4-methyl-6-((1-methyl-2-oxo-4-((2-(pyrimidin-2-yl)propan-2-yl)amino)-1,2-dihydroquinolin-6-yl)amino)pyrimidin-2-yl)-N,N-dimethylpiperidine-4-carboxamide;

1-(5-chloro-4-((4-((1-methoxy-2-methylpropan-2-yl)amino)-1-methyl-2-oxo-1,2-dihydroquinolin-6-yl)amino)pyrimidin-2-yl)-N,N-dimethylpiperidine-4-carboxamide;

6-((5-chloro-2-((2S,6R)-2,6-dimethylmorpholino)pyrimidin-4-yl)amino)-1-methyl-4-((1-(pyrimidin-2-yl)ethyl)amino)quinolin-2(1H)-one;

6-((5-chloro-2-(4,4-difluoropiperidin-1-yl)pyrimidin-4-yl)amino)-1-methyl-4-((1-(pyrimidin-2-yl)ethyl)amino)-1,8-naphthyridin-2(1H)-one;

1-(5-chloro-4-((1-methyl-2-oxo-4-((1-(pyrimidin-2-yl)ethyl)amino)-1,2-dihydroquinolin-6-yl)amino)pyrimidin-2-yl)-N,N-dimethylpiperidine-4-carboxamide;

6-((5-chloro-2-((2S,6R)-2,6-dimethylmorpholino)pyrimidin-4-yl)amino)-4-(((R)-1-cyclopropylethyl)amino)-1-methylquinolin-2(1H)-one;

2-(1-(5-chloro-4-((1-methyl-2-oxo-4-((1-(pyrimidin-2-yl)ethyl)amino)-1,2-dihydroquinolin-6-yl)amino)pyrimidin-2-yl)piperidin-4-yl)-N,N-dimethylacetamide;

6-((5-chloro-2-((pyridin-3-ylmethyl)amino)pyrimidin-4-yl)amino)-1-methyl-4-((1-(pyrimidin-2-yl)ethyl)amino)quinolin-2(1H)-one;

9-(5-chloro-4-((1-methyl-2-oxo-4-((1-(pyrimidin-2-yl)ethyl)amino)-1,2-dihydroquinolin-6-yl)amino)pyrimidin-2-yl)-2-methyl-2,9-diazaspiro[5.5]undecan-1-one;

6-((5-chloro-2-(7-oxa-2-azaspiro[3.5]nonan-2-yl)pyrimidin-4-yl)amino)-1-methyl-4-((1-(pyrimidin-2-yl)ethyl)amino)quinolin-2(1H)-one;

6-((5-chloro-2-(4,4-difluoropiperidin-1-yl)pyrimidin-4-yl)amino)-1-methyl-4-((1-(pyrimidin-2-yl)ethyl)amino)quinolin-2(1H)-one;

1-(5-chloro-4-((1-methyl-2-oxo-4-((1-(pyrimidin-2-yl)ethyl)amino)-1,2-dihydroquinolin-6-yl)amino)pyrimidin-2-yl)-3-methylazetidine-3-carbonitrile;

6-((5-chloro-2-(2-methyl-2,4,6,7-tetrahydro-5H-pyrazolo[4,3-c]pyridin-5-yl)pyrimidin-4-yl)amino)-1-methyl-4-((1-(pyrimidin-2-yl)ethyl)amino)quinolin-2(1H)-one;

2-methyl-4-((1-methyl-2-oxo-4-((1-(pyrimidin-2-yl)ethyl)amino)-1,2-dihydroquinolin-6-yl)amino)nicotinonitrile;

5-cyano-N,6-dimethyl-4-((1-methyl-2-oxo-4-((1-(pyrimidin-2-yl)ethyl)amino)-1,2-dihydroquinolin-6-yl)amino)picolinamide;

6-chloro-5-cyano-N,N-dimethyl-4-((1-methyl-2-oxo-4-((2-(pyrimidin-2-yl)propan-2-yl)amino)-1,2-dihydroquinolin-6-yl)amino)picolinamide;

6-chloro-5-cyano-N,N-dimethyl-4-((1-methyl-2-oxo-4-((1-(pyrimidin-2-yl)ethyl)amino)-1,2-dihydroquinolin-6-yl)amino)picolinamide;

5-cyano-N-methyl-4-((1-methyl-2-oxo-4-((1-(pyrimidin-2-yl)ethyl)amino)-1,2-dihydroquinolin-6-yl)amino)picolinamide;

2-chloro-4-((4-((1-methoxy-2-methylpropan-2-yl)amino)-1-methyl-2-oxo-1,2-dihydroquinolin-6-yl)amino)nicotinonitrile;

6-((5,6-dichloropyrimidin-4-yl)amino)-1-methyl-4-((1-(pyrimidin-2-yl)ethyl)amino)quinolin-2(1H)-one;

6-chloro-5-cyano-4-((4-((1-methoxy-2-methylbutan-2-yl)amino)-1-methyl-2-oxo-1,2-dihydroquinolin-6-yl)amino)-N-methylpicolinamide;

rac-6-chloro-5-cyano-4-((4-(((1S,2R)-2-methoxycyclopentyl)amino)-1-methyl-2-oxo-1,2-dihydroquinolin-6-yl)amino)-N-methylpicolinamide;

3-chloro-4-((1-methyl-2-oxo-4-((1-(pyrimidin-2-yl)ethyl)amino)-1,2-dihydroquinolin-6-yl)amino)picolinonitrile;

2-chloro-4-((1-methyl-2-oxo-4-((3-(pyrimidin-2-yl)tetrahydrofuran-3-yl)amino)-1,2-dihydroquinolin-6-yl)amino)nicotinonitrile;

2-chloro-4-((1-methyl-2-oxo-4-((1-(5-(pyridin-3-yl)pyrimidin-2-yl)ethyl)amino)-1,2-dihydroquinolin-6-yl)amino)nicotinonitrile;

N-(5-Chloro-4-((1-methyl-2-oxo-4-((1-(pyrimidin-2-yl)ethyl)amino)-1,2-dihydroquinolin-6-yl)amino)pyridin-2-yl)-N-methylacetamide;

rac-2-chloro-4-((4-(((1R,2S)-2-methoxycyclobutyl)amino)-1-methyl-2-oxo-1,2-dihydroquinolin-6-yl)amino)nicotinonitrile;

rac-2-chloro-4-((4-(((1R,2R)-2-methoxycyclobutyl)amino)-1-methyl-2-oxo-1,2-dihydroquinolin-6-yl)amino)nicotinonitrile;

rac-6-chloro-5-cyano-4-((4-(((1R,2R)-2-methoxycyclobutyl)amino)-1-methyl-2-oxo-1,2-dihydroquinolin-6-yl)amino)-N-methylpicolinamide;

rac-6-chloro-5-cyano-4-((4-(((1R,2S)-2-methoxycyclobutyl)amino)-1-methyl-2-oxo-1,2-dihydroquinolin-6-yl)amino)-N-methylpicolinamide;

6-chloro-5-cyano-4-((4-((1-cyanocyclopropyl)amino)-1-methyl-2-oxo-1,2-dihydroquinolin-6-yl)amino)-N-methylpicolinamide;

2-chloro-4-((4-((1-cyanocyclopropyl)amino)-1-methyl-2-oxo-1,2-dihydroquinolin-6-yl)amino)nicotinonitrile;

2-chloro-4-((1-methyl-2-oxo-4-((2-(pyrimidin-2-yl)butan-2-yl)amino)-1,2-dihydroquinolin-6-yl)amino)nicotinonitrile;

(R)-2-chloro-4-((5-((1-cyclopropylethyl)amino)-8-methyl-7-oxo-7,8-dihydro-1,8-naphthyridin-3-yl)amino)nicotinonitrile;

2-chloro-4-((4-((1-(isoquinolin-3-yl)ethyl)amino)-1-methyl-2-oxo-1,2-dihydroquinolin-6-yl)amino)nicotinonitrile;

2-chloro-4-((4-((1-(5-cyclobutylpyrimidin-2-yl)ethyl)amino)-1-methyl-2-oxo-1,2-dihydroquinolin-6-yl)amino)nicotinonitrile;

6-((5-chloro-2-((3R,5S)-4,4-difluoro-3,5-dimethylpiperidin-1-yl)pyrimidin-4-yl)amino)-1-methyl-4-((2-(pyrimidin-2-yl)propan-2-yl)amino)quinazolin-2(1H)-one;

(R)-6-((2-(azetidin-1-yl)-5-chloropyrimidin-4-yl)amino)-4-((1-cyclopropylethyl)amino)-1-methylquinolin-2(1H)-one;

6-((5-chloro-2-(2-(methoxymethyl)azetidin-1-yl)pyrimidin-4-yl)amino)-4-(((R)-1-cyclopropylethyl)amino)-1-methylquinolin-2(1H)-one;

6-((5-chloro-2-(1-methyl-1,4,5,7-tetrahydro-6H-pyrazolo[3,4-c]pyridin-6-yl)pyrimidin-4-yl)amino)-1-methyl-4-((1-(pyrimidin-2-yl)ethyl)amino)quinolin-2(1H)-one;

6-((5-chloro-2-(4,4-difluoro-3-(hydroxymethyl)piperidin-1-yl)pyrimidin-4-yl)amino)-1-methyl-4-((1-(pyrimidin-2-yl)ethyl)amino)quinolin-2(1H)-one;

6-[[5-chloro-2-[(2R,6S)-2,6-dimethylmorpholin-4-yl]pyrimidin-4-yl]amino]-1-methyl-4-(1-pyrimidin-2-ylethylamino)quinazolin-2-one;

6-[[5-chloro-2-[(2R,6S)-2,6-dimethylmorpholin-4-yl]pyrimidin-4-yl]amino]-1-methyl-4-[(1-methyl-1-pyrimidin-2-yl-ethyl)amino]quinazolin-2-one;

6-[[5-chloro-2-[(3R,5S)-3,5-dimethyl-1-piperidyl]pyrimidin-4-yl]amino]-1-methyl-4-[(1-methyl-1-pyrimidin-2-yl-ethyl)amino]quinazolin-2-one;
2-chloro-4-((1-methyl-2-oxo-4-((2-(pyrimidin-2-yl)propan-2-yl)amino)-1,2-dihydroquinolin-6-yl)amino)-6-(1-oxa-6-azaspiro[3.3]heptane-6-carbonyl)nicotinonitrile; or
2-chloro-6-(3-(cyanomethyl)azetidine-1-carbonyl)-4-((1-methyl-2-oxo-4-((2-(pyrimidin-2-yl)propan-2-yl)amino)-1,2-dihydroquinolin-6-yl)amino)nicotinonitrile.

Particular compounds of the present invention include any of the compounds exemplified in the present application, or a pharmaceutically acceptable salt or solvate thereof, and, in particular, any of the following:

2-Chloro-4-[[1-methyl-4-[(1-methyl-1-pyrimidin-2-yl-ethyl)amino]-2-oxo-6-quinolyl]amino]pyridine-3-carbonitrile;
2-chloro-4-[[1-methyl-2-oxo-4-(1-pyrimidin-2-ylethylamino)-6-quinolyl]amino]pyridine-3-carbonitrile;
2-chloro-4-[[1-[2-(2,5-dioxopyrrolidin-1-yl)ethyl]-2-oxo-4-(1-pyrimidin-2-ylethylamino)-6-quinolyl]amino]pyridine-3-carbonitrile;
2-chloro-4-[[2-oxo-4-(1-pyrimidin-2-ylethylamino)-1-(tetrahydropyran-4-ylmethyl)-6-quinolyl]amino]pyridine-3-carbonitrile;
2-chloro-4-[[1-methyl-2-oxo-4-[1-(1H-1,2,4-triazol-3-yl)ethylamino]-6-quinolyl]amino]pyridine-3-carbonitrile;
trans-2-chloro-4-[[4-[(3-hydroxycyclobutyl)amino]-1-methyl-2-oxo-6-quinolyl]amino]pyridine-3-carbonitrile;
2-chloro-4-[[1-methyl-2-oxo-4-[[(3S)-tetrahydrofuran-3-yl]amino]-6-quinolyl]amino]pyridine-3-carbonitrile;
2-chloro-4-[[1-methyl-4-[1-(5-methyl-1,2,4-oxadiazol-3-yl)ethylamino]-2-oxo-6-quinolyl]amino]pyridine-3-carbonitrile;
2-chloro-4-[[1-methyl-4-[1-(4-methylpyrimidin-2-yl)ethylamino]-2-oxo-6-quinolyl]amino]pyridine-3-carbonitrile;
2-chloro-4-[[1-methyl-2-oxo-4-(1-pyrazin-2-ylethylamino)-6-quinolyl]amino]pyridine-3-carbonitrile;
2-chloro-4-[[4-[(3-hydroxy-1-methyl-propyl)amino]-1-methyl-2-oxo-quinazolin-6-yl]amino]pyridine-3-carbonitrile;
2-chloro-4-[[4-[(2-hydroxy-1-methyl-ethyl)amino]-1-methyl-2-oxo-quinazolin-6-yl]amino]pyridine-3-carbonitrile;
2-chloro-4-[[1-methyl-4-[1-(5-methylisoxazol-3-yl)ethylamino]-2-oxo-6-quinolyl]amino]pyridine-3-carbonitrile;
2-chloro-4-[[4-[(2-hydroxy-1-methyl-ethyl)amino]-2-oxo-1H-quinazolin-6-yl]amino]pyridine-3-carbonitrile;
2-chloro-4-[[4-(ethylamino)-1-[2-(2-methoxyethoxy)ethyl]-2-oxo-6-quinolyl]amino]pyridine-3-carbonitrile;
2-chloro-4-[[1-methyl-4-(1-oxazol-2-ylethylamino)-2-oxo-6-quinolyl]amino]pyridine-3-carbonitrile;
2-chloro-4-[[1-methyl-2-oxo-4-(1-pyrimidin-4-ylethylamino)-6-quinolyl]amino]pyridine-3-carbonitrile;
2-chloro-4-[[1-[2-(2,5-dioxopyrrolidin-1-yl)ethyl]-4-(ethylamino)-2-oxo-6-quinolyl]amino]pyridine-3-carbonitrile;
2-chloro-4-[[1-methyl-2-oxo-4-(1-thiazol-2-ylethylamino)-6-quinolyl]amino]pyridine-3-carbonitrile;
2-chloro-4-[[1-methyl-2-oxo-4-[1-(1H-pyrazol-3-yl)ethylamino]-6-quinolyl]amino]pyridine-3-carbonitrile;
6-chloro-5-cyano-N-methyl-4-[[1-methyl-4-[(1-methyl-1-pyrimidin-2-yl-ethyl)amino]-2-oxo-6-quinolyl]amino]pyridine-2-carboxamide;
6-chloro-5-cyano-N-methyl-4-[[1-methyl-2-oxo-4-(1-pyrimidin-2-ylethylamino)-6-quinolyl]amino]pyridine-2-carboxamide;
2-chloro-6-methyl-4-[[1-methyl-2-oxo-4-(1-pyrimidin-2-ylethylamino)-6-quinolyl]amino]pyridine-3-carbonitrile;
2-chloro-4-[[8-methyl-5-[(1-methyl-1-pyrimidin-2-yl-ethyl)amino]-7-oxo-1,8-naphthyridin-3-yl]amino]pyridine-3-carbonitrile;
6-Chloro-5-cyano-4-[[4-(1-cyclopropylethylamino)-1-methyl-2-oxo-6-quinolyl]amino]pyridine-2-carboxylic acid;
6-chloro-5-cyano-4-[[4-(cyclopropylamino)-1-methyl-2-oxo-6-quinolyl]amino]pyridine-2-carboxylic acid;
6-chloro-5-cyano-4-[[1-methyl-4-[(1-methylcyclopropyl)amino]-2-oxo-6-quinolyl]amino]pyridine-2-carboxylic acid;
6-chloro-5-cyano-4-[[1-methyl-4-[(1-methylcyclopentyl)amino]-2-oxo-6-quinolyl]amino]pyridine-2-carboxylic acid;
(R)-2-((6-((2-Chloro-3-cyanopyridin-4-yl)amino)-1-methyl-2-oxo-1,2-dihydroquinolin-4-yl)amino)-N-((1-methyl-1H-pyrazol-4-yl)methyl)propanamide;
(R)-2-((6-((2-chloro-3-cyanopyridin-4-yl)amino)-1-methyl-2-oxo-1,2-dihydroquinolin-4-yl)amino)-N-(2-hydroxyethyl)propanamide;
2-Chloro-4-((1-methyl-4-((1-(3-methyl-1H-1,2,4-triazol-5-yl)ethyl)amino)-2-oxo-1,2-dihydroquinolin-6-yl)amino)nicotinonitrile;
(R)-2-((6-((2-Chloro-3-cyanopyridin-4-yl)amino)-1-methyl-2-oxo-1,2-dihydroquinolin-4-yl)amino)-N-cyclopentylpropanamide;
(R)-2-((6-((2-chloro-3-cyanopyridin-4-yl)amino)-1-methyl-2-oxo-1,2-dihydroquinolin-4-yl)amino)-N-(2-methoxyethyl)propanamide;
(R)—N-(But-3-yn-1-yl)-2-((6-((2-chloro-3-cyanopyridin-4-yl)amino)-1-methyl-2-oxo-1,2-dihydroquinolin-4-yl)amino)propanamide;
(S)-2-Chloro-4-((4-((1-hydroxypropan-2-yl)amino)-1-methyl-2-oxo-1,2-dihydroquinolin-6-yl)amino)nicotinonitrile;
2-((6-((2-Chloro-3-cyanopyridin-4-yl)amino)-1-methyl-2-oxo-1,2-dihydroquinolin-4-yl)amino)-N-ethyl-2-methylpropanamide;
(R)-2-((6-((2-Chloro-3-cyanopyridin-4-yl)amino)-1-methyl-2-oxo-1,2-dihydroquinolin-4-yl)amino)-N-(4-methoxycyclohexyl)propanamide;
(R)-2-chloro-4-((4-((1-hydroxypropan-2-yl)amino)-1-methyl-2-oxo-1,2-dihydroquinolin-6-yl)amino)nicotinonitrile;
rac-2-((6-((2-Chloro-3-cyanopyridin-4-yl)amino)-1-methyl-2-oxo-1,2-dihydroquinolin-4-yl)amino)-N-ethylpropanamide;
2-Chloro-4-((1-methyl-4-((1-(5-methyl-1,3,4-oxadiazol-2-yl)ethyl)amino)-2-oxo-1,2-dihydroquinolin-6-yl)amino)nicotinonitrile;
(R)-2-((6-((2-Chloro-3-cyanopyridin-4-yl)amino)-1-methyl-2-oxo-1,2-dihydroquinolin-4-yl)amino)-N-(2-(1-methyl-1H-pyrazol-4-yl)ethyl)propanamide;
(S)-2-Chloro-4-((4-((4-hydroxybutan-2-yl)amino)-1-methyl-2-oxo-1,2-dihydroquinolin-6-yl)amino)nicotinonitrile;
(R)-2-((6-((2-chloro-3-cyanopyridin-4-yl)amino)-1-methyl-2-oxo-1,2-dihydroquinolin-4-yl)amino)-N-methylpropanamide;
(R)-2-((6-((2-chloro-3-cyanopyridin-4-yl)amino)-2-oxo-1,2-dihydroquinolin-4-yl)amino)-N-methylpropanamide;
6-Chloro-5-cyano-4-[[4-(ethylamino)-1-methyl-2-oxo-6-quinolyl]amino]pyridine-2-carboxylic acid;
6-Chloro-5-cyano-4-[[4-(ethylamino)-1-methyl-2-oxo-6-quinolyl]amino]-N-methyl-pyridine-2-carboxamide;
6-[(2,3-Dichloro-4-pyridyl)amino]-1-methyl-4-(1-pyrimidin-2-ylethylamino)quinolin-2-one;

6-((2,3-dichloropyridin-4-yl)amino)-1-methyl-4-((2-(pyrimidin-2-yl)propan-2-yl)amino)quinolin-2(1H)-one;
6-((2,3-dichloropyridin-4-yl)amino)-1-methyl-4-((1-(pyrimidin-2-yl)ethyl)amino)quinazolin-2(1H)-one;
(R)-4-((1-cyclopropylethyl)amino)-6-((2,3-dichloropyridin-4-yl)amino)-1-methylquinazolin-2(1H)-one;
6-((2,3-dichloropyridin-4-yl)amino)-1-methyl-4-((1-(pyrimidin-2-yl)ethyl)amino)-1,8-naphthyridin-2(1H)-one;
(R)-4-((1-cyclopropylethyl)amino)-6-((2,3-dichloropyridin-4-yl)amino)-1-methyl-1,8-naphthyridin-2(1H)-one;
2-Chloro-4-((4-((2-(5-((2R,6S)-2,6-dimethylmorpholino)pyrimidin-2-yl)propan-2-yl)amino)-1-methyl-2-oxo-1,2-dihydroquinolin-6-yl)amino)nicotinonitrile;
6-chloro-5-cyano-4-((4-((1-cyclopropylethyl)amino)-1-methyl-2-oxo-1,2-dihydroquinolin-6-yl)amino)-N-methylpicolinamide;
4-((4-(tert-butylamino)-1-methyl-2-oxo-1,2-dihydroquinolin-6-yl)amino)-6-chloro-5-cyano-N-methylpicolinamide;
6-chloro-5-cyano-4-[[4-[(2-methoxy-1,1-dimethyl-ethyl)amino]-1-methyl-2-oxo-6-quinolyl]amino]-N-methylpyridine-2-carboxamide;
6-(Azetidine-1-carbonyl)-2-chloro-4-((1-methyl-2-oxo-4-((2-(pyrimidin-2-yl)propan-2-yl)amino)-1,2-dihydroquinolin-6-yl)amino)nicotinonitrile;
6-(azetidine-1-carbonyl)-2-chloro-4-((4-((2-(5-cyclopropylpyrimidin-2-yl)propan-2-yl)amino)-1-methyl-2-oxo-1,2-dihydroquinolin-6-yl)amino)nicotinonitrile;
(R)-6-(azetidine-1-carbonyl)-2-chloro-4-((4-((1-cyclopropylethyl)amino)-1-methyl-2-oxo-1,2-dihydroquinolin-6-yl)amino)nicotinonitrile;
2-chloro-4-((1-methyl-2-oxo-4-((2-(pyrimidin-2-yl)propan-2-yl)amino)-1,2-dihydroquinolin-6-yl)amino)-6-(3-(trifluoromethyl)azetidine-1-carbonyl)nicotinonitrile;
6-chloro-5-cyano-4-((4-((2-(5-cyclopropylpyrimidin-2-yl)propan-2-yl)amino)-1-methyl-2-oxo-1,2-dihydroquinolin-6-yl)amino)picolinic acid;
(R)-6-chloro-5-cyano-4-((4-((1-cyclopropylethyl)amino)-1-methyl-2-oxo-1,2-dihydroquinolin-6-yl)amino)picolinic acid;
6-chloro-5-cyano-4-((4-((2-fluoroethyl)amino)-1-methyl-2-oxo-1,2-dihydroquinolin-6-yl)amino)picolinic acid;
(S)-6-chloro-5-cyano-4-((4-((1-cyclopropylethyl)amino)-1-methyl-2-oxo-1,2-dihydroquinolin-6-yl)amino)picolinic acid;
6-chloro-5-cyano-4-((1-methyl-2-oxo-4-((2-(pyrimidin-2-yl)propan-2-yl)amino)-1,2-dihydroquinolin-6-yl)amino)picolinic acid;
6-chloro-5-cyano-4-((4-((1-cyanocyclopropyl)amino)-1-methyl-2-oxo-1,2-dihydroquinolin-6-yl)amino)picolinic acid;
6-chloro-5-cyano-4-((4-((1-ethynylcyclopropyl)amino)-1-methyl-2-oxo-1,2-dihydroquinolin-6-yl)amino)picolinic acid;
rac-6-chloro-5-cyano-4-((4-(((1R,2R)-2-ethylcyclopropyl)amino)-1-methyl-2-oxo-1,2-dihydroquinolin-6-yl)amino)picolinic acid;
6-chloro-5-cyano-4-((4-((2,2-dimethylcyclopropyl)amino)-1-methyl-2-oxo-1,2-dihydroquinolin-6-yl)amino)picolinic acid;
6-chloro-5-cyano-4-((4-((1-(hydroxymethyl)cyclopropyl)amino)-1-methyl-2-oxo-1,2-dihydroquinolin-6-yl)amino)picolinic acid;
6-chloro-5-cyano-4-((4-((cyclopropylmethyl)amino)-1-methyl-2-oxo-1,2-dihydroquinolin-6-yl)amino)picolinic acid;
6-chloro-5-cyano-4-((4-((1-methoxy-2-methylpropan-2-yl)amino)-1-methyl-2-oxo-1,2-dihydroquinolin-6-yl)amino)picolinic acid;
4-((4-(tert-butylamino)-1-methyl-2-oxo-1,2-dihydroquinolin-6-yl)amino)-6-chloro-5-cyanopicolinic acid;
6-chloro-5-cyano-4-((1-methyl-2-oxo-4-(tert-pentylamino)-1,2-dihydroquinolin-6-yl)amino)picolinic acid;
2-chloro-4-((4-((2-(5-cyclopropylpyrimidin-2-yl)propan-2-yl)amino)-1-methyl-2-oxo-1,2-dihydroquinolin-6-yl)amino)nicotinonitrile;
2-chloro-4-((4-((1-(5-((2S,6R)-2,6-dimethylmorpholino)pyrimidin-2-yl)ethyl)amino)-1-methyl-2-oxo-1,2-dihydroquinolin-6-yl)amino)nicotinonitrile;
2-chloro-4-((1-methyl-4-((1-(5-(1-methyl-1H-pyrazol-4-yl)pyrimidin-2-yl)ethyl)amino)-2-oxo-1,2-dihydroquinolin-6-yl)amino)nicotinonitrile;
2-chloro-4-((1-methyl-2-oxo-4-((1-(5-(2-(trifluoromethyl)morpholino)pyrimidin-2-yl)ethyl)amino)-1,2-dihydroquinolin-6-yl)amino)nicotinonitrile;
2-chloro-4-((4-((1-(5-cyclopropylpyrimidin-2-yl)ethyl)amino)-1-methyl-2-oxo-1,2-dihydroquinolin-6-yl)amino)nicotinonitrile;
2-chloro-4-((1-methyl-4-((1-(5-methylpyrimidin-2-yl)ethyl)amino)-2-oxo-1,2-dihydroquinolin-6-yl)amino)nicotinonitrile;
(R)-2-chloro-4-((1-methyl-2-oxo-4-((1-(pyrimidin-2-yl)ethyl)amino)-1,2-dihydroquinolin-6-yl)amino)nicotinonitrile;
2-chloro-4-((1-methyl-2-oxo-4-((1-(pyrimidin-2-yl)ethyl)amino)-1,2-dihydroquinazolin-6-yl)amino)nicotinonitrile;
(R)-6-chloro-5-cyano-4-((4-((1-cyclopropylethyl)amino)-1-methyl-2-oxo-1,2-dihydroquinolin-6-yl)amino)-N-methylpicolinamide;
4-((4-((1-(5-bromopyrimidin-2-yl)ethyl)amino)-1-methyl-2-oxo-1,2-dihydroquinolin-6-yl)amino)-2-chloronicotinonitrile;
2-chloro-4-((4-((1-(5-((3R,5S)-3,5-dimethylpiperidin-1-yl)pyrimidin-2-yl)ethyl)amino)-1-methyl-2-oxo-1,2-dihydroquinolin-6-yl)amino)nicotinonitrile;
2-chloro-4-((1-methyl-4-((1-(1-methyl-1H-1,2,4-triazol-3-yl)ethyl)amino)-2-oxo-1,2-dihydroquinolin-6-yl)amino)nicotinonitrile;
(R)-2-chloro-4-((4-((1-cyclopropylethyl)amino)-1-methyl-2-oxo-1,2-dihydroquinazolin-6-yl)amino)nicotinonitrile;
(R)-2-chloro-4-((4-((1-cyclopropylethyl)amino)-1-methyl-2-oxo-1,2-dihydroquinolin-6-yl)amino)nicotinonitrile;
2-chloro-4-((1-(cyclohexylmethyl)-2-oxo-4-((2-(pyrimidin-2-yl)propan-2-yl)amino)-1,2-dihydroquinolin-6-yl)amino)nicotinonitrile;
2-chloro-4-((4-((cyclopropyl(pyrimidin-2-yl)methyl)amino)-1-methyl-2-oxo-1,2-dihydroquinolin-6-yl)amino)nicotinonitrile;
ethyl 7-((1-methyl-2-oxo-4-((1-(pyrimidin-2-yl)ethyl)amino)-1,2-dihydroquinolin-6-yl)amino)pyrazolo[1,5-a]pyrimidine-5-carboxylate;
2-chloro-4-((8-methoxy-1-methyl-2-oxo-4-((2-(pyrimidin-2-yl)propan-2-yl)amino)-1,2-dihydroquinolin-6-yl)amino)nicotinonitrile;
(S)-2-chloro-4-((1-methyl-2-oxo-4-((1-(pyrimidin-2-yl)ethyl)amino)-1,2-dihydroquinolin-6-yl)amino)nicotinonitrile;
4-chloro-6-((1-methyl-2-oxo-4-((1-(pyrimidin-2-yl)ethyl)amino)-1,2-dihydroquinolin-6-yl)amino)pyrimidine-5-carbonitrile;

2-chloro-4-((1-methyl-2-oxo-4-((1-(pyrimidin-2-yl)cyclopropyl)amino)-1,2-dihydroquinolin-6-yl)amino)nicotinonitrile;
2-chloro-4-((1-(cyclohexylmethyl)-2-oxo-4-((1-(pyrimidin-2-yl)ethyl)amino)-1,2-dihydroquinolin-6-yl)amino)nicotinonitrile;
2-chloro-4-[[1-methyl-2-oxo-4-[1-(5-tetrahydropyran-4-yl)pyrimidin-2-yl)ethylamino]-6-quinolyl]amino]pyridine-3-carbonitrile;
2-chloro-4-((1-methyl-4-((1-(5-morpholinopyrimidin-2-yl)ethyl)amino)-2-oxo-1,2-dihydroquinolin-6-yl)amino)nicotinonitrile;
(S)-2-chloro-4-((4-((1-cyclopropyl-2-hydroxyethyl)amino)-1-methyl-2-oxo-1,2-dihydroquinolin-6-yl)amino)nicotinonitrile;
2-chloro-4-((1-methyl-2-oxo-4-((2-(pyridin-2-yl)propan-2-yl)amino)-1,2-dihydroquinolin-6-yl)amino)nicotinonitrile;
2-((6-((2-chloro-3-cyanopyridin-4-yl)amino)-1-methyl-2-oxo-1,2-dihydroquinolin-4-yl)amino)-2-methyl-N-((1-methyl-1H-pyrazol-4-yl)methyl)propanamide;
2-chloro-4-((1-methyl-2-oxo-4-((1-(pyridin-2-yl)ethyl)amino)-1,2-dihydroquinolin-6-yl)amino)nicotinonitrile;
(R)-6-((5-chloro-2-methoxypyrimidin-4-yl)amino)-4-((1-cyclopropylethyl)amino)-1-methylquinolin-2(1H)-one;
(S)-6-((5-chloro-2-methoxypyrimidin-4-yl)amino)-4-((1-cyclopropyl-2-hydroxyethyl)amino)-1-methylquinolin-2(1H)-one;
2-chloro-4-((4-((1-(2-methoxyethoxy)propan-2-yl)amino)-1-methyl-2-oxo-1,2-dihydroquinolin-6-yl)amino)nicotinonitrile;
6-((5-Chloro-2-(4,4-difluoropiperidin-1-yl)pyrimidin-4-yl)amino)-1-methyl-4-((1-(pyrimidin-2-yl)ethyl)amino)quinazolin-2(1H)-one;
(R)-1-(5-chloro-4-((4-((1-cyclopropylethyl)amino)-1-methyl-2-oxo-1,2-dihydroquinolin-6-yl)amino)pyrimidin-2-yl)-N,N-dimethylpiperidine-4-carboxamide;
1-(5-chloro-4-((8-methoxy-1-methyl-2-oxo-4-((2-(pyrimidin-2-yl)propan-2-yl)amino)-1,2-dihydroquinolin-6-yl)amino)pyrimidin-2-yl)-N,N-dimethylpiperidine-4-carboxamide;
1-(5-chloro-4-((1-methyl-2-oxo-4-((1-(pyrimidin-2-yl)ethyl)amino)-1,2-dihydroquinazolin-6-yl)amino)pyrimidin-2-yl)-N,N-dimethylpiperidine-4-carboxamide;
6-((5-chloro-2-((3R,5S)-3,5-dimethylpiperidin-1-yl)pyrimidin-4-yl)amino)-1-methyl-4-((1-(pyrimidin-2-yl)ethyl)amino)quinazolin-2(1H)-one;
6-((5-chloro-2-((2S,6R)-2,6-dimethylmorpholino)pyrimidin-4-yl)amino)-1-methyl-4-((2-(pyrimidin-2-yl)propan-2-yl)amino)quinolin-2(1H)-one;
6-((5-chloro-2-(4,4-difluoropiperidin-1-yl)pyrimidin-4-yl)amino)-1-methyl-4-((2-(pyrimidin-2-yl)propan-2-yl)amino)quinolin-2(1H)-one;
rac-6-((5-chloro-2-((3R,5S)-4,4-difluoro-3,5-dimethylpiperidin-1-yl)pyrimidin-4-yl)amino)-1-methyl-4-((1-(pyrimidin-2-yl)ethyl)amino)quinazolin-2(1H)-one;
1-methyl-4-((2-(pyrimidin-2-yl)propan-2-yl)amino)-6-((2,3,6-trichloropyridin-4-yl)amino)quinolin-2(1H)-one;
6-((5-chloro-6-methyl-2-(3-(trifluoromethyl)-1H-pyrazol-1-yl)pyrimidin-4-yl)amino)-1-methyl-4-((2-(pyrimidin-2-yl)propan-2-yl)amino)quinolin-2(1H)-one;
6-((5-chloro-2-(3,5-dimethyl-1H-pyrazol-1-yl)pyrimidin-4-yl)amino)-1-methyl-4-((1-(1-methyl-1H-1,2,4-triazol-3-yl)ethyl)amino)quinolin-2(1H)-one;
(R)-6-((5-chloro-2-(3,5-dimethyl-1H-pyrazol-1-yl)pyrimidin-4-yl)amino)-4-((1-cyclopropylethyl)amino)-1-methylquinolin-2(1H)-one;
6-((5-chloro-2-(3-(trifluoromethyl)-1H-pyrazol-1-yl)pyrimidin-4-yl)amino)-1-methyl-4-((2-(pyrimidin-2-yl)propan-2-yl)amino)quinolin-2(1H)-one;
6-((5-chloro-2-(3,5-dimethyl-1H-pyrazol-1-yl)pyrimidin-4-yl)amino)-4-((1-methoxy-2-methylpropan-2-yl)amino)-1-methylquinolin-2(1H)-one;
6-((5-chloro-2-(3,5-dimethyl-1H-pyrazol-1-yl)pyrimidin-4-yl)amino)-1-methyl-4-((1-(pyrimidin-2-yl)ethyl)amino)quinolin-2(1H)-one;
6-((5-Chloro-2-((S)-2-(methoxymethyl)pyrrolidine-1-carbonyl)pyridin-4-yl)amino)-4-(((R)-1-cyclopropylethyl)amino)-1-methylquinolin-2(1H)-one;
6-((5-chloro-2-(2-(2-methoxyethyl)pyrrolidine-1-carbonyl)pyridin-4-yl)amino)-4-(((R)-1-cyclopropylethyl)amino)-1-methylquinolin-2(1H)-one;
(S)-6-((5-chloro-2-methoxypyridin-4-yl)amino)-4-((1-cyclopropyl-2-hydroxyethyl)amino)-1-methylquinolin-2(1H)-one;
1-(5-chloro-4-((1-methyl-2-oxo-4-((2-(pyrimidin-2-yl)propan-2-yl)amino)-1,2-dihydroquinolin-6-yl)amino)pyrimidin-2-yl)-N,N-dimethylpiperidine-4-carboxamide;
1-(5-chloro-4-((4-((1-cyanocyclopropyl)amino)-1-methyl-2-oxo-1,2-dihydroquinolin-6-yl)amino)pyrimidin-2-yl)-N,N-dimethylpiperidine-4-carboxamide;
1-(5-chloro-4-methyl-6-((1-methyl-2-oxo-4-((2-(pyrimidin-2-yl)propan-2-yl)amino)-1,2-dihydroquinolin-6-yl)amino)pyrimidin-2-yl)-N,N-dimethylpiperidine-4-carboxamide;
1-(5-chloro-4-((4-((1-methoxy-2-methylpropan-2-yl)amino)-1-methyl-2-oxo-1,2-dihydroquinolin-6-yl)amino)pyrimidin-2-yl)-N,N-dimethylpiperidine-4-carboxamide;
6-((5-chloro-2-((2S,6R)-2,6-dimethylmorpholino)pyrimidin-4-yl)amino)-1-methyl-4-((1-(pyrimidin-2-yl)ethyl)amino)quinolin-2(1H)-one;
6-((5-chloro-2-(4,4-difluoropiperidin-1-yl)pyrimidin-4-yl)amino)-1-methyl-4-((1-(pyrimidin-2-yl)ethyl)amino)-1,8-naphthyridin-2(1H)-one;
1-(5-chloro-4-((1-methyl-2-oxo-4-((1-(pyrimidin-2-yl)ethyl)amino)-1,2-dihydroquinolin-6-yl)amino)pyrimidin-2-yl)-N,N-dimethylpiperidine-4-carboxamide;
6-((5-chloro-2-((2S,6R)-2,6-dimethylmorpholino)pyrimidin-4-yl)amino)-4-(((R)-1-cyclopropylethyl)amino)-1-methylquinolin-2(1H)-one;
2-(1-(5-chloro-4-((1-methyl-2-oxo-4-((1-(pyrimidin-2-yl)ethyl)amino)-1,2-dihydroquinolin-6-yl)amino)pyrimidin-2-yl)piperidin-4-yl)-N,N-dimethylacetamide;
6-((5-chloro-2-((pyridin-3-ylmethyl)amino)pyrimidin-4-yl)amino)-1-methyl-4-((1-(pyrimidin-2-yl)ethyl)amino)quinolin-2(1H)-one;
9-(5-chloro-4-((1-methyl-2-oxo-4-((1-(pyrimidin-2-yl)ethyl)amino)-1,2-dihydroquinolin-6-yl)amino)pyrimidin-2-yl)-2-methyl-2,9-diazaspiro[5.5]undecan-1-one;
6-((5-chloro-2-(7-oxa-2-azaspiro[3.5]nonan-2-yl)pyrimidin-4-yl)amino)-1-methyl-4-((1-(pyrimidin-2-yl)ethyl)amino)quinolin-2(1H)-one;
6-((5-chloro-2-(4,4-difluoropiperidin-1-yl)pyrimidin-4-yl)amino)-1-methyl-4-((1-(pyrimidin-2-yl)ethyl)amino)quinolin-2(1H)-one;
1-(5-chloro-4-((1-methyl-2-oxo-4-((1-(pyrimidin-2-yl)ethyl)amino)-1,2-dihydroquinolin-6-yl)amino)pyrimidin-2-yl)-3-methylazetidine-3-carbonitrile;
6-((5-chloro-2-(2-methyl-2,4,6,7-tetrahydro-5H-pyrazolo[4,3-c]pyridin-5-yl)pyrimidin-4-yl)amino)-1-methyl-4-((1-(pyrimidin-2-yl)ethyl)amino)quinolin-2(1H)-one;
2-methyl-4-((1-methyl-2-oxo-4-((1-(pyrimidin-2-yl)ethyl)amino)-1,2-dihydroquinolin-6-yl)amino)nicotinonitrile;

5-cyano-N,6-dimethyl-4-((1-methyl-2-oxo-4-((1-(pyrimidin-2-yl)ethyl)amino)-1,2-dihydroquinolin-6-yl)amino)picolinamide;

6-chloro-5-cyano-N,N-dimethyl-4-((1-methyl-2-oxo-4-((2-(pyrimidin-2-yl)propan-2-yl)amino)-1,2-dihydroquinolin-6-yl)amino)picolinamide;

6-chloro-5-cyano-N,N-dimethyl-4-((1-methyl-2-oxo-4-((1-(pyrimidin-2-yl)ethyl)amino)-1,2-dihydroquinolin-6-yl)amino)picolinamide;

5-cyano-N-methyl-4-((1-methyl-2-oxo-4-((1-(pyrimidin-2-yl)ethyl)amino)-1,2-dihydroquinolin-6-yl)amino)picolinamide;

2-chloro-4-((4-((1-methoxy-2-methylpropan-2-yl)amino)-1-methyl-2-oxo-1,2-dihydroquinolin-6-yl)amino)nicotinonitrile;

6-((5,6-dichloropyrimidin-4-yl)amino)-1-methyl-4-((1-(pyrimidin-2-yl)ethyl)amino)quinolin-2(1H)-one;

6-chloro-5-cyano-4-((4-((1-methoxy-2-methylbutan-2-yl)amino)-1-methyl-2-oxo-1,2-dihydroquinolin-6-yl)amino)-N-methylpicolinamide;

rac-6-chloro-5-cyano-4-((4-(((1S,2R)-2-methoxycyclopentyl)amino)-1-methyl-2-oxo-1,2-dihydroquinolin-6-yl)amino)-N-methylpicolinamide;

3-chloro-4-((1-methyl-2-oxo-4-((1-(pyrimidin-2-yl)ethyl)amino)-1,2-dihydroquinolin-6-yl)amino)picolinonitrile;

2-chloro-4-((1-methyl-2-oxo-4-((1-(5-(pyridin-3-yl)pyrimidin-2-yl)ethyl)amino)-1,2-dihydroquinolin-6-yl)amino)nicotinonitrile;

N-(5-Chloro-4-((1-methyl-2-oxo-4-((1-(pyrimidin-2-yl)ethyl)amino)-1,2-dihydroquinolin-6-yl)amino)pyridin-2-yl)-N-methylacetamide;

rac-2-chloro-4-((4-(((1R,2S)-2-methoxycyclobutyl)amino)-1-methyl-2-oxo-1,2-dihydroquinolin-6-yl)amino)nicotinonitrile;

rac-2-chloro-4-((4-(((1R,2R)-2-methoxycyclobutyl)amino)-1-methyl-2-oxo-1,2-dihydroquinolin-6-yl)amino)nicotinonitrile;

rac-6-chloro-5-cyano-4-((4-(((1R,2R)-2-methoxycyclobutyl)amino)-1-methyl-2-oxo-1,2-dihydroquinolin-6-yl)amino)-N-methylpicolinamide;

rac-6-chloro-5-cyano-4-((4-(((1R,2S)-2-methoxycyclobutyl)amino)-1-methyl-2-oxo-1,2-dihydroquinolin-6-yl)amino)-N-methylpicolinamide;

6-chloro-5-cyano-4-((4-((1-cyanocyclopropyl)amino)-1-methyl-2-oxo-1,2-dihydroquinolin-6-yl)amino)-N-methylpicolinamide;

2-chloro-4-((4-((1-cyanocyclopropyl)amino)-1-methyl-2-oxo-1,2-dihydroquinolin-6-yl)amino)nicotinonitrile;

2-chloro-4-((1-methyl-2-oxo-4-((2-(pyrimidin-2-yl)butan-2-yl)amino)-1,2-dihydroquinolin-6-yl)amino)nicotinonitrile;

(R)-2-chloro-4-((5-((1-cyclopropylethyl)amino)-8-methyl-7-oxo-7,8-dihydro-1,8-naphthyridin-3-yl)amino)nicotinonitrile; or 6-((5-chloro-2-((3R,5S)-4,4-difluoro-3,5-dimethylpiperidin-1-yl)pyrimidin-4-yl)amino)-1-methyl-4-((2-(pyrimidin-2-yl)propan-2-yl)amino)quinazolin-2(1H)-one.

Particular compounds of the present invention include any of the compounds exemplified in the present application, or a pharmaceutically acceptable salt or solvate thereof, and, in particular, any of the following:

2-chloro-4-[[1-methyl-4-[(1-methyl-1-pyrimidin-2-yl-ethyl)amino]-2-oxo-6-quinolyl]amino]pyridine-3-carbonitrile;

2-chloro-4-[[1-methyl-2-oxo-4-(1-pyrimidin-2-ylethylamino)-6-quinolyl]amino]pyridine-3-carbonitrile;

2-chloro-4-[[1-[2-(2,5-dioxopyrrolidin-1-yl)ethyl]-2-oxo-4-(1-pyrimidin-2-ylethylamino)-6-quinolyl]amino]pyridine-3-carbonitrile;

2-chloro-4-[[2-oxo-4-(1-pyrimidin-2-ylethylamino)-1-(tetrahydropyran-4-ylmethyl)-6-quinolyl]amino]pyridine-3-carbonitrile;

2-chloro-4-[[1-methyl-2-oxo-4-[1-(1H-1,2,4-triazol-3-yl)ethylamino]-6-quinolyl]amino]pyridine-3-carbonitrile;

trans-2-chloro-4-[[4-[(3-hydroxycyclobutyl)amino]-1-methyl-2-oxo-6-quinolyl]amino]pyridine-3-carbonitrile;

2-chloro-4-[[1-methyl-2-oxo-4-[[(3S)-tetrahydrofuran-3-yl]amino]-6-quinolyl]amino]pyridine-3-carbonitrile;

2-chloro-4-[[1-methyl-4-[1-(5-methyl-1,2,4-oxadiazol-3-yl)ethylamino]-2-oxo-6-quinolyl]amino]pyridine-3-carbonitrile;

2-chloro-4-[[1-methyl-4-[1-(4-methylpyrimidin-2-yl)ethylamino]-2-oxo-6-quinolyl]amino]pyridine-3-carbonitrile;

2-chloro-4-[[1-methyl-2-oxo-4-(1-pyrazin-2-ylethylamino)-6-quinolyl]amino]pyridine-3-carbonitrile;

2-chloro-4-[[4-[(3-hydroxy-1-methyl-propyl)amino]-1-methyl-2-oxo-quinazolin-6-yl]amino]pyridine-3-carbonitrile;

2-chloro-4-[[4-[(2-hydroxy-1-methyl-ethyl)amino]-1-methyl-2-oxo-quinazolin-6-yl]amino]pyridine-3-carbonitrile;

2-chloro-4-[[1-methyl-4-[1-(5-methylisoxazol-3-yl)ethylamino]-2-oxo-6-quinolyl]amino]pyridine-3-carbonitrile;

2-chloro-4-[[4-[(2-hydroxy-1-methyl-ethyl)amino]-2-oxo-1H-quinazolin-6-yl]amino]pyridine-3-carbonitrile;

2-chloro-4-[[4-(ethylamino)-1-[2-(2-methoxyethoxy)ethyl]-2-oxo-6-quinolyl]amino]pyridine-3-carbonitrile;

2-chloro-4-[[1-methyl-4-(1-oxazol-2-ylethylamino)-2-oxo-6-quinolyl]amino]pyridine-3-carbonitrile;

2-chloro-4-[[1-methyl-2-oxo-4-(1-pyrimidin-4-ylethylamino)-6-quinolyl]amino]pyridine-3-carbonitrile;

2-chloro-4-[[1-[2-(2,5-dioxopyrrolidin-1-yl)ethyl]-4-(ethylamino)-2-oxo-6-quinolyl]amino]pyridine-3-carbonitrile;

2-chloro-4-[[1-methyl-2-oxo-4-(1-thiazol-2-ylethylamino)-6-quinolyl]amino]pyridine-3-carbonitrile;

2-chloro-4-[[1-methyl-2-oxo-4-[1-(1H-pyrazol-3-yl)ethylamino]-6-quinolyl]amino]pyridine-3-carbonitrile;

6-chloro-5-cyano-N-methyl-4-[[1-methyl-4-[(1-methyl-1-pyrimidin-2-yl-ethyl)amino]-2-oxo-6-quinolyl]amino]pyridine-2-carboxamide;

6-chloro-5-cyano-N-methyl-4-[[1-methyl-2-oxo-4-(1-pyrimidin-2-ylethylamino)-6-quinolyl]amino]pyridine-2-carboxamide;

2-chloro-6-methyl-4-[[1-methyl-2-oxo-4-(1-pyrimidin-2-ylethylamino)-6-quinolyl]amino]pyridine-3-carbonitrile;

6-chloro-5-cyano-4-[[4-(1-cyclopropylethylamino)-1-methyl-2-oxo-6-quinolyl]amino]pyridine-2-carboxylic acid;

6-chloro-5-cyano-4-[[4-(cyclopropylamino)-1-methyl-2-oxo-6-quinolyl]amino]pyridine-2-carboxylic acid;

6-chloro-5-cyano-4-[[1-methyl-4-[(1-methylcyclopropyl)amino]-2-oxo-6-quinolyl]amino]pyridine-2-carboxylic acid;

6-chloro-5-cyano-4-[[1-methyl-4-[(1-methylcyclopentyl)amino]-2-oxo-6-quinolyl]amino]pyridine-2-carboxylic acid;

(R)-2-((6-((2-Chloro-3-cyanopyridin-4-yl)amino)-1-methyl-2-oxo-1,2-dihydroquinolin-4-yl)amino)-N-((1-methyl-1H-pyrazol-4-yl)methyl)propanamide;

(R)-2-((6-((2-chloro-3-cyanopyridin-4-yl)amino)-1-methyl-2-oxo-1,2-dihydroquinolin-4-yl)amino)-N-(2-hydroxyethyl)propanamide;

2-Chloro-4-((1-methyl-4-((1-(3-methyl-1H-1,2,4-triazol-5-yl)ethyl)amino)-2-oxo-1,2-dihydroquinolin-6-yl)amino)nicotinonitrile;
(R)-2-((6-((2-Chloro-3-cyanopyridin-4-yl)amino)-1-methyl-2-oxo-1,2-dihydroquinolin-4-yl)amino)-N-cyclopentylpropanamide;
(R)-2-(((6-((2-chloro-3-cyanopyridin-4-yl)amino)-1-methyl-2-oxo-1,2-dihydroquinolin-4-yl)amino)-N-(2-methoxyethyl)propanamide;
(R)—N-(But-3-yn-1-yl)-2-((6-((2-chloro-3-cyanopyridin-4-yl)amino)-1-methyl-2-oxo-1,2-dihydroquinolin-4-yl)amino)propanamide;
(S)-2-Chloro-4-((4-((1-hydroxypropan-2-yl)amino)-1-methyl-2-oxo-1,2-dihydroquinolin-6-yl)amino)nicotinonitrile;
2-((6-((2-Chloro-3-cyanopyridin-4-yl)amino)-1-methyl-2-oxo-1,2-dihydroquinolin-4-yl)amino)-N-ethyl-2-methylpropanamide;
(R)-2-((6-((2-Chloro-3-cyanopyridin-4-yl)amino)-1-methyl-2-oxo-1,2-dihydroquinolin-4-yl)amino)-N-(4-methoxycyclohexyl)propanamide;
(R)-2-chloro-4-((4-((1-hydroxypropan-2-yl)amino)-1-methyl-2-oxo-1,2-dihydroquinolin-6-yl)amino)nicotinonitrile;
rac-2-((6-((2-Chloro-3-cyanopyridin-4-yl)amino)-1-methyl-2-oxo-1,2-dihydroquinolin-4-yl)amino)-N-ethylpropanamide;
2-Chloro-4-((1-methyl-4-((1-(5-methyl-1,3,4-oxadiazol-2-yl)ethyl)amino)-2-oxo-1,2-dihydroquinolin-6-yl)amino)nicotinonitrile;
(R)-2-((6-((2-Chloro-3-cyanopyridin-4-yl)amino)-1-methyl-2-oxo-1,2-dihydroquinolin-4-yl)amino)-N-(2-(1-methyl-1H-pyrazol-4-yl)ethyl)propanamide;
(S)-2-Chloro-4-((4-((4-hydroxybutan-2-yl)amino)-1-methyl-2-oxo-1,2-dihydroquinolin-6-yl)amino)nicotinonitrile;
(R)-2-((6-((2-chloro-3-cyanopyridin-4-yl)amino)-1-methyl-2-oxo-1,2-dihydroquinolin-4-yl)amino)-N-methylpropanamide;
(R)-2-((6-((2-chloro-3-cyanopyridin-4-yl)amino)-2-oxo-1,2-dihydroquinolin-4-yl)amino)-N-methylpropanamide;
6-chloro-5-cyano-4-[[4-(ethylamino)-1-methyl-2-oxo-6-quinolyl]amino]pyridine-2-carboxylic acid;
6-chloro-5-cyano-4-[[4-(ethylamino)-1-methyl-2-oxo-6-quinolyl]amino]-N-methyl-pyridine-2-carboxamide;
6-[(2,3-dichloro-4-pyridyl)amino]-1-methyl-4-(1-pyrimidin-2-ylethylamino)quinolin-2-one; or
2-chloro-4-[[8-methyl-5-[(1-methyl-1-pyrimidin-2-yl-ethyl)amino]-7-oxo-1,8-naphthyridin-3-yl]amino]pyridine-3-carbonitrile.

The various functional groups and substituents making up the compounds of the Formula (I), or sub-formulae Ia to Ig, are typically chosen such that the molecular weight of the compound of the formula (I) does not exceed 1000. More usually, the molecular weight of the compound will be less than 900, for example less than 800, or less than 750, or less than 700, or less than 650. More preferably, the molecular weight is less than 600 and, for example, is 550 or less.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric methane sulfonate or maleic acid. In addition, a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a pharmaceutically acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess antiproliferative activity.

The present invention also encompasses compounds of the invention as defined herein which comprise one or more isotopic substitutions. For example, H may be in any isotopic form, including 1H, 2H(D), and 3H (T); C may be in any isotopic form, including 12C, 13C, and 14C; and O may be in any isotopic form, including 16O and 18O; and the like.

It is also to be understood that certain compounds of the Formula (I), or sub-formulae Ia to Ig, may exist in solvated as well as unsolvated forms such as, for example, hydrated forms. It is to be understood that the invention encompasses all such solvated forms that possess antiproliferative activity.

It is also to be understood that certain compounds of the Formula I, or sub-formulae Ia to Ig, may exhibit polymorphism, and that the invention encompasses all such forms that possess antiproliferative activity.

Compounds of the Formula I, or sub-formulae Ia to Ig, may exist in a number of different tautomeric forms and references to compounds of the Formula I, or sub-formulae Ia to Ig, include all such forms. For the avoidance of doubt, where a compound can exist in one of several tautomeric forms, and only one is specifically described or shown, all others are nevertheless embraced by Formula I, or sub-formulae Ia to Ig. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

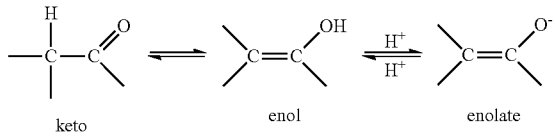

Compounds of the Formula I, or sub-formulae Ia to Ig, containing an amine function may also form N-oxides. A reference herein to a compound of the Formula I, or sub-formulae Ia to Ig, that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example Advanced Organic Chemistry, by Jerry March, 4th Edition, Wiley Interscience, pages. More particularly, N-oxides can be made by the procedure of L. W. Deady (Syn. Comm. 1977, 7, 509-514) in which the amine compound is reacted with m-chloroperoxybenzoic acid (mCPBA), for example, in an inert solvent such as dichloromethane.

The compounds of Formula (I), or sub-formulae Ia to Ig, may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the Formula (I), or sub-formulae Ia to Id, and in-vivo cleavable amide derivatives that may be formed at a carboxy group or an amino group in a compound of the Formula (I), or sub-formulae Ia to Ig.

Accordingly, the present invention includes those compounds of the Formula (I), or sub-formulae Ia to Ig, as defined hereinbefore, when made available by organic synthesis and when made available within the human or animal body by way of cleavage of a pro-drug thereof. Accordingly, the present invention includes those compounds of the Formula I, or sub-formulae Ia to Ig, that are produced by organic synthetic means and also such compounds that are produced in the human or animal body by way of metabolism of a precursor compound, that is a compound of the Formula (I), or sub-formulae Ia to Ig, may be a synthetically-produced compound or a metabolically-produced compound.

A suitable pharmaceutically acceptable pro-drug of a compound of the Formula (I), or sub-formulae Ia to Ig, is one that is based on reasonable medical judgement as being suitable for administration to the human or animal body without undesirable pharmacological activities and without undue toxicity.

Various forms of pro-drug have been described, for example in the following documents:—
a) Methods in Enzymology, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, Advanced Drug Delivery Reviews, 8, 1-38 (1992);
e) H. Bundgaard, et al., Journal of Pharmaceutical Sciences, 77, 285 (1988);
f) N. Kakeya, et al., Chem. Pharm. Bull., 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the Formula I, or sub-formulae Ia to Ig, that possesses a carboxy group is, for example, an in vivo cleavable ester thereof. An in vivo cleavable ester of a compound of the Formula I, or sub-formulae Ia to Ig, containing a carboxy group is, for example, a pharmaceutically acceptable ester which is cleaved in the human or animal body to produce the parent acid. Suitable pharmaceutically acceptable esters for carboxy include C1-6alkyl esters such as methyl, ethyl and tert-butyl, C1-6alkoxymethyl esters such as methoxymethyl esters, C1-6alkanoyloxymethyl esters such as pivaloyloxymethyl esters, 3-phthalidyl esters, C3-8cycloalkylcarbonyloxy-C1-6alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and C1-6alkoxycarbonyloxy-C1-6alkyl esters such as methoxycarbonyloxymethyl and 1-methoxycarbonyloxyethyl esters.

A suitable pharmaceutically acceptable pro-drug of a compound of the Formula (I), or sub-formulae Ia to Ig, that possesses a hydroxy group is, for example, an in vivo cleavable ester or ether thereof. An in vivo cleavable ester or ether of a compound of the Formula I, or sub-formulae Ia to Ig, containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include C1-10alkanoyl groups such as acetyl, benzoyl, phenylacetyl and substituted benzoyl and phenylacetyl groups, C1-10alkoxycarbonyl groups such as ethoxycarbonyl, N,N—(C1-6)2carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(C1-4alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the Formula (I), or sub-formulae Ia to Ig, that possesses a carboxy group is, for example, an in vivo cleavable amide thereof, for example an amide formed with an amine such as ammonia, a C1-4alkylamine such as methylamine, a (C1-4alkyl)2amine such as dimethylamine, N-ethyl-N-methylamine or diethylamine, a C1-4alkoxy-C2-

4alkylamine such as 2-methoxyethylamine, a phenyl-C1-4alkylamine such as benzylamine and amino acids such as glycine or an ester thereof.

A suitable pharmaceutically acceptable pro-drug of a compound of the Formula I, or sub-formulae Ia to Ig, that possesses an amino group is, for example, an in vivo cleavable amide derivative thereof. Suitable pharmaceutically acceptable amides from an amino group include, for example an amide formed with C1-10alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-(C1-4alkyl)piperazin-1-ylmethyl.

The in vivo effects of a compound of the Formula (I), or sub-formulae Ia to Ig, may be exerted in part by one or more metabolites that are formed within the human or animal body after administration of a compound of the Formula (I), or sub-formulae Ia to Ig. As stated hereinbefore, the in vivo effects of a compound of the Formula (I), or sub-formulae Ia to Ig, may also be exerted by way of metabolism of a precursor compound (a pro-drug).

Though the present invention may relate to any compound or particular group of compounds defined herein by way of optional, preferred or suitable features or otherwise in terms of particular embodiments, the present invention may also relate to any compound or particular group of compounds that specifically excludes said optional, preferred or suitable features or particular embodiments.

Suitably, the present invention excludes any individual compounds not possessing the biological activity defined herein.

Synthesis

The compounds of the present invention can be prepared by any suitable technique known in the art. Particular processes for the preparation of these compounds are described further in the accompanying examples.

In the description of the synthetic methods described herein and in any referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

It will be appreciated that during the synthesis of the compounds of the invention in the processes defined herein, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example boron tris(trifluoroacetate). A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively, an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with an acid, for example an organic acid such as trifluoroacetic acid, or for example a benzyl group which may be removed, for example, by hydrogenation over a catalyst such as palladium-on-carbon.

Resins may also be used as a protecting group.

The methodology employed to synthesise a compound of Formula (I), or sub-formulae Ia to Ig, will vary depending on the nature of $X_1$, $X_2$, $X_3$, $R^1$, $R^2$, $R^3$, $R^4$, $R^5$ and any substituent groups associated therewith. Suitable processes for their preparation are described further in the accompanying Examples.

Once a compound of Formula (I), or sub-formulae Ia to Id, has been synthesised by any one of the processes defined herein, the processes may then further comprise the additional steps of:

(i) removing any protecting groups present;
(ii) converting the compound Formula (I) into another compound of Formula (I);
(iii) forming a pharmaceutically acceptable salt, hydrate or solvate thereof; and/or
(iv) forming a prodrug thereof.

An example of (ii) above is when a compound of Formula (I) is synthesised and then one or more of the groups of $X_1$, $X_2$, $X_3$, $R^1$, $R^2$, $R^3$, $R^4$ and $R^5$ may be further reacted to change the nature of the group and provide an alternative compound of Formula (I). For example, the compound can be reacted to convert any R group into a substituent group other than hydrogen.

The resultant compounds of Formula (I), or sub-formulae Ia to Id, can be isolated and purified using techniques well known in the art.

The compounds of Formula (I) may be synthesised by the general synthetic routes (Schemes 1 to 6) below, specific examples of which are described in more detail in the Examples.

Scheme 1

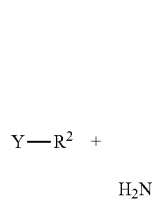

(A)

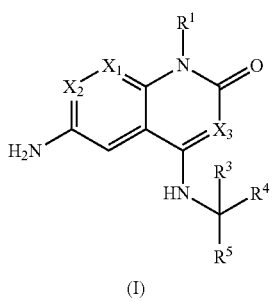

(I)

wherein, Y is a halogen such as Cl, Br, I or a suitable alternative such as OTf, and $R^1$, $R^2$, $R^3$, $R^4$, $R^5$, $X^1$, $X^2$, $X^3$ are suitable groups chosen from defined previously.

The reaction between aromatic amine (A) and aryl halide or equivalent $R^2$—Y to form compounds of formula (I) as shown in scheme 1 may be carried out at elevated temperature (e.g. 60-180° C.), using conventional or microwave heating, in a suitable solvent or solvent mixture, such as NMP, DMA, DMF or acetonitrile. The reaction is carried out in the presence of a base (such as triethylamine or DIPEA) or with no base. Alternative reaction conditions include the use of a transition metal catalyst such as $Pd_2(dba)_3$ combined with a suitable ligand such as Xantphos, in the presence of a base such as cesium carbonate at elevated temperature, using a suitable solvent or solvent mixture, such as toluene or mixtures of toluene and DMF or NMP.

Compounds (A) may be prepared using methods such as those described in scheme 2.

A compound of formula (I) may be converted to another compound of formula (I) by methods generally known to those skilled in the art.

Scheme 2

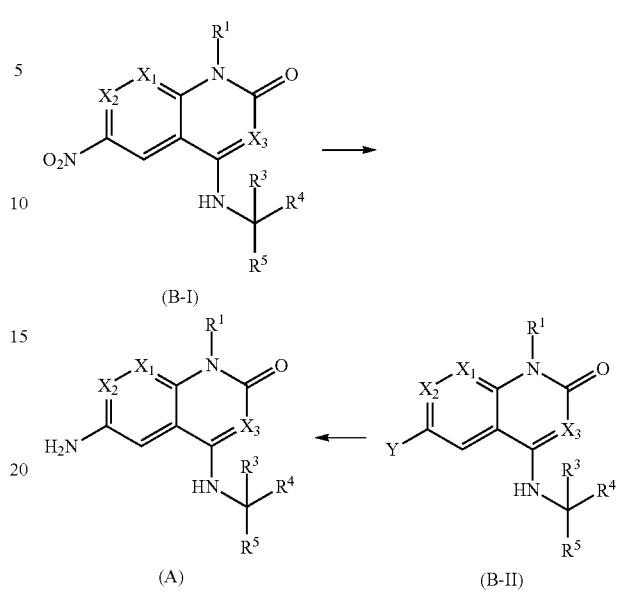

wherein, Y is a halogen such as Cl, Br, I or a suitable alternative such as OTf, and $R^1$, $R^3$, $R^4$, $R^5$, $X_1$, $X_2$, $X_3$ are suitable groups chosen from those defined previously.

The reduction of nitro compounds (B-I) to aromatic amines (A) may be carried out by numerous methods which are well known in the art. Hydrogenation can be carried out in the presence of a metal catalyst such as palladium, often in the form of palladium on carbon, in an appropriate solvent or mixture of solvents such as ethanol, methanol, ethyl acetate or ethanol/NMP at ambient or elevated temperature (such as 40-80° C.) using conventional or microwave heating. These reactions are carried out under a hydrogen atmosphere, or alternatively by "transfer hydrogenation" using a reagent such as ammonium formate or triethylsilane. An alternative method uses tin (II) chloride in an appropriate solvent or solvent mixture, such as ethanol and trifluoroethanol, at elevated temperatures such as 120° C. using conventional or microwave heating. A further method uses ammonium chloride and zinc metal dust, in an appropriate solvent such as methanol at elevated temperature such as 60° C. Many other approaches are known in the art such as iron or zinc metal mediated reductions.

Aromatic amines (A) may also be formed from aryl halides (B-II) by reaction with ammonia (for example, from ammonium hydroxide solution) in an appropriate solvent such as NMP, at elevated temperatures (such as 140° C.), using conventional or microwave heating. These reactions are typically catalysed using a metal catalyst such as copper (I) oxide. Particularly where $X_2$=N, reaction of (B-II) with aromatic amines $R^2$—$NH_2$ by known methods may provide another method to access compounds (I).

Further manipulation of compounds (A), (B-I) or (B-II) by known methods can be used to modify $R^1$, $R^3$, $R^4$, $R^5$, $X_1$, $X_2$, $X_3$.

Compounds (B-I) and (B-II) may be prepared by methods including those as shown in Schemes 3, 5, 6.

Scheme 3

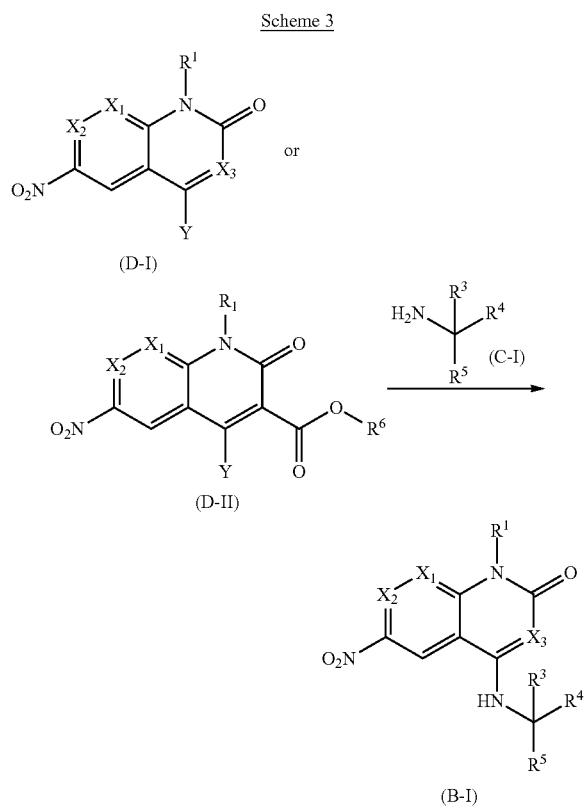

Scheme 4

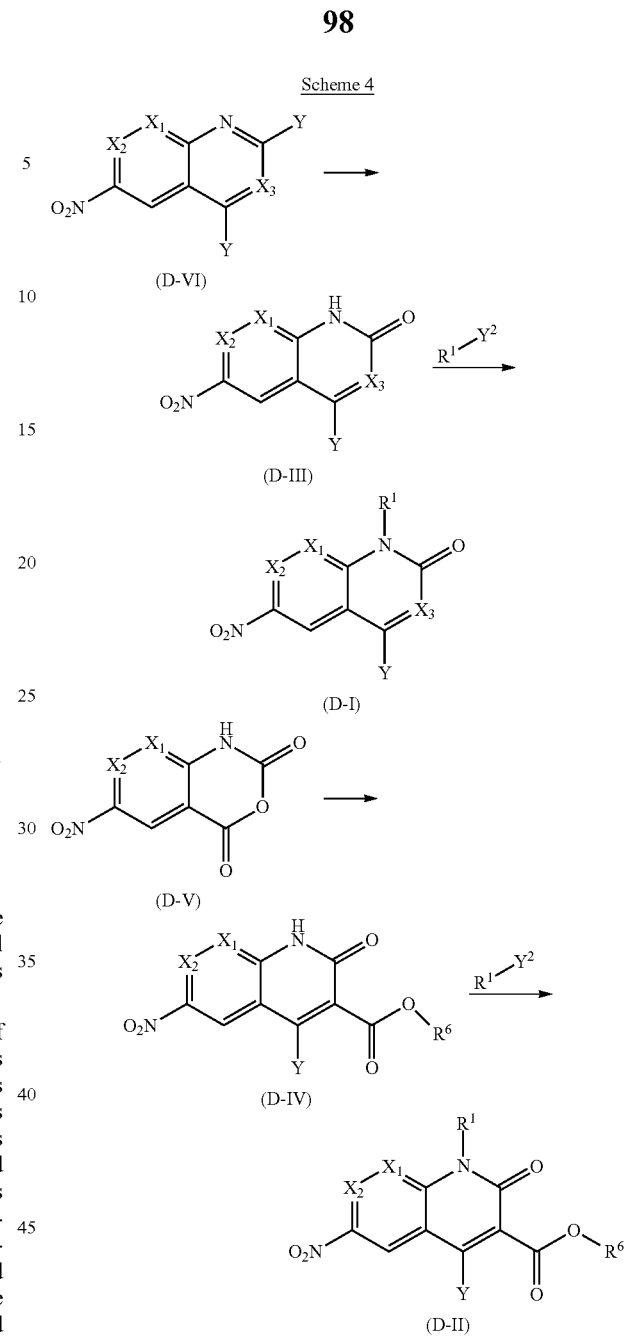

wherein, Y is a halogen such as Cl, Br, I or a suitable alternative such as OTf, $R^6$ is a small alkyl such as methyl or ethyl, and $R^1$, $R^3$, $R^4$, $R^5$, $X_1$, $X_2$, $X_3$ are suitable groups chosen from those defined previously.

Nitro compounds (B-I) can be prepared by the reaction of amines (C-I) with halo-aromatic or equivalent (D-I). This reaction can be carried out at elevated temperature (such as 80-200° C.) in a suitable solvent or solvent mixture such as NMP, NMP/THF or using the amine as solvent. Various additives such as bases (e.g DIPEA, triethylamine) and nucleophilic catalysts (e.g. DMAP) may be used. For less nucleophilic and more sterically hindered amines, alternative conditions may be required. For example, metal catalysed amination may be employed, using a metal source and ligand. Conditions for this type of reaction are known in the literature and include the use of palladium acetate and BINAP as described in Naik et al., *J. Med. Chem.*, 2014, 57, 5419. Reactions are typically carried out using a base such as cesium carbonate in an appropriate solvent or solvent mixture such as toluene, again at elevated temperatures. Alternatively, for the preparation of the subset of compounds (B-I) where $X_3$=CH, use of an ester functionality (D-II) can be used to aid the halogen displacement. Displacement of Y by (C-I) is carried out at elevated temperature (such as 160° C.) in a suitable solvent such as NMP, typically using a base such as DIPEA. Removal of the ester group can be carried out by known methods, such as the addition of lithium chloride to the reaction mixture and further heating (e.g. at 160° C.). Microwave or conventional heating may be employed for the above reactions.

Amines (C-I) were obtained from commercial suppliers or prepared by methods which are known in the art. Compounds (D-I) and (D-II) may be prepared as shown in scheme 4.

wherein, Y and $Y^2$ are halogens such as Cl, Br, I or a suitable alternative such as OTf or OTs, $R^6$ is a small alkyl such as methyl or ethyl, and $R^1$, $X_1$, $X_2$, $X_3$ are suitable groups chosen from those defined previously.

Introduction of $R^1$ group onto compounds (D-III) or (D-IV) may be carried out by alkylation to form compounds (D-I) or (D-II). Alkylation conditions are well known in the art, and include the use of an alkyl halide or equivalent ($Y^2$—$R^1$, such as iodomethane for $R^1$=Me) in an appropriate solvent such as DMF, in the presence of a base such as sodium hydride, or cesium carbonate, at ambient or elevated temperature (e.g. 80° C.). Alkylation may occur on oxygen or on nitrogen; choice of reaction conditions may modulate selectivity, and these regioisomers can typically be separated using known methods. For certain $R^1$ groups, particularly aromatic or heteroaromatic, metal catalysis (such as using copper or palladium based catalysis) may be required or beneficial, and such methods are documented in the literature. Aryl or heteroaryl halides or boronic acids can be used for reactions of this type. Compounds (D-III) are commercially available or can be prepared by known methods, such as the hydrolysis of dihalo derivatives (D-VI) using conditions including those shown in Naik et al. *J. Med. Chem.*, 2014, 57, 5419. Compounds (D-IV) may be prepared by a multistep process starting from compound (D-V), by analogy to a process described in the literature (Stadlbauer et al, *J. Het. Chem.* 1998 p 627; Coppola et al. *Synthesis* 1981, p 391, Tomassoli et al, *Monatsh. Chem.* 2016, p 1069, Ohashi et al, *Bioorg. Med. Chem.* 2012, p 5496, Tomassoli et al, *Eur. J. Med. Chem.* 2011, 46, p 1.

Scheme 6

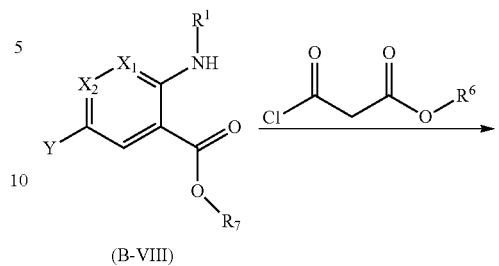

Scheme 5

[Scheme 5 structures: (D-V), (B-IV), (B-III), (D-VII), (D-VIII), (D-IX)]

wherein, $Y^2$ is a halogen such as Cl, Br, I or a suitable alternative such as OTs, and $R^1$, $R^3$, $R^4$, $R^5$, $X_1$, $X_2$ are suitable groups chosen from those defined previously.

Compounds of formula (B-III) [equivalent to compounds of formula (B-I) where $X_3$=N] can be prepared by a multistep procedure starting from dichloropyrimidines (D-V) which may be obtained from commercial suppliers or prepared by known methods. Reaction of (D-V) with an amine (C-I) at ambient or elevated temperature, in an appropriate solvent (e.g. THF) in the presence of an appropriate base (e.g. DIPEA and triethylamine) is followed by hydrolysis in the presence of acid (such as acetic acid) typically at elevated temperature, such as 70° C. to form compounds (B-IV). Alkylation may then be carried out using conditions such as those described in Scheme 4.

An alternative sequence avoids the need for a hydrolysis step. Compounds of formula (D-VII) which may be obtained from commercial suppliers or prepared by known methods may be nitrated using conditions well known in the art (for example, the use of sulfuric and nitric acid), then treated with phosphorus oxychloride. Displacement of the resulting chlorine atom in compound (D-IX) by an amine using conditions previously described gives an alternative method for formation of compounds (B-IV).

-continued

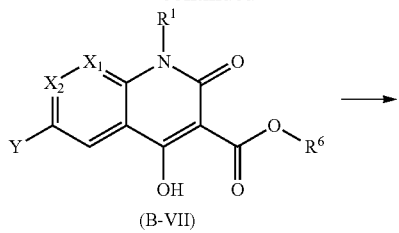

(B-VII)

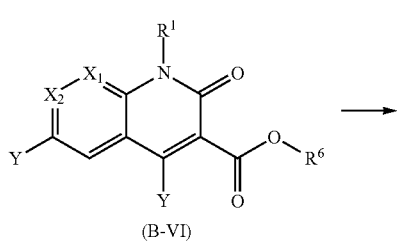

(B-VI)

-continued

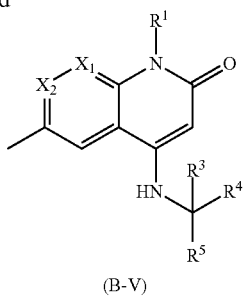

(B-V)

wherein, Y is a halogen such as Cl, Br, I or a suitable alternative such as OTf, $R^6$ is a small alkyl group such as methyl or ethyl, and $R^1$, $R^3$, $R^4$, $R^5$, $X_1$, $X_2$ are suitable groups chosen from those defined previously.

Compounds (B-V) may be prepared via reaction of (B-VI) with amines (C-I) as described in Scheme 3. Compounds (B-VI) are prepared by halogenation of compounds (B-VII). Methods for this sort of transformation are well known in the literature and include treatment with phosphorus oxychloride at elevated temperature, such as 100° C. Compounds (B-VII) can be prepared from compounds (B-VIII) by condensation with alkyl malonyl chlorides using known methods (such as the use of triethylamine in DCM at ambient or elevated temperatures), followed by cyclisation, for example by treatment with sodium alkoxide in an alcohol solvent at ambient temperature. Compounds (B-VIII) may be commercially available, or prepared by methods known in the art.

Biological Activity

The biological assays described in the Examples section herein may be used to measure the pharmacological effects of the compounds of the present invention.

Although the pharmacological properties of the compounds of Formula I vary with structural change, as expected, the compounds of the invention were found to be active in the HTRF in vitro assay described in the Examples section.

In general, as illustrated by the Example compound data in Table 1a and Table 1b, the compounds of the invention demonstrate an $IC_{50}$ of 1 µM or less, which corresponds to a $pIC_{50}$ of 6.0 or more, in the HTRF assay described in the Examples section. Preferred compounds of the invention demonstrate an $IC_{50}$ of 500 nM or less, which corresponds to a $pIC_{50}$ of 6.3 or more, with the most preferred compounds of the invention demonstrating an $IC_{50}$ of 250 nM or less, which corresponds to a $pIC_{50}$ of 6.6 or more.

In the NanoBRET cell assay described herein in the Examples section, as illustrated by the Example compound data in Table 2a and Table 2b, the compounds of Formula I typically demonstrate a $pIC_{50}$ of 4.5 or more (preferably 5.0 or more, most preferably 6.0 or more).

In the immunofluorescence assay described herein in the Examples section, certain compounds of the invention have been shown to enable degradation of BCL6. This is illustrated by the Example compound data shown in Table 2c.

In general, as illustrated by the Example compound data in Table 2d, compounds of the invention show inhibition of cell proliferation when tested in the assay described herein in the Examples section.

The following data were generated for the Examples:

TABLE 1a

Initially Generated Data from the HTRF in vitro Assay

| Example | HTRF $pIC_{50}$ | Example | HTRF $pIC_{50}$ |
|---|---|---|---|
| 1a | 7.38 | 2a | 6.78 |
| 1b | 6.88 | 2b | 6.41 |
| 1c | 6.63 | 2c | 6.36 |
| 1d | 6.58 | 2d | 6.51 |
| 1e | 6.50 | 3a | 6.93 |
| 1f | 6.37 | 3b | 6.73 |
| 1g | 6.10 | 3c | 6.65 |
| 1h | 6.40 | 3d | 6.62 |
| 1i | 6.31 | 3e | 6.59 |
| 1j | 6.27 | 3f | 6.48 |
| 1k | 6.19 | 3g | 6.43 |
| 1l | 6.18 | 3h | 6.40 |
| 1m | 6.15 | 3i | 6.36 |
| 1n | 6.10 | 3j | 6.05 |
| 1o | 6.09 | 3k | 6.17 |
| 1p | 6.06 | 3l | 6.16 |
| 1q | 6.10 | 3m | 6.06 |
| 1r | 6.05 | 3n | 6.31 |
| 1s | 6.03 | 3o | 6.16 |
| 1t | 6.00 | 3p | 6.61 |
| 1u | 7.44 | 4 | 6.06 |
| 1v | 6.76 | 5 | 6.21 |
| 1w | 6.29 | 6a | 6.36 |
| 1x | 6.68 | | |

TABLE 1b

Further Generated Data from the HTRF in vitro Assay

| Example | HTRF pIC50 |
|---|---|
| 1a | 7.33 |
| 1b | 6.93 |
| 1c | 6.73 |
| 1d | 6.58 |
| 1e | 6.08 |
| 1f | 6.27 |
| 1g | 6.13 |
| 1h | 6.38 |
| 1i | 6.26 |
| 1j | 6.29 |
| 1k | 5.95 |
| 1l | 5.98 |
| 1m | 5.88 |
| 1n | 6.35 |
| 1o | 6.15 |
| 1p | 5.96 |
| 1q | 6.29 |
| 1r | 6.25 |
| 1s | 6.07 |
| 1t | 5.84 |
| 1u | 7.51 |
| 1v | 7.31 |
| 1w | 6.90 |
| 1x | 7.20 |
| 2a | 6.85 |
| 2b | 6.55 |
| 2c | 6.38 |
| 2d | 6.65 |
| 3a | 7.05 |
| 3b | 6.57 |
| 3c | 6.50 |
| 3d | 6.61 |
| 3e | 6.42 |
| 3f | 6.71 |
| 3g | 6.39 |
| 3h | 6.41 |
| 3i | 6.42 |
| 3j | 6.14 |

TABLE 1b-continued

Further Generated Data from the HTRF in vitro Assay

| Example | HTRF pIC50 |
|---|---|
| 3l | 5.93 |
| 3n | 6.01 |
| 3o | 5.69 |
| 3p | 6.61 |
| 4 | 6.07 |
| 5 | 6.43 |
| 6a | 6.56 |
| 6b | 6.81 |
| 6c | 6.57 |
| 6d | 6.09 |
| 6e | 6.28 |
| 6f | 6.21 |
| 6g | 6.25 |
| 6h | 6.00 |
| 6i | 6.35 |
| 6j | 6.84 |
| 7a | 7.91 |
| 7b | 6.54 |
| 7c | 6.33 |
| 7d | 6.85 |
| 8a | 7.78 |
| 8b | 7.86 |
| 8c | 7.02 |
| 8d | 7.50 |
| 8e | 7.55 |
| 8f | 6.99 |
| 8g | 7.82 |
| 8h | 7.68 |
| 9a | 7.74 |
| 9b | 7.13 |
| 9c | 6.05 |
| 9d | 6.13 |
| 9f | 7.65 |
| 9g | 7.05 |
| 9h | 6.77 |
| 9i | 6.61 |
| 9j | 6.49 |
| 9k | 6.35 |
| 9l | 6.56 |
| 9m | 7.01 |
| 9n | 6.84 |
| 9o | 6.66 |
| 9p | 7.25 |
| 9q | 6.81 |
| 10a | 7.53 |
| 10b | 7.39 |
| 10c | 7.45 |
| 10d | 7.33 |
| 10e | 7.27 |
| 10f | 7.12 |
| 10g | 7.10 |
| 10h | 7.10 |
| 10i | 6.96 |
| 10j | 6.92 |
| 10k | 6.82 |
| 10l | 6.70 |
| 10m | 6.66 |
| 10n | 6.55 |
| 10o | 6.50 |
| 10p | 6.44 |
| 10q | 6.44 |
| 10r | 6.32 |
| 10s | 6.23 |
| 10t | 6.22 |
| 10u | 6.19 |
| 10v | 6.17 |
| 10w | 7.58 |
| 10x | 7.56 |
| 11a | 6.78 |
| 11b | 6.52 |
| 11c | 6.42 |
| 11d | 6.34 |
| 11e | 6.20 |
| 11f | 6.13 |
| 11g | 6.05 |
| 11h | 6.65 |
| 11i | 6.64 |
| 11j | 6.83 |
| 12a | 6.72 |
| 12b | 6.52 |
| 12c | 6.28 |
| 12d | 6.78 |
| 12e | 6.58 |
| 12f | 6.57 |
| 12g | 6.33 |
| 12h | 6.60 |
| 12i | 7.32 |
| 13 | 6.66 |
| 14a | 6.66 |
| 14b | 6.64 |
| 14c | 6.54 |
| 14d | 6.44 |
| 14e | 6.54 |
| 14f | 6.49 |
| 15a | 6.59 |
| 15b | 6.46 |
| 15c | 6.24 |
| 15d | 6.42 |
| 15e | 6.28 |
| 15f | 6.58 |
| 15g | 6.47 |
| 15h | 6.21 |
| 15i | 6.58 |
| 16a | 6.58 |
| 16b | 6.37 |
| 16c | 6.36 |
| 16d | 6.25 |
| 17a | 6.48 |
| 17b | 6.11 |
| 17c | 6.47 |
| 17d | 6.19 |
| 17e | 6.34 |
| 17f | 6.32 |
| 17g | 6.24 |
| 17h | 6.20 |
| 17i | 6.20 |
| 17j | 6.18 |
| 17k | 6.11 |
| 18a | 6.30 |
| 18b | 6.40 |
| 19a | 7.55 |
| 19b | 6.99 |
| 19c | 6.05 |
| 19d | 6.51 |
| 19e | 6.05 |
| 19f | 6.40 |
| 19g | 6.07 |
| 19h | 6.17 |
| 19i | 6.38 |
| 20 | 7.46 |
| 21 | 6.33 |
| 22a | 6.60 |
| 22b | 6.24 |
| 23a | 6.42 |
| 23b | 6.33 |
| 24a | 6.84 |
| 24b | 6.49 |
| 24c | 6.45 |
| 24d | 6.53 |
| 24e | 6.38 |
| 24f | 7.26 |
| 25a | 6.73 |
| 26a | 6.25 |
| 26b | 6.31 |
| 26c | 6.23 |
| 26d | 6.30 |
| 26e | 7.03 |

TABLE 1b-continued

Further Generated Data from the HTRF in vitro Assay

| Example | HTRF pIC50 |
|---|---|
| 26f | 6.99 |
| 26g | 6.54 |

TABLE 2a

Initially Generated Data from the NanoBRET cell assay

| Example | NanoBRET cell pIC$_{50}$ |
|---|---|
| 1a | 6.17 |
| 1b | 5.79 |
| 1d | 5.45 |

TABLE 2b

Further Generated Data from the NanoBRET cell assay

| Example | NanoBRET cell pIC50 |
|---|---|
| 1a | 6.33 |
| 1b | 5.92 |
| 1c | 4.65 |
| 1d | 5.45 |
| 1m | 5.27 |
| 1u | 6.28 |
| 1v | 6.03 |
| 1w | 5.80 |
| 1x | 5.80 |
| 3g | 4.68 |
| 6a | 5.55 |
| 6b | 5.86 |
| 6c | 5.26 |
| 6d | 5.74 |
| 6g | 5.13 |
| 6j | 5.92 |
| 7a | 6.46 |
| 7b | 5.95 |
| 7d | 6.01 |
| 8a | 6.26 |
| 8b | 6.13 |
| 8c | 6.30 |
| 8d | 6.62 |
| 8e | 6.17 |
| 8f | 5.28 |
| 10a | 6.29 |
| 10b | 6.31 |
| 10c | 6.31 |
| 10d | 6.23 |
| 10e | 6.02 |
| 10f | 5.97 |
| 10g | 5.83 |
| 10h | 5.05 |
| 10i | 5.75 |
| 10j | 5.91 |
| 10k | 5.82 |
| 10m | 5.56 |
| 10n | 5.89 |
| 10o | 5.64 |
| 10p | 5.63 |
| 10q | 5.57 |
| 10s | 5.61 |
| 10u | 5.06 |
| 10w | 6.04 |
| 10x | 5.90 |
| 11a | 5.47 |
| 11b | 5.89 |

TABLE 2b-continued

Further Generated Data from the NanoBRET cell assay

| Example | NanoBRET cell pIC50 |
|---|---|
| 11d | 5.36 |
| 11e | 5.46 |
| 11h | 5.55 |
| 11i | 5.68 |
| 11j | 4.96 |
| 12a | 5.63 |
| 12b | 5.89 |
| 12c | 5.48 |
| 12d | 4.95 |
| 12f | 5.61 |
| 13.00 | 5.77 |
| 14a | 5.41 |
| 14b | 5.08 |
| 14c | 6.05 |
| 14d | 5.69 |
| 14e | 5.00 |
| 15a | 5.70 |
| 15b | 5.66 |
| 15d | 5.75 |
| 15e | 5.37 |
| 15f | 5.64 |
| 15g | 5.14 |
| 15h | 5.16 |
| 15i | 5.81 |
| 16a | 5.58 |
| 16b | 5.30 |
| 16d | 5.04 |
| 17a | 5.75 |
| 17c | 5.43 |
| 17e | 5.46 |
| 17f | 5.49 |
| 17h | 5.38 |
| 17i | 5.55 |
| 17j | 5.31 |
| 18b | 5.15 |
| 19a | 5.56 |
| 19b | 5.28 |
| 19c | 4.53 |
| 19d | 5.06 |
| 19f | 5.53 |
| 19h | 4.82 |
| 19i | 5.03 |
| 20.00 | 6.32 |
| 21.00 | 5.17 |
| 22a | 5.63 |
| 23a | 5.17 |
| 24b | 5.32 |
| 24c | 5.29 |
| 24d | 5.35 |
| 24e | 5.46 |
| 24f | 5.79 |
| 26b | 5.57 |
| 26d | 5.42 |
| 26e | 5.54 |
| 26f | 6.17 |

TABLE 2c

Data Generated from the Immunofluorescence Assay

| Example | Degradation assay in SU-DHL4 (pDC50) |
|---|---|
| 12a | 6.30 |
| 12h | 6.71 |
| 25a | 7.32 |
| 26g | 6.93 |

TABLE 2d

Data Generated from the Cell Viability Assay

| Example | Cell proliferation assay in SU-DHL4 cells (GI$_{50}$) (µM) | Example | Cell proliferation assay in SU-DHL4 cells (GI$_{50}$) (µM) |
|---|---|---|---|
| 6b | 2.13 | 10w | 1.34 |
| 8d | 0.45 | 12h | 0.34 |
| 10b | 0.29 | 14c | 0.76 |
| 10c | 0.46 | 25a | 0.11 |
| 10d | 1.48 | 26f | 0.44 |
| 10e | 1.72 | | |

The following compounds were tested but did not exhibit the desired activity in the assays described in the Examples section:
2-chloro-4-((1-methyl-2-oxo-4-((2-oxopiperidin-3-yl)amino)-1,2-dihydroquinolin-6-yl)amino)nicotinonitrile;
2-chloro-4-((4-((1-(1-methyl-1H-pyrazol-4-yl)ethyl)amino)-2-oxo-1,2-dihydroquinolin-6-yl)amino)nicotinonitrile;
2-chloro-4-((4-((1-(dimethylamino)propan-2-yl)amino)-1-methyl-2-oxo-1,2-dihydroquinolin-6-yl)amino)nicotinonitrile; and
2-((6-((2-chloro-3-cyanopyridin-4-yl)amino)-2-oxo-1,2-dihydroquinolin-4-yl)amino)-N-methylacetamide.

Following further testing, the following compounds were discovered not to exhibit the preferred activity in the assays described in the Examples section:
2-chloro-4-[[1-methyl-2-oxo-4-(pyrimidin-2-ylmethylamino)-6-quinolyl]amino]pyridine-3-carbonitrile;
6-((5-chloro-2-((3S,5R)-3,5-dimethylpiperidin-1-yl)-6-(trifluoromethyl)pyrimidin-4-yl)amino)-1-methyl-4-((1-(pyrimidin-2-yl)ethyl)amino)quinolin-2(1H)-one;
2-chloro-4-((1-methyl-2-oxo-4-((pyrimidin-2-ylmethyl)amino)-1,2-dihydroquinolin-6-yl)amino)nicotinonitrile
2-chloro-4-((1-methyl-4-((1-methyl-2-oxopyrrolidin-3-yl)amino)-2-oxo-1,2-dihydroquinolin-6-yl)amino)nicotinonitrile; and
2-chloro-4-((8-(ethylamino)-5-methyl-6-oxo-5,6-dihydro-1,5-naphthyridin-2-yl)amino)nicotinonitrile.

In an embodiment, the compounds of the invention are compounds of Formula I as defined hereinbefore, with the proviso that the compound is not one of the compounds listed in the preceding paragraph.

Pharmaceutical Compositions

According to a further aspect of the invention there is provided a pharmaceutical composition which comprises a compound of the invention as defined hereinbefore, or a pharmaceutically acceptable salt, hydrate or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy is an amount sufficient to treat or prevent a proliferative condition referred to herein, slow its progression and/or reduce the symptoms associated with the condition.

The amount of active ingredient that is combined with one or more excipients to produce a single dosage form will necessarily vary depending upon the individual treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the conditions, the age and sex of the animal or patient and the route of administration, according to well-known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

The present invention provides compounds that function as inhibitors of BCL6.

The present invention therefore provides a method of inhibiting BCL6 activity in vitro or in vivo, said method comprising contacting a cell with an effective amount of a compound, or a pharmaceutically acceptable salt, hydrate or solvate thereof, as defined herein.

The present invention also provides a method of treating a disease or disorder in which BCL6 activity is implicated in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a method of inhibiting cell proliferation, in vitro or in vivo, said method comprising contacting a cell with an effective amount of a compound, or a pharmaceutically acceptable salt, hydrate or solvate thereof, as defined herein.

The present invention provides a method of treating a proliferative disorder in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a method of treating cancer in a patient in need of such treatment, said method comprising administering to said patient a therapeutically effective amount of a compound, or a pharmaceutically acceptable salt, hydrate or solvate thereof, or a pharmaceutical composition as defined herein.

The present invention provides a compound, or a pharmaceutically acceptable salt, hydrate or solvate thereof, or a pharmaceutical composition as defined herein for use in therapy.

The present invention provides a compound, or a pharmaceutically acceptable salt, hydrate or solvate thereof, or a pharmaceutical composition as defined herein for use in the treatment of a proliferative condition.

The present invention provides a compound, or a pharmaceutically acceptable salt, hydrate or solvate thereof, or a pharmaceutical composition as defined herein for use in the treatment of cancer. In a particular embodiment, the cancer is human cancer.

The present invention provides a compound, or a pharmaceutically acceptable salt, hydrate or solvate thereof, as defined herein for use in the inhibition of BCL6 activity (i.e. in the inhibition of BCL6 transcriptional repression and/or co-repressor binding).

Certain compounds of the present invention have been found to bind to BCL6 and initiated the degradation of BCL6. Thus, the present invention also provides a compound, or a pharmaceutically acceptable salt, hydrate or solvate thereof, as defined herein for use in the degradation of BCL6.

The present invention provides a compound, or a pharmaceutically acceptable salt, hydrate or solvate thereof, as defined herein for use in the treatment of a disease or disorder in which BCL6 activity is implicated.

The present invention provides a use of a compound, or a pharmaceutically acceptable salt, hydrate or solvate thereof, as defined herein in the manufacture of a medicament for the treatment of a proliferative condition.

The present invention provides a use of a compound, or a pharmaceutically acceptable salt, hydrate or solvate thereof, as defined herein in the manufacture of a medicament for the treatment of cancer. Suitably, the medicament is for use in the treatment of human cancers.

The present invention provides a use of a compound, or a pharmaceutically acceptable salt, hydrate or solvate thereof, as defined herein in the manufacture of a medicament for the inhibition of BCL6 activity (i.e. in the inhibition of BCL6 transcriptional repression and/or co-repressor binding).

The present invention provides a use of a compound, or a pharmaceutically acceptable salt, hydrate or solvate thereof, as defined herein in the manufacture of a medicament for the degradation of BCL6.

The present invention provides a use of a compound, or a pharmaceutically acceptable salt, hydrate or solvate thereof, as defined herein in the manufacture of a medicament for the treatment of a disease or disorder in which BCL6 activity is implicated.

The term "proliferative disorder" and "proliferative condition" are used interchangeably herein and pertain to an unwanted or uncontrolled cellular proliferation of excessive or abnormal cells which is undesired, such as, neoplastic or hyperplastic growth, whether in vitro ox in vivo. Examples of proliferative conditions include, but are not limited to, pre-malignant and malignant cellular proliferation, including but not limited to, malignant neoplasms and tumours, cancers (including breast cancer, non-small cell lung cancer (NSCLC) and squamous cell carcinomas (SCC) (including SCC of the head and neck, oesophagus, lung and ovary), leukemias (including acute lymphoblastic leukaemia (ALL) and chronic myeloid leukaemia (CML)), (including acute lymphoblastic leukaemia (ALL) and chronic myeloid leukaemia (CML)), psoriasis, bone diseases, fibroproliferative disorders (e.g., of connective tissues), and atherosclerosis. Any type of cell may be treated, including but not limited to, lymphatic, blood, lung, colon, breast, ovarian, prostate, liver, pancreas, brain, and skin.

The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

The compound of Formula (I), or a pharmaceutically acceptable salt thereof, being an inhibitor of BCL6, has potential therapeutic uses in a variety of BCL6-mediated disease states.

BCL6 expression has been linked to a variety of lymphomas (Wagner et al., *British J Haematology*, 2010, 152, 3-12). BCL6 is involved in chromosomal translocations in diffuse large B-cell lymphoma (DLBCL) and inhibitors of BCL6 have been reported to kill DLBCL cells (Cerchietti et al., *Cancer* Cell, 2010, 17, 400-411), primary low grade follicular lymphoma cells (Cardenas et al., *Clin Cancer* Res, 2017, 23(4), 885-893) and Burkitt lymphoma cells (Polo et al., *Nat Med*, 2004, 10, 1329-1335). BCL6 is required for the formation of follicular helper T cells (Hatzi et al., *J Exp* Med, 2015, 212(4), 539-553), which raises the possibility that BCL6 inhibitors may be used to treat angioimmunoblastic T-cell lymphoma (AITL), in which BCL6 is strongly expressed (Cortes & Palomero, *Curr Opin Hematol,* 2016, 23, 434-443).

BCL6 has also been implicated in leukaemia cells which have acquired resistance to tyrosine kinase inhibitors (TKIs). TKIs typically fail to eradicate leukaemia-initiating cells, which may often cause recurrence of leukaemia after initial treatment. BCL6 has been identified as an important component of the TKI drug-resistance pathway in both Ph+ acute lymphoblastic leukaemia (ALL) (Duy et al., *Nature,* 2011, 473, 384-388) and Ph+ chronic myeloid leukaemia (CML) (Hurtz et al., *J Exp* Med. 2011, 208(11), 2163-2174). Inhibitors of BCL6 may therefore be used to treat ALL and CML in combination with a TKI.

Further non-haematological, solid tumours may be treated with an inhibitor of BCL6. BCL6 is amplified in approximately 50% of breast tumours and is expressed in many breast cancer cell lines, including triple negative breast cancer cell lines (Walker et al., *Oncogene,* 2015, 34, 1073-1082). BCL6 is also important for the survival and proliferation of non-small cell lung cancer (NSCLC) cells, primarily due to repression of genes involved in DNA damage repair (Marullo et al., *Proc* 107$^{th}$ Annual Meeting AACR, 2016, Abstract nr 1271 and Deb et al., Cancer Res., 2017, Apr. 4, doi: 10.1158/0008-5472.CAN-15-3052). BCL6 amplification may also be prevalent in squamous cell carcinomas (SCC) (including SCC of the head & neck, oesophagus, lung and ovary). Furthermore, inhibition of BCL6 has recently been reported to be a suitable therapeutic target for glioma and glioblatoma (Xu et al., *Proc. Natl. Acad. Sci. U.S.A.,* 2017, 114(15), 3981-3986).

According to a further aspect of the specification there is provided a compound of Formula (I), or a pharmaceutically acceptable salt thereof, as defined hereinbefore for use in the treatment of haematological cancers such as lymphomas (including diffuse large B-cell lymphoma (DLBCL), follicular lymphoma (FL), Burkitt lymphoma (BL) and angioimmunoblastic T-cell lymphoma (AITL)), leukaemias (including acute lymphoblastic leukaemia (ALL) and chronic myeloid leukaemia (CML)) and multiple myeloma, and of solid tumours (including glioma, breast cancer, non-small cell lung cancer (NSCLC) and squamous cell carcinomas (SCC) (including SCC of the head and neck, oesophagus, lung and ovary)).

According to a further feature of this aspect of the specification there is provided a compound of Formula (I), or a pharmaceutically acceptable salt thereof, as defined hereinbefore for use in the treatment of lymphomas, including DLBCL, FL, BL and AITL.

According to a further feature of this aspect of the specification there is provided a compound of Formula (I), or a pharmaceutically acceptable salt thereof, as defined hereinbefore for use in the treatment of DLBCL and FL.

According to a further feature of this aspect of the specification there is provided a compound of Formula (I), or a pharmaceutically acceptable salt thereof, as defined hereinbefore for use in the treatment of leukaemias, including ALL and CML.

According to a further feature of this aspect of the specification there is provided a compound of Formula (I), or a pharmaceutically acceptable salt thereof, as defined hereinbefore for use in the treatment of solid tumours, including glioma, breast cancer, NSCLC and SCC.

According to a further feature of this aspect of the specification there is provided a method for treating haematological cancers such as lymphomas (including DLBCL, FL, BL and AITL), leukaemias (including ALL and CML) and multiple myeloma, and of solid tumours (including glioma, breast cancer, NSCLC and SCC (including SCC of the head and neck, oesophagus, lung and ovary)) in a warm-blooded animal such as man that is in need of such treatment, which comprises administering an effective amount of a compound of Formula (I), or a pharmaceutically acceptable salt thereof, as defined hereinbefore.

According to a further feature of this aspect of the specification there is provided a method for treating lymphomas, including DLBCL, FL, BL and AITL, in a warm-blooded animal such as man that is in need of such treatment, which comprises administering an effective amount of a compound of Formula (I), or a pharmaceutically acceptable salt thereof, as defined hereinbefore.

According to a further feature of this aspect of the specification there is provided a method for treating DLBCL and FL, in a warm-blooded animal such as man that is in need of such treatment, which comprises administering an effective amount of a compound of Formula (I), or a pharmaceutically acceptable salt thereof, as defined hereinbefore.

According to a further feature of this aspect of the specification there is provided a method for treating leukaemias, including ALL and CML, in a warm-blooded animal such as man that is in need of such treatment, which comprises administering an effective amount of a compound of Formula (I), or a pharmaceutically acceptable salt thereof, as defined hereinbefore.

According to a further feature of this aspect of the specification there is provided a method for treating solid tumours (including glioma, breast cancer, NSCLC and SCC (including SCC of the head and neck, oesophagus, lung and ovary)), in a warm-blooded animal such as man that is in need of such treatment, which comprises administering an effective amount of a compound of Formula (I), or a pharmaceutically acceptable salt thereof, as defined hereinbefore.

According to a further feature of this aspect of the specification there is provided the use of a compound of Formula (I), or a pharmaceutically acceptable salt thereof, as defined hereinbefore in the manufacture of a medicament for use in the treatment of haematological cancers such as lymphomas (including DLBCL, FL, BL and AITL), leukaemias (including ALL and CML) and multiple myeloma, and of solid tumours (including glioma, breast cancer, NSCLC and SCC (including SCC of the head and neck, oesophagus, lung and ovary)).

According to a further feature of this aspect of the specification there is provided the use of a compound of Formula (I), or a pharmaceutically acceptable salt thereof, as defined hereinbefore in the manufacture of a medicament for use in the treatment of lymphomas, including DLBCL, FL, BL and AITL.

According to a further feature of this aspect of the specification there is provided the use of a compound of Formula (I), or a pharmaceutically acceptable salt thereof, as defined hereinbefore in the manufacture of a medicament for use in the treatment of DLBCL and FL.

According to a further feature of this aspect of the specification there is provided the use of a compound of Formula (I), or a pharmaceutically acceptable salt thereof, as defined hereinbefore in the manufacture of a medicament for use in the treatment of leukaemias, including ALL and CML.

According to a further feature of this aspect of the specification there is provided the use of a compound of Formula (I), or a pharmaceutically acceptable salt thereof, as defined hereinbefore in the manufacture of a medicament for use in the treatment of solid tumours (including glioma, breast cancer, NSCLC and SCC (including SCC of the head and neck, oesophagus, lung and ovary)).

Routes of Administration

The compounds of the invention or pharmaceutical compositions comprising these compounds may be administered to a subject by any convenient route of administration, whether systemically, peripherally or topically (i.e., at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eye drops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intra-arterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The antiproliferative treatment defined hereinbefore may be applied as a sole therapy or may involve, in addition to the compound of the invention, conventional surgery or radiotherapy or chemotherapy. Such chemotherapy may include one or more of the following categories of antitumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example *vinca* alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), steroid hormones, including progestogens (for example megestrol acetate) and corticosteroids (for example dexamethasone, prednisone and prednisolone), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. (Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy) quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

In a particular embodiment, the antiproliferative treatment defined hereinbefore may involve, in addition to the compound of the invention, conventional surgery or radiotherapy or chemotherapy, wherein the chemotherapy may include one or more anti-tumour agents selected from procarbazine, carmustine, lomustine, irinotecan, temozolomide, cisplatin, carboplatin, methotrexate, etoposide, cyclophosphamide, ifosfamide, and vincristine.

In another particular embodiment, the antiproliferative treatment defined hereinbefore may involve, in addition to the compound of the invention, conventional surgery or radiotherapy or chemotherapy, wherein the chemotherapy may include one or more chemotherapeutic agents selected from a BCL-2 family inhibitor (e.g. Venetoclax and/or navitoclax), a BTK inhibitor (e.g. Ibrutinib, Acalabrutinib, Tirabrutinib (ONO/GS-4059), BGB-3111 or Spebrutinib (CC-292) or a TNF inhibitor (e.g. Lenalidomide).

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination for use in the treatment of a cancer (for example a cancer involving a solid tumour) comprising a compound of the invention as defined hereinbefore, or a pharmaceutically acceptable salt, hydrate or solvate thereof, and another anti-tumour agent.

According to this aspect of the invention there is provided a combination for use in the treatment of a proliferative condition, such as cancer (for example a cancer involving a solid tumour), comprising a compound of the invention as defined hereinbefore, or a pharmaceutically acceptable salt, hydrate or solvate thereof, and any one of the anti-tumour agents listed herein above.

According to this aspect of the invention there is provided a combination for use in the treatment of a cancer comprising a compound of the invention as defined hereinbefore, or a pharmaceutically acceptable salt, hydrate or solvate thereof, and a tyrosine kinase inhibitor.

According to this aspect of the invention there is provided a combination for use in the treatment of leukaemia (such as ALL or CML) comprising a compound of the invention as defined hereinbefore, or a pharmaceutically acceptable salt, hydrate or solvate thereof, and a tyrosine kinase inhibitor.

In a further aspect of the invention there is provided a compound of the invention or a pharmaceutically acceptable salt, hydrate or solvate thereof, for use in the treatment of cancer in combination with another anti-tumour agent, optionally selected from one listed herein above.

In a further aspect of the invention there is provided a compound of the invention or a pharmaceutically acceptable salt, hydrate or solvate thereof, for use in the treatment of cancer in combination with a tyrosine kinase inhibitor, optionally selected from one listed herein above.

In a further aspect of the invention there is provided a compound of the invention or a pharmaceutically acceptable salt, hydrate or solvate thereof, for use in the treatment of leukaemia (such as ALL or CML) in combination with a tyrosine kinase inhibitor, optionally selected from one listed herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of the invention, or a pharmaceutically acceptable salt, hydrate or solvate thereof, in combination with an anti-tumour agent (optionally selected from one listed herein above), in association with a pharmaceutically acceptable diluent or carrier.

EXAMPLES

Abbreviations

APCI Atmospheric pressure chemical ionization
AcOH acetic acid
aq. Aqueous
br broad (in NMR spectrum)
n-BuLi n-butyl lithium
conc. concentrated
d doublet (in NMR spectrum)
dba dibenzylideneacetone
DCM dichloromethane
DIPEA N,N-diisopropylethylamine
DMA dimethylacetamide
DME 1,2-dimethoxyethane
DMF N,N-dimethylformamide
DMSO dimethylsulfoxide
ESI electrospray ionisation
Et2O diethyl ether
EtOAc ethyl acetate
EtOH ethanol
h hour(s)
HATU N-[(Dimethylamino)-1H-1,2,3-triazolo-[4,5-b]pyridin-1-ylmethylene]-N-methylmethanaminium hexafluorophosphate N-oxide
Hex hexane
HPLC High Performance Liquid Chromatography
HRMS high resolution mass spectrometry
IPA iso-propyl alcohol
KOAc Potassium acetate
KP-Sil Biotage KP-Sil (50 uM irregular silica)
LCMS liquid chromatography and mass spectrometry
m-CPBA 3-chloroperbenzoic acid
MeOH methanol
MeCN acetonitrile
MS mass spectrometry
Ms mesyl (methanesulfonyl)
m multiplet (in NMR spectrum)
MHz megahertz
min minute(s)
mins minute(s)
mL milliliter(s)
MP macroporous polystyrene (solid support for polymer-bound reagents, such as Biotage MP-carbonate)
m/z mass to charge ratio
NMP N-methylpyrrolidinone
NMR nuclear magnetic resonance
NOESY nuclear Overhauser effect spectroscopy
Pd/C palladium on activated charcoal
PL-HCO3 polystyrene supported hydrogen carbonate (solid supported reagent)
ppm parts per million
q quartet (in NMR spectrum)
quin. quintet (in NMR spectrum)
Rt retention time (in LCMS)
rt room temperature s singlet (in NMR spectrum)
sat. saturated
SCX-2 strong cation exchange (e.g. Isolute® SCX-2 columns)
sex. sextet (in NMR spectrum)
Si-DMT silica bound equivalent of 2,4,6-trimercaptotriazine, commercially available e.g. from Silicycle or Biotage. Also known as Si-TMT
t triplet (in NMR spectrum)
TBAF tetrabutylammonium fluoride
TEA triethylamine
Tf triflate (trifluoromethane sulfonate)
TFA trifluoroacetic acid
TFE 2,2,2-trifluoroethanol
THF tetrahydrofuran
T3P propylphosphonic anhydride
Ts tosyl (4-toluenesulfonyl)
uL microlitres
Xantphos 4,5-Bis(diphenylphosphino)-9,9-dimethylxanthene
Analytical Methods: LCMS
Method T2

LC/MS and HRMS analysis was performed on an Agilent 1200 series HPLC and diode array detector coupled to a 6210 time of flight mass spectrometer with dual multimode APCI/ESI source. Analytical separation was carried out at 40° C. on a Merck Chromolith Flash column (RP-18e, 25×2 mm) using a flow rate of 1.5 mL/min in a 2 minute gradient elution with detection at 254 nm. The mobile phase was a mixture of methanol (solvent A) and water (solvent B), both containing formic acid at 0.1%. Gradient elution was as follows: 5:95 (A/B) to 100:0 (A/B) over 1.25 min, 100:0 (A/B) for 0.5 min, and then reversion back to 5:95 (A/B) over 0.05 min, finally 5:95 (A/B) for 0.2 min Method T4

As for method T2 except at 30° C., using a flow rate of 0.75 mL/min in a 4 minute gradient elution as follows: 5:95 (A/B) to 100:0 (A/B) over 2.5 min, 100:0 (A/B) for 1 min, and then reversion back to 5:95 (A/B) over 0.1 min, finally 5:95 (A/B) for 0.4 min.

Method X2

LC/MS and HRMS analysis was performed on a Waters Acquity UPLC and diode array detector coupled to a Waters G2 QToF mass spectrometer fitted with a multimode ESI/APCI source. Analytical separation was carried out at 30° C. on a Phenomenex Kinetex C18 column (30×2.1 mm, 2.6 u, 100 A) using a flow rate of 0.5 mL/min in a 2 minute gradient elution with detection at 254 nm. The mobile phase was a mixture of methanol (solvent A) and water (solvent B), both containing formic acid at 0.1%. Gradient elution was as follows: 10:90 (A/B) to 90:10 (A/B) over 1.25 min, 90:10 (A/B) for 0.5 min, and then reversion back to 10:90 (A/B) over 0.15 min, finally 10:90 (A/B) for 0.1 min.

Method X4

As for method $X_2$, except using a flow rate of 0.3 mL/min in a 4 minute gradient elution as follows: 10:90 (A/B) to 90:10 (A/B) over 3 min, 90:10 (A/B) for 0.5 min, and then reversion back to 10:90 (A/B) over 0.3 min, finally 10:90 (A/B) for 0.2 min.

Analytical Methods: NMR

NMR data was collected on a Bruker Avance 500 spectrometer equipped with a 5 mm BBO/QNP probe or on a Bruker Avance Neo 600 spectrometer equipped with a 5 mm TCI Cryo-Probe. The $^1$H and $^{13}$C spectra were referenced to the internal deuterated solvent. All NMR data were acquired at the temperature of 298 K. All data were acquired and processed using Bruker Topspin 2.1 or Bruker Topspin 4.

The $^1$H-NMR spectrum was acquired using a Bruker standard 1D zg30 pulse sequence with 16 scans. The sweep width was 20.5 ppm, and the FID contained 64 k time-domain data points.

Purification Methods

Unless otherwise described in the text, HPLC purification was carried out on an Agilent 6120 MS-Prep LC using an ACE 5 C18-PFP 250×21.2 mm column using a 15 min gradient of water:methanol (both modified with 0.1% formic acid)—for example 10-100%, 40-100%, 60-100% or 55-80%, at a flow rate of 20 mL per minute. Alternative column sizes and flow rates were used dependent on the scale of the purification, chosen from ACE 5 C18-PFP 250×10 mm (flow rate 5 mL per minute) or ACE 5 C18-PFP 250×30 mm (flow rate 40 mL per minute).

Flash column chromatography was carried out using prepacked Biotage™ SNAP KP-Sil columns. Reverse phase chromatography was carried out using a Biotage™ SNAP Ultra C18 12 g or 30 g column, using a gradient of water:methanol (both modified with 0.1% formic acid).

Example Compounds

Example 1a; 2-Chloro-4-[[1-methyl-4-[(1-methyl-1-pyridin-2-yl-ethyl)amino]-2-oxo-6-quinolyl]amino]pyridine-3-carbonitrile

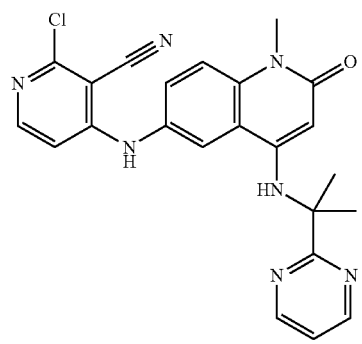 [SMILES: Cn1c(=O)cc(NC(C)(C)c2ncccn2)c2cc(Nc3ccnc(Cl)c3C#N)ccc21]

A mixture of 6-amino-1-methyl-4-[(1-methyl-1-pyrimidin-2-yl-ethyl)amino]quinolin-2-one (Intermediate A3a, 19.1 mg, 0.062 mmol), 2,4-dichloropyridine-3-carbonitrile (12.9 mg, 0.074 mmol), NMP (0.62 mL) and triethylamine (17.3 uL, 0.12 mmol) in a sealed vial was purged with argon for 5 mins, then heated in the microwave for 1 h at 160° C. DMSO (0.7 mL) was added to the sample which was purified directly using reverse-phase C18 column eluting from 20-100% methanol in water (each containing 0.1% formic acid) to give the title compound (16 mg) as a pale orange solid. $^1$H NMR (500 MHz, DMSO-d6) δ 9.59 (s, 1H), 8.82 (d, J=4.9 Hz, 2H), 8.25 (d, J=2.3 Hz, 1H), 8.05 (d, J=6.2 Hz, 1H), 7.51 (dd, J=9.0, 2.3 Hz, 1H), 7.46 (d, J=9.0 Hz, 1H), 7.39 (t, J=4.9 Hz, 1H), 6.85 (s, 1H), 6.61 (d, J=6.2

Hz, 1H), 4.69 (s, 1H), 3.41 (s, 3H), 1.76 (s, 6H). LCMS (Method T4) Rt=2.64 mins, m/z 446.1482 [M+H]+ expected 446.1491 for $C_{23}H_{21}ClN_7O$.

The following tabulated examples in Table 3 were prepared by a method analogous to that used for the preparation of example 1a, starting from the intermediate(s) shown.

TABLE 3

Compounds prepared by a method analogous to that used for the preparation of Example 1a

| Example | Data and comments | Intermediate |
|---|---|---|
| Example 1b: 2-chloro-4-[[1-methyl-2-oxo-4-(1-pyrimidin-2-ylethylamino)-6-quinolyl]amino]pyridine-3-carbonitrile | 1H NMR (500 MHz, DMSO-d6) δ 9.62 (s, 1H), 8.79 (d, J = 4.9 Hz, 2H), 8.29 (d, J = 2.2 Hz, 1H), 8.05 (d, J = 6.2 Hz, 1H), 7.56-7.44 (m, 2H), 7.40 (t, J = 4.9 Hz, 1H), 7.23 (d, J = 7.0 Hz, 1H), 6.61 (d, J = 6.2 Hz, 1H), 5.27 (s, 1H), 4.74 (app quin, J = 6.9 Hz, 1H), 3.46 (s, 3H), 1.60 (d, J = 6.9 Hz, 3H). LCMS (Method T4) Rt = 2.55 mins, m/z 432.1329 [M + H]+ expected 432.1334 for $C_{22}H_{19}ClN_7O$. | 6-amino-1-methyl-4-(1-pyrimidin-2-ylethylamino)quinolin-2-one (Intermediate A1b). |
| Example 1c: 2-chloro-4-[[1-[2-(2,5-dioxopyrrolidin-1-yl)ethyl]-2-oxo-4-(1-pyrimidin-2-ylethylamino)-6-quinolyl]amino]pyridine-3-carbonitrile | 1H NMR (500 MHz, Chloroform-d) δ 8.77 (d, J = 4.9 Hz, 2H), 8.07 (dd, J = 6.1, 0.7 Hz, 1H), 7.61 (d, J = 2.4 Hz, 1H), 7.55 (d, J = 8.9 Hz, 1H), 7.49 (dd, J = 8.9, 2.4 Hz, 1H), 7.26 (t, J = 4.9 Hz, 1H), 7.08 (s, 1H), 6.69 (d, J = 6.1 Hz, 1H), 6.54 (d, J = 6.4 Hz, 1H), 5.74 (s, 1H), 4.85 (app. quin., J = 6.6 Hz, 1H), 4.50-4.44 (m, 2H), 3.94-3.87 (m, 2H), 2.66 (s, 4H), 1.65 (d, J = 6.7 Hz, 3H). LCMS (Method T4) Rt = 2.31 mins, m/z 543.1665 [M + H]+ expected 543.1660 for $C_{27}H_{24}ClN_8O_3$. | 1-[2-[6-amino-2-oxo-4-(1-pyrimidin-2-ylethylamino)-1-quinolyl]ethyl]pyrrolidine-2,5-dione (Intermediate A1c). |
| Example 1d: 2-chloro-4-[[2-oxo-4-(1-pyrimidin-2-ylethylamino)-1-(tetrahydropyran-4-ylmethyl)-6-quinolyl]amino]pyridine-3-carbonitrile | 1H NMR (500 MHz, Chloroform-d) δ 8.77 (d, J = 4.9 Hz, 2H), 8.08 (d, J = 6.1 Hz, 1H), 7.60 (d, J = 2.3 Hz, 1H), 7.44 (dd, J = 9.0, 2.3 Hz, 1H), 7.40 (d, J = 9.0 Hz, 1H), 7.27 (t, J = 4.9 Hz, 1H), 7.03 (s, 1H), 6.68 (d, J = 6.1 Hz, 1H), 6.46 (d, J = 6.4 Hz, 1H), 5.83 (s, 1H), 4.89 (app. quin., J = 6.6 Hz, 1H), 4.21 (br. s, 2H), 4.02-3.91 (m, 2H), 3.36-3.26 (m, 2H), 2.15-2.04 (m, 1H), 1.66 (d, J = 6.7 Hz, 3H), 1.62-1.53 (m, 4H). LCMS (Method T4) Rt = 2.47 mins, m/z 516.1921 [M + H]+ expected 516.1915 for $C_{27}H_{27}ClN_7O_2$. | 6-amino-4-(1-pyrimidin-2-ylethylamino)-1-(tetrahydropyran-4-ylmethyl)quinolin-2-one (Intermediate A1d). |

TABLE 3-continued

Compounds prepared by a method analogous to that used for the preparation of Example 1a

| Example | Data and comments | Intermediate |
| --- | --- | --- |
| Example 1e: 2-chloro-4-[[1-methyl-2-oxo-4-[1-(1H-1,2,4-triazol-3-yl)ethylamino]-6-quinolyl]amino]pyridine-3-carbonitrile | $^1$H NMR (600 MHz, DMSO-d6) δ 13.87 (br. s, 1H), 9.60 (br. s, 1H), 8.41 (s, 1H), 8.21 (d, J = 1.9 Hz, 1H), 8.03 (d, J = 6.2 Hz, 1H), 7.52-7.46 (m, 2H), 7.07 (br. s, 1H), 6.60 (d, J = 6.2 Hz, 1H), 5.48 (s, 1H), 4.81 (br. s, 1H), 3.49 (s, 3H), 1.59 (d, J = 6.8 Hz, 3H). LCMS (Method T4) Rt = 2.45 mins m/z 421.1272 [M + H]$^+$ expected 421.1287 for $C_{20}H_{18}ClN_8O$. | 6-amino-1-methyl-4-[1-(1H-1,2,4-triazol-3-yl)ethylamino]quinolin-2-one (Intermediate A1e). |
| Example 1f: trans-2-chloro-4-[[4-[(3-hydroxycyclobutyl)amino]-1-methyl-2-oxo-6-quinolyl]amino]pyridine-3-carbonitrile | $^1$H NMR (500 MHz, Methanol-d$_4$) δ 8.05 (d, J = 2.4 Hz, 1H), 7.98 (d, J = 6.2 Hz, 1H), 7.64 (d, J = 9.0 Hz, 1H), 7.57 (dd, J = 9.0, 2.4 Hz, 1H), 6.69 (d, J = 6.2 Hz, 1H), 5.46 (s, 1H), 4.49-4.41 (m, 1H), 4.11-4.03 (m, 1H), 3.67 (s, 3H), 2.48-2.33 (m, 4H). LCMS (Method T4) Rt = 2.49 mins, m/z 396.1233 [M + H]$^+$ expected 396.1222 for $C_{20}H_{19}ClN_5O_2$. | trans-6-amino-4-[(3-hydroxycyclobutyl)amino]-1-methyl-quinolin-2-one (Intermediate A1f). |
| Example 1g: 2-chloro-4-[[1-methyl-2-oxo-4-[[(3S)-tetrahydrofuran-3-yl]amino]-6-quinolyl]amino]pyridine-3-carbonitrile | $^1$H NMR (500 MHz, Methanol-d$_4$) δ 8.07 (d, J = 2.3 Hz, 1H), 7.98 (d, J = 6.2 Hz, 1H), 7.66 (d, J = 9.0 Hz, 1H), 7.58 (dd, J = 9.0, 2.3 Hz, 1H), 6.68 (d, J = 6.2 Hz, 1H), 5.68 (s, 1H), 4.25-4.19 (m, 1H), 4.02-3.95 (m, 2H), 3.88-3.82 (m, 2H), 3.69 (s, 3H), 2.40-2.32 (m, 1H), 2.11-2.03 (m, 1H); LCMS (Method T4) Rt = 2.52 min, m/z calculated for $C_{20}H_{19}ClN_5O_2^+$ [M + H]$^+$: 396.1222, Found: 396.1212. | 6-amino-1-methyl-4-[[(3S)-tetrahydrofuran-3-yl]amino]quinolin-2-one (Intermediate A4o) |
| Example 1h: 2-chloro-4-[[1-methyl-4-[1-(5-methyl-1,2,4-oxadiazol-3-yl)ethylamino]-2-oxo-6-quinolyl]amino]pyridine-3-carbonitrile | $^1$H NMR (500 MHz, Chloroform-d) δ 8.03 (d, J = 6.0 Hz, 1H), 7.61 (d, J = 2.3 Hz, 1H), 7.44 (dd, J = 9.0, 2.3 Hz, 1H), 7.39 (d, J = 9.0 Hz, 1H), 7.12 (s, 1H), 6.58 (d, J = 6.0 Hz, 1H), 5.83 (s, 1H), 5.53 (d, J = 7.3 Hz, 1H), 4.88 (app. quin., J = 6.9 Hz, 1H), 3.63 (s, 3H), 2.57 (s, 3H), 1.71 (d, J = 6.8 Hz, 3H). LCMS (Method T4) Rt = 2.56 mins, m/z 436.1262 [M + H]$^+$ expected 436.1283 for $C_{21}H_{19}ClN_7O_2$. | 6-amino-1-methyl-4-[1-(5-methyl-1,2,4-oxadiazol-3-yl)ethylamino]quinolin-2-one (Intermediate A2a) |

TABLE 3-continued

Compounds prepared by a method analogous to that used for the preparation of Example 1a

| Example | Data and comments | Intermediate |
|---|---|---|
| Example 1i: 2-chloro-4-[[1-methyl-4-[1-(4-methylpyrimidin-2-yl)ethylamino]-2-oxo-6-quinolyl]amino]pyridine-3-carbonitrile | $^1$H NMR (500 MHz, Chloroform-d) δ 8.58 (d, J = 5.1 Hz, 1H), 8.07 (d, J = 6.0, 1H), 7.59 (d, J = 2.2 Hz, 1H), 7.44 (dd, J = 9.0, 2.2 Hz, 1H), 7.41 (d, J = 9.0 Hz, 1H), 7.09 (d, J = 5.1 Hz, 1H), 7.00 (s, 1H), 6.66 (d, J = 6.0 Hz, 1H), 6.50 (d, J = 6.4 Hz, 1H), 5.83 (s, 1H), 4.84 (app. quin., J = 6.6 Hz, 1H), 3.66 (s, 3H), 2.56 (s, 3H), 1.64 (d, J = 6.7 Hz, 3H). LCMS (Method T4) Rt = 2.63 mins, m/z 446.1471 [M + H]$^+$ expected 446.1491 for $C_{23}H_{21}ClN_7O$. | 6-amino-1-methyl-4-[1-(4-methylpyrimidin-2-yl)ethylamino]quinolin-2-one (Intermediate A1i) |
| Example 1j: 2-chloro-4-[[1-methyl-2-oxo-4-(1-pyrazin-2-ylethylamino)-6-quinolyl]amino]pyridine-3-carbonitrile | $^1$H NMR (500 MHz, DMSO-d$_6$) δ 9.63 (s, 1H), 8.71 (d, J = 1.6 Hz, 1H), 8.61 (dd, J = 2.5, 1.6 Hz, 1H), 8.54 (d, J = 2.5 Hz, 1H), 8.26 (d, J = 2.1 Hz, 1H), 8.05 (d, J = 6.2 Hz, 1H), 7.53 (dd, J = 9.0, 2.1 Hz, 1H), 7.50 (d, J = 9.0 Hz, 1H), 7.24 (d, J = 6.9 Hz, 1H), 6.66 (d, J = 6.2 Hz, 1H), 5.30 (s, 1H), 4.82 (app. quin., J = 6.9 Hz, 1H), 3.47 (s, 3H), 1.61 (d, J = 6.9 Hz, 3H). LCMS (Method T4) Rt = 2.56 mins, m/z 432.1316 [M + H]$^+$ expected 432.1334 for $C_{22}H_{19}ClN_7O$. | 6-amino-1-methyl-4-(1-pyrazin-2-ylethylamino)quinolin-2-one (Intermediate A1j). |
| Example 1k: 2-chloro-4-[[4-[(3-hydroxy-1-methyl-propyl)amino]-1-methyl-2-oxo-quinazolin-6-yl]amino]pyridine-3-carbonitrile | $^1$H NMR (500 MHz, Methanol-d$_4$) δ 8.11 (d, J = 2.3 Hz, 1H), 7.99 (d, J = 6.2 Hz, 1H), 7.66 (dd, J = 9.0, 2.3 Hz, 1H), 7.54 (d, J = 9.0 Hz, 1H), 6.74 (d, J = 6.2 Hz, 1H), 4.60 (app. sex., J = 6.7 Hz, 1H), 3.67-3.55 (m, 5H), 1.83 (app. q, J = 6.5 Hz, 2H), 1.31 (d, J = 6.6 Hz, 3H). LCMS (Method T4) Rt = 2.29 mins, m/z 399.1320 [M + H]$^+$ expected 399.1331 for $C_{19}H_{20}ClN_6O_2$. | 6-amino-4-[(3-hydroxy-1-methyl-propyl)amino]-1-methyl-quinazolin-2-one (Intermediate A1s). |
| Example 1l: 2-chloro-4-[[4-[(2-hydroxy-1-methyl-ethyl)amino]-1-methyl-2-oxo-quinazolin-6-yl]amino]pyridine-3-carbonitrile | $^1$H NMR (500 MHz, Methanol-d$_4$) δ 8.12 (d, J = 2.4 Hz, 1H), 8.00 (d, J = 6.2 Hz, 1H), 7.66 (dd, J = 9.0, 2.4 Hz, 1H), 7.55 (d, J = 9.0 Hz, 1H), 6.72 (d, J = 6.2 Hz, 1H), 4.60-4.50 (m, 1H), 3.69-3.59 (m, 5H), 1.28 (d, J = 6.8 Hz, 3H). LCMS (Method T4) Rt = 2.26 mins, m/z 385.1162 [M + H]$^+$ expected 385.1174 for $C_{18}H_{18}ClN_6O_2$ | 6-amino-4-[(2-hydroxy-1-methyl-ethyl)amino]-1-methyl-quinazolin-2-one A1t). |

TABLE 3-continued

Compounds prepared by a method analogous to that used for the preparation of Example 1a

| Example | Data and comments | Intermediate |
| --- | --- | --- |
| Example 1m: 2-chloro-4-[[1-methyl-4-[1-(5-methylisoxazol-3-yl)ethylamino]-2-oxo-6-quinolyl]amino]pyridine-3-carbonitrile | $^1$H NMR (500 MHz, Methanol-d$_4$) δ 8.11 (d, J = 2.3 Hz, 1H), 7.98 (d, J = 6.2 Hz, 1H), 7.63 (d, J = 9.0 Hz, 1H), 7.58 (dd, J = 9.0, 2.3 Hz, 1H), 6.71 (d, J = 6.2 Hz, 1H), 6.10 (app. d, J = 0.9 Hz, 1H), 5.69 (s, 1H), 4.85-4.80 (m, 1H), 3.64 (s, 3H), 2.36 (d, J = 0.9 Hz, 3H), 1.65 (d, J = 6.9 Hz, 3H). LCMS (Method T4) Rt = 2.65 mins, m/z 435.1314 [M + H]$^+$ expected 435.1331 for C$_{22}$H$_{20}$ClN$_6$O$_2$. | 6-amino-1-methyl-4-[1-(5-methylisoxazol-3-yl)ethylamino]quinolin-2-one (Intermediate A2o). |
| Example 1n: 2-chloro-4-[[4-[(2-hydroxy-1-methyl-ethyl)amino]-2-oxo-1H-quinazolin-6-yl]amino]pyridine-3-carbonitrile | $^1$H NMR (500 MHz, Methanol-d$_4$) δ 8.07 (d, J = 2.2 Hz, 1H), 7.99 (d, J = 6.2 Hz, 1H), 7.55 (dd, J = 8.7, 2.2 Hz, 1H), 7.32 (d, J = 8.7 Hz, 1H), 6.70 (d, J = 6.2 Hz, 1H), 4.62-4.52 (m, 1H), 3.65 (d, J = 5.7 Hz, 2H), 1.28 (d, J = 6.8 Hz, 3H). LCMS (Method T4) Rt = 2.08 mins, m/z 371.1009 [M + H]$^+$ expected 371.1018 for C$_{17}$H$_{16}$ClN$_6$O$_2$ | 6-amino-4-[(2-hydroxy-1-methyl-ethyl)amino]-1H-quinazolin-2-one (Intermediate A2n). |
| Example 1o: 2-chloro-4-[[4-(ethylamino)-1-[2-(2-methoxyethoxy)ethyl]-2-oxo-6-quinolyl]amino]pyridine-3-carbonitrile | $^1$H NMR (500 MHz, Chloroform-d) δ 7.97 (d, J = 6.1 Hz, 1H), 7.63-7.58 (m, 2H), 7.37 (dd, J = 9.1, 2.3 Hz, 1H), 7.32 (s, 1H), 6.59 (d, J = 6.1 Hz, 1H), 5.66 (s, 1H), 5.30 (t, J = 4.9 Hz, 1H), 4.43 (t, J = 6.2 Hz, 2H), 3.78 (t, J = 6.2 Hz, 2H), 3.61-3.55 (m, 2H), 3.48-3.44 (m, 2H), 3.30 (s, 3H), 3.25-3.19 (m, 2H), 1.33 (t, J = 7.2 Hz, 3H). LCMS (Method T4) Rt = 2.66 mins, m/z 442.1637 [M + H]$^+$ expected 442.1640 for C$_{22}$H$_{25}$ClN$_5$O$_3$. | 6-amino-4-(ethylamino)-1-[2-(2-methoxyethoxy)ethyl[quinolin-2-one (Intermediate A5). |
| Example 1p: 2-chloro-4-[[1-methyl-4-(1-oxazol-2-ylethylamino)-2-oxo-6-quinolyl]amino]pyridine-3-carbonitrile | $^1$H NMR (500 MHz, Methanol-d$_4$) δ 8.14 (d, J = 2.3 Hz, 1H), 7.99 (d, J = 6.3 Hz, 1H), 7.87 (d, J = 0.9 Hz, 1H), 7.65 (d, J = 9.0 Hz, 1H), 7.59 (dd, J = 9.0, 2.3 Hz, 1H), 7.13 (d, J = 0.9 Hz, 1H), 6.72 (d, J = 6.3 Hz, 1H), 5.67 (s, 1H), 4.98 (q, J = 7.0 Hz, 1H), 3.66 (s, 3H), 1.73 (d, J = 7.0 Hz, 3H). LCMS (Method T4) Rt = 2.56 mins, m/z 421.1169 [M + H]$^+$ expected 421.1174 for C$_{21}$H$_{18}$ClN$_6$O$_2$. | 6-amino-1-methyl-4-(1-oxazol-2-ylethylamino)quinolin-2-one (Intermediate A1u). |

TABLE 3-continued

Compounds prepared by a method analogous to that used for the preparation of Example 1a

| Example | Data and comments | Intermediate |
| --- | --- | --- |
| Example 1q: 2-chloro-4-[[1-methyl-2-oxo-4-(1-pyrimidin-4-ylethylamino)-6-quinolyl]amino]pyridine-3-carbonitrile | $^{1}$H NMR (500 MHz, Chloroform-d) δ 9.21 (d, J = 1.4 Hz, 1H), 8.72 (d, J = 5.2 Hz, 1H), 8.06 (d, J = 6.1 Hz, 1H), 7.63 (d, J = 2.2 Hz, 1H), 7.48 (dd, J = 9.0, 2.2 Hz, 1H), 7.43 (d, J = 9.0 Hz, 1H), 7.36 (dd, J = 5.2, 1.4 Hz, 1H), 7.09 (s, 1H), 6.63 (d, J = 6.1 Hz, 1H), 6.21 (d, J = 6.1 Hz, 1H), 5.71 (s, 1H), 4.73 (app. quin., J = 6.6 Hz, 1H), 3.65 (s, 3H), 1.63 (d, J = 6.7 Hz, 3H). LCMS (Method T4) Rt = 2.35 mins, m/z 432.1328 (M + H)$^{+}$ expected 432.1339 for $C_{22}H_{19}ClN_{7}O$ | 6-amino-1-methyl-4-(1-pyrimidin-4-ylethylamino)quinolin-2-one (Intermediate A1k) |
| Example 1r: 2-chloro-4-[[1-[2-(2,5-dioxopyrrolidin-1-yl)ethyl]-4-(ethylamino)-2-oxo-6-quinolyl]amino]pyridine-3-carbonitrile | $^{1}$H NMR (500 MHz, Methanol-d$_{4}$) δ 7.99 (d, J = 6.3 Hz, 1H), 7.97 (d, J = 2.4 Hz, 1H), 7.74 (d, J = 9.0 Hz, 1H), 7.57 (dd, J = 9.0, 2.4 Hz, 1H), 6.72 (d, J = 6.3 Hz, 1H), 5.56 (s, 1H), 4.52 (t, J = 5.8 Hz, 2H), 3.87 (t, J = 5.8 Hz, 2H), 3.27 (q, J = 7.2 Hz, 2H), 2.61 (s, 4H), 1.31 (t, J = 7.2 Hz, 3H). LCMS (Method T4) Rt = 2.51 mins, m/z 465.1421 [M + H]$^{+}$ expected 465.1436 for $C_{23}H_{22}ClN_{6}O_{3}$. | 1-[2-[6-amino-4-(ethylamino)-2-oxo-1-quinolyl]ethyl]pyrrolidine-2,5-dione (Intermediate A7) |
| Example 1s: 2-chloro-4-[[1-methyl-2-oxo-4-(1-thiazol-2-ylethylamino)-6-quinolyl]amino]pyridine-3-carbonitrile | $^{1}$H NMR (500 MHz, DMSO-d$_{6}$) δ 9.64 (s, 1H), 8.22 (d, J = 2.1 Hz, 1H), 8.05 (d, J = 6.2 Hz, 1H), 7.75 (d, J = 3.2 Hz, 1H), 7.60 (d, J = 3.2 Hz, 1H), 7.54 (dd, J = 9.0, 2.1 Hz 1H), 7.52 (d, J = 9.0 Hz, 1H), 7.33 (d, J = 6.7 Hz, 1H), 6.64 (d, J = 6.2 Hz, 1H), 5.46 (s, 1H), 5.05 (app. quin., J = 6.8 Hz, 1H), 3.49 (s, 3H), 1.66 (d, J = 6.8 Hz, 3H). LCMS (Method T4) Rt = 2.62 mins, m/z 437.0938 [M + H]$^{+}$ expected 437.0946 for $C_{21}H_{18}ClN_{6}OS$. | 6-amino-1-methyl-4-(1-thiazol-2-ylethylamino)quinolin-2-one (Intermediate A1l). |

TABLE 3-continued

Compounds prepared by a method analogous to that used for the preparation of Example 1a

| Example | Data and comments | Intermediate |
| --- | --- | --- |
| Example 1t: 2-chloro-4-[[1-methyl-2-oxo-4-[1-(1H-pyrazol-3-yl)ethylamino]-6-quinolyl]amino]pyridine-3-carbonitrile | $^1$H NMR (500 MHz, Methanol-d$_4$) δ 8.13 (d, J = 2.3 Hz, 1H), 7.98 (d, J = 6.2 Hz, 1H), 7.62 (d, J = 9.0 Hz, 1H), 7.57 (dd, J = 9.0, 2.3 Hz, 1H), 7.54 (d, J = 2.2 Hz, 1H), 6.72 (d, J = 6.2 Hz, 1H), 6.25 (d, J = 2.2 Hz, 1H), 5.65 (s, 1H), 4.84 (q, J = 6.8 Hz, 1H), 3.64 (s, 3H), 1.65 (d, J = 6.8 Hz, 3H). LCMS (Method T4) Rt = 2.55 mins, m/z 420.1328 [M + H]$^+$ expected 420.1334 for C$_{21}$H$_{19}$ClN$_7$O. | 6-amino-1-methyl-4-[1-(1H-pyrazol-3-yl)ethylamino]quinolin-2-one (Intermediate A1m). |
| Example 1u: 6-chloro-5-cyano-N-methyl-4-[[1-methyl-4-[(1-methyl-1-pyrimidin-2-yl-ethyl)amino]-2-oxo-6-quinolyl]amino]pyridine-2-carboxamide | $^1$H NMR (500 MHz, Methanol-d$_4$) δ 8.79 (d, J = 4.9 Hz, 2H), 8.16 (d, J = 2.1 Hz, 1H), 7.63 (d, J = 8.9 Hz, 1H), 7.60 (dd, J = 8.9, 2.1 Hz, 1H), 7.36 (t, J = 4.9 Hz, 1H), 7.35 (s, 1H), 5.08 (s, 1H), 3.60 (s, 3H), 2.88 (s, 3H), 1.85 (s, 6H). LCMS (Method X4) Rt = 2.58 mins, m/z 503.1717 [M + H]$^+$ expected 503.1711 for C$_{25}$H$_{24}$ClN$_8$O$_2$. | 6-amino-1-methyl-4-[(1-methyl-1-pyrimidin-2-yl-ethyl)amino]quinolin-2-one (Intermediate A3a) and 4,6-dichloro-5-cyano-N-methyl-pyridine-2-carboxamide (Intermediate E1A) |
| Example 1v: 6-chloro-5-cyano-N-methyl-4-[[1-methyl-2-oxo-4-(1-pyrimidin-2-ylethylamino)-6-quinolyl]amino]pyridine-2-carboxamide | $^1$H NMR (500 MHz, Chloroform-d) δ 8.76 (d, J = 4.9 Hz, 2H), 7.79 (d, J = 5.1 Hz, 1H), 7.60 (d, J = 2.3 Hz, 1H), 7.50 (s, 1H), 7.45 (dd, J = 8.9, 2.3 Hz, 1H), 7.41 (d, J = 8.9 Hz, 1H), 7.24 (t, J = 4.9 Hz, 1H), 7.20 (s, 1H), 6.42 (d, J = 6.6 Hz, 1H), 5.82 (s, 1H), 4.89 (app. quin, J = 6.6 Hz, 1H), 3.66 (s, 3H), 2.97 (d, J = 5.1 Hz, 3H), 1.67 (d, J = 6.7 Hz, 3H). LCMS (Method X4) Rt = 2.41 mins, m/z 489.1562 [M + H]$^+$ expected 489.1554 for C$_{24}$H$_{22}$ClN$_8$O$_2$. | 6-amino-1-methyl-4-(1-pyrimidin-2-ylethylamino)quinolin-2-one (Intermediate A1b) and 4,6-dichloro-5-cyano-N-methyl-pyridine-2-carboxamide (Intermediate E1a) |

TABLE 3-continued

Compounds prepared by a method analogous to that used for the preparation of Example 1a

| Example | Data and comments | Intermediate |
|---|---|---|
| Example 1w: 2-chloro-6-methyl-4-[[1-methyl-2-oxo-4-(1-pyrimidin-2-ylethylamino)-6-quinolyl]amino]pyridine-3-carbonitrile | $^1$H NMR (500 MHz, Chloroform-d) δ 8.78 (d, J = 4.9 Hz, 2H), 7.57 (d, J = 2.2 Hz, 1H), 7.46 (dd, J = 9.0, 2.2 Hz, 1H), 7.43 (d, J = 9.0 Hz, 1H), 7.27 (t, J = 4.9 Hz, 1H), 6.86 (s, 1H), 6.46 (s, 1H), 6.42 (d, J = 6.5 Hz, 1H), 5.85 (s, 1H), 4.90 (app. quin., J = 6.6 Hz, 1H), 3.68 (s, 3H), 2.38 (s, 3H), 1.67 (d, J = 6.7 Hz, 3H). LCMS (Method X4) Rt = 2.47 mins, m/z 446.1485 [M + H]$^+$ expected 446.1496 for $C_{23}H_{21}ClN_7O$ | 6-amino-1-methyl-4-(1-pyrimidin-2-ylethylamino)quinolin-2-one (Intermediate A1b) and 2,4-dichloro-6-methyl-pyridine-3-carbonitrile |
| Example 1x: 2-chloro-4-[[8-methyl-5-[(1-methyl-1-pyrimidin-2-yl-ethyl)amino]-7-oxo-1,8-naphthyridin-3-yl]amino]pyridine-3-carbonitrile | $^1$H NMR (500 MHz, Chloroform-d) δ 8.79 (d, J = 4.9 Hz, 2H), 8.53 (d, J = 2.4 Hz, 1H), 8.11 (d, J = 6.0 Hz, 1H), 7.92 (d, J = 2.4 Hz, 1H), 7.25 (t, J = 4.9 Hz, 1H), 7.04 (s, 1H), 6.81 (s, 1H), 6.61 (d, J = 6.0 Hz, 1H), 5.73 (s, 1H), 3.73 (s, 3H), 1.87 (s, 6H). LCMS (Method T4) Rt = 2.59 mins, m/z 447.1443 [M + H]$^+$ expected 447.1443 for $C_{22}H_{20}ClN_8O$. | 6-amino-1-methyl-4-[(1-methyl-1-pyrimidin-2-yl-ethyl)amino]-1,8-naphthyridin-2-one (Intermediate A9). |

Example 2a; 6-Chloro-5-cyano-4-[[4-(1-cyclopropylethylamino)-1-methyl-2-oxo-6-quinolyl]amino]pyridine-2-carboxylic acid

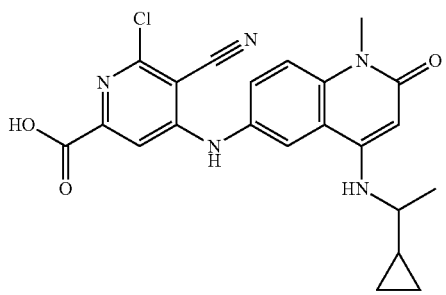 [SMILES: CC(Nc1cc(=O)n(C)c2ccc(Nc3cc(C(=O)O)nc(Cl)c3C#N)cc12)C1CC1]

A mixture of 6-amino-4-(1-cyclopropylethylamino)-1-methyl-quinolin-2-one (Intermediate A1g, 11.6 mg, 0.0452 mmol), 4,6-dichloro-5-cyano-pyridine-2-carboxylic acid (14.7 mg, 0.0678 mmol) and NMP (0.5 mL) in a sealed vial was purged with argon for 5 mins, then heated in the microwave for 2 h at 100° C. DMSO (0.8 mL) was added to the sample which was purified directly using reverse-phase C18 column eluting from 20-100% methanol in water (containing 0.1% formic acid) to give 6-chloro-5-cyano-4-[[4-(1-cyclopropylethylamino)-1-methyl-2-oxo-6-quinolyl]amino]pyridine-2-carboxylic acid (11 mg) as a pale yellow solid. $^1$H NMR (500 MHz, DMSO-d$_6$) δ 13.7 (v. br, 1H), 9.90 (s, 1H), 8.13 (d, J=2.2 Hz, 1H), 7.55 (dd, J=9.0, 2.2 Hz, 1H), 7.51 (d, J=9.0 Hz, 1H), 7.17 (s, 1H), 6.59 (d, J=7.9 Hz, 1H), 5.46 (s, 1H), 3.52 (s, 3H), 3.13 (app. sex., J=7.0 Hz, 1H), 1.23 (d, J=6.3 Hz, 3H), 1.12-1.02 (m, 1H), 0.49-0.43 (m, 1H), 0.43-0.36 (m, 1H), 0.29-0.17 (m, 2H). LCMS (Method T4) Rt=2.65 mins, m/z 438.1340 [M+H]$^+$ expected 438.1327 for $C_{22}H_{21}ClN_5O_3$.

The following tabulated examples were prepared by a method analogous to that used for the preparation of example 2a, starting from the intermediate shown in Table 4.

TABLE 4

Compounds prepared by a method analogous to that used for the preparation of Example 2a.

| Example | Data and comments | Intermediate |
| --- | --- | --- |
| Example 2b: 6-chloro-5-cyano-4-[[4-(cyclopropylamino)-1-methyl-2-oxo-6-quinolyl]amino]pyridine-2-carboxylic acid | $^1$H NMR (500 MHz, DMSO-$d_6$) δ 13.75 (br. s, 1H), 9.86 (s, 1H), 7.97 (s, 1H), 7.53-7.52 (m, 2H), 7.19-7.17 (m, 1H), 7.15 (s, 1H), 5.81 (s, 1H), 3.54 (s, 3H), 2.50-2.43 (m, 1H), 0.86-0.72 (m, 2H), 0.56-0.49 (m, 2H). LCMS (Method T4) Rt = 2.50 mins, m/z 410.1011 [M + H]$^+$ expected 410.1014 for $C_{20}H_{17}ClN_5O_3$. | 6-amino-4-(cyclopropyl-amino)-1-methyl-quinolin-2-one (Intermediate A1h). |
| Example 2c: 6-chloro-5-cyano-4-[[1-methyl-4-[(1-methylcyclopropyl)amino]-2-oxo-6-quinolyl]amino]pyridine-2-carboxylic acid | $^1$H NMR (500 MHz, DMSO-$d_6$) δ 13.73 (s, 1H), 9.84 (s, 1H), 7.96 (s, 1H), 7.55-7.49 (m, 2H), 7.26 (s, 1H), 7.17 (s, 1H), 5.75 (s, 1H), 3.53 (s, 3H), 1.34 (s, 3H), 0.78-0.67 (m, 4H). LCMS (Method T4) Rt = 2.56 mins, m/z 424.1179 [M + H]$^+$ expected 424.1171 for $C_{21}H_{19}ClN_5O_3$. | 6-amino-1-methyl-4-[(1-methylcyclo-propyl)amino]quinolin-2-one (Intermediate A1o). |
| Example 2d: 6-chloro-5-cyano-4-[[1-methyl-4-[(1-methylcyclopentyl)amino]-2-oxo-6-quinolyl]amino]pyridine-2-carboxylic acid | $^1$H NMR (500 MHz, DMSO-$d_6$) δ 13.48 (br. s, 1H), 9.83 (s, 1H), 8.14-8.10 (m, 1H), 7.58-7.46 (m, 2H), 7.16 (s, 1H), 6.12 (s, 1H), 5.57 (s, 1H), 3.52 (s, 3H), 2.19-2.10 (m, 2H), 1.74-1.57 (m, 6H), 1.42 (s, 3H). LCMS (Method T4) Rt = 2.78 mins, m/z 452.1496 [M + H]$^+$ expected 452.1484 for $C_{23}H_{23}ClN_5O_3$. | 6-amino-1-methyl-4-[(1-methylcyclo-pentyl)amino]quinolin-2-one (Intermediate A1n). |

Example 3a; (R)-2-((6-((2-Chloro-3-cyanopyridin-4-yl)amino)-1-methyl-2-oxo-1,2-dihydroquinolin-4-yl)amino)-N-((1-methyl-1H-pyrazol-4-yl)methyl) propanamide

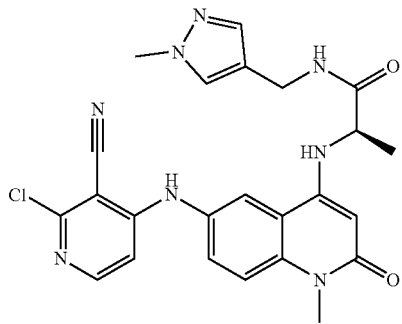 [SMILES: C[C@@H](Nc1cc(=O)n(C)c2ccc(Nc3ccnc(Cl)c3C#N)cc12)C(=O)NCc1cnn(C)c1]

A suspension of 2,4-dichloropyridine-3-carbonitrile (6.8 mg, 0.04 mmol), (2R)-2-[(6-amino-1-methyl-2-oxo-4-quinolyl)amino]-N-[(1-methylpyrazol-4-yl)methyl]propanamide (10 mg, 0.028 mmol) and DIPEA (0.015 mL, 0.085 mmol) in NMP (1.50 mL) was stirred under microwave irradiation at 160° C. for 1 h. Product was purified by preparative HPLC to give the title compound as a brown solid (2.5 mg). $^1$H NMR (500 MHz, Methanol-d4) δ 8.12 (d, J=2.3 Hz, 1H), 8.00 (d, J=6.2 Hz, 1H), 7.65 (d, J=9.0 Hz, 1H), 7.59 (dd, J=9.0, 2.3 Hz, 1H), 7.51 (s, 1H), 7.38 (s, 1H), 6.74 (d, J=6.3 Hz, 1H), 5.56 (s, 1H), 4.26 (m, 2H), 4.09 (q, J=7.0 Hz, 1H), 3.84 (s, 3H), 3.68 (s, 3H), 1.55 (d, J=7.0 Hz, 3H). LCMS (Method T4) Rt=2.49 mins, m/z 491.1704 [M+H]$^+$ expected 491.1705 for $C_{24}H_{24}ClN_8O_2$.

The following tabulated examples in Table 5 were prepared by an analogous method to that used for the preparation of example 3a, using the intermediates shown. Examples 3f and 3 g required 3 hours under microwave irradiation at 160° C., and example 3m required 2 hours under microwave irradiation at 160° C. Examples 3p, 3n, 3o, 3j used triethylamine instead of DIPEA. Example 3o required further purification by preparative TLC.

TABLE 5

| Compounds prepared by a method analogous to that used for the preparation of Example 3a. | | |
| --- | --- | --- |
| Example | Data and comments | Intermediate |
| Example 3b: (R)-2-((6-((2-chloro-3-cyanopyridin-4-yl)amino)-1-methyl-2-oxo-1,2-dihydroquinolin-4-yl)amino)-N-(2-hydroxyethyl)propanamide | $^1$H NMR (500 MHz, Methanol-d$_4$) δ 8.12 (d, J = 2.2 Hz, 1H), 8.00 (d, J = 6.2 Hz, 1H), 7.66 (d, J = 9.0 Hz, 1H), 7.60 (dd, J = 9.0, 2.2 Hz, 1H), 6.74 (d, J = 6.2 Hz, 1H), 5.59 (s, 1H), 4.15-4.09 (m, 1H), 3.68 (s, 3H), 3.65-3.52 (m, 2H), 3.40-3.30 (m, 2H), 1.57 (d, J = 7.0 Hz, 3H). LCMS (Method T4) Rt = 2.41 mins, m/z 441.1432 [M + H]$^+$ expected 441.1436 for $C_{21}H_{22}ClN_6O_3$ | Intermediate A2b: (2R)-2-[(6-amino-1-methyl-2-oxo-4-quinolyl)amino]-N-(2-hydroxyethyl) propanamide |
| Example 3c: 2-Chloro-4-((1-methyl-4-((1-(3-methyl-1H-1,2,4-triazol-5-yl)ethyl)amino)-2-oxo-1,2-dihydroquinolin-6-yl)amino)nicotinonitrile | $^1$H NMR (500 MHz, Methanol-d$_4$) δ 8.16 (d, J = 2.2 Hz, 1H), 8.01 (d, J = 6.2 Hz, 1H), 7.65 (d, J = 9.0 Hz, 1H), 7.59 (dd, J = 9.0, 2.2 Hz, 1H), 6.75 (d, J = 6.3 Hz, 1H), 5.64 (s, 1H), 4.84 (m, 1H), 3.66 (s, 3H), 2.41 (s, 3H), 1.69 (d, J = 6.9 Hz, 3H). LCMS (Method T4) Rt = 2.48 mins, m/z 435.1433 [M + H]$^+$ expected 435.1443 for $C_{21}H_{20}ClN_8O$. | Intermediate A2c: 6-amino-1-methyl-4-[1-(3-methyl-1H-1,2,4-triazol-5-yl)ethylamino] quinolin-2-one |

TABLE 5-continued

Compounds prepared by a method analogous to that used for the preparation of Example 3a.

| Example | Data and comments | Intermediate |
| --- | --- | --- |
| Example 3d: (R)-2-((6-((2-Chloro-3-cyanopyridin-4-yl)amino)-1-methyl-2-oxo-1,2-dihydroquinolin-4-yl)amino)-N-cyclopentylpropanamide | $^1$H NMR (500 MHz, Methanol-d$_4$) δ 8.10 (d, J = 2.2 Hz, 1H), 8.00 (d, J = 6.2 Hz, 1H), 7.65 (d, J = 9.0 Hz, 1H), 7.59 (dd, J = 9.0, 2.2 Hz, 1H), 6.73 (d, J = 6.2 Hz, 1H), 5.58 (s, 1H), 4.14-4.07 (m, 2H), 3.68 (s, 3H), 1.97-1.90 (m, 2H), 1.77-1.70 (m, 2H), 1.66-1.57 (m, 2H), 1.53 (d, J = 6.9 Hz, 3H), 1.52-1.43 (m, 2H). LCMS (Method T4) Rt = 2.74 mins, m/z 465.1792 [M + H]$^+$ expected 465.1800 for $C_{24}H_{26}ClN_6O_2$. | Intermediate A2d: (R)-2-((6-amino-1-methyl-2-oxo-1,2-dihydroquinolin-4-yl)amino)-N-cyclopentylpropanamide |
| Example 3e: (R)-2-((6-((2-chloro-3-cyanopyridin-4-yl)amino)-1-methyl-2-oxo-1,2-dihydroquinolin-4-yl)amino)-N-(2-methoxyethyl)propanamide | $^1$H NMR (500 MHz, Methanol-d$_4$) δ 8.11 (d, J = 2.2 Hz, 1H), 7.99 (d, J = 6.2 Hz, 1H), 7.63 (d, J = 9.0 Hz, 1H), 7.58 (dd, J = 9.0, 2.2 Hz, 1H), 6.73 (d, J = 6.2 Hz, 1H), 5.58 (s, 1H), 4.12 (q, J = 7.0 Hz, 1H), 3.67 (s, 3H), 3.46-3.43 (m, 2H), 3.42-3.38 (m, 1H), 3.36-3.33 (m, 1H), 3.32 (s, 3H), 1.56 (d, J = 7.0 Hz, 3H). LCMS (Method T4) Rt = 2.50 mins, m/z 455.1585 [M + H]$^+$ expected 455.1593 for $C_{22}H_{24}ClN_6O_3$. | Intermediate A2e: (R)-2-((6-amino-1-methyl-2-oxo-1,2-dihydroquinolin-4-yl)amino)-N-(2-methoxyethyl)propanamide |
| Example 3f: (R)-N-(But-3-yn-1-yl)-2-((6-((2-chloro-3-cyanopyridin-4-yl)amino)-1-methyl-2-oxo-1,2-dihydroquinolin-4-yl)amino)propanamide | $^1$H NMR (600 MHz, Methanol-d$_4$) δ 8.13 (d, J = 2.3 Hz, 1H), 8.01 (d, J = 6.3 Hz, 1H), 7.67 (d, J = 9.0 Hz, 1H), 7.61 (dd, J = 9.0, 2.3 Hz, 1H), 6.75 (d, J = 6.3 Hz, 1H), 5.59 (s, 1H), 4.11 (q, J = 6.9 Hz, 1H), 3.69 (s, 3H), 3.41 (dt, J = 13.5, 6.8 Hz, 1H), 3.33-3.27 (m, 1H), 2.40 (td, J = 6.9, 2.6 Hz, 2H), 2.26 (t, J = 2.6 Hz, 1H), 1.58 (d, J = 6.9 Hz, 3H). LCMS (Method T4) Rt = 2.53 mins, m/z 449.1488 [M + H]$^+$ expected 449.1487 for $C_{23}H_{22}ClN_6O_2$. | Intermediate A2f: (R)-2-((6-amino-1-methyl-2-oxo-1,2-dihydroquinolin-4-yl)amino)-N-(but-3-yn-1-yl)propanamide |

TABLE 5-continued

Compounds prepared by a method analogous to that used for the preparation of Example 3a.

| Example | Data and comments | Intermediate |
| --- | --- | --- |
| Example 3g: (S)-2-Chloro-4-((4-((1-hydroxypropan-2-yl)amino)-1-methyl-2-oxo-1,2-dihydroquinolin-6-yl)amino)nicotinonitrile 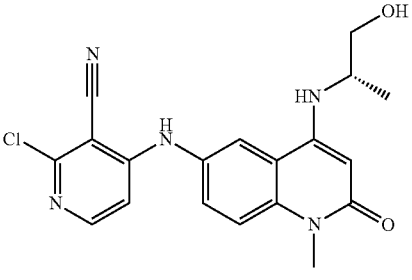 [SMILES: C[C@@H](CO)Nc1cc(=O)n(C)c2ccc(Nc3ccnc(Cl)c3C#N)cc12] | $^1$H NMR (600 MHz, DMSO-d6) δ 9.58 (s, 1H), 8.08 (s, 1H), 8.03 (d, J = 6.2 Hz, 1H), 7.51 (s, 2H), 6.60 (d, J = 6.2 Hz, 1H), 6.38 (d, J = 7.3 Hz, 1H), 5.55 (s, 1H), 3.61-3.50 (m, 2H), 3.52 (s, 3H), 3.37-3.34 (m, 1H), 3.33 (s, broad, 1H), 1.19 (d, J = 6.3 Hz, 3H). LCMS (Method T4) Rt = 2.48 mins, m/z 384.1213 [M + H]$^+$ expected 384.1222 for $C_{19}H_{19}ClN_5O_2$. | Intermediate A2g: (S)-6-Amino-4-((1-hydroxypropan-2-yl)amino)-1-methylquinolin-2(1H)-one |
| Example 3h: 2-((6-((2-Chloro-3-cyanopyridin-4-yl)amino)-1-methyl-2-oxo-1,2-dihydroquinolin-4-yl)amino)-N-ethyl-2-methylpropanamide 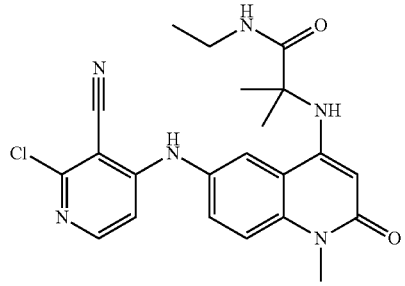 [SMILES: CCNC(=O)C(C)(C)Nc1cc(=O)n(C)c2ccc(Nc3ccnc(Cl)c3C#N)cc12] | $^1$H NMR (500 MHz, Methanol-d$_4$) δ 8.12 (d, J = 2.2 Hz, 1H), 8.00 (d, J = 6.2 Hz, 1H), 7.67 (d, J = 9.0 Hz, 1H), 7.60 (dd, J = 9.0, 2.2 Hz, 1H), 6.73 (d, J = 6.2 Hz, 1H), 5.51 (s, 1H), 3.68 (s, 3H), 3.23 (q, J = 7.2 Hz, 2H), 1.60 (s, 6H), 1.07 (t, J = 7.2 Hz, 3H). LCMS (Method T4) Rt = 2.52 mins, m/z 439.1626 [M + H]$^+$ expected 439.1644 for $C_{22}H_{24}ClN_6O_2$. | Intermediate A2h: 2-((6-amino-1-methyl-2-oxo-1,2-dihydroquinolin-4-yl)amino)-N-ethyl-2-methylpropanamide |
| Example 3i: (R)-2-((6-((2-Chloro-3-cyanopyridin-4-yl)amino)-1-methyl-2-oxo-1,2-dihydroquinolin-4-yl)amino)-N-(4-methoxycyclohexyl)propanamide 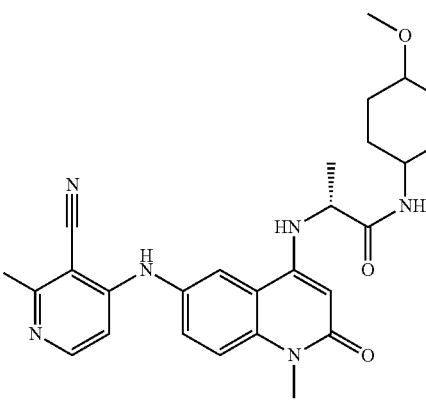 | $^1$H NMR (500 MHz, Methanol-d$_4$) δ 8.12 (d, J = 2.2 Hz, 1H), 8.01 (d, J = 6.2 Hz, 1H), 7.67 (d, J = 9.0 Hz, 1H), 7.61 (dd, J = 9.0, 2.2 Hz, 1H), 6.74 (d, J = 6.2 Hz, 1H), 5.58 (s, 1H), 4.08 (q, J = 6.9 Hz, 1H), 3.69 (s, 3H), 3.66-3.64 (m, 1H), 3.35 (s, 3H), 3.24-3.16 (m, 1H), 2.13-2.05 (m, 2H), 2.00-1.92 (m, 2H), 1.55 (d, J = 6.9 Hz, 3H), 1.34-1.20 (m, 4H). LCMS (Method T4) Rt = 2.65 mins, m/z 509.2089 [M + H]$^+$ expected 509.2062 for $C_{26}H_{30}ClN_6O_3$. | Intermediate A2i: (R)-2-((6-amino-1-methyl-2-oxo-1,2-dihydroquinolin-4-yl)amino)-N-(4-methoxycyclohexyl)propanamide |

TABLE 5-continued

Compounds prepared by a method analogous to that used for the preparation of Example 3a.

| Example | Data and comments | Intermediate |
| --- | --- | --- |
| Example 3j: (R)-2-chloro-4-((4-((1-hydroxypropan-2-yl)amino)-1-methyl-2-oxo-1,2-dihydroquinolin-6-yl)amino)nicotinonitrile 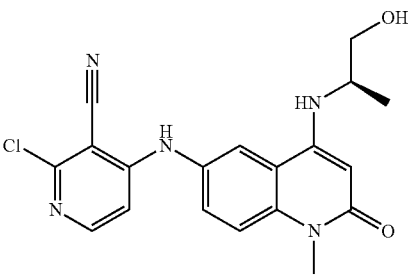 [SMILES: C[C@H](CO)Nc1cc(=O)n(C)c2ccc(Nc3ccnc(Cl)c3C#N)cc12] | $^1$H NMR (500 MHz, DMF-$d_7$) δ 8.23 (d, J = 2.2 Hz, 1H), 8.10 (d, J = 6.2 Hz, 1H), 7.64 (dd, J = 8.9, 2.2 Hz, 1H), 7.58 (d, J = 8.9 Hz, 1H), 6.79 (d, J = 6.2 Hz, 1H), 6.62-6.55 (m, broad, 1H), 5.65 (s, 1H), 3.74-3.68 (m, 1H + 1H), 3.63 (s, 3H), 3.56-3.50 (m, 1H), 1.29 (d, J = 6.2 Hz, 3H); LCMS (Method T4) Rt = 2.48 mins, m/z 384.1256 [M + H]$^+$ expected 384.1222 for $C_{19}H_{19}ClN_5O_2$. | Intermediate A2s: (R)-6-amino-4-((1-hydroxypropan-2-yl)amino)-1-methylquinolin-2(1H)-one |
| Example 3k: rac-2-((6-((2-Chloro-3-cyanopyridin-4-yl)amino)-1-methyl-2-oxo-1,2-dihydroquinolin-4-yl)amino)-N-ethylpropanamide 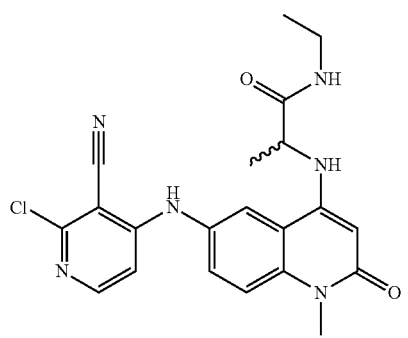 [SMILES: CCNC(=O)C(C)Nc1cc(=O)n(C)c2ccc(Nc3ccnc(Cl)c3C#N)cc12] | $^1$H NMR (500 MHz, Methanol-$d_4$) δ 8.12 (d, J = 2.2 Hz, 1H), 8.01 (d, J = 6.2 Hz, 1H), 7.67 (d, J = 9.0 Hz, 1H), 7.60 (dd, J = 9.0, 2.2 Hz, 1H), 6.75 (d, J = 6.2 Hz, 1H), 5.57 (s, 1H), 4.07 (q, J = 6.9 Hz, 1H), 3.69 (s, 3H), 3.25 (q, J = 7.2, 2H), 1.55 (d, J = 6.9 Hz, 3H), 1.14 (t, J = 7.2 Hz, 3H). LCMS (Method T4) Rt = 2.51 mins, m/z 425.1476 [M + H]$^+$ expected 425.1487 for $C_{21}H_{22}ClN_6O_2$. | Intermediate A2k: 2-((6-amino-1-methyl-2-oxo-1,2-dihydroquinolin-4-yl)amino)-N-ethylpropanamide |
| Example 3l: 2-Chloro-4-((1-methyl-4-((1-(5-methyl-1,3,4-oxadiazol-2-yl)ethyl)amino)-2-oxo-1,2-dihydroquinolin-6-yl)amino)nicotinonitrile 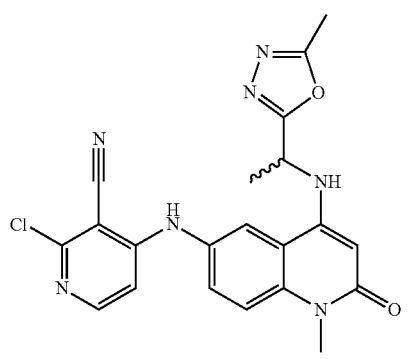 [SMILES: Cc1nnc(C(C)Nc2cc(=O)n(C)c3ccc(Nc4ccnc(Cl)c4C#N)cc23)o1] | $^1$H NMR (500 MHz, Methanol-$d_4$) δ 8.11 (d, J = 2.2 Hz, 1H), 8.00 (d, J = 6.2 Hz, 1H), 7.67 (d, J = 9.0 Hz, 1H), 7.60 (dd, J = 9.0, 2.2 Hz, 1H), 6.72 (d, J = 6.2 Hz, 1H), 5.78 (s, 1H), 5.12 (q, J = 6.9 Hz, 1H), 3.68 (s, 3H), 2.52 (s, 3H), 1.78 (d, J = 6.9 Hz, 3H). LCMS (Method T4) Rt = 2.48 mins, m/z 436.1271 [M + H]$^+$ expected 436.1283 for $C_{21}H_{19}ClN_7O_2$. | Intermediate A2l: 6-amino-1-methyl-4-((1-(5-methyl-1,3,4-oxadiazol-2-yl)ethyl)amino)quinolin-2(1H)-one |

TABLE 5-continued

Compounds prepared by a method analogous to that used for the preparation of Example 3a.

| Example | Data and comments | Intermediate |
|---|---|---|
| Example 3m: (R)-2-((6-((2-Chloro-3-cyanopyridin-4-yl)amino)-1-methyl-2-oxo-1,2-dihydroquinolin-4-yl)amino)-N-(2-(1-methyl-1H-pyrazol-4-yl)ethyl)propanamide 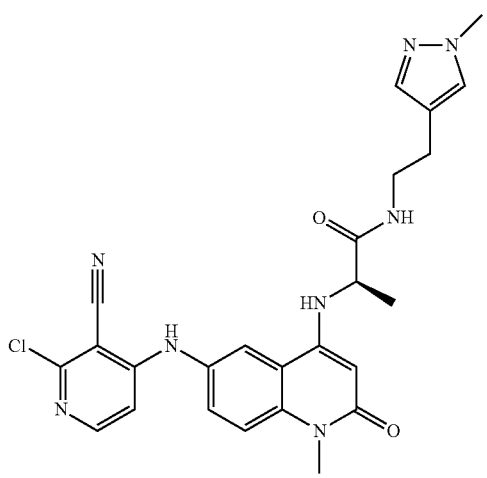 [SMILES: C[C@@H](Nc1cc(=O)n(C)c2ccc(Nc3ccnc(Cl)c3C#N)cc12)C(=O)NCCc1cnn(C)c1] | $^1$H NMR (500 MHz, Methanol-d$_4$) δ 8.10 (d, J = 2.2 Hz, 1H), 8.01 (d, J = 6.2 Hz, 1H), 7.67 (d, J = 9.0 Hz, 1H), 7.61 (dd, J = 9.0, 2.2 Hz, 1H), 7.40 (s, 1H), 7.29 (s, 1H), 6.74 (d, J = 6.2 Hz, 1H), 5.56 (s, 1H), 4.05 (q, J = 7.0 Hz, 1H), 3.78 (s, 3H), 3.70 (s, 3H), 3.51-3.37 (m, 2H), 2.74-2.58 (m, 2H), 1.52 (d, J = 7.0 Hz, 3H). LCMS (Method T2) Rt = 1.32 min; m/z 505 [M + H]$^+$. | Intermediate A2m: (R)-2-((6-amino-1-methyl-2-oxo-1,2-dihydroquinolin-4-yl)amino)-N-(2-(1-methyl-1H-pyrazol-4-yl)ethyl)propanamide |
| Example 3n: (S)-2-Chloro-4-((4-((4-hydroxybutan-2-yl)amino)-1-methyl-2-oxo-1,2-dihydroquinolin-6-yl)amino)nicotinonitrile 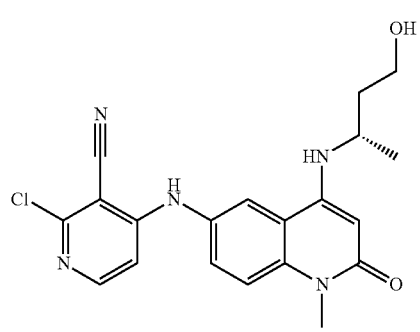 [SMILES: C[C@@H](CCO)Nc1cc(=O)n(C)c2ccc(Nc3ccnc(Cl)c3C#N)cc12] | $^1$H NMR (500 MHz, Methanol-d$_4$) δ 8.00 (d, J = 2.2 Hz, 1H), 7.99 (d, J = 6.3 Hz, 1H), 7.65 (d, J = 9.0 Hz, 1H), 7.58 (dd, J = 9.0, 2.2 Hz, 1H), 6.70 (d, J = 6.3 Hz, 1H), 5.75 (s, 1H), 3.90-3.83 (m, 1H), 3.75-3.65 (m, 1H + 1H), 3.69 (s, 3H), 1.99-1.91 (m, 1H), 1.85-1.78 (m, 1H), 1.31 (d, J = 6.4 Hz, 3H); LCMS (Method T4) Rt = 2.53 mins, m/z 398.1385 [M + H]$^+$ expected 398.1378 for $C_{20}H_{21}ClN_5O_2$. | Intermediate A2q: (S)-6-Amino-4-((4-hydroxybutan-2-yl)amino)-1-methylquinolin-2(1H)-one |
| Example 3o: (R)-2-((6-((2-chloro-3-cyanopyridin-4-yl)amino)-1-methyl-2-oxo-1,2-dihydroquinolin-4-yl)amino)-N-methylpropanamide 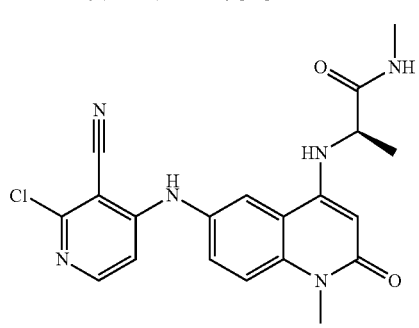 [SMILES: CNC(=O)[C@@H](C)Nc1cc(=O)n(C)c2ccc(Nc3ccnc(Cl)c3C#N)cc12] | $^1$H NMR (500 MHz, Methanol-d$_4$) δ 8.14 (d, J = 2.2 Hz, 1H), 8.02 (d, J = 6.2 Hz, 1H), 7.68 (d, J = 9.0 Hz, 1H), 7.62 (dd, J = 9.0, 2.2 Hz, 1H), 6.76 (d, J = 6.2 Hz, 1H), 5.57 (s, 1H), 4.09 (q, J = 7.0 Hz, 1H), 3.70 (s, 3H), 2.78 (s, 3H), 1.56 (d, J = 7.0 Hz, 3H); LCMS (Method T4) Rt = 2.43 mins, m/z 411.1337 [M + H]$^+$ expected 411.1331 for $C_{20}H_{20}ClN_6O_2$. | Intermediate A2r: (R)-2-((6-amino-1-methyl-2-oxo-1,2-dihydroquinolin-4-yl)amino)-N-methylpropanamide |

TABLE 5-continued

Compounds prepared by a method analogous to that used for the preparation of Example 3a.

| Example | Data and comments | Intermediate |
| --- | --- | --- |
| Example 3p: (R)-2-((6-((2-chloro-3-cyanopyridin-4-yl)amino)-2-oxo-1,2-dihydroquinolin-4-yl)amino)-N-methylpropanamide 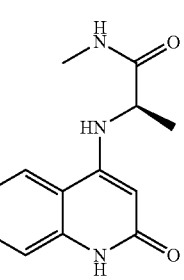 | $^1$H NMR (500 MHz, Methanol-$d_4$) δ 8.08 (d, J = 2.2 Hz, 1H), 8.00 (d, J = 6.2 Hz, 1H), 7.49 (dd, J = 8.7, 2.2 Hz, 1H), 7.43 (d, J = 8.7 Hz, 1H), 6.72 (d, J = 6.2 Hz, 1H), 5.45 (s, 1H), 4.09 (q, J = 7.0 Hz, 1H), 2.77 (s, 3H), 1.56 (d, J = 7.0 Hz, 3H); LCMS (Method T4) Rt = 2.30 mins, m/z 397.1167 [M + H]$^+$ expected 397.1174 for $C_{19}H_{18}ClN_6O_2$. | Intermediate A2p: (R)-2-((6-amino-2-oxo-1,2-dihydroquinolin-4-yl)amino)-N-methylpropanamide |

Example 4; 6-Chloro-5-cyano-4-[[4-(ethylamino)-1-methyl-2-oxo-6-quinolyl]amino]pyridine-2-carboxylic acid

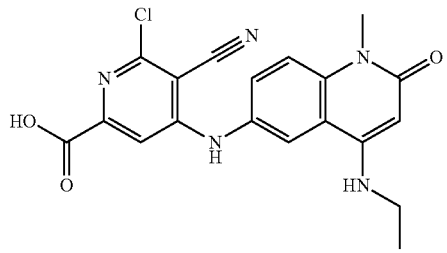 [SMILES: CCNc1cc(=O)n(C)c2ccc(Nc3cc(C(=O)O)nc(Cl)c3C#N)cc12]

A mixture of 4,6-dichloro-5-cyano-pyridine-2-carboxylic acid (8.2 mg, 0.038 mmol) and 6-amino-4-(ethylamino)-1-methyl-quinolin-2-one (Intermediate A6, 10.4 mg, 0.048 mmol) and NMP (0.38 mL) in a sealed vial was purged with argon for 5 mins, then heated in a heating block for 2 h at 100° C. Water (5 mL) was added to the reaction mixture. The resulting precipitate was filtered, washed with water (2×5 mL), methanol (3 mL) and diethyl ether (5 mL) affording 6-chloro-5-cyano-4-[[4-(ethylamino)-1-methyl-2-oxo-6-quinolyl]amino]pyridine-2-carboxylic acid (6 mg, 37%) as an orange solid. $^1$H NMR (500 MHz, DMSO-$d_6$) δ 13.68 (br s, 1H), 9.92 (s, 1H), 8.06-8.02 (m, 1H), 7.54-7.52 (m, 2H), 7.18 (s, 1H), 6.80 (t, J=5.0 Hz, 1H), 5.45 (s, 1H), 3.53 (s, 3H), 3.20-3.14 (m, 2H), 1.21 (t, J=7.1 Hz, 3H); LCMS (Method T4) Rt=2.45 mins, m/z 398.0992 [M+H]$^+$ expected 398.1014 for $C_{19}H_{17}ClN_5O_3^+$.

Example 5; 6-Chloro-5-cyano-4-[[4-(ethylamino)-1-methyl-2-oxo-6-quinolyl]amino]-N-methyl-pyridine-2-carboxamide

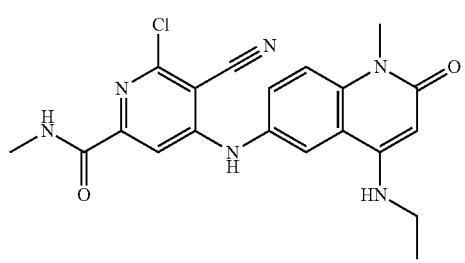 [SMILES: CCNc1cc(=O)n(C)c2ccc(Nc3cc(C(=O)NC)nc(Cl)c3C#N)cc12]

A mixture of 4,6-dichloro-5-cyano-N-methyl-pyridine-2-carboxamide (Intermediate E1a, 11 mg, 0.048 mmol), 6-amino-4-(ethylamino)-1-methyl-quinolin-2-one (Intermediate A6 as a 0.2M solution in NMP, 0.30 mL, 0.06 mmol) and DIPEA (8.8 uL, 0.051 mmol) was diluted with additional NMP (0.2 mL) and heated to 120° C. for 2 h, then purified by preparative HPLC (40-100% methanol in water, 0.1% formic acid modifier) to give the title compound (6.5 mg). $^1$H NMR (500 MHz, DMSO-$d_6$) δ 9.90 (s, 1H), 8.64 (q, J=5.6 Hz, 1H), 8.02 (s, 1H), 7.52 (m, 2H), 7.14 (s, 1H), 6.80 (t, J=5.1 Hz, 1H), 5.45 (s, 1H), 3.53 (s, 3H), 3.17 (qd, J=7.2, 4.9 Hz, 2H), 2.73 (d, J=4.8 Hz, 3H), 1.21 (t, J=7.2 Hz, 3H). LCMS (Method X4) Rt 2.43 min; m/z 411.1342 expected 411.1336 for $C_{20}H_{20}ClN_6O_2$ [M+H]$^+$.

Example 6a; 6-[(2,3-Dichloro-4-pyridyl)amino]-1-methyl-4-(1-pyrimidin-2-ylethylamino)quinolin-2-one

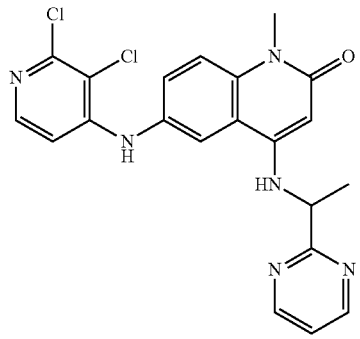 [SMILES: CC(Nc1cc(=O)n(C)c2ccc(Nc3ccnc(Cl)c3Cl)cc12)c1ncccn1]

To a mixture of 6-amino-1-methyl-4-(1-pyrimidin-2-ylethylamino)quinolin-2-one (Intermediate A1b, 8.0 mg, 0.027 mmol), 2,3-dichloro-4-iodo-pyridine (8.9 mg, 0.033 mmol), cesium carbonate (70.6 mg, 0.22 mmol), Pd$_2$(dba)$_3$ (2.5 mg, 0.0027 mmol), Xantphos (9.4 mg, 0.016 mmol) in a sealed vial was added toluene (0.42 mL) and DMF (0.13 mL) and the vial purged with argon for 5 mins. The vial was heated in the microwave at 80° C. for 1 h then diluted with water and extracted twice with ethyl acetate. Organic extracts were washed with brine then dried over magnesium sulfate. DMSO (0.8 mL) was added to the sample which was purified using reverse-phase C18 column eluting from 30-100% methanol in water (each containing 0.1% formic acid) to give the title compound (4.5 mg) as an off-white solid. ¹H NMR (500 MHz, Chloroform-d) δ 8.74 (d, J=4.9 Hz, 2H), 7.91 (d, J=5.7 Hz, 1H), 7.55 (d, J=2.3 Hz, 1H), 7.40 (dd, J=8.9, 2.3 Hz, 1H), 7.33 (d, J=8.9 Hz, 1H), 7.20 (t, J=4.9 Hz, 1H), 6.72 (s, 1H), 6.61 (d, J=5.7 Hz, 1H), 6.52 (d, J=6.6 Hz, 1H), 5.79 (s, 1H), 4.89 (app. quin., J=6.7 Hz, 1H), 3.63 (s, 3H), 1.67 (d, J=6.7 Hz, 3H). LCMS (Method X4) R$^t$ 2.56 min; m/z 441.1017 expected 441.0997 for $C_{21}H_{19}Cl_2N_6O$ [M+H]⁺.

The following tabulated examples in Table 6 were prepared by an analogous method to that used for the preparation of example 6a, using the intermediates shown.

TABLE 6

Compounds prepared by a method analogous to that used for the preparation of Example 6a.

| Example | Data and comments | Intermediate |
| --- | --- | --- |
| Example 6b: 6-((2,3-dichloropyridin-4-yl)amino)-1-methyl-4-((2-(pyrimidin-2-yl)propan-2-yl)amino)quinolin-2(1H)-one | ¹H NMR (500 MHz, Chloroform-d) δ 8.73 (d, J = 4.9 Hz, 2H), 7.92 (d, J = 5.7 Hz, 1H), 7.63 (d, J = 2.4 Hz, 1H), 7.38 (dd, J = 8.9, 2.4 Hz, 1H), 7.32 (d, J = 8.9 Hz, 1H), 7.17 (t, J = 4.9 Hz, 1H), 6.79 (s, 1H), 6.74 (s, 1H), 6.68 (d, J = 5.7 Hz, 1H), 5.60 (s, 1H), 3.60 (s, 3H), 1.86 (s, 6H). LCMS (Method T4) Rt = 2.76 mins, m/z 455.1129 [M + H]⁺ expected 455.1148 for $C_{22}H_{21}Cl_2N_6O$. | Intermediate A3a: 6-amino-1-methyl-4-((2-(pyrimidin-2-yl)propan-2-yl)amino)quinolin-2(1H)-one and 2,3-dichloro-4-iodo-pyridine |
| Example 6c: 6-((2,3-dichloropyridin-4-yl)amino)-1-methyl-4-((1-(pyrimidin-2-yl)ethyl)amino)quinazolin-2(1H)-one | ¹H NMR (500 MHz, Chloroform-d) δ 8.75-8.69 (m, 2H), 7.92-7.87 (m, 1H), 7.87-7.80 (m, 1H), 7.68 (d, J = 2.3 Hz, 1H), 7.53 (dt, J = 8.9, 2.7 Hz, 1H), 7.29-7.23 (m, 1H), 7.23-7.17 (m, 1H), 6.85 (s, 1H), 6.60 (t, J = 5.4 Hz, 1H), 5.67 (app. quin., J = 6.7 Hz, 1H), 3.62-3.57 (m, 3H), 1.66 (d, J = 6.7 Hz, 3H) LCMS (Method T4) Rt = 2.56 mins, m/z 442.0934 [M + H]⁺ expected 442.0944 for $C_{20}H_{18}Cl_2N_7O$. | Intermediate A4p: 6-amino-1-methyl-4-((1-(pyrimidin-2-yl)ethyl)amino) quinazolin-2(1H)-one and 2,3-dichloro-4-iodo-pyridine |
| Example 6d: (R)-4-((1-cyclopropylethyl)amino)-6-((2,3-dichloropyridin-4-yl)amino)-1-methylquinazolin-2(1H)-one | ¹H NMR (600 MHz, Chloroform-d) δ 7.96 (d, J = 2.4 Hz, 1H), 7.79 (d, J = 5.7 Hz, 1H), 7.48 (dd, J = 8.9, 2.3 Hz, 1H), 7.24 (d, J = 8.9 Hz, 1H), 7.08 (d, J = 8.0 Hz, 1H), 6.70 (s, 1H), 6.55 (d, J = 5.7 Hz, 1H), 3.95-3.85 (m, 1H), 3.59 (s, 3H), 1.28 (d, J = 6.6 Hz, 3H), 1.02-0.92 (m, 1H), 0.52-0.43 (m, 1H), 0.42-0.31 (m, 2H), 0.26-0.18 (m, 1H). LCMS (Method T4) Rt = 2.65 mins, m/z 404.1028 [M + H]⁺ expected 404.1039 for $C_{19}H_{20}Cl_2N_5O$. | Intermediate A4t: (R)-6-amino-4-((1-cyclopropylethyl)amino)-1-methylquinazolin-2(1H)-one and 2,3-dichloro-4-iodo-pyridine |

TABLE 6-continued

Compounds prepared by a method analogous to that used for the preparation of Example 6a.

| Example | Data and comments | Intermediate |
|---|---|---|
| Example 6e: 6-((2,3-dichloropyridin-4-yl)amino)-1-methyl-4-((1-(pyrimidin-2-yl)ethyl)amino)-1,8-naphthyridin-2(1H)-one 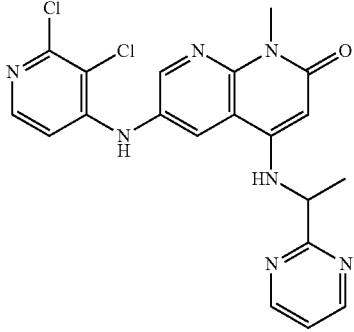 [SMILES: CC(Nc1cc(=O)n(C)c2ncc(Nc3ccnc(Cl)c3Cl)cc12)c1ncccn1] | $^1$H NMR (600 MHz, Methanol-d4) δ 8.80 (d, J = 4.9 Hz, 2H), 8.63 (d, J = 2.4 Hz, 1H), 8.61 (d, J = 2.4 Hz, 1H), 7.91 (d, J = 5.8 Hz, 1H), 7.40 (t, J = 4.9 Hz, 1H), 6.80 (d, J = 5.8 Hz, 1H), 5.52 (s, 1H), 4.92-4.88 (m, 1H), 3.71 (s, 3H), 1.71 (d, J = 6.9 Hz, 3H). LCMS (Method T4) Rt = 2.73 mins, m/z 442.0935 [M + H]$^+$ expected 442.0944 for $C_{20}H_{18}Cl_2N_7O$ | Intermediate A10b: 6-amino-1-methyl-4-(1-pyrimidin-2-ylethylamino)-1,8-naphthyridin-2-one and 2,3-dichloro-4-iodo-pyridine |
| Example 6f: (R)-4-((1-cyclopropylethyl)amino)-6-((2,3-dichloropyridin-4-yl)amino)-1-methyl-1,8-naphthyridin-2(1H)-one 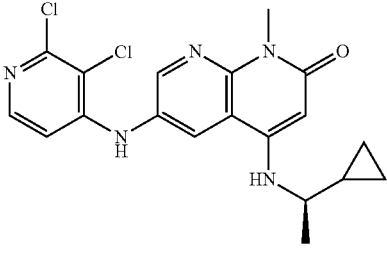 [SMILES: C[C@@H](Nc1cc(=O)n(C)c2ncc(Nc3ccnc(Cl)c3Cl)cc12)C1CC1] | $^1$H NMR (600 MHz, Methanol-d4) δ 8.60 (d, J = 2.4 Hz, 1H), 8.52 (d, J = 2.4 Hz, 1H), 7.89 (d, J = 5.8 Hz, 1H), 6.71 (d, J = 5.8 Hz, 1H), 5.67 (s, 1H), 3.76 (s, 3H), 3.19-3.07 (m, 1H), 1.36 (d, J = 6.4 Hz, 3H), 1.19-1.06 (m, 1H), 0.65-0.48 (m, 2H), 0.41-0.26 (m, 2H). LCMS (Method T4) Rt = 2.94 mins, m/z 404.1037 [M + H]$^+$ expected 404.1039 for $C_{19}H_{20}Cl_2N_5O$ | Intermediate A10a: 6-amino-4-[[(1R)-1-cyclopropylethyl]amino]-1-methyl-1,8-naphthyridin-2-one and 2,3-dichloro-4-iodo-pyridine |
| Example 6g: 1-(cyclopropylmethyl)-6-[(2,3-dichloro-4-pyridyl)amino]-4-(1-pyrimidin-2-ylethylamino)quinolin-2-one 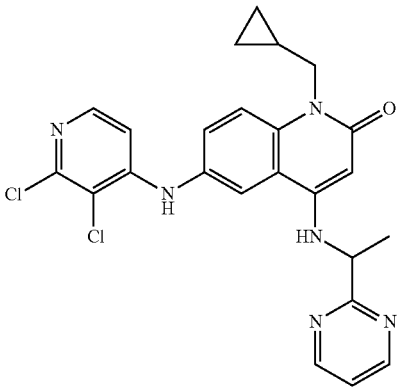 [SMILES: CC(Nc1cc(=O)n(CC2CC2)c2ccc(Nc3ccnc(Cl)c3Cl)cc12)c1ncccn1] | $^1$H NMR (500 MHz, Methanol-d$_4$) δ 8.80 (d, J = 4.9 Hz, 2H), 8.16 (d, J = 2.4 Hz, 1H), 7.87 (d, J = 5.8 Hz, 1H), 7.76 (d, J = 9.1 Hz, 1H), 7.60 (dd, J = 9.0, 2.4 Hz, 1H), 7.39 (t, J = 4.9 Hz, 1H), 6.80 (d, J = 5.8 Hz, 1H), 5.53 (s, 1H), 4.91-4.88 (m, 1H), 4.21 (d, J = 6.9 Hz, 2H), 1.70 (d, J = 6.9 Hz, 3H), 1.29-1.24 (m, 1H), 0.53-0.44 (m, 4H). LCMS (Method T4) Rt = 3.02 mins, m/z 481.1292 [M + H]$^+$ expected 481.1305 for $C_{24}H_{23}Cl_2N_6O$ | Intermediate A1w: 6-amino-1-(cyclopropyl-methyl)-4-((1-(pyrimidin-2-yl)ethyl)amino)quinolin-2(1H)-one and 2,3-dichloro-4-iodo-pyridine |

TABLE 6-continued

Compounds prepared by a method analogous to that used for the preparation of Example 6a.

| Example | Data and comments | Intermediate |
| --- | --- | --- |
| Example 6h: 6-((5-chloro-2-((2S,6R)-2,6-dimethylmorpholino)pyridin-4-yl)amino)-4-(((R)-1-cyclopropylethyl)amino)-1-methylquinolin-2(1H)-one 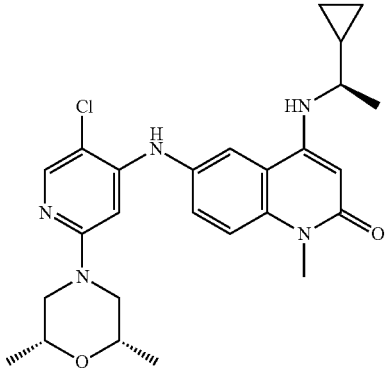 [SMILES: C[C@@H]1CN(c2cc(Nc3ccc4c(c3)c(N[C@H](C)C3CC3)cc(=O)n4C)c(Cl)cn2)C[C@H](C)O1] | 1H NMR (600 MHz, Chloroform-d) δ 8.03 (s, 1H), 7.51 (dd, J = 8.9, 2.3 Hz, 1H), 7.45 (d, J = 2.3 Hz, 1H), 7.42 (d, J = 8.9 Hz, 1H), 6.42 (s, 1H), 6.07 (s, 1H), 5.79 (s, 1H), 4.77-4.73 (m, 1H), 3.85-3.78 (m, 2H), 3.70 (s, 3H), 3.71-3.63 (m, 2H), 3.13-3.07 (m, 1H), 2.46-2.38 (m, 2H), 1.33 (d, J = 6.3 Hz, 3H), 1.22 (d, J = 6.3 Hz, 6H), 1.10-1.01 (m, 1H), 0.67-0.60 (m, 1H), 0.60-0.53 (m, 1H), 0.39-0.31 (m, 2H). LCMS (Method X4) Rt = 2.46 min, m/z 482.2320 [M + H]$^+$ expected 482.2323 for $C_{26}H_{33}ClN_5O_2$ | Intermediate A1a: (R)-6-amino-4-((1-cyclopropylethyl)amino)-1-methylquinolin-2(1H)-one and Intermediate E10c: (2S,6R)-4-(5-chloro-4-iodo-2-pyridyl)-2,6-dimethyl-morpholine |
| Example 6i: (R)-1-(5-chloro-4-((4-((1-cyclopropylethyl)amino)-1-methyl-2-oxo-1,2-dihydroquinolin-6-yl)amino)pyridin-2-yl)-N,N-dimethylpiperidine-4-carboxamide 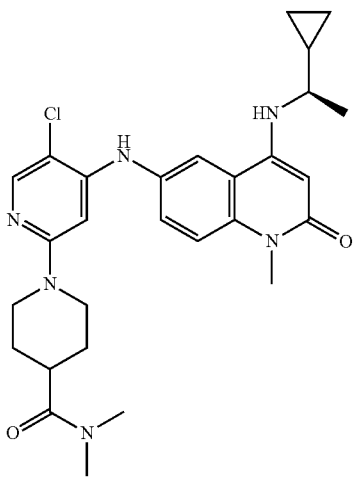 [SMILES: C[C@@H](Nc1cc(=O)n(C)c2ccc(Nc3cc(N4CCC(C(=O)N(C)C)CC4)ncc3Cl)cc12)C1CC1] | $^1$H NMR (600 MHz, Chloroform-d) δ 7.93 (s, 1H), 7.50 (d, J = 2.4 Hz, 1H), 7.44 (dd, J = 8.9, 2.3 Hz, 1H), 7.35 (d, J = 8.9 Hz, 1H), 6.38 (s, 1H), 6.05 (s, 1H), 5.70 (s, 1H), 5.10-4.96 (m, 1H), 4.16-4.04 (m, 2H), 3.66 (s, 3H), 3.07-3.01 (m, 4H), 2.91 (s, 3H), 2.82-2.74 (m, 2H), 2.70-2.64 (m, 1H), 1.81-1.72 (m, 2H), 1.71-1.65 (m, 2H), 1.28 (d, J = 6.3 Hz, 3H), 1.07-1.00 (m, 1H), 0.60-0.53 (m, 1H), 0.53-0.46 (m, 1H), 0.33-0.24 (m, 2H). LCMS (Method T4) Rt = 2.28 mins, m/z 523.2568 [M + H]$^+$ expected 523.2583 for $C_{28}H_{36}ClN_6O_2$ | Intermediate A1a: (R)-6-amino-4-((1-cyclopropylethyl)amino)-1-methylquinolin-2(1H)-one and Intermediate E10b: 1-(5-chloro-4-iodo-2-pyridyl)-N,N-dimethyl-piperidine-4-carboxamide |

TABLE 6-continued

Compounds prepared by a method analogous to that used for the preparation of Example 6a.

| Example | Data and comments | Intermediate |
| --- | --- | --- |
| Example 6j: 4-((2-(5-cyclopropylpyrimidin-2-yl)propan-2-yl)amino)-6-((2,3-dichloropyridin-4-yl)amino)-1-methylquinolin-2(1H)-one | $^1$H NMR (600 MHz, DMSO-d$_6$) δ 8.71 (s, 1H), 8.56 (s, 2H), 8.23 (d, J = 2.3 Hz, 1H), 7.88 (d, J = 5.7 Hz, 1H), 7.50 (dd, J = 8.9, 2.3 Hz, 1H), 7.45 (d, J = 8.9 Hz, 1H), 6.83 (s, 1H), 6.56 (d, J = 5.7 Hz, 1H), 4.71 (s, 1H), 3.42 (s, 3H), 1.96-1.90 (m, 1H), 1.73 (s, 6H), 1.05-1.00 (m, 2H), 0.86-0.82 (m, 2H); LCMS (Method X4) Rt = 2.97 mins, m/z 495.1465 [M + H]$^+$ expected 495.1467 for $C_{25}H_{25}Cl_2N_6O^+$. | Intermediate A4j: 6-amino-4-((2-(5-cyclopropyl-pyrimidin-2-yl)propan-2-yl)amino)-1-methylquinolin-2(1H)-one and 2,3-dichloro-4-iodo-pyridine |

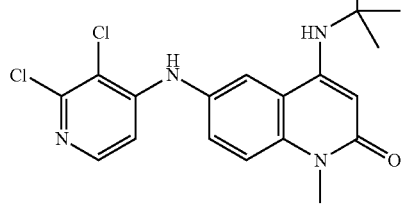

Example 7a: 2-Chloro-4-((4-((2-(5-((2R,6S)-2,6-dimethylmorpholino)pyrimidin-2-yl)propan-2-yl)amino)-1-methyl-2-oxo-1,2-dihydroquinolin-6-yl)amino)nicotinonitrile

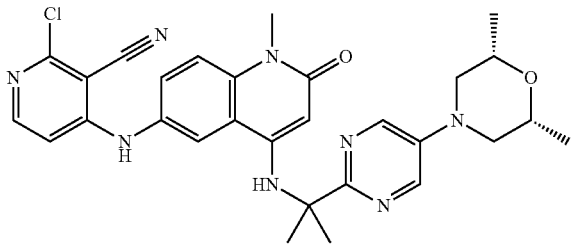 [SMILES: C[C@@H]1CN(c2cnc(C(C)(C)Nc3cc(=O)n(C)c4ccc(Nc5ccnc(Cl)c5C#N)cc34)nc2)C[C@H](C)O1]

To a 0.5-2 mL Biotage vial containing 6-amino-4-((2-(5-((2S,6R)-2,6-dimethylmorpholino)pyrimidin-2-yl)propan-2-yl)amino)-1-methylquinolin-2(1H)-one (Intermediate A8, 10.5 mg, 0.025 mmol) was added 2,4-dichloropyridine-3-carbonitrile (5.2 mg, 0.03 mmol), NMP (0.71 mL) and triethylamine (7 μL, 0.05 mmol). The vial was sealed and purged with argon for 5 mins. The vial was then heated in the microwave for 2 h at 120° C. DMSO (0.8 mL) was added to the sample which was purified by reverse-phase C18 column eluting from 30-100% methanol in water (containing 0.1% formic acid) to give 2-chloro-4-[[4-[[1-[5-[(2S,6R)-2,6-dimethylmorpholin-4-yl]pyrimidin-2-yl]-1-methyl-ethyl]amino]-1-methyl-2-oxo-6-quinolyl]amino]pyridine-3-carbonitrile (6 mg) as a pale brown solid. $^1$H NMR (600 MHz, DMSO-d$_6$) δ 9.57 (s, 1H), 8.47 (s, 2H), 8.22 (d, J=2.3 Hz, 1H), 8.04 (d, J=6.2 Hz, 1H), 7.50 (dd, J=8.9, 2.2 Hz, 1H), 7.45 (d, J=8.9 Hz, 1H), 6.75 (s, 1H), 6.61 (d, J=6.2 Hz, 1H), 4.77 (s, 1H), 3.75-3.64 (m, 4H), 3.42 (s, 3H), 2.34 (app. t, J=11.0 Hz, 2H), 1.72 (s, 6H), 1.14 (d, J=6.2 Hz, 6H). LCMS (Method T4) Rt=2.86 mins, m/z 559.2310 [M+H]$^+$ expected 559.2331 for $C_{29}H_{32}ClN_8O_2$.

The following tabulated examples in Table 7 were prepared by an analogous method to that used for the preparation of example 7a, using the quinolinone intermediate shown and 4,6-dichloro-5-cyano-N-methyl-pyridine-2-carboxamide (intermediate E1a).

TABLE 7

Compounds prepared by a method analogous to that used for the preparation of Example 7a.

| Example | Data | Intermediate |
| --- | --- | --- |
| Example 7b: 6-chloro-5-cyano-4-((4-((1-cyclopropylethyl)amino)-1-methyl-2-oxo-1,2-dihydroquinolin-6-yl)amino)-N-methylpicolinamide | $^1$H NMR (500 MHz, DMSO-d$_6$) δ 9.92 (s, 1H), 8.65 (q, J = 4.9 Hz, 1H), 8.12 (d, J = 1.8 Hz, 1H), 7.58-7.49 (m, 2H), 7.14 (s, 1H), 6.61 (d, J = 7.8 Hz, 1H), 5.47 (s, 1H), 3.53 (s, 3H), 3.13 (q, J = 7.2 Hz, 1H), 2.74 (d, J = 4.8 Hz, 3H), 1.24 (d, J = 6.3 Hz, 3H), 1.13-1.05 (m, 1H), 0.51-0.44 (m, 1H), 0.44-0.37 (m, 1H), 0.34-0.16 (m, 2H). LCMS (Method T4) Rt = 2.86 mins, m/z 451.1635 [M + H]$^+$ expected 451.1644 for $C_{23}H_{24}ClN_6O_2$ | Intermediate A1g: 6-amino-4-(1-cyclopropyl-ethylamino)-1-methyl-quinolin-2-one |

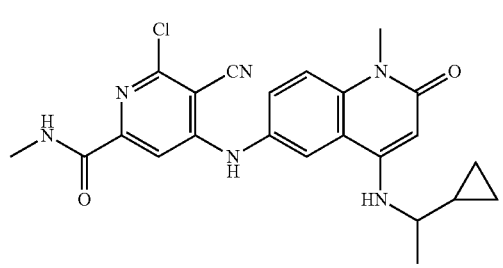 [SMILES: CNC(=O)c1cc(Nc2ccc3c(c2)c(NC(C)C2CC2)cc(=O)n3C)c(C#N)c(Cl)n1]

TABLE 7-continued

Compounds prepared by a method analogous to that used for the preparation of Example 7a.

| Example | Data | Intermediate |
| --- | --- | --- |
| Example 7c: 4-((4-(tert-butylamino)-1-methyl-2-oxo-1,2-dihydroquinolin-6-yl)amino)-6-chloro-5-cyano-N-methylpicolinamide | $^1$H NMR (500 MHz, DMSO-$d_6$) δ 9.85 (s, 1H), 8.65 (d, J = 5.0 Hz, 1H), 8.07 (s, 1H), 7.55-7.50 (m, 2H), 7.13 (s, 1H), 5.91 (s, 1H), 5.70 (s, 1H), 3.53 (s, 3H), 2.73 (d, J = 4.8 Hz, 3H), 1.42 (s, 9H). LCMS (Method T4) Rt = 2.86 mins, m/z 439.1635 [M + H]$^+$ expected 439.1644 for $C_{22}H_{24}ClN_6O_2$ | Intermediate A4c: 6-amino-4-(tert-butylamino)-1-methyl-quinolin-2-one |
| Example 7d: 6-chloro-5-cyano-4-[[4-[(2-methoxy-1,1-dimethyl-ethyl)amino]-1-methyl-2-oxo-6-quinolyl]amino]-N-methyl-pyridine-2-carboxamide | $^1$H NMR (500 MHz, Methanol-d4) δ 7.86 (d, J = 2.3 Hz, 1H), 7.68 (d, J = 9.0 Hz, 1H), 7.62 (dd, J = 9.0, 2.3 Hz, 1H), 7.38 (s, 1H), 6.01 (s, 1H), 3.71 (s, 3H), 3.53 (s, 2H), 3.41 (s, 3H), 2.89 (s, 3H), 1.49 (s, 6H). LCMS (Method T4) Rt = 2.84 mins, m/z 469.1734 [M + H]$^+$ expected 469.1749 for $C_{23}H_{26}ClN_6O_3$ | Intermediate A4e: 6-amino-4-[(2-methoxy-1,1-dimethyl-ethyl)amino]-1-methyl-quinolin-2-one |

Example 8a: 6-(Azetidine-1-carbonyl)-2-chloro-4-((1-methyl-2-oxo-4-((2-(pyrimidin-2-yl)propan-2-yl)amino)-1,2-dihydroquinolin-6-yl)amino)nicotinonitrile

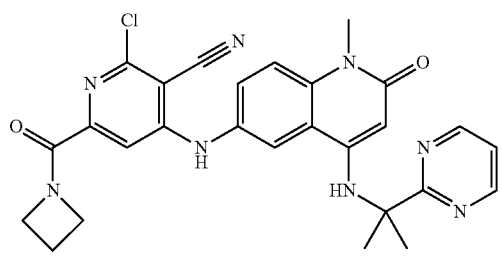 [SMILES: Cn1c(=O)cc(NC(C)(C)c2ncccn2)c2cc(Nc3cc(C(=O)N4CCC4)nc(Cl)c3C#N)ccc21]

T3P (50 wt % in EtOAc, 44 mg, 0.069 mmol), DIPEA (26 uL, 0.15 mmol) and azetidine (4 uL, 0.055 mmol) were added sequentially to a solution of 6-chloro-5-cyano-4-((1-methyl-2-oxo-4-((2-(pyrimidin-2-yl)propan-2-yl)amino)-1,2-dihydroquinolin-6-yl)amino)picolinic acid (Example 9f, 24 mg, 0.050 mmol) in DMF (0.26 mL). The reaction mixture was stirred at rt for 16 h. Water (10 mL) was added and the aqueous mixture was extracted with EtOAc (3×10 mL). The organic extracts were combined, dried ($Na_2SO_4$) and concentrated in vacuo. Purification by HPLC (ACE 5 C18-PFP 250×21.2 mm column; 15 min gradient of 60:40 to 0:100 $H_2O$:MeOH (both modified with 0.1% formic acid); flow rate 20 mLmin$^{-1}$; Agilent 6120 MS-Prep LC) afforded the title compound (6 mg, 21%) as a yellow solid. $^1$H NMR (600 MHz, Methanol-$d_4$) δ 8.79 (d, J=4.9 Hz, 2H), 8.15 (d, J=1.9 Hz, 1H), 7.62 (d, J=8.9 Hz, 1H), 7.59 (dd, J=8.9, 1.9 Hz, 1H), 7.36 (t, J=4.9 Hz, 1H), 7.26 (s, 1H), 5.07 (s, 1H), 4.69 (t, J=7.8 Hz, 2H), 4.14 (t, J=7.8 Hz, 2H), 3.60 (s, 3H), 2.36 (app. quin., J=7.8 Hz, 2H), 1.85 (s, 6H); LCMS (Method T4) Rt=2.80 mins, m/z 529.1819 [M+H]$^+$ expected 529.1862 for $C_{27}H_{26}ClN_8O_2^+$.

The following tabulated examples in Table 7 were prepared by an analogous method to that used for the preparation of example 8a using the intermediates shown. For example 8b, reaction time was 2 h. For example 8c, reaction time was 1 h. For example 8d, additional T3P and 3-(trifluoromethyl)azetidine was added after 16 h, and total reaction time was 21 h. For example 8e, reaction time was 90 mins and for example 8f, reaction time was 2 h.

TABLE 7

Compounds prepared by a method analogous to that used for the preparation of Example 8a.

| Example | Data | Intermediate |
|---|---|---|
| Example 8b:<br>6-(azetidine-1-carbonyl)-2-chloro-4-((4-((2-(5-cyclopropylpyrimidin-2-yl)propan-2-yl)amino)-1-methyl-2-oxo-1,2-dihydroquinolin-6-yl)amino)nicotinonitrile | $^1$H NMR (600 MHz, Chloroform-d) δ 8.51 (s, 2H), 7.61 (d, J = 2.3 Hz, 1H), 7.44 (dd, J = 8.9, 2.3 Hz, 1H), 7.43-7.38 (m, 2H), 7.12 (s, 1H), 6.71 (s, 1H), 5.70 (s, 1H), 4.75-4.65 (m, 2H), 4.23-4.14 (m, 2H), 3.65 (s, 3H), 2.40-2.32 (m, 2H), 1.91-1.85 (m, 7H), 1.15-1.10 (m, 2H), 0.85-0.81 (m, 2H).<br>LCMS (Method T4) Rt = 2.96 mins, m/z 569.2150 [M + H]$^+$ expected 569.2175 for $C_{30}H_{30}ClN_8O_2$. | Example 9a: 6-chloro-5-cyano-4-((4-((2-(5-cyclopropyl-pyrimidin-2-yl)propan-2-yl)amino)-1-methyl-2-oxo-1,2-dihydroquinolin-6-yl)amino)picolinic acid |
| Example 8c:<br>(R)-6-(azetidine-1-carbonyl)-2-chloro-4-((4-((1-cyclopropylethyl)amino)-1-methyl-2-oxo-1,2-dihydroquinolin-6-yl)amino)nicotinonitrile | $^1$H NMR (600 MHz, Chloroform-d) δ 7.44-7.37 (m, 4H), 6.97 (s, 1H), 5.74 (s, 1H), 4.71-4.65 (m, 3H), 4.19-4.13 (m, 2H), 3.66 (s, 3H), 3.06 (app. sex., J = 6.4 Hz, 1H), 2.38-2.30 (m, 2H), 1.31 (d, J = 6.3 Hz, 3H), 1.03 (qt, J = 7.8, 4.9 Hz, 1H), 0.64-0.52 (m, 2H), 0.37-0.29 (m, 2H).<br>LCMS (Method T4) Rt = 2.91 mins, m/z 477.1786 [M + H]$^+$ expected 477.1800 for $C_{25}H_{26}ClN_6O_2$. | Example 9b: (R)-6-chloro-5-cyano-4-((4-((1-cyclopropylethyl)amino)-1-methyl-2-oxo-1,2-dihydroquinolin-6-yl)amino)picolinic acid |
| Example 8d:<br>2-chloro-4-((1-methyl-2-oxo-4-((2-(pyrimidin-2-yl)propan-2-yl)amino)-1,2-dihydroquinolin-6-yl)amino)-6-(3-(trifluoromethyl)azetidine-1-carbonyl)nicotinonitrile | $^1$H NMR (500 MHz, Methanol-d$_4$) δ 8.79 (d, J = 4.9 Hz, 2 H), 8.15 (d, J = 2.2 Hz, 1 H), 7.63 (d, J = 8.9 Hz, 1 H), 7.59 (dd, J = 8.9, 2.2 Hz, 1 H), 7.36 (t, J = 4.9 Hz, 1 H), 7.30 (s, 1 H), 5.07 (s, 1 H), 4.94-4.89 (m, 1 H), 4.72 (dd, J = 11.4, 5.5 Hz, 1 H), 4.35-4.29 (m, 1 H), 4.12 (dd, J = 11.2, 5.3 Hz, 1 H), 3.60 (s, 3 H), 3.58-3.50 (m, 1 H), 1.86 (s, 6 H); LCMS (Method X4) Rt = 3.04 mins, m/z 597.1736 [M + H]$^+$ expected 597.1741 for $C_{28}H_{25}ClF_3N_8O_2^+$. | Example 9f: 6-chloro-5-cyano-4-((1-methyl-2-oxo-4-((2-(pyrimidin-2-yl)propan-2-yl)amino)-1,2-dihydroquinolin-6-yl)amino)picolinic acid |

TABLE 7-continued

Compounds prepared by a method analogous to that used for the preparation of Example 8a.

| Example | Data | Intermediate |
| --- | --- | --- |
| Example 8e: (S)-2-chloro-6-(2-(methoxymethyl)pyrrolidine-1-carbonyl)-4-((1-methyl-2-oxo-4-(2-(pyrimidin-2-yl)propan-2-yl)amino)-1,2-dihydroquinolin-6-yl)amino)nicotinonitrile<br>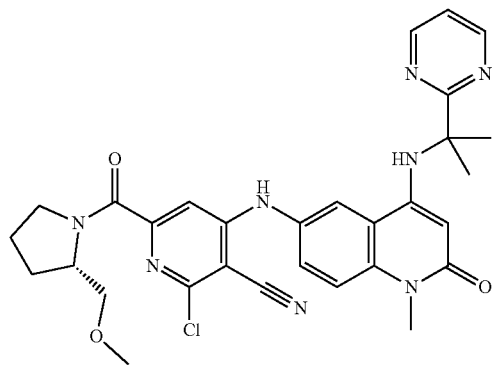 [SMILES: COC[C@@H]1CCCN1C(=O)c1cc(Nc2ccc3c(c2)c(NC(C)(C)c2ncccn2)cc(=O)n3C)c(C#N)c(Cl)n1]<br>Two amide rotamers observed; NMRs written up separately. | Rotamer A (Major): $^1$H NMR (600 MHz, chloroform-d) δ 8.80 (d, J = 4.9 Hz, 2 H), 7.61-7.59 (m, 1 H), 7.47-7.44 (m, 1 H), 7.41 (d, J = 3.3 Hz, 1 H), 7.24 (t, J = 4.9 Hz, 1 H), 7.09 (s, 1 H), 7.04 (s, 1 H), 6.66 (s, 1 H), 5.69 (s, 1 H), 4.36-4.31 (m, 1 H), 3.81-3.76 (m, 1 H), 3.65 (s, 3 H), 3.63-3.58 (m, 2 H), 3.46 (dd, J = 9.4, 7.0 Hz, 1 H), 3.33 (s, 3 H), 2.04-1.95 (m, 2 H), 1.95-1.91 (m, 1 H), 1.89(s, 6 H), 1.86-1.80 (m, 1 H);<br>Rotamer B (Minor): $^1$H NMR (600 MHz, chloroform-d) δ 8.80 (d, J = 4.9 Hz, 2 H), 7.61-7.59 (m, 1 H), 7.47-7.44 (m, 1 H), 7.40 (d, J = 3.4 Hz, 1 H), 7.23 (t, J = 4.9 Hz, 1 H), 7.12 (s, 1 H), 7.04 (s, 1 H), 6.68 (s, 1 H), 5.69 (s, 1 H), 4.73-4.67 (m, 1 H), 3.69-3.66 (m, 1 H), 3.65 (s, 3 H), 3.58-3.52 (m, 1 H), 3.38 (dd, J = 9.5, 5.3 Hz, 1 H), 3.23 (s, 3 H), 3.19 (dd, J = 9.5, 7.3 Hz, 1 H), 2.04-1.95 (m, 3 H), 1.95-1.91 (m, 1 H), 1.89 (s, 6 H);<br>LCMS (Method X4) Rt = 2.83 mins, m/z 587.2310 [M + H]$^+$ expected 587.2286 for $C_{30}H_{32}ClN_8O_3^+$. | Example 9f: 6-chloro-5-cyano-4-((1-methyl-2-oxo-4-((2-(pyrimidin-2-yl)propan-2-yl)amino)-1,2-dihydroquinolin-6-yl)amino)picolinic acid |
| Example 8f: 2-chloro-4-((4-((1-(5-cyclopropylpyrimidin-2-yl)ethyl)amino)-1-methyl-2-oxo-1,2-dihydroquinolin-6-yl)amino)-6-(3-(trifluoromethyl)azetidine-1-carbonyl)nicotinonitrile<br>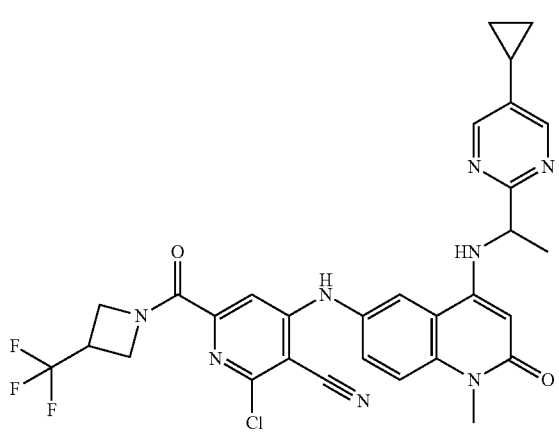 [SMILES: CC(Nc1cc(=O)n(C)c2ccc(Nc3cc(C(=O)N4CC(C(F)(F)F)C4)nc(Cl)c3C#N)cc12)c1ncc(C2CC2)cn1] | $^1$H NMR (600 MHz, Chloroform-d) δ 8.48 (s, 2H), 7.59-7.52 (m, 1H), 7.47-7.37 (m, 3H), 7.15 (s, 1H), 6.41-6.33 (m, 1H), 5.81 (s, 1H), 4.93-4.80 (m, 2H), 4.77-4.70 (m, 1H), 4.31-4.23 (m, 1H), 4.19 (dd, J = 11.4, 5.6 Hz, 1H), 3.65 (s, 3H), 3.37-3.26 (m, 1H), 1.90-1.82 (m, 1H), 1.63 (d, J = 6.4 Hz, 3H), 1.14-1.06 (m, 2H), 0.83-0.75 (m, 2H).<br>LCMS (Method X4) Rt = 3.17 min, m/z 623.1917 [M + H]$^+$ expected 623.1898 for $C_{30}H_{27}ClF_3N_8O_2$. | Example 9p: 6-chloro-5-cyano-4-((4-((1-(5-cyclopropyl-pyrimidin-2-yl)ethyl)amino)-1-methyl-2-oxo-1,2-dihydroquinolin-6-yl)amino)picolinic acid |

TABLE 7-continued

Compounds prepared by a method analogous to that used for the preparation of Example 8a.

| Example | Data | Intermediate |
| --- | --- | --- |
| Example 8g: 2-chloro-4-((1-methyl-2-oxo-4-((2-(pyrimidin-2-yl)propan-2-yl)amino)-1,2-dihydroquinolin-6-yl)amino)-6-(1-oxa-6-azaspiro[3.3]heptane-6-carbonyl)nicotinonitrile 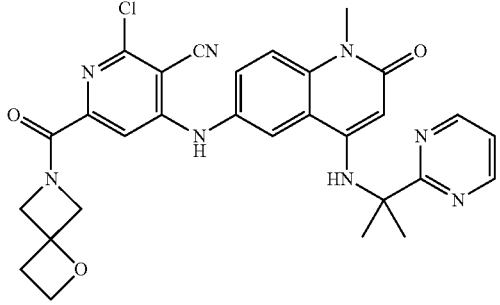 [SMILES: Cn1c(=O)cc(NC(C)(C)c2ncccn2)c2cc(Nc3cc(C(=O)N4CC5(CCO5)C4)nc(Cl)c3C#N)ccc21] | $^1$H NMR (600 MHz, chloroform-d) δ 8.78 (d, J = 4.9 Hz, 2 H), 7.59 (d, J = 2.0 Hz, 1 H), 7.44 (dd, J = 8.9, 2.0 Hz, 1 H), 7.42 (s, 1 H), 7.41 (d, J = 8.9 Hz, 1 H), 7.24 (t, J = 4.9 Hz, 1 H), 7.02 (s, 1 H), 6.66 (s, 1 H), 5.70 (s, 1 H), 4.88 (dd, J = 12.3, 1.6 Hz, 1 H), 4.81 (dd, J = 12.3, 1.4 Hz, 1 H), 4.58-4.52 (m, 2 H), 4.34 (dd, J = 12.3, 1.4 Hz, 1 H), 4.31 (dd, J = 12.3, 1.6 Hz, 1 H), 3.65 (s, 3 H), 2.93-2.85 (m, 2 H), 1.89 (s, 6 H); LCMS (Method X4) Rt = 2.70 mins, m/z 571.1994 [M + H]$^+$ expected 571.1973 for $C_{29}H_{28}ClN_8O_3^+$. | Example 9f: 6-chloro-5-cyano-4-((1-methyl-2-oxo-4-((2-(pyrimidin-2-yl)propan-2-yl)amino)-1,2-dihydroquinolin-6-yl)amino)picolinic acid |
| Example 8h: 2-chloro-6-(3-(cyanomethyl)azetidine-1-carbonyl)-4-((1-methyl-2-oxo-4-((2-(pyrimidin-2-yl)propan-2-yl)amino)-1,2-dihydroquinolin-6-yl)amino)nicotinonitrile 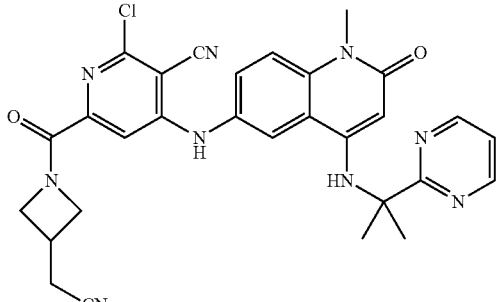 | $^1$H NMR (600 MHz Methanol-d$_4$) δ 8.81 (d, J = 4.9 Hz, 2 H), 8.16 (d, J = 2.2 Hz, 1 H), 7.65 (d, J = 9.0 Hz, 1 H), 7.61 (dd, J = 9.0, 2.2 Hz, 1 H), 7.38 (t, J = 4.9 Hz, 1 H), 7.30 (s, 1 H), 5.10 (s, 1 H), 4.87-4.85 (m, 1 H), 4.51-4.47 (m, 1 H), 4.34-4.29 (m, 1 H), 3.94-3.89 (m, 1 H), 3.62 (s, 3 H), 3.09-3.02 (m, 1 H), 2.84 (d, J = 6.6 Hz, 2 H), 1.88 (s, 6 H); LCMS (Method X4) Rt = 2.70 mins, m/z 568.1995 [M + H]$^+$ expected 568.1976 for $C_{29}H_{27}ClN_9O_2^+$. | Example 9f: 6-chloro-5-cyano-4-((1-methyl-2-oxo-4-((2-(pyrimidin-2-yl)propan-2-yl)amino)-1,2-dihydroquinolin-6-yl)amino)picolinic acid |

The following tabulated examples in Table 8 were prepared by a method analogous to that used for the preparation of example 2a, starting from the intermediate shown in the table. Note that the carboxylic acid signal observed at around 13.7 ppm in the NMR spectra is often very broad, and in some cases is too broad to be clearly observed. For example 9q, the reaction was heated to 140° C. for 1 h.

TABLE 8

Compounds prepared by a method analogous to that used for the preparation of Example 2a.

| Example | Data | Intermediate |
| --- | --- | --- |
| Example 9a:<br>6-chloro-5-cyano-4-((4-((2-(5-cyclopropylpyrimidin-2-yl)propan-2-yl)amino)-1-methyl-2-oxo-1,2-dihydroquinolin-6-yl)amino)picolinic acid | $^1$H NMR (600 MHz, DMSO-$d_6$) δ 13.68 (s, 1H), 9.91 (s, 1H), 8.57 (s, 2H), 8.25 (d, J = 2.2 Hz, 1H), 7.55 (dd, J = 8.9, 2.2 Hz, 1H), 7.48 (d, J = 8.9 Hz, 1H), 7.15 (s, 1H), 6.81 (s, 1H), 4.72 (s, 1H), 3.43 (s, 3H), 1.96-1.89 (m, 1H), 1.73 (s, 6H), 1.05-1.00 (m, 2H), 0.86-0.81 (m, 2H). LCMS (Method T4) Rt = 2.72 mins, m/z 530.1690 [M + H]$^+$ expected 530.1702 for $C_{27}H_{25}ClN_7O_3$. | Intermediate A4j: 6-amino-4-((2-(5-cyclopropyl-pyrimidin-2-yl)propan-2-yl)amino)-1-methylquinolin-2(1H)-one |
| Example 9b:<br>(R)-6-chloro-5-cyano-4-((4-((1-cyclopropylethyl)amino)-1-methyl-2-oxo-1,2-dihydroquinolin-6-yl)amino)picolinic acid | 1H NMR (500 MHz, DMSO-$d_6$) δ 13.69 (br, 1H), 9.90 (s, 1H), 8.13 (d, J = 2.2 Hz, 1H), 7.55 (dd, J = 9.0, 2.2 Hz, 1H), 7.51 (d, J = 9.0 Hz, 1H), 7.17 (s, 1H), 6.59 (d, J = 7.9 Hz, 1H), 5.46 (s, 1H), 3.52 (s, 3H), 3.13 (app. sex., J = 7.0 Hz, 1H), 1.23 (d, J = 6.3 Hz, 3H), 1.12-1.02 (m, 1H), 0.49-0.43 (m, 1H), 0.43-0.36 (m, 1H), 0.29-0.17 (m, 2H). LCMS (Method T4) Rt = 2.65 mins, m/z 438.1316 [M + H]$^+$ expected 438.1327 for $C_{22}H_{21}ClN_5O_3$. | Intermediate A1a: (R)-6-amino-4-((1-cyclopropylethyl)amino)-1-methylquinolin-2(1H)-one |
| Example 9c:<br>6-chloro-5-cyano-4-((4-((2-fluoroethyl)amino)-1-methyl-2-oxo-1,2-dihydroquinolin-6-yl)amino)picolinic acid | $^1$H NMR (500 MHz, DMSO-d6) δ 13.7 (1H, br), 9.89 (s, 1H), 8.06 (s, 1H), 7.55 (d, J = 1.9 Hz, 2H), 7.17 (s, 1H), 7.06-7.02 (m, 1H), 5.57 (s, 1H), 4.67 (t, J = 4.9 Hz, 1H), 4.58 (t, J = 4.8 Hz, 1H), 3.57-3.50 (m, 4H), 3.48 (d, J = 5.0 Hz, 1H). LCMS (Method T4) Rt = 2.42 mins, m/z 416.0919 [M + H]$^+$ expected 416.0920 for $C_{19}H_{16}ClFN_5O_3$ | Intermediate A4d: 6-amino-4-((2-fluoroethyl)amino)-1-methylquinolin-2(1H)-one |

TABLE 8-continued

Compounds prepared by a method analogous to that used for the preparation of Example 2a.

| Example | Data | Intermediate |
| --- | --- | --- |
| Example 9d:<br>(S)-6-chloro-5-cyano-4-((4-((1-cyclopropylethyl)amino)-1-methyl-2-oxo-1,2-dihydroquinolin-6-yl)amino)picolinic acid | $^1$H NMR (500 MHz, DMSO-d$_6$) δ 13.7 (br, 1H), 9.90 (s, 1H), 8.13 (d, J = 2.2 Hz, 1H), 7.55 (dd, J = 9.0, 2.2 Hz, 1H), 7.51 (d, J = 9.0 Hz, 1H), 7.17 (s, 1H), 6.59 (d, J = 7.9 Hz, 1H), 5.46 (s, 1H), 3.52 (s, 3H), 3.13 (app. sex., J = 7.0 Hz, 1H), 1.23 (d, J = 6.3 Hz, 3H), 1.12-1.02 (m, 1H), 0.49-0.43 (m, 1H), 0.43-0.36 (m, 1H), 0.29-0.17 (m, 2H).<br>LCMS (Method T4) Rt = 2.65 mins, m/z 438.1321 [M + H]$^+$ expected 438.1327 for C$_{22}$H$_{21}$ClN$_5$O$_3$. | Intermediate A11n: (S)-6-amino-4-((1-cyclopropylethyl)amino)-1-methylquinolin-2(1H)-one |
| Example 9f:<br>6-chloro-5-cyano-4-(1-methyl-2-oxo-4-((2-(pyrimidin-2-yl)propan-2-yl)amino)-1,2-dihydroquinolin-6-yl)amino)picolinic acid | $^1$H NMR (500 MHz, DMSO-d$_6$) δ 9.93 (br s, 1 H), 8.82 (d, J = 4.9 Hz, 2 H), 8.27 (d, J = 2.1 Hz, 1 H), 7.56 (dd, J = 9.0, 2.1 Hz, 1 H), 7.49 (d, J = 9.0 Hz, 1 H), 7.40 (t, J = 4.9 Hz, 1 H), 7.16 (s, 1 H), 6.85 (s, 1 H), 4.69 (s, 1 H), 3.43 (s, 3 H), 1.76 (s, 6 H); LCMS (Method T4) Rt = 2.51 mins, m/z 490.1380 [M + H]$^+$ expected 490.1389 for C$_{24}$H$_{21}$ClN$_7$O$_3$$^+$. | Intermediate A3a: 6-amino-1-methyl-4-((2-(pyrimidin-2-yl)propan-2-yl)amino)quinolin-2(1H)-one |
| Example 9g:<br>6-chloro-5-cyano-4-((4-((1-cyanocyclopropyl)amino)-1-methyl-2-oxo-1,2-dihydroquinolin-6-yl)amino)picolinic acid | $^1$H NMR (500 MHz, DMSO-d$_6$) δ 13.73 (br s, 1 H), 9.92 (s, 1 H), 7.88-7.85 (m, 2 H), 7.61-7.59 (m, 2 H), 7.18 (s, 1 H), 5.91 (s, 1 H), 3.58 (s, 3 H), 1.72-1.68 (m, 2 H), 1.33-1.29 (m, 2 H); LCMS (Method T4) Rt = 2.36 mins, m/z 435.0960 [M + H]$^+$ expected 435.0967 for C$_{21}$H$_{16}$ClN$_6$O$_3$$^+$. | Intermediate A3f: 1-((6-amino-1-methyl-2-oxo-1,2-dihydroquinolin-4-yl)amino)cyclopropane-1-carbonitrile |
| Example 9h:<br>6-chloro-5-cyano-4-((4-((1-ethynylcyclopropyl)amino)-1-methyl-2-oxo-1,2-dihydroquinolin-6-yl)amino)picolinic acid | $^1$H NMR (500 MHz, DMSO-d$_6$) δ 9.68 (br s, 1 H), 7.90 (br s, 1 H), 7.61 (br s, 1 H), 7.56-7.48 (m, 2 H), 7.09 (br s, 1 H), 5.92 (br s, 1 H), 3.55 (s, 3 H), 3.13 (s, 1 H), 1.29-1.21 (m, 2 H), 1.12-1.08 (m, 2 H); LCMS (Method T4) Rt = 2.49 mins, m/z 434.0998 [M + H]$^+$ expected 434.1014 for C$_{22}$H$_{17}$ClN$_5$O$_3$$^+$. | Intermediate A11: 6-amino-4-((1-ethynylcyclopropyl)amino)-1-methylquinolin-2(1H)-one |

TABLE 8-continued

Compounds prepared by a method analogous to that used for the preparation of Example 2a.

| Example | Data | Intermediate |
| --- | --- | --- |
| Example 9i:<br>rac-6-chloro-5-cyano-4-((4-(((1R,2R)-2-ethylcyclopropyl)amino)-1-methyl-2-oxo-1,2-dihydroquinolin-6-yl)amino)picolinic acid | $^1$H NMR (500 MHz, DMSO-d$_6$) δ 9.85 (br s, 1 H), 7.97 (br s, 1 H), 7.52 (br s, 2 H), 7.14 (br s, 2 H), 5.74 (br s, 1 H), 3.53 (s, 3 H), 2.25-2.19 (m, 1 H), 1.54-1.43 (m, 1 H), 1.29-1.20 (m, 1 H), 1.04-0.96 (m, 3 H), 0.92-0.85 (m, 1 H), 0.71-0.64 (m, 1 H), 0.64-0.58 (m, 1 H); LCMS (Method T4) Rt = 2.73 mins, m/z 438.1312 [M + H]$^+$ expected 438.1327 for C$_{22}$H$_{21}$ClN$_5$O$_3^+$. | Intermediate A3b: rac-6-amino-4-(((1R,2R)-2-ethylcyclopropyl)amino)-1-methylquinolin-2(1H)-one |
| Example 9j:<br>6-chloro-5-cyano-4-((4-((2,2-dimethylcyclopropyl)amino)-1-methyl-2-oxo-1,2-dihydroquinolin-6-yl)amino)picolinic acid | $^1$H NMR (500 MHz, DMSO-d$_6$) δ 9.86 (br s, 1 H), 8.05 (s, 1 H), 7.53 (s, 2 H), 7.19 (s, 1 H), 7.07 (s, 1 H), 5.58 (s, 1 H), 3.54 (s, 3 H), 2.28-2.22 (m, 1 H), 1.17 (s, 3 H), 0.96 (s, 3 H), 0.80-0.74 (m, 1 H), 0.61-0.56 (m, 1H); LCMS (Method T4) Rt = 2.70 mins, m/z 438.1318 [M + H]$^+$ expected 438.1327 for C$_{22}$H$_{21}$ClN$_5$O$_3^+$. | Intermediate A3e: 6-amino-4-((2,2-dimethylcyclopropyl)amino)-1-methylquinolin-2(1H)-one |
| Example 9k:<br>6-chloro-5-cyano-4-((4-((1-(hydroxymethyl)cyclopropyl)amino)-1-methyl-2-oxo-1,2-dihydroquinolin-6-yl)amino)picolinic acid | $^1$H NMR (500 MHz, DMSO-d$_6$) δ 9.89 (br s, 1 H), 8.06 (s, 1 H), 7.52 (s, 2 H), 7.24 (s, 1 H), 7.18 (s, 1 H), 5.76 (s, 1 H), 4.81 (br s, 1 H), 3.53-3.50 (m, 5 H), 0.90-0.85 (m, 2 H), 0.71-0.67 (m, 2 H); LCMS (Method T4) Rt = 2.37 mins, m/z 440.1110 [M + H]$^+$ expected 440.1120 for C$_{21}$H$_{19}$ClN$_5$O$_4^+$. | Intermediate A3c: 6-amino-4-((1-(hydroxymethyl)cyclopropyl)amino)-1-methylquinolin-2(1H)-one |
| Example 9l:<br>6-chloro-5-cyano-4-((4-((cyclopropylmethyl)amino)-1-methyl-2-oxo-1,2-dihydroquinolin-6-yl)amino)picolinic acid | $^1$H NMR (500 MHz, DMSO-d6) δ 9.93 (s, 1H), 8.08 (d, J = 2.1 Hz, 1H), 7.57-7.50 (m, 2H), 7.20 (s, 1H), 6.95 (t, J = 5.3 Hz, 1H), 5.48 (s, 1H), 3.53 (s, 3H), 3.06-2.97 (m, 2H), 0.62-0.41 (m, 2H), 0.29-0.13 (m, 2H). LCMS (Method T4) Rt = 2.86 mins, m/z 424.1165 [M + H]$^+$ expected 424.1171 for C$_{21}$H$_{19}$ClN$_5$O$_3$ | Intermediate A4b: 6-amino-4-((cyclopropylmethyl)amino)-1-methylquinolin-2(1H)-one |

TABLE 8-continued

Compounds prepared by a method analogous to that used for the preparation of Example 2a.

| Example | Data | Intermediate |
| --- | --- | --- |
| Example 9m:<br>6-chloro-5-cyano-4-((4-((1-methoxy-2-methylpropan-2-yl)amino)-1-methyl-2-oxo-1,2-dihydroquinolin-6-yl)amino)picolinic acid<br>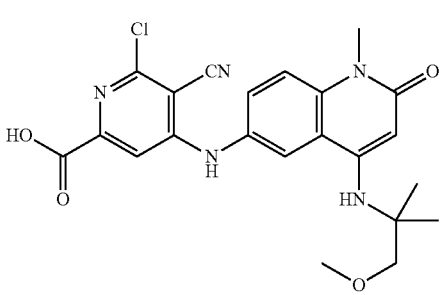 [SMILES: COCC(C)(C)Nc1cc(=O)n(C)c2ccc(Nc3cc(C(=O)O)nc(Cl)c3C#N)cc12] | $^1$H NMR (500 MHz, Methanol-d4) δ 7.88 (d, J = 2.2 Hz, 1H), 7.69 (d, J = 9.0 Hz, 1H), 7.63 (dd, J = 9.0, 2.3 Hz, 1H), 7.40 (s, 1H), 6.01 (s, 1H), 3.71 (s, 3H), 3.53 (s, 2H), 3.41 (s, 3H), 1.49 (s, 6H)<br>LCMS (Method T4) Rt = 2.69 mins, m/z 456.1423 [M + H]$^+$ expected 456.1466 for C$_{22}$H$_{23}$ClN$_5$O$_4$ | Intermediate A4e:<br>6-amino-4-[(2-methoxy-1,1-dimethyl-ethyl)amino]-1-methyl-quinolin-2-one |
| Example 9n:<br>4-((4-(tert-butylamino)-1-methyl-2-oxo-1,2-dihydroquinolin-6-yl)amino)-6-chloro-5-cyanopicolinic acid<br>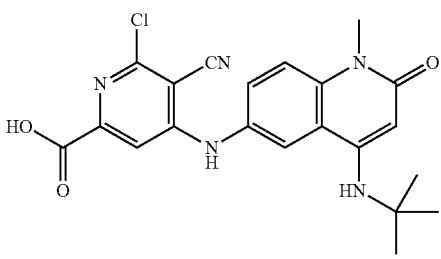 [SMILES: Cn1c(=O)cc(NC(C)(C)C)c2cc(Nc3cc(C(=O)O)nc(Cl)c3C#N)ccc21] | $^1$H NMR (500 MHz, Methanol-d4) δ 8.03 (d, J = 2.3 Hz, 1H), 7.68 (d, J = 9.0 Hz, 1H), 7.64-7.57 (m, 1H), 7.36 (s, 1H), 5.98 (s, 1H), 3.70 (s, 3H), 1.52 (s, 9H).<br>LCMS (Method T4) Rt = 2.73 mins, m/z 426.1326 [M + H]$^+$ expected 426.1327 for C$_{21}$H$_{21}$ClN$_5$O$_3$ | Intermediate A4c:<br>6-amino-4-(tert-butylamino)-1-methyl-quinolin-2-one |
| Example 9o:<br>6-chloro-5-cyano-4-((1-methyl-2-oxo-4-(tert-pentylamino)-1,2-dihydroquinolin-6-yl)amino)picolinic acid<br>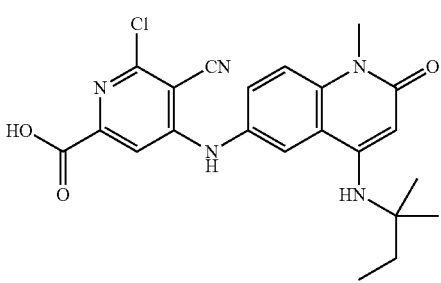 [SMILES: CCC(C)(C)Nc1cc(=O)n(C)c2ccc(Nc3cc(C(=O)O)nc(Cl)c3C#N)cc12] | $^1$H NMR (500 MHz, Methanol-d4) δ 8.07 (s, 1H), 7.67 (d, J = 8.9 Hz, 1H), 7.64-7.58 (m, 1H), 7.47 (s, 1H), 5.97 (s, 1H), 3.70 (s, 3H), 1.89 (q, J = 7.4 Hz, 2H), 1.46 (s, 6H), 0.90 (t, J = 7.4 Hz, 3H).<br>LCMS (Method T4) Rt = 2.82 mins, m/z 440.1475 [M + H]$^+$ expected 440.1484 for C$_{22}$H$_{23}$ClN$_5$O$_3$ | Intermediate A4a:<br>6-amino-1-methyl-4-(tert-pentylamino)quinolin-2(1H)-one |

TABLE 8-continued

Compounds prepared by a method analogous to that used for the preparation of Example 2a.

| Example | Data | Intermediate |
| --- | --- | --- |
| Example 9p:<br>6-chloro-5-cyano-4-((4-((1-(5-cyclopropylpyrimidin-2-yl)ethyl)amino)-1-methyl-2-oxo-1,2-dihydroquinolin-6-yl)amino)picolinic acid | $^1$H NMR (600 MHz, DMSO-$d_6$) δ 13.78 (br. s, 1H), 9.83 (br. s, 1H), 8.54 (s, 2H), 8.29 (d, J = 2.3 Hz, 1H), 7.54 (dd, J = 8.9, 2.3 Hz, 1H), 7.49 (d, J = 8.9 Hz, 1H), 7.18 (d, J = 6.9 Hz, 1H), 7.13 (s, 1H), 5.28 (s, 1H), 4.70 (app. quin., J = 6.9 Hz, 1H), 3.46 (s, 3H), 1.94-1.87 (m, 1H), 1.57 (d, J = 6.9 Hz, 3H), 1.06-0.95 (m, 2H), 0.88-0.78 (m, 2H).<br>LCMS (Method X4) Rt = 2.52 min, m/z 516.1558 [M + H]$^+$ expected 516.1551 for $C_{26}H_{23}ClN_7O_3$ | Intermediate A1q: 6-amino-4-((1-(5-cyclopropyl-pyrimidin-2-yl)ethyl)amino)-1-methylquinolin-2(1H)-one |
| Example 9q:<br>4-((1-benzyl-2-oxo-4-((1-(pyrimidin-2-yl)ethyl)amino)-1,2-dihydroquinolin-6-yl)amino)-6-chloro-5-cyanopicolinic acid | 1H NMR (600 MHz, Methanol-$d_4$) δ 8.82 (d, J = 4.9 Hz, 2H), 8.21 (s, 1H), 7.52-7.44 (m, 2H), 7.41 (t, J = 4.9 Hz, 1H), 7.35 (s, 1H), 7.30 (t, J = 7.6 Hz, 2H), 7.23 (d, J = 7.4 Hz, 1H), 7.18 (d, J = 7.6 Hz, 2H), 5.67 (s, 1H), 5.53 (s, 2H), 4.95 (q, J = 6.9 Hz, 1H), 1.74 (d, J = 6.9 Hz, 3H).<br>LCMS (Method X4) Rt = 2.62 mins, m/z 552.1569 [M + H]$^+$ expected 552.1551 for $C_{29}H_{23}ClN_7O_3{}^+$. | Intermediate A3g: 6-amino-1-benzyl-4-((1-(pyrimidin-2-yl)ethyl)amino)quinolin-2(1H)-one |

The following tabulated examples in Table 9 were prepared by a method analogous to that used for the preparation of example 1a, starting from the intermediate(s) shown in the table.

TABLE 9

Compounds prepared by a method analogous to that used for the preparation of Example 1a.

| Example | Data | Intermediate |
| --- | --- | --- |
| Example 10a:<br>2-chloro-4-((4-((2-(5-cyclopropylpyrimidin-2-yl)propan-2-yl)amino)-1-methyl-2-oxo-1,2-dihydroquinolin-6-yl)amino)nicotinonitrile<br>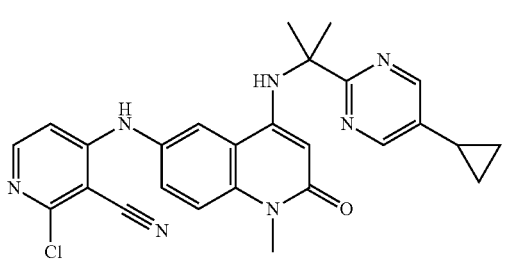 [SMILES: Cn1c(=O)cc(NC(C)(C)c2ncc(C3CC3)cn2)c2cc(Nc3ccnc(Cl)c3C#N)ccc21] | $^1$H NMR (600 MHz, DMSO-d$_6$) δ 9.58 (s, 1H), 8.56 (s, 2H), 8.24 (d, J = 2.3 Hz, 1H), 8.05 (d, J = 6.2 Hz, 1H), 7.51 (dd, J = 9.0, 2.3 Hz, 1H), 7.45 (d, J = 9.0 Hz, 1H), 6.81 (s, 1H), 6.61 (d, J = 6.2 Hz, 1H), 4.71 (s, 1H), 3.42 (s, 3H), 1.96-1.89 (m, 1H), 1.73 (s, 6H), 1.06-0.98 (m, 2H), 0.87-0.81 (m, 2H). LCMS (Method T4) Rt = 2.80 mins, m/z 486.1788 [M + H]$^+$ expected 486.1804 for C$_{26}$H$_{26}$ClN$_7$O. | Intermediate A4j: 6-amino-4-((2-(5-cyclopropyl-pyrimidin-2-yl)propan-2-yl)amino)-1-methylquinolin-2(1H)-one and 2,4-dichloropyridine-3-carbonitrile |
| Example 10b:<br>2-chloro-4-((4-((1-(5-((2S,6R)-2,6-dimethylmorpholino)pyrimidin-2-yl)ethyl)amino)-1-methyl-2-oxo-1,2-dihydroquinolin-6-yl)amino)nicotinonitrile<br>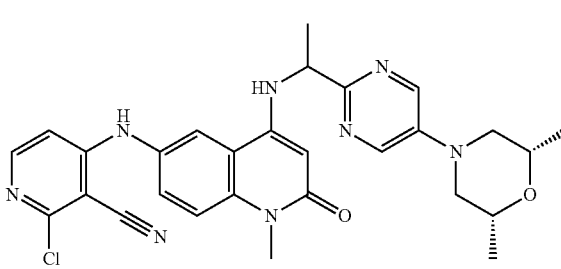 | $^1$H NMR (600 MHz, Chloroform-d) δ 8.36 (s, 2H), 8.06 (d, J = 6.1 Hz, 1H), 7.58 (d, J = 2.3 Hz, 1H), 7.44 (dd, J = 8.9, 2.3 Hz, 1H), 7.40 (d, J = 8.9 Hz, 1H), 7.03 (s, 1H), 6.64 (d, J = 6.1 Hz, 1H), 6.44 (d, J = 6.3 Hz, 1H), 5.81 (s, 1H), 4.81 (app. quin., J = 6.3 Hz, 1H), 3.84-3.77 (m, 2H), 3.65 (s, 3H), 3.52-3.40 (m, 2H), 2.55-2.46 (m, 2H), 1.63 (d, J = 6.6 Hz, 3H), 1.28 (d, J = 6.3 Hz, 6H). LCMS (Method T4) Rt = 2.80 mins, m/z 545.2148 [M + H]$^+$ expected 545.2175 for C$_{28}$H$_{30}$ClN$_8$O$_2$. | Intermediate A1r: 6-amino-4-((1-(5-((2S,6R)-2,6-dimethylmorpholino)pyrimidin-2-yl)ethyl)amino)-1-methylquinolin-2(1H)-one and 2,4-dichloropyridine-3-carbonitrile |
| Example 10c:<br>2-chloro-4-((1-methyl-4-((1-(5-(1-methyl-1H-pyrazol-4-yl)pyrimidin-2-yl)ethyl)amino)-2-oxo-1,2-dihydroquinolin-6-yl)amino)nicotinonitrile<br>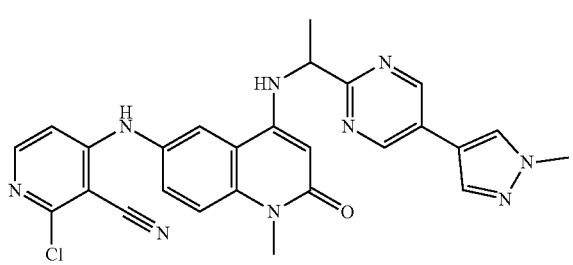 [SMILES: CC(Nc1cc(=O)n(C)c2ccc(Nc3ccnc(Cl)c3C#N)cc12)c1ncc(-c2cnn(C)c2)cn1] | $^1$H NMR (500 MHz, Chloroform-d) δ 8.83 (s, 2H), 8.06 (d, J = 6.1 Hz, 1H), 7.79 (s, 1H), 7.71 (s, 1H), 7.60 (d, J = 2.2 Hz, 1H), 7.45 (dd, J = 8.9, 2.2 Hz, 1H), 7.41 (d, J = 8.9 Hz, 1H), 7.09 (s, 1H), 6.63 (d, J = 6.1 Hz, 1H), 6.42 (d, J = 6.5 Hz, 1H), 5.83 (s, 1H), 4.88 (app. quin., J = 6.6 Hz, 1H), 3.99 (s, 3H), 3.65 (s, 3H), 1.67 (d, J = 6.7 Hz, 3H). LCMS (Method T4) Rt = 2.65 mins, m/z 512.1698 [M + H]$^+$ expected 512.1709 for C$_{26}$H$_{23}$ClN$_9$O. | Intermediate A4s: 6-amino-1-methyl-4-((1-(5-(1-methyl-1H-pyrazol-4-yl)pyrimidin-2-yl)ethyl)amino) quinolin-2(1H)-one and 2,4-dichloropyridine-3-carbonitrile |

TABLE 9-continued

Compounds prepared by a method analogous to that used for the preparation of Example 1a.

| Example | Data | Intermediate |
| --- | --- | --- |
| Example 10d:<br>2-chloro-4-((1-methyl-2-oxo-4-((1-(5-(2-(trifluoromethyl)morpholino)pyrimidin-2-yl)ethyl)amino)-1,2-dihydroquinolin-6-yl)amino)nicotinonitrile (1:1 mixture of diastereomers)<br>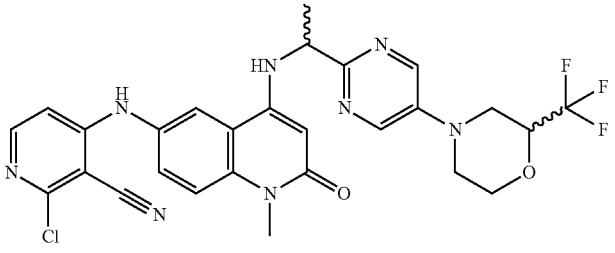 [SMILES: CC(Nc1cc(=O)n(C)c2ccc(Nc3ccnc(Cl)c3C#N)cc12)c1ncc(N2CCOC(C(F)(F)F)C2)cn1]<br>Please note that NMR data is for the diastereomeric mixture. Peaks are described above as they are observed, but apparent multiplets may in fact be made up of overlapping signals from diastereoisomeric protons. | $^1$H NMR (600 MHz, Chloroform-d) δ 8.41 (s, 2H), 8.05 (app. br. d, J = 6.1 Hz, 1H), 7.56 (d, J = 2.3 Hz, 1H), 7.45 (app. dt, J = 9.0, 2.3 Hz, 1H), 7.40 (app. dd, J = 9.0, 2.6 Hz, 1H), 7.06 (s, 1H), 6.62 (app. dd, J = 6.1, 2.9 Hz, 1H), 6.33 (app. dd, J = 9.2, 6.5 Hz, 1H), 5.80 (s, 1H), 4.83 (app. quin., J = 6.6 Hz, 1H), 4.23-4.17 (m, 1H), 4.15-4.07 (m, 1H), 3.90-3.82 (m, 1H), 3.69-3.61 (m, 4H), 3.51-3.43 (m, 1H), 3.08-3.00 (m, 1H), 2.99-2.91 (m, 1H), 1.63 (d, J = 6.7 Hz, 3H). LCMS (Method X4) Rt = 2.83 mins, m/z 585.1743 [M + H]$^+$ expected 585.1741 for $C_{27}H_{25}ClF_3N_8O_2$. | Intermediate A1p: 6-amino-1-methyl-4-((1-(5-(2-(trifluoromethyl) morpholino) pyrimidin-2-yl)ethyl)amino) quinolin-2(1H)-one and 2,4-dichloropyridine-3-carbonitrile |
| Example 10e:<br>2-chloro-4-((4-((1-(5-cyclopropylpyrimidin-2-yl)ethyl)amino)-1-methyl-2-oxo-1,2-dihydroquinolin-6-yl)amino)nicotinonitrile<br>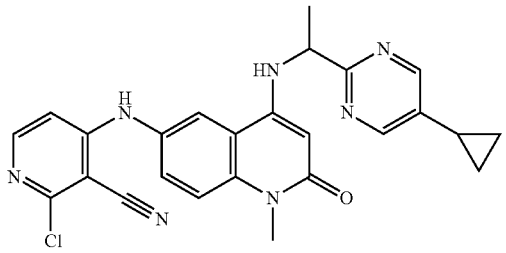 [SMILES: CC(Nc1cc(=O)n(C)c2ccc(Nc3ccnc(Cl)c3C#N)cc12)c1ncc(C2CC2)cn1] | $^1$H NMR (600 MHz, Chloroform-d) δ 8.47 (s, 2H), 8.06 (d, J = 6.1 Hz, 1H), 7.58 (d, J = 2.4 Hz, 1H), 7.44 (dd, J = 8.9, 2.4 Hz, 1H), 7.40 (d, J = 8.9 Hz, 1H), 7.09 (s, 1H), 6.63 (d, J = 6.1 Hz, 1H), 6.43 (d, J = 6.4 Hz, 1H), 5.80 (s, 1H), 4.83 (app. quin., J = 6.6 Hz, 1H), 3.65 (s, 3H), 1.90-1.83 (m, 1H), 1.62 (d, J = 6.7 Hz, 3H), 1.15-1.06 (m, 2H), 0.83-0.74 (m, 2H). LCMS (Method T4) Rt = 2.73 mins, m/z 472.1633 [M + H]$^+$ expected 472.1633 for $C_{25}H_{23}ClN_7O$. | Intermediate A1q: 6-amino-4-((1-(5-cyclopropyl-pyrimidin-2-yl)ethyl)amino)-1-methylquinolin-2(1H)-one and 2,4-dichloropyridine-3-carbonitrile |
| Example 10f:<br>2-chloro-4-(1-methyl-4-((1-(5-methylpyrimidin-2-yl)ethyl)amino)-2-oxo-1,2-dihydroquinolin-6-yl)amino)nicotinonitrile<br>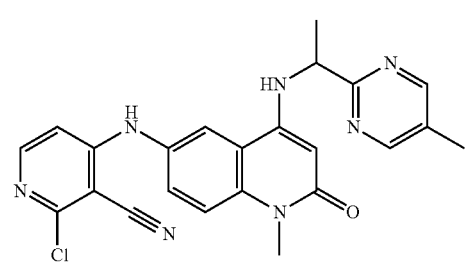 [SMILES: Cc1cnc(C(C)Nc2cc(=O)n(C)c3ccc(Nc4ccnc(Cl)c4C#N)cc23)nc1] | $^1$H NMR (600 MHz, Chloroform-d) δ 8.61 (s, 2H), 8.10 (d, J = 6.1 Hz, 1H), 7.60 (d, J = 2.2 Hz, 1H), 7.48 (dd, J = 8.9, 2.2 Hz, 1H), 7.44 (d, J = 8.9 Hz, 1H), 7.00 (s, 1H), 6.67 (d, J = 6.1 Hz, 1H), 6.41 (d, J = 6.4 Hz, 1H), 5.85 (s, 1H), 4.88 (app. quin., J = 6.6 Hz, 1H), 3.69 (s, 3H), 2.36 (s, 3H), 1.67 (d, J = 6.7 Hz, 3H). LCMS (Method T4) Rt = 2.61 mins, m/z 446.1480 [M + H]$^+$ expected 446.1491 for $C_{23}H_{21}ClN_7O$. | Intermediate A4u: 6-amino-1-methyl-4-((1-(5-methylpyrimidin-2-yl)ethyl)amino) quinolin-2(1H)-one and 2,4-dichloropyridine-3-carbonitrile |

TABLE 9-continued

Compounds prepared by a method analogous to that used for the preparation of Example 1a.

| Example | Data | Intermediate |
| --- | --- | --- |
| Example 10g:<br>(R)-2-chloro-4-((1-methyl-2-oxo-4-((1-(pyrimidin-2-yl)ethyl)amino)-1,2-dihydroquinolin-6-yl)amino)nicotinonitrile | 1H NMR (500 MHz, DMSO-d6) δ 9.62 (s, 1H), 8.79 (d, J = 4.9 Hz, 2H), 8.29 (d, J = 2.2 Hz, 1H), 8.05 (d, J = 6.2 Hz, 1H), 7.56-7.44 (m, 2H), 7.40 (t, J = 4.9 Hz, 1H), 7.23 (d, J = 7.0 Hz, 1H), 6.61 (d, J = 6.2 Hz, 1H), 5.27 (s, 1H), 4.74 (p, J = 6.9 Hz, 1H), 3.46 (s, 3H), 1.60 (d, J = 6.9 Hz, 3H). LCMS (Method T4) Rt = 2.53 mins, m/z 432.1309 [M + H]$^+$ expected 432.1334 for $C_{22}H_{19}ClN_7O$. | Intermediate A4q: (R)-6-amino-1-methyl-4-((1-(pyrimidin-2-yl)ethyl)amino)quinolin-2(1H)-one and 2,4-dichloropyridine-3-carbonitrile |
| Example 10h:<br>2-chloro-4-(1-methyl-2-oxo-4-((1-(pyrimidin-2-yl)ethyl)amino)-1,2-dihydroquinazolin-6-yl)amino)nicotinonitrile | $^1$H NMR (500 MHz, Chloroform-d) δ 8.72 (d, J = 4.9 Hz, 2H), 8.05 (d, J = 6.1 Hz, 1H), 7.80 (d, J = 6.6 Hz, 1H), 7.75 (d, J = 2.3 Hz, 1H), 7.59 (dd, J = 9.0, 2.3 Hz, 1H), 7.49 (s, 1H), 7.32 (d, J = 9.0 Hz, 1H), 7.22 (t, J = 4.9 Hz, 1H), 6.65 (d, J = 6.1 Hz, 1H), 5.62 (app. quin., J = 6.7 Hz, 1H), 3.63 (s, 3H), 1.65 (d, J = 6.8 Hz, 3H). LCMS (Method T4) Rt = 2.42 mins, m/z 433.1283 [M + H]$^+$ expected 433.1287 for $C_{21}H_{18}ClN_8O$. | Intermediate A4p: 6-amino-1-methyl-4-((1-(pyrimidin-2-yl)ethyl)amino)quinazolin-2(1H)-one and 2,4-dichloropyridine-3-carbonitrile |
| Example 10i:<br>(R)-6-chloro-5-cyano-4-((4-((1-cyclopropylethyl)amino)-1-methyl-2-oxo-1,2-dihydroquinolin-6-yl)amino)-N-methylpicolinamide | $^1$H NMR (500 MHz, DMSO-d$_6$) δ 9.91 (s, 1H), 8.64 (q, J = 4.8 Hz, 1H), 8.12 (d, J = 2.1 Hz, 1H), 7.57-7.47 (m, 2H), 7.14 (s, 1H), 6.60 (d, J = 7.8 Hz, 1H), 5.47 (s, 1H), 3.52 (s, 3H), 3.12 (app. sex., J = 6.9 Hz, 1H), 2.73 (d, J = 4.8 Hz, 3H), 1.23 (d, J = 6.3 Hz, 3H), 1.13-1.03 (m, 1H), 0.51-0.42 (m, 1H), 0.44-0.35 (m, 1H), 0.31-0.18 (m, 2H). LCMS (Method T4) Rt = 2.79 mins, m/z 451.1635 [M + H]$^+$ expected 451.1644 for $C_{23}H_{24}ClN_6O_2$. | Intermediate A1a: (R)-6-amino-4-((1-cyclopropylethyl)amino)-1-methylquinolin-2(1H)-one and Intermediate E1a: 4,6-dichloro-5-cyano-N-methyl-pyridine-2-carboxamide |
| Example 10j:<br>4-((4-((1-(5-bromopyrimidin-2-yl)ethyl)amino)-1-methyl-2-oxo-1,2-dihydroquinolin-6-yl)amino)-2-chloronicotinonitrile | $^1$H NMR (500 MHz, Chloroform-d) δ 8.79 (s, 2H), 8.06 (d, J = 6.1 Hz, 1H), 7.58 (d, J = 2.2 Hz, 1H), 7.46 (dd, J = 8.9, 2.2 Hz, 1H), 7.42 (d, J = 8.9 Hz, 1H), 7.10 (s, 1H), 6.63 (d, J = 6.1 Hz, 1H), 6.12 (d, J = 6.8 Hz, 1H), 5.79 (s, 1H), 4.86 (app. quin., J = 6.7 Hz, 1H), 3.65 (s, 3H), 1.65 (d, J = 6.7 Hz, 3H). LCMS (Method X4) Rt = 2.73 mins, m/z 510.0451 [M + H]$^+$ expected 510.0445 for $C_{22}H_{18}^{79}Br^{35}ClN_7O$. | Intermediate A2w: 6-amino-4-((1-(5-bromopyrimidin-2-yl)ethyl)amino)-1-methylquinolin-2(1H)-one and 2,4-dichloropyridine-3-carbonitrile |

TABLE 9-continued

Compounds prepared by a method analogous to that used for the preparation of Example 1a.

| Example | Data | Intermediate |
| --- | --- | --- |
| Example 10k: 2-chloro-4-((4-((1-(5-((3R,5S)-3,5-dimethylpiperidin-1-yl)pyrimidin-2-yl)ethyl)amino)-1-methyl-2-oxo-1,2-dihydroquinolin-6-yl)amino)nicotinonitrile 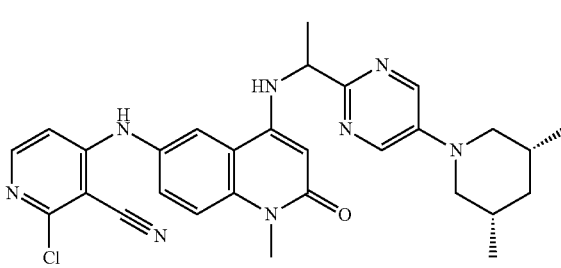 | $^1$H NMR (600 MHz, Chloroform-d) δ 8.35 (s, 2H), 8.05 (d, J = 6.1 Hz, 1H), 7.56 (d, J = 2.3 Hz, 1H), 7.42 (dd, J = 8.9, 2.3 Hz, 1H), 7.38 (d, J = 8.9 Hz, 1H), 7.05 (s, 1H), 6.60 (d, J = 6.1 Hz, 1H), 6.50 (d, J = 6.3 Hz, 1H), 5.81 (s, 1H), 4.78 (app. quin., J = 6.5 Hz, 1H), 3.64 (s, 3H), 3.64-3.58 (m, 2H), 2.36-2.24 (m, 2H), 1.91-1.70 (m, 4H), 1.61 (d, J = 6.6 Hz, 3H), 0.95 (d, J = 6.6 Hz, 6H). LCMS (Method T4) Rt = 3.10 mins, m/z 543.2369 [M + H]$^+$ expected 543.2382 for $C_{29}H_{32}ClN_8O$. | Intermediate A4w: 6-amino-4-((1-(5-((3S,5R)-3,5-dimethylpiperidin-1-yl)pyrimidin-2-yl)ethyl)amino)-1-methylquinolin-2(1H)-one and 2,4-dichloropyridine-3-carbonitrile |
| Example 10l: 2-chloro-4-((1-methyl-4-((1-(1-methyl-1H-1,2,4-triazol-3-yl)ethyl)amino)-2-oxo-1,2-dihydroquinolin-6-yl)amino)nicotinonitrile 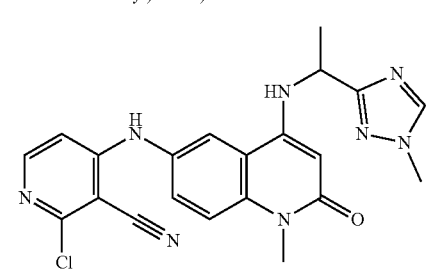 | $^1$H NMR (500 MHz, Chloroform-d) δ 8.04 (d, J = 6.1 Hz, 1H), 7.95 (s, 1H), 7.56 (d, J = 2.4 Hz, 1H), 7.40 (dd, J = 9.0, 2.4 Hz, 1H), 7.35 (d, J = 9.0 Hz, 1H), 7.12 (s, 1H), 6.58 (d, J = 6.1 Hz, 1H), 5.81 (s, 1H), 5.78 (d, J = 6.8 Hz, 1H), 4.85 (app. quin., J = 6.7 Hz, 1H), 3.89 (s, 3H), 3.61 (s, 3H), 1.66 (d, J = 6.7 Hz, 3H). LCMS (Method T4) Rt = 2.47 mins, m/z 435.1440 [M + H]$^+$ expected 435.1443 for $C_{21}H_{20}ClN_8O$. | Intermediate A4l: 6-amino-1-methyl-4-((1-(1-methyl-1H-1,2,4-triazol-3-yl)ethyl)amino)quinolin-2(1H)-one and 2,4-dichloropyridine-3-carbonitrile |
| Example 10m: (R)-2-chloro-4-((4-((1-cyclopropylethyl)amino)-1-methyl-2-oxo-1,2-dihydroquinazolin-6-yl)amino)nicotinonitrile 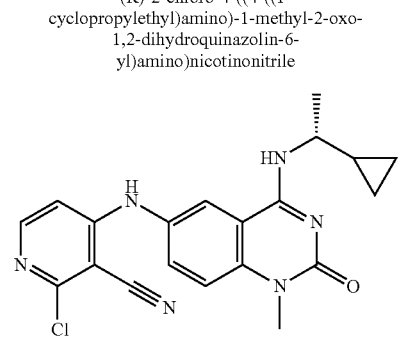 | $^1$H NMR (600 MHz, Chloroform-d) δ 8.02 (d, J = 6.1 Hz, 1H), 7.90 (d, J = 2.3 Hz, 1H), 7.52 (dd, J = 9.0, 2.3 Hz, 1H), 7.28 (d, J = 9.0 Hz, 1H), 7.24 (s, 1H), 6.73(d, J = 7.7 Hz, 1H), 6.64 (d, J = 6.1 Hz, 1H), 3.91-3.82 (m, 1H), 3.60 (s, 3H), 1.28 (d, J = 6.6 Hz, 3H), 1.02-0.95 (m, 1H), 0.53-0.45 (m, 1H), 0.44-0.38 (m, 1H), 0.38-0.30 (m, 1H), 0.24-0.17 (m, 1H). LCMS (Method T4) Rt = 2.50 mins, m/z 395.1371 [M + H]$^+$ expected 395.1382 for $C_{20}H_{20}ClN_6O$. | Intermediate A4t: (R)-6-amino-4-((1-cyclopropylethyl)amino)-1-methylquinazolin-2(1H)-one and 2,4-dichloropyridine-3-carbonitrile |

TABLE 9-continued

Compounds prepared by a method analogous to that used for the preparation of Example 1a.

| Example | Data | Intermediate |
|---|---|---|
| Example 10n:<br>(R)-2-chloro-4-((4-((1-cyclopropylethyl)amino)-1-methyl-2-oxo-1,2-dihydroquinolin-6-yl)amino)nicotinonitrile<br>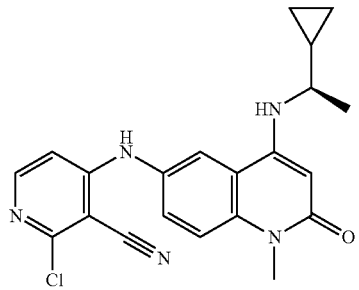 [SMILES: C[C@@H](Nc1cc(=O)n(C)c2ccc(Nc3ccnc(Cl)c3C#N)cc12)C1CC1] | $^1$H NMR (500 MHz, Chloroform-d) δ 8.05 (d, J = 6.1 Hz, 1H), 7.48 (d, J = 2.2 Hz, 1H), 7.45 (dd, J = 8.9, 2.2 Hz, 1H), 7.41 (d, J = 8.9 Hz, 1H), 7.02 (s, 1H), 6.61 (d, J = 6.1 Hz, 1H), 5.73 (s, 1H), 4.79 (d, J = 6.3 Hz, 1H), 3.66 (s, 3H), 3.10-3.00 (m, 1H), 1.31 (d, J = 6.3 Hz, 3H), 1.10-0.99 (m, 1H), 0.65-0.56 (m, 1H), 0.59-0.50 (m, 1H), 0.38-0.28 (m, 2H). LCMS (Method T4) Rt = 2.75 mins, m/z 394.1426 [M + H]$^+$ expected 394.1429 for $C_{21}H_{21}ClN_5O$. | Intermediate A1a: (R)-6-amino-4-((1-cyclopropylethyl)amino)-1-methylquinolin-2(1H)-one and 2,4-dichloropyridine-3-carbonitrile |
| Example 10o:<br>2-chloro-4-((1-(cyclohexylmethyl)-2-oxo-4-((2-(pyrimidin-2-yl)propan-2-yl)amino)-1,2-dihydroquinolin-6-yl)amino)nicotinonitrile<br>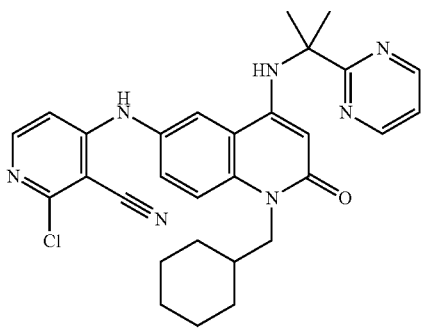 [SMILES: CC(C)(Nc1cc(=O)n(CC2CCCCC2)c2ccc(Nc3ccnc(Cl)c3C#N)cc12)c1ncccn1] | 1H NMR (500 MHz, Chloroform-d) δ 8.77 (d, J = 4.9 Hz, 2H), 8.08 (d, J = 6.1 Hz, 1H), 7.62 (d, J = 2.1 Hz, 1H), 7.40 (dd, J = 9.0, 2.1 Hz, 1H), 7.37 (d, J = 9.0 Hz, 1H), 7.24 (t, J = 4.9 Hz, 1H), 7.06 (s, 1H), 6.77 (s, 1H), 6.72 (d, J = 6.1 Hz, 1H), 5.70 (s, 1H), 4.11 (s, 2H), 1.87 (s, 6H), 1.85-1.56 (m, 7H), 1.21-1.11 (m, 4H). LCMS (Method T4) Rt = 3.08 mins, m/z 528.2273 [M + H]$^+$ expected 528.2279 for $C_{29}H_{31}ClN_7O$. | Intermediate A4i: 6-amino-1-(cyclohexylmethyl)-4-((2-(pyrimidin-2-yl)propan-2-yl)amino)quinolin-2(1H)-one and 2,4-dichloropyridine-3-carbonitrile |
| Example 10p:<br>2-chloro-4-((4-((cyclopropyl(pyrimidin-2-yl)methyl)amino)-1-methyl-2-oxo-1,2-dihydroquinolin-6-yl)amino)nicotinonitrile<br>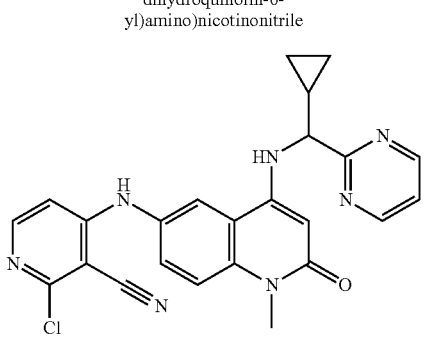 | $^1$H NMR (500 MHz, DMSO-d$_6$) δ 9.64 (s, 1H), 8.80 (d, J = 4.9 Hz, 2H), 8.36 (d, J = 2.2 Hz, 1H), 8.05 (d, J = 6.2 Hz, 1H), 7.52 (dd, J = 9.0, 2.2 Hz, 1H), 7.49 (d, J = 6.8 Hz, 1H), 7.47 (d, J = 9.0 Hz, 1H), 7.40 (t, J = 4.9 Hz, 1H), 6.61 (d, J = 6.2 Hz, 1H), 5.22 (s, 1H), 3.83 (dd, J = 9.3, 6.8 Hz, 1H), 3.44 (s, 3H), 1.57-1.48 (m, 1H), 0.67-0.57 (m, 1H), 0.54-0.41 (m, 3H). LCMS (Method T4) Rt = 2.64 mins, m/z 458.1476 [M + H]$^+$ expected 458.1491 for $C_{24}H_{21}ClN_7O$. | Intermediate A4m: 6-amino-4-((cyclopropyl(pyrimidin-2-yl)methyl)amino)-1-methylquinolin-2(1H)-one and 2,4-dichloropyridine-3-carbonitrile |

TABLE 9-continued

Compounds prepared by a method analogous to that used for the preparation of Example 1a.

| Example | Data | Intermediate |
| --- | --- | --- |
| Example 10q:<br>ethyl 7-((1-methyl-2-oxo-4-((1-(pyrimidin-2-yl)ethyl)amino)-1,2-dihydroquinolin-6-yl)amino)pyrazolo[1,5-a]pyrimidine-5-carboxylate | $^1$H NMR (500 MHz, Chloroform-d) δ 8.74 (d, J = 4.9 Hz, 2H), 8.33 (s, 1H), 8.20 (d, J = 2.4 Hz, 1H), 7.74 (d, J = 2.3 Hz, 1H), 7.63 (dd, J = 9.0, 2.3 Hz, 1H), 7.46 (d, J = 9.0 Hz, 1H), 7.22 (t, J = 4.9 Hz, 1H), 6.98 (s, 1H), 6.85 (d, J = 2.4 Hz, 1H), 6.52 (d, J = 6.6 Hz, 1H), 5.86 (s, 1H), 4.91 (app. quin., J = 6.6 Hz, 1H), 4.46 (q, J = 7.1 Hz, 2H), 3.69 (s, 3H), 1.67 (d, J = 6.6 Hz, 3H), 1.41 (t, J = 7.1 Hz, 3H). LCMS (Method T4) Rt = 2.64 mins, m/z 485.2043 [M + H]$^+$ expected 485.2044 for $C_{25}H_{25}N_8O_3$. | ethyl 7-chloropyrazolo[1,5-a]pyrimidine-5-carboxylate and Intermediate A1b: 6-amino-1-methyl-4-((1-(pyrimidin-2-yl)ethyl)amino)quinolin-2(1H)-one |
| Example 10r:<br>2-chloro-4-((8-methoxy-1-methyl-2-oxo-4-((2-(pyrimidin-2-yl)propan-2-yl)amino)-1,2-dihydroquinolin-6-yl)amino)nicotinonitrile | $^1$H NMR (500 MHz, Chloroform-d) δ 8.76 (d, J = 4.9 Hz, 2H), 8.10 (d, J = 6.1 Hz, 1H), 7.25 (d, J = 2.2 Hz, 1H), 7.23 (t, J = 4.9 Hz, 1H), 7.01 (s, 1H), 6.89 (d, J = 2.2 Hz, 1H), 6.78 (d, J = 6.1 Hz, 1H), 6.64 (s, 1H), 5.71 (s, 1H), 3.89 (s, 3H), 3.82 (s, 3H), 1.86 (s, 6H). LCMS (Method T4) Rt = 2.71 mins, m/z 476.1588 [M + H]$^+$ expected 476.1596 for $C_{24}H_{23}ClN_7O_2$. | Intermediate A10c: 6-amino-8-methoxy-1-methyl-4-((2-(pyrimidin-2-yl)propan-2-yl)amino)quinolin-2(1H)-one and 2,4-dichloropyridine-3-carbonitrile |
| Example 10s:<br>(S)-2-chloro-4-((1-methyl-2-oxo-4-((1-(pyrimidin-2-yl)ethyl)amino)-1,2-dihydroquinolin-6-yl)amino)nicotinonitrile | $^1$H NMR (500 MHz, DMSO-d6) δ 9.62 (s, 1H), 8.79 (d, J = 4.9 Hz, 2H), 8.29 (d, J = 2.2 Hz, 1H), 8.05 (d, J = 6.2 Hz, 1H), 7.56-7.44 (m, 2H), 7.40 (t, J = 4.9 Hz, 1H), 7.23 (d, J = 7.0 Hz, 1H), 6.61 (d, J = 6.2 Hz, 1H), 5.27 (s, 1H), 4.74 (p, J = 6.9 Hz, 1H), 3.46 (s, 3H), 1.60 (d, J = 6.9 Hz, 3H). LCMS (Method T4) Rt = 2.54 mins, m/z 432.1304 [M + H]$^+$ expected 432.1334 for $C_{22}H_{19}ClN_7O$. | Intermediate A4r: (S)-6-amino-1-methyl-4-((1-(pyrimidin-2-yl)ethyl)amino)quinolin-2(1H)-one and 2,4-dichloropyridine-3-carbonitrile |

TABLE 9-continued

Compounds prepared by a method analogous to that used for the preparation of Example 1a.

| Example | Data | Intermediate |
|---|---|---|
| Example 10t:<br>4-chloro-6-((1-methyl-2-oxo-4-((1-(pyrimidin-2-yl)ethyl)amino)-1,2-dihydroquinolin-6-yl)amino)pyrimidine-5-carbonitrile<br>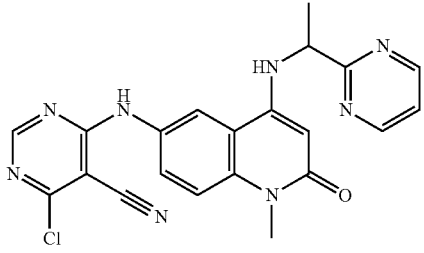 [SMILES: CC(Nc1cc(=O)n(C)c2ccc(Nc3ncnc(Cl)c3C#N)cc12)c1ncccn1] | $^1$H NMR (500 MHz, Chloroform-d) δ 8.76 (d, J = 4.9 Hz, 2H), 8.57 (s, 1H), 7.90 (d, J = 2.4 Hz, 1H), 7.80 (s, 1H), 7.72 (dd, J = 9.0, 2.4 Hz, 1H), 7.37 (d, J = 9.0 Hz, 1H), 7.25 (t, J = 4.9 Hz, 1H), 6.41 (d, J = 6.5 Hz, 1H), 5.80 (s, 1H), 4.89 (app. quin., J = 6.6 Hz, 1H), 3.64 (s, 3H), 1.66 (d, J = 6.7 Hz, 3H). LCMS (Method T4) Rt = 2.55 mins, m/z 433.1282 [M + H]$^+$ expected 433.1287 for $C_{21}H_{18}ClN_8O$. | Intermediate A1b: 6-amino-1-methyl-4-((1-(pyrimidin-2-yl)ethyl)amino) quinolin-2(1H)-one and 4,6-dichloropyrimidine-5-carbonitrile |
| Example 10u:<br>2-chloro-4-((1-methyl-2-oxo-4-((1-(pyrimidin-2-yl)cyclopropyl)amino)-1,2-dihydroquinolin-6-yl)amino)nicotinonitrile<br>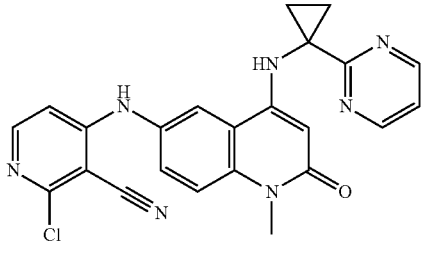 [SMILES: Cn1c(=O)cc(NC2(c3ncccn3)CC2)c2cc(Nc3ccnc(Cl)c3C#N)ccc21] | $^1$H NMR (500 MHz, DMSO-d$_6$) δ 9.61 (s, 1H), 8.69 (d, J = 4.9 Hz, 2H), 8.12 (d, J = 2.0 Hz, 1H), 8.06 (d, J = 6.2 Hz, 1H), 7.86 (s, 1H), 7.57-7.48 (m, 2H), 7.30 (t, J = 4.9 Hz, 1H), 6.64 (d, J = 6.2 Hz, 1H), 5.34 (s, 1H), 3.49 (s, 3H), 1.70 (br. s, 2H), 1.36 (br. s, 2H). LCMS (Method T4) Rt = 2.58 mins, m/z 444.1322 [M + H]$^+$ expected 444.1334 for $C_{23}H_{19}ClN_7O$. | Intermediate A4g: 6-amino-1-methyl-4-((1-(pyrimidin-2-yl)cyclopropyl) amino)quinolin-2(1H)-one and 2,4-dichloropyridine-3-carbonitrile |
| Example 10v:<br>2-chloro-4-((1-(cyclohexylmethyl)-2-oxo-4-((1-(pyrimidin-2-yl)ethyl)amino)-1,2-dihydroquinolin-6-yl)amino)nicotinonitrile<br>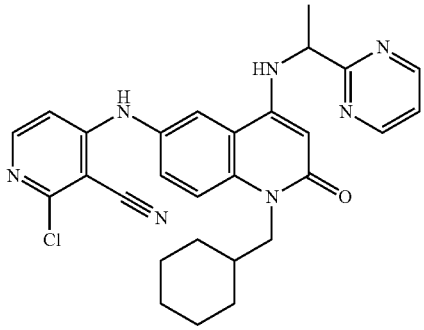 [SMILES: CC(Nc1cc(=O)n(CC2CCCCC2)c2ccc(Nc3ccnc(Cl)c3C#N)cc12)c1ncccn1] | $^1$H NMR (500 MHz, Chloroform-d) δ 8.77 (d, J = 4.9 Hz, 2H), 8.06 (d, J = 6.1 Hz, 1H), 7.58 (d, J = 2.2 Hz, 1H), 7.42 (dd, J = 9.0, 2.2 Hz, 1H), 7.38 (d, J = 9.0 Hz, 1H), 7.25 (t, J = 4.9 Hz, 1H), 7.08 (s, 1H), 6.67 (d, J = 6.1 Hz, 1H), 6.43 (d, J = 6.4 Hz, 1H), 5.82 (s, 1H), 4.89 (app. quin., J = 6.6 Hz, 1H), 4.13 (br. s, 2H), 1.87-1.59 (m, 10H), 1.22-1.13 (m, 4H). LCMS (Method T4) Rt = 3.04 mins, m/z 514.2109 [M + H]$^+$ expected 514.2117 for $C_{28}H_{29}ClN_7O$. | Intermediate A4h: 6-amino-1-(cyclohexylmethyl)-4-((1-(pyrimidin-2-yl)ethyl)amino) quinolin-2(1H)-one and 2,4-dichloropyridine-3-carbonitrile |

TABLE 9-continued

Compounds prepared by a method analogous to that used for the preparation of Example 1a.

| Example | Data | Intermediate |
| --- | --- | --- |
| Example 10w:<br>2-chloro-4-[[1-methyl-2-oxo-4-[1-(5-tetrahydropyran-4-ylpyrimidin-2-yl)ethylamino]-6-quinolyl]amino]pyridine-3-carbonitrile | 1H NMR (600 MHz, Chloroform-d) δ 8.63 (s, 2H), 8.06 (d, J = 6.1 Hz, 1H), 7.60 (d, J = 2.2 Hz, 1H), 7.46 (dd, J = 8.9, 2.2 Hz, 1H), 7.42 (d, J = 8.9 Hz, 1H), 7.07 (s, 1H), 6.65 (d, J = 6.1 Hz, 1H), 6.42 (d, J = 6.4 Hz, 1H), 5.84 (s, 1H), 4.88 (app. quin., J = 6.5 Hz, 1H), 4.14-4.07 (m, 2H), 3.67 (s, 3H), 3.54 (td, J = 11.5, 3.0 Hz, 2H), 2.87-2.77 (m, 1H), 1.87-1.77 (m, 4H), 1.65 (d, J = 6.7 Hz, 3H). LCMS (Method T4) Rt = 2.66 mins, m/z 516.1895 [M + H]$^+$ expected 516.1909 for $C_{27}H_{27}ClN_7O_2$. | Intermediate B21: 6-amino-1-methyl-4-((1-(5-(tetrahydro-2H-pyran-4-yl)pyrimidin-2-yl)ethyl)amino)quinolin-2(1H)-one and 2,4-dichloropyridine-3-carbonitrile |
| Example 10x:<br>2-chloro-4-((1-methyl-4-((1-(5-morpholinopyrimidin-2-yl)ethyl)amino)-2-oxo-1,2-dihydroquinolin-6-yl)amino)nicotinonitrile | $^1$H NMR (600 MHz, Chloroform-d) δ 8.37 (s, 2H), 8.06 (d, J = 6.1 Hz, 1H), 7.56 (d, J = 2.2 Hz, 1H), 7.45 (dd, J = 8.9, 2.2 Hz, 1H), 7.41 (d, J = 8.9 Hz, 1H), 7.00 (s, 1H), 6.63 (d, J = 6.1 Hz, 1H), 6.33 (d, J = 6.4 Hz, 1H), 5.82 (s, 1H), 4.82 (app. quin., J = 6.6 Hz, 1H), 3.91-3.86 (m, 4H), 3.66 (s, 3H), 3.22 (dd, J = 6.3, 3.7 Hz, 4H), 1.62 (m, 3H). LCMS (Method T4) Rt = 2.64 mins, m/z 517.1839 [M + H]$^+$ expected 517.1862 for $C_{26}H_{26}ClN_8O_2$. | Intermediate A4v: 6-amino-1-methyl-4-((1-(5-morpholinopyrimidin-2-yl)ethyl)amino)quinolin-2(1H)-one and 2,4-dichloropyridine-3-carbonitrile |

The following tabulated examples in Table 10 were prepared by an analogous method to that used for the preparation of example 3a, using the intermediates shown. For examples 11e, 11f, 11h, 11i and 11j the reactions were heated to 140° C.

TABLE 10

Compounds prepared by a method analogous to that used for the preparation of Example 3a.

| Example | Data and comments | Intermediate |
| --- | --- | --- |
| Example 11a:<br>(S)-2-chloro-4-((4-((1-cyclopropyl-2-hydroxyethyl)amino)-1-methyl-2-oxo-1,2-dihydroquinolin-6-yl)amino)nicotinonitrile | $^1$H NMR (600 MHz, Methanol-d$_4$) δ 8.11 (d, J = 2.2 Hz, 1H), 8.00 (d, J = 6.3 Hz, 1H), 7.67 (d, J = 9.0 Hz, 1H), 7.60 (dd, J = 9.0, 2.2 Hz, 1H), 6.71 (d, J = 6.3 Hz, 1H), 5.74 (s, 1H), 3.85 (dd, J = 11.4, 4.6 Hz, 1H), 3.75 (dd, J = 11.4, 5.9 Hz, 1H), 3.69 (s, 3H), 3.20-3.14 (m, 1H), 1.20-1.12 (m, 1H), 0.63-0.58 (m, 1H), 0.56-0.50 (m, 1H), 0.38-0.35 (dt, J = 4.8, 2.0 Hz, 2H). LCMS (Method T4) Rt = 2.58 mins, m/z 410.1367 [M + H]$^+$ expected 410.1378 for $C_{21}H_{21}ClN_5O_2$. | Intermediate A12b: (S)-6-amino-4-((1-cyclopropyl-2-hydroxyethyl)amino)-1-methylquinolin-2(1H-one and 2,4-dichloropyridine-3-carbonitrile |

TABLE 10-continued

Compounds prepared by a method analogous to that used for the preparation of Example 3a.

| Example | Data and comments | Intermediate |
| --- | --- | --- |
| Example 11b:<br>2-chloro-4-((1-methyl-2-oxo-4-((2-(pyridin-2-yl)propan-2-yl)amino)-1,2-dihydroquinolin-6-yl)amino)nicotinonitrile:formic acid (1:1) | $^1$H NMR (500 MHz, DMF-d$_7$) δ 8.80 (ddd, J = 4.8, 1.8, 0.9 Hz, 1H), 8.58 (d, J = 2.3 Hz, 1H), 8.30 (d, J = 6.1 Hz, 1H), 7.95 (td, J = 7.7, 1.8 Hz, 1H), 7.82 (dd, J = 9.0, 2.3 Hz, 1H), 7.79-7.76 (dt, J = 8.0, 1.1 Hz, 1H), 7.73 (d, J = 9.0 Hz, 1H), 7.46 (ddd, J = 7.7, 4.8, 1.1 Hz, 1H), 7.19 (s, broad, 1H), 7.00 (d, J = 6.1 Hz, 1H), 5.09 (s, 1H) 3.71 (s 3H) 1.96 (s 6H).<br>LCMS (Method T4) Rt = 2.51 mins, m/z 445.1532 [M + H]$^+$ expected 445.1538 for C$_{24}$H$_{22}$ClN$_6$O. | Intermediate A2v: 6-amino-1-methyl-4-((2-(pyridin-2-yl)amino)quinolin-2(1H)-one and 2,4-dichloropyridine-3-carbonitrile |
| Example 11c:<br>2-((6--((2-chloro-3-cyanopyridin-4-yl)amino)-1-methyl-2-oxo-1,2-dihydroquinolin-4-yl)amino)-2-methyl-N-((1-methyl-1H-pyrazol-4-yl)methyl)propanamide | $^1$H NMR (500 MHz, Methanol-d$_4$) δ 8.09 (d, J = 2.3 Hz, 1H), 7.99 (d, J = 6.2 Hz, 1H), 7.65 (d, J = 9.0 Hz, 1H), 7.58 (dd, J = 9.0, 2.3 Hz, 1H), 7.46 (s, 1H), 7.28 (s, 1H), 6.71 (d, J = 6.2 Hz, 1H), 5.47 (s, 1H), 4.24 (s, 2H), 3.82 (s, 3H), 3.67 (s, 3H), 1.61 (s, 6H).<br>LCMS (Method T4) Rt = 2.50 mins, m/z 505.1852 [M + H]$^+$ expected 505.1862 for C$_{25}$H$_{26}$ClN$_8$O$_2$. | Intermediate A2u: 2-(6-amino-1-methyl-2-oxo-1,2-dihydroquinolin-4-yl)amino)-2-methyl-N-((1-methyl-1H-pyrazol-4-yl)methyl)propanamide and 2,4-dichloropyridine-3-carbonitrile |
| Example 11d:<br>2-chloro-4-((1-methyl-2-oxo-4-((1-(pyridin-2-yl)ethyl)amino)-1,2-dihydroquinolin-6-yl)amino)nicotinonitrile: formic acid (1:1) | $^1$H NMR (500 MHz, Methanol-d$_4$) δ 8.60-8.52 (m, 1H), 8.43 (br s, 1H), 8.23 (d, J = 2.2 Hz, 1H), 8.04 (d, J = 6.2 Hz, 1H), 7.81 (td, J = 7.6, 1.7 Hz, 1H), 7.66 (d, J = 9.0 Hz, 1H), 7.62 (dd, J = 9.0, 2.2 Hz, 1H), 7.49 (d, J = 7.9 Hz, 1H), 7.33 (ddd, J = 7.6, 4.9, 1.2 Hz, 1H), 6.78 (d, J = 6.2 Hz, 1H), 5.46 (s, 1H), 4.77 (q, J = 6.8 Hz, 1H), 3.64 (s, 3H), 1.67 (d, J = 6.8 Hz, 3H).<br>LCMS (Method T4) Rt = 2.48 mins, m/z 431.1363 [M + H]$^+$ expected 431.1382 for C$_{23}$H$_{20}$ClN$_6$O. | Intermediate A2t: 6-amino-1-methyl-4-((1-(pyridin-2-yl)ethyl)amino)quinoline-2(1H)-one and 2,4-dichloropyridine-3-carbonitrile |

TABLE 10-continued

Compounds prepared by a method analogous to that used for the preparation of Example 3a.

| Example | Data and comments | Intermediate |
| --- | --- | --- |
| Example 11e:<br>(R)-6-((5-chloro-2-methoxypyrimidin-4-yl)amino-4-((1-cyclopropylethyl)amino)-1-methylquinolin-2(1H)-one | $^1$H NMR (600 MHz, Methanol-$d_4$) δ 8.34 (d, J = 2.3 Hz, 1H), 8.13 (s, 1H), 7.88 (dd, J = 9.1, 2.3 Hz, 1H), 7.56 (d, J = 9.1 Hz, 1H), 5.65 (s, 1H), 3.88 (s, 3H), 3.67 (s, 3H), 3.16-3.08 (m, 1H), 1.36 (d, J = 6.4 Hz, 3H), 1.17-1.10 (m, 1H), 0.63-0.57 (m, 1H), 0.57-0.52 (m, 1H), 0.39-0.30 (m, 2H).<br>LCMS (Method T4) Rt = 2.81 mins, m/z 400.1568 [M + H]$^+$ expected 400.1535 for $C_{20}H_{23}ClN_5O_2$. | Intermediate A1a:<br>(R)-6-amino-4-((1-cyclopropylethyl)amino)-1-methylquinoline-2(1H)-one- and 4,5-dichloro-2-methoxypyrimidine |
| Example 11f:<br>(S)-6-((5-chloro-2-methoxypyrimidin-4-yl)amino)-4-((1-cyclopropyl-2-hydroxyethyl)amino)-1-methylquinolin-2(1H)-one | 1H NMR (500 MHz, Methanol-$d_4$) δ 8.34 (m, 1H), 8.14 (s, 1H), 7.90 (dd, J = 9.1, 2.3 Hz, 1H), 7.59 (d, J = 9.1 Hz, 1H), 5.72 (s, 1H), 3.88 (s, 3H), 33.85 (dd, J = 11.3, 4.6 Hz, 1H), 3.75 (dd, J = 11.3, 5.4 Hz, 1H), 3.68 (s, 3H), 3.20-3.13 (m, 1H), 1.20-1.12 (m, 1H), 0.64-0.59 (m, 1H), 0.58-0.51 (m, 1H), 0.42-0.34 (m, 2H).<br>LCMS (Method T4) Rt = 2.61 mins, m/z 4.16.1471 [M + H]$^+$ expected 416.1484 for $C_{20}H_{23}ClN_5O_3$. | Intermediate A12b:<br>(S)-6-amino-4-((1-cyclopropyl-2-hydroxyethyl)amino-1-methylquinolin-2(1H)-one and 4,5-dichloro-2-methoxypyrimidine |
| Example 11g:<br>2-chloro-4-((4-((1-(2-methoxyethoxy)propan-2-yl)amino)-1-methyl-2-oxo-1,2-dihydroquinolin-6-yl)amino)nicotinonitrile | $^1$H NMR (600 MHz, Methanol-$d_4$) δ 8.04 (d, J = 2.3 Hz, 1H), 8.00 (d, J = 6.2 Hz, 1H), 7.66 (d, J = 9.0 Hz, 1H), 7.59 (dd, J = 9.0, 2.3 Hz, 1H), 6.70 (d, J = 6.2 Hz, 1H), 5.75 (s, 1H), 3.91-3.85 (m, 1H), 3.69 (s, 3H), 3.68-3.62 (m, 3H), 3.60 (dd, J = 9.8, 5.1 Hz, 1H), 3.57-3.53 (m, 2H), 3.34 (s, 3H), 1.32 (d, J = 6.5 Hz, 3H).<br>LCMS (Method T4) Rt = 2.63 mins, m/z 442.1647 [M + H]$^+$ expected 442.1640 for $C_{22}H_{25}ClN_5O_3$. | Intermediate A12c:<br>6-amino-4-((1-(2-methoxyethoxy)propan-2-yl)amino)-1-methylquinolin-2(1H)-one and 2,4-dichloropyridine-3-carbonitrile |

TABLE 10-continued

Compounds prepared by a method analogous to that used for the preparation of Example 3a.

| Example | Data and comments | Intermediate |
| --- | --- | --- |
| Example 11h: 2-chloro-4-((1-(cyclopropylmethyl)-2-oxo-4-((1-(pyrimidin-2-yl)ethyl)amino)-1,2-dihydroquinolin-6-yl)amino)nicotinonitrile | $^1$H NMR (600 MHz, Methanol-$d_4$) δ 8.80 (d, J = 4.9 Hz, 2H), 8.19 (d, J = 2.3 Hz, 1H), 8.03 (d, J = 6.2 Hz, 1H), 7.78 (d, J = 9.0 Hz, 1H), 7.61 (dd, J = 9.0, 2.3 Hz, 1H), 7.40 (t, J = 4.9 Hz, 1H), 6.79 (d, J = 6.3 Hz, 1H), 5.53 (s, 1H), 4.93-4.89 (m, 1H), 4.21 (d, J = 6.8 Hz, 2H), 1.71 (d, J = 6.9 Hz, 3H), 1.36-1.20 (m, 1H), 0.52-0.43 (m, 4H). LCMS (Method T4) Rt = 2.71 min, m/z 472.1650 [M + H]$^+$ expected 472.1653 for $C_{25}H_{23}ClN_7O^+$. | Intermediate A1w: 6-amino-1-(cyclopropylmethyl)-4-((1-(pyrimidin-2-yl)ethyl)amino) quinolin-2(1H)-one and 2,4-dichloropyridine-3-carbonitrile |
| Example 11i: 2-chloro-4((1-(cyclobutylmethyl)-2-oxo-4-((1-(pyrimidin-2-yl)ethyl)amino)-1,2-dihydroquinolin-6-yl)amino)nicotinonitrile | $^1$H NMR (600 MHz, Methanol-$d_4$) δ 8.80 (d, J = 4.9 Hz, 2H), 8.17 (d, J = 2.3 Hz, 1H), 8.03 (d, J = 6.2 Hz, 1H), 7.63 (d, J = 9.1 Hz, 1H), 7.58 (dd, J = 9.0, 2.4 Hz, 1H), 7.40 (t, J = 4.9 Hz, 1H), 6.78 (d, J = 6.2 Hz, 1H), 5.53 (s, 1H), 4.92 - 4.88 (m, 1H), 4.36 (d, J = 7.1 Hz, 2H), 2.85 - 2.75 (m, 1H), 2.06 - 1.81 (m, 6H), 1.71 (d, J = 6.9 Hz, 3H). LCMS (Method X4) Rt = 2.89 mins, m/z 486.1804 [M + H]+ expected 486.1809 for $C_{26}H_{25}ClN_7O^+$. | Intermediate A3h: 6-amino-1-(cyclobutylmethyl)-yl)-4-((1-(pyrimidin-2-yl)ethyl)amino) quinolin-2(1H)-one and 2,4-dichloropyridine-3-carbonitrile |
| Example 11j: 2-chloro-4-((1-(2-hydroxyethyl)-2-oxo-4-((1-(pyrimidin-2-yl)ethyl)amino)-1,2-dihydroquinolin-6-yl)amino)nicotinonitrile | 1H NMR (600 MHz, Methanol-d4) δ 8.80 (d, J = 4.9 Hz, 2H), 8.18 (d, J = 2.4 Hz, 1H), 8.03 (d, J = 6.2 Hz, 1H), 7.78 (d, J = 9.1 Hz, 1H), 7.58 (dd, J = 9.0, 2.4 Hz, 1H), 7.40 (t, J = 4.9 Hz, 1H), 6.78 (d, J = 6.2 Hz, 1H), 5.55 (d, J = 1.6 Hz, 1H), 4.92-4.88 (m, 1H), 4.40 (q, J = 6.3 Hz, 2H), 3.81 (t, J = 6.3 Hz, 2H), 1.71 (d, J = 6.9 Hz, 3H). LCMS (Method X4) Rt = 2.24 mins, m/z 462.1438 [M + H]$^+$ expected 462.1445 for $C_{23}H_{21}ClN_7O_2^+$. Purification by SCX-2 column leads to deprotection of the silyl group, to give the free alcohol product shown. | Intermediate A3i: 6-amino-1-(2-((tert-butyldimethylsilyl)oxy)ethyl)-4-((1-(pyrimidin-2-yl)ethyl)amino) quinolin-2(1H)-one and 2,4-dichloropyridine-3-carbonitrile |

Example 12a: 6-((5-Chloro-2-(4,4-difluoropiperidin-1-yl)pyrimidin-4-yl)amino)-1-methyl-4-((1-(pyrimidin-2-yl)ethyl)amino)quinazolin-2(1H)-one

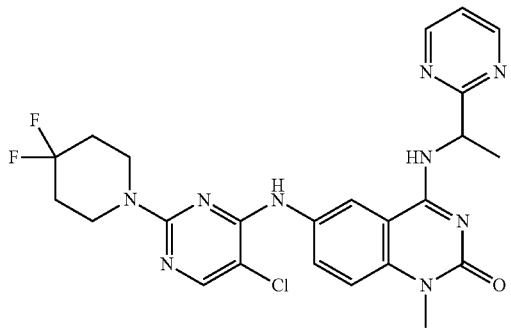 [SMILES: CC(Nc1nc(=O)n(C)c2ccc(Nc3nc(N4CCC(F)(F)CC4)ncc3Cl)cc12)c1ncccn1]

A mixture of 6-amino-1-methyl-4-(1-pyrimidin-2-ylethylamino)quinazolin-2-one (Intermediate A4p, 20 mg, 0.068 mmol), 2,4,5-trichloropyrimidine (15 mg, 0.08 mmol), NMP (0.67 mL) and DIPEA (47 uL, 0.27 mmol) were heated in the microwave for 1 h at 140° C. After this time 4,4-difluoropiperidine hydrochloride (31.9 mg, 0.20 mmol) and DIPEA (47 uL, 0.2700 mmol) were added to the mixture, which was then heated in the microwave for a further 1 h at 140° C. Once cooled, DMSO (0.7 mL) was added to the sample which was purified using reverse-phase C18 column eluting from 30-100% methanol in water (each containing 0.1% formic acid) to give the title compound (27 mg) as an off-white solid. $^1$H NMR (600 MHz, Chloroform-d) δ 8.75 (d, J=4.9 Hz, 2H), 8.05 (d, J=2.4 Hz, 1H), 8.03 (s, 1H), 7.74 (dd, J=9.0, 2.4 Hz, 1H), 7.55 (d, J=6.6 Hz, 1H), 7.27-7.22 (m, 2H), 7.16 (s, 1H), 5.75 (app. quin., J=6.4 Hz, 1H), 3.92-3.82 (m, 4H), 3.64 (s, 3H), 1.96-1.86 (m, 4H), 1.67 (d, J=6.8 Hz, 3H). LCMS (Method T4) Rt=2.81 mins, m/z 528.1816 [M+H]$^+$ expected 528.1833 for $C_{24}H_{25}ClF_2N_9O$.

The following tabulated examples in Table 11 were prepared by an analogous method to that used for the preparation of example 12a, using the intermediate shown and the appropriate amine. (4,4-Difluoro-3-piperidyl)methanol, used in the preparation of example 12i, was prepared by hydrogenation of commercial (1-benzyl-4,4-difluoro-3-piperidyl)methanol using palladium hydroxide in ethanol.

TABLE 11

| Compounds prepared by a method analogous to that used for the preparation of Example 12a. | | |
|---|---|---|
| Example | Data | Intermediate |
| Example 12b: (R)-1-(5-chloro-4-((4-((1-cyclopropylethyl)amino)-1-methyl-2-oxo-1,2-dihydroquinolin-6-yl)amino)pyrimidin-2-yl)-N,N-dimethylpiperidine-4-carboxamide | 1H NMR (500 MHz, Chloroform-d) δ 7.99 (s, 1H), 7.78 (d, J = 2.3 Hz, 1H), 7.69 (dd, J = 9.0, 2.3 Hz, 1H), 7.32 (d, J = 9.0 Hz, 1H), 7.01 (s, 1H), 5.71 (s, 1H), 4.71 yl) (d, J = 6.3 Hz, 1H), 4.69-4.58 (m, 2H), 3.65 (s, 3H), 3.10-3.00 (m, 4H), 2.97-2.89 (m, 5H), 2.82-2.71 (m, 1H), 1.83-1.66 (m, 4H), 1.30 (d, J = 6.3 Hz, 3H), 1.08-0.97 (m, 1H), 0.65-0.56 (m, 1H), 0.58-0.48 (m, 1H), 0.37-0.27 (m, 2H). LCMS (Method X4) Rt = 2.40 mins, m/z 524.2560 [M + H]$^+$ expected 524.2541 for $C_{27}H_{35}ClN_7O_2$. | Intermediate A1a: (R)-6-amino-4-((1-cyclopropylethyl)amino)-1-methylquinolin-2(1H)-one |
| Example 12c: 1-(5-chloro-4-((8-methoxy-1-methyl-2-oxo-4((2-(pyrimidin-2-Apropan-2-yl)amino)-1,2-dihydroquinolin-6-yl)amino)pyrimidin-2-yl)-N,N-dimethylpiperidine-4-carboxamide | $^1$H NMR (500 MHz, Chloroform-d) δ 8.74 (d, J = 4.8 Hz, 2H), 8.01 (s, 1H), 7.48 (d, J = 2.2 Hz, 1H), 7.38 (d, J = 2.2 Hz, 1H), 7.20 (t, J = 4.9 Hz, 1H), 7.03 (s, 1H), 6.40 (s, 1H), 5.59 (s, 1H), 4.73-4.66 (m, 2H), 3.88 (s, 3H), 3.80 (s, 3H), 3.05 (s, 3H), 2.92 (s, 3H), 2.91-2.80 (m, 2H), 2.76-2.66 (m, 1H), 1.86 (s, 6H), 1.73-1.66 (m, 4H). LCMS (Method X4) Rt = 2.57 mins, m/z 606.2709 [M + H]+ expected 606.2708 for $C_{30}H_{37}ClN_9O_3$. | Intermediate A10c: 6-amino-8-methoxy-1-methyl-4-(((2-(pyrimidin-2-yl)propan-2-yl)amino)quinolin-2(1H)-one |

TABLE 11-continued

Compounds prepared by a method analogous to that used for the preparation of Example 12a.

| Example | Data | Intermediate |
|---|---|---|
| Example 12d: 1-(5-chloro-4-((1-methyl-2-oxo-4((1-(pyrimidin-2-yl)ethyl)amino)-1,2-dihydroquinazolin-6-yl)amino)pyrimidin-2-yl)-N,N-dimethylpiperidine-4-carboxamide | $^1$H NMR (600 MHz, Methanol-d$_4$) δ 8.77 (d, J = 4.9 Hz, 2H), 8.35 (t, J = 2.3 Hz, 1H), 8.00-7.93 (m, 2H), 7.47-7.42 (m, 1H), 7.36 (t, J = 4.9 Hz, 1H), 5.65 (q, J = 7.1 Hz, 1H), 4.64-4.55 (m, 2H), 3.59 (s, 3H), 3.10 (s, 3H), 2.99-2.86 (m, 6H), 1.74-1.66 (m, 5H), 1.66-1.56 (m, 2H). LCMS (Method T4) Rt = 2.34 mins, m/z 563.2346 [M + H]$^+$ expected 563.2393 for C$_{27}$H$_{32}$ClN$_{10}$O$_2$ | Intermediate A4p: 6-amino-1-methyl-4-((1-(pyrimidin-2-yl)ethyl)amino)quinazolin-2(1H)-one |
| Example 12e: 6-((5-chloro-2-((3R,5S)-3,5-dimethylpiperidin-1-yl)pyrimidin-4-yl)amino)-1-methyl-4-((1-(pyrimidin-2-yl)ethyl)amino)quinazolin-2(1H)-one:formic acid (1:1) | $^1$H NMR 600 MHz, Methanol-d$_4$) δ 8.79 (d, J = 4.8 Hz, 2H), 8.36-8.30 (m, 1H), 8.21 (s, 1H), 7.99 (dd, J = 9.1, 2.3 Hz, 1H), 7.95 (d, J = 2.2 Hz, 1H), 7.47 (dd, J = 9.1, 4.1 Hz, 1H), 7.39 (t, J = 4.9 Hz, 1H), 5.70-5.59 (m, 1H), 4.55-4.44 (m, 2H), 3.62 (s, 3H), 2.32-2.18 (m, 2H), 1.81-1.73(m, 1H), 1.71 (d, J = 7.0 Hz, 2H), 1.59-1.46 (m, 2H), 0.89-0.79 (m, 6H), 0.79-0.68 (m, 1H). LCMS (Method T4) Rt = 2.88 mins, m/z 520.2263 [M + H]$^+$ expected 520.2335 for C$_{26}$H$_{31}$ClN$_9$O | Intermediate A4p: 6-amino-1-methyl-4-((1-(pyrimidin-2-yl)ethyl)amino)quinazolin-2(1H)-one |
| Example 12f: 6-((5-chloro-2-((2S,6R)-2,6-dimethylmorpholino)pyrimidin-4-yl)amino)-1-methyl-4-((2-(pyrimidin-2-yl)propan-2-yl)amino)quinolin-2(1H)-one | $^1$H NMR (500 MHz, Methanol-d$_4$) δ 8.80 (d, J = 4.9 Hz, 2H), 8.26 (d, J = 2.0 Hz, 1H), 8.00 (d, J = 1.3 Hz, 1H), 7.93 (dd, J = 9.1, 2.3 Hz, 1H), 7.53 (dd, J = 9.2, 2.2 Hz, 1H), 7.38 (t, J = 4.7 Hz, 1H), 5.22 (s, 1H), 4.43-4.34 (m, 2H), 3.61 (s, 3H), 3.57-3.43 (m, 2H), 2.48 (dd, J = 13.1, 10.6 Hz, 2H), 1.89 (d, J = 3.7 Hz, 6H), 1.14 (d, J = 6.2 Hz, 6H). LCMS (Method T4) Rt = 2.97 mins, m/z 535.2230 [M + H]$^+$ expected 535.2331 for C$_{27}$H$_{32}$ClN$_8$O$_2$ | Intermediate A3a: 6-amino-1-methyl-4-((2-(pyrimidin-2-yl)propan-2-yl)amino)quinolin-2(1H)-one |

TABLE 11-continued

Compounds prepared by a method analogous to that used for the preparation of Example 12a.

| Example | Data | Intermediate |
|---|---|---|
| Example 12g: 6-((5-chloro-2-(4,4-difluoropiperidin-1-yl)pyrimidin-4-yl)amino)-1-methyl-4-((2-(pyrimidin-2-yl)propan-2-yl)amino)quinolin-2(1H)-one.<br>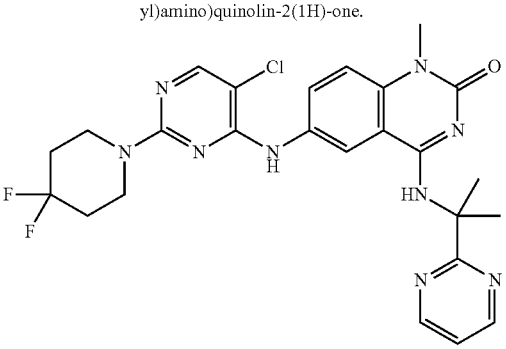 | $^1$H NMR (500 MHz, Methanol-d$_4$) δ 8.80 (d, J = 4.9 Hz, 2H), 8.30 (d, J = 2.3 Hz, 1H), 8.02 (s, 1H), 7.90 (dd, J = 9.1, 2.4 Hz, 1H), 7.53 (d, J = 9.1 Hz, 1H), 7.37 (t, J = 4.9 Hz, 1H), 5.17 (s, 1H), 3.88-3.76 (m, 4H), 3.60 (s, 3H), 2.00-1.90 (m, 4H), 1.88 (s, 6H). LCMS (Method T4) Rt = 3.04 mins, m/z 541.1978 [M + H]$^+$ expected 541.2037 for $C_{26}H_{28}ClF_2N_8O$ | Intermediate A3a: 6-amino-1-methyl-4-((2-(pyrimidin-2-yl)propan-2-yl)amino)quinolin-2(1H)-one |
| Example 12h: rac-6-((5-chloro-2-((3R,5S)-4,4-difluoro-3,5-dimethylpiperidin-1-yl)pyrimidin-4-yl)amino)-1-methyl-4-((1-(pyrimidin-2-yl)ethyl)amino)quinazolin-2(1H)-one<br>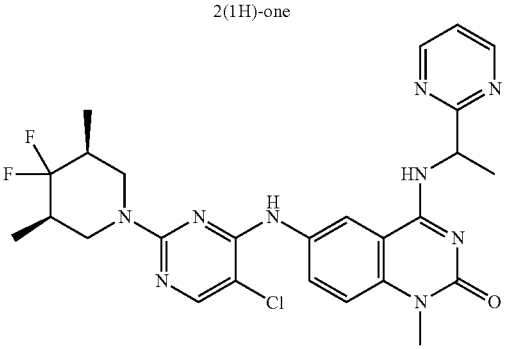 | $^1$H NMR (600 MHz, Methanol-d$_4$) δ 8.78 (d, J = 4.9 Hz, 2H), 8.35 (d, J = 2.3 Hz, 1H), 8.02 (s, 1H), 7.95 (dd, J = 9.1, 2.3 Hz, 1H), 7.50 (d, J = 9.1 Hz, 1H), 7.39 (t, J = 4.9 Hz, 1H), 5.68 (q, J = 7.0 Hz, 1H), 4.53 (m, 2H), 3.63 (s, 3H), 2.81-2.58 (m, 2H), 2.05-1.78 (m, 2H), 1.71 (d, J = 7.0 Hz, 3H), 0.95 (d, J = 7.3 Hz, 6H). LCMS (Method T4) Rt = 3.16 mins, m/z 556.2122 [M + H]$^+$ expected 556.2146 for $C_{26}H_{29}ClF_2N_9O$ | Intermediate A4p: 6-amino-1-methyl-4-((1-(pyrimidin-2-yl)ethyl)amino)quinazolin-2(1H)-one |
| Example 12i: 6-((5-chloro-2-(4,4-difluoro-3-(hydroxymethyl)piperidin-1-yl)pyrimidin-4-yl)amino)-1-methyl-4-((2-(pyrimidin-2-yl)propan-2-yl)amino)quinazolin-2(1H)-one<br>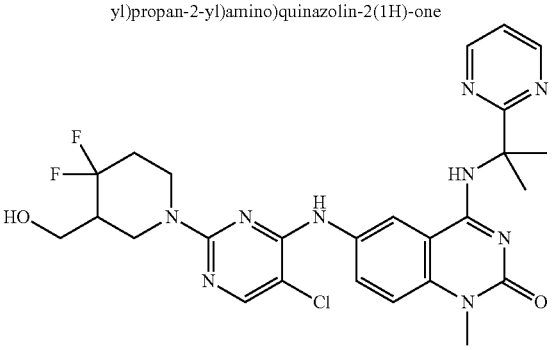 | $^1$H NMR (600 MHz, Methanol-d$_4$) δ 8.77 (d, J = 4.9 Hz, 2H), 8.33 (d, J = 2.3 Hz, 1H), 8.05-8.00 (m, 2H), 7.44 (d, J = 9.1 Hz, 1H), 7.35 (t, J = 4.9 Hz, 1H), 4.61 (d, J = 13.7 Hz, 1H), 4.41-4.29 (m, 1H), 3.90 (dd, J = 11.1, 4.0 Hz, 1H), 3.57 (s, 3H), 3.53-3.44 (m, 1H), 3.41-3.34 (m, 1H), 3.26-3.16 (m, 1H), 2.15-2.06 (m, 1H), 2.04-1.98 (m, 1H), 1.96 (d, J = 3.3 Hz, 6H), 1.93-1.81 (m, 1H). LCMS (Method X4) Rt = 2.77 mins, m/z 572.2110 [M + H]+ expected 572.2101 or $C_{26}H_{29}ClF_2N_9O_2^+$. | Intermediate F1i: 6+(((2,5-dichloropyrimidin-4-yl)amino)-1-methyl-4-((2-(pyrimidin-2-yl)propan-2-yl)amino)quinazolin-2-(1H)-one |

Example 13; 1-methyl-4-((2-(pyrimidin-2-yl)propan-2-yl)amino)-6-((2,3,6-trichloropyridin-4-yl)amino)quinolin-2(1H)-one

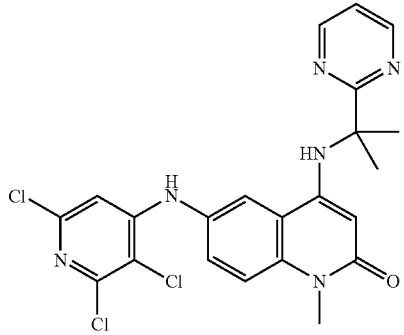 [SMILES: Cn1c(=O)cc(NC(C)(C)c2ncccn2)c2cc(Nc3cc(Cl)nc(Cl)c3Cl)ccc21]

A mixture of 6-amino-1-methyl-4-((2-(pyrimidin-2-yl)propan-2-yl)amino)quinolin-2(1H)-one (Intermediate A3a, 100 mg, 0.32 mmol), 2,3,4,6-tetrachloropyridine (84 mg, 0.39 mmol), NMP (3.2 mL) and triethylamine (90 uL, 0.65 mmol) was sealed in a vial and purged with argon for 5 mins. The vial was then heated in the microwave for 6 h at 140° C. Once cooled, DMSO (0.4 mL) was added to the sample which was purified directly using reverse-phase C18 column eluting from 30-100% methanol in water (each containing 0.1% formic acid) to give the title compound (52 mg) as a pale brown solid. $^1$H NMR (600 MHz, DMSO-$d_6$) δ 9.08 (s, 1H), 8.82 (d, J=4.9 Hz, 2H), 8.25 (d, J=2.3 Hz, 1H), 7.53 (dd, J=8.9, 2.3 Hz, 1H), 7.47 (d, J=8.9 Hz, 1H), 7.39 (t, J=4.9 Hz, 1H), 6.87 (s, 1H), 6.43 (s, 1H), 4.69 (s, 1H), 3.42 (s, 3H), 1.76 (s, 6H). LCMS (Method T4) Rt=2.95 mins, m/z 489.0749 [M+H]$^+$ expected 489.0759 for $C_{22}H_{20}Cl_3N_6O$.

Example 14a: 6-((5-chloro-6-methyl-2-(3-(trifluoromethyl)-1H-pyrazol-1-yl)pyrimidin-4-yl)amino)-1-methyl-4-((2-(pyrimidin-2-yl)propan-2-yl)amino)quinolin-2(1H)-one

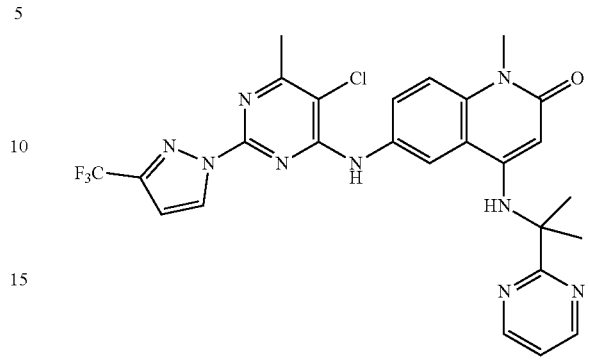

A mixture of 6-[(2,5-dichloro-6-methyl-pyrimidin-4-yl)amino]-1-methyl-4-[(1-methyl-1-pyrimidin-2-yl-ethyl)amino]quinolin-2-one (Intermediate F1g, 20 mg, 0.04 mmol), 5-(trifluoromethyl)-1H-pyrazole (29 mg, 0.21 mmol), and Cesium Carbonate (70 mg, 0.21 mmol) in NMP (0.60 mL) was heated in the MW at 180° C. for 1 h. The reaction mixture was purified via Biotage reverse-phase chromatography (C18, 12 g, 35-100% MeOH in water), yielding 6-((5-chloro-6-methyl-2-(3-(trifluoromethyl)-1H-pyrazol-1-yl)pyrimidin-4-yl)amino)-1-methyl-4-((2-(pyrimidin-2-yl)propan-2-yl)amino)quinolin-2(1H)-one (2 mg) as a brown solid. $^1$H NMR (600 MHz, Methanol-d4) δ 8.75 (d, J=4.9 Hz, 2H), 8.56 (dd, J=2.7, 1.1 Hz, 1H), 8.50 (d, J=2.4 Hz, 1H), 7.93 (dd, J=9.0, 2.4 Hz, 1H), 7.61 (d, J=9.1 Hz, 1H), 6.73 (d, J=2.7 Hz, 1H), 5.25 (s, 1H), 3.64 (s, 3H), 3.37 (s, 2H), 2.65 (s, 3H), 1.88 (s, 6H). LCMS (Method T4) Rt=3.28 mins, m/z 570.1763 [M+H]$^+$ expected 570.1744 for $C_{26}H_{23}ClF_3N_9O$.

The following tabulated examples in Table 12 were prepared by an analogous method to that used for the preparation of example 14a using the intermediates shown. For example 14b, reaction time was 7 h. For example 14e, reaction time was 9 h. For reaction 14f, reaction time was 3 h.

TABLE 12

Compounds prepared by a method analogous to that used for the preparation of Example 14a.

| Example | Data | Intermediate |
|---|---|---|
| Example 14b:<br>6-((5-chloro-6-(3,5-dimethyl-1H-pyrazol-1-yl)pyrimidin-4-yl)amino)-1-methyl-4-((1-(1-methyl-1H-1,2,4-triazol-3-yl)ethyl)amino)quinolin-2(1H)-one | $^1$H NMR (500 MHz, Chloroform-d) δ 8.38 (s, 1H), 7.82 (d, J = 2.3 Hz, 1H), 7.79 (s, 1H), 7.51 (dd, J = 9.0, 2.3 Hz, 1H), 7.35 (s, 1H), 7.19 (d, J = 9.0 Hz, 1H), 6.16 (br. s, 1H), 5.89 (s, 1H), 5.75 (s, 1H), 4.84 (app. quin., J = 6.7 Hz, 1H), 3.82 (s, 3H), 3.57 (s, 3H), 2.27 (s, 3H), 2.21 (s, 3H), 1.63 (d, J = 6.8 Hz, 3H). LCMS (Method T4) Rt = 2.70 mins, m/z 505.1961 [M + H]$^+$ expected 505.1974 for $C_{24}H_{26}ClN_{10}O$. | Intermediate F1d: 6-((2,5-dichloropyrimidin-4-yl)amino)-1-methyl-4-((1-(1-methyl-1H-1,2,4-triazol-3-yl)ethyl)amino)quinolin-2(1H)-one |

TABLE 12-continued

Compounds prepared by a method analogous to that used for the preparation of Example 14a.

| Example | Data | Intermediate |
|---|---|---|
| Example 14c: (R)-6-((5-chloro-2-(3,5-dimethyl-1H-pyrazol-1-yl)pyrimidin-4-yl)amino)-4-((1-cyclopropylethyl)amino)-1-methylquinolin-2(1H)-one 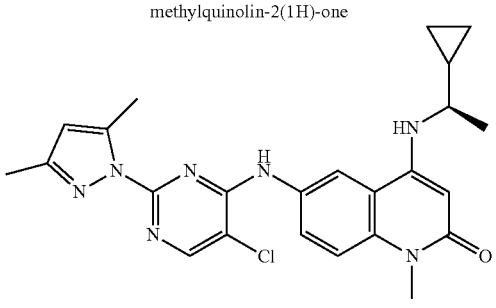 | 1H NMR (500 MHz, Chloroform-d) δ 8.39 (s, 1H), 7.82 (d, J = 2.3 Hz, 1H), 7.62 (dd, J = 9.0, 2.3 Hz, 1H), 7.35 (d, J = 9.0 Hz, 1H), 7.30 (s, 1H), 5.94 (s, 1H), 5.72 (s, 1H), 4.72 (d, J = 6.4 Hz, 1H), 3.66 (s, 3H), 3.10-3.00 (m, 1H), 2.31 (br. s, 3H), 2.29 (s, 3H), 1.28 (d, J = 6.4 Hz, 3H), 1.03-0.92 (m, 1H), 0.61-0.52 (m, 1H), 0.54-0.42 (m, 1H), 0.34-0.24 (m, 2H). LCMS (Method T4) Rt = 2.93 mins, m/z 464.1956 [M + H]+ expected 464.1960 for $C_{24}H_{27}ClN_7O$. | Intermediate F1e: (R)-4-((1-cyclopropylethyl)amino)-6-((2,5-dichloropyrimidin-4-yl)amino)-1-methylquinolin-2(1H)-one |
| Example 14d: 6-((5-chloro-2-(3-(trifluoromethyl)-1H-pyrazol-1-yl)pyrimidin-4-yl)amino)-1-methyl-4-((2-(pyrimidin-2-yl)propan-2-yl)amino)quinolin-2(1H)-one 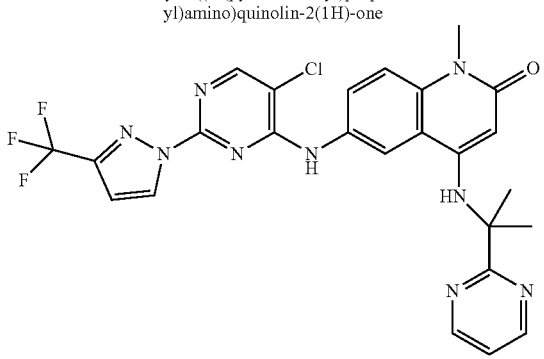 | $^1$H NMR (600 MHz, Methanol-$d_4$) δ 8.73 (d, J = 4.8 Hz, 2 H), 8.53 (br s, 1H), 8.50 (br s, 1H), 8.43 (s, 1H), 7.91 (d, J = 8.9 Hz, 1 H), 7.58 (d, J = 8.9 Hz, 1 H), 7.32 (t, J = 4.8 Hz, 1 H), 6.71 (d, J = 1.8 Hz, 1 H), 5.23 (s, 1 H), 3.62 (s, 3 H), 1.86 (s, 6 H); (Method T4) Rt = 3.01 mins, m/z 556.1496 [M + H]+ expected 556.1588 for $C_{25}H_{22}ClF_3N_9O^+$. | Intermediate F1a: 6-((2,5-dichloropyrimidin-4-yl)amino)-1-methyl-4-((2-(pyrimidin-2-yl)propan-2-yl)amino)quinolin-2(1H)-one |
| Example 14e: 6-((5-chloro-2-(3,5-dimethyl-1H-pyrazol-1-yl)pyrimidin-4-yl)amino)-4-((1-methoxy-2-methylpropan-2-yl)amino)-1-methylquinolin-2(1H)-one 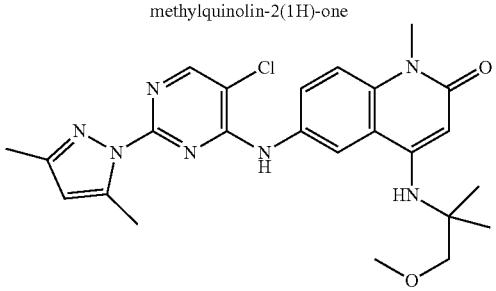 | $^1$H NMR (600 MHz, Methanol-d4) δ 8.39 (s, 1H), 8.11 (d, J = 2.3 Hz, 1H), 7.80 (dd, J = 9.0, 2.3 Hz, 1H), 7.60 (d, J = 8.9 Hz, 1H), 6.04 (s, 1H), 5.99 (s, 1H), 3.69 (s, 3H), 3.46 (s, 2H), 3.29 (s, 3H), 2.27 (s, 3H), 2.25 (s, 3H), 1.47 (s, 6H). LCMS (Method T4) Rt = 2.99 mins, m/z 482.2055 [M + H]+ expected 82.2066 for $C^{24}H^{29}ClN^7O^2$ | Intermediate F1f: 6-((2,5-dichloropyrimidin-4-yl)amino)-4-((1-methoxy-2-methylpropan-2-yl)amino)-1-methylquinolin-2(1H)-one |

TABLE 12-continued

Compounds prepared by a method analogous to that used for the preparation of Example 14a.

| Example | Data | Intermediate |
|---|---|---|
| Example 14f:<br>6-((5-chloro-2-(3,5-dimethyl-1H-pyrazol-1-yl)pyrimidin-4-yl)amino)-1-methyl-4-((1-(pyrimidin-2-yl)ethyl)amino)quinolin-2(1H)-one<br>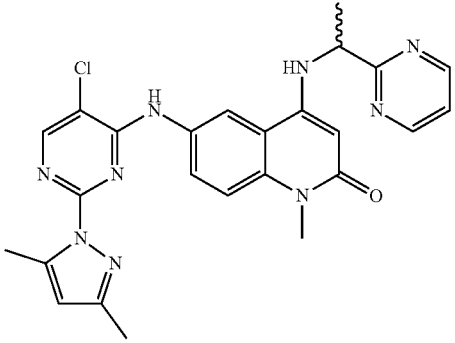 [SMILES: Cc1cc(C)n(-c2ncc(Cl)c(Nc3ccc4c(c3)c(NC(C)c3ncccn3)cc(=O)n4C)n2)n1] | $^1$H NMR (500 MHz, Methanol-d$_4$) 8.74 (d, J = 4.9 Hz, 2H), 8.40 (s, 1H), 8.36 (s, 1H), 7.78 (d, J = 10.0 Hz, 1H), 7.60 (d, J = 8.9 Hz, 1H), 7.37 (t, J = 4.9 Hz, 1H), 5.98 (s, 1H), 5.58 (s, 1H), 4.7 (q, 1H), 3.65 (s, 3H), 2.23 (s, 3H), 2.22 (s, 3H), 1.67 (d, J = 6.9 Hz, 3H).<br>LCMS (Method T4) Rt = 2.76 mins, m/z 502.1838 [M + H]$^+$ expected 502.1865 for C$_{25}$H$_{25}$ClN$_9$O. | Intermediate F1c: 6-((2,5-dichloropyrimidin-4-yl)amino)-4-((1-(4,5-dihydropyrimidin-2-yl)ethyl)amino)-1-methylquinolin-2(1H)-one |

Example 15a: 6-((5-Chloro-2-((S)-2-(methoxymethyl)pyrrolidine-1-carbonyl)pyridin-4-yl)amino)-4-(((R)-1-cyclopropylethyl)amino)-1-methylquinolin-2(1H)-one

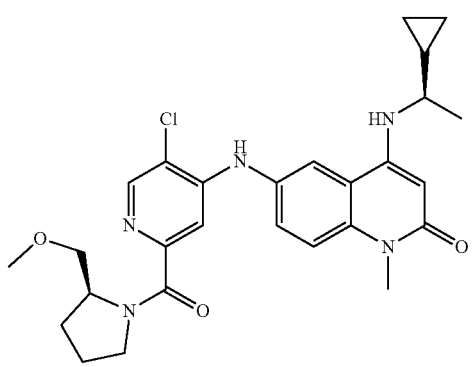 [SMILES: COC[C@@H]1CCCN1C(=O)c1cc(Nc2ccc3c(c2)c(N[C@H](C)C2CC2)cc(=O)n3C)c(Cl)cn1]

A mixture of cesium carbonate (111.4 mg, 0.342 mmol), (5-diphenylphosphanyl-9,9-dimethyl-xanthen-4-yl)-diphenyl-phosphane (14.8 mg, 0.026 mmol), 6-amino-4-[[(1F)-1-cyclopropylethyl]amino]-1-methyl-quinolin-2-one (Intermediate A1a, 11.0 mg, 0.043 mmol), (4,5-dichloro-2-pyridyl)-[(2S)-2-(methoxymethyl)pyrrolidin-1-yl] methanone (intermediate E6a, 11.7 mg, 0.041 mmol) and Pd$_2$(dba)$_3$ (3.9 mg, 0.004 mmol) was suspended in DMF (0.5 mL)/toluene (1.5 mL). The resulting suspension was stirred under microwave irradiation at 140° C. for an hour. The suspension was filtered, the solvent was conc. The crude was then purified by hplc and gave 6-[[5-chloro-2-[(2S)-2-(methoxymethyl)pyrrolidine-1-carbonyl]-4-pyridyl]amino]-4-[[(1R)-1-cyclopropylethyl]amino]-1-methyl-quinolin-2-one (2 mg, 9%, 0.004 mmol) as a light yellow oil. LCMS (Method T4) Rt=2.82 mins, m/z 510.2269 [M+H]$^+$ expected 510.2266 for C$_{27}$H$_{33}$ClN$_5$O$_3$. NMR showed two sets of signals, confirmed as rotamers using NOE experiments as described in *J. Org. Chem.* 77, 11, 5198-5202.

Rotamer A: $^1$H NMR (600 MHz, Methanol-d$_4$) δ 8.32 (s, 1H), 8.07 (t, J=1.9 Hz, 1H), 7.65 (dd, J=9.0, 2.0 Hz, 1H), 7.60 (dd, J=9.0, 2.0 Hz, 1H), 7.02 (d, J=15.0 Hz, 1H), 5.66 (s, 1H), 4.35-4.25 (m, 1H), 3.69 (s, 3H), 3.62-3.56 (m, 2H), 3.56-3.48 (m, 2H), 3.35 (s, 3H), 3.17-3.13 (m, 1H), 2.10-1.90 (m, 3H), 1.85-1.75 (m, 1H), 1.36 (d, J=6.4 Hz, 3H), 1.12-1.10 (m, 1H), 0.62-0.50 (m, 2H), 0.40-0.25 (m, 2H).
Rotamer B: $^1$H NMR (600 MHz, Methanol-d$_4$) δ 8.32 (s, 1H), 8.07 (t, J=1.9 Hz, 1H), 7.65 (dd, J=9.0, 2.0 Hz, 1H), 7.60 (dd, J=9.0, 2.0 Hz, 1H), 7.02 (d, J=15.0 Hz, 1H), 5.66 (s, 1H), 4.60-4.52 (m, 1H), 3.69 (s, 3H), 3.62-3.56 (m, 2H), 3.56-3.48 (m, 2H), 3.28-3.24 (m, 1H), 3.13 (s, 3H), 2.10-1.90 (m, 4H), 1.36 (d, J=6.4 Hz, 3H), 1.12-1.10 (m, 1H), 0.62-0.50 (m, 2H), 0.40-0.25 (m, 2H).

The following tabulated compounds were prepared by an analogous method to that used for the preparation of example 15a using the intermediates shown in Table 12b.

TABLE 12b

Compounds prepared by a method analogous to that used for the preperation of Example 15a.

| Example | Data and comments | Intermediate |
| --- | --- | --- |
| Example 15b: 6-((5-chloro-2-(2-(2-methoxyethyl)pyrrolidine-1-carbonyl)pyridin-4-yl)amino-4-(((R)-1-cyclopropylethyl)amino)-1-methylquinolin-2(1H)-one | Rotamer A: $^1$H NMR (600 MHz, Methanol-d$_4$) δ 8.32 (d, J = 1.2 Hz, 1H), 8.08 (dd, J = 2.3, 0.9 Hz, 1H), 7.65 (d, J = 9.0 Hz, 1H), 7.60 (dt, J = 9.0, 2.2 Hz, 1H), 6.99 (d, J = 7.3 Hz, 1H), 5.65 (s, 1H), 4.27-4.20 (m, 1H), 3.69 (s, 3H), 3.64-3.55 (m, 1H), 3.51-3.44 (m, 2H), 3.29 (s, 3H), 3.26-3.18 (m, 1H), 3.15-3.09 (m, 1H), 2.25-2.15 (m, 1H), 2.10-2.00 (m, 1H), 2.20-1.90 (m, 1H), 1.85-1.75 (m, 1H), 1.75-1.60 (m, 1H), 1.55-1.45 (m,1H), 1.36 (d, J = 4.5 Hz, 3H), 1.20-1.10 (m, 1H), 0.62-0.46 (m, 2H), 0.40-0.26 (m, 2H). Rotamer B: $^1$H NMR (600 MHz, Methanol-d$_4$) δ 8.33 (d, J = 1.2 Hz, 1H), 8.07 (dd, J = 2.3, 0.9 Hz, 1H), 7.65 (d, J = 9.0 Hz, 1H), 7.60 (dt, J = 9.0, 2.2 Hz, 1H), 7.01 (d, J = 1.8 Hz, 1H), 5.65 (s, 1H), 4.55-4.45 (m, 1H), 3.69 (s, 3H), 3.64-3.55 (m, 1H), 3.51-3.44 (m, 2H), 3.16 (s, 3H), 3.26-3.18 (m, 1H), 3.15-3.09 (m, 1H), 2.25-2.15 (m, 1H), 2.10-2.00 (m, 1H), 2.20-1.90 (m, 1H), 1.95-1.85 (m, 1H), 1.85-1.75 (m, 1H), 1.75-1.60 (m, 1H), 1.37 (d, J = 4.5 Hz, 3H), 1.20-1.10 (m, 1H), 0.62-0.46 (m, 2H), 0.40-0.26 (m, 2H). LCMS (Method T4) Rt = 2.84 mins, m/z 524.2407 [M + H]$^+$ expected 524.2423 for C$_{28}$H$_{35}$ClN$_5$O$_3$. | Intermediate A1a: (R)-6-amino-4-((1-cyclopropylethyl)amino)-1-methylquinolin-2(1H)-one and Intermediate E6b: (4,5-dichloropyridin-2-yl)(2-(2-methoxyethyl)pyrrolidin-1-yl)methanone. |
| Example 15c: (S)-6-((5-chloro-2-methoxypyridin-4-yl)amino)4-4((1-cyclopropyl-2-hydroxyethyl)amino)-1-methylquinoline-2(1H)-one | $^1$H NMR (600 MHz, DMF-d$_7$) δ 8.26 (s, 1H), 8.23 (d, J = 2.3 Hz, 1H), 8.02 (s, 1H), 7.60 (dd, J = 8.9, 2.3 Hz, 1H), 7.55 (d, J = 8.9 Hz, 1H), 6.67 (d, J = 7.8 Hz, 1H), 6.03 (s, 1H), 5.63 (s, 1H), 3.82-3.78 (dd + s, 1H + 3H), 3.75 (dd, J = 11.1, 5.8 Hz, 1H), 3.62 (s, 3H), 3.28-3.21 (m, 1H), 1.20 (m, 1H), 0.55-0.48 (m, 1H), 0.48-0.40 (m, 1H), 0.42-0.32 (m, 2H). LCMS (Method T4 Rt = 2.53 mins, m/z 415.1530 [M + H]$^+$ expected 415.1531 for C$_{21}$H$_{24}$ClN$_4$O$_3$. | Intermediate A12b: (S)-6-amino-4-((1-cyclopropyl-2-hydroxyethyl)amino)-1-methylquinolin-2(1H)-one and 4-bromo-5-chloro-2-methoxy-pyridine |
| Example 15d: (R)-6-((2-(azetidine-1-carbonyl)-5-chloropyridin-4-yl)amino)-4-((1-cyclopropylethyl)amino)-1-methylquinolin-2(1H)-one | $^1$H NMR (600 MHz, Methanol-d$_4$) δ 8.33 (s, 1H), 8.07 (d, J = 2.2 Hz, 1H), 7.64 (d, J = 8.9 Hz, 1H), 7.59 (dd, J = 8.9, 2.2 Hz, 1H), 7.33 (s, 1H), 5.65 (s, 1H), 4.71-4.55 (m, 2H), 4.14 (dd, J = 8.6, 7.0 Hz, 2H), 3.69 (s, 3H), 3.17-3.07 (m, 1H), 2.40-2.27 (m, 2H), 1.35 (d, J = 6.4 Hz, 3H), 1.15-1.07 (m, 1H), 0.60-0.54 (m, 1H), 0.54-0.48 (m, 1H), 0.38-0.33 (m, 1H), 0.33-0.27 (m, 1H). LCMS (Method T4) Rt = 2.79 mins, m/z 452.1841 [M + H]$^+$ expected 452.1848 for C$_{24}$H$_{27}$ClN$_5$O$_2$ | Intermediate A1a: (R)-6-amino-4-((1-cyclopropylethyl)amino)-1-methylquinolin-2(1H)-one and Intermediate E8a: azetidin-1-yl(4,5-dichloropyridin-2-yl)methanone |

TABLE 12b-continued

Compounds prepared by a method analogous to that used for the preperation of Example 15a.

| Example | Data and comments | Intermediate |
| --- | --- | --- |
| Example 15e: 6-((5-chloro-2-((2S,6R)-2,6-dimethylmorpholino)pyridin-4-yl)amino)-1-methyl-4-((1-(pyrimidin-2-yl)ethyl)amino)quinolin-2(1H)-one | $^1$H NMR (600 MHz, Methanol-d$_4$) δ 8.80 (d, J = 4.9 Hz, 2H), 8.10 (s, 1H), 7.92 (s, 1H), 7.62 (d, J = 2.2 Hz, 2H), 7.39 (t, J = 4.9 Hz, 1H), 6.22 (s, 1H), 5.57 (s, 1H), 4.90 (m, 1H), 3.88-3.74 (m, 2H), 3.65 (s, 3H), 3.70-3.58 (m, 2H), 2.37 (dd, J = 12.5, 10.5 Hz, 2H), 1.71 (d, J = 6.9 Hz, 3H), 1.16 (dd, J = 6.3, 1.5 Hz, 6H). LCMS (Method T4) Rt = 2.30 mins, m/z 520.2204 [M + H]$^+$ expected 520.2222 for C$_{27}$H$_{31}$ClN$_7$O$_2$ | Intermediate A1b: 6-amino-1-methyl-4-(1-pyrimidin-2-ylethylamino)quinolin-2-one and Intermediate E10c: (2S,6R)-4-(5-chloro-4-iodo-2-pyridyl)-2,6-dimethyl-morpholine |
| Example 15f: (R)-6-((5-chloro-2-(4-(2-hydroxyethyl)-1H-pyrazol-1-yl)pyridin-4-yl)amino)-4-((1-cyclopropylethyl)amino)-1-methylquinolin-2(1H)-one | $^1$H NMR (600 MHz, Methanol-d$_4$) δ 8.31 (d, J = 0.9 Hz, 1H), 8.16 (s, 1H), 8.12 (s, 1H), 7.71-7.59 (m, 2H), 7.52 (s, 1H), 7.29 (s, 1H), 5.65 (s, 1H), 3.72 (t, J = 6.7 Hz, 2H), 3.70 (s, 3H), 3.18-3.06 (m, 1H), 2.72 (t, J = 6.7 Hz, 2H), 1.34 (d, J = 6.4 Hz, 3H), 1.14-1.05 (m, 1H), 0.60-0.53 (m, 1H), 0.53-0.45 (m, 1H), 0.38-0.32 (m, 1H), 0.32-0.26 (m, 1H). LCMS (Method T4) Rt = 2.88 mins, m/z 479.1963 [M + H]$^+$ expected 479.1957 for C$_{25}$H$_{28}$ClN$_6$O$_2$ | Intermediate A1a: (R)-6-amino-4-((1-cyclopropylethyl)amino)-1-methylquinolin-2(1H)-one and Intermediate E9: 2-(1-(5-chloro-4-iodopyridin-2-yl)-1H-pyrazol-4-yl)ethan-1-ol |
| Example 15g: 1-(5-chloro-4-((1-methyl-2-oxo-4-((1-(pyrimidin-2-yl)ethyl)amino)-1,2-dihydroquinolin-6-yl)amino)pyridin-2-yl)-N,N-dimethylpiperidine-4-carboxamide | $^1$H NMR (600 MHz, Methanol-d$_4$) δ 8.79 (d, J = 4.9 Hz, 2H), 8.14 (dd, J = 1.8, 0.9 Hz, 1H), 7.91 (s, 1H), 7.62 (d, J = 1.8 Hz, 2H), 7.38 (t, J = 4.9 Hz, 1H), 6.23 (s, 1H), 5.55 (s, 1H), 4.90 (m, 1H), 4.05 (dd, J = 13.0, 3.6 Hz, 2H), 3.65 (s, 3H), 3.12 (s, 3H), 2.91 (s, 3H), 2.90-2.83 (m, 3H), 1.75-1.66 (m, 4H), 1.70 (d, J = 6.8 Hz, 3H). LCMS (Method T4) Rt = 2.11 mins, m/z 561.2432 [M + H]$^+$ expected 561.2488 for C$_{29}$H$_{34}$ClN$_8$O$_2$ | Intermediate A1b: 6-amino-1-methyl-4-(1-pyrimidin-2-ylethylamino)quinolin-2-one and Intermediate E10b: 1-(5-chloro-4-iodo-2-pyridll)-N,N-dimethyl-piperidine-4-carboxamide |

TABLE 12b-continued

Compounds prepared by a method analogous to that used for the preperation of Example 15a.

| Example | Data and comments | Intermediate |
|---|---|---|
| Example 15h: 6-((5-chloro-2-(4,4-difluoropiperidin-1-yl)pyridin-4-yl)amino)-1-methyl-4-((1-(pyrimidin-2-yl)ethyl)amino)quinolin-2(1H)-one | 1H NMR (600 MHz, Methanol-$d_4$) δ 8.79 (d, J = 4.9 Hz, 2H), 8.12 (s, 1H), 7.93 (s, 1H), 7.62 (d, J = 2.2 Hz, 2H), 7.39 (t, J = 4.9 Hz, 1H), 6.30 (s, 1H), 5.56 (s, 1H), 4.90 (m, 1H), 3.65 (s, 3H), 3.57-3.50 (m, 4H), 2.00-1.92 (m, 4H), 1.70 (d, J = 6.9 Hz, 3H). LCMS (Method T4) Rt = 2.35 mins, m/z 526.1899 [M + H]$^+$ expected 526.1928 for $C_{26}H_{27}ClF_2N_7O$ | Intermediate A1b: 6-amino-1-methyl-4-(1-pyrimidin-2-ylethylamino)quinolin-2-one and Intermediate E10a: 5-chloro-2-(4,4-difluoro-1-piperidyl)-4-iodo-pyridine |
| Example 15i: 6-((5-chloro-2-(4-(2-hydroxyethyl)-1H-pyrazol-1-yl)pyridin-4-yl)amino)-1-methyl-4-((1-(pyrimidin-2-yl)ethyl)amino)quinoline-2(1H)-one | $^1$H NMR (600 MHz, Methanol-$d_4$) δ 8.77 (d, J = 4.9 Hz, 2H), 8.33 (s, 1H), 8.18 (s, 1H), 8.16 (d, J = 1.9 Hz, 1H), 7.71-7.62 (m, 2H), 7.53 (s, 1H), 7.37 (t, J = 4.9 Hz, 1H), 7.32 (s, 1H), 5.58 (s, 1H), 4.89 (m, 1H), 3.73 (t, J = 6.7 Hz, 2H), 3.67 (s, 3H). LCMS (Method T4) Rt = 2.70 mins, m/z 517.1842 [M + H]$^+$ expected 517.1862 for $C_{26}H_{26}ClN_8O_2$ | Intermediate A1b: 6-amino-1-methyl-4-(1-pyrimidin-2-ylethylamino)quinolin-2-one and Intermediate E9: 2-(1-(5-chloro-4-iodopyridin-2-yl)-1H-pyrazol-4-yl)ethan-1-ol |

Example 16a: 1-(5-chloro-4-((1-methyl-2-oxo-4-((2-(pyrimidin-2-yl)propan-2-yl)amino)-1,2-dihydroquinolin-6-yl)amino)pyrimidin-2-yl)-N,N-dimethylpiperidine-4-carboxamide

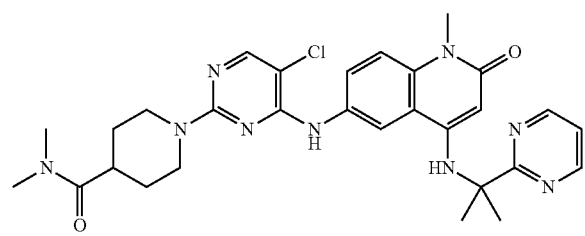 [SMILES: CN(C)C(=O)C1CCN(c2ncc(Cl)c(Nc3ccc4c(c3)c(NC(C)(C)c3ncccn3)cc(=O)n4C)n2)CC1]

An oven-dried microwave vial (0.5-2.0 mL volume) was charged with 6-((2,5-dichloropyrimidin-4-yl)amino)-1-methyl-4-((2-(pyrimidin-2-yl)propan-2-yl)amino)quinolin-2(1H)-one (Intermediate F1a; 17 mg, 0.038 mmol), cesium carbonate (64 mg, 0.196 mmol) and N,N-dimethylpiperidine-4-carboxamide hydrochloride (35 mg, 0.181 mmol). The reaction vial was flushed with Ar, sealed with a cap and then further flushed with Ar. Anhydrous NMP (0.6 mL) was added. The reaction mixture was heated at 160° C. under microwave irradiation for 1 h. The reaction mixture was dissolved in DMSO (0.8 mL) and directly purified by reverse-phase chromatography (Biotage reverse-phase 12 g C-18 column; 10-100% MeOH in $H_2O$ (containing 0.1% formic acid)), affording the title compound (13 mg, 61%) as a pale yellow solid. $^1$H NMR (600 MHz, Methanol-$d_4$) δ 8.80 (d, J=4.8 Hz, 2H), 8.29 (d, J=1.6 Hz, 1H), 7.98 (s, 1H), 7.92 (dd, J=9.0, 1.6 Hz, 1H), 7.52 (d, J=9.0 Hz, 1H), 7.37 (t, J=4.8 Hz, 1H), 5.17 (s, 1H), 4.62 (d, J=13.1 Hz, 2H), 3.60 (s, 3H), 3.12 (s, 3H), 2.97-2.89 (m, 6H), 1.88 (s, 6H), 1.75-1.70 (m, 2H), 1.65-1.57 (m, 2H); LCMS (Method T4) Rt=2.43 mins, m/z 576.2597 [M+H]$^+$ expected 576.2552 for $C_{29}H_{35}ClN_9O_2$.

The following tabulated examples in Table 13 were prepared by an analogous method to that used for the preparation of example 16a, using the intermediates shown. For examples 16c and 16d reaction temperature was 180° C.

TABLE 13

Compounds prepared by a method analogous to that used for the preparation of Example 16a.

| Example | Data and comments | Intermediate |
| --- | --- | --- |
| Example 16b: 1-(5-chloro-4-((4-((1-cyanocyclopropyl)amino)-1-methyl-2-oxo-1,2-dihydroquinolin-6-yl)amino)pyrimidin-2-yl)-N,N-dimethylpiperidine-4-carboxamide | $^1$H NMR (500 MHz, chloroform-d) δ 7.92 (s, 1 H), 7.89 (d, J = 2.1 Hz, 1 H), 7.64 (dd, J = 9.1, 2.1 Hz, 1 H), 7.33 (d, J = 9.1 Hz, 1 H), 7.09 (br s, 1 H), 6.25 (s, 1 H), 6.06 (br s, 1 H), 4.64-4.57 (m, 2 H), 3.69 (s, 3 H), 3.09 (s, 3 H), 2.95 (s, 3 H), 2.93-2.88 (m, 2 H), 2.85-2.78 (m, 1 H), 1.77-1 73 (m, 4 H), 1.62-1.59 (m, 2 H), 1.40-1.35 (m, 2 H); LCMS (Method T4) Rt = 2.28 mins, m/z 521.2160 [M + H]+ expected 521.2175 for $C_{26}H_{30}ClN_8O_2^+$. | Intermediate F1b: 1-((6-((2,5-dichloropyrimidin-4-yl)amino)-1-methyl-2-oxo-1,2-dihydroquinolin-4-yl)amino)cyclopropane-1-carbonitrile |
| Example 16c: 1-(5-chloro-4-methyl-6-((1-methyl-2-oxo-4-((2-(pyrimidin-2-yl)propan-2-yl)amino)-1,2-dihydroquinolin-6-yl)amino)pyrimidin-2-yl)-N,N-dimethylpiperidine-4-carboxamide | $^1$H NMR (600 MHz, Methanol-d4) δ 8.80 (d, J = 4.9 Hz, 2H), 8.28 (d, J = 2.3 Hz, 1H), 7.94 (dd, J = 9.1, 2.3 Hz, 1H), 7.51 (d, J = 9.1 Hz, 1H), 7.38 (t, J = 4.9 Hz, 1H), 5.17 (s, 1H), 4.68 (dt, J = 13.4, 3.3 Hz, 2H), 3.60 (s, 3H), 3.12 (s, 3H), 2.96-2.86 (m, 6H), 2.40 (s, 3H), 1.89 (s, 6H), 1.76-1.69 (m, 2H), 1.66-1.55 (m, 2H). LCMS (Method T4) Rt = 2.26 mins, m/z 590.2778 [M + H]+ expected 590.2759 for $C_{30}H_{37}ClN_9O_2$ | Intermediate F1g: 6-((2,5-dichloro-6-methylpyrimidin-4-yl)amino)-1-methyl-4-((2-(pyrimidin-2-yl)propan-2-yl)amino)quinolin-2(1H)-one |
| Example 16d: 1-(5-chloro-4-((4-((1-methoxy-2-methylpropan-2-yl)amino)-1-methyl-2-oxo-1,2-dihydroquinolin-6-yl)amino)pyrimidin-2-yl)-N,N-dimethylpiperidine-4-carboxamide | $^1$H NMR (500 MHz, DMSO-d6) δ 8.80 (s, 1H), 8.06 (d, J = 2.2 Hz, 1H), 8.04 (s, 1H), 7.77 (dd, J = 9.1, 2.2 Hz, 1H), 7.40 (d, J = 9.1 Hz, 1H), 5.63 (s, 1H), 4.59-4.31 (m, 2H), 3.50 (s, 3H), 3.47 (s, 2H), 3.31 (s, 3H), 3.02 (d, J = 2.8 Hz, 3H), 2.86 (td, J = 12.6, 2.8 Hz, 3H), 2.83-2.73 (m, 4H), 1.64-1.55 (m, 2H), 1.48-1.39 (m, 2H), 1.37 (s, 6H). LCMS (Method T4) Rt = 2.61 mins, m/z 542.2628 [M + H]+ expected 542.2641 for $C_{27}H_{37}ClN_7O_3$ | Intermediate F1f: 6-((2,5-dichloropyrimidin-4-yl)amino)-4-((1-methoxy-2-methylpropan-2-yl)amino)-1-methylquinolin-2(1H)-one |

Example 17a: 6-((5-chloro-2-((2S,6R)-2,6-dimethyl-morpholino)pyrimidin-4-yl)amino)-1-methyl-4-((1-(pyrimidin-2-yl)ethyl)amino)quinolin-2(1H)-one

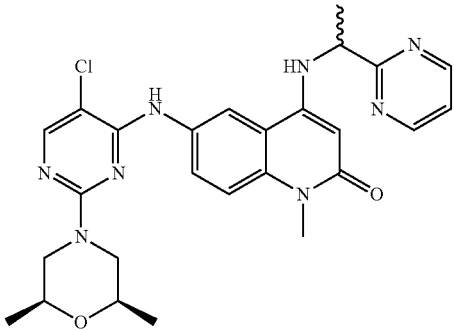 [SMILES: CC(Nc1cc(=O)n(C)c2ccc(Nc3nc(N4C[C@@H](C)O[C@@H](C)C4)ncc3Cl)cc12)c1ncccn1]

A mixture of 6-[(2,5-dichloropyrimidin-4-yl)amino]-1-methyl-4-(1-pyrimidin-2-ylethylamino)quinolin-2-one (Intermediate F1c, 8.6 mg, 0.019 mmol) and (2R,6S)-2,6-dimethylmorpholine (11.2 mg, 0.097 mmol) in NMP (1.50 mL) was stirred under microwave irradiation at 140° C. for 1 h. HPLC purification gave 6-[[5-chloro-2-[(2R,6S)-2,6-dimethylmorpholin-4-yl]pyrimidin-4-yl]amino]-1-methyl-4-(1-pyrimidin-2-ylethylamino)quinolin-2-one (4 mg). $^1$H NMR (600 MHz, methanol-$d_4$) δ 8.81 (d, J=4.9 Hz, 2H), 8.27 (d, J=2.0 Hz, 1H), 7.99 (s, 1H), 7.89 (dd, J=9.1, 2.0 Hz, 1H), 7.54 (d, J=9.1 Hz, 1H), 7.40 (t, J=4.9 Hz, 1H), 5.60 (s, 1H), 4.93-4.89 (m, 1H), 4.40-4.39 (m, 2H), 3.64 (s, 3H), 3.60-3.49 (m, 2H), 2.55-2.44 (m, 2H), 1.71 (d, J=6.8 Hz, 3H), 1.13 (d, J=6.1 Hz, 6H); LCMS (Method T4) Rt=2.78 mins, m/z 521.2156 [M+H]+ expected 521.2175 for $C_{26}H_{30}ClN_8O_2$.

The following tabulated examples in Table 14 were prepared by an analogous method to that used for the preparation of example 17a, using an appropriate amine. Example 17g was prepared using amine Intermediate C3: 2-methyl-2,9-diazaspiro[5.5]undecan-1-one.

TABLE 14

Compounds prepared by a method analogous to that ised for the preparation of Example 17a.

| Example | Data | Intermediate |
| --- | --- | --- |
| Eample 17b: 6-((5-chloro-2-(4,4-difluoropiperidin-1-yl)pyrimidin-4-yl)amino)-1-methyl-4-((1-(pyrimidin-2-yl)ethyl)amino)-4,/-naphthyridin-2(1H)-one | $^1$H NMR (600 MHz, Methanol-d4) δ 8.87-8.72 (m, 4H), 8.05 (s, 1H), 7.39 (t, J = 4.9 Hz, 1H), 5.58 (s, 1H), 4.94-4.88 (m, 1H), 3.86 (t, J = 5.8 Hz, 4H), 3.70 (s, 3H), 2.09-1.86 (m, 4H), 1.71 (d, J = 6.8 Hz, 3H). LCMS (Method T4) Rt = 3.05 mins, m/z 528.1817 [M + H]+ expected 528.1833 for $C_{24}H_{25}ClF_2N_9O$ | 6-((2,5-dichloropyrimidin-4-yl)amino)-4-((1-(4,5-dihydropyrimidin-2-yl)ethyl)amino)-1-methyl-1,8-naphthyridin-2(1H)-one (Intermediate F1h) |
| Example 17c: 1-(5-chloro-4-((-methyl-2-oxo-4-((1-(pyrimidin-2yl)ethyl)amino)-1,2-dihydroquinolin-6-yl)amino)pyrimidin-2-yl)-N,N-dimethylpiperidine-4-carboxamide | $^1$H NMR (500 MHz, Methanol-$d_4$) δ 8.80 (d, J = 4.9 Hz, 2H), 8.28 (d, J = 2.2 Hz, 1H), 7.97 (s, 1H), 7.91 (dd, J = 9.1, 2.2 Hz, 1H), 7.52 (d, J = 9.1 Hz, 1H), 7.39 (t, J = 4.9 Hz, 1H), 5.56 (s, 1H), 4.86 (q, 1H), 4.66-4.60 (m, 2H), 3.62 (s, 3H), 3.12 (s, 3H), 2.98-2.90 (m, 1H + 2H), 2.91 (s, 3H), 1.78-1.68 (m, 2H), 1.71 (d, J = 6.9 Hz, 3H), 1.68-1.58 (m, 2H). LCMS (Method T4) Rt = 2.36 mins, m/z 562.2432 [M + H]+ expected 562.2440 for $C_{28}H_{33}ClN_9O_2$. | 6-[(2,5-dichloropyrimidin-4-yl)amino]-1-methyl-4-(1-pyrimidin-2-ylethylamino)quinolin-2-one (Intermediate F1c) |

TABLE 14-continued

Compounds prepared by a method analogous to that ised for the preparation of Example 17a.

| Example | Data | Intermediate |
| --- | --- | --- |
| Example 17d: 6-((5-chloro-2-((2S,6R)-2,6-dimethylmorpholino)pyrimidin-4-yl)amino)-4-(((R)-1-cyclopropylethyl)amino)-1-methylquinolin-2(1H)-one:formic acid (1:1) | $^1$H NMR (600 MHz, Methanol-$d_4$) δ 8.38 (s, 1H), 8.16 (d, J = 2.3 Hz, 1H), 7.98 (s, 1H), 7.88 (dd, J = 9.1, 2.3 Hz, 1H), 7.56 (d, J = 9.1 Hz, 1H), 5.66 (s, 1H), 4.38-4.32 (m, 2H), 3.68 (s, 3H), 3.62-3.50 (m, 2H), 3.20-3.12 (m, 1H), 2.55-2.45 (m, 2H), 1.37 (d, J = 6.4 Hz, 3H), 1.17-1.15 (m, 1H), 1.15 (d, J = 6.2 Hz, 6H), 0.65-0.48 (m, 2H), 0.42-0.30 (m, 2H). LCMS (Method T4) Rt = 2.98 mins, m/z 483.2231 [M + H]$^+$ expected 483.2270 for $C_{25}H_{32}ClN_6O_2$. | (R)-4-((1-cyclopropylethyl)amino)-6-((2,5-dichloropyrimidin-4-yl)amino)-1-methylquinolin-2(1H)-one (Intermediate F1e) |
| Example 17e: 2-(1-(5-chloro-4-((1-methyl-2-oxo-4-((1-(pyrimidin-2-yl)ethyl)amino)-1,2-dihydroquinolin-6-yl)amino)pyrimidin-2-yl)piperidin-4-yl)-N,N-dimethylacetamide:formic acid (1:1) | $^1$H NMR (500 MHz, Methanol-$d_4$) δ 8.81 (d, J = 4.9 Hz, 2H), 8.32 (d, J = 2.2 Hz, 1H), 8.27 (s, 1H), 7.96 (s, 1H), 7.93 (dd, J = 9.0, 2.2 Hz, 1H), 7.54 (d, J = 9.0 Hz, 1H), 7.40 (t, J = 4.9 Hz, 1H), 5.59 (s, 1H), 4.94-4.83 (m, 1H), 4.66-4.52 (m, 2H), 3.64 (s, 3H), 3.04 (s, 3H), 2.93 (s, 3H), 2.87 (dd, J = 14.1, 11.6 Hz, 2H), 2.30 (d, J = 7.0 Hz, 2H), 2.08-1.94 (m, 1H), 1.80-1.74 (m, 2H), 1.72 (d, J = 6.8 Hz, 3H), 1.19 (m, 2H). LCMS (Method T4) Rt = 2.43 mins, m/z 576.2585 [M + H]$^+$ expected 576.2597 for $C_{29}H_{35}ClN_9O_2$. | 6-[((2,5-dichloropyrimidin-4-yl)amino]-1-methyl-4-(1-pyrimidin-2-ylethylamino)quinolin-2-one (Intermediate F1c) |
| Example 17f: 6-((5-chloro-2-((pyridin-3-ylmethyl)amino)pyrimidin-4-yl)amino)-1-methyl-4((1-(pyrimidin-2-yl)ethyl)amino)quinolin-2(1H)-one:formic acid (1:1) | $^1$H NMR (500 MHz, Methanol-$d_4$) δ 8.77 (d, J = 4.9 Hz, 2H), 8.37 (br, 1H), 8.35-8.21 (m, broad, 3H), 7.94 (s, 1H), 7.78 (broad, 1H), 7.64 (broad, 1H), 7.48-7.40 (m, 1H), 7.37 (t, J = 4.9 Hz, 1H), 7.28-7.20 (broad, 1H), 5.56 (s, 1H), 4.85 (q, 1H), 4.58-4.41 (m, 2H), 3.63 (s, 3H), 1.70 (d, J = 6.8 Hz, 3H). LCMS (Method T4) Rt = 1.97 mins, m/z 514.1846 [M + H]$^+$ expected 514.1865 for $C_{26}H_{25}ClN_9O$. | 6-[(2,5-dichloropyrimidin-4-yl)amino]-1-methyl-4-(1-pyrimidin-2-ylethylamino)quinolin-2-one (Intermediate F1c) |

TABLE 14-continued

Compounds prepared by a method analogous to that ised for the preparation of Example 17a.

| Example | Data | Intermediate |
| --- | --- | --- |
| Example 17g: 9-(5-chloro-4-((1-methyl-2-oxo-4((1-(pyrimidin-2-yl)ethyl)amino)-1,2-dihydroquinolin-6-yl)amino)pyrimidin-2-yl)-2-methyl-2,9-diazaspiro[5.5]undecan-1-one | $^1$H NMR (500 MHz, Methanol-d$_4$) δ 8.79 (d, J = 4.9 Hz, 2H), 8.32 (d, J = 2.3 Hz, 1H), 7.96 (s, 1H), 7.90 (dd, J = 9.1, 2.4 Hz, 1H), 7.52 (d, J = 9.1 Hz, 1H), 7.38 (t, J = 4.9 Hz, 1H), 5.56 (s, 1H), 4.85 (q, 1H), 4.47-4.12 (m, 2H), 3.62 (s, 3H), 3.36-3.31 (m, 2H), 3.31 -3.21 (m, 2H), 2.87 (s, 3H), 2.16-1.98 (m, 2H), 1.90-1.80 (m, 4H), 1.70 (d, J = 6.8 Hz, 3H), 1.54-1.45 (m, 2H). LCMS (Method T4) Rt = 2.47 mins, m/z 588.2576 [M + H]$^+$ expected 588.2597 for C$_{30}$H$_{35}$ClN$_9$O$_2$. | 6-[((2,5-dichloropyrimidin-4-yl)amino]-1-methyl-4-(1-pyrimidin-2-ylethylamino) quinolin-2-one (Intermediate F1c) |
| Example 17h: 6-((5-chloro-2-(7-oxa-2-azaspiro[3.5]nonan-2-yl)pyrimidin-4-yl)amino)-1-methyl-4((1-(pyrimidin-2-yl)ethyl)amino)quinolin-2(1H)-one:formic acid (1:1) | $^1$H NMR (500 MHz, Methanol-d$_4$) δ 8.82 (d, J = 4.9 Hz, 2H), 8.48 (d, J = 2.4 Hz, 1H), 8.20 (1H, br), 7.98 (dd, J = 9.1, 2.4 Hz, 1H), 7.96 (s, 1H), 7.53 (d, J = 9.1 Hz, 1H), 7.40 (t, J = 4.9 Hz, 1H), 5.60 (s, 1H), 4.85 (q, 1H), 3.87 (q, J = 8.5 Hz, 4H), 3.63 (s, 3H), 3.62-3.58 (m, 4H), 1.80-1.75 (m, 4H), 1.73 (d, J = 6.9 Hz, 3H). LCMS (Method T4) Rt = 2.41 mins, m/z 533.2162 [M + H]$^+$ expected 533.2175 for C$_{27}$H$_{30}$ClN$_8$O$_2$. | 6-[((2,5-dichloropyrimidin-4-yl)amino]-1-methyl-4-(1-pyrimidin-2-ylethylamino) quinolin-2-one (Intermediate F1c) |
| Example 17i: 6-((5-chloro-2-(4,4-difluoropiperidin-1-yl)pyrimidin-4-yl)amino)-1-methyl-4-((1-(pyrimidin-2-yl)ethyl)amino)quinolin-2(1H)-one | $^1$H NMR (500 MHz, Methanol-d$_4$) δ 8.80 (d, J = 4.9 Hz, 2H), 8.32 (d, J = 2.3 Hz, 1H), 8.01 (s, 1H), 7.88 (dd, J = 9.1, 2.3 Hz, 1H), 7.55 (d, J = 9.1 Hz, 1H), 7.39 (t, J = 4.9 Hz, 1H), 5.58 (s, 1H), 4.91 (d, 1H), 3.89-3.82 (m, 4H), 3.64 (s, 3H), 2.09-1.82 (m, 4H), 1.71 (d, J = 6.8 Hz, 3H). LCMS (Method T4) Rt = 2.90 mins, m/z 527.1879 [M + H]$^+$ expected 527.1881 for C$_{25}$H$_{26}$ClF$_2$N$_8$O. | 6-[(2,5-dichloropyrimidin-4-yl)amino]-1-methyl-4-(1-pyrimidin-2-ylethylamino) quinloin-2-one (Intermediate F1c) |

TABLE 14-continued

Compounds prepared by a method analogous to that ised for the preparation of Example 17a.

| Example | Data | Intermediate |
|---|---|---|
| Example 17j: 1-(5-chloro-4-((1-methyl-2-oxo-4-((11-(pyrimidin-2-yl)ethyl)amino)-1,2-dihydroquinoline-6-yl)amino)pyrimidin-2-yl)-3-methylazetidine-3-carbonitrile 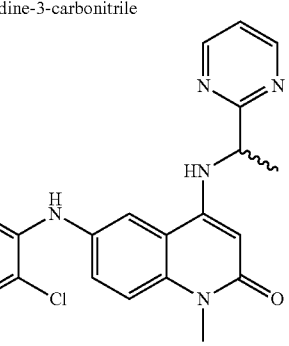 | $^1$H NMR (500 MHz, Methanol-d$_4$) δ 8.82 (d, J = 4.9 Hz, 2H), 8.54 (t, J = 1.8 Hz, 1H), 8.02 (s, 1H), 7.87 (dd, J = 9.1, 2.3 Hz, 1H), 7.54 (d, J = 9.1 Hz, 1H), 7.39 (t, J = 4.9 Hz, 1H), 5.60 (s, 1H), 4.93 (q, 1H), 4.44 (dd, J = 15.1, 8.6 Hz, 2H), 4.05 (t, J = 8.1 Hz, 2H), 3.63 (s, 3H), 1.73 (d, J = 6.8 Hz, 3H), 1.67 (s, 3H). LCMS (Method T4) Rt = 2.59 mins, m/z 502.1842 [M + H]$^+$ expected 502.1865 for C$_{25}$H$_{25}$ClN$_9$O. | 6-[(2,5-dichloropyrimidin-4-yl)amino]-1-methyl-4-(1-pyrimidin-2-ylethylamino)quinloin-2-one (Intermediate F1c) |
| Example 17k: 6-((5-chloro-2-(2-methyl-2,4,6,7-tetrahydro-5H-pyrazolo[4,3-c]pyridin-5-yl)pyrimidin-4-yl)amino)-1-methyl-4-((1-(pyrimidin-2-yl)ethyl)amino)quinolin-2(1H)-one 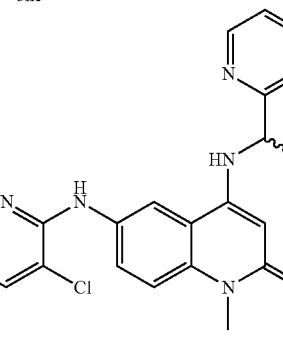 | $^1$H NMR (500 MHz, Methanol-d$_4$) δ 8.77 (d, J = 4.9 Hz, 2H), 8.35 (d, J = 2.4 Hz, 1H), 8.01 (s, 1H), 7.92 (dd, J = 9.1, 2.4 Hz, 1H), 7.58 (d, J = 9.1 Hz, 1H), 7.35 (t, J = 4.9 Hz, 1H), 4.92 (q, 1H), 4.74-4.58 (m, 2H), 4.13-4.03 (m, 1H), 4.02-3.93 (m, 1H), 3.79 (s, 3H), 3.66 (s, 3H), 2.74-2.70 (m, 2H), 1.69 (d, J = 6.8 Hz, 3H). LCMS (Method T4) Rt = 2.63 mins, m/z 543.2109 [M + H]$^+$ expected 543.2131 for C$_{27}$H$_{28}$ClN$_{10}$O. | 6-[(2,5-dichloropyrimidin-4-yl)amino]-1-methyl-4-(1-pyrimidin-2-ylethylamino)quinloin-2-one (Intermediate F1c) |

Example 18a: 2-methyl-4-((1-methyl-2-oxo-4-((1-(pyrimidin-2-yl)ethyl)amino)-1,2-dihydroquinolin-6-yl)amino)nicotinonitrile

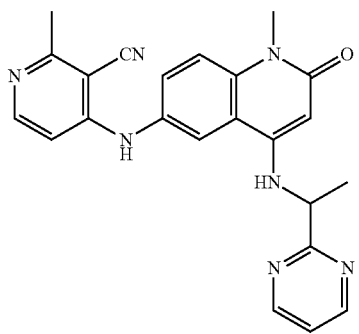 [SMILES: Cc1nccc(Nc2ccc3c(c2)c(NC(C)c2ncccn2)cc(=O)n3C)c1C#N]

To a sealed microwave vial under nitrogen containing 2-chloro-4-[[1-methyl-2-oxo-4-(1-pyrimidin-2-ylethylamino)-6-quinolyl]amino]pyridine-3-carbonitrile (Example 1b, 10 mg, 0.023 mmol) and methylboronic acid (2.1 mg, 0.035 mmol) in degassed dioxane (3 mL) was added Bis(triphenylphosphine)palladium(II) chloride (3.3 mg, 0.0046 mmol) followed by degassed 2M aq sodium carbonate (0.035 mL, 0.07 mmol) and the reaction was heated in the MW at 120° C. for 1 h. LCMS showed starting material still present. Under nitrogen, Bis(triphenylphosphine)palladium (II) chloride (3.3 mg, 0.0046 mmo), methylboronic acid (2.1 mg, 0.035 mmol) and 2M aq sodium carbonate (0.05 mL, 0.0232 mmol) were further added and the reaction was degassed for 5 min before being heated in the MW at 120° C. for 2 h. The crude reaction mixture was filtered, and the filtrate was concentrated under reduced pressure. The resulting residue was purified via reverse-phase Biotage chromatography (12-80% MeOH in water) to yield the title compound (4 mg) as a white solid. $^1$H NMR (500 MHz, Methanol-d4) δ 8.80 (d, J=4.9 Hz, 2H), 8.16 (d, J=2.1 Hz, 1H), 8.11 (d, J=6.3 Hz, 1H), 7.63 (d, J=9.0 Hz, 1H), 7.60 (dd, J=9.0, 2.2 Hz, 1H), 7.40 (t, J=5.0 Hz, 1H), 6.72 (d, J=6.3 Hz, 1H), 5.54 (s, 1H), 4.96-4.82 (m, 1H), 3.64 (s, 3H), 2.66 (s, 3H), 1.71 (d, J=6.9 Hz, 3H). LCMS (Method T4) Rt=1.87 mins, m/z 412.1869 [M+H]$^+$ expected 412.1880 for C$_{23}$H$_{22}$N$_7$O.

Example 18b: 5-cyano-N, 6-dimethyl-4-((1-methyl-2-oxo-4-((1-(pyrimidin-2-yl)ethyl)amino)-1,2-dihydroquinolin-6-yl)amino)picolinamide

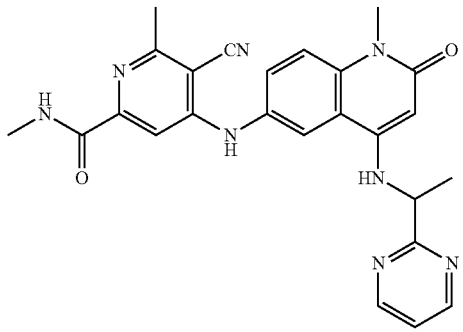 [SMILES: CNC(=O)c1cc(Nc2ccc3c(c2)c(NC(C)c2ncccn2)cc(=O)n3C)c(C#N)c(C)n1]

Prepared by an analogous method to that used for the preparation of example 18a, using Example 1 v: 6-chloro-5-cyano-N-methyl-4-[[1-methyl-2-oxo-4-(1-pyrimidin-2-ylethylamino)-6-quinolyl]amino]pyridine-2-carboxamide.
$^1$H NMR (600 MHz, Methanol-d4) δ 8.79 (d, J=4.9 Hz, 2H), 8.15 (d, J=2.3 Hz, 1H), 7.65 (d, J=9.0 Hz, 1H), 7.62 (dd, J=8.9, 2.3 Hz, 1H), 7.39 (t, J=4.9 Hz, 1H), 7.33 (s, 1H), 5.57 (s, 1H), 4.93-4.89 (m, 1H), 3.66 (s, 3H), 2.92 (s, 3H), 2.71 (s, 3H), 1.70 (d, J=6.9 Hz, 3H). LCMS (Method T4) Rt=2.6 mins, m/z 469.2078 [M+H]$^+$ expected 469.2095 for $C_{25}H_{25}N_8O_2$ Example 19a: 6-chloro-5-cyano-N,N-dimethyl-4-((1-methyl-2-oxo-4-((2-(pyrimidin-2-yl)propan-2-yl)amino)-1,2-dihydroquinolin-6-yl)amino)picolinamide

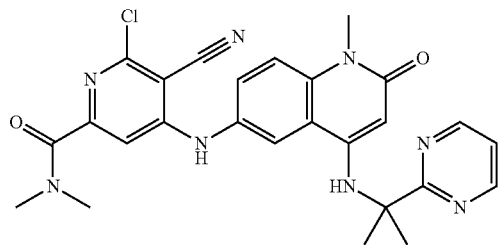 [SMILES: CN(C)C(=O)c1cc(Nc2ccc3c(c2)c(NC(C)(C)c2ncccn2)cc(=O)n3C)c(C#N)c(Cl)n1]

An oven-dried microwave vial (0.5-2.0 mL volume) was charged with 6-amino-1-methyl-4-((2-(pyrimidin-2-yl)propan-2-yl)amino)quinolin-2(1H)-one (Intermediate A3a; 16 mg, 0.052 mmol) and 4,6-dichloro-5-cyano-N,N-dimethylpicolinamide (Intermediate E1b; 19 mg, 0.079 mmol). The reaction vial was flushed with Ar, sealed with a cap and then further flushed with Ar. Anhydrous NMP (0.6 mL) was added followed by DIPEA (18 uL, 0.10 mmol). The reaction mixture was heated at 140° C. under microwave irradiation for 1 h. The reaction mixture was allowed to cool to rt. The mixture was diluted with DMSO (0.8 mL) and directly purified by reverse-phase chromatography (Biotage reverse-phase 12 g C-18 column; 10-100% methanol in water (containing 0.1% formic acid)). The product containing fractions were combined, concentrated in vacuo and re-purified by flash chromatography (10 g KP-sil; 0% to 10% methanol in dichloromethane). The product containing fractions were combined, concentrated in vacuo and then re-dissolved in a 1:1 mixture of MeCN/DMSO (1.5 mL). Purification by HPLC (ACE 5 C18-PFP 250×21.2 mm column; 15 min gradient of 45:55 to 20:80 $H_2O$:MeOH (both modified with 0.1% formic acid); flow rate 20 mLmin$^-$$_1$; Agilent 6120 MS-Prep LC) afforded the title compound (6 mg, 20%) as a pale yellow solid. $^1$H NMR (600 MHz, Methanol-d$_4$) δ 8.79 (d, J=4.8 Hz, 2H), 8.16 (s, 1H), 7.64-7.57 (m, 2H), 7.36 (t, J=4.8 Hz, 1H), 6.83 (s, 1H), 5.05 (s, 1H), 3.59 (s, 3H), 3.02 (s, 3H), 2.99 (s, 3H), 1.85 (s, 6H); LCMS (Method T4) Rt=2.54 mins, m/z 517.1837 [M+H]$^+$ expected 517.1862 for $C_{26}H_{26}ClN_8O_2^+$.

The following tabulated examples in Table 15 were prepared by an analogous method to that used for the preparation of example 19a, using the intermediates shown. For example 19c, the reaction was heated to 140° C. for 2 h, then further heated to 160° C. for 1 hr. For example 19e, a reaction time of 0.5 h at temperature of 120° C. was used. For example 19h, a reaction time of 0.5 h at temperature of 220° C. was used.

TABLE 15

Compounds prepared by a method analogous to that used for the preparation of Example 19a.

| Example | Data | Intermediate |
| --- | --- | --- |
| Example 19b: 6-chloro-5-cyano-N,N-dimethyl-4-((1-methyl-2-oxo-4-(0-(pyrimidin-2-yl)ethyl)amino)-1,2-dihydroquinolin-6-yl)amino)picolinamide | $^1$H NMR (600 MHz, Methanol-d4) δ 8.79 (d, J = 4.9 Hz, 2H), 8.19 (d, J = 2.3 Hz, 1H), 7.68-7.58 (m, 2H), 7.39 (t, J = 4.8 Hz, 1H), 6.86 (s, 1H), 5.54 (s, 1H), 4.91-4.88 (m, 1H), 3.64 (s, 3H), 3.04 (s, 3H), 3.01 (s, 3H), 1.71 (d, J = 6.9 Hz, 3H) LCMS (Method T4) Rt = 2.54 mins, m/z 503.1695 [M + H]$^+$ expected 503.1705 for $C_{25}H_{24}ClN_8O_2$ | Intermediate A1b: 6-amino-1-methyl-4-((1-(pyrimidin-2-yl)ethyl)amino)quinolin-2(1H)-one and Intermediate E1b: 4,6-dichloro-5-cyano-N,N-dimethylpicolinamide |

TABLE 15-continued

Compounds prepared by a method analogous to that used for the preparation of Example 19a.

| Example | Data | Intermediate |
|---|---|---|
| Example 19c: 5-cyano-N-methyl-4-(0-methyl-2-oxo-4-(0-(pyrimidin-2-yl)ethyl)amino)-1,2-dihydroquinolin-6-yl)amino)picolinamide 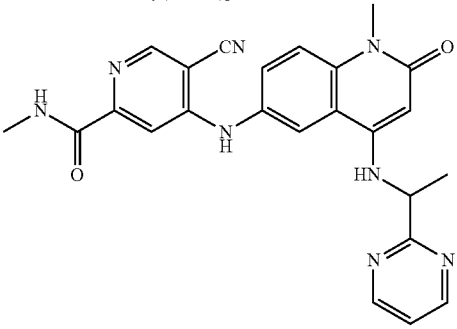 | $^1$H NMR (600 MHz, Methanol-d4) δ 8.79 (d, J = 4.9 Hz, 2H), 8.58 (s, 1H), 8.17 (d, J = 2.2 Hz, 1H), 7.66 (d, J = 8.9 Hz, 1H), 7.63 (dd, J = 9.0, 2.2 Hz, 1H), 7.48 (s, 1H), 7.38 (t, J = 4.9 Hz, 1H), 5.57 (s, 1H), 4.95-4.86 (m, 1H), 3.66 (s, 3H), 2.92 (s, 3H), 1.70 (d, J = 6.9 Hz, 3H). LCMS (Method T4) Rt = 2.40 mins, m/z 55.1931 [M + H]$^+$ expected 455.1938 for $C_{24}H_{23}N_8O_2$ | Intermediate A1b: 6-amino-1-methyl-4-((1-(pyrimidin-2-yl)ethyl)amino) quinolin-2(1H)-one and Intermediate E7: 4-chloro-5-cyano-N-methylpicolinamide |
| Example 19d: 2-chloro-4-((4-((1-methoxy-2-methylpropan-2-yl)amino)-1-methyl-2-oxo-1,2-dihydroquinolin-6-yl)amino)nicotinonitrile 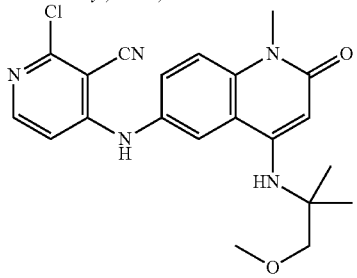 | $^1$H NMR (600 MHz, DMSO-d6) δ 9.55 (s, 1H), 8.03 (d, J = 6.2 Hz, 1H), 7.97 (d, J = 2.1 Hz, 1H), 7.52 (dd, J = 8.9, 2.0 Hz, 1H), 7.50 (d, J = 8.9 Hz, 1H), 6.63 (d, J = 6.2 Hz, 1H), 5.76 (s, 1H), 5.73 (s, 1H), 3.52 (s, 3H), 3.49 (s, 2H), 3.31 (s, 3H), 1.39 (s, 6H). LCMS (Method T4) Rt = 2.81 mins, m/z 412.1540 [M + H]$^+$ expected 412.1535 for $C_{21}H_{23}ClN_5O_2$ | Intermediate A4e: 6-amino-4-((1-methoxy-2-methylpropan-2-yl)amino)-1-methylquinolin-2(1H)-one and 2,4-dichloropyridine-3-carbonitrile (commercial) |
| Example 19e: 6-((5,6-dichloropyrimidin-4-yl)amino)-1-methyl-4-((1-(pyrimidin-2-yl)ethyl)amino)quinolin-2(1H)-one 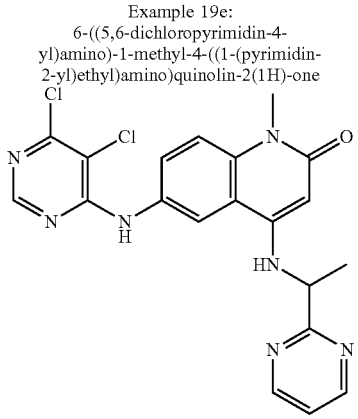 | $^1$H NMR (500 MHz, Methanol-d4) δ 8.81 (d, J = 5.0 Hz, 2H), 8.31 (s, 1H), 8.30 (d, J = 2.3 Hz, 1H), 7.91 (dd, J = 9.1, 2.4 Hz, 1H), 7.57 (d, J = 9.1 Hz, 1H), 7.40 (t, J = 4.9 Hz, 1H), 5.58 (s, 1H), 4.94-4.91 (m, 1H), 3.64 (s, 3H), 1.72 (d, J = 6.9 Hz, 3H) LCMS (Method T4) Rt = 2.74 mins, m/z 442.0932 [M + H]$^+$ expected 442.0944 for $C_{20}H_{18}Cl_2N_7O$ | Intermediate A1b: 6-amino-1-methyl-4-((1-(pyrimidin-2-yl)ethyl)amino) quinolin-2(1H)-one and 4,5,6-trichloropyrimidine |

TABLE 15-continued

Compounds prepared by a method analogous to that used for the preparation of Example 19a.

| Example | Data | Intermediate |
|---|---|---|
| Example 19f:<br>6-chloro-5-cyano-4-((4-((1-methoxy-2-methylbutan-2-yl)amino)-1-methyl-2-oxo-1,2-dihydroquinolin-6-yl)amino)-N-methylpicolinamide<br>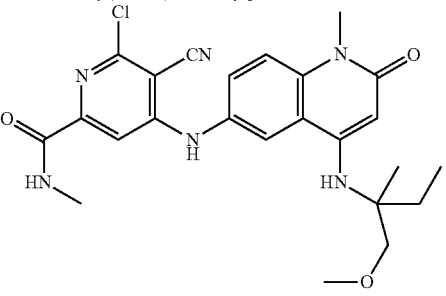 | $^1$H NMR (500 MHz, Methanol-d4) δ 7.90 (d, J = 2.3 Hz, 1H), 7.66 (d, J = 9.0 Hz, 1H), 7.61 (dd, J = 9.0, 2.3 Hz, 1H), 7.39 (s, 1H), 6.00 (s, 1H), 3.69 (s, 3H), 3.63 (d, J = 9.3 Hz, 1H), 3.45 (d, J = 9.4 Hz, 1H), 3.38 (s, 3H), 2.89 (s, 3H), 1.98-1.82 (m, 2H), 1.44 (s, 3H), 0.91 (t, J = 7.5 Hz, 3H).<br>LCMS (Method T4) Rt = 2.92 mins, m/z 483.1892 [M + H]$^+$ expected 483.1906 for $C_{24}H_{28}ClN_6O_3$ | Intermediate A4f: 6-amino-4-((1-methoxy-2-methylbutan-2-yl)amino)-1-methylquinolin-2(1H)-one and Intermediate E1a: 4,6-Dichloro-5-cyano-N-methyl-pyridine-2-carboxamide |
| Example 19g:<br>rac-6-chloro-5-cyano-4((4-(((1S,2R)-2-methoxycyclopentyl)amino)-1-methyl-2-oxo-1,2-dihydroquinolin-6-yl)amino)-N-methylpicolinamide<br>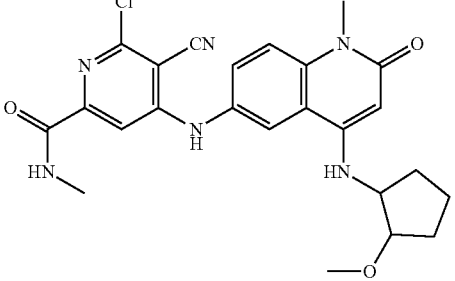 | $^1$H NMR (600 MHz, Methanol-d4) δ 7.93 (d, J = 2.4 Hz, 1H), 7.67 (d, J = 8.9 Hz, 1H), 7.65-7.55 (m, 1H), 7.41 (d, J = 2.6 Hz, 1H), 5.75 (s, 1H), 4.04 - 3.94 (m, 1H), 3.94-3.84 (m, 1H), 3.71 (s, 3H), 3.33 (d, J = 1.7 Hz, 3H), 2.89 (d, J = 2.4 Hz, 3H), 2.19-2.08 (m, 1H), 1.97-1.59 (m, 5H).<br>LCMS (Method T4) Rt = 2.88 mins, m/z 481.1738 [M + H]$^+$ expected 481.1749 for $C_{24}H_{26}ClN_6O_3$ | Intermediate A4x: rac-6-amino-4-(((1S,2R)-2-methoxycyclopentyl)amino)-1-methylquinolin-2(1H)-one and Intermediate E1a: 4,6-Dichloro-5-cyano-N-methyl-pyridine-2-carboxamide |
| Example 19h:<br>3-chloro-4-((1-methyl-2-oxo-4-((1-(pyrimidin-2-yl)ethyl)amino)-1,2-dihydroquinolin-6-yl)amino)picolinonitrile<br>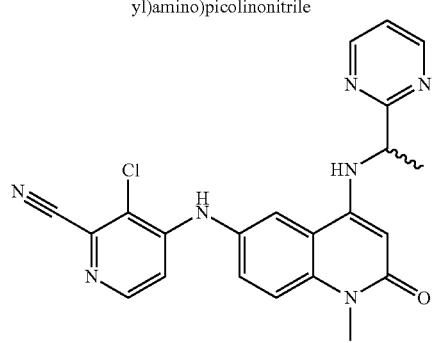 | $^1$H NMR (600 MHz, Methanol-d$_4$) δ 8.80 (d, J = 4.9 Hz, 2H), 8.19 (d, J = 2.3 Hz, 1H), 8.14 (d, J = 5.8 Hz, 1H), 7.66 (d, J = 9.0 Hz, 1H), 7.62 (dd, J = 9.0, 2.3 Hz, 1H), 7.40 (t, J = 4.9 Hz, 1H), 7.01 (d, J = 5.8 Hz, 1H), 5.55 (s, 1H), 4.85 (q, 1H), 3.65 (s, 3H), 1.71 (d, J = 6.9 Hz, 3H).<br>LCMS (Method T4) Rt = 2.55 mins, m/z 432.1323 [M + H]+ expected 432.1334 for $C_{22}H_{19}ClN_7O$. | Intermediate A1b: 6-amino-1-methyl-4-(1-pyrimidin-2-ylethylamino) quinolin-2-one and Intermediate E5: 3,4-dichloropicolinonitrile (added as a solution in NMP) |

TABLE 15-continued

Compounds prepared by a method analogous to that used for the preparation of Example 19a.

| Example | Data | Intermediate |
| --- | --- | --- |
| Example 19i: 2-chloro-4-((1-methyl-2-oxo-4-((3-(pyrimidin-2-yl)tetrahydrofuran-3-yl)amino)-1,2-dihydroquinolin-6-yl)amino)nicotinonitrile | $^{1}$H NMR (600 MHz, Methanol-$d_4$) δ 8.81 (d, J = 4.9 Hz, 2H), 8.24 (d, J = 2.3 Hz, 1H), 8.03 (d, J = 6.2 Hz, 1H), 7.65 (d, J = 9.0 Hz, 1H), 7.61 (dd, J = 9.0, 2.3 Hz, 1H), 7.39 (t, J = 4.9 Hz, 1H), 6.77 (d, J = 6.2 Hz, 1H), 5.24 (s, 1H), 4.48-4.39 (m, 2H), 4.22-4.10 (m, 2H), 3.62 (s, 3H), 3.07-2.99 (m, 1H), 2.74-2.65 (m, 1H). LCMS (Method T4) Rt = 2.57 min, m/z 474.1383 [M + H]$^{+}$ expected 474.1440 for $C_{24}H_{21}ClN_{7}O_{2}$ | 6-amino-1-methyl-4-[(3-pyrimidin-2-yltetrahydrofuran-3-yl)amino]quinolin-2-one (Intermediate A1v) |

Example 20: 2-chloro-4-((1-methyl-2-oxo-4-((1-(5-(pyridin-3-yl)pyrimidin-2-yl)ethyl)amino)-1,2-dihydroquinolin-6-yl)amino)nicotinonitrile

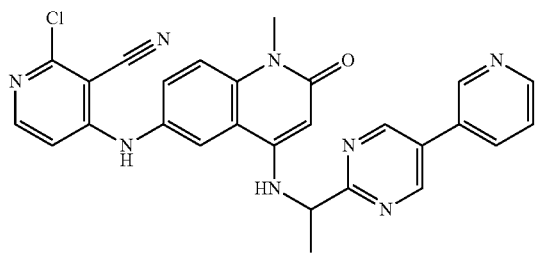 [SMILES: CC(Nc1cc(=O)n(C)c2ccc(Nc3ccnc(Cl)c3C#N)cc12)c1ncc(-c2cccnc2)cn1]

A mixture of 4-[[4-[1-(5-bromopyrimidin-2-yl)ethylamino]-1-methyl-2-oxo-6-quinolyl]amino]-2-chloro-pyridine-3-carbonitrile (Example 10j, 5.5 mg, 0.011 mmol), 3-pyridineboronic acid pinacol ester (2.65 mg, 0.013 mmol), tetrakis(triphenylphosphine)palladium(0) (1.24 mg, 0.0011 mmol), sodium carbonate (2M aq.) (19 uL, 0.038 mmol) and DMF (0.6 mL) was added to a vial which was sealed and purged with argon. The mixture was heated in the microwave to 140° C. for 1 h. The mixture was passed through a syringe filter then loaded directly onto a reverse-phase C18 column eluting from 30-100% methanol in water (each containing 0.1% formic acid). The sample was then further purified by Biotage KP-Sil 10 g eluting 0-8% methanol in DCM affording the title compound (1.7 mg) as an off-white solid. $^{1}$H NMR (600 MHz, Chloroform-d) δ 8.97 (s, 2H), 8.85 (d, J=1.9 Hz, 1H), 8.73 (dd, J=4.8, 1.6 Hz, 1H), 8.08 (d, J=6.1 Hz, 1H), 7.92-7.88 (m, 1H), 7.61 (d, J=2.3 Hz, 1H), 7.50-7.46 (m, 2H), 7.44 (d, J=9.0 Hz, 1H), 7.01 (s, 1H), 6.65 (d, J=6.1 Hz, 1H), 6.29 (d, J=6.6 Hz, 1H), 5.87 (s, 1H), 4.98 (app. quin., J=6.7 Hz, 1H), 3.68 (s, 3H), 1.72 (d, J=6.7 Hz, 3H). LCMS (Method T4) Rt=2.56 mins, m/z 509.1584 [M+H]$^{+}$ expected 509.1600 for $C_{27}H_{22}ClN_{8}O$.

Example 21: N-(5-Chloro-4-((1-methyl-2-oxo-4-((1-(pyrimidin-2-yl)ethyl)amino)-1,2-dihydroquinolin-6-yl)amino)pyridin-2-yl)-N-methylacetamide

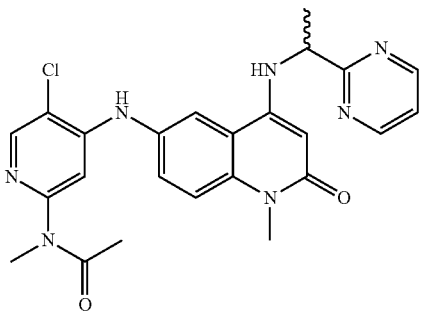 [SMILES: CC(=O)N(C)c1cc(Nc2ccc3c(c2)c(NC(C)c2ncccn2)cc(=O)n3C)c(Cl)cn1]

A suspension of palladium acetate (0.51 mg, 0.002 mmol), (5-diphenylphosphanyl-9,9-dimethyl-xanthen-4-yl)-diphenyl-phosphane (7.9 mg, 0.014 mmol), 6-amino-1-methyl-4-(1-pyrimidin-2-ylethylamino)quinolin-2-one (Intermediate A1b, 10.1 mg, 0.034 mmol), N-(4-bromo-5-chloro-2-pyridyl)-N-methyl-acetamide (Intermediate E3, 6.0 mg, 0.023 mmol) and cesium carbonate (22.3 mg, 0.068 mmol) in dioxane (2.0 mL) was stirred at under microwave irradiation at 140° C. for 1 h. After filtration, the solvent was removed under reduced pressure. The crude was then purified by HPLC, yielding N-[5-chloro-4-[[1-methyl-2-oxo-4-(1-pyrimidin-2-ylethylamino)-6-quinolyl]amino]-2-pyridyl]-N-methyl-acetamide (1.5 mg) as a yellow oil.
$^{1}$H NMR (500 MHz, Methanol-$d_4$) δ 8.78 (d, J=5.0 Hz, 2H), 8.25 (s, 1H), 8.20-8.05 (m, 1H), 7.62 (d, J=1.0 Hz, 2H), 7.38 (t, J=4.9 Hz, 1H), 6.86 (s, broad, 1H), 5.54 (s, 1H), 4.80 (q, 1H), 3.63 (s, 3H), 3.24 (s, broad, 3H), 2.03 (s, broad, 3H), 1.70 (d, J=6.9 Hz, 3H). LCMS (Method T4) Rt=2.46 mins, m/z 478.1742 [M+H]$^{+}$ expected 478.1753 for $C_{24}H_{25}ClN_{7}O_{2}$.

The following tabulated examples in Table 16 were prepared by an analogous method to that used for the preparation of example 19a. Examples 22a and 22b represent a pair of diastereoisomers where one is cis and one is trans across the cyclobutane ring. The compounds can be clearly distinguished from one another by NMR, but it has not been unambiguously determined which is the cis and which is the trans structure. Both compounds are racemic.

TABLE 16

Compounds prepared by a method analogous to that used for the preparation of Example 19a.

| Example | Data | Intermediate |
| --- | --- | --- |
| Example 22a: rac-2-chloro-4-((4-(((1R,2S)-2-methoxycyclobutyl)amino)-1-methyl-2-oxo-1,2-dihydroquinolin-6-yl)amino)nicotinonitrile or rac-2-chloro-4-((4-(((1R,2R)-2-methoxycyclobutyl)amino)-1-methyl-2-oxo-1,2-dihydroquinolin-6-yl)amino)nicotinonitrile | $^1$H NMR (600 MHz, Methanol-d4) δ 8.13 (d, J = 2.3 Hz, 1H), 8.03 (d, J = 6.2 Hz, 1H), 7.77 (d, J = 9.0 Hz, 1H), 7.66 (dd, J = 9.0, 2.4 Hz, 1H), 6.75 (d, J = 6.2 Hz, 1H), 6.00 (s, 1H), 3.92 (td, J = 6.2, 5.0, 2.5 Hz, 2H), 3.77 (s, 3H), 3.34 (s, 3H), 2.34-2.27 (m, 1H), 2.26-2.19 (m, 1H), 1.72-1.58 (m, 2H). LCMS (Method T4) Rt = 2.69 mins, m/z 432.1198 [M + Na]$^+$ expected 432.1198 for $C_{21}H_{20}ClN_5NaO_2$ | Intermediate A13a: rac-6-amino-4-(((1R,2S)-2-methoxycyclobutyl)amino)-1-methylquinolin-2(1H)-one or rac-6-amino-4-(((1R,2R)-2-methoxycyclobutyl)amino)-1-methylquinolin-2(1H)-one |
| Example 22b: rac-2-chloro-4-((4-(((1R,2S)-2-methoxycyclobutyl)amino)-1-methyl-2-oxo-1,2-dihydroquinolin-6-yl)amino)nicotinonitrile or rac-2-chloro-4-((4-(((1R,2R)-2-methoxycyclobutyl)amino)-1-methyl-2-oxo-1,2-dihydroquinolin-6-yl)amino)nicotinonitrile | $^1$H NMR (500 MHz, Methanol-d4) δ 8.01 (d, J = 6.3 Hz, 1H), 7.96 (d, J = 2.2 Hz, 1H), 7.66 (d, J = 9.0 Hz, 1H), 7.62 (d, J = 2.4 Hz, 1H), 6.76 (d, J = 6.2 Hz, 1H), 5.62 (s, 1H), 4.28-4.17 (m, 2H), 3.69 (s, 3H), 3.32 (s, 3H), 2.31-2.18 (m, 2H), 2.18-2.11 (m, 1H), 2.11-2.03 (m, 1H). LCMS (Method T4) Rt = 2.69 mins, m/z 432.1188 [M + Na]$^+$ expected 432.1198 for $C_{21}H_{20}ClN_5NaO_2$ | Intermediate A13b: rac-6-amino-4-(((1R,2S)-2-methoxycyclobutyl)amino)-1-methylquinolin-2(1H)-one or rac-6-amino-4-(((1R,2R)-2-methoxycyclobutyl)amino)-1-methylquinolin-2(1H)-one |

The following tabulated examples in Table 17 were prepared by an analogous method to that used for the preparation of example 19a, using Intermediate E1a: 4,6-dichloro-5-cyano-N-methyl-pyridine-2-carboxamide. Examples 23a and 23b represent a pair of diastereoisomers where one is cis and one is trans across the cyclobutane ring. The compounds can be clearly distinguished from one another by NMR, but it has not been unambiguously determined which is the cis and which is the trans structure. Both compounds are racemic.

TABLE 17

Compounds prepared by a method analogous to that used for the preparation of Example 19a.

| Example | Data | Intermediate |
|---|---|---|
| Example 23a: rac-6-chloro-5-cyano 4-((4-(((1R,2R)-2-methoxycyclobutyl)amino)-1-methyl-2-oxo-1,2-dihydroquinolin-6-yl)amino)-N-methylpicolinamide or rac-6-chloro-5-cyano-4-((4-(((1R,2S)-2-methoxycyclobutyl)amino)-1-methyl-2-oxo-1,2-dihydroquinolin-6-yl)amino)-N-methylpicolinamide 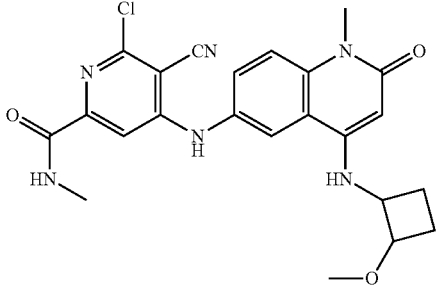 [SMILES: CNC(=O)c1cc(Nc2ccc3c(c2)c(NC2CCC2OC)cc(=O)n3C)c(C#N)c(Cl)n1] | $^1$H NMR (600 MHz, DMSO-d6) δ 9.87 (br, 1H, NH), 8.65 (q, J = 4.9 Hz, 1H), 8.08 (s, 1H), 7.54 (m, 2H), 7.14 (s, 1H), 7.01 (d, J = 6.4 Hz, 1H), 5.61 (s, 1H), 3.87 (q, J = 7.2 Hz, 1H), 3.78 (d, J = 7.9 Hz, 1H), 3.54 (s, 3H), 3.21 (s, 3H), 2.74 (d, J = 4.8 Hz, 3H), 2.23-2.14 (m, 1H), 2.13-2.04 (m, 1H), 1.59-1.50 (m, 1H), 1.50-1.40 (m, 1H). LCMS (Method T4) Rt = 2.74 mins, m/z 467.1586 [M + H]$^+$ expected 467.1593 for C$_{23}$H$_{24}$ClN$_6$O$_5$ | Intermediate A13a: rac-6-amino-4-(((1R,2S)-2-methoxycyclobutyl)amino)-1-methylquinolin-2(1H)-one or rac-6-amino-4-(((1R,2R)-2-methoxycyclobutyl)amino)-1-methylquinolin-2(1H)-one |
| Example 23b: rac-6-chloro-5-cyano 4-((4-(((1R,2R)-2-methoxycyclobutyl)amino)-1-methyl-2-oxo-1,2-dihydroquinolin-6-yl)amino)-N-methylpicolinamide or rac-6-chloro-5-cyano-4-((4-(((1R,2S)-2-methoxycyclobutyl)amino)-1-methyl-2-oxo-1,2-dihydroquinolin-6-yl)amino)-N-methylpicolinamide 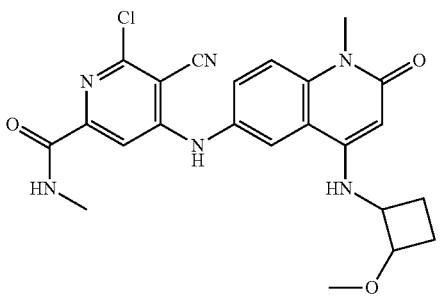 [SMILES: CNC(=O)c1cc(Nc2ccc3c(c2)c(NC2CCC2OC)cc(=O)n3C)c(C#N)c(Cl)n1] | $^1$H NMR (500 MHz, Methanol-d4) δ 7.98 (d, J = 2.2 Hz, 1H), 7.66 (t, J = 6.4 Hz, 1H), 7.63-7.55 (m, 1H), 7.40 (d, J = 1.0 Hz, 1H), 5.61 (s, 1H), 4.30-4.10 (m, 2H), 3.70 (s, 3H), 3.29 (s, 3H), 2.90-2.86 (m, 3H), 2.33-1.92 (m, 4H). LCMS (Method T4) Rt = 2.80 mins, m/z 489.1411 [M + Na]$^+$ expected 489.1411 for C$_{23}$H$_{23}$ClN$_6$NaO$_3$ | Intermediate A13b: rac-6-amino-4-(((1R,2S)-2-methoxycyclobutyl)amino)-1-methylquinolin-2(1H)-one or rac-6-amino-4-(((1R,2R)-2-methoxycyclobutyl)amino)-1-methylquinolin-2(1H)-one |

The following tabulated examples in Table 18 were prepared by a method analogous to that used for the preparation of example 1a, starting from the intermediate(s) shown in the table. For example 24d, 2h reaction time was required.

TABLE 18

Compounds prepared by a method analogous to that used for the preparation of Example 1a.

| Example | Data | Intermediate |
| --- | --- | --- |
| Example 24a:<br>6-chloro-5-cyano-4-((4-((1-cyanocyclopropyl)amino)-1-methyl-2-oxo-1,2-dihydroquinolin-6-yl)amino)-N-methylpicolinamide | $^1$H NMR (500 MHz, DMSO-d$_6$) δ 9.92 (br s, 1 H), 8.61 (s, 1 H), 7.91-7.77 (m, 2 H), 7.62-7.50 (m, 2 H), 7.11 (s, 1 H), 5.90 (s, 1 H), 3.58 (s, 3 H), 2.73 (d, J = 4.3 Hz, 3 H), 1.72-1.65 (m, 2 H), 1.35-1.28 (m, 2 H);<br>LCMS (Method T4) Rt = 2.52 mins, m/z 448.1271 [M + H]$^+$ expected 448.1283 for C$_{22}$H$_{19}$ClN$_7$O$_2^+$. | Intermediate A3f: 1-((6-amino-1-methyl-2-oxo-1,2-dihydroquinolin-4-yl)amino)cyclopropane-1-carbonitrile and Intermediate E1a: 4,6-dichloro-5-cyano-N-methylpicolinamide |
| Example 24b:<br>2-chloro-4-((4-((1-cyanocyclopropyl)amino)-1-methyl-2-oxo-1,2-dihydroquinolin-6-yl)amino)nicotinonitrile | $^1$H NMR (500 MHz, DMSO-d$_6$) δ 9.60 (br s, 1 H), 8.05 (d, J = 6.2 Hz, 1 H), 7.87-7.84 (m, 2 H), 7.58 (d, J = 9.0 Hz, 1 H), 7.55 (d, J = 9.0, 2.0 Hz, 1 H), 6.66 (d, J = 6.2 Hz, 1 H), 5.90 (s, 1 H), 3.57 (s, 3 H), 1.72-1.67 (m, 2 H), 1.33-1.28 (m, 2 H); LCMS (Method T4) Rt = 2.47 mins, m/z 391.1057 [M + H]$^+$ expected 391.1069 for C$_{20}$H$_{16}$ClN$_6$O$^+$. | Intermediate A3f: 1-((6-amino-1-methyl-2-oxo-1,2-dihydroquinolin-4-yl)amino)cyclopropane-1-carbonitrile |
| Example 24c:<br>2-chloro-4-((1-methyl-2-oxo-4-((2-(pyrimidin-2-yl)butan-2-yl)amino)-1,2-dihydroquinolin-6-yl)amino)nicotinonitrile | $^1$H NMR (500 MHz, DMSO-d$_6$) δ 9.61 (br s, 1 H), 8.84 (d, J = 4.8 Hz, 2 H), 8.20 (br s, 1 H), 8.05 (d, J = 6.2 Hz, 1 H), 7.55-7.44 (m, 2 H), 7.41 (t, J = 4.8 Hz, 1 H), 6.79 (br s, 1 H), 6.65 (s, 1 H), 4.84 (s, 1 H), 3.43 (s, 3 H), 2.31-2.15 (m, 2 H), 1.73 (s, 3 H), 0.69 (t, J = 7.1 Hz, 3 H); LCMS (Method T4) Rt = 2.74 mins, m/z 460.1630 [M + H]$^+$ expected 460.1647 for C$_{24}$H$_{23}$ClN$_7$O$^+$. | Intermediate A3d: 6-amino-1-methyl-4-((2-(pyrimidin-2-yl)butan-2-yl)amino)quinolin-2(1H)-one |
| Example 24d:<br>(R)-2-chloro-4-((5-((1-cyclopropylethyl)amino)-8-methyl-7-oxo-7,8-dihydro-1,8-naphthyridin-3-yl)amino)nicotinonitrile | $^1$H NMR (600 MHz, Methanol-d4) δ 8.60 (d, J = 2.4 Hz, 1H), 8.54 (d, J = 2.4 Hz, 1H), 8.04 (d, J = 6.2 Hz, 1H), 6.73 (d, J = 6.2 Hz, 1H), 5.67 (s, 1H), 3.75 (s, 3H), 3.19-3.07 (m, 1H), 1.36 (d, J = 6.4 Hz, 3H), 1.16-1.05 (m, 1H), 0.63-0.49 (m, 2H), 0.40-0.26 (m, 2H).<br>LCMS (Method T4) Rt = 2.73 mins, m/z 395.1382 [M + H]$^+$ expected 395.1344 for C$_{20}$H$_{20}$ClN$_6$O | Intermediate A10a: (R)-6-amino-4-((1-cyclopropylethyl)amino)-1-methyl-1,8-naphthyridin-2(1H)-one |

TABLE 18-continued

Compounds prepared by a method analogous to that used for the preparation of Example 1a.

| Example | Data | Intermediate |
| --- | --- | --- |
| Example 24e:<br>2-chloro-4-((4-((1-(isoquinolin-3-yl)ethyl)amino)-1-methyl-2-oxo-1,2-dihydroquinolin-6-yl)amino)nicotinonitrile<br>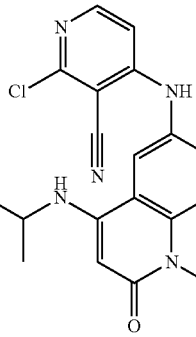 | $^1$H NMR (600 MHz, Chloroform-d) δ 9.23 (s, 1H), 7.97 (d, J = 6.1 Hz, 1H), 7.90-7.82 (m, 2H), 7.79-7.73 (m, 2H), 7.62-7.54 (m, 2H), 7.29-7.23 (m, 2H), 7.21 (d, J = 8.9 Hz, 1H), 7.03 (s, 1H), 6.92 (s, 1H), 6.39 (d, J = 6.1 Hz, 1H), 5.81 (s, 1H), 4.91 (app. quin., J = 6.6 Hz, 1H), 3.52 (s, 3H), 1.78 (d, J = 6.7 Hz, 3H).<br>LCMS (Method T4) Rt = 2.74 mins, m/z 481.1516 [M + H]$^+$ expected 481.1538 for $C_{27}H_{22}ClN_6O$ | Intermediate A1x: 6-amino-4-((1-(isoquinolin-3-yl)ethyl)amino)-1-methylquinolin-2(1H)-one |
| Example 24f:<br>2-chloro-4-((4-((1-(5-cyclobutylpyrimidin-2-yl)ethyl)amino)-1-methyl-2-oxo-1,2-dihydroquinolin-6-yl)amino)nicotinonitrile<br>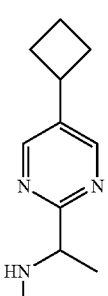 | $^1$H NMR (600 MHz, DMSO-d$_6$) δ 9.62 (s, 1H), 8.69 (s, 2H), 8.29 (d, J = 2.2 Hz, 1H), 8.04 (d, J = 6.2 Hz, 1H), 7.51 (dd, J = 9.0, 2.2 Hz, 1H), 7.47 (d, J = 9.0 Hz, 1H), 7.21 (d, J = 7.0 Hz, 1H), 6.61 (d, J = 6.2 Hz, 1H), 5.28 (s, 1H), 4.72 (app. quin., J = 6.9 Hz, 1H), 3.52 (app. quin., J = 8.8 Hz, 1H), 3.45 (s, 3H), 2.32-2.24 (m, 2H), 2.21-2.12 (m, 2H), 2.06-1.94 (m, 1H), 1.89-1.80 (m, 1H), 1.58 (d, J = 6.9 Hz, 3H).<br>LCMS (Method X4) Rt = 2.89 mins, m/z 486.1816 [M + H]$^+$ expected 486.1809 for $C_{26}H_{25}ClN_7O$ | Intermediate A1y: 6-amino-4-((1-(5-cyclobutylpyrimidin-2-yl)ethyl)amino)-1-methylquinolin-2(1H)-one |

Example 25a: 6-((5-chloro-2-((3R,5S)-4,4-difluoro-3,5-dimethylpiperidin-1-yl)pyrimidin-4-yl)amino)-1-methyl-4-((2-(pyrimidin-2-yl)propan-2-yl)amino)quinazolin-2(1H)-one

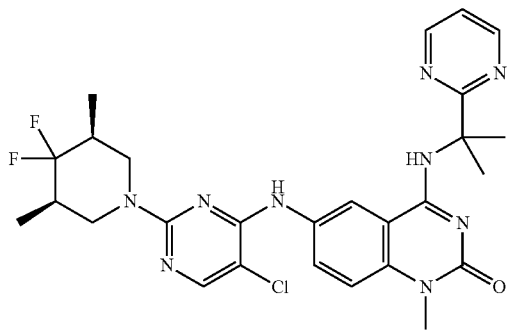 [SMILES: C[C@@H]1CN(c2ncc(Cl)c(Nc3ccc4c(c3)c(NC(C)(C)c3ncccn3)nc(=O)n4C)n2)C[C@H](C)C1(F)F]

A mixture of 6-[(2,5-dichloropyrimidin-4-yl)amino]-1-methyl-4-[(1-methyl-1-pyrimidin-2-yl-ethyl)amino]quinazolin-2-one (Intermediate F1i, 6 mg, 0.013 mmol), (3R, 5S)-4,4-difluoro-3,5-dimethyl-piperidine (5.9 mg, 0.04 mmol) and N,N-diisopropylethylamine (0.02 mL, 0.11 mmol) in NMP (0.5 mL) was heated under microwave irradiation to 140° C. for 3 h. The crude reaction mixture was purified via reverse-phase Biotage chromatography (12 g, Ultra C18, 20-100% methanol in water, 0.1% formic acid modifier) to give the title compound as a cream solid (2.4 mg). $^1$H NMR (600 MHz, Methanol-d4)) δ 8.78 (d, J=4.9 Hz, 2H), 8.32 (d, J=2.3 Hz, 1H), 8.03 (s, 1H), 7.95 (dd, J=9.1, 2.3 Hz, 1H), 7.48 (d, J=9.0 Hz, 1H), 7.36 (t, J=4.9 Hz, 1H), 4.56 (m, 2H), 3.60 (s, 3H), 2.66 (m, 2H), 1.99 (s, 6H), 1.98-1.84 (m, 2H), 0.96 (d, J=6.7 Hz, 6H). LCMS (Method T4) Rt=3.24 mins, m/z 570.2283 [M+H]$^+$ expected 570.2303 for $C_{27}H_{31}ClF_2N_9O$.

The following tabulated examples in Table 18b were prepared by a method analogous to that used for the preparation of example 17a, starting from the intermediate(s) shown in the table. Example 26e was heated to 180° C.

TABLE 18b

Compounds prepared by a method analogous to that used for the preparation of Example 17a.

| Example | Data and comments | Intermediates |
| --- | --- | --- |
| Example 26a: (R)-6-((2-(azetidin-1-yl)-5-chloropyrimidin-4-yl)amino)-4-((1-cyclopropylethyl)amino)-1-methylquinolin-2(1H)-one: formic acid (1:1) | 1H NMR (600 MHz, Methanol-$d_4$) δ 8.38 (d, J = 2.3 Hz, 1H), 8.19 (br s, 1H), 7.95 (dd, J = 9.1, 2.4 Hz, 1H), 7.92 (s, 1H), 7.52 (d, J = 9.1 Hz, 1H), 5.64 (s, 1H), 4.23-3.99 (m, 4H), 3.66 (s, 3H), 3.15-3.05 (m, 1H), 2.34 (p, J = 7.5 Hz, 2H), 1.36 (d, J = 6.4 Hz, 3H), 1.15-1.05 (m, 1H), 0.68-0.57 (m, 1H), 0.57-0.48 (m, 1H), 0.46-0.26 (m, 2H). LCMS (Method T4) Rt = 2.50 mins, m/z 425.1908 [M + H]$^+$ expected 425.1850 for $C_{22}H_{26}ClN_6O$ | Intermediate F1e: (R)-4-((1-cyclopropylethyl)amino)-6-((2,5-dichloropyrimidin-4-yl)amino)-1-methylquinolin-2(1H)-one and azetidine |
| Example 26b: 6-((5-chloro-2-(2-(methoxymethyl)azetidin-1-yl)pyrimidin-4-yl)amino)-4-(((R)-1-cyclopropylethyl)amino)-1-methylquinolin-2(1H)-one: formic acid (1:1) | Rotamer A: $^1$H NMR (600 MHz, Methanol-$d_4$) δ 8.29 (s, 1H), 8.17 (s, 1H), 7.93 (s, 1H), 7.90 (dd, J = 9.1, 2.4 Hz, 1H), 7.55 (s, 1H), 5.64 (s, 1H), 4.48-4.38 (m, 1H), 4.00-3.90 (m, 2H), 3.67 (s, 3H), 3.68-3.64 (m, 1H), 3.56-3.45 (m, 1H), 3.24 (s, 3H), 3.16-3.08 (m, 1H), 2.38-2.25 (m, 2H), 1.36 (d, J = 6.4 Hz, 3H), 1.18-1.10 (m, 1H), 0.68-0.57 (m, 1H), 0.57-0.50 (m, 1H), 0.40-0.30 (m, 2H). Rotamer B: $^1$H NMR (600 MHz, Methanol-$d_4$) δ 8.26 (s, 1H), 8.17 (s, 1H), 7.87 (dd, J = 9.1, 2.4 Hz, 1H), 7.53 (s, 1H), 5.65 (s, 1H), 4.48-4.38 (m, 1H), 4.00-3.90 (m, 2H), 3.67 (s, 3H), 3.68-3.64 (m, 1H), 3.56-3.45 (m, 1H), 3.25 (s, 3H), 3.16-3.08 (m, 1H), 2.38-2.25 (m, 2H), 1.36 (d, J = 6.4 Hz, 3H), 1.18-1.10 (m, 1H), 0.68-0.57 (m, 1H), 0.57-0.50 (m, 1H), 0.40-0.30 (m, 2H). LCMS (Method T4) Rt = 2.51 mins, m/z 469.2153 [M + H]+ expected 469.2113 for $C_{24}H_{30}ClN_6O_2$ | Intermediate F1e: (R)-4-((1-cyclopropylethyl)amino)-6-((2,5-dichloropyrimidin-4-yl)amino)-1-methylquinolin-2(1H)-one and 2-(methoxymethyl)azetidine |
| Example 26c: 6-((5-chloro-2-(1-methyl-1,4,5,7-tetrahydro-6H-pyrazolo[3,4-c]pyrimidin-6-yl)pyrimidin-4-yl)amino)-1-methyl-4-((1-pyrimidin-2-yl)ethyl)amino)quinolin-2(1H)-one | $^1$H NMR (600 MHz, Methanol-$d_4$) δ 8.78 (d, J = 4.9 Hz, 2H), 8.35 (d, J = 2.3 Hz, 1H), 8.02 (s, 1H), 7.93 (dd, J = 9.1, 2.3 Hz, 1H), 7.58 (d, J = 9.1 Hz, 1H), 7.36 (t, J = 4.9 Hz, 1H), 7.31 (s, 1H), 5.62 (s, 1H), 4.93 (q, J = 6.8 Hz, 1H), 4.68 (q, J = 15.5 Hz, 2H), 4.08 (dt, J = 13.4, 5.7 Hz, 1H), 3.99 (dt, J = 13.4, 5.7 Hz, 1H), 3.80 (s, 3H), 3.67 (s, 3H), 2.73 (t, J = 5.7 Hz, 2H), 1.70 (d, J = 6.8 Hz, 3H). LCMS (Method T4) Rt = 2.62 mins, m/z 543.2051 [M + H]$^+$ expected 543.2131 for $C_{27}H_{28}ClN_{10}O$ | Intermediate F1c: 6-((2,5-dichloropyrimidin-4-yl)amino)-1-methyl-4-((1-(pyrimidin-2-yl)ethyl)amino) quinolin-2(1H)-one and 1-methyl-4,5,6,7-tetrahydropyrazolo[3,4-c]pyridine hydrochloride |

TABLE 18b-continued

Compounds prepared by a method analogous to that used for the preparation of Example 17a.

| Example | Data and comments | Intermediates |
|---|---|---|
| Example 26d:<br>6-((5-chloro-2-(4,4-difluoro-3-(hydroxymethyl)piperidin-1-yl)pyrimidin-4-yl)amino)-1-methyl-4-((1-pyrimidin-2-yl)ethyl)amino)quinolin-2(1H)-one | Diastereomer A: $^1$H NMR (600 MHz, Methanol-d$_4$) δ 8.81 (d, J = 4.9 Hz, 2H), 8.26 (dd, J = 9.1, 2.3 Hz, 1H), 8.02 (m, 2H), 7.55 (d, J = 9.1 Hz, 1H), 7.40 (t, J = 4.9 Hz, 1H), 5.57 (s, 1H), 4.91 (m, 1H), 4.53-4.44 (m, 1H), 4.30-4.24 (m, 1H), 3.92-3.86 (m, 1H), 3.64 (s, 3H), 3.57-3.24 (m, 3H), 3.24-2.08 (m, 1H), 2.08-1.97 (m, 1H), 1.97-1.84 (m, 1H), 1.72 (d, J = 6.9, 3H).<br>Diastereomer B: $^1$H NMR (600 MHz, Methanol-d$_4$) δ 8.81 (d, J = 4.9 Hz, 2H), 8.26 (dd, J = 9.1, 2.3 Hz, 1H), 8.02 (m, 2H), 7.55 (d, J = 9.1 Hz, 1H), 7.40 (t, J = 4.9 Hz, 1H), 5.56 (s, 1H), 4.91 (m, 1H), 4.61-4.54 (m, 1H), 4.36-4.31 (m, 1H), 3.99-3.92 (m, 1H), 3.64 (s, 3H), 3.57-3.24 (m, 3H), 3.24-2.08 (m, 1H), 2.08-1.97 (m, 1H), 1.97-1.84 (m, 1H), 1.72 (d, J = 6.9, 3H).<br>LCMS (Method T4) Rt = 2.73 mins, m/z 557.1968 [M + H]$^+$ expected 557.1986 for C$_{26}$H$_{28}$ClF$_2$N$_8$O$_2$ | Intermediate F1c: 6-((2,5-dichloropyrimidin-4-yl)amino)-1-methyl-4-((1-(pyrimidin-2-yl)ethyl)amino)quinolin-2(1H)-one and (4,4-difluoro-3-piperidyl)methanol (prepared by hydrogenation of commercial (1-benzyl-4,4-difluoro-3-piperidyl)methanol using palladium hydroxide in ethanol |
| Example 26e:<br>6-[[5-chloro-2-[(2R,6S)-2,6-dimethylmorpholin-4-yl]pyrimidin-4-yl]amino)-1-methyl-4-(1-pyrimidin-2-ylethylamino)quinazolin-2-one | 1H NMR (600 MHz, Methanol-d$_4$) δ 8.79 (d, J = 4.9 Hz, 2H), 8.34 (dd, J = 2.3, 1.2 Hz, 1H), 8.00 (d, J = 0.9 Hz, 1H), 7.96 (dd, J = 9.1, 2.4 Hz, 1H), 7.48 (dd, J = 9.1, 1.2 Hz, 1H), 7.39 (t, J = 4.9 Hz, 1H), 5.66 (q, J = 7.0 Hz, 1H), 4.45-4.27 (m, 2H), 3.62 (s, 3H), 3.59-3.49 (m, 2H), 2.57-2.44 (m, 2H), 1.71 (d, J = 7.0 Hz, 3H), 1.11 (dd, J = 6.2, 2.9 Hz, 6H).<br>LCMS (Method T4) Rt = 2.77 min, m/z 523.2046 [M + H]$^+$ expected 523.2127 for C$_{25}$H$_{29}$ClN$_9$O$_2$ | Intermediate F1j: 6-((2,5-dichloropyrimidin-4-yl)amino)-1-methyl-4-((1-(pyrimidin-2-yl)ethyl)amino)quinazolin-2(1H)-one and (2R,6S)-2,6-dimethylmorpholine |
| Example 26f:<br>6-[[5-chloro-2-[(2R,6S)-2,6-dimethylmorpholin-4-yl]pyrimidin-4-yl]amino-1-methyl-4-[(1-methyl-1-pyrimidin-2-yl)ethyl)amino]quinazolin-2-one:formic acid (1:1) | $^1$H NMR (600 MHz, Methanol-d$_4$) δ 8.79 (d, J = 4.9 Hz, 2H), 8.34 (d, J = 2.3 Hz, 1H), 8.15 (br s, 1H), 8.02 (s, 1H), 7.94 (dd, J = 9.1, 2.3 Hz, 1H), 7.47 (d, J = 9.1 Hz, 1H), 7.37 (t, J = 4.9 Hz, 1H), 4.38 (t, J = 11.9 Hz, 2H), 3.59 (s, 3H), 3.52 (ddd, J = 10.6, 6.2, 2.5 Hz, 2H), 2.47 (dd, J = 13.2, 10.6 Hz, 2H), 1.99 (s, 6H), 1.12 (d, J = 6.2 Hz, 6H).<br>LCMS (Method T4) Rt = 2.89 min, m/z 536.2272 [M + H]$^+$ expected 536.2284 for C$_{26}$H$_{31}$ClN$_9$O$_2$ | Intermediate F1i: 6-((2,5-dichloropyrimidin-4-yl)amino)-1-methyl-4-((2-(pyrimidin-2-yl)propan-2-yl)amino)quinazolin-2(1H)-one and and (2R,6S)-2,6-dimethylmorpholine |

TABLE 18b-continued

Compounds prepared by a method analogous to that used for the preparation of Example 17a.

| Example | Data and comments | Intermediates |
|---|---|---|
| Example 26g: 6-[[5-chloro-2-[(3R,5S)-3,5-dimethyl-1-piperidyl]pyrimidin-4-yl]amino-1-methyl-4-[(1-methyl-1-pyrimidin-2-yl)ethyl)amino]quinazolin-2-one:formic acid (1:1) | $^1$H NMR (600 MHz, Methanol-d4) δ 8.78 (d, J = 4.8 Hz, 2H), 8.34 (m, 1H), 8.23 (br s, 1H), 7.99 (d, J = 2 Hz), 7.97 (s, 1H), 7.46 (dd, J = 9.2, 1.3 Hz, 1H), 7.37 (t, J = 4.9 Hz, 1H), 4.59-4.47 (m, 2H), 3.60 (s, 3H), 2.23 (t, J = 12.2 Hz, 2H), 1.99 (s, 6H), 1.82-1.69 (m, 1H), 1.59-1.44 (m, 2H), 0.84 (d, J = 6.6 Hz, 6H), 0.73 (q, J = 12.1 Hz, 1H) LCMS (Method T4) RT = 3.02 min, m/z 534.2473 [M + H]$^+$ expected 534.2491 for $C_{27}H_{33}ClN_9O$ | Intermediate F1i: 6-((2,5-dichloropyrimidin-4-yl)amino)-1-methyl-4-((2-(pyrimidin-2-yl)propan-2-yl)amino)quinazolin-2(1H)-one and (3R,5S)-3,5-dimethylpiperidine |

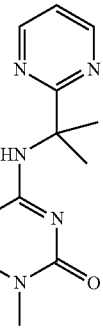

INTERMEDIATES USED IN THE PREPARATION OF EXAMPLES

Intermediate A1a: (R)-6-amino-4-((1-cyclopropylethyl)amino)-1-methylquinolin-2(1H)-one

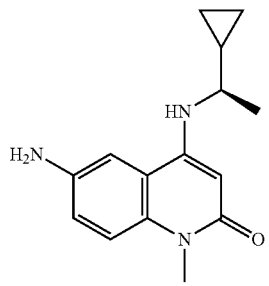

To a solution of 4-[[(1R)-1-cyclopropylethyl]amino]-1-methyl-6-nitro-quinolin-2-one (340 mg, 1.18 mmol) in ethanol (4 mL) was added ammonium formate (746 mg, 11.8 mmol) and Pd/C (10 wt %, 126 mg, 0.118 mmol). The reaction vessel was sealed and evacuated then refilled with argon three times, then placed into a drysyn block which had been preheated to 60° C. and stirred until complete by LCMS analysis (30 minutes). LCMS (Method T2) showed consumption of SM and formation of product (Rt=0.92 mins, m/z 258.16 (M+H)$^+$). After cooling to room temperature, the mixture was filtered through Celite™ and washed with ethanol (~50 mL). The solvent was evaporated under reduced pressure. The residue was diluted with DCM, washed with half-saturated sodium bicarbonate, dried and evaporated under reduced pressure affording 6-amino-4-[[(1R)-1-cyclopropylethyl]amino]-1-methyl-quinolin-2-one (261 mg) as a pale brown solid.

The following tabulated intermediates in Table 19 were prepared by methods analogous to that used in the preparation of intermediate A1a, using the nitro starting material as shown in the table. Products were further purified using an SCX-2 column or by reverse-phase chromatography where required.

TABLE 19 compounds prepared by methods analogous to that used in the preparation of Intermediate A1a.

| Name | Structure | Characterisation | Starting material (nitro) |
|---|---|---|---|
| Intermediate A1b: 6-amino-1-methyl-4-(1-pyrimidin-2-ylethylamino)quinolin-2-one | 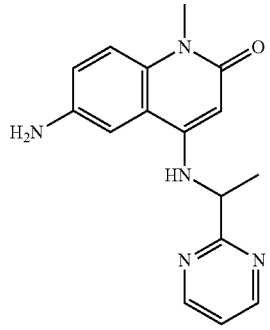 [SMILES: CC(Nc1cc(=O)n(C)c2ccc(N)cc12)c1ncccn1] | LCMS (Method T2) Rt = 0.54 mins, m/z 296.15 [M + H]$^+$. | 1-methyl-6-nitro-4-(1-pyrimidin-2-ylethylamino)quinolin-2-one (Intermediate B1b). |

TABLE 19-continued compounds prepared by methods analogous to that used in the preparation of Intermediate A1a.

| Name | Structure | Characterisation | Starting material (nitro) |
|---|---|---|---|
| Intermediate A1c: 1-[2-[6-amino-2-oxo-4-(1-pyrimidin-2-ylethylamino)-2-quinolyl]ethyl]pyrrolidine-2,5-dione | 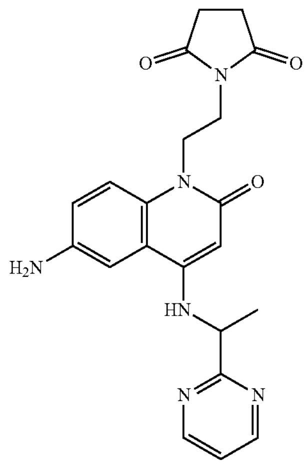 [SMILES: CC(Nc1cc(=O)n(CCN2C(=O)CCC2=O)c2ccc(N)cc12)c1ncccn1] | LCMS (Method T2) Rt = 0.78 mins, m/z 407.18 [M + H]+. | 1-[2-[6-nitro-2-oxo-4-(1-pyrimidin-2-ylethylamino)-1-quinolyl]ethyl]pyrrolidine-2,5-dione (Intermediate B1c). |
| Intermediate A1d: 6-amino-4-(1-pyrimidin-2-ylethylamino)-1-(tetrahydropyran-4-ylmethyl)quinolin-2-one | 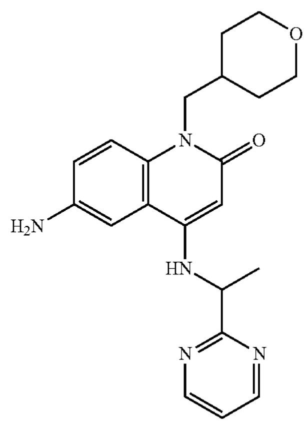 [SMILES: CC(Nc1cc(=O)n(CC2CCOCC2)c2ccc(N)cc12)c1ncccn1] | LCMS (Method T2) Rt = 0.99 mins, m/z 380.21 [M + H]+. | 6-nitro-4-(1-pyrimidin-2-ylethylamino)-1-(tetrahydropyran-4-ylmethyl)quinolin-2-one (Intermediate B1d). |
| Intermediate A1e: 6-amino-1-methyl-4-[1-(4H-1,2,4-triazol-3-yl)ethylamino]quinolin-2-one | 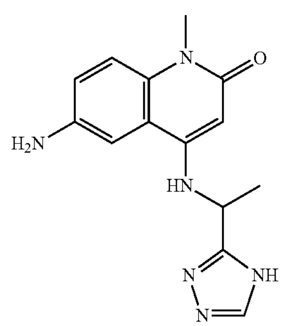 [SMILES: CC(Nc1cc(=O)n(C)c2ccc(N)cc12)c1nnc[nH]1] | LCMS (Method T2) Rt = 0.22 mins, m/z 285.15 [M + H]+. | 1-methyl-6-nitro-4-[1-(4H-1,2,4-triazol-3-yl)ethylamino]quinolin-2-one (Intermediate B2a, used as a solution in DMSO-d6). |
| Intermediate A1f: trans-6-amino-4-[(3-hydroxycyclobutyl)amino]-1-methyl-quinolin-2-one | 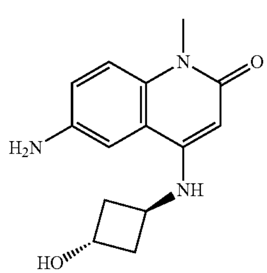 [SMILES: Cn1c(=O)cc(N[C@H]2C[C@H](O)C2)c2cc(N)ccc21] | LCMS (Method T2) Rt = 0.27 mins. m/z 260.14 [M + H]+. | trans-4-[(3-hydroxycyclobutyl)amino]-1-methyl-6-nitro-quinolin-2-one (Intermediate B2f). |

TABLE 19-continued compounds prepared by methods analogous to that used in the preparation of Intermediate A1a.

| Name | Structure | Characterisation | Starting material (nitro) |
|---|---|---|---|
| Intermediate A1g: 6-amino-4-(1-cyclopropylethylamino)-1-methyl-quinolin-2-one | 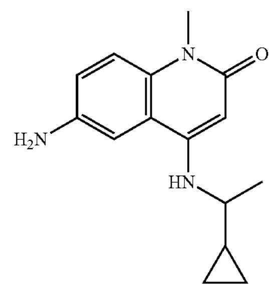 [SMILES: CC(Nc1cc(=O)n(C)c2ccc(N)cc12)C1CC1] | LCMS (Method T2) Rt = 0.94 mins, m/z 258.16 [M + H]$^+$. | 4-(1-cyclopropylethylamino)-1-methyl-6-nitro-quinolin-2-one (Intermediate B6a). |
| Intermediate A1h: 6-amino-4-(cyclopropylamino)-1-methyl-quinolin-2-one | 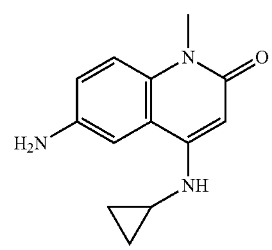 [SMILES: Cn1c(=O)cc(NC2CC2)c2cc(N)ccc21] | LCMS (Method T2) Rt = 0.45 mins, m/z 230.13 [M + H]$^+$. | 4-(cyclopropylamino)-1-methyl-6-nitro-quinolin-2-one (Intermediate B6b). |
| Intermediate A1i: 6-amino-1-methyl-4-[1-(4-methylpyrimidin-2-yl)ethylamino]quinolin-2-one | 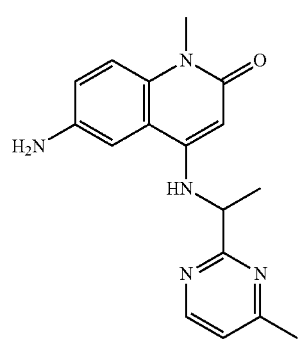 [SMILES: Cc1ccnc(C(C)Nc2cc(=O)n(C)c3ccc(N)cc23)n1] | LCMS (Method T2) Rt = 0.87 mins, m/z 310.17 [M + H]$^+$. | 1-methyl-4-[1-(4-methylpyrimidin-2-yl)ethylamino]-6-nitro-quinolin-2-one (Intermediate B1i). |
| Intermediate A1j: 6-amino-1-methyl-4-(1-pyrazin-2-ylethylamino)quinolin-2-one | 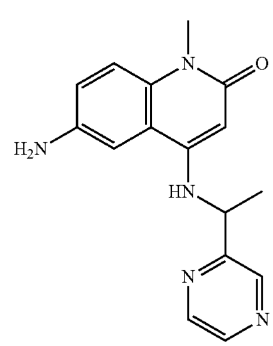 [SMILES: CC(Nc1cc(=O)n(C)c2ccc(N)cc12)c1cnccn1] | LCMS (Method T2) Rt = 0.57 mins, m/z 296.15 [M + H]$^+$. | 1-methyl-6-nitro-4-(1-pyrazin-2-ylethylamino)quinolin-2-one (Intermediate B1j). |

249
250

TABLE 19-continued compounds prepared by methods analogous to that used in the preparation of Intermediate A1a.

| Name | Structure | Characterisation | Starting material (nitro) |
|---|---|---|---|
| Intermediate A1k: 6-amino-1-methyl-4-(1-pyrimidin-4-ylethylamino)quinolin-2-one | 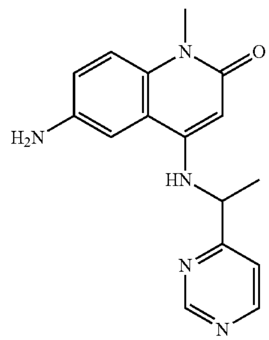 [SMILES: CC(Nc1cc(=O)n(C)c2ccc(N)cc12)c1ccncn1] | LCMS (Method T2) Rt = 0.49 mins, m/z 296.15 [M + H]$^+$. | 1-methyl-6-nitro-4-(1-pyrimidin-4-ylethylamino)quinolin-2-one (Intermediate B1f). |
| Intermediate A1l: 6-amino-1-methyl-4-(1-thiazol-2-ylethylamino)quinolin-2-one | 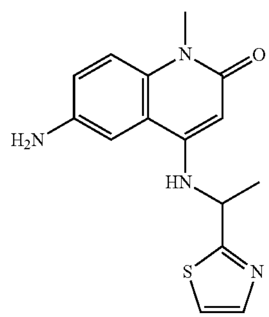 [SMILES: CC(Nc1cc(=O)n(C)c2ccc(N)cc12)c1nccs1] | LCMS (Method T2) Rt = 0.88 mins, m/z 301.1118 [M + H]$^+$. | 1-methyl-6-nitro-4-(1-thiazol-2-ylethylamino)quinolin-2-one (Intermediate B1g). |
| Intermediate A1m: 6-amino-1-methyl-4-[1-(1H-pyrazol-5-yl)ethylamino]quinolin-2-one | 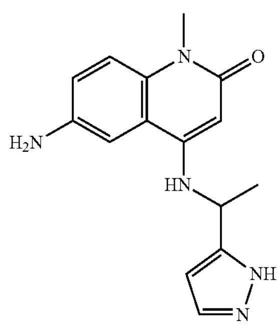 [SMILES: CC(Nc1cc(=O)n(C)c2ccc(N)cc12)c1ccn[nH]1] | LCMS (Method T2) Rt = 0.52 mins, m/z 284.15 [M + H]$^+$. | 1-methyl-6-nitro-4-[1-(1H-pyrazol-5-yl)ethylamino]quinolin-2-one (Intermediate B2e, as a solution in DMSO-d6) |
| Intermediate A1n: 6-amino-1-methyl-4-[(1-methylcyclopentyl)amino]quinolin-2-one | 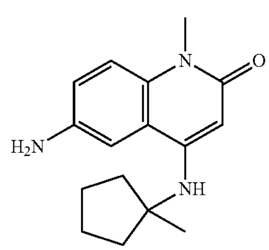 [SMILES: Cn1c(=O)cc(NC2(C)CCCC2)c2cc(N)ccc21] | LCMS (Method T2) Rt = 1.09 mins, m/z 272.18 [M + H]$^+$. | 1-methyl-4-[(1-methylcyclopentyl)amino]-6-nitro-quinolin-2-one (Intermediate B1h). |
| Intermediate A1o: 6-amino-1-methyl-4-[(1-methylcyclopropyl)amino]quinolin-2-one | 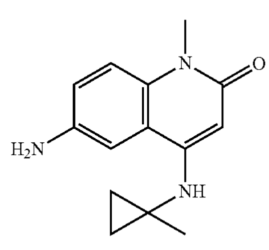 [SMILES: Cn1c(=O)cc(NC2(C)CC2)c2cc(N)ccc21] | LCMS (Method T2) Rt = 0.70 mins, m/z 244.15 [M + H]$^+$. | 1-methyl-4-[(1-methylcyclopropyl)amino]-6-nitro-quinolin-2-one (Intermediate B2c). |

TABLE 19-continued compounds prepared by methods analogous to that used in the preparation of Intermediate A1a.

| Name | Structure | Characterisation | Starting material (nitro) |
|---|---|---|---|
| Intermediate A1p: 6-amino-1-methyl-4-((1-(5-(2-(trifluoromethyl)morpholine)pyrimidin-2-yl)ethyl)amino)quinolin-2(1H)-one | 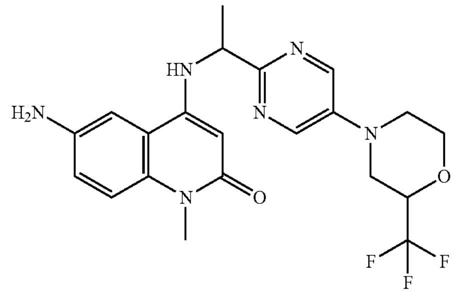 [SMILES: CC(Nc1cc(=O)n(C)c2ccc(N)cc12)c1ncc(N2CCOC(C(F)(F)F)C2)cn1] | LCMS (Method T2) Rt = 1.15 mins, m/z 449.19 [M + H]⁺. | Intermediate B15b: 1-methyl-6-nitro-4-((1-(5-(2-(trifluoromethyl)morpholino)pyrimidin-2-yl)ethyl)amino)quinolin-2(1H)-one |
| Intermediate A1q: 6-amino-4-((1-(5-cyclopropylpyrimidin-2-yl)ethyl)amino)-1-methylquinolin-2(1H)-one | 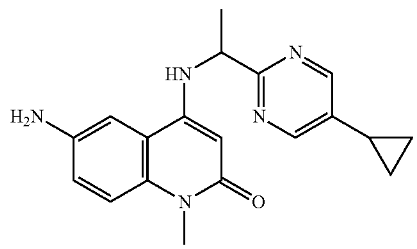 [SMILES: CC(Nc1cc(=O)n(C)c2ccc(N)cc12)c1ncc(C2CC2)cn1] | LCMS (Method T2) Rt = 1.04 mins, m/z 336.18 [M + H]⁺. | Intermediate B18a: 4-((1-(5-cyclopropylpyrimidin-2-yl)ethyl)amino)-1-methyl-6-nitroquinolin-2(1H)-one |
| Intermediate A1r: 6-amino-4-((1-(5-((2R,6S)-2,6-dimethylmorpholino)pyrimidin-2-yl)ethyl)amino)-1-methylquinolin-2(1H)-one | 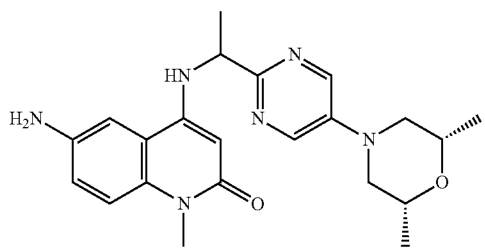 [SMILES: CC(Nc1cc(=O)n(C)c2ccc(N)cc12)c1ncc(N2C[C@@H](C)O[C@@H](C)C2)cn1] | LCMS (Method T2) Rt = 1.12 mins, m/z 409.23 [M + H]⁺. | Intermediate B15d: 4-((1-(5-((2R,6S)-2,6-dimethylmorpholino)pyrimidin-2-yl)ethyl)amino)-1-methyl-6-nitroquinolin-2(1H)-one |
| Intermediate A1s: 6-Amino-4-[(3-hydroxy-1-methyl-propyl)amino]-1-methyl-quinazolin-2-one | 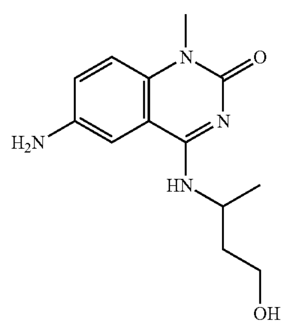 [SMILES: CC(CCO)Nc1nc(=O)n(C)c2ccc(N)cc12] | LCMS (Method T2) Rt = 0.19 mins, m/z 263.15 [M + H]+ | 4-[(3-hydroxy-1-methyl-propyl)amino]-1-methyl-6-nitrio-quinazolin-2-one (Intermediate B3a) |
| Intermediate A1t: 6-Amino-4-[(2-hydroxy-1-methyl-ethyl)amino]-1-methyl-quinazolin-2-one | 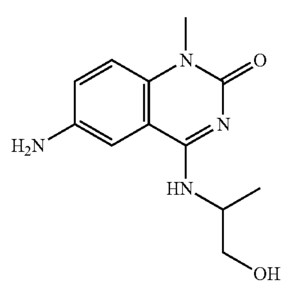 [SMILES: CC(CO)Nc1nc(=O)n(C)c2ccc(N)cc12] | LCMS (Method T2) Rt = 0.14 mins, m/z 249.13 [M + H]+. | 4-[(2-hydroxy-1-methyl-ethyl)amino]-1-methyl-6-nitro-quinazolin-2-one (Intermediate B3b) |

TABLE 19-continued compounds prepared by methods analogous to that used in the preparation of Intermediate A1a.

| Name | Structure | Characterisation | Starting material (nitro) |
|---|---|---|---|
| Intermediate A1u: 6-Amino-1-methyl-4-[1-(1-methylimidazol-2-yl)ethylamino]quinolin-2-one | 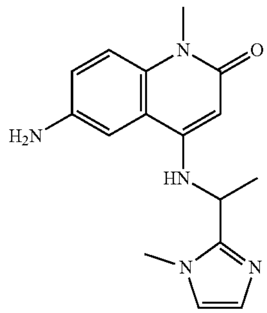 [SMILES: CC(Nc1cc(=O)n(C)c2ccc(N)cc12)c1nccn1C] | LCMS (Method T2) Rt = 0.11 mins, m/z 298.17 | 1-methyl-4-[1-(1-methylimidazol-2-yl)ethylamino]-6-nitro-quinolin-2-one (Intermediate B1e) |
| Intermediate A1v: 6-amino-1-methyl-4-((3-(pyrimidin-2-yl)tetrahydrofuran-3-yl)amino)quinolin-2(1H)-one | 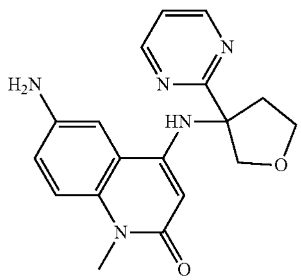 [SMILES: Cn1c(=O)cc(NC2(c3ncccn3)CCOC2)c2cc(N)ccc21] | LCMS (Method T2) Rt = 0.50 min, m/z 338 [M + H]+. | Intermediate B7l: 1-methyl-6-nitro-4-((3-(pyrimidin-2-yl)tetrahydrofuran-3-yl)amino)quinolin-2(1H)-one |
| Intermediate A1w: 6-amino-1-(cyclopropylmethyl)-4-((1-(pyrimidin-2-yl)ethyl)amino)quinolin-2(1H)-one | 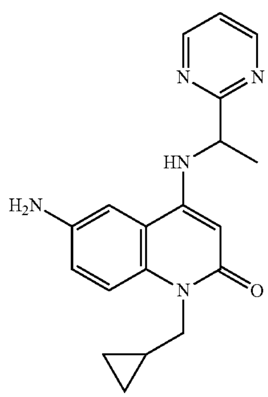 [SMILES: CC(Nc1cc(=O)n(CC2CC2)c2ccc(N)cc12)c1ncccn1] | LCMS (Method T2) Rt = 1.01 min, m/z 336 [M + H]+. | Intermediate B1k: 1-(cyclopropylmethyl)-6-nitro-4-((1-(pyrimidin-2-yl)ethyl)amino)quinolin-2(1H)-one |
| Intermediate A1x: 6-amino-4-((1-(isoquinolin-3-yl)ethyl)amino)-1-methylquinolin-2(1H)-one | 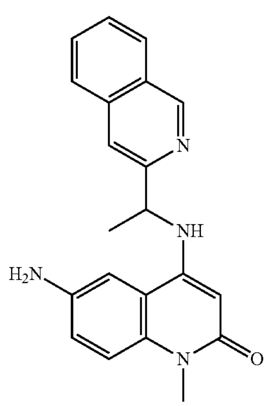 [SMILES: CC(Nc1cc(=O)n(C)c2ccc(N)cc12)c1cc2ccccc2cn1] | LCMS (Method T2) Rt = 1.01 min, m/z 345.17 [M + H]+. | Intermediate B12c: 4-((1-(isoquinolin-3-yl)ethyl)amino)-1-methyl-6-nitroquinolin-2(1H)-one |

TABLE 19-continued compounds prepared by methods analogous to that used in the preparation of Intermediate A1a.

| Name | Structure | Characterisation | Starting material (nitro) |
|---|---|---|---|
| Intermediate A1y: 6-amino-4-((1-(5-cyclobutylpyrimidin-2-yl)ethyl)amino)-1-methylquinolin-2(1H)-one | 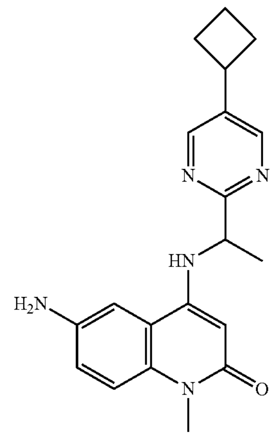 [SMILES: CC(Nc1cc(=O)n(C)c2ccc(N)cc12)c1ncc(C2CCC2)cn1] | LCMS (Method T2) Rt = 1.15 min, m/z 350.19 [M + H]+. | Intermediate B23a: 4-((1-(5-cyclobutylpyrimidin-2-yl)ethyl)amino)-1-methyl-6-nitroquinolin-2(1H)-one |

Intermediate A2a; 6-amino-1-methyl-4-[1-(5-methyl-1,2,4-oxadiazol-3-yl)ethylamino]quinolin-2-one

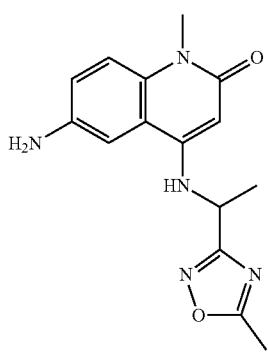 [SMILES: Cc1nc(C(C)Nc2cc(=O)n(C)c3ccc(N)cc23)no1]

A mixture of 1-methyl-4-[1-(5-methyl-1,2,4-oxadiazol-3-yl)ethylamino]-6-nitro-quinolin-2-one (Intermediate B2b, 21 mg, 0.064 mmol) and tin(II) chloride (48.4 mg, 0.26 mmol) in ethanol (0.48 mL) and 2,2,2-trifluoroethanol (0.16 mL) was heated in a microwave at 120° C. for 1 h. LCMS (Method T2) Rt=0.61 mins, m/z 300.15 [M+H]$^+$. The mixture was purified by passing through an SCX-2 cartridge. The product was eluted with methanolic ammonia, affording 6-amino-1-methyl-4-[1-(5-methyl-1,2,4-oxadiazol-3-yl)ethylamino]-quinolin-2-one.

The following intermediates in Table 19 were prepared by a method analogous to that used for the preparation of Intermediate A2a, using the nitro-starting material shown.

TABLE 19 compounds prepared by a method analogous to that used for the preparation of Intermediate A2a.

| Name | Structure | Characterisation | Starting material (nitro) |
|---|---|---|---|
| Intermediate A2b: (2R)-2-((6-amino-1-methyl-2-oxo-1,2-dihydroquinolin-4-yl)amino)-N-(2-hydroxyethyl)propanamide | 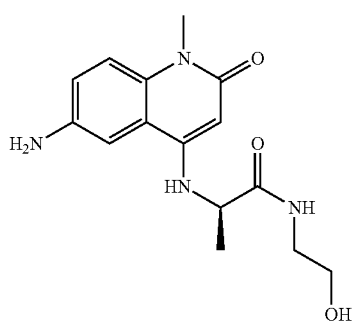 | LCMS (Method T2), Rt = 0.19 mins, m/z 305.1 (M + H)$^+$. | Intermediate B7b (2R)-N-(2-hydroxyethyl)-2-[(1-methyl-6-nitro-2-oxo-4-quinolyl)amino]propanamide |

TABLE 19-continued compounds prepared by a method analogous to that used for the preparation of Intermediate A2a.

| Name | Structure | Characterisation | Starting material (nitro) |
|---|---|---|---|
| Intermediate A2c: 6-Amino-1-methyl-4-((1-(3-methyl-1H-1,2,4-triazol-5-yl)ethyl)amino)quinolin-2(1H)-one | 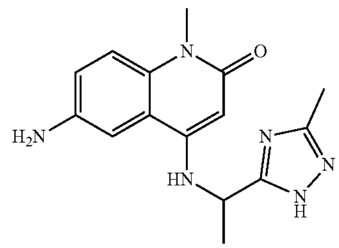 [SMILES: Cc1n[nH]c(C(C)Nc2cc(=O)n(C)c3ccc(N)cc23)n1] | LCMS (Method T2), Rt = 0.27 mins, m/z 299.2 (M + H)+. | Intermediate B7c 1-methyl-4-[1-(3-methyl-1H-1,2,4-triazol-5-yl)ethylamino]-6-nitro-quinolin-2-one |
| Intermediate A2d: (R)-2-((6-amino-1-methyl-2oxo-1,2-dihydroquinolin-4-yl)amino)-N-cyclopentylpropanamide | 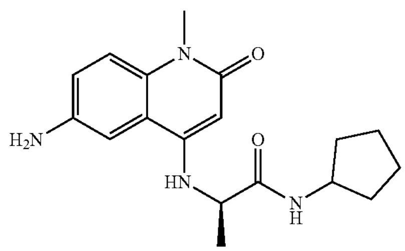 | LCMS (Method T2), Rt = 0.98 mins, m/z 329.2 (M + H)+. | Intermediate B7d (2R)-N-cyclopentyl-2-[(1-methyl-6-nitro-2-oxo-4-quinolyl)amino]propan-amide |
| Intermediate A2e: (R)-2-((6-amino-1-methyl-2-oxo-1,2-dihydroquinolin-4-yl)amino)-N-(2-methoxyethyl)propana-mide | 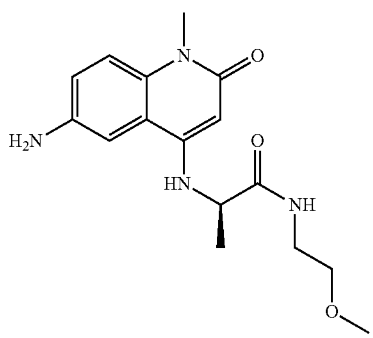 [SMILES: COCCNC(=O)[C@@H](C)Nc1cc(=O)n(C)c2ccc(N)cc12] | LCMS (Method X2), Rt = 0.56 mins, m/z 319.1 (M + H)+. | Intermediate B7e (2R)-N-(2-methoxyethyl)-2-[(1-methyl-6-nitro-2-oxo-4-quinolyl)amino]propan-amide |
| Intermediate A2f: (R)-2-((6-amino-1-methyl-2-oxo-1,2-dihydroquinolin-4-yl)amino)-N-(but-3-yn-1-yl)propanamide | 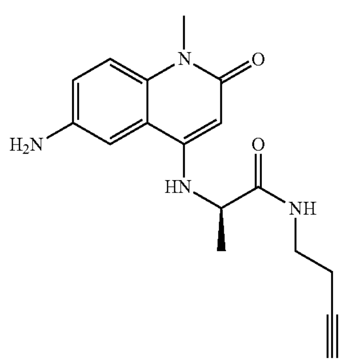 | LCMS (Method T2), Rt = 0.44 mins, m/z 313.2 (M + H)+. | Intermediate B7f (2R)-N-but-3-ynyl-2-[(1-methyl-6-nitro-2-oxo-4-quinolyl)amino]propan-amide |
| Intermediate A2g: (S)-6-Amino-4-((1-hydroxypropan-2-yl)amino)-1-methylquinolin-2(1H)-one | 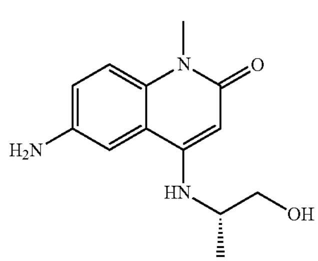 [SMILES: C[C@@H](CO)Nc1cc(=O)n(C)c2ccc(N)cc12] | LCMS (Method T2), Rt = 0.24 min, m/z 248.1 (M + H)+. | Intermediate B8 4-[[(1S)-2-hydroxy-1-methyl-ethyl]amino]-1-methyl-6-nitro-quinolin-2-one |

TABLE 19-continued compounds prepared by a method analogous to that used for the preparation of Intermediate A2a.

| Name | Structure | Characterisation | Starting material (nitro) |
|---|---|---|---|
| Intermediate A2h: 2-((6-Amino-1-methyl-2-oxo-1,2-dihydroquinolin-4-yl)amino)-N-ethyl-2-methylpropanamide | 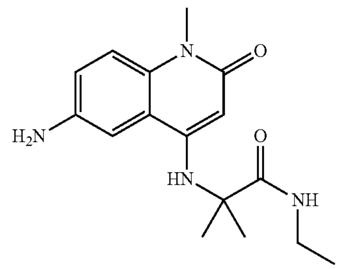 | LCMS (Method T2), Rt = 0.41 mins, m/z 303.2 (M + H)+. | Intermediate B7h 2-[(6-amino-1-methyl-2-oxo-4-quinolyl)amino]-N-ethyl-2-methyl-propanamide |
| Intermediate A2i: (R)-2-((6-amino-1-methyl-2-oxo-1,2-dihydroquinolin-4-yl)amino)-N-(4-methoxycyclohexyl)pro-panamide | | LCMS (Method T2), Rt = 0.97 mins, m/z 373.2 (M + H)+. | Intermediate B7i (2R)-N-(4-methoxycyclohexyl)-2-[(1-methyl-6-nitro-2-oxo-4-quinolyl)amino]propan-amide |
| Intermediate A2j: (2R)-2-((6-Amino-1-methyl-2-oxo-1,2-dihydroquinolin-4-yl)amino)-N-((1-methyl-1H-pyrazol-4-yl)methyl)propanamide | 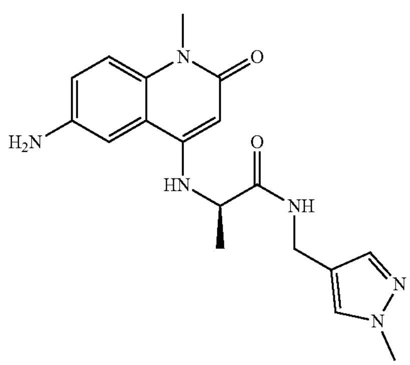 [SMILES: C[C@@H](Nc1cc(=O)n(C)c2ccc(N)cc12)C(=O)NCc1cnn(C)c1] | LCMS (Method X2), Rt = 0.61 mins, m/z 355.2 (M + H)+. | Intermediate B7a (2R)-2-[(1-methyl-6-nitro-2-oxo-4-quinolyl)amino]-N-[(1-methylpyrazol-4-yl)methyl]propanamide |
| Intermediate A2k: 2-((6-Amino-1-methyl-2-oxo-1,2-dihydroquinolin-4-yl)amino)-N-ethylpropanamide | 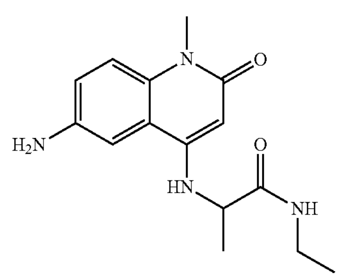 [SMILES: CCNC(=O)C(C)Nc1cc(=O)n(C)c2ccc(N)cc12] | LCMS (Method T2), Rt = 0.32 mins, m/z 289.2 (M + H)+. | Intermediate B7k N-ethyl-2-(((1-methyl-6-nitro-2-oxo-1,2-dihydroquinolin-4-yl)amino)-propanamide |
| Intermediate A2l: 6-Amino-1-methyl-4-((1-(5-methyl-1,3,4-oxadiazol-2-yl)ethyl)amino)quinolin-2(1H)-one | 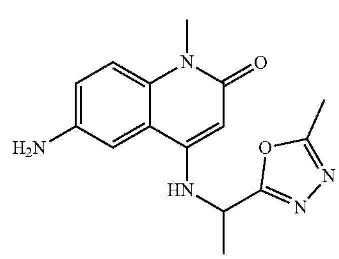 | LCMS (Method T2), Rt = 0.47 mins, m/z 300.1 (M + H)+. | Intermediate B7j 1-methyl-4-((1-(5-methyl-1,3,4-oxadiazol-2-yl)ethyl)amino)-6-nitroquinolin-2(1H)-one |

TABLE 19-continued compounds prepared by a method analogous to that used for the preparation of Intermediate A2a.

| Name | Structure | Characterisation | Starting material (nitro) |
|---|---|---|---|
| Intermediate A2m: (R)-2-((6-amino-1-methyl-2-oxo-1,2-dihydroquinolin-4-yl)amino)-N-(2-(1-methyl-1H-pyrazol-4-yl)ethyl)propanamide | 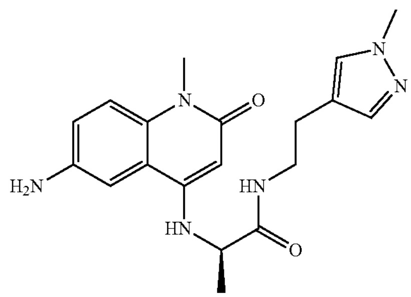 [SMILES: C[C@@H](Nc1cc(=O)n(C)c2ccc(N)cc12)C(=O)NCCc1cnn(C)c1] | LCMS (Method T2), Rt = 0.71 mins, m/z 369.2 (M + H)+. | Intermediate B7g (2R)-2-[(1-methyl-6-nitro-2-oxo-4-quinolyl)amino]-N-[2-(1-methylpyrazol-4-yl)ethyl]propanamide |
| Intermediate A2n: 6-amino-4-[(2-hydroxy-1-methyl-ethyl)amino]-1H-quinazolin-2-one | 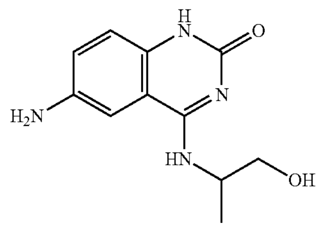 [SMILES: CC(CO)Nc1nc(=O)[nH]c2ccc(N)cc12] | LCMS (Method T2), Rt = 0.11 mins, m/z 235.1181 (M + H)+. | Intermediate B3c 4-[(2-hydroxy-1-methyl-ethyl)amino]-6-nitro-1H-quinazolin-2-one |
| Intermediate A2o: 6-amino-1-methyl-4-[1-(5-methylisoxazol-3-yl)ethylamino]quinolin-2-one | 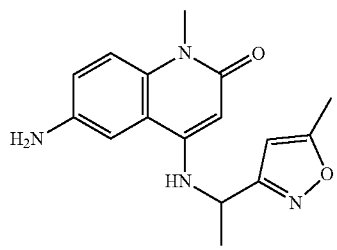 [SMILES: Cc1cc(C(C)Nc2cc(=O)n(C)c3ccc(N)cc23)no1] | LCMS (Method T2), Rt = 0.88 mins, m/z 299.1488 (M + H)+. | Intermediate B2d 6-amino-1-methyl-4-[1-(5-methylisoxazol-3-yl)ethylamino]quinolin-2-one |
| Intermediate A2p: (2R)-2-[(6-amino-2-oxo-1H-quinazolin-4-yl)amino]-N-methyl-propanamide/ | 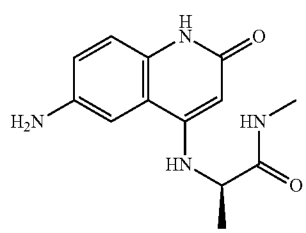 [SMILES: CNC(=O)[C@@H](C)Nc1cc(=O)[nH]c2ccc(N)cc12] | LCMS (Method T2), Rt = 0.09 mins, m/z 261.1 (M + H)+. | Intermediate B4a (2R)-N-methyl-2-[(6-nitro-2-oxo-1H-quinolin-4-yl)amino]propanamide |
| Intermediate A2q: (2S)-6-Amino-4-((4-hydroxybutan-2-yl)amino)-1-methylquinolin-2(1H)-one | 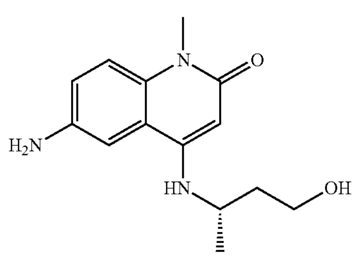 [SMILES: C[C@@H](CCO)Nc1cc(=O)n(C)c2ccc(N)cc12] | LCMS (Method T2), Rt = 0.33 mins, m/z 262.2 (M + H)+. | Intermediate B4b (S)-4-((4-Hydroxybutan-2-yl)amino)-1-methyl-6-nitroquinolin-2(1H)-one |
| Intermediate A2r: (2R)-2-((6-amino-1-methyl-2-oxo-1,2-dihydroquinolin-4-yl)amino)-N-methylpropanamide | 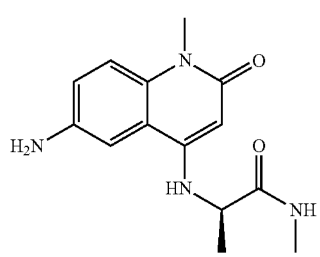 [SMILES: CNC(=O)[C@@H](C)Nc1cc(=O)n(C)c2ccc(N)cc12] | LCMS (Method T2), Rt = 0.21 mins, m/z 275.2 (M + H)+. | Intermediate B4c (2R)-N-methyl-2-[(1-methyl-6-nitro-2-oxo-4-quinolyl)amino]propanamide |

TABLE 19-continued compounds prepared by a method analogous to that used for the preparation of Intermediate A2a.

| Name | Structure | Characterisation | Starting material (nitro) |
|---|---|---|---|
| Intermediate A2s: (2R)-6-amino-4-((1-hydroxypropan-2-yl)amino)-1-methylquinolin-2(1H)-one | 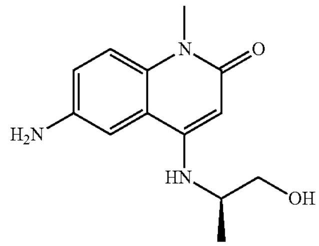 [SMILES: C[C@H](CO)Nc1cc(=O)n(C)c2ccc(N)cc12] | LCMS (Method T2), Rt = 0.23 mins, m/z 248.1 (M + H)+. | Intermediate B4d (2R)-4-((1-Hydroxypropan-2-yl)amino)-1-methyl-6-nitroquinolin-2(1H)-one |
| Intermediate A2t: 6-amino-1-methyl-4-((1-(pyridin-2-yl)ethyl)amino)quinolin-2(1H)-one | 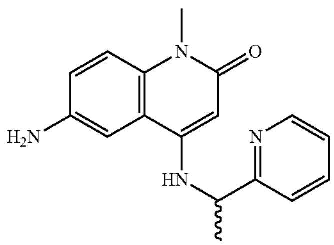 [SMILES: CC(Nc1cc(=O)n(C)c2ccc(N)cc12)c1ccccn1] | LCMS (Method T2), Rt = 0.29 mins, m/z 295.2 (M + H)+. | Intermediate B16: 1-methyl-6-nitro-4-((1-(pyridin-2-yl)ethyl)amino)quinolin-2(1H)-one |
| Intermediate A2u: 2-((6-amino-1-methyl-2-oxo-1,2-dihydroquinolin-4-yl)amino)-2-methyl-N-((1-methyl-1H-pyrazol-4-yl)methyl)propanamide | 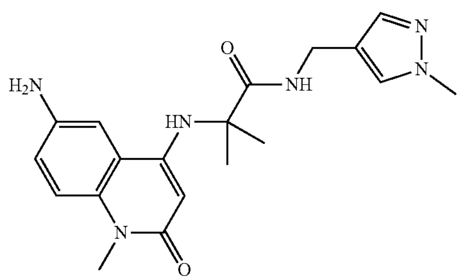 [SMILES: Cn1cc(CNC(=O)C(C)(C)Nc2cc(=O)n(C)c3ccc(N)cc23)cn1] | LCMS (Method T2), Rt = 0.48 mins, m/z 369.2 (M + H)+. | Intermediate B9a: 2-methyl-N-((1-methyl-1H-pyrazol-4-yl)methyl)-2-((1-methyl-6-nitro-2-oxo-1,2-dihydroquinolin-4-yl)amino)propanamide |
| Intermediate A2v: 6-amino-1-methyl-4-((2-(pyridin-2-yl)propan-2-yl)amino)quinolin-2(1H)-one | 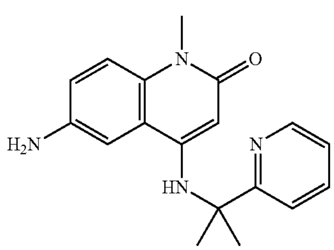 [SMILES: Cn1c(=O)cc(NC(C)(C)c2ccccn2)c2cc(N)ccc21] | LCMS (Method T2), Rt = 0.35 mins, m/z 309.2 (M + H)+. | Intermediate B9b: 1-methyl-6-nitro-4-((2-(pyridin-2-yl)propan-2-yl)amino)quinolin-2(1H)-one |
| Intermediate A2w: 6-amino-4-((1-(5-bromopyrimidin-2-yl)ethyl)amino)-1-methylquinolin-2(1H)-one | 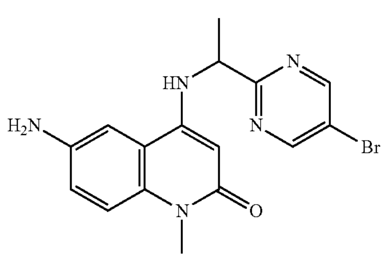 [SMILES: CC(Nc1cc(=O)n(C)c2ccc(N)cc12)c1ncc(Br)cn1] | LCMS (Method T2), Rt = 1.99 mins, m/z 374.06 (M + H)+. | Intermediate B12a: 4-((1-(5-bromopyrimidin-2-yl)ethyl)amino)-1-methyl-6-nitroquinolin-2(1H)-one |

Intermediate A3a; 6-amino-1-methyl-4-[(1-methyl-1-pyrimidin-2-yl-ethyl)amino]quinolin-2-one

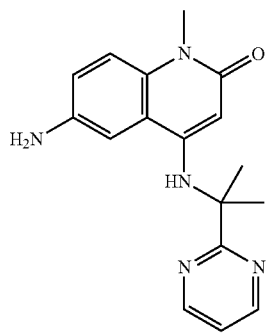 [SMILES: Cn1c(=O)cc(NC(C)(C)c2ncccn2)c2cc(N)ccc21]

A microwave vial (10-20 mL volume) was charged with 1-methyl-4-[(1-methyl-1-pyrimidin-2-yl-ethyl)amino]-6-nitro-quinolin-2-one (Intermediate B1a; 1.02 g, 3 mmol), Pd/C (10 wt %; 93 mg) and ammonium formate (1.02 g, 16 mmol). The reaction vial was flushed with Ar, sealed with a cap and then further flushed with Ar. Anhydrous methanol (15 mL) was added and the reaction mixture was heated at 80° C. for 20 min. The reaction mixture was allowed to cool to rt, filtered through Celite™ and the solids washed with MeOH (100 mL). The filtrate was concentrated in vacuo, and dry-loaded onto silica gel. Purification by flash chromatography (25 g KP-sil; 0% to 15% methanolic ammonia [1.4 M] in $CH_2Cl_2$) afforded the title compound (630 mg, 68%) as a brown solid. LCMS (Method T2) RT 0.67 min; m/z 310.1677 $[M+H]^+$.

The following tabulated intermediates in Table 20 were prepared by methods analogous to that used in the preparation of intermediate A3a, using the nitro starting material as shown.

TABLE 20 compounds prepared by a method analogous to that used for the preparation of Intermediate A3a.

| Name | Structure | Characterisation | Starting material (nitro) |
|---|---|---|---|
| Intermediate A3b: rac-6-amino-4-(((1R,2R)-2-ethylcyclopropyl)amino)-1-methylquinolin-2(1H)-one | 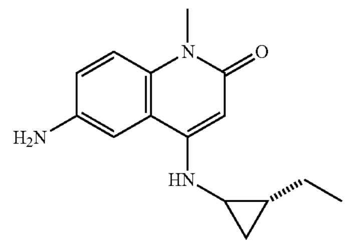 [SMILES: CC[C@@H]1CC1Nc1cc(=O)n(C)c2ccc(N)cc12] | LCMS (Method T2) Rt 1.10 min; m/z 258.1623 $[M + H]^+$. | Intermediate B9n: rac-4-(((1R,2R)-2-ethylcyclopropyl)amino)-1-methyl-6-nitroquinolin-2(1H)-one |
| Intermediate A3c: 6-amino-4-((1-(hydroxymethyl)cyclopropyl)amino)-1-methylquinolin-2(1H)-one | 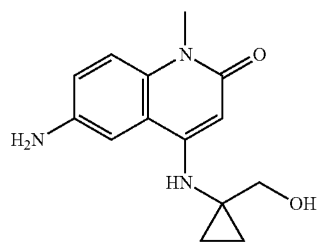 [SMILES: Cn1c(=O)cc(NC2(CO)CC2)c2cc(N)ccc21] | LCMS (Method T2) RT 0.33 min; m/z 260.1362 $[M + H]^+$. | Intermediate B9m: 4-((1-(hydroxymethyl)cyclopropyl)amino)-1-methyl-6-nitroquinolin-2(1H)-one |
| Intermediate A3d: 6-amino-1-methyl-4-((2-pyrimidin-2-yl)butan-2-yl)amino)quinolin-2(1H)-one | 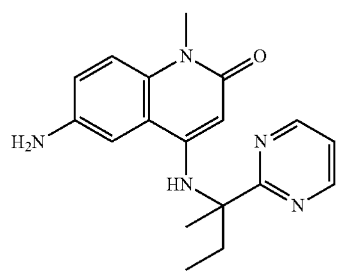 [SMILES: CCC(C)(Nc1cc(=O)n(C)c2ccc(N)cc12)c1ncccn1] | LCMS (Method X2) RT 0.83 min; m/z 324.1824 $[M + H]^+$. | Intermediate B9d: 1-methyl-4-[(1-methyl-1-pyrimidin-2-yl-propyl)amino]-6-nitro-quinolin-2-one |
| Intermediate A3e: 6-amino-4-((2,2-dimethylcyclopropyl)amino)-1-methylquinolin-2(1H)-one | 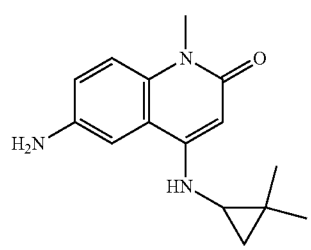 [SMILES: Cn1c(=O)cc(NC2CC2(C)C)c2cc(N)ccc21] | LCMS (Method X2) RT 0.92 min; m/z 258.1424 $[M + H]^+$. | Intermediate B9e: 4-[(2,2-dimethylcyclopropyl)amino]-1-methyl-6-nitro-quinolin-2-one |

TABLE 20-continued compounds prepared by a method analogous to that used for the preparation of Intermediate A3a.

| Name | Structure | Characterisation | Starting material (nitro) |
| --- | --- | --- | --- |
| Intermediate A3f: 1-((6-amino-1-methyl-2-oxo-1,2-dihydroquinolin-4-yl)amino)cyclopropane-1-carbonitrile | 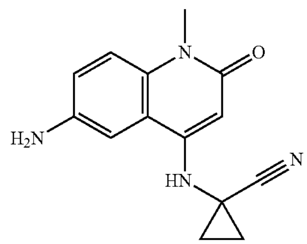 [SMILES: Cn1c(=O)cc(NC2(C#N)CC2)c2cc(N)ccc21] | LCMS (Method T2) RT 0.36 min; m/z 255.1208 [M + H]$^+$. | Intermediate B13: 1-((1-methyl-6-nitro-2-oxo-1,2-dihydroquinolin-4-yl)amino)cyclopropane-1-carbonitrile |
| Intermediate A3g: 6-amino-1-benzyl-4-((1-(pyrimidin-2-yl)ethyl)amino)quinolin-2(1H)-one | 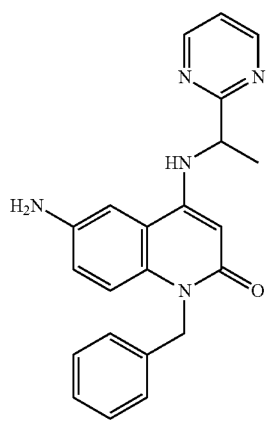 [SMILES: CC(Nc1cc(=O)n(Cc2ccccc2)c2ccc(N)cc12)c1ncccn1] | LCMS (Method T2) m/z 372.1814 expected 372.1824 [M + H]+ | Intermediate B24a: 1-benzyl-6-nitro-4-((1-(pyrimidin-2-yl)ethyl)amino)quinolin-2(1H)-one |
| Intermediate A3h: 6-amino-1-(cyclobutylmethyl)-4-((1-(pyrimidin-2-yl)ethyl)amino)quinolin-2(1H)-one | 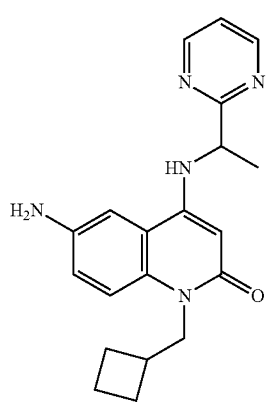 [SMILES: CC(Nc1cc(=O)n(CC2CCC2)c2ccc(N)cc12)c1ncccn1] | LCMS (Method T2) Rt = 1.09 min, m/z 350 [M + H]$^+$. | Intermediate B24b: 1-(cyclobutylmethyl)-6-nitro-4-((1-(pyrimidin-2-yl)ethyl)amino)quinolin-2(1H)-one |

TABLE 20-continued compounds prepared by a method analogous to that used for the preparation of Intermediate A3a.

| Name | Structure | Characterisation | Starting material (nitro) |
|---|---|---|---|
| Intermediate A3i: 6-amino-1-(2-((tert-butyldimethylsilyl)oxy)eth-yl)-4-((1-(pyrimidin-2-yl)ethyl)amino)quinolin-2(1H)-one | | LCMS (Method T2) Rt = 1.41 mins, m/z 440 [M + H]$^+$. | Intermediate B1l: 1-(2-((tert-butyldimethylsilyl)oxy)ethyl)-6-nitro-4-((1-(pyrimidin-2-yl)ethyl)amino)quinolin-2(1H)-one |

The following tabulated intermediates in Table 21 were prepared by methods analogous to that used in the preparation of intermediate A3a, using the nitro starting material as shown.

TABLE 21 compounds prepared by a method analogous to that used for the preparation of Intermediate A3a.

| Name | Structure | Characterisation | Starting material (nitro) |
|---|---|---|---|
| Intermediate A4a: 6-amino-1-methyl-4-(tert-pentylamino)quinolin-2(1H)-one | 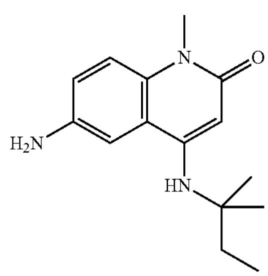 [SMILES: CCC(C)(C)Nc1cc(=O)n(C)c2ccc(N)cc12] | LCMS (Method T2) Rt = 1.04 min, m/z 260 [M + H]$^+$. | Intermediate B14a: 1-methyl-6-nitro-4-(tert-pentylamino)quinolin-2(1H)-one |
| Intermediate A4b: 6-amino-4-((cyclopropylmethyl)amino)-1-methylquinolin-2(1H)-one | 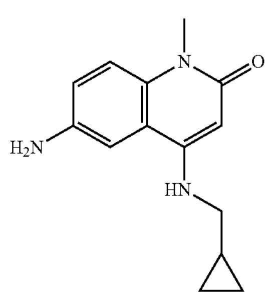 [SMILES: Cn1c(=O)cc(NCC2CC2)c2cc(N)ccc21] | LCMS (Method T2) Rt = 0.82 min, m/z 244 [M + H]$^+$. | Intermediate B14b: 4-((cyclopropylmethyl)amino)-1-methyl-6-nitroquinolin-2(1H)-one |

TABLE 21-continued compounds prepared by a method analogous to that used for the preparation of Intermediate A3a.

| Name | Structure | Characterisation | Starting material (nitro) |
|---|---|---|---|
| Intermediate A4c: 6-amino-4-(tert-butylamino)-1-methylquinolin-2(1H)-one | 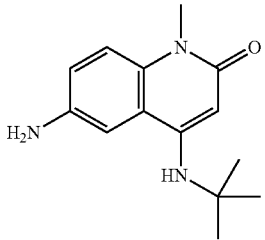 [SMILES: Cn1c(=O)cc(NC(C)(C)C)c2cc(N)ccc21] | LCMS (Method T2) Rt = 0.88 min, m/z 246 [M + H]+. | Intermediate B14c: 4-(tert-butylamino)-1-methyl-6-nitroquinolin-2(1H)-one |
| Intermediate A4d: 6-amino-4-((2-fluoroethyl)amino)-1-methylquinolin-2(1H)-one | 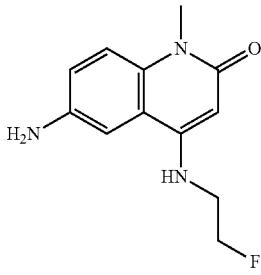 | LCMS (Method T2) Rt = 0.20 min, m/z 236 [M + H]+. | Intermediate B14d: 4-((2-fluoroethyl)amino)-1-methyl-6-nitroquinolin-2(1H)-one |
| Intermediate A4e: 6-amino-4-((1-methoxy-2-methylpropan-2-yl)amino)-1-methylquinolin-2(1H)-one | 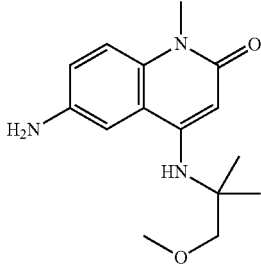 [SMILES: COCC(C)(C)Nc1cc(=O)n(C)c2ccc(N)cc12] | LCMS (Method T2) Rt = 0.91 min, m/z 276 [M + H]+. | Intermediate B14e: 4-((1-methoxy-2-methylpropan-2-yl)amino)-1-methyl-6-nitroquinolin-2(1H)-one |
| Intermediate A4f: 6-amino-4-((1-methoxy-2-methylbutan-2-yl)amino)-1-methylquinolin-2(1H)-one | 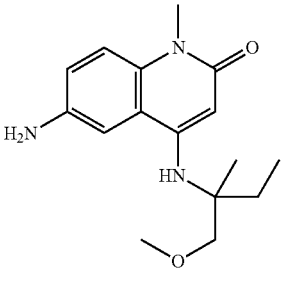 [SMILES: CCC(C)(COC)Nc1cc(=O)n(C)c2ccc(N)cc12] | LCMS (Method T2) Rt = 1.01 min, m/z 290 [M + H]+. | Intermediate B9i: 4-((1-methoxy-2-methylbutan-2-yl)amino)-1-methyl-6-nitroquinolin-2(1H)-one |
| Intermediate A4g: 6-amino-1-methyl-4-((1-(pyrimidin-2-yl)cyclopropyl)amino)quinolin-2(1H)-one | 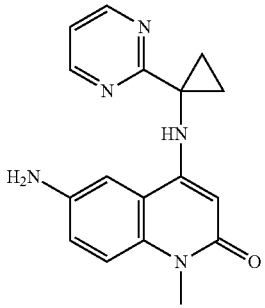 | LCMS (Method T2) Rt = 0.51 mins, m/z 308.15 [M + H]+. | Intermediate B14f: 1-methyl-6-nitro-4-((1-(pyrimidin-2-yl)cyclopropyl)amino)quinolin-2(1H)-one |

TABLE 21-continued compounds prepared by a method analogous to that used for the preparation of Intermediate A3a.

| Name | Structure | Characterisation | Starting material (nitro) |
|---|---|---|---|
| Intermediate A4h: 6-amino-1-(cyclohexylmethyl)-4-((1-(pyrimidin-2-yl)ethyl)amino)quinolin-2(1H)-one | 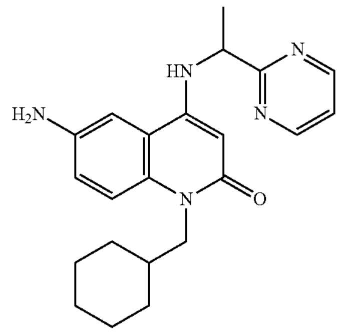 [SMILES: CC(Nc1cc(=O)n(CC2CCCCC2)c2ccc(N)cc12)c1ncccn1] | LCMS (Method T2) Rt = 1.30 mins, m/z 378.23 [M + H]+. | Intermediate B14g: 1-(cyclohexylmethyl)-6-nitro-4-((1-(pyrimidin-2-yl)ethyl)amino)quinolin-2(1H)-one |
| Intermediate A4i: 6-amino-1-(cyclohexylmethyl)-4-((2-(pyrimidin-2-yl)propan-2-yl)amino)quinolin-2(1H)-one | 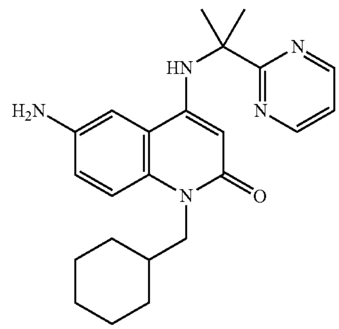 [SMILES: CC(C)(Nc1cc(=O)n(CC2CCCCC2)c2ccc(N)cc12)c1ncccn1] | LCMS (Method T2) Rt = 1.33 mins, m/z 392.24 [M + H]+. | Intermediate B14h: 1-(cyclohexylmethyl)-6-nitro-4-((2-(pyrimidin-2-yl)propan-2-yl)amino)quinolin-2(1H)-one |
| Intermediate A4j: 6-amino-4-((2-(5-cyclopropylpyrimidin-2-yl)propan-2-yl)amino)-1-methylquinolin-2(1H)-one | 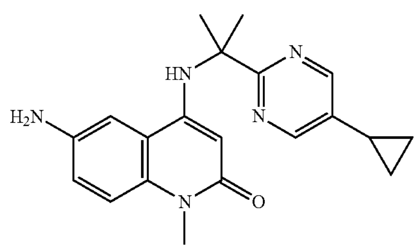 [SMILES: Cn1c(=O)cc(NC(C)(C)c2ncc(C3CC3)cn2)c2cc(N)ccc21] | LCMS (Method T2) Rt = 1.07 mins, m/z 350.20 [M + H]+. | Intermediate B18d: 4-((2-(5-cyclopropylpyrimidin-2-yl)propan-2-yl)amino)-1-methyl-6-nitroquinolin-2(1H)-one |
| Intermediate A4l: 6-amino-1-methyl-4-((1-(1-methyl-1H-1,2,4-triazol-3-yl)ethyl)amino)quinolin-2(1H)-one | 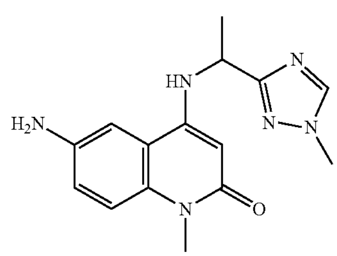 [SMILES: CC(Nc1cc(=O)n(C)c2ccc(N)cc12)c1ncn(C)n1] | LCMS (Method T2) Rt = 0.54 mins, m/z 299.16 [M + H]+. | Intermediate B9p: 1-methyl-4-((1-(1-methyl-1H-1,2,4-triazol-3-yl)ethyl)amino)-6-nitroquinolin-2(1H)-one |
| Intermediate A4m: 6-amino-4-((cyclopropyl(pyrimidin-2-yl)methyl)amino)-1-methylquinolin-2(1H)-one | 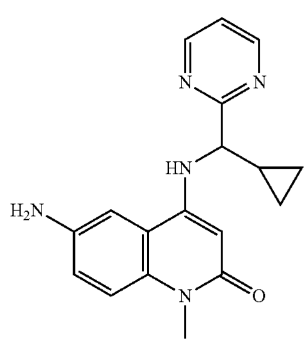 [SMILES: Cn1c(=O)cc(NC(c2ncccn2)C2CC2)c2cc(N)ccc21] | LCMS (Method T2) Rt = 0.85 mins, m/z 322.17 [M + H]+. | Intermediate B9l: 4-((cyclopropyl(pyrimidin-2-yl)methyl)amino)-1-methyl-6-nitroquinolin-2(1H)-one |

TABLE 21-continued compounds prepared by a method analogous to that used for the preparation of Intermediate A3a.

| Name | Structure | Characterisation | Starting material (nitro) |
|---|---|---|---|
| Intermediate A4n: (S)-6-amino-4-((1-cyclopropylethyl)amino)-1-methylquinolin-2(1H)-one | 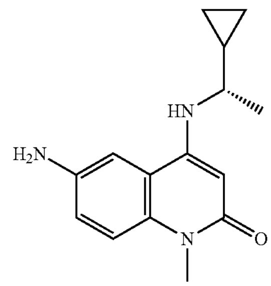 [SMILES: C[C@H](Nc1cc(=O)n(C)c2ccc(N)cc12)C1CC1] | LCMS (Method T2) Rt = 0.92 mins, m/z 258.16 [M + H]+ | Intermediate B10b: (S)-4-((1-cyclopropylethyl)amino)-1-methyl-6-nitroquinolin-2(1H)-one |
| Intermediate A4o: 6-Amino-1-methyl-4-[[(3S)-tetrahydrofuran-3-yl]amino]quinolin-2-one | 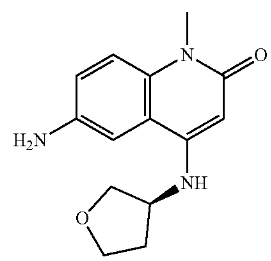 [SMILES: Cn1c(=O)cc(N[C@H]2CCOC2)c2cc(N)ccc21] | LCMS (Method T2); Rt 0.42 min; m/z 260.1390 [M + H]+ | 1-methyl-6-nitro-4-[[(3S)-tetrahydrofuran-3-yl]amino]quinolin-2-one (Intermediate B5 |
| Intermediate A4p: 6-amino-1-methyl-4-((1-(pyrimidin-2-yl)ethyl)amino)quinazolin-2(1H)-one | 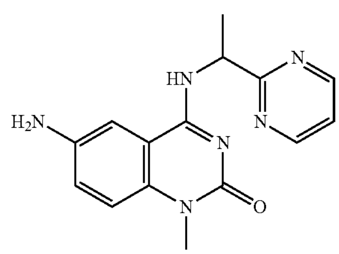 [SMILES: CC(Nc1nc(=O)n(C)c2ccc(N)cc12)c1ncccn1] | LCMS (Method T2) Rt = 0.49 mins, m/z 297.15 [M + H]+. | Intermediate B20b: 1-methyl-6-nitro-4-((1-(pyrimidin-2-yl)ethyl)amino)quinazolin-2(1H)-one |
| Intermediate A4q: (S)-6-amino-1-methyl-4-((1-(pyrimidin-2-yl)ethyl)amino)quinolin-2(1H)-one | 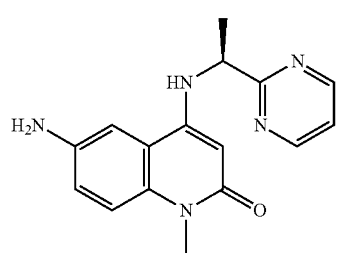 [SMILES: C[C@H](Nc1cc(=O)n(C)c2ccc(N)cc12)c1ncccn1] | LCMS (Method T2) Rt = 0.52 mins, m/z 296.15 [M + H]+. | Intermediate B11s: (S)-1-methyl-6-nitro-4-((1-(pyrimidin-2-yl)ethyl)amino)quinolin-2(1H)-one |
| Intermediate A4r: (R)-6-amino-1-methyl-4-((1-(pyrimidin-2-yl)ethyl)amino)quinolin-2(1H)-one | 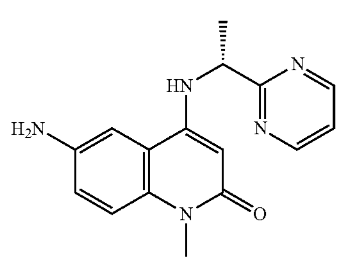 [SMILES: C[C@@H](Nc1cc(=O)n(C)c2ccc(N)cc12)c1ncccn1] | LCMS (Method T2) Rt = 0.54 mins, m/z 296.15 [M + H]+. | Intermediate B11r: (R)-1-methyl-6-nitro-4-((1-(pyrimidin-2-yl)ethyl)amino)quinolin-2(1H)-one |

TABLE 21-continued compounds prepared by a method analogous to that used for the preparation of Intermediate A3a.

| Name | Structure | Characterisation | Starting material (nitro) |
|---|---|---|---|
| Intermediate A4s: 6-amino-1-methyl-4-((1-(5-(1-methyl-1H-pyrazol-4-yl)pyrimidin-2-yl)ethyl)amino)quinolin-2(1H)-one | 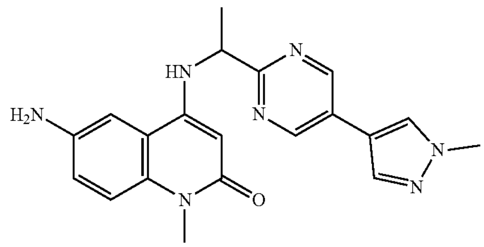 [SMILES: CC(Nc1cc(=O)n(C)c2ccc(N)cc12)c1ncc(-c2cnn(C)c2)cn1] | LCMS (Method T2) Rt = 1.01 mins, m/z 376.19 [M + H]⁺. | Intermediate B18b: 1-methyl-4-((1-(5-(1-methyl-1H-pyrazol-4-yl)pyrimidin-2-yl)ethyl)amino)-6-nitroquinolin-2(1H)-one |
| Intermediate A4t: (R)-6-amino-4-((1-cyclopropylethyl)amino)-1-methylquinazolin-2(1H)-one | 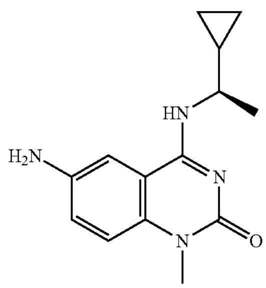 [SMILES: C[C@@H](Nc1nc(=O)n(C)c2ccc(N)cc12)C1CC1] | LCMS (Method T2) Rt = 0.39 mins, m/z 259.15 [M + H]⁺. | Intermediate B20a: (R)-4-((1-cyclopropylethyl)amino)-1-methyl-6-nitroquinazolin-2(1H)-one |
| Intermediate A4u: 6-amino-1-methyl-4-((1-(5-methylpyrimidin-2-yl)ethyl)amino)quinolin-2(1H)-one | 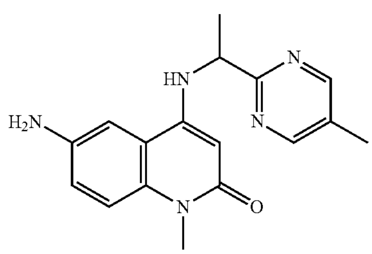 [SMILES: Cc1cnc(C(C)Nc2cc(=O)n(C)c3ccc(N)cc23)nc1] | LCMS (Method T2) Rt = 0.87 mins, m/z 310.16 [M + H]⁺. | Intermediate B19a: 1-methyl-4-((1-(5-methylpyrimidin-2-yl)ethyl)amino)-6-nitroquinolin-2(1H)-one |
| Intermediate A4v: 6-amino-1-methyl-4-((1-(5-morpholinopyrimidin-2-yl)ethyl)amino)quinolin-2(1H)-one | 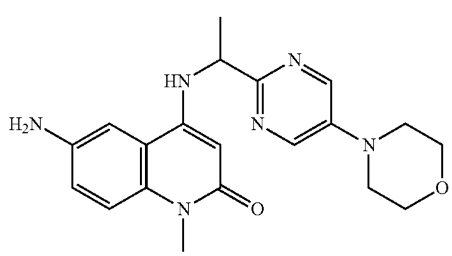 [SMILES: CC(Nc1cc(=O)n(C)c2ccc(N)cc12)c1ncc(N2CCOCC2)cn1] | LCMS (Method T2) Rt = 0.98 mins, m/z 381.20 [M + H]⁺. | Intermediate B15a: 1-methyl-4-((1-(5-morpholinopyrimidin-2-yl)ethyl)amino)-6-nitroquinolin-2(1H)-one |
| Intermediate A4w: 6-amino-4-((1-(5-((3S,5R)-3,5-dimethylpiperidin-1-yl)pyrimidin-2-yl)ethyl)amino)-1-methylquinolin-2(1H)-one | 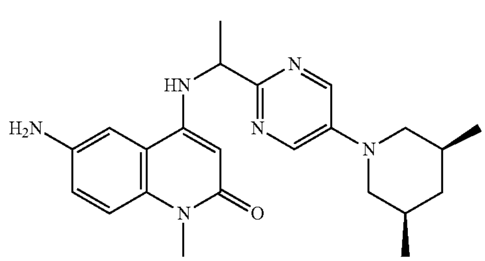 [SMILES: CC(Nc1cc(=O)n(C)c2ccc(N)cc12)c1ncc(N2C[C@H](C)C[C@H](C)C2)cn1] | LCMS (Method T2) Rt = 1.38 mins, m/z 407.25 [M + H]⁺. | Intermediate B15c: 4-((1-(5-((3S,5R)-3,5-dimethylpiperidin-1-yl)pyrimidin-2-yl)ethyl)amino)-1-methyl-6-nitroquinolin-2(1H)-one |

TABLE 21-continued compounds prepared by a method analogous to that used for the preparation of Intermediate A3a.

| Name | Structure | Characterisation | Starting material (nitro) |
|---|---|---|---|
| Intermediate A4x: rac-6-amino-4-(((1S,2R)-2-methoxycyclopentyl)amino)-1-methylquinolin-2(1H)-one | 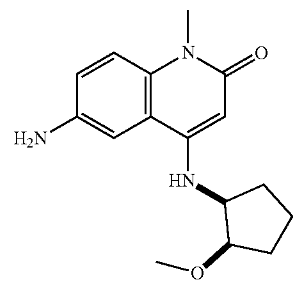 [SMILES: CO[C@@H]1CCC[C@@H]1Nc1cc(=O)n(C)c2ccc(N)cc12] | LCMS (Method T2) Rt = 0.99 min, m/z 288 [M + H]⁺. | Intermediate B9q: 4-((2-methoxycyclopentyl)amino)-1-methyl-6-nitroquinolin-2(1H)-one |
| Intermediate A4y: 6-amino-1-methyl-4-((2-(pyrimidin-2-yl)propan-2-yl)amino)quinazolin-2(1H)-one | 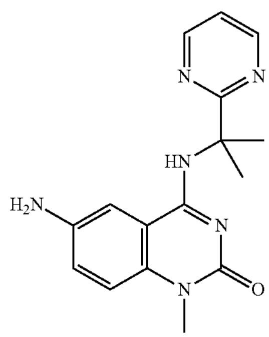 [SMILES: Cn1c(=O)nc(NC(C)(C)c2ncccn2)c2cc(N)ccc21] | LCMS (Method T2) Rt = 0.69 min, m/z 311 [M + H]⁺. | Intermediate B20c: 1-methyl-6-nitro-4-((2-(pyrimidin-2-yl)propan-2-yl)amino)quinazolin-2(1H)-one |

Intermediate A5: 6-amino-4-(ethylamino)-1-[2-(2-methoxyethoxy)ethyl]quinolin-2-one

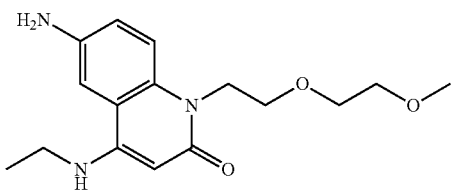 [SMILES: CCNc1cc(=O)n(CCOCCOC)c2ccc(N)cc12]

Step 1: 4-chloro-1-[2-(2-methoxyethoxy)ethyl]-6-nitro-quinolin-2-one

A mixture of 4-chloro-6-nitro-1H-quinolin-2-one (Intermediate D3, 337 mg, 1.5 mmol), 1-(2-bromoethoxy)-2-methoxy-ethane (412 mg, 2.25 mmol), cesium carbonate (977 mg, 3 mmol) and DMF (15.0 mL, 0.1 M) was stirred at 80° C. for 2 hours. LCMS (Method T2) Rt=1.41 mins, m/z 327.07 [M+H]+. Once cooled, water was added then the mixture was extracted with EtOAc. The organic extracts were washed with water and brine then dried over MgSO₄, filtered and concentrated in vacuo. The residue was purified by Biotage KP-Sil 25 g column eluting 20-80% EtOAc in cyclohexane affording 4-chloro-1-[2-(2-methoxyethoxy) ethyl]-6-nitro-quinolin-2-one (237 mg) as a white solid.

Step 2: 4-(ethylamino)-1-[2-(2-methoxyethoxy) ethyl]-6-nitro-quinolin-2-one

A mixture of 4-chloro-1-[2-(2-methoxyethoxy)ethyl]-6-nitro-quinolin-2-one (32.0 mg, 0.098 mmol) and ethylamine (2.0 M in THF) (0.49 mL, 0.98 mmol) in NMP (0.98 mL) was heated to 160° C. for 2 h. LCMS (Method T2) Rt=1.34 mins, m/z 336.15 [M+H]+. The solution was taken forward without further manipulation.

Step 3: 6-amino-4-(ethylamino)-1-[2-(2-methoxyethoxy)ethyl]quinolin-2-one

A mixture of 4-(ethylamino)-1-[2-(2-methoxyethoxy) ethyl]-6-nitro-quinolin-2-one (32.8 mg, 0.058 mmol (0.1 M in NMP)) in Ethanol (1.00 mL) was added Pd/C (10 wt %) (10.0 mg) and ammonium formate (61.7 mg, 0.98 mmol). The vial was sealed and evacuated then refilled with argon three times. The vial was then placed into a drysyn block preheated to 60° C. for 30 mins. LCMS (Method T2) Rt=0.91 mins, m/z 306.18 [M+H]⁺. Once cooled, the mixture was purified by passing through a bed of Celite™ on an SCX-2 cartridge. The product was eluted with methanolic ammonia, affording 6-amino-4-(ethylamino)-1-[2-(2-methoxyethoxy)ethyl]quinolin-2-one.

Intermediate A6:
6-Amino-4-(ethylamino)-1-methyl-quinolin-2-one

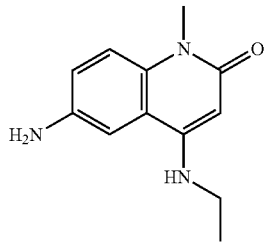

Step 1:
4-(ethylamino)-1-methyl-6-nitro-quinolin-2-one

A suspension of ethylamine (2.0M in THF, 31 mL, 63 mmol) and 4-chloro-1-methyl-6-nitro-quinolin-2-one (Intermediate D1, 1.5 g, 6.3 mmol) in NMP (21 mL) was divided equally into three microwave vials (10-20 mL volume). The reaction vials were sealed with caps and then heated thermally at 160° C. for 2 h. The reaction mixtures were allowed to cool to rt. Water was added to each of the reaction mixtures. After 1 min, a precipitate formed, which was filtered. The combined precipitates were washed with water affording 4-(ethylamino)-1-methyl-6-nitro-quinolin-2-one (1.3 g) as a yellow/orange solid which was used without further purification. LCMS (Method X2); Rt 1.09 min; m/z 248.1035 [M+H]$^+$

Step 2:
6-amino-4-(ethylamino)-1-methyl-quinolin-2-one

A mixture of 4-(ethylamino)-1-methyl-6-nitro-quinolin-2-one (0.45 g, 1.8 mmol), ammonium formate (1.07 g, 16.9 mmol) and 10 wt % Pd/C (87 mg) in ethanol (10 mL) and NMP (2 mL) was evacuated and refilled with nitrogen three times, then heated at 60° C. for 30 min. The reaction mixture was allowed to cool to rt, then filtered through Celite™, and the resulting solids were washed with ethanol. The filtrate was concentrated in vacuo to yield a solution of the product in NMP, which was purified using an SCX column then further purified by flash column chromatography (silica, 0 to 15% methanol in DCM) to give the title compound (260 mg) as an off-white solid which was used without further purification. LCMS (Method X2); RT 0.27 min; m/z 218.1292 [M+H]$^+$.

Intermediate A7; 1-[2-[6-Amino-4-(ethylamino)-2-oxo-1-quinolyl]ethyl]pyrrolidine-2,5-dione

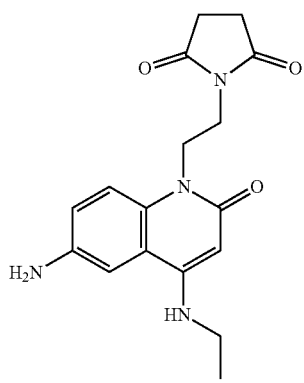 [SMILES: CCNc1cc(=O)n(CCN2C(=O)CCC2=O)c2ccc(N)cc12]

A mixture of 1-[2-(4-chloro-6-nitro-2-oxo-1-quinolyl) ethyl]pyrrolidine-2,5-dione (Intermediate D5, 30 mg, 0.086 mmol) and ethylamine (2.0M in THF, 0.43 mL, 0.86 mmol) in NMP (0.86 mL) was heated to 160° C. for 1 h. LCMS (Method T2) Rt=1.21 mins, m/z 359.13 [M+H]$^+$. The resulting solution was diluted with ethanol (0.86 mL), and Pd/C (10 wt %, 4.6 mg) and ammonium formate (54.1 mg, 0.86 mmol) were added. The vial was sealed and evacuated then refilled with argon three times. The vial was then placed into a drysyn block preheated to 60° C. for 45 mins. LCMS (Method T2) Rt=0.47 mins, m/z 329.1612 [M+H]$^+$. Once cooled, the mixture was purified by passing through a bed of Celite™ on an SCX-2 cartridge. The product was eluted with methanolic ammonia, affording 1-[2-[6-amino-4-(ethylamino)-2-oxo-1-quinolyl]ethyl]pyrrolidine-2,5-dione.

Intermediate A8: 6-amino-4-((2-(5-((2R,6S)-2,6-dimethylmorpholino)pyrimidin-2-yl)propan-2-yl) amino)-1-methylquinolin-2(1H)-one

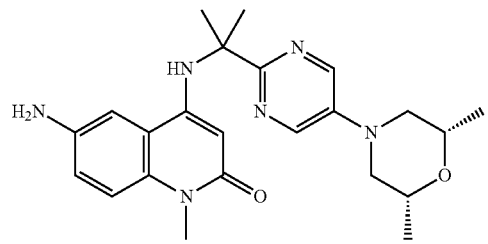 [SMILES: C[C@@H]1CN(c2cnc(C(C)(C)Nc3cc(=O)n(C)c4ccc(N)cc34)nc2)C[C@H](C)O1]

Step 1: 4-((2-(5-((2R,6S)-2,6-dimethylmorpholino) pyrimidin-2-yl)propan-2-yl)amino)-1-methyl-6-nitroquinolin-2(1H)-one To a vial was added 4-[[1-(5-bromopyrimidin-2-yl)-1-methyl-ethyl]amino]-1-methyl-6-nitro-quinolin-2-one (Intermediate B17, 100 mg, 0.24 mmol), (2R,6S)-2,6-dimethylmorpholine (35 uL, 0.29 mmol), cesium carbonate (620 mg, 1.9 mmol), tris(dibenzylideneacetone)-dipalladium(0) (22 mg, 0.024 mmol), Xantphos (83 mg, 0.14 mmol) and a stirrer bar. The vial was sealed, toluene (3.67 mL) and DMF (1.12 mL) were added and the vial purged with argon for 5 mins. The vial was heated in the microwave at 80° C. overnight. Once cooled to rt, the mixture was purified by passing through a syringe filter, concentrated to remove the toluene then the residue was purified by flash column chromatography (Biotage KP-Sil 25 g, eluting 0-10% MeOH in DCM) affording 4-((2-(5-((2R,6S)-2,6-dimethylmorpholino)pyrimidin-2-yl)propan-2-yl)amino)-1-methyl-6-nitroquinolin-2(1H)-one (100 mg, 92%, 0.2210 mmol) as a pale brown solid. LCMS: Rt=1.45 mins, mass not observed.

Step 2; 6-amino-4-((2-(5-((2R,6S)-2,6-dimethylmorpholino)pyrimidin-2-yl)propan-2-yl)amino)-1-methylquinolin-2(1H)-one To a solution of 4-((2-(5-((2R,6S)-2,6-dimethylmorpholino)pyrimidin-2-yl)propan-2-yl)amino)-1-methyl-6-nitroquinolin-2(1H)-one (from step 1, 100 mg, 0.22 mmol) in ethanol (2.2 mL) was added ammonium formate (140 mg, 2.21 mmol) and Pd/C (10 wt %) (24 mg, 0.022 mmol). The vial was sealed and evacuated then refilled with argon three times. The vial was then placed into a drysyn block preheated to 60° C. After cooling to r.t. the mixture was filtered through Celite™ and washed with ethanol. The solvent was evaporated under reduced pressure. The residue was diluted with DCM, washed with half-saturated sodium bicarbonate, dried and evaporated under reduced pressure affording 6-amino-4-[[1-[5-[(2R,6S)-2,6-dimethylmorpholin-4-yl]pyrimidin-2-yl]-1-methyl-ethyl]amino]-1-methyl-quinolin-2-one (72 mg, 77%, 0.1704 mmol) as an pale orange solid. LCMS (Method T2) Rt=1.15 mins, m/z 423.50 [M+H]$^+$.

Intermediate A9; 6-Amino-1-methyl-4-[(1-methyl-1-pyrimidin-2-yl-ethyl)amino]-1,8-naphthyridin-2-one

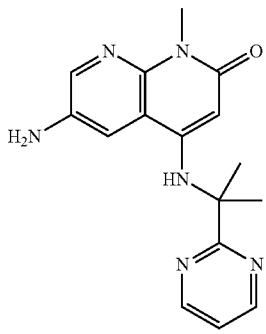

Step 1; 6-bromo-1-methyl-4-[(1-methyl-1-pyrimidin-2-yl-ethyl)amino]-1,8-naphthyridin-2-one A mixture of ethyl 6-bromo-4-chloro-1-methyl-2-oxo-1,8-naphthyridine-3-carboxylate (Intermediate D7, 80 mg, 0.23 mmol), 2-pyrimidin-2-ylpropan-2-amine dihydrochloride (73 mg, 0.35 mmol) and DIPEA (0.16 mL, 0.93 mmol) in NMP (1.16 mL) in a sealed vessel was heated in a microwave at 160° C. for 1 h. LCMS (Method T2) Rt=1.53 mins, m/z 446.09 [M+H]$^+$. Lithium chloride (58.9 mg, 1.39 mmol) was added to the mixture, the vessel was resealed and heated in a drysyn heating block at 160° C. for 3 h. LCMS (Method T2) Rt=1.41 mins, m/z 374.06 [M+H]$^+$. Once cooled, the sample was purified directly using reverse-phase C18 column eluting from 10-100% methanol in water (containing 0.1% formic acid) to give ethyl 6-bromo-1-methyl-4-[(1-methyl-1-pyrimidin-2-yl-ethyl)amino]-1,8-naphthyridin-2-one (59 mg) as an off-white solid. $^1$H NMR (500 MHz, Chloroform-d) δ 8.80 (d, J=4.9 Hz, 2H), 8.60 (d, J=2.3 Hz, 1H), 8.12 (d, J=2.3 Hz, 1H), 7.25 (t, J=4.9 Hz, 1H), 6.60 (s, 1H), 5.64 (s, 1H), 3.68 (s, 3H), 1.87 (s, 6H).

Step 2; 6-amino-1-methyl-4-[(1-methyl-1-pyrimidin-2-yl-ethyl)amino]-1,8-naphthyridin-2-one A mixture of 6-bromo-1-methyl-4-[(1-methyl-1-pyrimidin-2-yl-ethyl)amino]-1,8-naphthyridin-2-one (from Step 1, 30 mg, 0.080 mmol), copper(I) oxide (2.3 mg, 0.016 mmol), ammonium hydroxide solution (28-30% NH$_3$, 1.00 mL, 25.7 mmol) and NMP (0.8 mL) was heated in microwave at 140° C. for 2 h. Additional copper(I) oxide (5.0 mg. 0.035 mmol) was then added and heating continued in microwave continued at 140° C. for 1.5 h. The mixture was concentrated in vacuo. The resulting NMP solution was then passed through a 5 g SCX-2 cartridge and washed through with MeOH and water. The product was eluted using methanolic ammonia then concentrated in vacuo affording 6-amino-1-methyl-4-[(1-methyl-1-pyrimidin-2-yl-ethyl)amino]-1,8-naphthyridin-2-one (25 mg) as a brown oil. LCMS (Method T2) Rt=1.01 mins, m/z 311.16 [M+H]$^+$.

Intermediate A10a: (R)-6-Amino-4-((1-cyclopropylethyl)amino)-1-methyl-1,8-naphthyridin-2(1H)-one

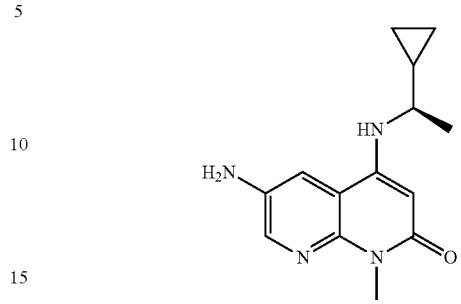

To a vial containing 6-bromo-4-[[(1R)-1-cyclopropylethyl]amino]-1-methyl-1,8-naphthyridin-2-one (Intermediate B9j, 60 mg, 0.19 mmol) in ammonium hydroxide solution (28-30% NH$_3$, 2.3 mL, 59.3 mmol) and NMP (0.8 mL) was added copper(I) oxide (5.3 mg, 0.037 mmol) and the reaction was heated in the MW at 140° C. for 2 h. The reaction mixture was concentrated under reduced pressure to remove the aqueous ammonium hydroxide. The resulting NMP solution was loaded onto a 5 g SCX-2 column and washed with MeOH and water. The product was then eluted with 2M methanolic ammonia, and concentrated under reduced pressure to give 6-bromo-4-[[(1R)-1-cyclopropylethyl]amino]-1-methyl-1,8-naphthyridin-2-one (53 mg, 89%, 0.164 mmol) as a brown oil. Compound was used in the next steps with no further purification. $^1$H NMR (500 MHz, Methanol-d4) δ 8.18 (d, J=2.6 Hz, 1H), 7.66 (d, J=2.6 Hz, 1H), 5.58 (s, 1H), 3.66 (s, 3H), 3.12-3.01 (m, 1H), 1.34 (d, J=6.4 Hz, 3H), 1.23-1.05 (m, 1H), 0.62-0.45 (m, 2H), 0.40-0.22 (m, 2H). LCMS (Method T2) Rt=1.14 mins, m/z 259 [M+H]$^+$.

Intermediate A10b: 6-Amino-1-methyl-4-((1-(pyrimidin-2-yl)ethyl)amino)-7,8-naphthyridin-2(1H)-one

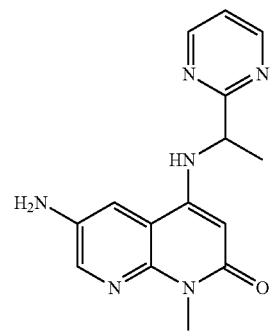 [SMILES: CC(Nc1cc(=O)n(C)c2ncc(N)cc12)c1ncccn1]

Prepared by a method analogous to that used in the preparation of intermediate A10a, using Intermediate B12b: 6-bromo-1-methyl-4-((1-(pyrimidin-2-yl)ethyl)amino)-1,8-naphthyridin-2(1H)-one
$^1$H NMR (500 MHz, Methano) δ 8.79 (d, J=4.9 Hz, 2H), 8.20 (dd, J=2.7, 1.3 Hz, 1H), 7.73 (d, J=2.7 Hz, 1H), 7.38 (t, J=4.9 Hz, 1H), 5.50 (d, J=1.4 Hz, 1H), 3.63 (s, 3H), 1.71 (d, J=6.9 Hz, 3H). LCMS (Method T2) Rt=0.94 mins, m/z 297 [M+H]$^+$.

Intermediate A10c: 6-Amino-8-methoxy-1-methyl-4-((2-(pyrimidin-2-yl)propan-2-yl)amino)quinolin-2(1H)-one

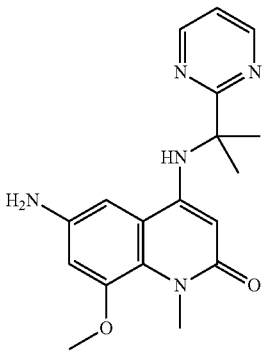 [SMILES: COc1cc(N)cc2c(NC(C)(C)c3ncccn3)cc(=O)n(C)c12]

Prepared by a method analogous to that used in the preparation of intermediate A10a, using Intermediate D8: 6-bromo-8-methoxy-1-methyl-4-((2-(pyrimidin-2-yl)propan-2-yl)amino)quinolin-2(1H)-one LCMS (Method T2) Rt=1.01 mins, m/z 340.17 [M+H]$^+$.

Intermediate A11: 6-Amino-4-((1-ethynylcyclopropyl)amino)-1-methylquinolin-2(1H)-one

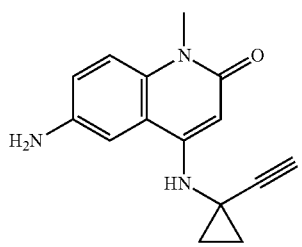 [SMILES: C#CC1(Nc2cc(=O)n(C)c3ccc(N)cc23)CC1]

An oven dried microwave vial (0.5-2.0 mL volume) was charged with 4-((1-ethynylcyclopropyl)amino)-1-methyl-6-nitroquinolin-2(1H)-one (Intermediate B9f; 25 mg, 0.09 mmol), ammonium chloride (35 mg, 0.65 mmol) and zinc dust (6 mg, 0.09 mmol). The reaction vial was flushed with Ar, sealed with a cap and then further flushed with Ar. Anhydrous methanol (1 mL) was added and the reaction mixture was sonicated for 5 min, stirred at rt for 1 h, then heated at 60° C. for 3 h. After this time, additional Zn dust (7 mg) was added and the reaction mixture was heated at 60° C. for a further 2 h. The reaction mixture was cooled to rt and filtered through Celite™. The solid residue was washed with MeOH (40 mL) and the filtrate was concentrated in vacuo. The crude product was dissolved in DMSO (1.4 mL) and directly purified using Biotage reverse-phase 12 g C-18 column eluting 10-10% MeOH in water (containing 0.1% formic acid), affording the title compound (5 mg, 24%) as a yellow solid. LCMS (Method X2) RT 0.70 min; m/z 254.1048 [M+H]$^+$.

Intermediate A12a: 6-amino-4-((1-cyclopropyl-2-hydroxyethyl)amino)-1-methylquinolin-2(1H)-one

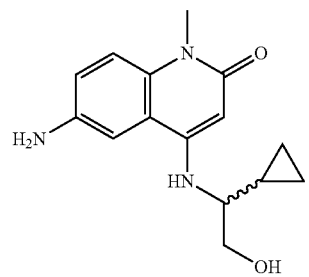 [SMILES: Cn1c(=O)cc(NC(CO)C2CC2)c2cc(N)ccc21]

4-[(1-Cyclopropyl-2-hydroxy-ethyl)amino]-1-methyl-6-nitro-quinolin-2-one (Intermediate B9c, 33.0 mg, 0.109 mmol) and palladium/C (2.32 mg, 0.022 mmol) were suspended in ethanol (4 mL). The mixture was hydrogenated at 1 atm for 16 h. After filtration and removal of solvent, 6-amino-4-[(1-cyclopropyl-2-hydroxy-ethyl)amino]-1-methyl-quinolin-2-one (28 mg, 94%, 0.102 mmol) was obtained as a brown oil. It was used in the next step without further purification. LCMS (Method T2) Rt=0.61 mins, m/z 274.2 [M+H]$^+$.

The following tabulated intermediates in Table 22 were prepared by methods analogous to that used in the preparation of intermediate A12a, using the nitro starting material as shown.

TABLE 22 compounds prepared by a method analogous to that used for the preparation of Intermediate A12a.

| Name | Structure | Characterisation | Starting material (nitro) |
|---|---|---|---|
| Intermediate A12b: (S)-6-amino-4-((1-cyclopropyl-2-hydroxyethyl)amino)-1-methylquinolin-2(1H)-one | 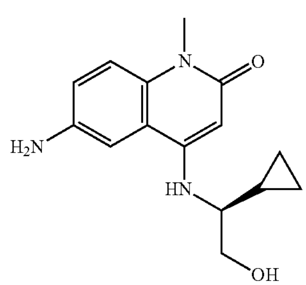 [SMILES: Cn1c(=O)cc(N[C@H](CO)C2CC2)c2cc(N)ccc21] | LCMS (Method T2), Rt = 0.63 mins, m/z 274.2 (M + H)$^+$. | Intermediate B9o: (S)-4-((1-cyclopropyl-2-hydroxyethyl)amino)-1-methyl-6-nitroquinolin-2(1H)-one |

TABLE 22-continued compounds prepared by a method analogous to that used for the preparation of Intermediate A12a.

| Name | Structure | Characterisation | Starting material (nitro) |
|---|---|---|---|
| Intermediate A12c: 6-amino-4-(((1-(2-methoxyethoxy)propan-2-yl)amino)-1-methylquinolin-2(1H)-one | | LCMS (Method T2), Rt = 0.87 mins, m/z 306.2 (M + H)+. | Intermediate B9g: 4-((1-(2-methoxyethoxy)propan-2-yl)amino)-1-methyl-6-nitroquinolin-2(1H)-one |

Intermediates A13a and A13b represent a pair of diastereoisomers where one is cis and one is trans across the cyclobutane ring. The compounds can be clearly distinguished from one another by NMR, but it has not been unambiguously determined which is the cis and which is the trans structure. Both compounds are racemic.

Intermediate A13a: rac-6-amino-4-(((1R,2S)-2-methoxycyclobutyl)amino)-1-methylquinolin-2(1H)-one or rac-6-amino-4-(((1R,2R)-2-methoxycyclobutyl)amino)-1-methylquinolin-2(1H)-one

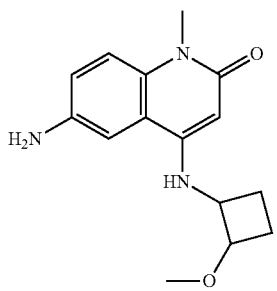 [SMILES: COC1CCC1Nc1cc(=O)n(C)c2ccc(N)cc12]

Prepared by a method analogous to that used for Intermediate A1a, starting from Intermediate B22a: rac-4-(((1R,2S)-2-methoxycyclobutyl)amino)-1-methyl-6-nitroquinolin-2(1H)-one or rac-4-(((1R,2R)-2-methoxycyclobutyl)amino)-1-methyl-6-nitroquinolin-2(1H)-one. $^1$H NMR (500 MHz, Chloroform-d) δ 7.19 (d, J=8.9 Hz, 1H), 6.97 (dd, J=8.9, 2.5 Hz, 1H), 6.81 (d, J=2.5 Hz, 1H), 5.82 (s, 1H), 4.79 (d, J=6.1 Hz, 1H), 3.93-3.83 (m, 1H), 3.83-3.75 (m, 1H), 3.62 (s, 3H), 3.34 (s, 3H), 2.44-2.31 (m, 1H), 2.20 (dddd, J=11.7, 8.3, 6.5, 1.6 Hz, 1H), 1.70 (tdd, J=10.9, 9.4, 8.2 Hz, 1H), 1.44-1.30 (m, 1H). LCMS (Method X2) Rt=0.73 min, m/z 274 [M+H]+.

Intermediate A13b: rac-6-amino-4-(((1R,2S)-2-methoxycyclobutyl)amino)-1-methylquinolin-2(1H)-one or rac-6-amino-4-(((1R,2R)-2-methoxycyclobutyl)amino)-1-methylquinolin-2(1H)-one

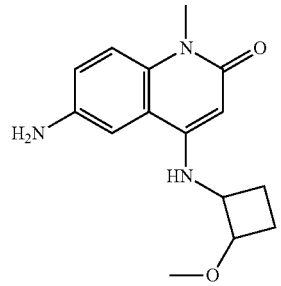 [SMILES: COC1CCC1Nc1cc(=O)n(C)c2ccc(N)cc12]

Prepared by a method analogous to that used for Intermediate A1a, starting from Intermediate B22b: rac-4-(((1R,2S)-2-methoxycyclobutyl)amino)-1-methyl-6-nitroquinolin-2(1H)-one or rac-4-(((1R,2R)-2-methoxycyclobutyl)amino)-1-methyl-6-nitroquinolin-2(1H)-one. $^1$H NMR (500 MHz, Methano-d4) δ 7.35 (d, J=9.7 Hz, 1H), 7.16-7.04 (m, 2H), 5.51 (s, 1H), 4.28-4.21 (m, 1H), 4.21-4.13 (m, 1H), 3.61 (s, 3H), 3.36 (s, 3H), 2.28-2.15 (m, 2H), 2.16-1.99 (m, 2H). LCMS (Method T2) Rt=0.84 min, m/z 274 [M+H]+.

Intermediate B1a; 1-Methyl-4-[(1-methyl-1-pyrimidin-2-yl-ethyl)amino]-6-nitro-quinolin-2-one

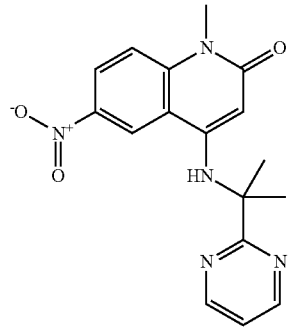

A mixture of 4-chloro-1-methyl-6-nitro-quinolin-2-one (Intermediate D1, 60.0 mg, 0.251 mmol), 2-pyrimidin-2- ylpropan-2-amine dihydrochloride (79.2 mg, 0.378 mmol), cesium carbonate (492 mg, 1.51 mmol), rac-BINAP (31.3 mg, 0.050 mmol) and palladium(II) acetate (11.3 mg, 0.050 mmol) in toluene (1.26 mL) in a sealed vessel was purged with argon then heated in a microwave at 120° C. for 3 h. LCMS (Method T2) Rt=1.30 mins, m/z 340.14 [M+H]+. Once cooled, the mixture was diluted with water and extracted twice with EtOAc. The organic extract was washed with brine then dried over MgSO$_4$. The residue was purified using a reverse-phase C18 column eluting from 20-100% methanol in water (both containing 0.1% formic acid) to give 1-methyl-4-[(1-methyl-1-pyrimidin-2-yl-ethyl)amino]-6-nitro-quinolin-2-one (21 mg) as a brown solid. $^1$H NMR (500 MHz, Chloroform-d) δ 8.81 (d, J=4.9 Hz, 2H), 8.73 (d, J=2.5 Hz, 1H), 8.38 (dd, J=9.4, 2.5 Hz, 1H), 7.39 (d, J=9.4 Hz, 1H), 7.25 (t, J=4.9 Hz, 2H), 6.92 (s, 1H), 5.65 (s, 1H), 3.65 (s, 3H), 1.89 (s, 6H).

The following intermediates in Table 23 were prepared by a method analogous to that used for the preparation of Intermediate B1a, starting from the appropriate amine and chloroquinolinone as shown.

TABLE 23 compounds prepared by a method analogous to that used for the preparation of Intermediate B1a.

| Intermediate | Structure | Data | Starting materials |
| --- | --- | --- | --- |
| Intermediate B1b: 1-methyl-6-nitro-4-(1-pyrimidin-2-ylethylamino)quinolin-2-one | 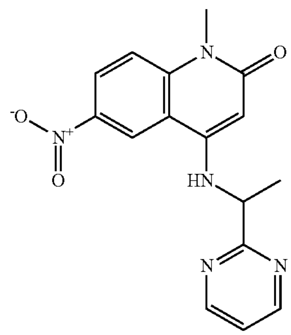 | LCMS (Method X2) Rt = 1.11 mins, m/z 326.13 [M + H]+. | 1-pyrimidin-2-ylethanamine and 4-chloro-1-methyl-6-nitro-quinolin-2-one (intermediate D1) |
| Intermediate B1c: 1-[2-[6-nitro-2-oxo-4-(1-pyrimidin-2-ylethylamino)-1-quinolyl]ethyl]pyrrolidine-2,5-dione | 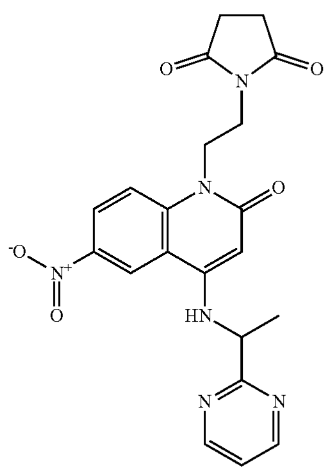 | LCMS (Method T2) Rt = 1.20 mins, m/z 437.16 [M + H]+. | 1-pyrimidin-2-ylethanamine and 1-[2-(4-chloro-6-nitro-2-oxo-1-quinolyl)ethyl]pyrrolidine-2,5-dione (Intermediate D5). |
| Intermediate B1d: 6-nitro-4-(1-pyrimidin-2-ylethylamino)-1-(tetrahydropyran-4-ylmethyl)quinolin-2-one | 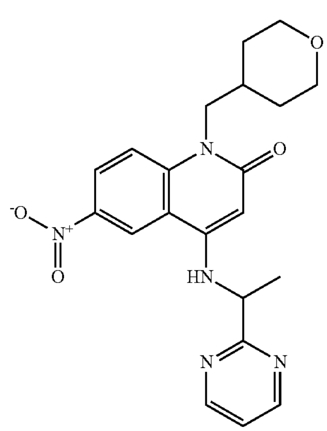 | LCMS (Method T2) Rt = 1.34 mins, m/z 410.18 [M + H]+. | 1-pyrimidin-2-ylethanamine and 4-chloro-6-nitro-1-(tetrahydropyran-4-ylmethyl)quinolin-2-one (Intermediate D4). |

TABLE 23-continued compounds prepared by a method analogous to that used for the preparation of Intermediate B1a.

| Intermediate | Structure | Data | Starting materials |
|---|---|---|---|
| Intermediate B1e: 1-methyl-4-[1-(1-methylimidazol-2-yl)ethylamino]-6-nitro-quinolin-2-one | 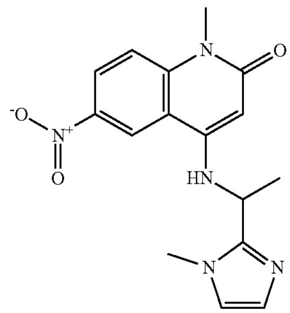 | LCMS (Method T2) Rt = 0.67 mins, m/z 328.14 [M + H]$^+$. | 1-(1-methylimidazol-2-yl)ethanamine and 4-chloro-1-methyl-6-nitro-quinolin-2-one (Intermediate D1) |
| Intermediate B1f: 1-methyl-6-nitro-4-(1-pyrimidin-4-ylethylamino) quinolin-2-one | 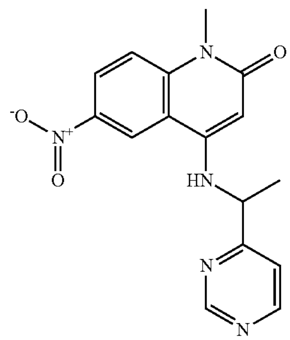 | LCMS (Method T2) Rt = 1.22 mins, m/z 326.13 [M + H]$^+$. | 1-pyrimidin-4-ylethanamine dihydrochloride and 4-chloro-1-methyl-6-nitro-quinolin-2-one (Intermediate D1) |
| Intermediate B1g: 1-methyl-6-nitro-4-(1-thiazol-2-ylethylamino) quinolin-2-one | 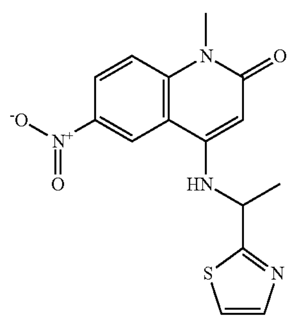 | LCMS (Method T2) Rt = 1.30 mins, m/z 331.09 [M + H]$^+$. | 1-thiazol-2-ylethanamine hydrochloride and 4-chloro-1-methyl-6-nitro-quinolin-2-one (Intermediate D1) |
| Intermediate B1h 1-methyl-4-[(1-methylcyclopentyl)amino]-6-nitro-quinolin-2-one | 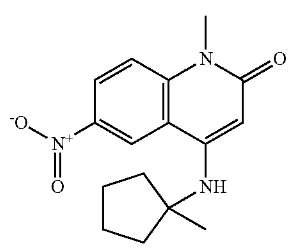 | LCMS (Method T2), Rt = 1.48 mins, m/z 302.1485 (M + H)$^+$. | 1-methylcyclopentanamine hydrochloride and 4-chloro-1-methyl-6-nitro-quinolin-2-one (Intermediate D1) |
| Intermediate B1i: 1-methyl-4-[1-(4-methylpyrimidin-2-yl)ethylamino]-6-nitro-quinolin-2-one | 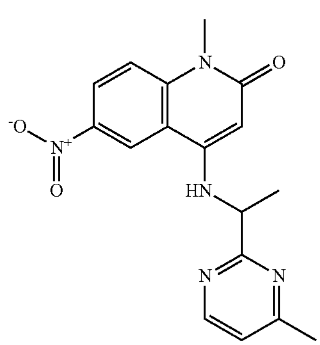 | LCMS (Method T2) Rt = 1.30 mins, m/z 340.14 [M + H]$^+$. | 1-(4-methylpyrimidin-2-yl)ethanamine dihydrochloride and 4-chloro-1-methyl-6-nitro-quinolin-2-one (Intermediate D1) |

TABLE 23-continued compounds prepared by a method analogous to that used for the preparation of Intermediate B1a.

| Intermediate | Structure | Data | Starting materials |
| --- | --- | --- | --- |
| Intermediate B1j:<br>1-methyl-6-nitro-4-<br>(1-pyrazin-2-<br>ylethylamino)<br>quinolin-2-one | | LCMS (Method T2)<br>Rt = 1.24 mins, m/z<br>326.12 [M + H]$^+$ | 1-pyrazin-2-<br>ylethanamine and 4-<br>chloro-1-methyl-6-nitro-<br>quinolin-2-one<br>(Intermediate D1) |
| Intermediate B1k:<br>1-(cyclopropyl-<br>methyl)-6-nitro-4-<br>((1-(pyrimidin-2-<br>yl)ethyl)amino)<br>quinolin-2(1H)-one | | LCMS (Method T2)<br>Rt = 1.42 min, m/z<br>366 [M + H]+. | 1-pyrimidin-2-<br>ylethanamine and 4-<br>chloro-1-<br>(cyclopropylmethyl)-6-<br>nitro-quinolin-2-one<br>(Intermediate D11) |
| Intermediate B1l:<br>1-(2-((tert-<br>butyldimethylsilyl)<br>oxy)ethyl)-6-nitro-<br>4-((1-(pyrimidin-2-<br>yl)ethyl)amino)<br>quinolin-2(1H)-one | | LCMS (Method T2)<br>Rt = 1.61 mins, m/z<br>470 [M + H]$^+$. | Intermediate D12: 1-(2-<br>((tert-<br>butyldimethylsilyl)oxy)<br>ethyl)-4-chloro-6-<br>nitroquinolin-2(1H)-one |

Intermediate B2a; 1-Methyl-6-nitro-4-[7,2,4-triazol-5-yl)ethylamino]quinolin-2-one

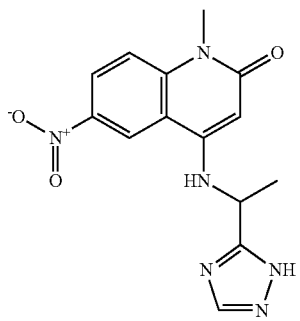

A mixture of ethyl 4-chloro-1-methyl-6-nitro-2-oxo-quinoline-3-carboxylate (Intermediate D2, 50 mg, 0.16 mmol), 1-(1H-1,2,4-triazol-5-yl)ethanamine hydrochloride (48 mg, 0.32 mmol), DIPEA (84 µL, 0.48 mmol, 3 equiv.) and NMP (1.61 mL) in a sealed vessel was heated in a microwave at 160° C. for 1 h. LCMS (Method T2) Rt=1.24 mins, m/z 387.14 [M+H]$^+$. Lithium chloride was added the mixture, the vessel was resealed and heated in a drysyn heating block at 160° C. for 2.5 h. LCMS (Method T2) Rt=1.15 mins, m/z 315.12 [M+H]$^+$. Once cooled, DMSO (0.4 mL) was added to the sample which was purified using reverse-phase C18 column eluting from 10-100% methanol in water (containing 0.1% formic acid) to give 1-methyl-6-nitro-4-[1-(1H-1,2,4-triazol-5-yl)ethylamino]quinolin-2-one (30 mg) as a brown solid. $^1$H NMR (500 MHz, DMSO-d$_6$) δ 13.84 (br. s, 1H), 9.25 (d, J=2.5 Hz, 1H), 8.37 (dd, J=9.3, 2.5 Hz, 1H), 8.30 (br. s, 1H), 7.76 (d, J=6.9 Hz, 1H), 7.59 (d, J=9.3 Hz, 1H), 5.55 (s, 1H), 4.86 (br. s, 1H), 3.51 (s, 3H), 1.65 (d, J=6.9 Hz, 3H).

The following intermediates in Table 24 were prepared by a method analogous to that used for the preparation of Intermediate B2a, starting from the appropriate amine and chloroquinolinone as shown.

TABLE 24 compounds prepared by a method analogous to that used for the preparation of Intermediate B2a

| Intermediate | Structure | Data | Starting materials |
|---|---|---|---|
| Intermediate B2b: 1-methyl-4-[1-(5-methyl-1,2,4-oxadiazol-3-yl)ethylamino]-6-nitro-quinolin-2-one | 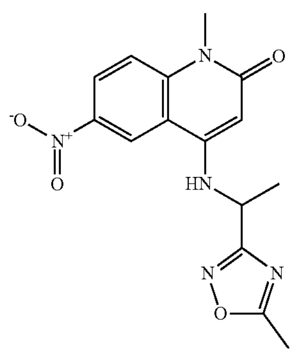 | LCMS (Method T2) Rt = 1.25 mins, m/z 330.12 [M + H]+. $^1$H NMR (500 MHz, Chloroform-d) δ 8.57 (d, J = 2.5 Hz, 1H), 8.39 (dd, J = 9.4, 2.5 Hz, 1H), 7.40 (d, J = 9.4 Hz, 1H), 5.85 (s, 1H), 5.41 (d, J = 7.4 Hz, 1H), 4.91 (app. quin., J = 6.9 Hz, 1H), 3.67 (s, 3H), 2.60 (s, 3H), 1.76 (d, J = 6.8 Hz, 3H). | 1-(5-methyl-1,2,4-oxadiazol-3-yl)ethanamine hydrochloride. |
| Intermediate B2c: 1-methyl-4-[(1-methylcyclopropyl)amino]-6-nitro-quinolin-2-one | 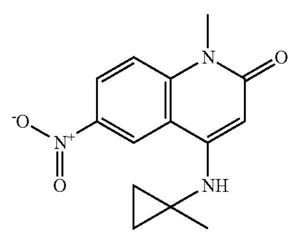 | LCMS (Method T2) Rt = 1.34 mins, m/z 274.12 [M + H]+. $^1$H NMR (500 MHz, Chloroform-d) δ 8.46 (d, J = 2.5 Hz, 1H), 8.37 (dd, J = 9.3, 2.5 Hz, 1H), 7.40 (d, J = 9.3 Hz, 1H), 6.19 (s, 1H), 5.51 (s, 1H), 3.70 (s, 3H), 1.45 (s, 3H), 0.97 - 0.85 (m, 2H), 0.88 - 0.77 (m, 2H). | 1-methylcyclopropan amine (3 equiv.). |
| Intermediate B2d: 1-methyl-4-[1-(5-methylisoxazol-3-yl)ethylamino]-6-nitro-quinolin-2-one | 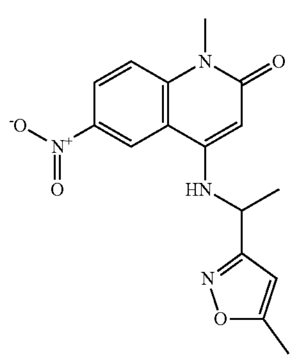 | LCMS (Method T2) Rt = 1.31 mins, m/z 329.13 [M + H]+. $^1$H NMR (500 MHz, Chloroform-d) δ 8.56 (d, J = 2.5 Hz, 1H), 8.39 (dd, J = 9.3, 2.5 Hz, 1H), 7.40 (d, J = 9.3 Hz, 1H), 5.96 (br. q, J = 0.8 Hz, 1H), 5.82 (s, 1H), 5.44 (br. d, J = 6.5 Hz, 1H), 4.81 (app. quin., J = 6.8 Hz, 1H), 3.67 (s, 3H), 2.42 (d, J = 0.8 Hz, 3H), 1.71 (d, J = 6.8 Hz, 3H). | 1-(5-methylisoxazol-3-yl)ethanamine hydrochloride |

TABLE 24-continued compounds prepared by a method analogous to that used for the preparation of Intermediate B2a

| Intermediate | Structure | Data | Starting materials |
|---|---|---|---|
| Intermediate B2e: 1-methyl-6-nitro-4-[1-(1H-pyrazol-5-yl)ethylamino]quinolin-2-one | 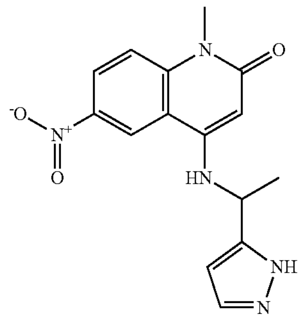 | LCMS (Method T2) Rt = 1.25 mins, m/z 314.12 [M + H]+. $^1$H NMR (500 MHz, DMSO-$d_6$) δ 9.20 (d, J = 2.5 Hz, 1H), 8.36 (dd, J = 9.3, 2.5 Hz, 1H), 7.61-7.53 (m, 3H), 6.17 (d, J = 2.1 Hz, 1H), 5.57 (s, 1H), 4.75 (app. quin., J = 6.8 Hz, 1H), 3.51 (s, 3H), 1.60 (d, J = 6.8 Hz, 3H). | 1-(1H-pyrazol-5-yl)ethanamine dihydrochloride, |
| Intermediate B2f: trans-4-[(3-hydroxy-cyclobutyl)amino]-1-methyl-6-nitro-quinolin-2-one | 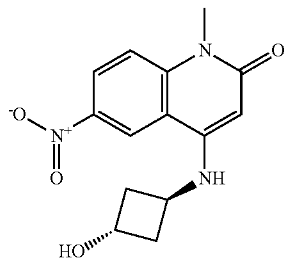 | LCMS (Method T2) Rt = 1.20 mins, m/z 290.11 [M + H]. $^1$H NMR (500 MHz, DMSO-$d_6$) δ 9.13 (d, J = 2.5 Hz, 1H), 8.36 (dd, J = 9.4, 2.5 Hz, 1H), 7.59 (d, J = 9.4 Hz, 1H), 7.49 (d, J = 4.8 Hz, 1H), 5.25 (s, 1H), 5.14 (br. s, 1H), 4.36 (app. quin., J = 6.4 Hz, 1H), 3.98-3.88 (m, 1H), 3.54 (s, 3H), 2.43-2.35 (m, 2H), 2.29-2.19 (m, 2H). | trans-3-aminocyclobutanol hydrochloride |

Intermediate B3a; 4-[(3-Hydroxy-1-methyl-propyl)amino]-1-methyl-6-nitro-quinazolin-2-one

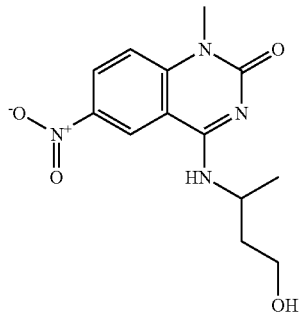

Step 1; 4-[(3-hydroxy-1-methyl-propyl)amino]-6-nitro-1H-quinazolin-2-one

A mixture of 2,4-dichloro-6-nitro-quinazoline (80 mg, 0.33 mmol), THF (3.3 mL), 3-aminobutan-1-ol (35 mg, 0.39 mmol) and DIPEA (0.14 mL, 0.82 mmol) was stirred at RT for 1 h. LCMS (Method T2) Rt=1.18 mins, m/z 297.08 [M+H]$^+$. Acetic acid (4 mL) was added directly to the mixture which was stirred at 70° C. for 16 h. LCMS (Method T2) Rt=0.85 mins, m/z 279.08 [M+H]$^+$. The solution was concentrated and the residue was taken up in methanol (5 mL). The solution was then purified using SCX-2 cartridge. The product was eluted with methanolic ammonia, affording 4-[(3-hydroxy-1-methyl-propyl)amino]-6-nitro-1H-quinazolin-2-one (50 mg).

Step 2; 4-[(3-hydroxy-1-methyl-propyl)amino]-1-methyl-6-nitro-quinazolin-2-one

Sodium hydride (60% in mineral oil) (3.32 mg, 0.083 mmol) was added to a solution containing 4-[(3-hydroxy-1-methyl-propyl)amino]-6-nitro-1H-quinazolin-2-one (21 mg, 0.076 mmol) in DMF (0.75 mL). The mixture was stirred at RT for 10 mins then iodomethane (5 μL, 0.08 mmol) was added. The mixture was stirred at rt for 1 hour. LCMS (Method T2) Rt=1.07 mins, m/z 293.12 [M+H]$^+$. Water was added to the mixture then passed through SCX-2 cartridge. The product was eluted with methanolic ammonia, affording 4-[(3-hydroxy-1-methyl-propyl)amino]-1-methyl-6-nitro-quinazolin-2-one (22 mg) as a yellow solid. $^1$H NMR (500 MHz, Chloroform-d) δ 8.89 (d, J=2.4 Hz, 1H), 8.42 (dd, J=9.4, 2.4 Hz, 1H), 7.97 (d, J=7.8 Hz, 1H), 7.29 (d, J=9.4 Hz, 1H), 4.70-4.57 (m, 1H), 4.27 (s, 1H), 3.76-3.67 (m, 2H), 3.65 (s, 3H), 2.01-1.91 (m, 1H), 1.78-1.68 (m, 1H), 1.35 (d, J=6.7 Hz, 3H).

Intermediate B3b; 4-[(2-Hydroxy-1-methyl-ethyl)amino]-1-methyl-6-nitro-quinazolin-2-one

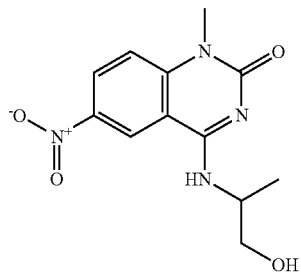

Prepared by a two-step process analogous to that used for the preparation of intermediate B3a, starting from 2-aminopropan-1-ol. LCMS (Method T2) Rt=1.02 mins, m/z 279.11 [M+H]$^+$. $^1$H NMR (500 MHz, Chloroform-d) δ 8.90 (d, J=2.4 Hz, 1H), 8.44 (dd, J=9.3, 2.4 Hz, 1H), 8.03 (s, 1H), 7.59 (d, J=7.5 Hz, 1H), 7.31 (d, J=9.3 Hz, 1H), 4.68-4.54 (m, 1H), 3.81 (dd, J=11.5, 4.0 Hz, 1H), 3.73 (dd, J=11.5, 6.3 Hz, 1H), 3.69 (s, 3H), 1.30 (d, J=6.7 Hz, 3H).

Intermediate B3c;
4-(Ethylamino)-1-methyl-6-nitro-quinazolin-2-one

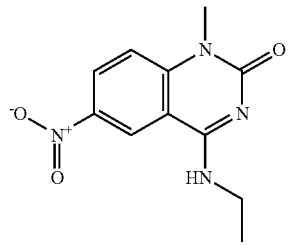

Prepared by a two-step process analogous to that used for the preparation of intermediate B3a, starting from ethylamine (2.0M in THF). LCMS (Method T2) Rt=1.05 mins, m/z 249.10 [M+H]$^+$. $^1$H NMR (500 MHz, DMSO-d$_6$) δ 9.10 (d, J=2.5 Hz, 1H), 8.86-8.79 (m, 1H, N/7), 8.43 (dd, J=9.4, 2.5 Hz, 1H), 7.50 (d, J=9.4 Hz, 1H), 3.51-3.43 (m, 5H), 1.20 (t, J=7.3 Hz, 3H).

Intermediate B4a; (R)—N-Methyl-2-((6-nitro-2-oxo-1,2-dihydroquinolin-4-yl)amino)propanamide

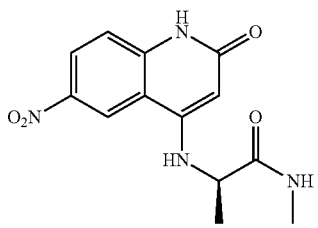 [SMILES: CNC(=O)[C@@H](C)Nc1cc(=O)[nH]c2ccc([N+](=O)[O-])cc12]

A suspension of 4-chloro-6-nitro-1H-quinolin-2-one (Intermediate D3, 70 mg, 0.31 mmol), (2R)-2-amino-N-methyl-propanamide hydrochloride (78 mg, 0.56 mmol), DMAP (19 mg, 0.16 mmol) and triethylamine (0.13 mL, 0.94 mmol) in NMP (1.5 mL) was stirred at 160° C. under microwave irradiation for 16 h. HPLC purification gave the title compound (9 mg, 10%) as a yellow solid. LCMS (Method T2) Rt=1.00 mins, m/z 291.1 [M+H]$^+$.

Intermediate B4b; 4-[[(1S)-3-Hydroxy-1-methylpropyl]amino]-1-methyl-6-nitro-quinolin-2-one

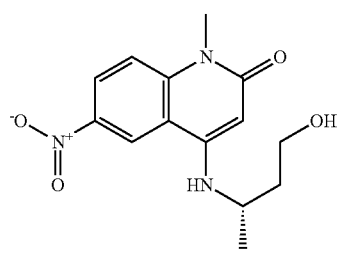

Prepared by a method analogous to that used for the preparation of example B4a, starting from Intermediate D1 4-chloro-1-methyl-6-nitro-quinolin-2-one and (3S)-3-aminobutan-1-ol. The microwave irradiation was stirred at 200° C. for 1 h. LCMS (Method T2) Rt=1.21 mins, m/z 292.1 [M+H]$^+$.

Intermediate B4c; (2R)—N-Methyl-2-[(1-methyl-6-nitro-2-oxo-4-quinolyl)amino]propanamide

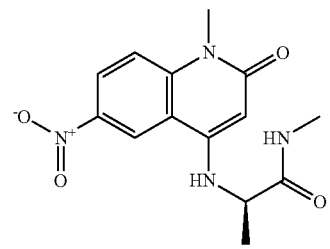

Prepared by a method analogous to that used for the preparation of example B4a, starting from Intermediate D1 4-chloro-1-methyl-6-nitro-quinolin-2-one and (2R)-2-amino-N-methyl-propanamide hydrochloride. LCMS (Method T2) Rt=1.11 mins, m/z 305.1 [M+H]$^+$.

Intermediate B4d; 4-[[(1R)-2-Hydroxy-1-methylethyl]amino]-1-methyl-6-nitro-quinolin-2-one

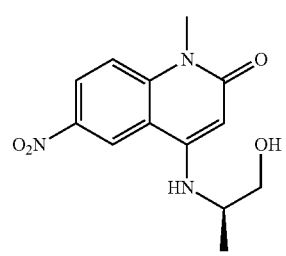 [SMILES: C[C@H](CO)Nc1cc(=O)n(C)c2ccc([N+](=O)[O-])cc12]

Prepared by a method analogous to that used for the preparation of example B4a, starting from Intermediate D1 4-chloro-1-methyl-6-nitro-quinolin-2-one and (2R)-2-aminopropan-1-ol. The microwave irradiation was stirred at 200° C. for 1 h. LCMS (Method T2) Rt=1.18 mins, m/z 278.1 [M+H]$^+$.

Intermediate B5; 1-Methyl-6-nitro-4-[[(3S)-tetrahydrofuran-3-yl]amino]quinolin-2-one

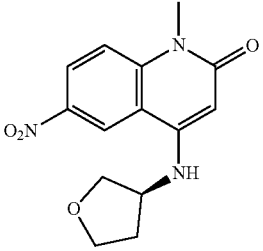

To a mixture of 4-chloro-1-methyl-6-nitro-quinolin-2-one (Intermediate D1, 58 mg, 0.24 mmol) and (3S)-tetrahydrofuran-3-amine hydrochloride (62 mg, 0.50 mmol) in NMP (1 mL) under argon was added DIPEA (0.21 mL, 1.2 mmol). The reaction mixture was heated at 160° C. under microwave irradiation for 1 h, followed by 200° C. under microwave irradiation for a further 1 h. The reaction mixture was allowed to cool to rt. Water (5 mL) was added and the resulting suspension was stirred for 5 min. The precipitate was filtered and washed with water (10 mL). The filtrate was passed through an SCX-2 cartridge (2 g), eluting with methanol (20 mL) followed by 2N methanolic ammonia (20 mL). The methanolic ammonia fraction was concentrated in vacuo affording 1-methyl-6-nitro-4-[[(3S)-tetrahydrofuran-3-yl]amino]quinolin-2-one (14 mg, 19%) as a red solid which was used without further purification. LCMS (Method T2); Rt 1.21 min; m/z 290.1127 [M+H]$^+$.

Intermediate B6a; 4-(1-Cyclopropylethylamino)-1-methyl-6-nitro-quinolin-2-one

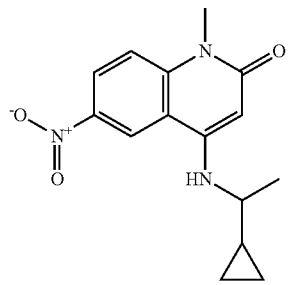

A mixture of 4-chloro-1-methyl-6-nitro-quinolin-2-one (Intermediate D1, 60.0 mg, 0.251 mmol), 1-cyclopropylethanamine (107 mg, 1.26 mmol) and DIPEA (87.6 uL, 0.503 mmol) in NMP (2.5 mL) was stirred at 160° C. for 18 h. Further portion of 1-cyclopropylethylamine (107 mg, 1.26 mmol) was added and heating continued at 160° C. for 3 h. LCMS (Method T2) Rt=1.40 mins, m/z 288.13 [M+H]$^+$. Once cooled, water was added then the mixture was extracted with ethyl acetate. The organic extracts were washed with water and brine then dried over MgSO$_4$, filtered and concentrated in vacuo. The residue was purified by Biotage KP-Sil 10 g column eluting 50-100% EtOAc in cyclohexane affording 4-(1-cyclopropylethylamino)-1-methyl-6-nitro-quinolin-2-one (13 mg) as a dark yellow solid. $^1$H NMR (500 MHz, Chloroform-d) δ 8.52 (d, J=2.5 Hz, 1H), 8.38 (dd, J=9.3, 2.5 Hz, 1H), 7.40 (d, J=9.3 Hz, 1H), 5.74 (s, 1H), 4.97 (d, J=6.4 Hz, 1H), 3.68 (s, 3H), 3.09-3.01 (m, 1H), 1.34 (d, J=6.3 Hz, 3H), 1.10 (app. qt, J=8.1, 5.0 Hz, 1H), 0.70-0.56 (m, 2H), 0.37-0.33 (m, 2H).

Intermediate B6b; 4-(Cyclopropylamino)-1-methyl-6-nitro-quinolin-2-one

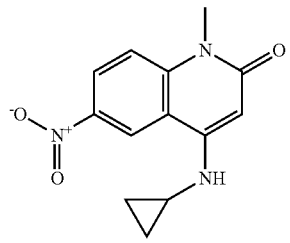

A mixture of 4-chloro-1-methyl-6-nitro-quinolin-2-one (Intermediate D1, 60 mg, 0.25 mmol) and cyclopropylamine (88 μL, 1.27 mmol) and DIPEA (88 μL, 0.50 mmol) in NMP (1.9 mL) was stirred at 160° C. for 2 h in microwave. LCMS (Method T2) Rt=1.30 mins, m/z 260.10 [M+H]$^+$. Mixture then purified directly using reverse-phase C18 column eluting from 10-100% methanol in water (containing 0.1% formic acid) to give 4-(cyclopropylamino)-1-methyl-6-nitro-quinolin-2-one (37 mg) as a brown solid. $^1$H NMR (500 MHz, DMSO-d$_6$) δ 9.01 (d, J=2.6 Hz, 1H), 8.36 (dd, J=9.4, 2.6 Hz, 1H), 7.75 (d, J=2.0 Hz, 1H), 7.61 (d, J=9.4 Hz, 1H), 5.87 (s, 1H), 3.56 (s, 3H), 2.52-2.47 (m, 1H), 0.85-0.80 (m, 2H), 0.62-0.57 (m, 2H).

Intermediate B7a; (2R)-2-[(1-Methyl-6-nitro-2-oxo-4-quinolyl)amino]-N-[(1-methylpyrazol-4-yl)methyl]propanamide

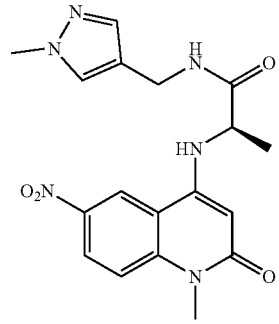 [SMILES: C[C@@H](Nc1cc(=O)n(C)c2ccc([N+](=O)[O-])cc12)C(=O)NCc1cnn(C)c1]

A suspension of ethyl 4-chloro-1-methyl-6-nitro-2-oxo-quinoline-3-carboxylate (Intermediate D2, 55 mg, 0.18 mmol), (2R)-2-amino-N-[(1-methylpyrazol-4-yl)methyl]propanamide (Intermediate C1b, 38 mg, 0.21 mmol) and DIPEA (0.07 mL, 0.42 mmol) in NMP (1.5 mL) was stirred at 160° C. under microwave irradiation for 1 h. Lithium chloride (52.8 mg, 1.25 mmol) was added and the resulting mixture stirred under microwave irradiation at 160° C. for 1 h. Purification by HPLC gave the title compound as a light brown solid (12 mg). LCMS (Method T2) Rt=1.16 mins, m/z 385.2 [M+H]$^+$.

The following intermediates in Table 25 were prepared by a method analogous to that used for the preparation of Intermediate B7a, using the amine starting material shown. Extended microwave irradiation times were required after the addition of lithium chloride were required for intermediates B7b, B7c, B7f and B7h: second microwave irradiation for 6 h. Starting amines for B7c, B7h, B7j and B7k were obtained from commercial suppliers.

TABLE 25 compounds prepared by a method analogous to that used for the preparation of Intermediate B7a.

| Name | Structure | Characterisation | Starting material (nitro) |
| --- | --- | --- | --- |
| Intermediate B7b: (2R)-N-(2-hydroxyethyl)-2-[(1-methyl-6-nitro-2-oxo-4-quinolyl)amino]propanamide | 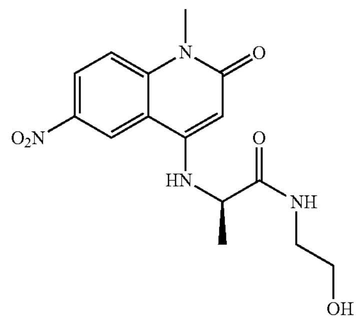 [SMILES: C[C@@H](Nc1cc(=O)n(C)c2ccc([N+](=O)[O-])cc12)C(=O)NCCO] | LCMS (Method T2), Rt = 1.09 mins, m/z 335.1 [M + H]+ | Intermediate C1a: (2R)-2-amino-N-(2-hydroxyethyl)propanamide |
| Intermediate B7c: 1-Methyl-4-((1-(3-methyl-1H-1,2,4-triazol-5-yl)ethyl)amino)-6-nitroquinolin-2(1H)-one | 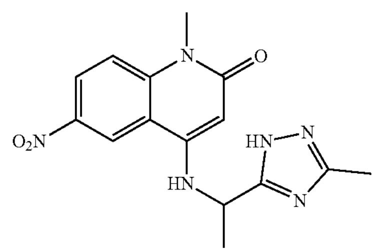 [SMILES: Cc1n[nH]c(C(C)Nc2cc(=O)n(C)c3ccc([N+](=O)[O-])cc23)n1] | LCMS (Method T2), Rt = 1.16 mins, m/z 329.1 [M + H]+ | 1-(3-methyl-1H-1,2,4-triazol-5-yl)ethanamine hydrochloride |
| Intermediate B7d: (R)-N-cyclopentyl-2-((1-methyl-6-nitro-2-oxo-1,2-dihydroquinolin-4-yl)amino)propanamide | 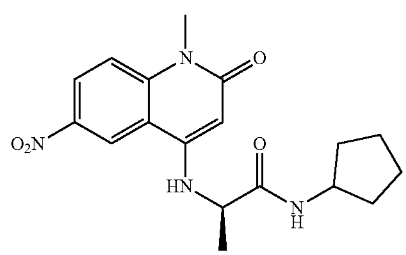 [SMILES: C[C@@H](Nc1cc(=O)n(C)c2ccc([N+](=O)[O-])cc12)C(=O)NC1CCCC1] | LCMS (Method T2), Rt = 1.36 mins, m/z 359.2 [M + H]+ | Intermediate C1d: (2R)-2-amino-N-cyclopentyl-propanamide |
| Intermediate B7e: (R)-N-(2-methoxyethyl)-2-((1-methyl-6-nitro-2-oxo-1,2-dihydroquinolin-4-yl)amino)propanamide | 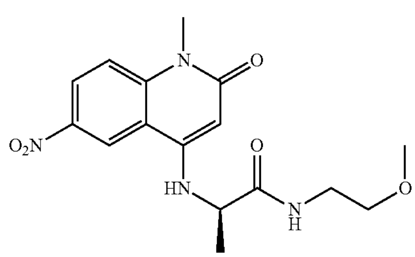 [SMILES: COCCNC(=O)[C@@H](C)Nc1cc(=O)n(C)c2ccc([N+](=O)[O-])cc12] | LCMS (Method T2), Rt = 1.18 mins, m/z 349.2 [M + H]+ | Intermediate C1e: (2R)-2-amino-N-(2-methoxyethyl)propanamide |
| Intermediate B7f: (R)-N-(but-3-yn-1-yl)-2-((1-methyl-6-nitro-2-oxo-1,2-dihydroquinolin-4-yl)amino-propanamide | 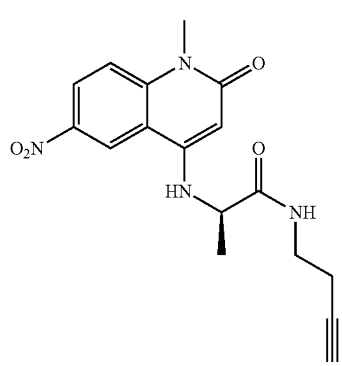 [SMILES: C#CCCNC(=O)[C@@H](C)Nc1cc(=O)n(C)c2ccc([N+](=O)[O-])cc12] | LCMS (Method T2), Rt = 1.20 mins, m/z 343.1 [M + H]+ | Intermediate C1f: (2R)-2-amino-N-but-3-ynyl-propanamide |

TABLE 25-continued compounds prepared by a method analogous to that used for the preparation of Intermediate B7a.

| Name | Structure | Characterisation | Starting material (nitro) |
|---|---|---|---|
| Intermediate B7g: (2R)-2-[(1-methyl-6-nitro-2-oxo-4-quinolyl)amino]-N-[2-(1-methylpyrazol-4-yl)ethyl]propanamide | 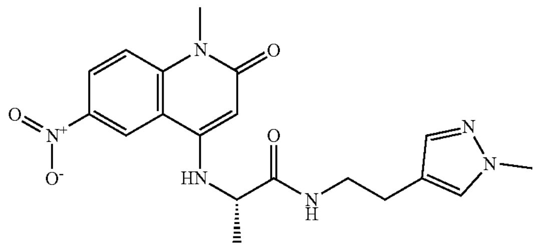 [SMILES: C[C@H](Nc1cc(=O)n(C)c2ccc([N+](=O)[O-])cc12)C(=O)NCCc1cnn(C)c1] | LCMS (Method T2) Rt = 1.19 mins, m/z 399.2 [M + H]$^+$ | Intermediate C1c: (2R)-2-amino-N-[2-(1-methylpyrazol-4-yl)ethyl]propanamide |
| Intermediate B7h: N-ethyl-2-methyl-2-((1-methyl-6-nitro-2-oxo-1,2-dihydroquinolin-4-yl)amino)propanamide | 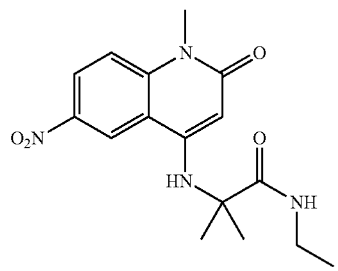 [SMILES: CCNC(=O)C(C)(C)Nc1cc(=O)n(C)c2ccc([N+](=O)[O-])cc12] | LCMS (Method T2), Rt = 1.20 mins, m/z 333.2 [M + H]$^+$ | 2-amino-N-ethyl-2-methyl-propanamide hydrochloride |
| Intermediate B7i: (R)-N-(4-methoxycyclohexyl)-2-((1-methyl-6-nitro-2-oxo-1,2-dihydroquinolin-4-yl)amino)propanamide | 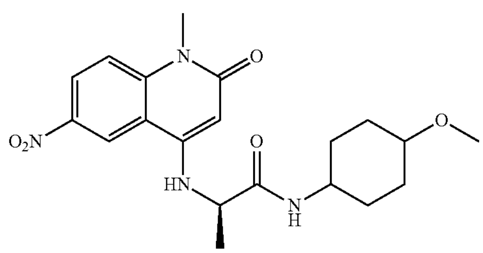 [SMILES: COC1CCC(NC(=O)[C@@H](C)Nc2cc(=O)n(C)c3ccc([N+](=O)[O-])cc23)CC1] | LCMS (Method T2), Rt = 1.30 mins, m/z 403.2 [M + H]$^+$ | Intermediate C1g: (2R)-2-amino-N-(4-methoxycyclohexyl) propanamide |
| Intermediate B7j: 1-methyl-4-((1-(5-methyl-1,3,4-oxadiazol-2-yl)ethyl)amino)-6-nitroquinolin-2(1H)-one | 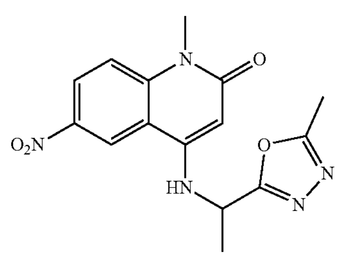 [SMILES: Cc1nnc(C(C)Nc2cc(=O)n(C)c3ccc([N+](=O)[O-])cc23)o1] | LCMS (Method T2) Rt = 1.19 mins, m/z 330.1 [M + H]$^+$ | 1-(5-methyl-1,3,4-oxadiazol-2-yl)ethanamine hydrochloride |
| Intermediate B7k: N-ethyl-2-((1-methyl-6-nitro-2-oxo-1,2-dihydroquinolin-4-yl)amino)-propanamide | 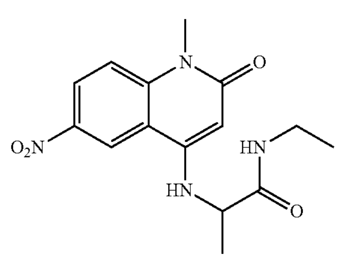 [SMILES: CCNC(=O)C(C)Nc1cc(=O)n(C)c2ccc([N+](=O)[O-])cc12] | LCMS (Method T2), Rt = 1.29 mins, m/z 319.2 [M + H]$^+$ | 2-amino-N-ethyl-propanamide hydrochloride |

TABLE 25-continued compounds prepared by a method analogous to that used for the preparation of Intermediate B7a.

| Name | Structure | Characterisation | Starting material (nitro) |
|---|---|---|---|
| Intermediate B71: 1-methyl-6-nitro-4-((3-(pyrimidin-2-yl)tetrahydrofuran-3-yl)amino)quinolin-2(1H)-one | 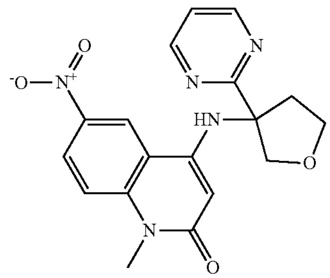 | LCMS (Method T2), Rt = 1.21 min, m/z 368 [M + H]+ | 3-pyrimidin-2-yltetrahydrofuran-3-amine dihydrochloride |

Intermediate B8; 4-[[(1S)-2-Hydroxy-1-methyl-ethyl]amino]-1-methyl-6-nitro-quinolin-2-one

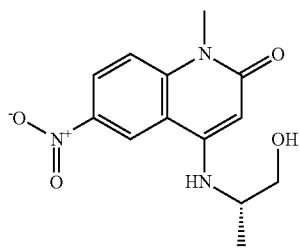

A suspension of 4-chloro-1-methyl-6-nitro-quinolin-2-one (Intermediate D1, 37 mg, 0.1 mmol), DIPEA (0.05 mL, 0.31 mmol) and (2S)-2-aminopropan-1-ol (35 mg, 0.47 mmol) in NMP (1.50 mL) was heated thermally to 160° C. for 14 h, then purified by HPLC and washed with diethyl ether to give the title compound (15.5 mg) as a cream solid. LCMS (Method T2) Rt=1.18 mins, m/z 278.1 [M+H]+.

The following intermediates in Table 26 were prepared by a method analogous to that used for the preparation of Intermediate B7a, using an appropriate amine intermediate and Intermediate D2. For intermediate B9a, temperature of 180° C. was used for the first step. For intermediate B9e and B9f, temperature of 140° C. was used for the first step. For intermediates B9l and B9m, temperature of 120° C. was used for the first step. For intermediate B9j, ethyl 6-bromo-4-chloro-1-methyl-2-oxo-1,8-naphthyridine-3-carboxylate (Intermediate D7) was used instead of Intermediate D2.

TABLE 26 compounds prepared by a method analogous to that used for the preparation of Intermediate B7a.

| Name | Structure | Characterisation |
|---|---|---|
| Intermediate B9a: 2-methyl-N-((1-methyl-1H-pyrazol-4-yl)methyl)-2-((1-methyl-6-nitro-2-oxo-1,2-dihydroquinolin-4-yl)amino)propanamide | 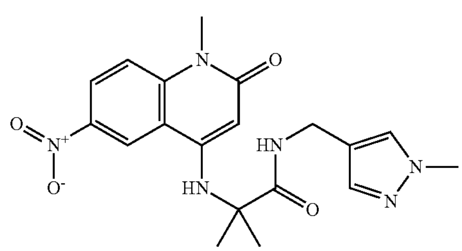 [SMILES: Cn1cc(CNC(=O)C(C)(C)Nc2cc(=O)n(C)c3ccc([N+](=O)[O-])cc23)cn1] | LCMS (Method T2), Rt = 1.19 mins, m/z 399.2 [M + H]+ |
| Intermediate B9b: 1-methyl-6-nitro-4-((2-(pyridin-2-yl)propan-2-yl)amino)quinolin-2(1H)-one | 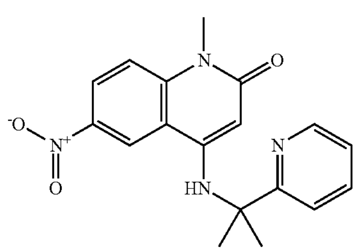 | LCMS (Method T2), Rt = 1.21 mins, m/z 339.1 [M + H]+ |

TABLE 26-continued compounds prepared by a method analogous to that used for the preparation of Intermediate B7a.

| Name | Structure | Characterisation |
| --- | --- | --- |
| Intermediate B9c: 4-[(1-cyclopropyl-2-hydroxy-ethyl)amino]-1-methyl-6-nitro-quinolin-2-one | 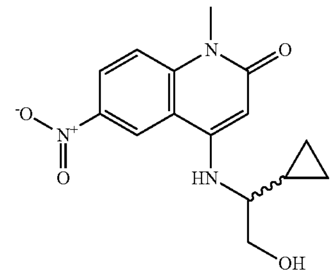 | LCMS (Method T2), Rt = 1.28 mins, m/z 304.1 [M + H]$^+$ |
| Intermediate B9d: 1-methyl-4-[(1-methyl-1-pyrimidin-2-yl-propyl)amino]-6-nitro-quinolin-2-one | 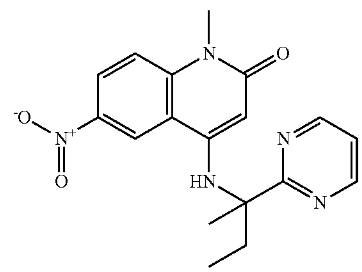 | LCMS (Method T2) RT 1.39 min; m/z 354.1511 [M + H]$^+$; |
| Intermediate B9e: 4-[(2,2-dimethylcyclopropyl)amino]-1-methyl-6-nitro-quinolin-2-one | 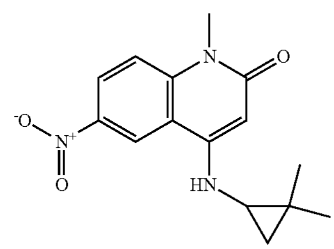 | LCMS (Method T2) RT 1.43 min; m/z 288.1304 [M + H]$^+$; |
| Intermediate B9f: 4-((1-ethynylcyclopropyl)amino)-1-methyl-6-nitroquinolin-2(1H)-one | 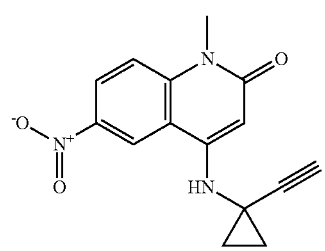 | LCMS (Method T2) RT 1.30 min; m/z 284.1026 [M + H]$^+$; |
| Intermediate B9g: 4-((1-(2-methoxyethoxy)propan-2-yl)amino)-1-methyl-6-nitroquinolin-2(1H)-one | 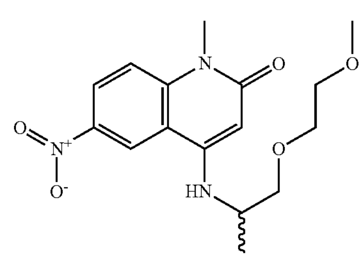 [SMILES: COCCOCC(C)Nc1cc(=O)n(C)c2ccc([N+](=O)[O-])cc12] | LCMS (Method T2), Rt = 1.31 mins, m/z 336.2 [M + H]$^+$ |

TABLE 26-continued compounds prepared by a method analogous to that used for the preparation of Intermediate B7a.

| Name | Characterisation |
|---|---|
| Intermediate B9i: 4-((1-methoxy-2-methylbutan-2-yl)amino)-1-methyl-6-nitroquinolin-2(1H)-one | LCMS (Method T2) Rt = 1.42 min, m/z 320 [M + H]+. |
| Intermediate B9j: 6-bromo-4-[[(1R)-1-cyclopropylethyl]amino]-1-methyl-1,8-naphthyridin-2-one | LCMS (Method T2) Rt = 1.52 min, m/z 322 [M + H]+. |
| Intermediate B9l: 4-((cyclopropyl(pyrimidin-2-yl)methyl)amino)-1-methyl-6-nitroquinolin-2(1H)-one | LCMS (Method T2) Rt = 1.32 mins, m/z 352.14 [M + H]+ |
| Intermediate B9m: 4-((1-(hydroxymethyl)cyclopropyl)amino)-1-methyl-6-nitroquinolin-2(1H)-one | LCMS (Method T2) RT 1.21 min; m/z 290.1079 [M + H]+; |
| Intermediate B9n: rac-4-(((1R,2R)-2-ethylcyclopropyl)amino)-1-methyl-6-nitroquinolin-2(1H)-one | LCMS (Method T2) RT 1.46 min; m/z 288.1337 [M + H]+; |

TABLE 26-continued compounds prepared by a method analogous to that used for the preparation of Intermediate B7a.

| Name | Structure | Characterisation |
| --- | --- | --- |
| Intermediate B9o: (S)-4-((1-cyclopropyl-2-hydroxyethyl)amino)-1-methyl-6-nitroquinolin-2(H)-one | 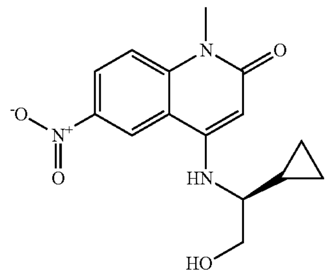 | LCMS (Method T2), Rt = 1.27 mins, m/z 304.1 [M + H]⁺ |
| Intermediate B9p: 1-methyl-4-((1-(1-methyl-1H-1,2,4-triazol-3-yl)ethyl)amino)-6-nitroquinolin-2(1H)-one | 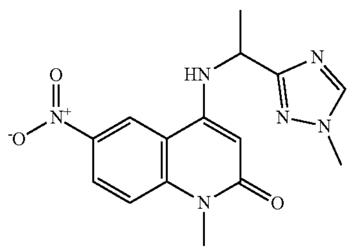 | LCMS (Method T2) Rt = 1.19 mins, m/z 329.13 [M + H]⁺ |
| Intermediate B9q: rac-4-(((1S,2R)-2-methoxycyclopentyl)amino)-1-methyl-6-nitroquinolin-2(1H)-one | 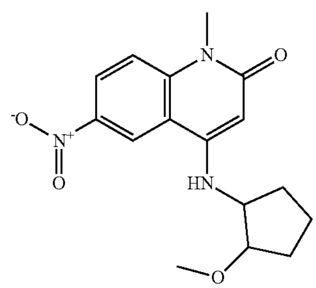 | LCMS (Method T2) Rt = 1.41 min, m/z 318 [M + H]⁺. |

Intermediate B10a: (R)-4-((1-cyclopropylethyl)amino)-1-methyl-6-nitroquinolin-2(1H)-one

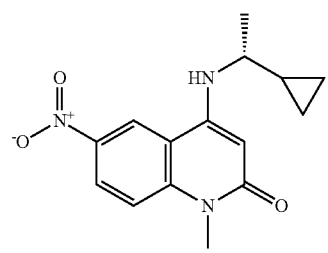

A suspension of ethyl 4-chloro-1-methyl-6-nitro-2-oxoquinoline-3-carboxylate (Intermediate D2, 100 mg, 0.32 mmol), (1R)-1-cyclopropylethanamine (69 uL, 0.64 mmol) and DIPEA (169 uL, 0.97 mmol) in NMP (1.61 mL) was stirred at 120° C. for 1 h in MW. Once cooled to rt, lithium chloride (82 mg, 1.9 mmol) was added to the mixture and heated to 120° C. for 20 h in heating block. The residue was taken up in water and extracted twice with EtOAc. The organic extracts were washed with water and brine then dried over MgSO₄. The residue was purified by Biotage KP-Sil 10 g eluting 0-10% MeOH in DCM affording 4-[[(1R)-1-cyclopropylethyl]amino]-1-methyl-6-nitro-quinolin-2-one (53 mg, 57%, 0.1845 mmol) as a dark yellow solid. LCMS (Method T2) Rt=1.40 mins, m/z 288.13 [M+H]⁺.

Intermediate B10b: (S)-4-((1-cyclopropylethyl)amino)-1-methyl-6-nitroquinolin-2(1H)-one

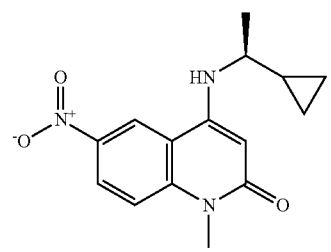

Prepared by a method analogous to that used for the preparation of Intermediate B10a. LCMS (Method T2) Rt=1.40 mins, m/z 288.13 [M+H]⁺.

Intermediate B11r: (R)-1-methyl-6-nitro-4-((1-(pyrimidin-2-yl)ethyl)amino)quinolin-2(1H)-one

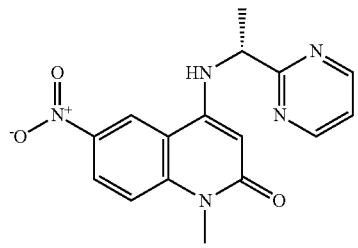

A suspension of ethyl 4-chloro-1-methyl-6-nitro-2-oxo-quinoline-3-carboxylate (Intermediate D2, 50 mg, 0.16 mmol), (1R)-1-(pyrimidin-2-yl)ethan-1-amine (30 mg, 0.24 mmol) and DIPEA (84 uL, 0.48 mmol) in NMP (0.80 mL) was stirred at 80° C. overnight in a heating block. Once cooled to rt, lithium chloride (41 mg, 0.97 mmol) was added to the mixture and heated to 120° C. for 6 h in the microwave. The residue was taken up in water and extracted twice with EtOAc. The organic extracts were washed with water and brine then dried over MgSO$_4$. The residue was purified by Biotage reverse-phase 12 g C-18 column eluting with 30-100% MeOH in water (containing 0.1% formic acid) affording (R)-1-methyl-6-nitro-4-((1-(pyrimidin-2-yl)ethyl)amino)quinolin-2(1H)-one (29 mg, 55%, 0.0891 mmol) as a pale brown solid. LCMS (Method T2) Rt=1.23 mins, m/z 326.13 [M+H]$^+$.

Intermediate B11s: (S)-1-methyl-6-nitro-4-((1-(pyrimidin-2-yl)ethyl)amino)quinolin-2(1H)-one

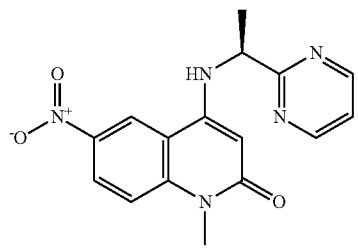

Prepared by a method analogous to that used for the preparation of Intermediate B11r. LCMS (Method T2) Rt=1.23 mins, m/z 326.13 [M+H]$^+$.

Intermediate B12a: 4-((1-(5-bromopyrimidin-2-yl)ethyl)amino)-1-methyl-6-nitroquinolin-2(1H)-one

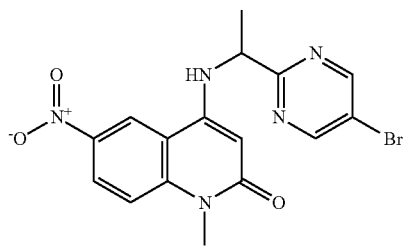

A mixture of ethyl 4-chloro-1-methyl-6-nitro-2-oxo-quinoline-3-carboxylate (Intermediate D2, 1.2 g, 3.9 mmol), 1-(5-bromopyrimidin-2-yl)ethanamine (940 mg, 4.6 mmol) and DIPEA (2 mL, 11.6 mmol) in NMP (9.7 mL) was stirred at 80° C. overnight. Once cooled to rt, lithium chloride (980 mg, 23 mmol) was added to the mixture which was then heated to 160° C. for 2 h. The residue was taken up in water and extracted twice with EtOAc. The organic extracts were washed twice with 1M aq. NaOH, brine then dried over MgSO$_4$. The residue was purified by Biotage KP-Sil 50 g eluting 50-100% EtOAc in cyclohexane. 4-((1-(5-bromopyrimidin-2-yl)ethyl)amino)-1-methyl-6-nitroquinolin-2(1H)-one (895 mg) was isolated as a mustard solid. LCMS (Method T2) Rt=1.38 mins, m/z 404.03 [M+H]$^+$.

Intermediate B12b: 6-bromo-1-methyl-4-((1-(pyrimidin-2-yl)ethyl)amino)-7,8-naphthyridin-2(1H)-one

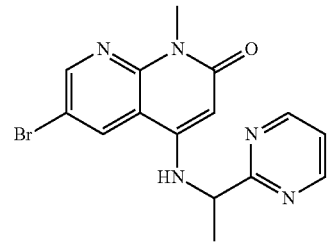 [SMILES: CC(Nc1cc(=O)n(C)c2ncc(Br)cc12)c1ncccn1]

This compound was prepared by a method analogous to that used for the preparation of Intermediate B12a, using Intermediate D7: Ethyl 6-bromo-4-chloro-1-methyl-2-oxo-1,8-naphthyridine-3-carboxylate instead of Intermediate D2. $^1$H NMR (500 MHz, Methanol-d4) δ 8.88-8.81 (m, 3H), 8.68-8.63 (m, 1H), 7.40 (s, 1H), 5.48 (s, 1H), 4.86-4.81 (m, 1H), 3.62 (s, 3H), 1.73 (d, J=6.7 Hz, 3H). LCMS (Method T2) Rt=1.36 min, m/z 360 [M+H]$^+$.

Intermediate B12c: 4-((1-(isoquinolin-3-yl)ethyl)amino)-1-methyl-6-nitroquinolin-2(1H)-one

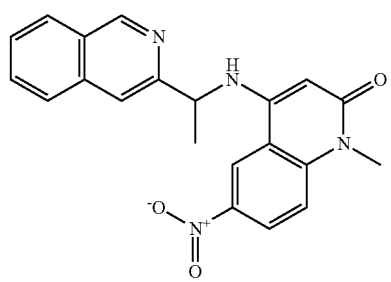

This compound was prepared by a method analogous to that used for the preparation of Intermediate B12a, using Intermediate D2 (Ethyl 4-chloro-1-methyl-6-nitro-2-oxo-quinoline-3-carboxylate) and intermediate C7a. LCMS (Method T2) Rt=1.38 min, m/z 375.14 [M+H]$^+$.

Intermediate B13: 1-((1-methyl-6-nitro-2-oxo-1,2-dihydroquinolin-4-yl)amino)cyclopropane-1-carbonitrile

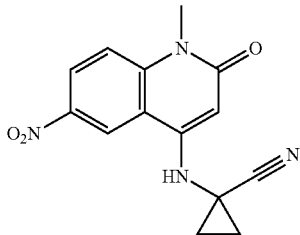 [SMILES: Cn1c(=O)cc(NC2(C#N)CC2)c2cc([N+](=O)[O-])ccc21]

A microwave vial (2.0-5.0 mL volume) was charged with ethyl 4-chloro-1-methyl-6-nitro-2-oxo-quinoline-3-carboxylate (Intermediate D2; 117 mg, 0.38 mmol) and 1-aminocyclopropanecarbonitrile hydrochloride (134 mg, 1.13 mmol). The reaction vial was flushed with Ar, sealed with a cap and then further flushed with Ar. Anhydrous NMP (2.5 mL) was added followed by DIPEA (0.33 mL, 1.89 mmol). The reaction mixture was heated at 140° C. in a heating block for 22 h. The reaction mixture was allowed to cool to rt, the cap was removed and lithium chloride (97 mg, 2.29 mmol) was added. The vial was sealed with a cap and heated at 160° C. in a heating block for 4 h. The reaction mixture was cooled to rt, diluted with DMSO (0.7 mL) and purification by reverse phase column chromatography (2 batches; Biotage 12 g C-18 column, 30% MeOH in water to 100% MeOH (both modified with 0.1% formic acid)) afforded the title compound (36 mg, 34%) as a pale yellow solid. $^1$H NMR (500 MHz, DMSO-$d_6$) δ 8.95 (d, J=2.5 Hz, 1H), 8.42 (dd, J=9.4, 2.5 Hz, 1H), 8.38 (s, 1H), 7.69 (d, J=9.4 Hz, 1H), 5.97 (s, 1H), 3.61 (s, 3H), 1.76-1.71 (m, 2H), 1.40-1.36 (m, 2H); LCMS (Method T2) RT 1.19 min; m/z 285.0962 $[M+H]^+$.

The following intermediates in Table 27 were prepared by a method analogous to that used for the preparation of intermediate B1a, starting from the appropriate amine (obtained from commercial supplier), and 4-chloro-1-methyl-6-nitro-quinolin-2-one (Intermediate D1). For examples B14g and B14h, Intermediate D10 was used instead of Intermediate D1.

TABLE 27 compounds prepared by a method analogous to that used for the preparation of Intermediate B1a.

| Intermediate | Structure | Data |
|---|---|---|
| Intermediate B14a: 1-methyl-6-nitro-4-(tert-pentylamino)quinolin-2(1H)-one | 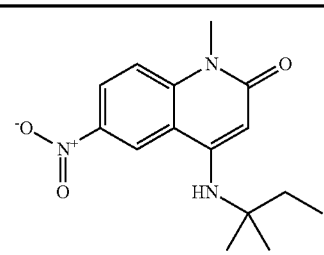 | LCMS (Method T2) Rt = 1.45 min, m/z 290 $[M + H]^+$. |
| Intermediate B14b: 4-((cyclopropylmethyl)amino)-1-methyl-6-nitroquinolin-2(1H)-one | 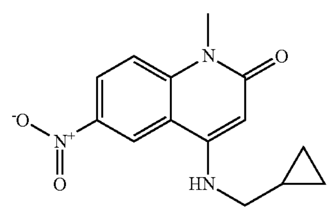 | LCMS (Method T2) Rt = 1.36 min, m/z 274 $[M + H]^+$. |
| Intermediate B14c: 4-(tert-butylamino)-1-methyl-6-nitroquinolin-2(1H)-one | 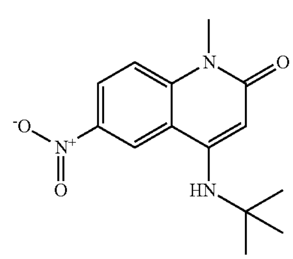 | LCMS (Method T2) Rt = 1.38 min, m/z 276 $[M + H]^+$. |
| Intermediate B14d: 4-((2-fluoroethyl)amino)-1-methyl-6-nitroquinolin-2(1H)-one | 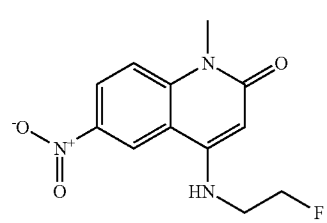 | Does not ionise well. $^1$H NMR (500 MHz, DMSO-d6) δ 9.10 (d, J = 2.6 Hz, 1H), 8.39 (dd, J = 9.3, 2.5 Hz, 1H), 7.70-7.57 (m, 2H), 5.66 (s, 1H), 4.71 (t, J = 4.8 Hz, 1H), 4.62 (t, J = 4.8 Hz, 1H), 3.60-3.55 (m, 4H), 3.52 (d, J = 5.0 Hz, 1H). |

TABLE 27-continued compounds prepared by a method analogous to that used for the preparation of Intermediate B1a.

| Intermediate | Structure | Data |
| --- | --- | --- |
| Intermediate B14e: 4-((1-methoxy-2-methylpropan-2-yl)amino)-1-methyl-6-nitroquinolin-2(1H)-one | 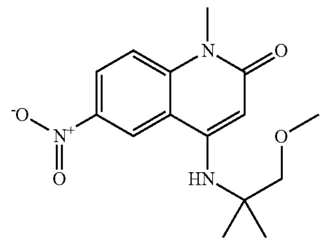 | LCMS (Method T2) Rt = 1.37 min, m/z 306 [M + H]$^+$. |
| Intermediate B14f: 1-methyl-6-nitro-4-((1-(pyrimidin-2-yl)cyclopropyl)amino)quinolin-2(1H)-one | 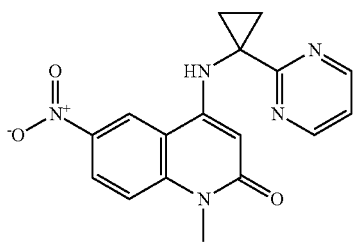 | LCMS (Method T2) Rt = 1.27 mins, m/z 338.12 [M + H]$^+$ |
| Intermediate B14g: 1-(cyclohexylmethyl)-6-nitro-4-((1-(pyrimidin-2-yl)ethyl)amino)quinolin-2(1H)-one | 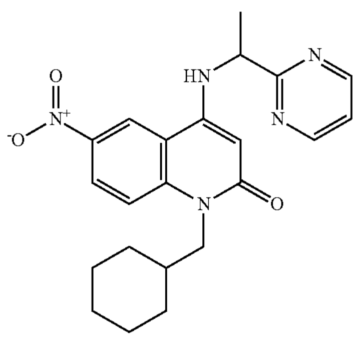 | LCMS (Method T2) Rt = 1.58 mins, m/z 408.20 [M + H]$^+$ |
| Intermediate B14h: 1-(cyclohexylmethyl)-6-nitro-4-((2-(pyrimidin-2-yl)propan-2-yl)amino)quinolin-2(1H)-one | 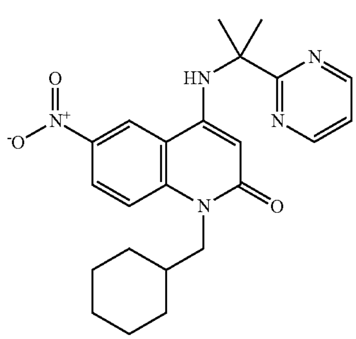 | LCMS (Method T2) Rt = 1.60 mins, m/z 422.21 [M + H]$^+$ |

Intermediate B15a: 1-methyl-4-((1-(5-morpholino-pyrimidin-2-yl)ethyl)amino)-6-nitroquinolin-2(1H)-one

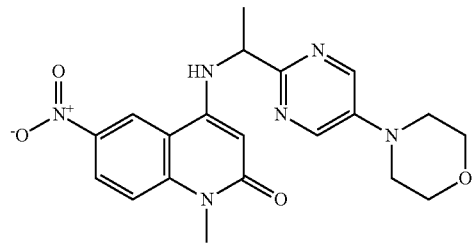

4-[1-(5-bromopyrimidin-2-yl)ethylamino]-1-methyl-6-nitro-quinolin-2-one (Intermediate B12a, 25 mg, 0.06 mmol), morpholine (6.5 uL, 0.07 mmol), cesium carbonate (161 mg, 0.49 mmol), Pd$_2$(dba)$_3$ (5.7 mg, 0.006 mmol), Xantphos (21.5 mg, 0.037 mmol) and a stirrer bar were added to a vial. The vial was sealed, toluene (0.95 mL) and DMF (0.29 mL) were added and the vial purged with argon for 5 mins. The vial was heated in MW at 80° C. for 1 h. The mixture was purified by passing through a syringe filter, concentrated to remove the toluene, diluted with DMSO (0.8 mL), then loaded directly onto a Biotage reverse-phase 12 g C-18 column, eluting 30-100% MeOH in water (containing 0.1% formic acid). 1-methyl-4-((1-(5-morpholinopyrimidin-2-yl)ethyl)amino)-6-nitroquinolin-2(1H)-one (10 mg, 39%, 0.0244 mmol) was obtained as a pale yellow solid. LCMS (Method T2) Rt=1.32 mins, m/z 411.175 [M+H]$^+$.

The following intermediates in Table 28 were prepared by a method analogous to that used for the preparation of intermediate B15a.

TABLE 28 compounds prepared by a method analogous to that used for the preparation of Intermediate B15a.

| Name | Structure | Characterisation |
|---|---|---|
| Intermediate B15b: 1-methyl-6-nitro-4-((1-(5-(2-(trifluoromethyl)morpholino)pyrimidin-2-yl)ethyl)amino)quinolin-2(1H)-one | 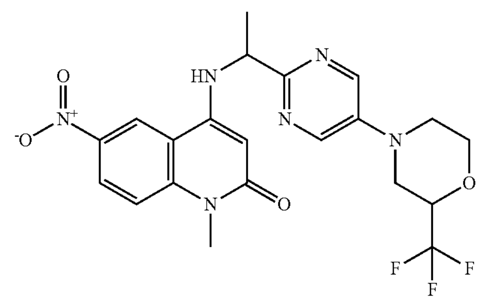 | LCMS (Method T2) Rt = 1.44 mins, m/z 479.16 [M + H]$^+$ |
| Intermediate B15c: 4-((1-(5-((3S,5R)-3,5-dimethylpiperidin-1-yl)pyrimidin-2-yl)ethyl)amino)-1-methyl-6-nitroquinolin-2(1H)-one | 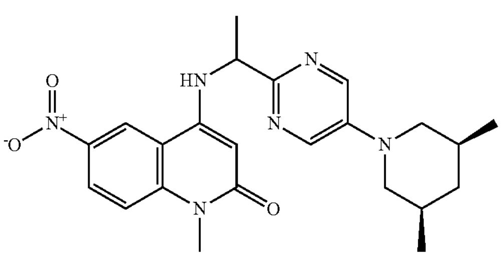 | LCMS (Method T2) Rt = 1.60 mins, m/z 437.23 [M + H]$^+$ |
| Intermediate B15d: 4-((1-(5-((2R,6S)-2,6-dimethylmorpholino)pyrimidin-2-yl)ethyl)amino)-1-methyl-6-nitroquinolin-2(1H)-one | 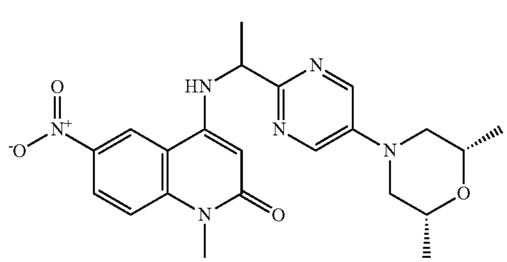 | LCMS (Method T2) Rt = 1.42 mins, m/z 439.20 [M + H]$^+$ |

Intermediate B16: 1-Methyl-6-nitro-4-((1-(pyridin-2-yl)ethyl)amino)quinolin-2(1H)-one

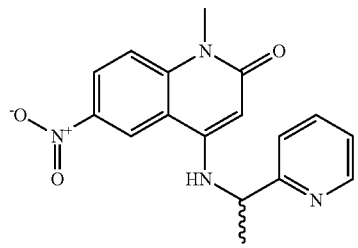

A suspension of N-ethyl-N-isopropyl-propan-2-amine (0.09 mL, 0.492 mmol), 4-chloro-1-methyl-6-nitro-quinolin-2-one (Intermediate D1, 47.0 mg, 0.197 mmol) and 1-(2-pyridyl)ethanamine (36 mg, 0.295 mmol) in NMP (1.5 mL) was stirred thermally at 160° C. for 1 h. When cooled, direct hplc purification gave 1-methyl-6-nitro-4-[1-(2-pyridyl)ethylamino]quinolin-2-one (8.5 mg, 13%, 0.026 mmol) as a cream solid. $^1$H NMR (500 MHz, Methanol-d4) δ 9.26 (d, J=2.5 Hz, 1H), 8.55 (ddd, J=4.9, 1.8, 0.9 Hz, 1H), 8.48 (dd, J=9.4, 2.5 Hz, 1H), 7.81 (td, J=7.5, 1.8 Hz, 1H), 7.69 (d, J=9.4 Hz, 1H), 7.50 (dt, J=8.0, 1.2 Hz, 1H), 7.32 (ddd, J=7.5, 5.0, 1.2 Hz, 1H), 5.48 (s, 1H), 4.78 (q, J=6.9 Hz, 1H), 3.64 (s, 3H), 1.73 (d, J=6.9 Hz, 3H). LCMS (Method T2), Rt=1.17 mins, m/z 325.1 [M+H]$^+$

Intermediate B17: 4-((2-(5-Bromopyrimidin-2-yl)propan-2-yl)amino)-1-methyl-6-nitroquinolin-2(1H)-one

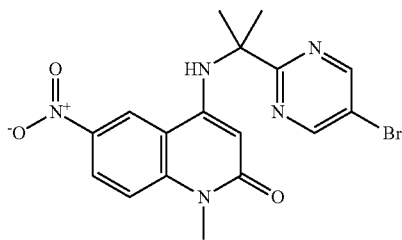

A suspension of ethyl 4-chloro-1-methyl-6-nitro-2-oxoquinoline-3-carboxylate (Intermediate D2, 0.5 g, 1.61 mmol), 1-(5-bromopyrimidin-2-yl)-1-methylethylamine hydrochloride (513 mg, 1.93 mmol) and DIPEA (1.1 mL, 6.44 mmol) was stirred at 120° C. for 6 h in heating block. Once cooled to rt, lithium chloride (409 mg, 9.66 mmol) was added to the mixture and heated to 160° C. overnight. Once cooled to rt, the residue was taken up in water and extracted twice with EtOAc. The combined organic extracts were washed with water and brine then dried over MgSO$_4$. The residue was purified by flash column chromatography (Biotage KP-Sil 25 g eluting 0-10% MeOH in DCM). A second purification was required so the residue was purified again (Biotage KP-Sil 25 g eluting 20-100% EtOAc in cyclohexane) affording 4-((2-(5-bromopyrimidin-2-yl)propan-2-yl)amino)-1-methyl-6-nitroquinolin-2(1H)-one (405 mg) as a yellow solid. LCMS (Method T2) Rt=1.42 mins, m/z 418.05 [M+H]$^+$.

Intermediate B18a: 4-((1-(5-Cyclopropylpyrimidin-2-yl)ethyl)amino)-1-methyl-6-nitroquinolin-2(1H)-one

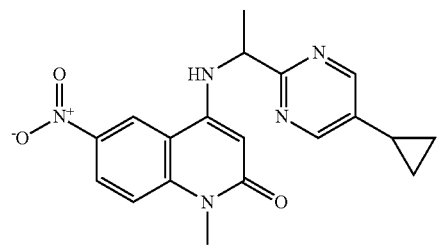

4-[1-(5-bromopyrimidin-2-yl)ethylamino]-1-methyl-6-nitro-quinolin-2-one (Intermediate B12a, 25.00 mg, 0.0618 mmol), Cyclopropylboronic acid (26.56 mg, 0.309 mmol), tetrakis(triphenylphosphine)palladium(0) (7.1 mg, 0.006 mmol), sodium carbonate (108 uL, 0.22 mmol) and DMF (0.64 mL) were added to a vial which was sealed and purged with argon. The mixture was heated in the microwave to 140° C. for 1 h. Once cooled to rt, the mixture was diluted with water and extracted with EtOAc. The combined organic extracts were washed with water and brine then dried over MgSO$_4$. The residue was purified by reverse-phase flash chromatography (12 g SNAP Ultra C-18 column, eluting 30-100% MeOH in water (containing 0.1% formic acid)) affording 17.5 mg of product, which contained residual triphenylphosphine oxide. No further purification was performed. LCMS (Method T2) Rt=1.39 mins, m/z 366.15 [M+H]$^+$.

The following intermediates in Table 29 were prepared by a method analogous to that used for the preparation of intermediate B18a.

TABLE 29 compounds prepared by a method analogous to that used for the preparation of Intermediate B18a.

| Name | Structure | Characterisation | Starting material |
|---|---|---|---|
| Intermediate B18b: 1-methyl-4-((1-(5-(1-methyl-1H-pyrazol-4-yl)pyrimidin-2-yl)ethyl)amino)-6-nitroquinolin-2(1H)-one | 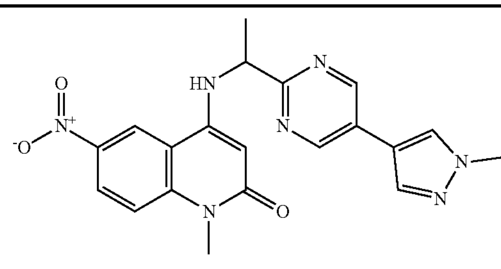 | LCMS (Method T2) Rt = 1.32 mins, m/z 406.13 [M + H]$^+$ | 4-[1-(5-bromopyrimidin-2-yl)ethylamino]-1-methyl-6-nitro-quinolin-2-one (Intermediate B12a) |

TABLE 29-continued compounds prepared by a method analogous to that used for the preparation of Intermediate B18a.

| Name | Structure | Characterisation | Starting material |
|---|---|---|---|
| Intermediate B18c: 4-((1-(5-(3,6-dihydro-2H-pyran-4-yl)pyrimidin-2-yl)ethyl)amino)-1-methyl-6-nitroquinolin-2(1H)-one | 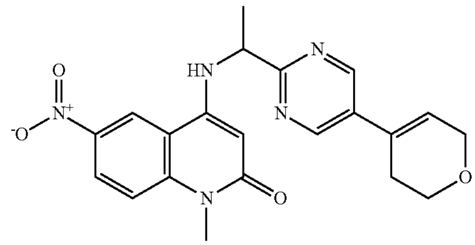 | LCMS (Method T2) Rt = 1.36 mins, m/z 408.16 [M + H]⁺ | 4-[1-(5-bromopyrimidin-2-yl)ethylamino]-1-methyl-6-nitro-quinolin-2-one (Intermediate B12a) |
| Intermediate B18d: 4-((2-(5-cyclopropylpyrimidin-2-yl)propan-2-yl)amino)-1-methyl-6-nitroquinolin-2(1H)-one | 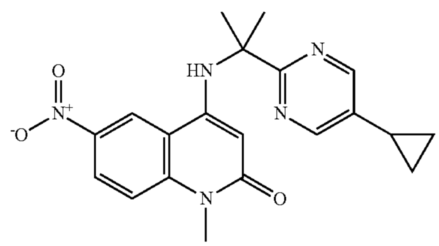 | LCMS (Method T2) Rt = 1.43 mins, m/z 380.17 [M + H]⁺ | Intermediate B17: 4-((2-(5-bromopyrimidin-2-yl)propan-2-yl)amino)-1-methyl-6-nitroquinolin-2(1H)-one |

Intermediate B19a: 1-Methyl-4-((1-(5-methylpyrimidin-2-yl)ethyl)amino)-6-nitroquinolin-2(1H)-one

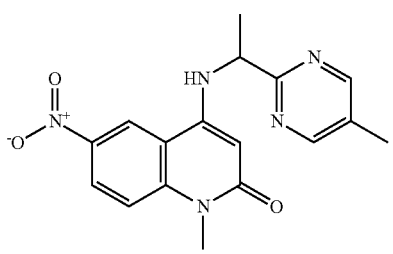

To an oven dried and sealed vial containing 4-[1-(5-bromopyrimidin-2-yl)ethylamino]-1-methyl-6-nitro-quinolin-2-one (Intermediate B12a, 22 mg, 0.054 mmol), Bis(triphenylphosphine)palladium(II) chloride (19 mg, 0.027 mmol) and methylboronic acid (32.6 mg, 0.54 mmol) was added dioxane (0.54 mL) and 2M aq sodium carbonate (0.14 mL, 0.28 mmol). The vial was then degassed with argon for 5 mins. The mixture was then heated with stirring in the microwave at 120° C. for 2 h. Once cooled to rt, the reaction mixture was filtered through a syringe filter, and the resulting filtrate was concentrated under reduced pressure. DMSO (0.5 mL) was added to the sample which was purified using reverse-phase C18 column eluting from 10-100% MeOH in water (containing 0.1% formic acid). 1-methyl-4-((1-(5-methylpyrimidin-2-yl)ethyl)amino)-6-nitroquinolin-2(1H)-one (5 mg, 27%, 0.0147 mmol) was obtained as an off-white solid. LCMS (Method T2) Rt=1.30 mins, m/z 340.14 [M+H]⁺

Intermediate B20a: (R)-4-((1-Cyclopropylethyl)amino)-1-methyl-6-nitroquinazolin-2(1H)-one

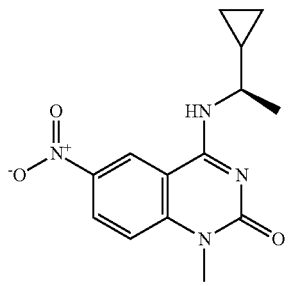

Triethylamine (2.5 mL, 18.1 mmol) was added to a solution of 1-methyl-6-nitro-quinazoline-2,4-dione (Intermediate D9, 1 g, 4.5 mmol) in phosphorus(V) oxychloride (6.0 mL, 64 mmol) which was then heated to 100° C. with stirring for 3 h. Once cooled to rt, the solution was concentrated in vacuo, leaving a residue which was diluted with DCM and poured into 1M aq. NaOH. The organic layer was separated and the aqueous layer extracted once more with DCM. The combined organic extracts were dried over sodium sulfate, filtered and concentrated in vacuo. The residue was diluted with NMP (9 mL) then (1R)-1-cyclopropylethan-1-amine (0.51 mL, 4.75 mmol) and triethylamine (2.5 mL, 18 mmol) were added. The solution was stirred at rt overnight. The solution was diluted with water and extracted with EtOAc. The combined organic extracts were washed twice with water and once with brine then dried over MgSO₄, filtered and concentrated in vacuo. The residue was purified by flash column chromatography (Biotage KP-Sil 25 g eluting 0-10% MeOH in DCM) affording (R)-4-((1-cyclopropylethyl)amino)-1-methyl-6-nitroquinazolin-2

(1H)-one (884 mg) as a brown solid. LCMS (Method T2) Rt=1.27 mins, m/z 289.13 [M+H]+.

Intermediate B20b: 1-Methyl-6-nitro-4-((1-(pyrimidin-2-yl)ethyl)amino)quinazolin-2(1H)-one

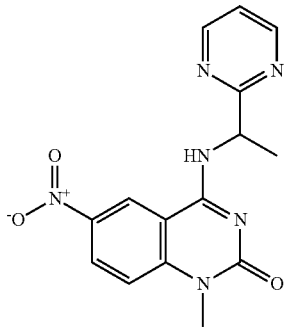

Prepared by a method analogous to that used for the preparation of Intermediate B20a. LCMS (Method T2) Rt=1.13 mins, m/z 327.12 [M+H]+.

Intermediate B20c: 1-Methyl-6-nitro-4-((1-(pyrimidin-2-yl)ethyl)amino)quinazolin-2(1H)-one

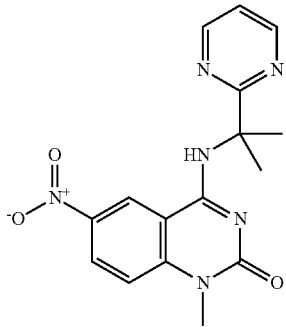

Prepared by a method analogous to that used for the preparation of Intermediate B20a. LCMS (Method T2) Rt=1.19 mins, m/z 341 [M+H]+.

Intermediate B21: 6-Amino-1-methyl-4-((1-(5-(tetrahydro-2H-pyran-4-yl)pyrimidin-2-yl)ethyl)amino)quinolin-2(1H)-one

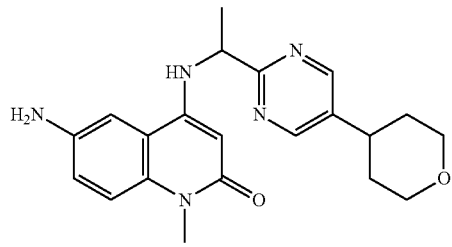 [SMILES: CC(Nc1cc(=O)n(C)c2ccc(N)cc12)c1ncc(C2CCOCC2)cn1]

To a solution of 4-[1-[5-(3,6-dihydro-2H-pyran-4-yl)pyrimidin-2-yl]ethylamino]-1-methyl-6-nitro-quinolin-2-one (Intermediate B18c, 45 mg, 0.1105 mmol) (containing residual triphenylphosphine oxide) in ethanol (4 mL) was added Pd/C (10 wt %) (25 mg, 0.024 mmol). The flask was placed under an atmosphere of hydrogen and heated to 60° C. with stirring overnight. The mixture was purified using a 5 g SCX column affording 6-amino-1-methyl-4-((1-(5-(tetrahydro-2H-pyran-4-yl)pyrimidin-2-yl)ethyl)amino)quinolin-2(1H)-one (19 mg) as a pale orange solid. LCMS (Method T2) Rt=1.00 mins, m/z 380.20 [M+H]+.

Intermediates B22a and B22b represent a pair of diastereoisomers where one is cis and one is trans across the cyclobutane ring. The compounds can be clearly distinguished from one another by NMR, but it has not been unambiguously determined which is the cis and which is the trans structure. Both compounds are racemic.

Intermediate B22a: rac-4-(((1R,2S)-2-methoxycyclobutyl)amino)-1-methyl-6-nitroquinolin-2(1H)-one or rac-4-(((1R,2R)-2-methoxycyclobutyl)amino)-1-methyl-6-nitroquinolin-2(1H)-one

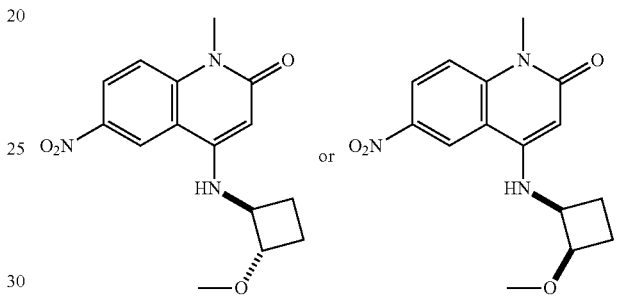

Prepared by a method analogous to that used for Intermediate B7a, starting from Intermediate C5a. 1H NMR (500 MHz, Chloroform-d) δ 8.52 (d, J=2.5 Hz, 1H), 8.41 (dd, J=9.3, 2.5 Hz, 1H), 7.43 (d, J=9.3 Hz, 1H), 5.98 (s, 1H), 5.17 (s, 1H), 3.87 (q, J=7.2 Hz, 1H), 3.71 (s, 3H), 3.43-3.38 (m, 1H), 3.36 (s, 3H), 2.86 (s, 1H), 2.44-2.36 (m, 2H), 2.31-2.22 (m, 1H), 2.08-1.99 (m, 2H), 1.79-1.69 (m, 2H), 1.52-1.46 (m, 1H). LCMS (Method T2) Rt=1.31 min, m/z 304 [M+H]+.

Intermediate B22b: rac-4-(((1R,2S)-2-methoxycyclobutyl)amino)-1-methyl-6-nitroquinolin-2(1H)-one or rac-4-(((1R,2R)-2-methoxycyclobutyl)amino)-1-methyl-6-nitroquinolin-2(1H)-one

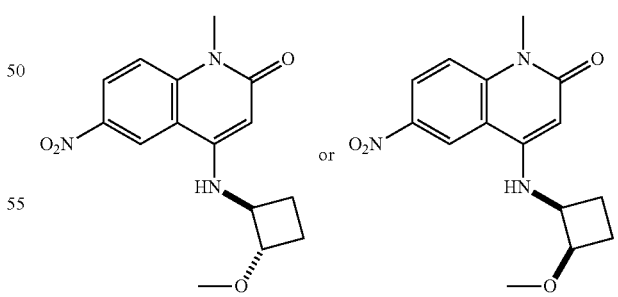

Prepared by a method analogous to that used for Intermediate B7a, starting from intermediate C5b. 1H NMR (500 MHz, Chloroform-d) δ 8.53 (d, J=2.5 Hz, 1H), 8.41 (dd, J=9.3, 2.4 Hz, 1H), 7.43 (d, J=9.3 Hz, 1H), 5.92 (d, J=4.9 Hz, 1H), 5.64 (s, 1H), 4.30-4.19 (m, 1H), 4.15 (s, 1H), 3.71 (s, 3H), 3.43 (s, 3H), 2.32-2.22 (m, 1H), 2.22-2.12 (m, 2H), 2.04-1.91 (m, 1H). LCMS (Method T2) Rt=1.34 min, m/z 304 [M+H]+.

Intermediate B23a: 4-((1-(5-cyclobutylpyrimidin-2-yl)ethyl)amino)-1-methyl-6-nitroquinolin-2(1H)-one

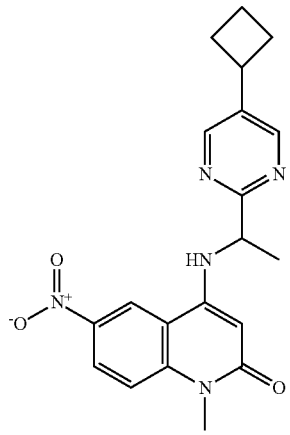

Potassium cyclobutyltrifluoroborate (54 mg, 0.31 mmol), 4-[1-(5-bromopyrimidin-2-yl)ethylamino]-1-methyl-6-nitro-quinolin-2-one (Intermediate B12a, 50 mg, 0.21 mmol), Pd(OAc)$_2$ (0.94 mg, 0.0042 mmol), RuPhos (3.9 mg, 0.0084 mmol) and potassium carbonate (87 mg, 0.63 mmol) were added to a vial and sealed. The vial was evacuated and flushed with argon three times then toluene (1.9 mL) and Water (0.19 mL) were added. The vial was heated to 80° C. for 64 hours. Once cooled, the mixture was diluted with water and extracted with EtOAc. Organic extracts combined and washed with brine, dried (MgSO$_4$) and concentrated in vacuo. The residue was passed through a 2 g SCX-2 column and eluted with 2M methanolic ammonia. The sample was then purified using Biotage reverse-phase 12 g C-18 column eluting 30-100% MeOH in water (each containing 0.1% formic acid) affording 4-[1-(5-cyclobutylpyrimidin-2-yl)ethylamino]-1-methyl-6-nitro-quinolin-2-one (27 mg) as a white solid. $^1$H NMR (500 MHz, Chloroform-d) δ 8.70 (d, J=2.4 Hz, 1H), 8.64-8.63 (m, 2H), 8.40 (dd, J=9.3, 2.4 Hz, 1H), 7.40 (d, J=9.3 Hz, 1H), 6.59 (d, J=6.6 Hz, 1H), 5.83 (s, 1H), 4.89 (app. quin., J=6.7 Hz, 1H), 3.68 (s, 3H), 3.57 (p, J=8.5 Hz, 1H), 2.49-2.39 (m, 2H), 2.27-2.07 (m, 3H), 2.01-1.92 (m, 1H), 1.68 (d, J=6.7 Hz, 3H). LCMS (Method T2) Rt=1.46 min, m/z 380.17 [M+H]$^+$.

Intermediate B24a: 1-benzyl-6-nitro-4-((1-(pyrimidin-2-yl)ethyl)amino)quinolin-2(1H)-one

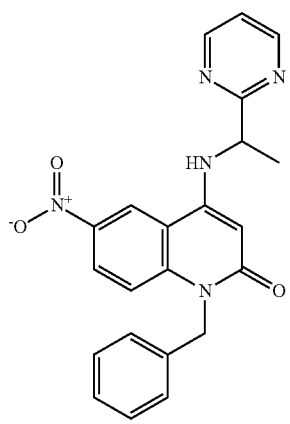

To 1-benzyl-4-chloro-6-nitro-quinolin-2-one (Intermediate D14, 70 mg, 0.22 mmol), 1-pyrimidin-2-ylethanamine hydrochloride (71 mg, 0.44 mmol), dicesium carbonate (0.58 g, 1.78 mmol), Xantphos (77 mg, 0.13 mmol) and Pd(dba)$_2$ (41 mg, 0.045 mmol) in a sealed vial under argon were added toluene (1.5 mL) and DMF (0.5 mL) were added. The reaction was heated in the microwave at 80° C. for 1 h, then to 140° C. for a further 1 h. The reaction was partitioned between EtOAc and water and the organic layer was separated and washed with brine. The organic layer was dried and concentrated under reduced pressure, then purified by column chromatography (12-100% EtOAc in cyclohexane) to give the title compound, m/z 402.1557 [M+H]+

Intermediate B24b: 1-(cyclobutylmethyl)-6-nitro-4-((1-(pyrimidin-2-yl)ethyl)amino)quinolin-2(1H)-one

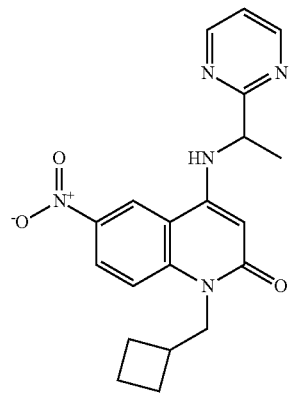

Prepared by an analogous method to that used in the preparation of intermediate B24a, starting from 4-chloro-1-(cyclobutylmethyl)-6-nitroquinolin-2(1H)-one (Intermediate D13). LCMS (Method T2) RT=1.70 min; m/z 380 [M+H]$^+$.

Intermediate C1a; (R)-2-Amino-N-(2-hydroxyethyl)propanamide

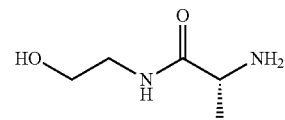

A solution of 2-aminoethanol (97 mg, 1.59 mmol), (2R)-2-(tert-butoxycarbonyl-amino)propanoic acid (100 mg, 0.53 mmol), DIPEA (0.18 mL, 1.06 mmol) and [dimethylamino-(3-oxidotriazolo[4,5-b]pyridin-3-ium-1-yl)methylene]-dimethyl-ammonium hexafluorophosphate (241 mg, 0.63 mmol) in DMF (2 mL) was stirred at rt for 24 h. Water (1 mL) was added and the mixed solution was stirred with 0.1 g MS-carbonate resin for an hour. After decanting, the solution was passed through a SCX-2 column (5 G) and washed with MeOH. After all the solvents were removed, the residue was dried in vacuo for 24 h. DCM was then added to the residue and filtered. TFA (0.6 mL) was added to the filtrate at rt. The resulting solution was stirred at rt for 16 h. After removal of all solvents, the residue was purified by scx-2 column. (R)-2-amino-N-(2-hydroxyethyl)propanamide (60 mg, 86%, 0.454 mmol) was obtained as a colourless oil. $^1$H NMR (500 MHz, Methanol-$d_4$) δ 3.81 (q, J=7.0 Hz, 1H), 3.68-3.56 (m, 2H), 3.41-3.33 (m, 2H), 1.46 (d, J=7.0 Hz, 3H).

The following intermediates in Table 30 were prepared by a method analogous to that used in the preparation of Intermediate C1a.

Intermediate C2:2-Amino-2-methyl-N-((1-methyl-1H-pyrazol-4-yl)methyl)propanamide

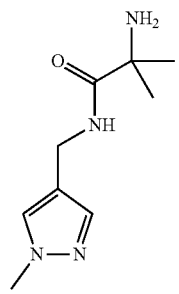

TABLE 30 compounds prepared by a method analogous to that used for the preparation of Intermediate C1a

| Intermediate | Structure | Data |
|---|---|---|
| Intermediate C1b: (R)-2-amino-N-((1-methyl-1H-pyrazol-4-yl)methyl)propanamide | 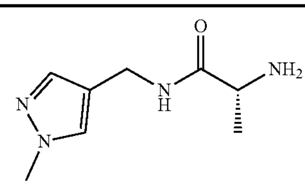 | $^1$H NMR (500 MHz, Methanol-$d_4$) δ 7.57 (s, 1H), 7.43 (s, 1H), 4.28 (s, 2H), 3.86 (s, 3H), 3.81 (q, J = 7.0 Hz, 1H), 1.46 (d, J = 7.0 Hz, 3H). |
| Intermediate C1c: (R)-2-amino-N-(2-(1-methyl-1H-pyrazol-4-yl)ethyl)propanamide | 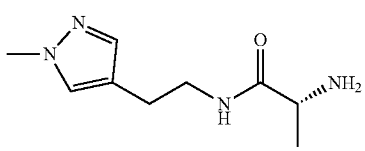 | $^1$H NMR (500 MHz, Methanol-$d_4$) δ 7.45 (s, 1H), 7.34 (s, 1H), 3.84 (s, 3H), 3.49 (q, J = 6.9 Hz, 1H), 3.42-3.29 (m, 2H), 2.68 (t, J = 7.2 Hz, 2H), 1.28 (d, J = 6.9 Hz, 3H). |
| Intermediate C1d: (R)-2-amino-N-cyclopentylpropanamide | 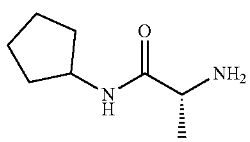 | $^1$H NMR (500 MHz, Methanol-$d_4$) δ 4.10 (p, J = 6.8 Hz, 1H), 3.38 (q, J = 6.9 Hz, 1H), 2.03-1.87 (m, 2H), 1.81-1.68 (m, 2H), 1.68-1.56 (m, 2H), 1.54-1.40 (m, 2H), 1.25 (d, J = 6.9 Hz, 3H). |
| Intermediate C1e: (R)-2-amino-N-(2-methoxyethyl)propanamide | 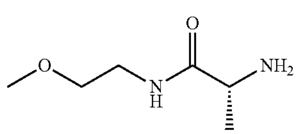 | $^1$H NMR (500 MHz, Methanol-$d_4$) δ 3.64 (q, J = 7.0 Hz, 1H), 3.53-3.45 (m, 2H), 3.40 (t, J = 5.6 Hz, 2H), 3.36 (s, 3H), 1.37 (d, J = 7.0 Hz, 3H). |
| Intermediate C1f: (R)-2-amino-N-(but-3-yn-1-yl)propanamide | 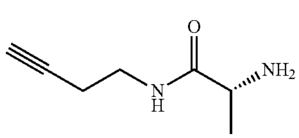 | $^1$H NMR (500 MHz, Methanol-$d_4$) δ 3.63 (q, J = 7.0 Hz, 1H), 3.47-3.24 (m, 2H), 2.43-2.38 (m, 2H), 2.32 (t, J = 2.6 Hz, 1H), 1.38 (d, J = 7.0 Hz, 3H). |
| Intermediate C1g: (R)-2-amino-N-(4-methoxycyclohexyl)propanamide | 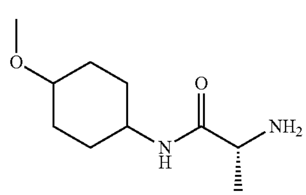 | $^1$H NMR (500 MHz, Methanol-$d_4$) δ 3.68-3.63 (m, 1H), 3.62 (q, J = 7.0 Hz, 1H), 3.35 (s, 3H), 3.24-3.15 (m, 1H), 2.13-2.02 (m, 2H), 2.02-1.89 (m, 2H), 1.37 (d, J = 7.0 Hz, 3H), 1.34-1.27 (m, 4H). |

A solution of 2-(tert-butoxycarbonylamino)-2-methylpropanoic acid (200.0 mg, 0.984 mmol), (1-methylpyrazol-4-yl)methanamine (131 mg, 1.18 mmol), [dimethylamino-(3-oxidotriazolo[4,5-b]pyridin-3-ium-1-yl)methylene]-dimethyl-ammonium hexafluorophosphate (449 mg, 1.18 mmol) and DIPEA (0.34 mL, 1.97 mmol) in DMF (3.0 mL) was stirred at 25° C. for 48 h. Water (1 mL) was added and the mixed solution was stirred with 0.1 g MP-carbonate resin for 1 h. After decanting, the solution was passed through a SCX-2 column (5G) and washed with MeOH. After all the solvents were removed, the residue was dried in vacuo for 24 h. DCM was then added to the residue and filtered. TFA (0.6 mL) was added to the filtrate at rt. The resulting solution was stirred at rt for 12 h. After that, all solvents were removed and the residue was purified by scx-2 (5G) column, yielding 2-amino-2-methyl-N-[(1-methylpyrazol-4-yl)methyl]propanamide (178 mg). $^1$H NMR (500 MHz, Methanol-$d_4$) δ 7.54 (s, 1H), 7.42 (s, 1H), 4.25 (s, 2H), 3.85 (s, 3H), 1.43 (s, 6H).

Intermediate C3:2-Methyl-2,9-diazaspiro[5.5]undecan-1-one

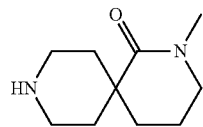

Step 1; tert-butyl 2-methyl-1-oxo-2,9-diazaspiro[5.5]undecane-9-carboxylate

A mixture of tert-butyl 1-oxo-2,9-diazaspiro[5.5]undecane-9-carboxylate (220 mg, 0.82 mmol) and sodium hydride (39.4 mg, 0.98 mmol) was stirred at 25° C. in DMF (8.0 mL) for 15 min, iodomethane (0.26 mL, 4.1 mmol) was then added. The resulting brown solution was stirred at 25° C. for 16 h. Brine was added and extracted with EtOAc. The organic layer was then washed with brine and dried with $Na_2SO_4$. After removal of solvent, tert-butyl 2-methyl-1-oxo-2,9-diazaspiro[5.5]undecane-9-carboxylate (219 mg) was obtained as a yellow oil. $^1$H NMR (500 MHz, Methanol-$d_4$) δ 3.84 (dtd, J=13.6, 4.8, 1.1 Hz, 2H), 3.40-3.34 (m, 2H), 3.24-3.05 (m, broad, 2H), 2.91 (s, 3H), 2.02-1.95 (m, 2H), 1.50-1.43 (m, 4H), 1.47 (s+m, 9+2H).

Step 2; 2-Methyl-2,9-diazaspiro[5.5]undecan-1-one tert-butyl 2-methyl-1-oxo-2,9-diazaspiro[5.5]undecane-9-carboxylate (219 mg, 0.78 mmol) was dissolved in DCM (8.0 mL) and trifluoroacetic acid (0.50 mL, 0.776 mmol) was added at 25° C. The solution was stirred at this temp for 16 h. After the removal of the volatiles, the crude was purified by scx-2 column, gave 2-methyl-2,9-diazaspiro[5.5]undecan-1-one (106 mg, 75%, 0.582 mmol) as a colourless oil. $^1$H NMR (500 MHz, Methanol-$d_4$) δ 3.48-3.29 (m, 2H), 2.93 (dt, J=13.2, 4.3 Hz, 2H), 2.90 (s, 3H), 2.76 (ddd, J=13.2, 11.1, 3.1 Hz, 2H), 2.05 (ddd, J=13.7, 11.1, 4.3 Hz, 2H), 1.95-1.82 (m, 4H), 1.58-1.39 (m, 2H).

Intermediate C4:2-methoxycyclopentan-1-amine hydrochloride

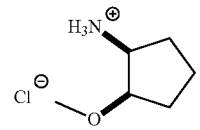

Step 1; tert-butyl N-(2-hydroxycyclopentyl)carbamate

Di-tert-butyl dicarbonate (1.64 g, 7.27 mmol) was added to a solution of cis-2-aminocyclopentanol hydrochloride (500 mg, 3.63 mmol) and triethylamine (1.02 mL, 7.27 mmol) in DCM (5.0 mL) and the reaction was stirred for 16 h at rt. The reaction was quenched upon addition of water (5 mL) and the mixture was passed through a phase separator cartridge. The organic layer was concentrated under reduced pressure and the crude residue was purified via flash column chromatography (0-50% EtOAc in cyclohexane) to give tert-butyl N-(2-hydroxycyclopentyl)carbamate (700 mg) as a white solid. $^1$H NMR (500 MHz, Chloroform-d) δ 4.84 (s, 1H), 4.18 (td, J=4.9, 2.5 Hz, 1H), 3.81 (s, 1H), 2.03-1.78 (m, 2H), 1.78-1.63 (m, 2H), 1.63-1.49 (m, 2H), 1.47 (s, 9H).

Step 2; tert-butyl N-(2-methoxycyclopentyl)carbamate

Iodomethane (0.62 mL, 9.94 mmol) was added dropwise to a solution of tert-butyl N-(2-hydroxycyclopentyl)carbamate (400 mg, 2 mmol) and tetrabutylammonium hydrogen sulfate (102 mg, 0.3 mmol) in 50% aqueous Sodium Hydroxide (3 mL, 2 mmol) and THF (3 mL). The reaction was stirred at room temperature for 10 days. The reaction was diluted with water and extracted with ethyl acetate (2×15 mL). The combined organic layers were washed with water, dried and concentrated under reduced pressure. The crude mixture was purified via flash column chromatography (25 g, 0-30% EtOAc in cyclohexane) to give tert-butyl N-(2-methoxycyclopentyl)carbamate (278 mg) as a colourless oil. $^1$H NMR (500 MHz, Chloroform-d) δ 5.06 (s, 1H), 3.88 (s, 1H), 3.64 (dt, J=5.1, 3.2 Hz, 1H), 3.33 (s, 3H), 2.03-1.92 (m, 1H), 1.82-1.68 (m, 2H), 1.65-1.50 (m, 2H), 1.52-1.40 (m, 10H).

Step 3; 2-methoxycyclopentan-1-amine hydrochloride tert-Butyl N-(2-methoxycyclopentyl)carbamate (278 mg, 1.29 mmol) was stirred in DCM (2 mL), acetonitrile (2 mL) and 3M aq. HCl (10 mL) at room temperature for 16 h. The reaction solvent was concentrated under reduced pressure, and the crude residue was taken to be quantitative and used in the next step with no further purification. $^1$H NMR (500 MHz, Deuterium Oxide) δ 3.82 (td, J=5.2, 3.4 Hz, 1H), 3.54 (td, J=7.6, 5.0 Hz, 1H), 3.27 (s, 3H), 1.98 (dt, J=8.0, 4.1 Hz, 1H), 1.82-1.65 (m, 3H), 1.65-1.48 (m, 2H).

Intermediates C5a and C5b represent a pair of diastereoisomers where one is cis and one is trans across the cyclobutane ring. The compounds can be clearly distinguished from one another by NMR, but it has not been unambiguously determined which is the cis and which is the trans structure. Both compounds are racemic.

Intermediate C5a: rac-(1 S,2R)-2-methoxycyclobutan-1-aminium chloride or rac-(1 S,2S)-2-methoxycyclobutan-1-aminium chloride

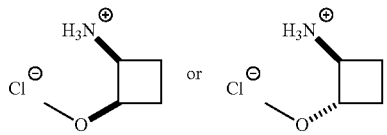

Tert-butyl N-(2-methoxycyclobutyl)carbamate (Intermediate C6a, 85 mg, 0.42 mmol) was stirred in acetonitrile (3 mL) and 3M aq. HCl (3 mL) at room temperature overnight. The reaction was concentrated under reduced pressure and the residue was assumed to be quantitative, and used with no further purification. $^1$H NMR (500 MHz, Deuterium Oxide) δ 3.98-3.85 (m, 1H), 3.61-3.52 (m, 1H), 3.24 (s, 3H), 2.26-2.13 (m, 1H), 2.13-1.98 (m, 1H), 1.69-1.47 (m, 2H).

Intermediate C5b: rac-(1S,2R)-2-methoxycyclobutan-1-aminium chloride or rac-(1 S,2S)-2-methoxycyclobutan-1-aminium chloride

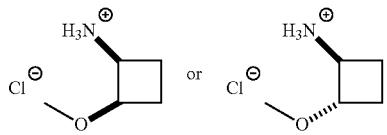

Prepared by a method analogous to that used for Intermediate C5a, starting from Intermediate C6b. $^1$H NMR (500 MHz, Deuterium Oxide) δ 4.11-4.01 (m, 1H), 3.86 (q, J=6.4, 4.9 Hz, 1H), 3.24 (s, 3H), 2.28-2.15 (m, 1H), 2.15-1.98 (m, 2H), 1.94-1.80 (m, 1H).

Intermediates C6a and C6b represent a pair of diastereoisomers where one is cis and one is trans across the cyclobutane ring. These were separated by flash column chromatography as described in the preparation below. The compound which elutes first has been labelled Intermediate C6b, which was used to prepare Intermediate C5b, leading to intermediates B22b, A13b and Examples 22b and 23b. The later eluting compound has been labelled Intermediate C6a, which was used to prepare Intermediate C5a, leading to intermediates B22a, A13a and Examples 22a and 23a. The compounds can be clearly distinguished from one another by NMR, but it has not been unambiguously determined which is the cis and which is the trans structure. Both compounds are racemic.

Intermediate C6a and C6b: rac-tert-butyl ((1S,2R)-2-methoxycyclobutyl)carbamatetert-butyl (2-methoxycyclobutyl)carbamate and rac-tert-butyl ((1S,2S)-2-methoxycyclobutyl)carbamate

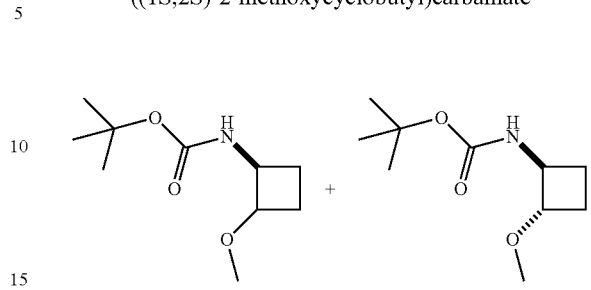

Step 1; tert-butyl N-(2-hydroxycyclobutyl)carbamate, mixture of diastereoisomers Di-tert-butyl dicarbonate (1.82 g, 8.1 mmol) was added to a solution of 2-aminocyclobutanol hydrochloride (0.5 g, 4 mmol) and triethylamine (1.14 mL, 8.1 mmol) in DCM (5 mL) and the reaction was stirred at rt for 16 h. The reaction was quenched by addition of water (5 mL) and the mixture was passed through a phase separator cartridge. The filtrate was concentrated under reduced pressure and the crude residue was purified via flash column chromatography (0-50% EtOAc in cyclohexane) to give tert-butyl N-(2-hydroxycyclobutyl)carbamate (600 mg) as a white solid (mixture of diastereoisomers).

Step 2; rac-tert-butyl ((1S,2R)-2-methoxycyclobutyl)carbamatetert-butyl (2-methoxycyclobutyl) carbamate and rac-tert-butyl ((1S,2S)-2-methoxycyclobutyl)carbamate Iodomethane (0.5 mL, 8 mmol) was added dropwise to a solution of tert-butyl N-(2-hydroxycyclobutyl)carbamate (300 mg, 1.6 mmol) (mixture of diasereoisomers) and tetrabutylammonium hydrogen sulfate (82 mg, 0.24 mmol) in 50% aqueous sodium hydroxide (9 mL) and THF (9 mL). The reaction was stirred at room temperature for 4 days. The reaction was diluted with water and extracted with EtOAc (2×5 mL). The combined organic layers were washed with water, dried and concentrated under reduced pressure. The crude residue was purified via Biotage column chromatography (KP-Sil 12 g, 0-30% EtOAc in cyclohexane over 50 CV) to elute Intermediate C6b (96 mg, 28%, 0.45 mmol). Further elution gave Intermediate C6a (85 mg, 26%, 0.42 mmol).

Data for Intermediate C6a: $^1$H NMR (500 MHz, Chloroform-d) δ 4.84 (s, 1H), 4.03-3.84 (m, 1H), 3.69-3.57 (m, 1H), 3.32 (s, 3H), 2.18-2.07 (m, 1H), 2.07-1.97 (m, 1H), 1.58-1.39 (m, 10H), 1.38-1.25 (m, 1H).

Data for Intermediate C6b: $^1$H NMR (500 MHz, Chloroform-d) δ 5.28 (s, 1H), 5.11-5.00 (m, 1H), 4.31-4.15 (m, 1H), 4.08-3.91 (m, 1H), 3.30 (s, 3H), 2.19-2.06 (m, 1H), 2.07-1.95 (m, 1H), 1.95-1.82 (m, 1H), 1.46 (s, 9H).

Intermediate C7a: 1-(3-isoquinolyl)ethanamine

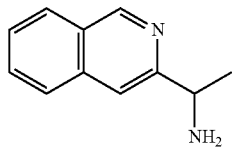

Step 1; N-(3-isoquinolylmethylene)-2-methyl-propane-2-sulfinamide

To a solution of isoquinoline-3-carbaldehyde (0.25 g, 1.59 mmol) and rac-2-Methyl-2-propanesulfinamide (0.21 g, 1.75 mmol) in DCM (8 mL) was added Cesium Carbonate (0.62 g, 1.9 mmol). The mixture was stirred overnight at rt. The mixture was diluted with DCM and washed with water, brine then dried over MgSO$_4$. The residue was purified by Biotage KP-Sil 10 g eluting 20-60% EtOAc in cyclohexane affording N-(3-isoquinolylmethylene)-2-methyl-propane-2-sulfinamide (335 mg) as a pale yellow solid. $^1$H NMR (500 MHz, Chloroform-d) δ 9.37 (s, 1H), 8.85 (s, 1H), 8.31 (s, 1H), 8.08-8.02 (m, 1H), 8.00-7.94 (m, 1H), 7.83-7.76 (m, 1H), 7.76-7.70 (m, 1H), 1.33 (s, 9H). LCMS (Method T2), Rt=1.41 mins, m/z 261.10 (M+H)$^+$.

Step 2; N-[1-(3-isoquinolyl)ethyl]-2-methyl-propane-2-sulfinamide

To a solution of N-(3-isoquinolylmethylene)-2-methyl-propane-2-sulfinamide (step 1, 0.25 g, 0.96 mmol) in THF (9.6 mL) under argon and cooled to −78° C. was added methylmagnesium bromide (3 M in diethyl ether, 0.19 mL) dropwise. The solution was stirred at −78° C. for 2 hours then 0° C. for 1 h. A further portion of Methylmagnesium bromide (3 M in diethyl ether, 1 mL) was added dropwise at 0° C. and solution stirred for 1 h. LCMS (Method T2), Rt=1.20 mins, m/z 277.13 (M+H)$^+$. The solution was quenched by addition of sat. aq. NH$_4$Cl. The mixture was extracted with EtOAc, the organic extracts washed with brine then dried over MgSO$_4$. The residue was taken forward to the next step.

Step 3; 1-(3-isoquinolyl)ethanamine

To a solution of N-[1-(3-isoquinolyl)ethyl]-2-methyl-propane-2-sulfinamide (0.27 g, 0.96 mmol) in methanol (4.8 mL) at rt was added HCl (4M in dioxane, 4 mL) dropwise. The solution was stirred at rt for 30 mins. The solution was concentrated in vacuo. The residue was then taken up in EtOAc and washed with sat. aq. NaHCO$_3$. The organic extracts were washed with brine, dried over MgSO$_4$ and concentrated in vacuo affording 1-(3-isoquinolyl)ethanamine (203 mg) as a brown oil. $^1$H NMR (500 MHz, Chloroform-d) δ 9.21 (s, 1H), 8.01-7.90 (m, 1H), 7.81-7.75 (m, 1H), 7.70-7.61 (m, 1H), 7.61 (s, 1H), 7.58-7.50 (m, 1H), 4.31 (q, J=6.7 Hz, 1H), 2.16 (br. s, 2H), 1.52 (d, J=6.7 Hz, 3H). LCMS (Method T2), Rt=0.32 mins, m/z 173.11 (M+H)$^+$.

Intermediate D1; 4-Chloro-1-methyl-6-nitro-quinolin-2-one

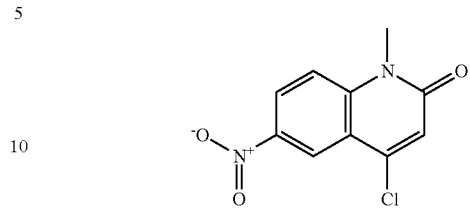

To a solution of 4-chloro-6-nitro-1H-quinolin-2-one (Intermediate D3, 5. g, 22.3 mmol) in DMF (96 mL) at 0-10° C. was added sodium hydride (60% in mineral oil) (1.78 g, 44.5 mmol) followed by a further portion of DMF (40 mL). After 20 mins iodomethane (2.77 mL, 44.5 mmol) was added dropwise. The mixture was stirred for 1 h at rt. LCMS (Method X2) Rt=1.17 mins, m/z 239.02 [M+H]$^+$. Water was added with care to the reaction mixture and stirred for 5 mins, forming a yellow precipitate which was filtered under suction. The yellow solid was washed several times with water before drying overnight under high vacuum. 4-chloro-1-methyl-6-nitro-quinolin-2-one (5.29 g) was isolated as a yellow solid.

Intermediate D2; Ethyl 4-chloro-1-methyl-6-nitro-2-oxo-quinoline-3-carboxylate

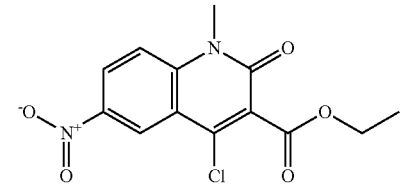

A mixture of ethyl 4-chloro-6-nitro-2-oxo-1H-quinoline-3-carboxylate (Intermediate D6, 2.29 g, 7.72 mmol) and sodium hydride (0.43 g, 10.81 mmol in mineral oil) in DMF (15 mL) was stirred at 0° C. for 15 min, iodomethane (2.40 mL, 38.6 mmol) was added. The resulting solution was stirred at 25° C. for 4 h. Water wad added, the ppt was filtered and dried. Ethyl 4-chloro-1-methyl-6-nitro-2-oxo-quinoline-3-carboxylate (2.36 g, 98%, 7.596 mmol) was obtained as a yellow solid. $^1$H NMR (500 MHz, DMSO-d$_6$) δ 8.73 (d, J=2.6 Hz, 1H), 8.56 (dd, J=9.4, 2.6 Hz, 1H), 7.89 (d, J=9.4 Hz, 1H), 4.39 (q, J=7.1 Hz, 2H), 3.70 (s, 3H), 1.32 (t, J=7.1 Hz, 3H); LCMS (Method T2) Rt=1.43 mins, m/z 311.0 [M+H]$^+$.

Intermediate D3; 4-Chloro-6-nitro-1H-quinolin-2-one

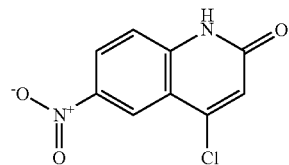

Step 1; 4-chloro-1H-quinolin-2-one

To a stirred solution of 2,4-dichloroquinoline (24.9 g, 126 mmol) in 1,4-dioxane (126 mL) was added conc. HCl (83.8 mL, 1.01 mol) drop-wise. The reaction mixture was refluxed for 18 h. The mixture was cooled to room temperature, poured into excess ice water and allowed to stir for 1 h. The precipitate was filtered and dried under vacuum to afford 4-chloro-1H-quinolin-2-one (19.2 g) as an off-white solid. LCMS (Method T2) Rt=1.25 mins, m/z 180.03 [M+H]$^+$.

Step 2; 4-chloro-6-nitro-1H-quinolin-2-one

A mixture of 4-chloro-1H-quinolin-2-one (17.8 g, 98.9 mmol) in sulfuric acid (52.7 mL, 989 mmol) was cooled to 0° C. Nitric acid (70%) (9.90 mL, 109 mmol) was added dropwise. The solution was stirred at 0° C. for 1 h and then poured onto ice water. The yellow precipitate that formed was filtered and washed with water, methanol, ethyl acetate and diethyl ether before being stirred under vacuum at 120° C. for 10 mins affording 4-chloro-6-nitro-1H-quinolin-2-one (21.5 g) as a pale yellow solid. LCMS (Method T2) Rt=1.27 mins, m/z 225.01 [M+H]$^+$.

Intermediate D4; 4-Chloro-6-nitro-1-(tetrahydropyran-4-ylmethyl)quinolin-2-one

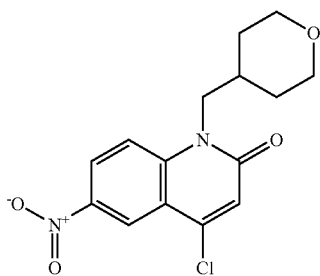

To a suspension of 4-chloro-6-nitro-1H-quinolin-2-one (Intermediate D3, 1.22 g, 5.43 mmol) in DMF (13.6 mL) was added sodium hydride (60% in mineral oil, 435 mg, 10.9 mmol). The mixture was stirred at RT for 30 mins then 4-(bromomethyl)tetrahydropyran (1.07 mL, 8.15 mmol) was added, the vial sealed and purged with argon. The solution was heated at 140° C. for 8 h. LCMS (Method T2) Rt=1.43 mins, m/z 332.16 [M+H]$^+$. The reaction was performed twice and combined of purification. Once cooled, water was added then the mixture was extracted with EtOAc. The organic extracts were washed with water and brine then dried over MgSO$_4$, filtered and concentrated in vacuo. The residue was purified by Biotage KP-Sil 100 g column eluting 20-100% EtOAc in cyclohexane affording 4-chloro-6-nitro-1-(tetrahydropyran-4-ylmethyl)quinolin-2-one (660 mg) as a yellow solid.

Intermediate D5; 1-[2-(4-Chloro-6-nitro-2-oxo-1-quinolyl)ethyl]pyrrolidine-2,5-dione

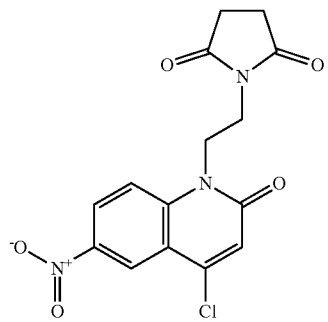

A mixture of 4-chloro-6-nitro-1H-quinolin-2-one (Intermediate D3, 270 mg, 1.20 mmol), 1-(2-bromoethyl)pyrrolidine-2,5-dione (371 mg, 1.80 mmol), cesium carbonate (783 mg, 2.40 mmol) and DMF (12.0 mL, 0.1 M) was stirred at 80° C. for 2 h. LCMS (Method T2) Rt=1.26 mins, m/z 350.05 [M+H]$^+$. Once cooled, water was added then the mixture was extracted with EtOAc. The organic extracts were washed with water and brine then dried over MgSO$_4$, filtered and concentrated in vacuo. The residue was purified by Biotage KP-Sil 25 g column eluting 20-80% EtOAc in cyclohexane affording 1-[2-(4-chloro-6-nitro-2-oxo-1-quinolyl)ethyl]pyrrolidine-2,5-dione (106 mg) as an off-white solid.

Intermediate D6; Ethyl 4-chloro-6-nitro-2-oxo-1,2-dihydroquinoline-3-carboxylate

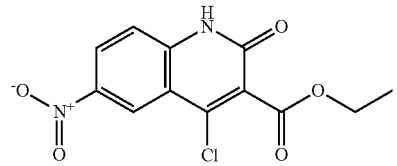

Step 1; Ethyl 4-hydroxy-6-nitro-2-oxo-1H-quinoline-3-carboxylate

6-Nitro-1H-3,1-benzoxazine-2,4-dione (10.1 g, 48.7 mmol) was dissolved in DMF (100 mL) and cooled at 0° C., diethyl malonate (37 mL, 243 mmol) was added. Sodium hydride in 4 portions was added within 30 min (3.9 g in total, 97 mmol). DMF was topped up to 200 mL during the period of adding sodium hydride. The resulting suspension was stirred at room temperature for 12 h and at 86° C. for 5 h. When cooled, water (200 mL in total) was added and the deep yellow suspension was slowly acidified with 3M HCl to pH 5, yielding a light-yellow suspension. After filtration, the solids were dried and washed with ether. The title compound (11.07 g) was obtained as a light yellow solid. $^1$H NMR (500 MHz, DMSO-d$_6$) δ 11.98 (s, 1H), 8.73 (d, J=2.6 Hz, 1H), 8.39 (dd, J=9.1, 2.6 Hz, 1H), 7.40 (d, J=9.1 Hz, 1H), 4.31 (q, J=7.1 Hz, 2H), 1.29 (t, J=7.1 Hz, 3H); LCMS (Method T2) Rt=1.42 mins, m/z 279.1 [M+H]$^+$.

Step 2; Ethyl 2,4-dichloro-6-nitroquinoline-3-carboxylate

Ethyl 4-hydroxy-6-nitro-2-oxo-1H-quinoline-3-carboxylate (from Step 1, 10 g, 36 mmol) was suspended in phosphorus (V) oxychloride (4 mL, 36 mmol). The mixture was stirred at 110° C. for 6 h, yielding a yellow solution. When cooled, POCl$_3$ was removed and the residue was dried under vacuo for 4 h. The solids were washed with ether, filtered and dried, to give the title compound (7.48 g) as a yellow solid. $^1$H NMR (500 MHz, DMSO-d$_6$) δ 8.98 (d, J=2.5 Hz, 1H), 8.67 (dd, J=9.1, 2.5 Hz, 1H), 8.30 (d, J=9.1 Hz, 1H), 4.53 (q, J=7.1 Hz, 2H), 1.39 (t, J=7.1 Hz, 3H).

Step 3; Ethyl 4-chloro-6-nitro-2-oxo-1,2-dihydroquinoline-3-carboxylate

Ethyl 2,4-dichloro-6-nitroquinoline-3-carboxylate (from Step 2, 8.4 g, 27 mmol) and sodium acetate (2.4 g, 29 mmol) were suspended in AcOH (15.0 mL). The mixture was stirred at 120° C. for 10 h. Water was added and the ppt was filtered and dried. The title compound (6.83 g) was obtained as a yellow solid. $^1$H NMR (500 MHz, DMSO-d$_6$) δ 13.00 (s, 1H), 8.67 (d, J=2.5 Hz, 1H), 8.50 (dd, J=9.1, 2.5 Hz, 1H), 7.56 (d, J=9.1 Hz, 1H), 4.38 (q, J=7.1 Hz, 2H), 1.32 (t, J=7.1 Hz, 3H); LCMS (Method T2) Rt=1.43 mins, m/z 297.0 [M+H]$^+$.

Intermediate D7: Ethyl 6-bromo-4-chloro-1-methyl-2-oxo-1,8-naphthyridine-3-carboxylate

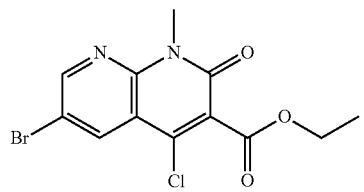 [SMILES: CCOC(=O)c1c(Cl)c2cc(Br)cnc2n(C)c1=O]

Step 1; methyl 5-bromo-2-(methylamino)pyridine-3-carboxylate

To a mixture of methyl 5-bromo-2-chloronicotinate (5.00 g, 20.0 mmol) in THF (100 mL) was added methylamine (2M in THF, 20 mL, 40 mmol). The mixture was stirred at rt for 21 h then additional methylamine (2M in THF, 5 mL, 10 mmol) was added and stirred for further 24 h. The mixture was concentrated in vacuo. The residue was diluted with water and extracted with EtOAc. The organic extracts were washed with water and brine then dried over MgSO$_4$, filtered and concentrated in vacuo. The residue was purified by Biotage Ultra 100 g eluting 1-50% EtOAc in cyclohexane affording methyl 5-bromo-2-(methylamino)pyridine-3-carboxylate (4.38 g) as a pale yellow solid. LCMS (Method T2) Rt=1.46 mins, m/z 244.99 [M+H]$^+$.

Step 2; ethyl 6-bromo-4-hydroxy-1-methyl-2-oxo-1,8-naphthyridine-3-carboxylate To a solution of methyl 5-bromo-2-(methylamino)pyridine-3-carboxylate (Step 1, 1 g, 4.08 mmol) in DCM (40.8 mL) was added triethylamine (1.14 mL, 8.16 mmol) followed by ethyl 3-chloro-3-oxo-propanoate (0.78 mL, 6.12 mmol). The solution was stirred at rt for 18 h. The temperature was raised to 60° C. and triethylamine (2.28 mL, 16.3 mmol) was added and the mixture stirred for 2 h then concentrated in vacuo. The residue was then dissolved in ethanol (40 mL) and sodium ethoxide solution (21 wt. % in ethanol) (3.05 mL, 8.16 mmol) was added at RT. The solution was stirred at rt for 18 h. LCMS (Method X2) Rt=1.49 mins, m/z 327.00 [M+H]$^+$. The solution was concentrated in vacuo. The residue was treated with water (100 mL) and 10% aq. HCl (25 mL) then extracted with DCM (2×100 mL). The combined organic extracts were washed with brine, dried over MgSO$_4$, filtered and concentrated in vacuo. The residue was purified by Biotage KP-Sil 50 g eluting 20-80% EtOAc in cyclohexane affording ethyl 6-bromo-4-hydroxy-1-methyl-2-oxo-1,8-naphthyridine-3-carboxylate (868 mg, 59%, 2.39 mmol) as a sticky yellow solid.

Step 3; ethyl 6-bromo-4-chloro-1-methyl-2-oxo-1,8-naphthyridine-3-carboxylate A solution of ethyl 6-bromo-4-hydroxy-1-methyl-2-oxo-1,8-naphthyridine-3-carboxylate (Step 2, 868 mg, 2.65 mmol) in phosphorus (V) oxychloride (10.0 mL, 107 mmol) was heated to 100° C. for 1 h. The mixture was concentrated in vacuo. The residue was taken up in DCM and washed with sat. aq. NaHCO$_3$. The organic layer was washed with brine, dried over MgSO$_4$, filtered and concentrated in vacuo. The residue was purified by Biotage KP-Sil 25 g eluting 40-100% EtOAc in cyclohexane affording ethyl 6-bromo-4-chloro-1-methyl-2-oxo-1,8-naphthyridine-3-carboxylate (502 mg, 55%, 1.45 mmol) as a yellow solid. $^1$H NMR (500 MHz, Chloroform-d) δ 8.69 (d, J=2.3 Hz, 1H), 8.41 (d, J=2.3 Hz, 1H), 4.47 (q, J=7.2 Hz, 2H), 3.79 (s, 3H), 1.41 (t, J=7.2 Hz, 3H). LCMS (Method T2) Rt=1.52 mins, m/z 344.97 [M+H]$^+$.

Intermediate D8: 6-Bromo-8-methoxy-1-methyl-4-((2-(pyrimidin-2-yl)propan-2-yl)amino)quinolin-2(1H)-one

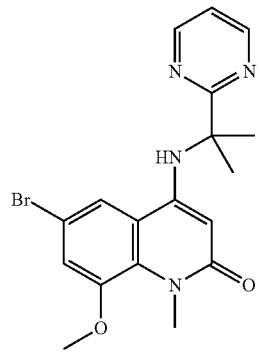 [SMILES: COc1cc(Br)cc2c(NC(C)(C)c3ncccn3)cc(=O)n(C)c12]

Step 1; methyl 5-bromo-3-methoxy-2-(methylamino)benzoate

Sodium hydride (60% in mineral oil, 0.22 g, 5.5 mmol) was added to a solution of methyl 2-amino-5-bromo-3-methoxy-benzoate (1.19 g, 4.6 mmol) in DMF (22.87 mL, 0.20 M), cooled to 0° C. After stirring at 0° C. for 30 mins, iodomethane (0.30 mL, 4.80 mmol) was added dropwise. The solution was stirred with warming to rt for 1 h. LCMS (Method T2) Rt=1.28 mins, m/z 274.01 [M+H]⁺. Reaction was quenched by careful addition of water (150 mL). The mixture was extracted with EtOAc (2×200 mL). The combined organic extracts were washed with water (2×100 mL) and brine (50 mL), dried over MgSO₄, filtered and concentrated in vacuo. Residue was purified by Biotage KP-Sil 25 g eluting 0-10% EtOAc in cyclohexane. Isolated material contained desired product and residual starting material. Fractions combined and residue further purified (in two batches) using Biotage reverse-phase 12 g C-18 column eluting 40-100% MeOH in water (containing 0.1% formic acid) affording methyl 5-bromo-3-methoxy-2-(methylamino)benzoate (427 mg).

Step 2; ethyl 6-bromo-4-hydroxy-8-methoxy-1-methyl-2-oxo-1,2-dihydroquinoline-3-carboxylate To a solution of methyl 5-bromo-3-methoxy-2-(methylamino)benzoate (427 mg, 1.56 mmol) in DCM (15.6 mL) was added ethyl 3-chloro-3-oxo-propanoate (0.30 mL, 2.34 mmol) followed by triethylamine (0.43 mL, 3.12 mmol). The solution was heated to 60° C. and stirred for 1 h. The solution was concentrated in vacuo then the residue was then dissolved in ethanol (15.6 mL) and sodium ethoxide solution (21 wt. % in ethanol, 8.31 mL, 4.67 mmol) added at rt. The solution was stirred at rt for 18 h. The solution was concentrated in vacuo. Residue was treated with water (100 mL) and 10% aq. HCl (25 mL) then extracted twice with DCM (2×100 mL). The combined organic extracts were washed with brine, dried over MgSO₄, filtered and concentrated in vacuo. The residue was purified by flash column chromatography using a Biotage KP-Sil 25 g column, eluting 20-100% EtOAc in cyclohexane affording ethyl 6-bromo-4-hydroxy-8-methoxy-1-methyl-2-oxo-1,2-dihydroquinoline-3-carboxylate (406 mg) as a crystalline yellow solid. LCMS (Method T2) Rt=1.64 mins, m/z 356.01 [M+H]⁺.

Step 3; ethyl 6-bromo-4-chloro-8-methoxy-1-methyl-2-oxo-1,2-dihydroquinoline-3-carboxylate Phosphorus oxychloride (4 mL, 42.8 mmol) was added to ethyl 6-bromo-4-hydroxy-8-methoxy-1-methyl-2-oxo-1,2-dihydroquinoline-3-carboxylate (400 mg, 1.12 mmol). The resulting mixture was then heated to 80° C. with stirring under argon for 3 h. The mixture was concentrated in vacuo, then the residue was dissolved in ethyl acetate and extracted with water. The organic layer was washed with brine then dried over MgSO₄ and concentrated in vacuo. The residue was purified by flash column chromatography using a Biotage KP-Sil 25 g column eluting with 10-80% EtOAc in cyclohexane affording ethyl 6-bromo-4-chloro-8-methoxy-1-methyl-2-oxo-1,2-dihydroquinoline-3-carboxylate (281 mg) as a white solid. LCMS (Method T2) Rt=1.60 mins, m/z 373.98 [M+H]⁺.

Step 4; 6-bromo-8-hydroxy-1-methyl-4-((2-(pyrimidin-2-yl)propan-2-yl)amino)quinolin-2(1H)-one A suspension of ethyl 6-bromo-4-chloro-8-methoxy-1-methyl-2-oxo-1,2-dihydroquinoline-3-carboxylate (80 mg, 0.21 mmol), 2-pyrimidin-2-ylpropan-2-amine dihydrochloride (67 mg, 0.32 mmol) and DIPEA (0.19 mL, 1.07 mmol) in NMP (1.07 mL) was heated to 160° C. for 1 h. LCMS (Method T2) Rt=1.57 mins, m/z 475.10 [M+H]⁺. Lithium chloride (54 mg, 1.28 mmol) was added to the mixture and heated to 160° C. for 4 h in heating block. LCMS (Method T2) Rt=1.38 mins, m/z 389.06 [M+H]⁺. The mixture was purified using a Biotage 12 g C-18 reverse phase column eluting from 40-100% MeOH in water (containing 0.1% formic acid) affording 6-bromo-8-hydroxy-1-methyl-4-((2-(pyrimidin-2-yl)propan-2-yl)amino)quinolin-2(1H)-one (23 mg) as an orange solid.

Step 5; 6-bromo-8-methoxy-1-methyl-4-((2-(pyrimidin-2-yl)propan-2-yl)amino)quinolin-2(1H)-one To a mixture of 6-bromo-8-hydroxy-1-methyl-4-((2-(pyrimidin-2-yl)propan-2-yl)amino)quinolin-2(1H)-one (23 mg, 0.06 mmol), potassium carbonate (24.5 mg, 0.18 mmol) in acetone (2 mL) was added dimethylsulfate (6.7 uL, 0.071 mmol). The mixture was stirred at rt for 18 h after which time a further 1.2 equiv. dimethylsulfate (6.7 uL, 0.07 mmol) was added and stirring continued for 6 h. Methanol was added to the mixture which was filtered through a pad of Celite™ and washed through with methanol. The filtrate was concentrated in vacuo then purified using Biotage reverse-phase 12 g C-18 column eluting 40-100% MeOH in water (containing 0.1% formic acid) affording 6-bromo-8-methoxy-1-methyl-4-((2-(pyrimidin-2-yl)propan-2-yl)amino)quinolin-2(1H)-one (17 mg) as an orange solid. LCMS (Method T2) Rt=1.46 mins, m/z 403.08 [M+H]⁺.

Intermediate D9: 1-methyl-6-nitroquinazoline-2,4(1H,3H)-dione

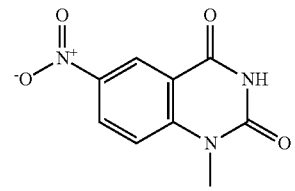

Step 1; 1-methylquinazoline-2,4(1H,3H)-dione

Ethyl chloroformate (20 mL, 209 mmol) was added to 2-(methylamino)benzamide (10 g, 67 mmol). The vial was sealed and heated to 100° C. for 4 h. The ethyl chloroformate was removed under vacuum and the residue loaded onto Biotage 50 g KP-Sil column (2 batches) and eluted with 20-100% EtOAc in cyclohexane followed by 0-20% MeOH in DCM. 1-methylquinazoline-2,4(1H,3H)-dione (5.27 g) was obtained as a white solid. LCMS (Method T2) Rt=0.83 mins, m/z 177.06 [M+H]⁺.

Step 2; 1-methyl-6-nitroquinazoline-2,4(1H,3H)-dione

A solution of 1-methylquinazoline-2,4(1H,3H)-dione (5.27 g, 29.91 mmol) in sulfuric acid (80 mL, 1501 mmol) was cooled to 0° C. and nitric acid (70%, 2.99 mL, 32.91 mmol) was added dropwise. The solution was stirred at 0° C. with warming to rt over 2.5 h. The solution was poured onto ice water. The yellow precipitate that formed was filtered and washed with water (500 mL). 1-methyl-6-nitroquinazoline-2,4(1H,3H)-dione (6.38 g, 96%, 28.847 mmol) was obtained as an off-white powder. LCMS (Method T2) Rt=0.90 mins, m/z 222.05 [M+H]⁺.

Intermediate D10: 4-Chloro-1-(cyclohexylmethyl)-6-nitroquinolin-2(1H)-one

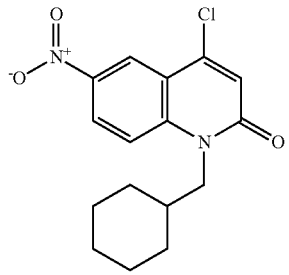

To a mixture of 4-chloro-6-nitro-1H-quinolin-2-one (Intermediate D3, 1.20 g, 5.343 mmol) and cesium carbonate (2.61 g, 8.014 mmol) in DMF (10.68 mL) was added bromomethylcyclohexane (1.89 g, 10.69 mmol) and the resulting mixture stirred at 140° C. for 1 h. Once cooled to rt, water was added to the mixture then extracted with EtOAc. Combined organic extracts were washed with water and brine, dried over MgSO$_4$. The residue was purified by Biotage KP-Sil 50 g eluting 0-30% EtOAc in cyclohexane affording 4-chloro-1-(cyclohexylmethyl)-6-nitroquinolin-2(1H)-one (461 mg) as a pale yellow solid. LCMS (Method T2) Rt=1.66 mins, m/z 321.10 [M+H]$^+$.

Intermediate D11: 4-chloro-1-(cyclopropylmethyl)-6-nitro-quinolin-2-one

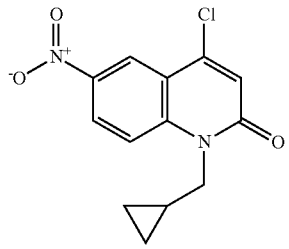

To a suspension of 4-chloro-6-nitro-1H-quinolin-2-one (Intermediate D3, 100 mg, 0.445 mmol) in DMF (2 mL) was added bromomethyl cyclopropane (0.09 mL, 0.89 mmol) and Cesium Carbonate (219 mg, 0.67 mmol). The reaction was stirred at rt for 21 h, before being diluted with DCM and washed with 1 M aq HCl, and brine. The organic layer was dried over MgSO$_4$ and concentrated under reduced pressure to give a residue with some DMF remaining. Purification via Biotage KP-Sil 25 g eluting 12-100% EtOac in cyclohexane afforded 4-chloro-4-chloro-1-(cyclopropylmethyl)-6-nitroquinolin-2-one (62.3 mg) as a yellow solid. LCMS (Method T2) Rt=1.51 mins, m/z 279 [M+H]$^+$.

Intermediate D12:1-(2-((tert-butyldimethylsilyl)oxy)ethyl)-4-chloro-6-nitroquinolin-2(1H)-one

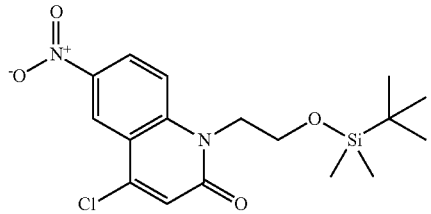

Prepared by a method analogous to that used in the preparation of Intermediate D11, starting from 4-chloro-6-nitro-1H-quinolin-2-one (Intermediate D3) and (2-bromoethoxy)(tert-butyl)dimethylsilane. LCMS (Method T2) Rt=1.68 mins, m/z 383 [M+H]$^+$.

Intermediate D13:4-chloro-1-(cyclobutylmethyl)-6-nitroquinolin-2(1H)-one

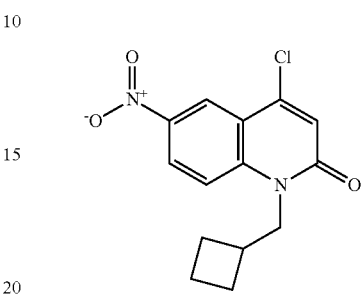

Prepared by a method analogous to that used in the preparation of Intermediate D11, starting from 4-chloro-6-nitro-1H-quinolin-2-one (Intermediate D3) and (bromomethyl)cyclobutane LCMS (Method T2) Rt=1.56 mins, m/z 293 [M+H]$^+$.

Intermediate D14: 1-benzyl-4-chloro-6-nitro-quinolin-2-one

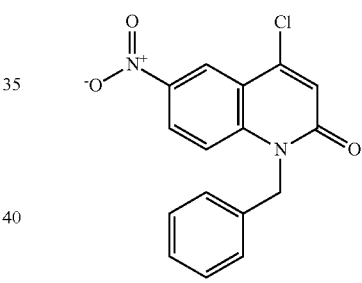

Prepared by a method analogous to that used in the preparation of Intermediate D11, starting from 4-chloro-6-nitro-1H-quinolin-2-one (Intermediate D3) and benzyl bromide $^1$H NMR (500 MHz, Chloroform-d) δ 8.94 (d, J=2.6 Hz, 1H), 8.33 (dd, J=9.3, 2.6 Hz, 1H), 7.42 (d, J=9.3 Hz, 1H), 7.37-7.32 (m, 2H), 7.32-7.29 (m, 1H), 7.22-7.18 (m, 2H), 7.13 (s, 1H), 5.59 (s, 2H).

Intermediate E1; 4,6-Dichloro-5-cyano-N-methyl-pyridine-2-carboxamide

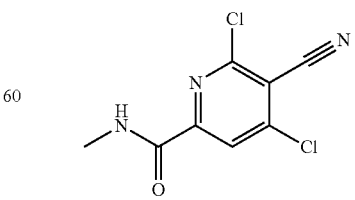

4,6-dichloro-5-cyano-pyridine-2-carboxylic acid (310 mg, 1.43 mmol) was suspended in DCM (15 mL) and DMF (0.06 mL) under argon and cooled to 0° C. Oxalyl chloride 2M in DCM (1.50 mL, 3 mmol) was added dropwise over 15 mins. The mixture was stirred at rt for 1 h under nitrogen, after which time all material was in solution, then cooled again to 0° C. Methanamine 2M in THF (3.50 mL, 7 mmol) was added dropwise over 10 mins and the resulting mixture continued to stir at 0° C. for 1.5 h, then warmed to rt and opened to air. After 1 h, pH was adjusted to pH6 using 10% citric acid/sat. sodium bicarbonate solution as required, then the resulting mixture extracted with DCM, using a phase separator cartridge to separate and dry aqueous. Resulting solution was evaporated under reduced pressure to give 4,6-dichloro-5-cyano-N-methyl-pyridine-2-carboxamide as beige solid (280 mg). $^1$H NMR (500 MHz, DMSO-d$_6$) δ 8.98 (q, J=4.4 Hz, 1H), 8.25 (s, 1H), 2.82 (d, J=4.7 Hz, 3H).

Intermediate E1b:
4,6-dichloro-5-cyano-N,N-dimethylpicolinamide

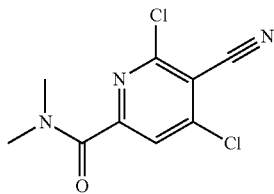

Prepared by a method analogous to that used for the preparation of intermediate E1a. $^1$H NMR (500 MHz, Chloroform-d) δ 7.82 (s, 1H), 3.16 (s, 3H), 3.14 (s, 3H).

Intermediate E2:
N-(4-Bromo-5-chloropyridin-2-yl)acetamide

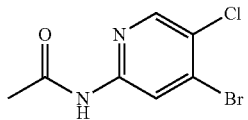

To a solution of 4-bromo-5-chloro-pyridin-2-amine (300 mg, 1.45 mmol), N,N-dimethylpyridin-4-amine (53 mg, 0.43 mmol) and acetyl chloride (0.31 mL, 4.34 mmol) in DMF (10.0 mL) was added triethylamine (0.40 mL, 2.89 mmol). The resulting solution was stirred at 25° C. for overnight. Brine was added and the precipitated N-(4-bromo-5-chloro-2-pyridyl)acetamide (126 mg) was collected and dried. The material was used in the next step without further purification. LCMS (Method T2) Rt=1.31 mins, m/z 250.9 [M+H]$^+$.

Intermediate E3:
N-(4-Bromo-5-chloropyridin-2-yl)-N-methylacetamide

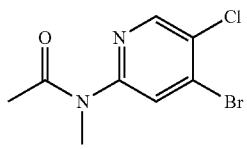

A mixture of N-(4-bromo-5-chloro-2-pyridyl)acetamide (46 mg, 0.184 mmol) and sodium hydride (10.3 mg, 0.258 mmol) was stirred at 25° C. in DMF (2.00 mL) for 15 min, iodomethane (0.06 mL, 0.922 mmol) was then added. The resulting brown solution was stirred at 25° C. for 1 h. Brine was added and extracted with EtOAc. The crude was then purified by HPLC. N-(4-bromo-5-chloro-2-pyridyl)-N-methyl-acetamide (12 mg) was obtained as an orange oil. $^1$H NMR (500 MHz, Methanol-d$_4$) δ 8.53 (s, 1H), 8.01 (s, 1H), 3.39 (s, 3H), 2.17 (s, 3H). LCMS (Method T2) Rt=1.26 mins, m/z 262.9 [M+H]$^+$.

Intermediate E4: 3,4-Dichloropicolinamide

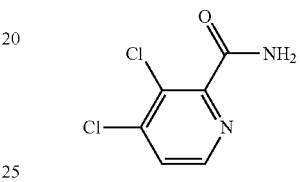

3,4-Dichloropyridine-2-carboxylic acid (238 mg, 1.24 mmol) was suspended in DCE (4.0 mL) and thionyl chloride (0.90 mL, 12.40 mmol) was then added. The resulting suspension was stirred under microwave irradiation at 100° C. for 8 h. When cooled, all volatiles were removed, an dark orange oil was obtained and dried in vacuo for 15 min. DCM (6.0 mL) was introduced to the residue and conc. NH$_3$ (4.0 mL) was added and the mixture was stirred at rt for 16 h. The resulting mixture was washed with NaHCO>3 solution and water and dried with Na$_2$SO$_4$. After filtration and removal of the solvent, 3,4-dichloropyridine-2-carboxamide (29 mg, 12%, 0.152 mmol) were obtained as a brown solid, washed with ether and dried. $^1$H NMR (500 MHz, DMSO-d$_6$) δ 8.49 (d, J=5.2 Hz, 1H), 8.10-8.06 (s, broad, 1H), 7.85-7.82 (s, broad, 1H), 7.83 (d, J=5.2 Hz, 1H). LCMS (Method T2) Rt=0.40 mins, m/z 192.9 [M+H]$^+$.

Intermediate E5: 3,4-Dichloropicolinonitrile

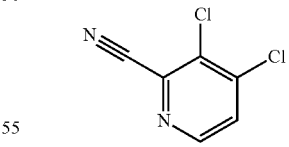

To a solution of 3,4-dichloropyridine-2-carboxamide (29 mg, 0.152 mmol) and triethylamine (0.15 mL, 1.063 mmol) in ethyl acetate (4.0 mL) at 0° C., trifluoroacetic anhydride (0.15 mL, 1.063 mmol) in ethyl acetate (1 mL) was added. The solution was stirred at this temperature for 1 h, then volatiles were removed and the crude was dried under vacuum for 30 min. The crude was then dissolved in 2 mL of NMP and divided into aliquots which were used in subsequent reactions without further purification. LCMS (Method T2) Rt=1.11 mins, m/z 195.1 [M+Na]$^+$.

Intermediate E6a: (S)-(4,5-Dichloropyridin-2-yl)(2-(methoxymethyl)pyrrolidin-1-yl)methanone

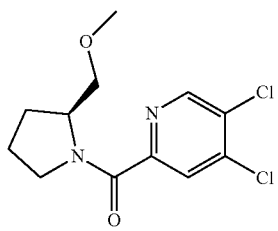 [SMILES: COC[C@@H]1CCCN1C(=O)c1cc(Cl)c(Cl)cn1]

A mixture of HATU (0.15 g, 0.41 mmol), 4,5-dichloro-pyridine-2-carboxylic acid (39 mg, 0.20 mmol) and (2S)-2-(methoxymethyl)pyrrolidine (1.32 mL, 1.02 mmol) was stirred at 25° C. for 16 h. HPLC purification gave (4,5-dichloro-2-pyridyl)-[(2S)-2-(methoxymethyl)pyrrolidin-1-yl]methanone (39 mg) as a colourless oil. LCMS (Method T2) Rt=1.39 mins, m/z 289.1 [M+H]$^+$. NMR showed two rotamers: Rota me r A. $^1$H NMR (500 MHz, Methanol-d$_4$) δ 8.71 (s, 1H), 7.96 (s, 1H), 4.44-4.38 (m, 1H), 3.82-3.75 (m, 1H), 3.68-3.64 (m, 2H), 3.40 (s, 3H), 2.14-1.96 (m, 5H). Rotamer B: δ 8.69 (s, 1H), 7.95 (s, 1H), 4.85-4.78 (m, 1H), 3.75-3.69 (m, 1H), 3.63-3.58 (m, 2H), 3.17 (s, 3H), 2.14-1.96 (m, 4H), 1.94-1.80 (m, 1H).

Intermediate E6b: rac-(4,5-Dichloropyridin-2-yl)(2-(2-methoxyethyl)pyrrolidin-1-yl)methanone

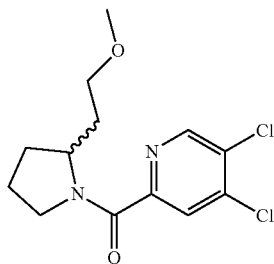 [SMILES: COCCC1CCCN1C(=O)c1cc(Cl)c(Cl)cn1]

Prepared by a method analogous to that used in the preparation of example E6a. NMR showed two rotamers: Rotamer A: $^1$H NMR (500 MHz, Methanol-d$_4$) δ 8.71 (s, 1H), 7.94 (s, 1H), 4.40-4.30 (m, 1H), 3.82-3.74 (m, 1H), 3.64-3.57 (m, 1H), 3.56-3.50 (m, 2H), 3.36 (s, 3H), 2.34-2.24 (m, 1H), 2.15-1.98 (m, 2H), 1.90-1.80 (m, 2H), 1.76-1.68 (m, 1H). Rotamer B: δ 8.72 (s, 1H), 7.97 (s, 1H), 4.71-4.65 (m, 1H), 3.74-3.64 (m, 2H), 3.31-3.22 (m, 2H), 3.15 (s, 3H), 2.15-1.98 (m, 3H), 1.97-1.91 (m, 1H), 1.76-1.68 (m, 1H), 1.64-1.56 (m, 1H). LCMS (Method T2) Rt=1.42 mins, m/z 303.1 [M+H]$^+$.

Intermediate E7:
4-Chloro-5-cyano-N-methylpicolinamide

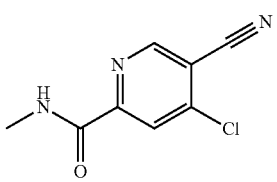

To a suspension of 4-chloro-5-cyano-pyridine-2-carboxylic acid (50 mg, 0.27 mmol) in DCM (15 mL) and anhydrous DMF (0.06 mL) under argon at 0° C., oxalyl chloride (0.05 mL, 0.575 mmol) was added dropwise over 15 mins. The reaction was stirred at rt for 1 h before being cooled to 0° C. Methanamine (2M in THF, 0.67 mL, 1.34 mmol) was added and the resulting mixture continued to stir at rt for 2.5 h before the reaction was opened to air. After 1 h, the pH was adjusted to pH 6 using 10% citric acid/sat. aq. sodium bicarbonate solution as required, then the resulting mixture extracted with DCM, using a phase separator cartridge to separate and dry aqueous. The resulting filtrate was evaporated under reduced pressure to give 4-chloro-5-cyano-N-methyl-pyridine-2-carboxamide (50 mg, 89%, 0.243 mmol). $^1$H NMR (500 MHz, DMSO-d6) δ 9.20 (d, J=1.6 Hz, 1H), 9.08 (s, 1H), 8.27 (d, J=2.4 Hz, 1H), 2.84 (d, J=4.8 Hz, 3H).

The following tabulated intermediates in Table 31 were prepared by methods analogous to that used in the preparation of Example 19a, using the amino starting material as shown in the table and the appropriate chloropyrimidine obtained from commercial suppliers.

TABLE 31 compounds prepared by a method analogous to that used for the preparation of Example 19a

| Name | Structure | Characterisation | Starting material |
|---|---|---|---|
| Intermediate F1a: 6-((2,5-dichloropyrimidin-4-yl)amino)-1-methyl-4-((2-(pyrimidin-2-yl)propan-2-yl)amino)quinolin-2(1H)-one | 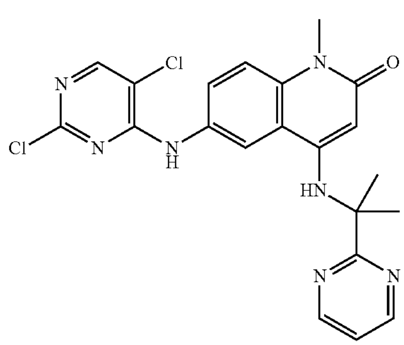 [SMILES: Cn1c(=O)cc(NC(C)(C)c2ncccn2)c2cc(Nc3nc(Cl)ncc3Cl)ccc21] | LCMS (Method T2) RT 1.45 min; m/z 456.1047 [M + H]$^+$. | Intermediate A3a: 6-amino-1-methyl-4-((2-(pyrimidin-2-yl)propan-2-yl)amino)quinolin-2(1H)-one |

TABLE 31-continued compounds prepared by a method analogous to that used for the preparation of Example 19a

| Name | Structure | Characterisation | Starting material |
|---|---|---|---|
| Intermediate F1b: 1-((6-((2,5-dichloropyrimidin-4-yl)amino)-1-methyl-2-oxo-1,2-dihydroquinolin-4-yl)amino)cyclopropane-1-carbonitrile | 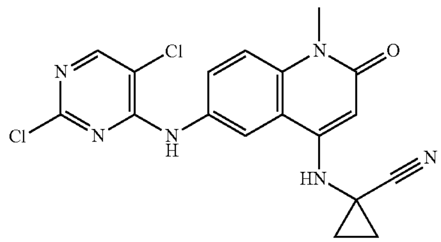 [SMILES: Cn1c(=O)cc(NC2(C#N)CC2)c2cc(Nc3nc(Cl)ncc3Cl)ccc21] | LCMS (Method T2) RT 1.35 min; m/z 401.0637 [M + H]⁺ | Intermediate A3f: 1-((6-amino-1-methyl-2-oxo-1,2-dihydroquinolin-4-yl)amino)cyclopropane-1-carbonitrile |
| Intermediate F1c: 6-((2,5-dichloropyrimidin-4-yl)amino)-1-methyl-4-((1-(pyrimidin-2-yl)ethyl)amino)quinolin-2(1H)-one | 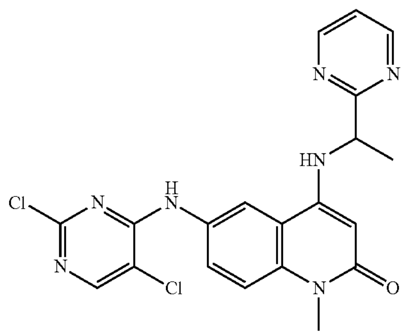 [SMILES: CC(Nc1cc(=O)n(C)c2ccc(Nc3nc(Cl)ncc3Cl)cc12)c1ncccn1] | LCMS (Method T4) Rt = 2.68 mins, m/z 442.09 [M + H]⁺. | Intermediate A1b: 6-amino-1-methyl-4-(1-pyrimidin-2-ylethylamino)quinolin-2-one |
| Intermediate F1d: 6-((2,5-dichloropyrimidin-4-yl)amino)-1-methyl-4-((1-(1-methyl-1H-1,2,4-triazol-3-yl)ethyl)amino)quinolin-2(1H)-one | 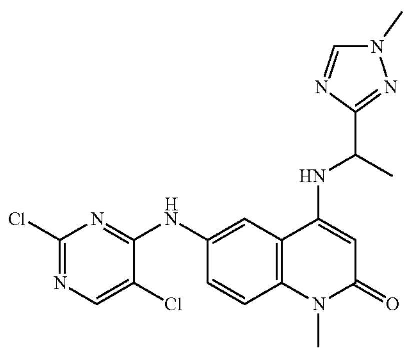 [SMILES: CC(Nc1cc(=O)n(C)c2ccc(Nc3nc(Cl)ncc3Cl)cc12)c1ncn(C)n1] | LCMS (Method T2) Rt = 1.37 mins, m/z 445.10 [M + H]⁺. | Intermediate A4l: 6-amino-1-methyl-4-((1-(1-methyl-1H-1,2,4-triazol-3-yl)ethyl)amino)quinolin-2(1H)-one |
| Intermediate F1e: (R)-4-((1-cyclopropylethyl)amino)-6-((2,5-dichloropyrimidin-4-yl)amino)-1-methylquinolin-2(1H)-one | 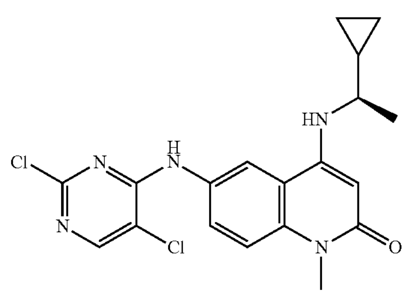 [SMILES: C[C@@H](Nc1cc(=O)n(C)c2ccc(Nc3nc(Cl)ncc3Cl)cc12)C1CC1] | LCMS (Method T4) Rt = 2.91 mins, m/z 404.10 [M + H]⁺. | Intermediate A1a: (R)-6-amino-4-((1-cyclopropylethyl)amino)-1-methylquinolin-2(1H)-one |
| Intermediate F1f: 6-((2,5-dichloropyrimidin-4-yl)amino)-4-((1-methoxy-2-methylpropan-2-yl)amino)-1-methylquinolin-2(1H)-one | 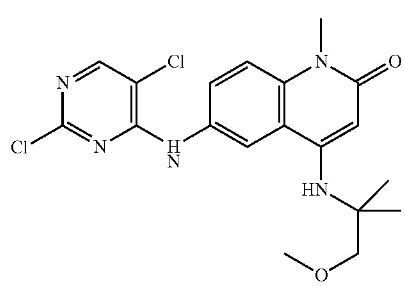 [SMILES: COCC(C)(C)Nc1cc(=O)n(C)c2ccc(Nc3nc(Cl)ncc3Cl)cc12] | LCMS (Method T2) Rt = 1.50 min, m/z 422 [M + H]⁺. | Intermediate A4e: 6-amino-4-((1-methoxy-2-methylpropan-2-yl)amino)-1-methylquinolin-2(1H)-one |

TABLE 31-continued compounds prepared by a method analogous to that used for the preparation of Example 19a

| Name | Structure | Characterisation | Starting material |
|---|---|---|---|
| Intermediate F1g: 6-((2,5-dichloro-6-methylpyrimidin-4-yl)amino)-1-methyl-4-((2-(pyrimidin-2-yl)propan-2-yl)amino)quinolin-2(1H)-one | 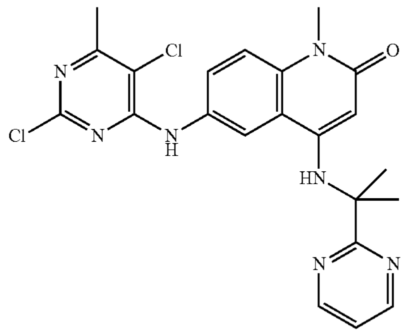 [SMILES: Cc1nc(Cl)nc(Nc2ccc3c(c2)c(NC(C)(C)c2ncccn2)cc(=O)n3C)c1Cl] | LCMS (Method T2) Rt = 1.50 min, m/z 470 [M + H]$^+$. | Intermediate A3a: 6-amino-1-methyl-4-((2-(pyrimidin-2-yl)propan-2-yl)amino)quinolin-2(1H)-one |
| Intermediate F1h: 6-((2,5-dichloropyrimidin-4-yl)amino)-4-((1-(4,5-dihydropyrimidin-2-yl)ethyl)amino)-1-methyl-1,8-naphthyridin-2(1H)-one | 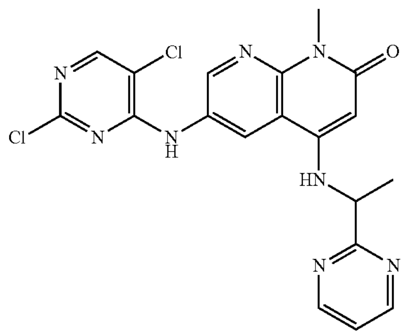 [SMILES: CC(Nc1cc(=O)n(C)c2ncc(Nc3nc(Cl)ncc3Cl)cc12)c1ncccn1] | LCMS (Method T2) Rt = 1.40 min, m/z 443 [M + H]$^+$. | Intermediate A10b: 6-amino-1-methyl-4-((1-(pyrimidin-2-yl)ethyl)amino)-1,8-naphthyridin-2(1H)-one |
| Intermediate F1i: 6-((2,5-dichloropyrimidin-4-yl)amino)-1-methyl-4-((2-(pyrimidin-2-yl)propan-2-yl)amino)quinazolin-2(1H)-one | 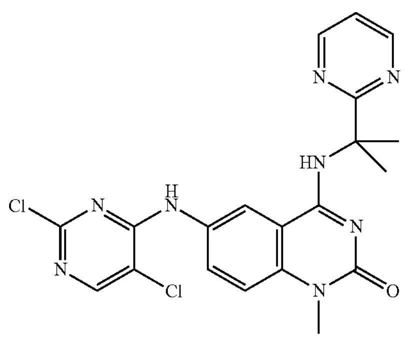 [SMILES: Cn1c(=O)nc(NC(C)(C)c2ncccn2)c2cc(Nc3nc(Cl)ncc3Cl)ccc21] | LCMS (Method T2) Rt = 1.40 min, m/z 457 [M + H]$^+$. | Intermediate A4y: 6-amino-1-methyl-4-((2-(pyrimidin-2-yl)propan-2-yl)amino)quinazolin-2(1H)-one |

Biological Assays

HTRF Assay

Each 15 μL HTRF reaction in a 384-well black Proxiplate (Perkin Elmer) contained either 1 nM (data in table 1b) or 10 nM (data in table 1a) Trx-6xHis-BCL6 (in house-produced, human BCL6 BTB domain covering amino-acid sequence 5-129), 300 nM BCOR-AF633 peptide (RSEIISTAPSS-WWPGP-Cys-AlexaFluor 633-amide, Cambridge Research Biochemical) and 0.5 (data in table 1b) or 1 nM (data in table 1a) anti-6xHis-Terbium cryptate (CisBio Bioassays, France), in assay buffer (25 mM Hepes pH8, 100 mM NaCl, 0.05% Tween20, 0.5 mM TCEP, 0.05% bovine serum albumin). Test compounds in DMSO or DMSO alone were added to the wells using an ECHO550 acoustic dispenser (Labcyte Inc) to give the appropriate test concentration in 0.7% v/v DMSO final. After 2 hours incubation at room temperature the plate was read on an Envision plate reader (Perkin Elmer) with 337 nm laser excitation, a first emission filter APC 665 nm and a second emission filter Europium 615 nm. The % inhibition at each concentration was calculated by normalising FRET ratio to the appropriate high (DMSO with all reagents) and low (DMSO without BCL6) controls. The compound $IC_{50}S$ were determined using GraphPad Prism 6.0 or Dotmatics (Bishops Storford, UK) software by fitting the normalised data to a sigmoidal four-parameter logistic fit equation.

The results of this assay are shown in Tables 1a and 1b above.

NanoBRET Assay

A cellular nano-Bioluminescence Resonance Energy Transfer (nanoBRET) assay (Promega NanoBRET Nano-Glo Detection System, catalogue number N1662) was used to detect inhibition of the BCL6-NCOR2(SMRT) corepressor protein-protein interaction. DNA encoding full length BCL6 and NCOR2 were inserted into pFC32K.NanoLuc and pFC14K.HaloTag vectors (Promega) to produce C-terminal tagged fusion proteins BCL6-nanoLuc and NCOR2-HaloTag, respectively. HEK293T cells were plated (5×10$^5$) in T75 tissue culture flask and bulk transfected 48 hours later with Fugene 6 (Promega cat. #E2691) reagent and 18 μg total DNA plasmids encoding BCL6-nanoLuc as donor and NCOR2-HaloTag as acceptor, at a donor:acceptor DNA ratio of 1:25. At 24 hr post-transfection, HEK293T cells were collected and stored in liquid nitrogen in 90% FBS (PAN Biotech UK) and 10% DMSO. At the time of assay, compounds (100 nL/well) and NanoBRET 618 ligand (10 nL of 1 mg/ml stock solution per well) were dispensed in a dry 384-well NUNC white assay plate (ThermoScientific NUNC cat. #10080681) using Echo550 acoustic dispensing (Labcyte Inc.). Frozen transfected HEK293T cells were thawed, centrifuged and freezing medium was replaced by phenol red-free OptiMEM+4% FBS (Life Technology). The cell density was adjusted to $3 \times 10^5$ cells/ml and 20 μL (6000 cells) were plated in each well containing test compounds (0.0125-50 μM) in DMSO or DMSO alone and 0.5 μg/ml NanoBRET 618 fluorescence ligand, in 0.55% v/v DMSO final concentration. Cells were incubated for 6 hr at 37° C./5% $CO_2$ then NanoBRET furimazine substrate (Promega) was added to give a final concentration of 10 μM. After a short centrifugation the plates were read on an Envision (Perkin Elmer) plate reader equipped with a LUM/D600 Dual mirror, Lum 450/40 nm bandpass and D605 nm longpass filters, with a 0.2 sec reading to determine the BRET ratio. The % inhibition at each test concentration was calculated by normalising the BRET ratio to the appropriate high and low controls. The compound $IC_{50}S$ were determined using Graphpad Prism 6.0 or Dotmatics software by fitting the normalised data to a sigmoidal four-parameter logistic fit equation The results obtained using this assay are shown in Tables 2a and 2b above.

Immunofluorescence-Based BCL6 Degradation Assay $DC_{50}$ values (compound concentration at which 50% of endogenous BCL6 protein is degraded) were determined in SUDHL-4 cells (American Type Culture Collection) in an immunofluorescence-based assay using an InCell2200 high content imaging system (GE Healthcare). Briefly, 40 μL of lymphoma suspension cells cultured in RPMI 1640-10% FBS (Sigma-Aldrich or PAN Biotech UK Ltd) were platted on fibronectin (Sigma catalogue F1141)-coated 384 well Cell Carrier Ultra plate (Perkin Elmer catalogue 6057300) at 1.2 104 cells/well. After 20 hours cell culture at 37° C./C02 incubator, compounds were dispensed in the cell culture plate using ECHO550 acoustic dispenser (Labcyte, Inc.), as 8 point-concentration response (ranging from 5 nM to 10 μM) in 0.67% final DMSO concentration. Cells were incubated with compound for 2 hours at 37° C./C02 incubator followed by fixation in 4.5% formaldehyde (37% formaldehyde solution, Sigma catalogue F8775) at room temperature for 15 min. After fixing, cells were washed in 1×TBS (Tris Buffer Saline) using a Power Washer 384 (Tecan Group Ltd). Blocking and cell permeabilisation were performed by incubating the fixed cells for 1 hour at room temperature in 1×TBS, 5% BSA, 1% Triton $X_{100}$, followed by three washes on PW384 plate washer. Primary and secondary antibodies were prepared in 1×TBS, 1% BSA, 0.2% Triton $X_{100}$. BCL6 expression was detected by incubating the cells for 1 h30 with BCL6 rabbit polyclonal antibody (Sigma Catalogue HPA004899) at 1:250, 0.8 μg/ml, followed by 1 hour in chicken anti-Rabbit Alexa 488 conjugated antibody (Life Technology) at 1:500. After incubation in each antibody, cells were washes four times in 1×TBS-0.05% tween on PW384 plate washer. Cells were finally incubated for 60 min with nuclear staining RedDot2 dye (Biotium) at 0.5× the stock concentration in 1×TBS. BCL6 expression in the absence or presence of compound was detected on InCell2200 with 20× objective and quantified on InCell Analyser 3.7.2 workstation (GE Healthcare). The % response at each concentration was calculated by normalising BCL6 expression in the presence of compound to the appropriate high (DMSO) and low (DMSO with 7 μM CCT369260) controls. The compound DC50s were determined using GraphPad Prism 6.0 or Dotmatics (Bishops Storford, UK) software by fitting the normalised data to a sigmoidal four-parameter logistic fit equation.

14-Day Cell Proliferation Assay

SU-DHL-4 cells were seeded in 96-well culture plates at a density of 2000 cells/well in RPMI-1640 medium (Sigma-Aldrich) supplemented with 10% FBS (Gibco). Compounds were initially dispensed into 96-well U-bottom plates using an Echo 550 acoustic dispenser (Labcyte Inc.), then diluted in RPMI-1640 medium and transferred onto the cells. Cells were treated with 8 compound concentrations in duplicate, ranging from 1 nM to 10 μM, in a final DMSO concentration of 0.1% and final volume of 100 μl. Cells were incubated with compound for 14 days, with medium changes at days 3, 7 and 10 carried out as follows: fresh 96-well cell culture plates were prepared containing 100 μl medium plus compound at the assay concentrations (white plates were used on day 10 to optimise luminescence measurement). Assay plates containing cells were vortexed to mix and cell density in one control well was counted using a Coulter Z2 cell counter (Beckman Coulter). The volume of medium containing 2000 cells in the control well was calculated and this volume of cells was transferred from every well of the assay plates to the corresponding well of the fresh plates containing compound. After 14 days, CellTiter Glo reagent (Promega) was added to the medium in each well of the assay plate at a ratio of 1:2, mixed on a plate shaker, then incubated at room temperature for 10 minutes. Luminescence was measured using an Envision plate reader (Perkin Elmer) and the relative luminescence at each compound concentration, compared to DMSO alone, was calculated. IC50 were determined using a 4-parameter curve fit in Dotmatics (Bishops Stortford, UK).

While specific embodiments of the invention have been described herein for the purpose of reference and illustration, various modifications will be apparent to a person skilled in the art without departing from the scope of the invention as defined by the appended claims.

The invention claimed is:

1. A compound of Formula (I), or a pharmaceutically acceptable salt or solvate thereof, as shown below:

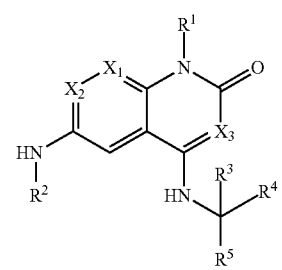

Formular (I)

wherein:
X₁ is selected from N or $CR^a$, wherein $R^a$ is selected from hydrogen, (1-2C)alkyl, halogen, hydroxy, (1-2C)alkoxy, (1-2C)haloalkyl, (1-2C)haloalkoxy, (2-4C)alkenyl, (2-4C)alkynyl, nitro, cyano or $NR^bR^c$, wherein $R^b$ and $R^c$ are each independently selected from hydrogen or (1-2C)alkyl;
X₂ is selected from N, CH, CF, CCl or C—CH₃;
X₃ is selected from N or $CR^d$, wherein $R^d$ is selected from hydrogen, fluoro, chloro or methyl;

R$^1$ is selected from hydrogen or a group of the formula:

-L-Y-Z wherein:
  L is absent or (1-5C)alkylene optionally substituted by one or more substituents selected from (1-2C)alkyl or oxo;
  Y is absent or O, S, SO, SO$_2$, N(R$^e$), C(O), C(O)O, OC(O), C(O)N(R$^e$), N(R$^e$)C(O), N(R$^e$)C(O)N(R$^f$), N(R$^e$)C(O)O, OC(O)N(R$^e$), S(O)$_2$N(R$^e$), or N(R$^e$)SO$_2$, wherein R$^e$ and R$^f$ are each independently selected from hydrogen or (1-4C)alkyl; and
  Z is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Z is optionally further substituted by one or more substituent groups independently selected from oxo, (1-4C)alkyl, halo, (1-4C)haloalkyl, (1-4C)haloalkoxy, amino, (1-4C)aminoalkyl, cyano, hydroxy, carboxy, carbamoyl, sulphamoyl, mercapto, ureido, NR$^g$R$^h$, OR$^g$, C(O)R$^g$, C(O)OR$^g$, OC(O)R$^g$, C(O)N(R$^g$)R$^h$, N(R$^g$)C(O)R$^h$, S(O)$_y$R$^g$ (where y is 0, 1 or 2), SO$_2$N(R$^g$)R$^h$, N(R$^g$)SO$_2$R$^g$, Si(R$^g$)R$^h$)R$^i$ or (CH$_2$)$_z$NR$^g$R$^h$ (where z is 1, 2 or 3); wherein R$^g$, R$^h$ and R$^i$ are each independently selected from hydrogen, (1-6C)alkyl or (3-6C)cycloalkyl; or R$^g$ and R$^h$ can be linked such that, together with the nitrogen atom to which they are attached, they form a 4-9 membered heterocyclic ring which is optionally substituted by one or more substituents selected from (1-4C)alkyl, halo, (1-4C)haloalkyl, (1-4C)haloalkoxy, (1-4C)alkoxy, (1-4C)alkylamino, amino, cyano or hydroxy;
R$^2$ is selected from:
  i) a group of Formula A shown below:

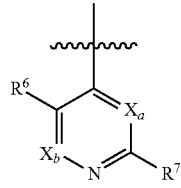

Formula A wherein:
  ⟋⟍ denotes the point of attachment;
  X$_a$ and X$_b$ are each independently selected from N or CR$^{x1}$, wherein R$^{x1}$ is selected from hydrogen, fluoro, chloro, bromo, (1-2C)alkyl, (1-2C)alkoxy, cyano, nitro, acetylenyl, CH$_2$F, CF$_2$H or CF$_3$;
  R$^6$ is selected from hydrogen, fluoro, chloro, bromo, (1-2C)alkyl, (1-2C)alkoxy, cyano, nitro, acetylenyl, CH$_2$F, CF$_2$H or CF$_3$;
  R$^7$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_3$—Z$_3$ wherein:
  Y$_3$ is absent or O, S, SO, SO$_2$, N(R$^j$)(CR$^j$R$^k$)$_{q1}$ (where q$_1$ is 0, 1 or 2), C(O), C(O)O, OC(O), C(O)N(R$^j$), N(R$^j$)C(O), N(R$^j$)C(O)N(R$^k$), N(R$^j$)C(O)O, OC(O)N(R$^j$), S(O)$_2$N(R$^j$) or N(R$^j$)SO$_2$, wherein R$^j$ and R$^k$ are each independently selected from hydrogen or (1-4C)alkyl; and
  Z$_3$ is hydrogen, (1-6C)alkyl, aryl, (3-6C)cycloalkyl, (2-4C)alkenyl, (2-4C)alkynyl, (3-6C)cycloalkenyl, heteroaryl or a 4 to 11-membered heterocyclyl; wherein Z$_3$ is optionally further substituted by one or more substituent groups independently selected from oxo, (1-4C)alkyl, (3-6C)cycloalkyl, halo, (1-4C)haloalkyl, (1-4C)haloalkoxy, (1-4C)hydroxyalkyl, amino, cyano, hydroxy, carboxy, carbamoyl, sulphamoyl, mercapto, C(O)NR$^l$R$^m$, NR$^l$R$^m$ or OR, wherein R$^l$ and R$^m$ are each independently selected from hydrogen, (1-4C)alkyl or (3-6C)cycloalkyl; and/or Z$^3$ is optionally further substituted by a group of the formula:

-L$_Z$-W$_Z$ wherein:
  L$_Z$ is absent or a (1-5C)alkylene optionally substituted by one or more substituents selected from (1-2C)alkyl or oxo; and
  W$_Z$ is aryl, heteroaryl, 4- to 7-membered heterocyclyl, (3-6C)cycloalkyl, halo, (1-4C)haloalkyl, (1-4C)haloalkoxy, cyano, hydroxy, (1-4C)alkoxy, C(O)R$^x$a, COOR$^{xa}$, C(O)NR$^{xa}$R$^{xb}$ or NR$^{xa}$R$^{xb}$, wherein R$^{xa}$ and R$^{xb}$ are each independently selected from hydrogen or (1-4C)alkyl; and wherein each aryl, heteroaryl, 4- to 7-membered heterocyclyl or (3-6C)cycloalkyl is optionally further substituted by one or more substituent groups independently selected from (1-4C)alkyl, halo, (1-4C)haloalkyl, amino, cyano or hydroxy;
  ii) a group of Formula B shown below:

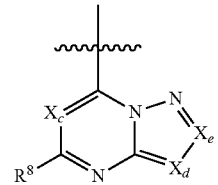

Formula B wherein:
  ⟋⟍ denotes the point of attachment;
  X$_c$, X$_d$ and X$_e$ are each independently selected from N, CH, CF, CCl, C—CN or CCH$_3$;
  R$^8$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_5$—Z$_5$ wherein:
  Y$_5$ is absent or O, N(R″), C(O), C(O)O, OC(O), C(O)N(R″), N(R″)C(O), N(R″)C(O)N(R°), N(R″)C(O)O, OC(O)N(R″), S(O)$_2$N(R″), or N(R″)SO$_2$, wherein R″ and R° are each independently selected from hydrogen or (1-4C)alkyl; and
  Z$_5$ is hydrogen, (1-6C)alkyl, aryl, (3-8C)cycloalkyl, (3-8C)cycloalkenyl, heteroaryl or heterocyclyl; wherein $Z_5$ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, $NR^pR^q$, or $OR^p$, wherein $R^p$ and $R^q$ are each independently selected from hydrogen, (1-4C)alkyl or (3-6C)cycloalkyl; and iii) a group of Formula C shown below:

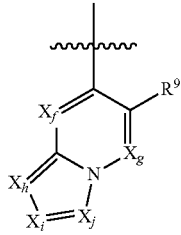

Formula C wherein:

denotes the point of attachment;

$R^9$ is selected from fluoro, chloro, bromo, (1-2C)alkyl, (1-2C)alkoxy, cyano, nitro, (2-4C)alkenyl, (2-4C)alkynyl, $CH_2F$, $CF_2H$ or $CF_3$;

$X_f$ and $X_g$ are each independently selected from N or $CR^{10}$, wherein $R^{10}$ is selected from hydrogen, fluoro, chloro, (1-2C)alkyl, (1-2C)haloalkyl or (1-2C)haloalkoxy;

$X_h$, $X_i$ and $X_j$ are each independently selected from N or $CR^{11}$, wherein $R^{11}$ is selected from hydrogen, halo, (1-2C)alkyl, (1-2C)alkoxy, (1-2C)haloalkyl or (1-2C)haloalkoxy;

$R^3$ is selected from hydrogen, (1-2C)alkyl, (3-4C)cycloalkyl, (1-2C)haloalkyl, cyano, (2-4C)alkenyl or (2-4C)alkynyl;

$R^4$ is selected from (1-4C)alkyl, cyano, (1-4C)haloalkyl or a group of the formula:

$Y_5$-$L_5$-$Z_5$ wherein:

$Y_5$ is absent or selected from C(O), C(O)O, OC(O), C(O)N(R') or S(O)$_2$N(R'), wherein R' is selected from hydrogen or (1-2C)alkyl;

$L_5$ is absent or (1-2C)alkylene, optionally substituted by one or more substituents selected from (1-2C)alkyl or oxo; and $Z_5$ is hydrogen, (1-6C)alkyl, (2-4C)alkenyl, (2-4C)alkynyl, aryl, (3-6C)cycloalkyl, (3-6C)cycloalkenyl, heteroaryl or heterocyclyl; wherein $Z_5$ is optionally substituted by one or more substituents selected from oxo, (1-4C)alkyl, halo, (1-4C)haloalkyl, (1-4C)haloalkoxy, (1-4C)alkoxy, (1-4C)alkylamino, amino, cyano, nitro, hydroxy, C(O)$R^s$, C(O)O$R^s$, OC(O)$R^s$, C(O)N(R$^s$)R$^t$, or NR$^s$C(O)R$^t$, wherein R$^s$ and R$^t$ are each independently selected from hydrogen, (1-4C)alkyl or (3-6C)cycloalkyl; or $Z_5$ is optionally substituted by a group of the formula:

$Q_5$-$L_5$-$W_5$ wherein:

$Q_5$ is absent or selected from O or N(R$^{x3}$), wherein R$^{x3}$ is selected from hydrogen or (1-2C)alkyl;

$L_5$ is absent or (1-2C)alkylene, optionally substituted by one or more substituents selected from (1-2C)alkyl or oxo; and $W_5$ is selected from (1-4C)alkyl, aryl, (3-6C)cycloalkyl, (3-6C)cycloalkenyl, 5- or 6-membered heteroaryl or a 5- or 6-membered heterocyclyl, and wherein $W_5$ is optionally further substituted by one or more substituents selected from (1-4C)alkyl, halo, (1-4C)haloalkyl, (1-4C)haloalkoxy, (1-4C)alkoxy, (1-4C)alkylamino, amino, cyano, nitro or hydroxy; or $R^3$ and $R^4$ are linked such that, together with the carbon atom to which they are attached, they form a 3-10 membered carbocyclic ring or a 4-10 membered heterocyclic ring, which is optionally substituted by one or more substituents selected from oxo, (1-2C)alkyl, halo, (1-2C)haloalkyl, (1-2C)haloalkoxy, (1-2C)alkoxy, (1-2C)alkylamino, amino, cyano, nitro or hydroxy; or the 3-10 membered carbocyclic or 4-10 membered heterocyclic ring is optionally fused to a 5 or 6 membered heteroaryl or phenyl ring, and the 5 or 6 membered heteroaryl or phenyl ring is optionally substituted by (1-2C)alkyl, halo, (1-2C)haloalkyl, (1-2C)haloalkoxy, (1-2C)alkoxy, (1-2C)alkylamino, amino, cyano, nitro or hydroxy; and $R^5$ is selected from hydrogen, (1-4C)alkyl, (1-2C)haloalkyl, (1-2C)alkoxy, (1-2C)haloalkoxy, cyano, nitro, acetylenyl, phenyl or 5- or 6-membered heteroaryl, wherein said (1-4C)alkyl, phenyl or 5- or 6-membered heteroaryl are independently optionally substituted by one or more substituents selected from halo, hydroxy or amino;

with the proviso that:

(i) no more than two of $X_1$, $X_2$ and $X_3$ are nitrogen;

(ii) when $R^2$ is a group of Formula B, no more than two of $X_c$, $X_d$ and $X_e$ are nitrogen; and (iii) when $R^2$ is a group of Formula C, no more than three of $X_f$, $X_g$, $X_h$, $X_i$ and $X_j$ are nitrogen.

2. A compound, or a pharmaceutically acceptable salt or solvate thereof, according to claim 1, wherein $X_2$ is selected from N or CH.

3. A compound, or a pharmaceutically acceptable salt or solvate thereof, according to claim 1, wherein $R^3$ is selected from hydrogen, (1-2C)alkyl, cyclopropyl, (1-2C)haloalkyl, cyano, (2-4C)alkenyl or (2-4C)alkynyl.

4. A compound, or a pharmaceutically acceptable salt or solvate thereof, according to claim 1, wherein the compound has the structural formula Ib$_2$ shown below:

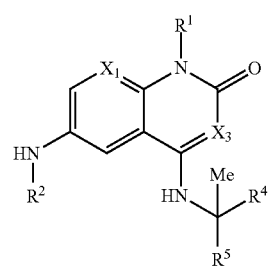

Formula Ib$_2$ wherein each of $X_1$, $X_3$, $R^1$, $R^2$, $R^4$ and $R^5$ are as defined in claim 1 above.

5. A compound, or a pharmaceutically acceptable salt or solvate thereof, according to claim 1, wherein $X_{10}$ is selected from N or $CR^a$, wherein $R^a$ is selected from hydrogen, methyl, fluoro, chloro, hydroxy, $OCH_3$, $CH_2F$, $CHF_2$, $CF_3$, $OCF_3$, acetylenyl, cyano or $NH_2$.

6. A compound, or a pharmaceutically acceptable salt or solvate thereof, according to claim 5, wherein $X_1$ is CH.

7. A compound, or a pharmaceutically acceptable salt or solvate thereof, according to claim 1, wherein $X_3$ is selected from N or CH.

8. A compound, or a pharmaceutically acceptable salt or solvate thereof, according to claim 1, wherein $R^1$ is selected from hydrogen or a group of the formula:

-L-Y—Z wherein:
L is absent or (1-5C)alkylene optionally substituted by one or more substituents selected from (1-2C)alkyl;
Y is absent or O, S, SO, $SO_2$, $N(R^e)$, C(O), C(O)O, OC(O), $C(O)N(R^e)$, $N(R^e)C(O)$, $S(O)_2N(R^e)$, or $N(R^e)SO_2$, wherein $R^e$ is selected from hydrogen or (1-4C)alkyl; and
Z is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Z is optionally further substituted by one or more substituent groups independently selected from oxo, (1-4C)alkyl, halo, (1-4C)haloalkyl, (1-4C)haloalkoxy, amino, (1-4C)aminoalkyl, cyano, hydroxy, carboxy, carbamoyl, sulphamoyl, mercapto, ureido, $NR^gR^g$, $C(O)R^g$, $C(O)OR^g$, $OC(O)R^g$, $C(O)N(R^g)R^h$, $N(R^g)C(O)R^h$, $S(O)_yR^g$ (where y is 0, 1 or 2), $SO_2N(R^g)R^h$, $N(R^g)SO_2R^g$, $Si(R^g)R^h)R^i$ or $(CH_2)_zNR^gR^h$ (where z is 1, 2 or 3); wherein $R^g$, $R^h$ and $R^i$ are each independently selected from hydrogen, (1-6C)alkyl or (3-6C)cycloalkyl; or $R^g$ and $R^h$ can be linked such that, together with the nitrogen atom to which they are attached, they form a 4-9 membered heterocyclic ring.

9. A compound, or a pharmaceutically acceptable salt or solvate thereof, according to claim 1, wherein $R^1$ is selected from hydrogen or a group of the formula:

-L-Y—Z wherein:
L is absent or (1-5C)alkylene;
Y is absent or O, $SO_2$, C(O), C(O)O, $C(O)N(R^e)$ or $S(O)_2N(R^e)$, wherein $R^e$ is selected from hydrogen or (1-4C)alkyl; and
Z is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Z is optionally further substituted by one or more substituent groups independently selected from oxo, (1-2C)alkyl, halo, (1-2C)haloalkyl, (1-2C)haloalkoxy, amino, (1-2C)aminoalkyl, cyano, hydroxy, $NR^gR^h$ or $OR^g$;
wherein $R^g$, $R^h$ and $R^i$ are each independently selected from hydrogen or (1-4C)alkyl.

10. A compound, or a pharmaceutically acceptable salt or solvate thereof, according to claim 1, wherein $R^2$ is selected from:

i) a group of Formula A shown below:

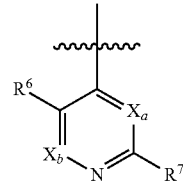

Formula A wherein:

denotes the point of attachment;
$X_a$ and $X_b$ are each independently selected from N or $CR^{x1}$, wherein $R^{x1}$ is selected from hydrogen, fluoro, chloro, bromo, (1-2C)alkyl, (1-2C)alkoxy, cyano, nitro, acetylenyl, $CH_2F$, $CF_2H$ or $CF_3$;
$R^6$ is selected from hydrogen, fluoro, chloro, bromo, methyl, $OCH_3$, cyano, nitro, acetylenyl, $CH_2F$ or $CF_2H_3$;
$R^7$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_3$—$Z_3$ wherein:
$Y_3$ is absent or O, $N(R^j)CH_2)_{q1}$ (where $q_1$ is 0 or 1), C(O), C(O)O, OC(O), $C(O)N(R^j)$, $N(R^j)C(O)$, $S(O)_2N(R^j)$, $N(R^j)SO_2$, wherein $R^j$ is selected from hydrogen or (1-4C)alkyl; and
$Z_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or a 4 to 11-membered heterocyclyl; wherein $Z_3$ is optionally further substituted by one or more substituent groups independently selected from oxo, (1-4C)alkyl, halo, (1-4C)haloalkyl, (1-4C)haloalkoxy, amino, cyano, hydroxy, carboxy, carbamoyl, sulphamoyl, mercapto, $C(O)NR^lR^m$, $NR^lR^m$ or $OR^l$, wherein $R^l$ and $R^m$ are each independently selected from hydrogen, (1-4C)alkyl or (3-6C)cycloalkyl; or $Z^3$ is optionally further substituted by a group of the formula:

-$L_Z$-$W_Z$ wherein:
$L_Z$ is absent or a (1-3C)alkylene; and
$W_Z$ is aryl, 5- or 6-membered heteroaryl, 5- or 6-membered heterocycyl, halo, (1-4C)haloalkyl, (1-4C)haloalkoxy, cyano, hydroxy, (1-4C)alkoxy, $C(O)R^{xa}$, $COOR^{xa}$, $C(O)NR^{xa}R^{xb}$ or $NR^{xa}R^{xb}$, wherein $R^{xa}$ and $R^{xb}$ are each independently selected from hydrogen or (1-4C)alkyl;

i) a group of Formula A shown below:

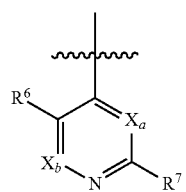

Formula A wherein:

↘↙ denotes the point of attachment;

$X_a$ and $X_b$ are each independently selected from N or $CR^{x1}$, wherein $R^{x1}$ is selected from hydrogen, fluoro, chloro, bromo, (1-2C)alkyl, (1-2C)alkoxy, cyano, nitro, acetylenyl, $CH_2F$, $CF_2H$ or $CF_3$;

$R^6$ is selected from hydrogen, fluoro, chloro, bromo, methyl, $OCH_3$, cyano, nitro, acetylenyl, $CH_2F$ or $CF_2H_3$;

$R^7$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_3$—$Z_3$ wherein:

$Y_3$ is absent or O, $N(R^j)CH_2)_{q1}$ (where $q_1$ is 0 or 1), C(O), C(O)O, OC(O), C(O)N($R^j$), N($R^j$)C(O), S(O)$_2$N($R^j$), or N($R^j$)SO$_2$, wherein $R^j$ is selected from hydrogen or (1-4C)alkyl; and $Z_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or a 4 to 11-membered heterocyclyl; wherein $Z_3$ is optionally further substituted by one or more substituent groups independently selected from oxo, (1-4C)alkyl, halo, (1-4C)haloalkyl, (1-4C)haloalkoxy, amino, cyano, hydroxy, carboxy, carbamoyl, sulphamoyl, mercapto, C(O)NR$^l$R$^m$, NR$^l$R$^m$ or OR$^l$, wherein R$^l$ and R$^m$ are each independently selected from hydrogen, (1-4C)alkyl or (3-6C)cycloalkyl; or $Z^3$ is optionally further substituted by a group of the formula:

-$L_Z$-$W_Z$ wherein:

$L_Z$ is absent or a (1-3C)alkylene; and $W_Z$ is aryl, 5- or 6-membered heteroaryl, 5- or 6-membered heterocycyl, halo, (1-4C)haloalkyl, (1-4C)haloalkoxy, cyano, hydroxy, (1-4C)alkoxy, C(O)R$^{xa}$, COOR$^{xa}$, C(O)NR$^{xa}$R$^{xb}$ or NR$^{xa}$R$^{xb}$, wherein R$^{xa}$ and R$^{xb}$ are each independently selected from hydrogen or (1-4C)alkyl; or ii) a group of Formula B shown below:

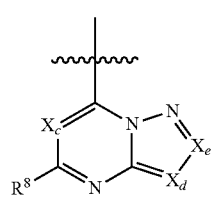

Formula B ii) a group of Formula B shown below:

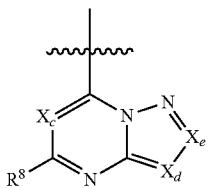

Formula B wherein:

↘↙ denotes the point of attachment;

$X_c$, $X_d$ and $X_e$ are each independently selected from N, CH, CF, CCl, C—CN or CCH$_3$;

$R^8$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—$Y_5$—$Z_5$ wherein:

$Y_5$ is absent or O, N(R″), C(O), C(O)O, C(O)N(R″) or S(O)$_2$N(R″), wherein R″ is selected from hydrogen or (1-4C)alkyl; and $Z_5$ is hydrogen, (1-6C)alkyl, aryl, (3-8C)cycloalkyl, (3-8C)cycloalkenyl, heteroaryl or heterocyclyl; wherein $Z_5$ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, NR$^p$R$^q$ or OR$^p$, wherein R$^p$ and R$^q$ are each independently selected from hydrogen, (1-4C)alkyl or (3-6C)cycloalkyl; and iii) a group of Formula C shown below:

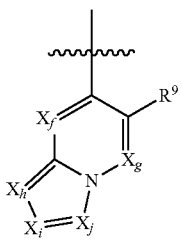

Formula C wherein:

↘↙ denotes the point of attachment;

$R^9$ is selected from fluoro, chloro, bromo, methyl, $OCH_3$, cyano, acetylenyl, $CH_2F$, $CF_2H$ or $CF_3$;

$X_f$ and $X_g$ are independently selected from N or CR$^{10}$, wherein R$^{10}$ is selected from hydrogen, fluoro, chloro, methyl, $CH_2F$, $CF_2H$ or $CF_3$;

$X_h$, $X_i$ and $X_j$ are each independently selected from N or CR$^{11}$, R$^{11}$ is selected from hydrogen, halo, (1-2C)alkyl, (1-2C)alkoxy, (1-2C)haloalkyl or (1-2C)haloalkoxy.

11. A compound, or a pharmaceutically acceptable salt or solvate thereof, according to claim 1, wherein $R^2$ is selected from:

wherein:

 denotes the point of attachment;
$X_c$, $X_d$ and $X_e$ are each independently selected from N, CH, CF, CCl, C—CN or CCH$_3$;
$R^8$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_5$—Z$_5$ wherein:
Y$_5$ is absent or O, N(R″), C(O), C(O)O, C(O)N(R″) or S(O)$_2$N(R″), wherein R″ is selected from hydrogen or (1-4C)alkyl; and
Z$_5$ is hydrogen, (1-6C)alkyl, aryl, (3-8C)cycloalkyl, (3-8C)cycloalkenyl, heteroaryl or heterocyclyl; wherein Z$_5$ is optionally further substituted by one or more substituent groups independently selected from (1-4C)alkyl, halo, (1-4C)haloalkyl, (1-4C)haloalkoxy, amino, cyano, hydroxy, amido, carboxy, carbamoyl, sulphamoyl, mercapto, NR$^p$R$^q$ or OR$^p$, wherein R$^p$ and R$^q$ are each independently selected from hydrogen, (1-4C)alkyl or (3-6C)cycloalkyl.

12. A compound, or a pharmaceutically acceptable salt or solvate thereof, according to claim 1, wherein R$^2$ is a group of Formula A shown below:

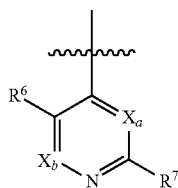

Formula A wherein:

 denotes the point of attachment;
$X_a$ and $X_b$ are each independently selected from N or CR$^{x1}$, wherein R$^{x1}$ is selected from hydrogen, fluoro, chloro, bromo, methyl, OCH$_3$, cyano or acetylenyl;
R$^6$ is selected from fluoro, chloro, bromo, methyl, OCH$_3$, cyano or acetylenyl;
R$^7$ is selected from hydrogen, halo, (1-4C)alkyl, (1-4C)alkoxy, (1-4C)haloalkyl, (1-4C)haloalkoxy, cyano, nitro, (2-4C)alkenyl, (2-4C)alkynyl or a group of the formula:

—Y$_3$—Z$_3$ wherein:
Y$_3$ is absent or O, N(R$^j$)CH$_2$)$_{q1}$ (where q$_1$ is 0 or 1), C(O), C(O)O, C(O)N(R$^j$) or S(O)$_2$N(R$^j$), wherein R$^j$ is selected from hydrogen or (1-4C)alkyl; and
Z$_3$ is hydrogen, (1-6C)alkyl, aryl, (3-6C)cycloalkyl, (2-4C)alkenyl, (2-4C)alkynyl, (3-6C)cycloalkenyl, 5- or 6-membered heteroaryl or a 4 to 11-membered heterocyclyl; wherein Z$_3$ is optionally further substituted by one or more substituent groups independently selected from (1-2C)alkyl, halo, (1-2C)haloalkyl, (1-2C)haloalkoxy, amino, cyano, hydroxy, amido, carboxy, C(O)NR$^l$R$^m$, NR$^l$R$^m$ or OR$^l$, wherein R$^l$ and R$^m$ are each independently selected from hydrogen, (1-4C)alkyl or cyclopropyl; or Z$^3$ is optionally further substituted by a group of the formula:

-L$_Z$-W$_Z$ wherein:
L$_Z$ is absent or a (1-3C)alkylene; and
W$_Z$ is aryl, 5- or 6-membered heteroaryl, 5- or 6-membered heterocycyl, halo, (1-4C)haloalkyl, (1-4C)haloalkoxy, cyano, hydroxy, (1-4C)alkoxy, C(O)R$^{xa}$, COOR$^{xa}$, C(O)NR$^{xa}$R$^{xb}$ or NR$^{xa}$R$^{xb}$, wherein R$^{xa}$ and R$^{xb}$ are each independently selected from hydrogen or (1-4C)alkyl.

13. A compound, or a pharmaceutically acceptable salt or solvate thereof, according to claim 1, wherein R$^4$ is selected from (1-4C)alkyl, cyano, (1-4C)haloalkyl or a group of the formula:

Y$_5$-L$_5$-Z$_5$ wherein:
Y$_5$ is absent or selected from C(O)O or C(O)N(R$^r$), wherein R$^r$ is selected from hydrogen or (1-2C)alkyl;
L$_5$ is absent or (1-2C)alkylene, optionally substituted by one or more substituents selected from (1-2C)alkyl; and
Z$_5$ is hydrogen, (1-6C)alkyl, (2-4C)alkynyl, aryl, (3-6C)cycloalkyl, (3-6C)cycloalkenyl, 5 or 6 membered heteroaryl or 5 or 6 membered heterocyclyl; wherein Z$_5$ is optionally substituted by one or more substituents selected from (1-2C)alkyl, halo, (1-2C)haloalkyl, (1-2C)haloalkoxy, (1-2C)alkoxy, (1-2C)alkylamino, amino, cyano, nitro, hydroxy, C(O)OR$^s$, C(O)N(R$^s$)R$^t$, NR$^s$C(O)R$^t$, wherein R$^s$ and R$^t$ are each independently selected from hydrogen or (1-2C)alkyl; or
R$^3$ and R$^4$ are linked such that, together with the carbon atom to which they are attached, they form a 3-7 membered carbocyclic ring or a 4-7 membered heterocyclic ring.

14. A compound, or a pharmaceutically acceptable salt or solvate thereof, according to claim 1, wherein R$^5$ is selected from hydrogen, (1-4C)alkyl, OCH$_3$, cyano or acetylenyl, wherein said (1-4C)alkyl is optionally substituted by one or more substituents selected from fluoro, chloro or hydroxy.

15. A compound, or a pharmaceutically acceptable salt or solvate thereof, according to claim 14, wherein R$^5$ is selected from hydrogen or (1-4C)alkyl.

16. A compound, or a pharmaceutically acceptable salt or solvate thereof, selected from one of the following:
2-Chloro-4-[[1-methyl-4-[(1-methyl-1-pyrimidin-2-ylethyl)amino]-2-oxo-6-quinolyl]amino]pyridine-3-carbonitrile;
2-chloro-4-[[1-methyl-2-oxo-4-(1-pyrimidin-2-ylethylamino)-6-quinolyl]amino]pyridine-3-carbonitrile;
2-chloro-4-[[1-[2-(2,5-dioxopyrrolidin-1-yl)ethyl]-2-oxo-4-(1-pyrimidin-2-ylethylamino)-6-quinolyl]amino]pyridine-3-carbonitrile;
2-chloro-4-[[2-oxo-4-(1-pyrimidin-2-ylethylamino)-1-(tetrahydropyran-4-ylmethyl)-6-quinolyl]amino]pyridine-3-carbonitrile;
2-chloro-4-[[1-methyl-2-oxo-4-[1-(1H-1,2,4-triazol-3-yl)ethylamino]-6-quinolyl]amino]pyridine-3-carbonitrile;
trans-2-chloro-4-[[4-[(3-hydroxycyclobutyl)amino]-1-methyl-2-oxo-6-quinolyl]amino]pyridine-3-carbonitrile;
2-chloro-4-[[1-methyl-2-oxo-4-[[(3S)-tetrahydrofuran-3-yl]amino]-6-quinolyl]amino]pyridine-3-carbonitrile;
2-chloro-4-[[1-methyl-4-[1-(5-methyl-1,2,4-oxadiazol-3-yl)ethylamino]-2-oxo-6-quinolyl]amino]pyridine-3-carbonitrile;

2-chloro-4-[[1-methyl-4-[1-(4-methylpyrimidin-2-yl)ethylamino]-2-oxo-6-quinolyl]amino]pyridine-3-carbonitrile;
2-chloro-4-[[1-methyl-2-oxo-4-(1-pyrazin-2-ylethylamino)-6-quinolyl]amino]pyridine-3-carbonitrile;
2-chloro-4-[[4-[(3-hydroxy-1-methyl-propyl)amino]-1-methyl-2-oxo-quinazolin-6-yl]amino]pyridine-3-carbonitrile;
2-chloro-4-[[4-[(2-hydroxy-1-methyl-ethyl)amino]-1-methyl-2-oxo-quinazolin-6-yl]amino]pyridine-3-carbonitrile;
2-chloro-4-[[1-methyl-4-[1-(5-methylisoxazol-3-yl)ethylamino]-2-oxo-6-quinolyl]amino]pyridine-3-carbonitrile;
2-chloro-4-[[4-[(2-hydroxy-1-methyl-ethyl)amino]-2-oxo-1H-quinazolin-6-yl]amino]pyridine-3-carbonitrile;
2-chloro-4-[[4-(ethylamino)-1-[2-(2-methoxyethoxy)ethyl]-2-oxo-6-quinolyl]amino]pyridine-3-carbonitrile;
2-chloro-4-[[1-methyl-4-(1-oxazol-2-ylethylamino)-2-oxo-6-quinolyl]amino]pyridine-3-carbonitrile;
2-chloro-4-[[1-methyl-2-oxo-4-(1-pyrimidin-4-ylethylamino)-6-quinolyl]amino]pyridine-3-carbonitrile;
2-chloro-4-[[1-[2-(2,5-dioxopyrrolidin-1-yl)ethyl]-4-(ethylamino)-2-oxo-6-quinolyl]amino]pyridine-3-carbonitrile;
2-chloro-4-[[1-methyl-2-oxo-4-(1-thiazol-2-ylethylamino)-6-quinolyl]amino]pyridine-3-carbonitrile;
2-chloro-4-[[1-methyl-2-oxo-4-[1-(1H-pyrazol-3-yl)ethylamino]-6-quinolyl]amino]pyridine-3-carbonitrile;
6-chloro-5-cyano-N-methyl-4-[[1-methyl-4-[(1-methyl-1-pyrimidin-2-yl-ethyl)amino]-2-oxo-6-quinolyl]amino]pyridine-2-carboxamide;
6-chloro-5-cyano-N-methyl-4-[[1-methyl-2-oxo-4-(1-pyrimidin-2-ylethylamino)-6-quinolyl]amino]pyridine-2-carboxamide;
2-chloro-6-methyl-4-[[1-methyl-2-oxo-4-(1-pyrimidin-2-ylethylamino)-6-quinolyl]amino]pyridine-3-carbonitrile;
2-chloro-4-[[8-methyl-5-[(1-methyl-1-pyrimidin-2-yl-ethyl)amino]-7-oxo-1,8-naphthyridin-3-yl]amino]pyridine-3-carbonitrile;
6-Chloro-5-cyano-4-[[4-(1-cyclopropylethylamino)-1-methyl-2-oxo-6-quinolyl]amino]pyridine-2-carboxylic acid;
6-chloro-5-cyano-4-[[4-(cyclopropylamino)-1-methyl-2-oxo-6-quinolyl]amino]pyridine-2-carboxylic acid;
6-chloro-5-cyano-4-[[1-methyl-4-[(1-methylcyclopropyl)amino]-2-oxo-6-quinolyl]amino]pyridine-2-carboxylic acid;
6-chloro-5-cyano-4-[[1-methyl-4-[(1-methylcyclopentyl)amino]-2-oxo-6-quinolyl]amino]pyridine-2-carboxylic acid;
(R)-2-((6-((2-Chloro-3-cyanopyridin-4-yl)amino)-1-methyl-2-oxo-1,2-dihydroquinolin-4-yl)amino)-N-((1-methyl-1H-pyrazol-4-yl)methyl)propanamide;
(R)-2-((6-((2-chloro-3-cyanopyridin-4-yl)amino)-1-methyl-2-oxo-1,2-dihydroquinolin-4-yl)amino)-N-(2-hydroxyethyl)propanamide;
2-Chloro-4-((1-methyl-4-((1-(3-methyl-1H-1,2,4-triazol-5-yl)ethyl)amino)-2-oxo-1,2-dihydroquinolin-6-yl)amino)nicotinonitrile;
(R)-2-((6-((2-Chloro-3-cyanopyridin-4-yl)amino)-1-methyl-2-oxo-1,2-dihydroquinolin-4-yl)amino)-N-cyclopentylpropanamide;
(R)-2-((6-((2-chloro-3-cyanopyridin-4-yl)amino)-1-methyl-2-oxo-1,2-dihydroquinolin-4-yl)amino)-N-(2-methoxyethyl)propanamide;
(R)—N-(But-3-yn-1-yl)-2-((6-((2-chloro-3-cyanopyridin-4-yl)amino)-1-methyl-2-oxo-1,2-dihydroquinolin-4-yl)amino)propanamide;
(S)-2-Chloro-4-((4-((1-hydroxypropan-2-yl)amino)-1-methyl-2-oxo-1,2-dihydroquinolin-6-yl)amino)nicotinonitrile;
2-((6-((2-Chloro-3-cyanopyridin-4-yl)amino)-1-methyl-2-oxo-1,2-dihydroquinolin-4-yl)amino)-N-ethyl-2-methylpropanamide;
(R)-2-((6-((2-Chloro-3-cyanopyridin-4-yl)amino)-1-methyl-2-oxo-1,2-dihydroquinolin-4-yl)amino)-N-(4-methoxycyclohexyl)propanamide;
(R)-2-chloro-4-((4-((1-hydroxypropan-2-yl)amino)-1-methyl-2-oxo-1,2-dihydroquinolin-6-yl)amino)nicotinonitrile;
rac-2-((6-((2-Chloro-3-cyanopyridin-4-yl)amino)-1-methyl-2-oxo-1,2-dihydroquinolin-4-yl)amino)-N-ethylpropanamide;
2-Chloro-4-((1-methyl-4-((1-(5-methyl-1,3,4-oxadiazol-2-yl)ethyl)amino)-2-oxo-1,2-dihydroquinolin-6-yl)amino)nicotinonitrile;
(R)-2-((6-((2-Chloro-3-cyanopyridin-4-yl)amino)-1-methyl-2-oxo-1,2-dihydroquinolin-4-yl)amino)-N-(2-(1-methyl-1H-pyrazol-4-yl)ethyl)propanamide;
(S)-2-Chloro-4-((4-((4-hydroxybutan-2-yl)amino)-1-methyl-2-oxo-1,2-dihydroquinolin-6-yl)amino)nicotinonitrile;
(R)-2-((6-((2-chloro-3-cyanopyridin-4-yl)amino)-1-methyl-2-oxo-1,2-dihydroquinolin-4-yl)amino)-N-methylpropanamide;
(R)-2-((6-((2-chloro-3-cyanopyridin-4-yl)amino)-2-oxo-1,2-dihydroquinolin-4-yl)amino)-N-methylpropanamide;
6-Chloro-5-cyano-4-[[4-(ethylamino)-1-methyl-2-oxo-6-quinolyl]amino]pyridine-2-carboxylic acid;
6-Chloro-5-cyano-4-[[4-(ethylamino)-1-methyl-2-oxo-6-quinolyl]amino]-N-methyl-pyridine-2-carboxamide;
6-[(2,3-Dichloro-4-pyridyl)amino]-1-methyl-4-(1-pyrimidin-2-ylethylamino)quinolin-2-one;
6-((2,3-dichloropyridin-4-yl)amino)-1-methyl-4-((2-(pyrimidin-2-yl)propan-2-yl)amino)quinolin-2(1H)-one;
6-((2,3-dichloropyridin-4-yl)amino)-1-methyl-4-((1-(pyrimidin-2-yl)ethyl)amino)quinazolin-2(1H)-one;
(R)-4-((1-cyclopropylethyl)amino)-6-((2,3-dichloropyridin-4-yl)amino)-1-methylquinazolin-2(1H)-one;
6-((2,3-dichloropyridin-4-yl)amino)-1-methyl-4-((1-(pyrimidin-2-yl)ethyl)amino)-1,8-naphthyridin-2(1H)-one;
(R)-4-((1-cyclopropylethyl)amino)-6-((2,3-dichloropyridin-4-yl)amino)-1-methyl-1,8-naphthyridin-2(1H)-one;
1-(cyclopropylmethyl)-6-[(2,3-dichloro-4-pyridyl)amino]-4-(1-pyrimidin-2-ylethylamino)quinolin-2-one;
6-((5-chloro-2-((2S,6R)-2,6-dimethylmorpholino)pyridin-4-yl)amino)-4-(((R)-1-cyclopropylethyl)amino)-1-methylquinolin-2(1H)-one;
(R)-1-(5-chloro-4-((4-((1-cyclopropylethyl)amino)-1-methyl-2-oxo-1,2-dihydroquinolin-6-yl)amino)pyridin-2-yl)-N,N-dimethylpiperidine-4-carboxamide;
4-((2-(5-cyclopropylpyrimidin-2-yl)propan-2-yl)amino)-6-((2,3-dichloropyridin-4-yl)amino)-1-methylquinolin-2(1H)-one;

2-Chloro-4-((4-((2-(5-((2R,6S)-2,6-dimethylmorpholino) pyrimidin-2-yl)propan-2-yl)amino)-1-methyl-2-oxo-1, 2-dihydroquinolin-6-yl)amino)nicotinonitrile;
6-chloro-5-cyano-4-((4-((1-cyclopropylethyl)amino)-1-methyl-2-oxo-1,2-dihydroquinolin-6-yl)amino)-N-methylpicolinamide;
4-((4-(tert-butylamino)-1-methyl-2-oxo-1,2-dihydroquinolin-6-yl)amino)-6-chloro-5-cyano-N-methylpicolinamide;
6-chloro-5-cyano-4-[[4-[(2-methoxy-1,1-dimethyl-ethyl) amino]-1-methyl-2-oxo-6-quinolyl]amino]-N-methyl-pyridine-2-carboxamide;
6-(Azetidine-1-carbonyl)-2-chloro-4-((1-methyl-2-oxo-4-((2-(pyrimidin-2-yl)propan-2-yl)amino)-1,2-dihydroquinolin-6-yl)amino)nicotinonitrile;
6-(azetidine-1-carbonyl)-2-chloro-4-((4-((2-(5-cyclopropylpyrimidin-2-yl)propan-2-yl)amino)-1-methyl-2-oxo-1,2-dihydroquinolin-6-yl)amino)nicotinonitrile;
(R)-6-(azetidine-1-carbonyl)-2-chloro-4-((4-((1-cyclopropylethyl)amino)-1-methyl-2-oxo-1,2-dihydroquinolin-6-yl)amino)nicotinonitrile;
2-chloro-4-((1-methyl-2-oxo-4-((2-(pyrimidin-2-yl)propan-2-yl)amino)-1,2-dihydroquinolin-6-yl)amino)-6-(3-(trifluoromethyl)azetidine-1-carbonyl)nicotinonitrile;
(S)-2-chloro-6-(2-(methoxymethyl)pyrrolidine-1-carbonyl)-4-((1-methyl-2-oxo-4-((2-(pyrimidin-2-yl)propan-2-yl)amino)-1,2-dihydroquinolin-6-yl)amino) nicotinonitrile;
2-chloro-4-((4-((1-(5-cyclopropylpyrimidin-2-yl)ethyl) amino)-1-methyl-2-oxo-1,2-dihydroquinolin-6-yl) amino)-6-(3-(trifluoromethyl)azetidine-1-carbonyl) nicotinonitrile;
6-chloro-5-cyano-4-((4-((2-(5-cyclopropylpyrimidin-2-yl)propan-2-yl)amino)-1-methyl-2-oxo-1,2-dihydroquinolin-6-yl)amino)picolinic acid;
(R)-6-chloro-5-cyano-4-((4-((1-cyclopropylethyl) amino)-1-methyl-2-oxo-1,2-dihydroquinolin-6-yl) amino)picolinic acid;
6-chloro-5-cyano-4-((4-((2-fluoroethyl)amino)-1-methyl-2-oxo-1,2-dihydroquinolin-6-yl)amino)picolinic acid;
(S)-6-chloro-5-cyano-4-((4-((1-cyclopropylethyl)amino)-1-methyl-2-oxo-1,2-dihydroquinolin-6-yl)amino)picolinic acid;
6-chloro-5-cyano-4-((1-methyl-2-oxo-4-((2-(pyrimidin-2-yl)propan-2-yl)amino)-1,2-dihydroquinolin-6-yl) amino)picolinic acid;
6-chloro-5-cyano-4-((4-((1-cyanocyclopropyl)amino)-1-methyl-2-oxo-1,2-dihydroquinolin-6-yl)amino)picolinic acid;
6-chloro-5-cyano-4-((4-((1-ethynylcyclopropyl)amino)-1-methyl-2-oxo-1,2-dihydroquinolin-6-yl)amino)picolinic acid;
rac-6-chloro-5-cyano-4-((4-(((1R,2R)-2-ethylcyclopropyl)amino)-1-methyl-2-oxo-1,2-dihydroquinolin-6-yl)amino)picolinic acid;
6-chloro-5-cyano-4-((4-((2,2-dimethylcyclopropyl) amino)-1-methyl-2-oxo-1,2-dihydroquinolin-6-yl) amino)picolinic acid;
6-chloro-5-cyano-4-((4-((1-(hydroxymethyl)cyclopropyl) amino)-1-methyl-2-oxo-1,2-dihydroquinolin-6-yl) amino)picolinic acid;
6-chloro-5-cyano-4-((4-((cyclopropylmethyl)amino)-1-methyl-2-oxo-1,2-dihydroquinolin-6-yl)amino)picolinic acid;
6-chloro-5-cyano-4-((4-((1-methoxy-2-methylpropan-2-yl)amino)-1-methyl-2-oxo-1,2-dihydroquinolin-6-yl) amino)picolinic acid;
4-((4-(tert-butylamino)-1-methyl-2-oxo-1,2-dihydroquinolin-6-yl)amino)-6-chloro-5-cyanopicolinic acid;
6-chloro-5-cyano-4-((1-methyl-2-oxo-4-(tert-pentylamino)-1,2-dihydroquinolin-6-yl)amino)picolinic acid;
6-chloro-5-cyano-4-((4-((1-(5-cyclopropylpyrimidin-2-yl)ethyl)amino)-1-methyl-2-oxo-1,2-dihydroquinolin-6-yl)amino)picolinic acid;
4-((1-benzyl-2-oxo-4-((1-(pyrimidin-2-yl)ethyl)amino)-1,2-dihydroquinolin-6-yl)amino)-6-chloro-5-cyanopicolinic acid;
2-chloro-4-((4-((2-(5-cyclopropylpyrimidin-2-yl)propan-2-yl)amino)-1-methyl-2-oxo-1,2-dihydroquinolin-6-yl)amino)nicotinonitrile;
2-chloro-4-((4-((1-(5-((2S,6R)-2,6-dimethylmorpholino) pyrimidin-2-yl)ethyl)amino)-1-methyl-2-oxo-1,2-dihydroquinolin-6-yl)amino)nicotinonitrile;
2-chloro-4-((1-methyl-4-((1-(5-(1-methyl-1H-pyrazol-4-yl)pyrimidin-2-yl)ethyl)amino)-2-oxo-1,2-dihydroquinolin-6-yl)amino)nicotinonitrile;
2-chloro-4-((1-methyl-2-oxo-4-((1-(5-(2-(trifluoromethyl)morpholino)pyrimidin-2-yl)ethyl)amino)-1,2-dihydroquinolin-6-yl)amino)nicotinonitrile;
2-chloro-4-((4-((1-(5-cyclopropylpyrimidin-2-yl)ethyl) amino)-1-methyl-2-oxo-1,2-dihydroquinolin-6-yl) amino)nicotinonitrile;
2-chloro-4-((1-methyl-4-((1-(5-methylpyrimidin-2-yl) ethyl)amino)-2-oxo-1,2-dihydroquinolin-6-yl)amino) nicotinonitrile;
(R)-2-chloro-4-((1-methyl-2-oxo-4-((1-(pyrimidin-2-yl) ethyl)amino)-1,2-dihydroquinolin-6-yl)amino)nicotinonitrile;
2-chloro-4-((1-methyl-2-oxo-4-((1-(pyrimidin-2-yl) ethyl)amino)-1,2-dihydroquinazolin-6-yl)amino)nicotinonitrile;
(R)-6-chloro-5-cyano-4-((4-((1-cyclopropylethyl) amino)-1-methyl-2-oxo-1,2-dihydroquinolin-6-yl) amino)-N-methylpicolinamide;
4-((4-((1-(5-bromopyrimidin-2-yl)ethyl)amino)-1-methyl-2-oxo-1,2-dihydroquinolin-6-yl)amino)-2-chloronicotinonitrile;
2-chloro-4-((4-((1-(5-((3R,5S)-3,5-dimethylpiperidin-1-yl)pyrimidin-2-yl)ethyl)amino)-1-methyl-2-oxo-1,2-dihydroquinolin-6-yl)amino)nicotinonitrile;
2-chloro-4-((1-methyl-4-((1-(1-methyl-1H-1,2,4-triazol-3-yl)ethyl)amino)-2-oxo-1,2-dihydroquinolin-6-yl) amino)nicotinonitrile;
(R)-2-chloro-4-((4-((1-cyclopropylethyl)amino)-1-methyl-2-oxo-1,2-dihydroquinazolin-6-yl)amino)nicotinonitrile;
(R)-2-chloro-4-((4-((1-cyclopropylethyl)amino)-1-methyl-2-oxo-1,2-dihydroquinolin-6-yl)amino)nicotinonitrile;
2-chloro-4-((1-(cyclohexylmethyl)-2-oxo-4-((2-(pyrimidin-2-yl)propan-2-yl)amino)-1,2-dihydroquinolin-6-yl)amino)nicotinonitrile;
2-chloro-4-((4-((cyclopropyl(pyrimidin-2-yl)methyl) amino)-1-methyl-2-oxo-1,2-dihydroquinolin-6-yl) amino)nicotinonitrile;
ethyl 7-((1-methyl-2-oxo-4-((1-(pyrimidin-2-yl)ethyl) amino)-1,2-dihydroquinolin-6-yl)amino)pyrazolo[1,5-a]pyrimidine-5-carboxylate;

2-chloro-4-((8-methoxy-1-methyl-2-oxo-4-((2-(pyrimidin-2-yl)propan-2-yl)amino)-1,2-dihydroquinolin-6-yl)amino)nicotinonitrile;
(S)-2-chloro-4-((1-methyl-2-oxo-4-((1-(pyrimidin-2-yl)ethyl)amino)-1,2-dihydroquinolin-6-yl)amino)nicotinonitrile;
4-chloro-6-((1-methyl-2-oxo-4-((1-(pyrimidin-2-yl)ethyl)amino)-1,2-dihydroquinolin-6-yl)amino)pyrimidine-5-carbonitrile;
2-chloro-4-((1-methyl-2-oxo-4-((1-(pyrimidin-2-yl)cyclopropyl)amino)-1,2-dihydroquinolin-6-yl)amino)nicotinonitrile;
2-chloro-4-((1-(cyclohexylmethyl)-2-oxo-4-((1-(pyrimidin-2-yl)ethyl)amino)-1,2-dihydroquinolin-6-yl)amino)nicotinonitrile;
2-chloro-4-[[1-methyl-2-oxo-4-[1-(5-tetrahydropyran-4-ylpyrimidin-2-yl)ethylamino]-6-quinolyl]amino]pyridine-3-carbonitrile;
2-chloro-4-((1-methyl-4-((1-(5-morpholinopyrimidin-2-yl)ethyl)amino)-2-oxo-1,2-dihydroquinolin-6-yl)amino)nicotinonitrile;
(S)-2-chloro-4-((4-((1-cyclopropyl-2-hydroxyethyl)amino)-1-methyl-2-oxo-1,2-dihydroquinolin-6-yl)amino)nicotinonitrile;
2-chloro-4-((1-methyl-2-oxo-4-((2-(pyridin-2-yl)propan-2-yl)amino)-1,2-dihydroquinolin-6-yl)amino)nicotinonitrile;
2-((6-((2-chloro-3-cyanopyridin-4-yl)amino)-1-methyl-2-oxo-1,2-dihydroquinolin-4-yl)amino)-2-methyl-N-((1-methyl-1H-pyrazol-4-yl)methyl)propanamide;
2-chloro-4-((1-methyl-2-oxo-4-((1-(pyridin-2-yl)ethyl)amino)-1,2-dihydroquinolin-6-yl)amino)nicotinonitrile;
(R)-6-((5-chloro-2-methoxypyrimidin-4-yl)amino)-4-((1-cyclopropylethyl)amino)-1-methylquinolin-2(1H)-one;
(S)-6-((5-chloro-2-methoxypyrimidin-4-yl)amino)-4-((1-cyclopropyl-2-hydroxyethyl)amino)-1-methylquinolin-2(1H)-one;
2-chloro-4-((4-((1-(2-methoxyethoxy)propan-2-yl)amino)-1-methyl-2-oxo-1,2-dihydroquinolin-6-yl)amino)nicotinonitrile;
2-chloro-4-((1-(cyclopropylmethyl)-2-oxo-4-((1-(pyrimidin-2-yl)ethyl)amino)-1,2-dihydroquinolin-6-yl)amino)nicotinonitrile;
2-chloro-4-((1-(cyclobutylmethyl)-2-oxo-4-((1-(pyrimidin-2-yl)ethyl)amino)-1,2-dihydroquinolin-6-yl)amino)nicotinonitrile;
2-chloro-4-((1-(2-hydroxyethyl)-2-oxo-4-((1-(pyrimidin-2-yl)ethyl)amino)-1,2-dihydroquinolin-6-yl)amino)nicotinonitrile;
6-((5-Chloro-2-(4,4-difluoropiperidin-1-yl)pyrimidin-4-yl)amino)-1-methyl-4-((1-(pyrimidin-2-yl)ethyl)amino)quinazolin-2(1H)-one;
(R)-1-(5-chloro-4-((4-((1-cyclopropylethyl)amino)-1-methyl-2-oxo-1,2-dihydroquinolin-6-yl)amino)pyrimidin-2-yl)-N,N-dimethylpiperidine-4-carboxamide;
1-(5-chloro-4-((8-methoxy-1-methyl-2-oxo-4-((2-(pyrimidin-2-yl)propan-2-yl)amino)-1,2-dihydroquinolin-6-yl)amino)pyrimidin-2-yl)-N,N-dimethylpiperidine-4-carboxamide;
1-(5-chloro-4-((1-methyl-2-oxo-4-((1-(pyrimidin-2-yl)ethyl)amino)-1,2-dihydroquinazolin-6-yl)amino)pyrimidin-2-yl)-N,N-dimethylpiperidine-4-carboxamide;
6-((5-chloro-2-((3R,5S)-3,5-dimethylpiperidin-1-yl)pyrimidin-4-yl)amino)-1-methyl-4-((1-(pyrimidin-2-yl)ethyl)amino)quinazolin-2(1H)-one;
6-((5-chloro-2-((2S,6R)-2,6-dimethylmorpholino)pyrimidin-4-yl)amino)-1-methyl-4-((2-(pyrimidin-2-yl)propan-2-yl)amino)quinolin-2(1H)-one;
6-((5-chloro-2-(4,4-difluoropiperidin-1-yl)pyrimidin-4-yl)amino)-1-methyl-4-((2-(pyrimidin-2-yl)propan-2-yl)amino)quinolin-2(1H)-one;
rac-6-((5-chloro-2-((3R,5S)-4,4-difluoro-3,5-dimethylpiperidin-1-yl)pyrimidin-4-yl)amino)-1-methyl-4-((1-(pyrimidin-2-yl)ethyl)amino)quinazolin-2(1H)-one;
6-((5-chloro-2-(4,4-difluoro-3-(hydroxymethyl)piperidin-1-yl)pyrimidin-4-yl)amino)-1-methyl-4-((2-(pyrimidin-2-yl)propan-2-yl)amino)quinazolin-2(1H)-one;
1-methyl-4-((2-(pyrimidin-2-yl)propan-2-yl)amino)-6-((2,3,6-trichloropyridin-4-yl)amino)quinolin-2(1H)-one;
6-((5-chloro-6-methyl-2-(3-(trifluoromethyl)-1H-pyrazol-1-yl)pyrimidin-4-yl)amino)-1-methyl-4-((2-(pyrimidin-2-yl)propan-2-yl)amino)quinolin-2(1H)-one;
6-((5-chloro-2-(3,5-dimethyl-1H-pyrazol-1-yl)pyrimidin-4-yl)amino)-1-methyl-4-((1-(1-methyl-1H-1,2,4-triazol-3-yl)ethyl)amino)quinolin-2(1H)-one;
(R)-6-((5-chloro-2-(3,5-dimethyl-1H-pyrazol-1-yl)pyrimidin-4-yl)amino)-4-((1-cyclopropylethyl)amino)-1-methylquinolin-2(1H)-one;
6-((5-chloro-2-(3-(trifluoromethyl)-1H-pyrazol-1-yl)pyrimidin-4-yl)amino)-1-methyl-4-((2-(pyrimidin-2-yl)propan-2-yl)amino)quinolin-2(1H)-one;
6-((5-chloro-2-(3,5-dimethyl-1H-pyrazol-1-yl)pyrimidin-4-yl)amino)-4-((1-methoxy-2-methylpropan-2-yl)amino)-1-methylquinolin-2(1H)-one;
6-((5-chloro-2-(3,5-dimethyl-1H-pyrazol-1-yl)pyrimidin-4-yl)amino)-1-methyl-4-((1-(pyrimidin-2-yl)ethyl)amino)quinolin-2(1H)-one;
6-((5-Chloro-2-((S)-2-(methoxymethyl)pyrrolidine-1-carbonyl)pyridin-4-yl)amino)-4-(((R)-1-cyclopropylethyl)amino)-1-methylquinolin-2(1H)-one;
6-((5-chloro-2-(2-(2-methoxyethyl)pyrrolidine-1-carbonyl)pyridin-4-yl)amino)-4-(((R)-1-cyclopropylethyl)amino)-1-methylquinolin-2(1H)-one;
(S)-6-((5-chloro-2-methoxypyridin-4-yl)amino)-4-((1-cyclopropyl-2-hydroxyethyl)amino)-1-methylquinolin-2(1H)-one;
(R)-6-((2-(azetidine-1-carbonyl)-5-chloropyridin-4-yl)amino)-4-((1-cyclopropylethyl)amino)-1-methylquinolin-2(1H)-one;
6-((5-chloro-2-((2S,6R)-2,6-dimethylmorpholino)pyridin-4-yl)amino)-1-methyl-4-((1-(pyrimidin-2-yl)ethyl)amino)quinolin-2(1H)-one;
(R)-6-((5-chloro-2-(4-(2-hydroxyethyl)-1H-pyrazol-1-yl)pyridin-4-yl)amino)-4-((1-cyclopropylethyl)amino)-1-methylquinolin-2(1H)-one;
1-(5-chloro-4-((1-methyl-2-oxo-4-((1-(pyrimidin-2-yl)ethyl)amino)-1,2-dihydroquinolin-6-yl)amino)pyridin-2-yl)-N,N-dimethylpiperidine-4-carboxamide;
6-((5-chloro-2-(4,4-difluoropiperidin-1-yl)pyridin-4-yl)amino)-1-methyl-4-((1-(pyrimidin-2-yl)ethyl)amino)quinolin-2(1H)-one;
6-((5-chloro-2-(4-(2-hydroxyethyl)-1H-pyrazol-1-yl)pyridin-4-yl)amino)-1-methyl-4-((1-(pyrimidin-2-yl)ethyl)amino)quinolin-2(1H)-one;
1-(5-chloro-4-((1-methyl-2-oxo-4-((2-(pyrimidin-2-yl)propan-2-yl)amino)-1,2-dihydroquinolin-6-yl)amino)pyrimidin-2-yl)-N,N-dimethylpiperidine-4-carboxamide;

1-(5-chloro-4-((4-((1-cyanocyclopropyl)amino)-1-methyl-2-oxo-1,2-dihydroquinolin-6-yl)amino)pyrimidin-2-yl)-N,N-dimethylpiperidine-4-carboxamide;
1-(5-chloro-4-methyl-6-((1-methyl-2-oxo-4-((2-(pyrimidin-2-yl)propan-2-yl)amino)-1,2-dihydroquinolin-6-yl)amino)pyrimidin-2-yl)-N,N-dimethylpiperidine-4-carboxamide;
1-(5-chloro-4-((4-((1-methoxy-2-methylpropan-2-yl)amino)-1-methyl-2-oxo-1,2-dihydroquinolin-6-yl)amino)pyrimidin-2-yl)-N,N-dimethylpiperidine-4-carboxamide;
6-((5-chloro-2-((2S,6R)-2,6-dimethylmorpholino)pyrimidin-4-yl)amino)-1-methyl-4-((1-(pyrimidin-2-yl)ethyl)amino)quinolin-2(1H)-one;
6-((5-chloro-2-(4,4-difluoropiperidin-1-yl)pyrimidin-4-yl)amino)-1-methyl-4-((1-(pyrimidin-2-yl)ethyl)amino)-1,8-naphthyridin-2(1H)-one;
1-(5-chloro-4-((1-methyl-2-oxo-4-((1-(pyrimidin-2-yl)ethyl)amino)-1,2-dihydroquinolin-6-yl)amino)pyrimidin-2-yl)-N,N-dimethylpiperidine-4-carboxamide;
6-((5-chloro-2-((2S,6R)-2,6-dimethylmorpholino)pyrimidin-4-yl)amino)-4-(((R)-1-cyclopropylethyl)amino)-1-methylquinolin-2(1H)-one;
2-(1-(5-chloro-4-((1-methyl-2-oxo-4-((1-(pyrimidin-2-yl)ethyl)amino)-1,2-dihydroquinolin-6-yl)amino)pyrimidin-2-yl)piperidin-4-yl)-N,N-dimethylacetamide;
6-((5-chloro-2-((pyridin-3-ylmethyl)amino)pyrimidin-4-yl)amino)-1-methyl-4-((1-(pyrimidin-2-yl)ethyl)amino)quinolin-2(1H)-one;
9-(5-chloro-4-((1-methyl-2-oxo-4-((1-(pyrimidin-2-yl)ethyl)amino)-1,2-dihydroquinolin-6-yl)amino)pyrimidin-2-yl)-2-methyl-2,9-diazaspiro[5.5]undecan-1-one;
6-((5-chloro-2-(7-oxa-2-azaspiro[3.5]nonan-2-yl)pyrimidin-4-yl)amino)-1-methyl-4-((1-(pyrimidin-2-yl)ethyl)amino)quinolin-2(1H)-one;
6-((5-chloro-2-(4,4-difluoropiperidin-1-yl)pyrimidin-4-yl)amino)-1-methyl-4-((1-(pyrimidin-2-yl)ethyl)amino)quinolin-2(1H)-one;
1-(5-chloro-4-((1-methyl-2-oxo-4-((1-(pyrimidin-2-yl)ethyl)amino)-1,2-dihydroquinolin-6-yl)amino)pyrimidin-2-yl)-3-methylazetidine-3-carbonitrile;
6-((5-chloro-2-(2-methyl-2,4,6,7-tetrahydro-5H-pyrazolo[4,3-c]pyridin-5-yl)pyrimidin-4-yl)amino)-1-methyl-4-((1-(pyrimidin-2-yl)ethyl)amino)quinolin-2(1H)-one;
2-methyl-4-((1-methyl-2-oxo-4-((1-(pyrimidin-2-yl)ethyl)amino)-1,2-dihydroquinolin-6-yl)amino)nicotinonitrile;
5-cyano-N,6-dimethyl-4-((1-methyl-2-oxo-4-((1-(pyrimidin-2-yl)ethyl)amino)-1,2-dihydroquinolin-6-yl)amino)picolinamide;
6-chloro-5-cyano-N,N-dimethyl-4-((1-methyl-2-oxo-4-((2-(pyrimidin-2-yl)propan-2-yl)amino)-1,2-dihydroquinolin-6-yl)amino)picolinamide;
6-chloro-5-cyano-N,N-dimethyl-4-((1-methyl-2-oxo-4-((1-(pyrimidin-2-yl)ethyl)amino)-1,2-dihydroquinolin-6-yl)amino)picolinamide;
5-cyano-N-methyl-4-((1-methyl-2-oxo-4-((1-(pyrimidin-2-yl)ethyl)amino)-1,2-dihydroquinolin-6-yl)amino)picolinamide;
2-chloro-4-((4-((1-methoxy-2-methylpropan-2-yl)amino)-1-methyl-2-oxo-1,2-dihydroquinolin-6-yl)amino)nicotinonitrile;
6-((5,6-dichloropyrimidin-4-yl)amino)-1-methyl-4-((1-(pyrimidin-2-yl)ethyl)amino)quinolin-2(1H)-one;
6-chloro-5-cyano-4-((4-((1-methoxy-2-methylbutan-2-yl)amino)-1-methyl-2-oxo-1,2-dihydroquinolin-6-yl)amino)-N-methylpicolinamide;
rac-6-chloro-5-cyano-4-((4-(((1S,2R)-2-methoxycyclopentyl)amino)-1-methyl-2-oxo-1,2-dihydroquinolin-6-yl)amino)-N-methylpicolinamide;
3-chloro-4-((1-methyl-2-oxo-4-((1-(pyrimidin-2-yl)ethyl)amino)-1,2-dihydroquinolin-6-yl)amino)picolinonitrile;
2-chloro-4-((1-methyl-2-oxo-4-((3-(pyrimidin-2-yl)tetrahydrofuran-3-yl)amino)-1,2-dihydroquinolin-6-yl)amino)nicotinonitrile;
2-chloro-4-((1-methyl-2-oxo-4-((1-(5-(pyridin-3-yl)pyrimidin-2-yl)ethyl)amino)-1,2-dihydroquinolin-6-yl)amino)nicotinonitrile;
N-(5-Chloro-4-((1-methyl-2-oxo-4-((1-(pyrimidin-2-yl)ethyl)amino)-1,2-dihydroquinolin-6-yl)amino)pyridin-2-yl)-N-methylacetamide;
rac-2-chloro-4-((4-(((1R,2S)-2-methoxycyclobutyl)amino)-1-methyl-2-oxo-1,2-dihydroquinolin-6-yl)amino)nicotinonitrile;
rac-2-chloro-4-((4-(((1R,2S)-2-methoxycyclobutyl)amino)-1-methyl-2-oxo-1,2-dihydroquinolin-6-yl)amino)nicotinonitrile;
rac-6-chloro-5-cyano-4-((4-(((1R,2R)-2-methoxycyclobutyl)amino)-1-methyl-2-oxo-1,2-dihydroquinolin-6-yl)amino)-N-methylpicolinamide;
rac-6-chloro-5-cyano-4-((4-(((1R,2S)-2-methoxycyclobutyl)amino)-1-methyl-2-oxo-1,2-dihydroquinolin-6-yl)amino)-N-methylpicolinamide;
6-chloro-5-cyano-4-((4-((1-cyanocyclopropyl)amino)-1-methyl-2-oxo-1,2-dihydroquinolin-6-yl)amino)-N-methylpicolinamide;
2-chloro-4-((4-((1-cyanocyclopropyl)amino)-1-methyl-2-oxo-1,2-dihydroquinolin-6-yl)amino)nicotinonitrile;
2-chloro-4-((1-methyl-2-oxo-4-((2-(pyrimidin-2-yl)butan-2-yl)amino)-1,2-dihydroquinolin-6-yl)amino)nicotinonitrile;
(R)-2-chloro-4-((5-((1-cyclopropylethyl)amino)-8-methyl-7-oxo-7,8-dihydro-1,8-naphthyridin-3-yl)amino)nicotinonitrile;
2-chloro-4-((4-((1-(isoquinolin-3-yl)ethyl)amino)-1-methyl-2-oxo-1,2-dihydroquinolin-6-yl)amino)nicotinonitrile;
2-chloro-4-((4-((1-(5-cyclobutylpyrimidin-2-yl)ethyl)amino)-1-methyl-2-oxo-1,2-dihydroquinolin-6-yl)amino)nicotinonitrile;
6-((5-chloro-2-((3R,5S)-4,4-difluoro-3,5-dimethylpiperidin-1-yl)pyrimidin-4-yl)amino)-1-methyl-4-((2-(pyrimidin-2-yl)propan-2-yl)amino)quinazolin-2(1H)-one;
(R)-6-((2-(azetidin-1-yl)-5-chloropyrimidin-4-yl)amino)-4-((1-cyclopropylethyl)amino)-1-methylquinolin-2(1H)-one;
6-((5-chloro-2-(2-(methoxymethyl)azetidin-1-yl)pyrimidin-4-yl)amino)-4-(((R)-1-cyclopropylethyl)amino)-1-methylquinolin-2(1H)-one;
6-((5-chloro-2-(1-methyl-1,4,5,7-tetrahydro-6H-pyrazolo[3,4-c]pyridin-6-yl)pyrimidin-4-yl)amino)-1-methyl-4-((1-(pyrimidin-2-yl)ethyl)amino)quinolin-2(1H)-one;
6-((5-chloro-2-(4,4-difluoro-3-(hydroxymethyl)piperidin-1-yl)pyrimidin-4-yl)amino)-1-methyl-4-((1-(pyrimidin-2-yl)ethyl)amino)quinolin-2(1H)-one;
6-[[5-chloro-2-[(2R,6S)-2,6-dimethylmorpholin-4-yl]pyrimidin-4-yl]amino]-1-methyl-4-(1-pyrimidin-2-ylethylamino)quinazolin-2-one;

6-[[5-chloro-2-[(2R,6S)-2,6-dimethylmorpholin-4-yl]pyrimidin-4-yl]amino]-1-methyl-4-[(1-methyl-1-pyrimidin-2-yl-ethyl)amino]quinazolin-2-one;

6-[[5-chloro-2-[(3R,5S)-3,5-dimethyl-1-piperidyl]pyrimidin-4-yl]amino]-1-methyl-4-[(1-methyl-1-pyrimidin-2-yl-ethyl)amino]quinazolin-2-one;

2-chloro-4-((1-methyl-2-oxo-4-((2-(pyrimidin-2-yl)propan-2-yl)amino)-1,2-dihydroquinolin-6-yl)amino)-6-(1-oxa-6-azaspiro[3.3]heptane-6-carbonyl)nicotinonitrile; or 2-chloro-6-(3-(cyanomethyl)azetidine-1-carbonyl)-4-((1-methyl-2-oxo-4-((2-(pyrimidin-2-yl)propan-2-yl)amino)-1,2-dihydroquinolin-6-yl)amino)nicotinonitrile.

17. A pharmaceutical composition comprising a compound according to claim 1, or a pharmaceutically acceptable salt or hydrate thereof and a pharmaceutically acceptable carrier or excipient.

18. A method for the treatment of cancer in a subject in need of such treatment, said method comprising administering a therapeutically effective amount of i) a compound according to claim 1, or a pharmaceutically acceptable salt or hydrate thereof, or ii) a pharmaceutical composition comprising a compound according to claim 1, or a or a pharmaceutically acceptable salt or hydrate thereof and a pharmaceutically acceptable carrier or excipient.

19. The method according to claim 18, wherein said cancer is diffuse large B-cell lymphoma (DLBCL), follicular lymphoma (FL), Burkitt lymphoma (BL), angioimmunoblastic T-cell lymphoma (AITL), acute lymphoblastic leukaemia (ALL), chronic myeloid leukaemia (CML), multiple myeloma, breast cancer, non-small cell lung cancer (NSCLC) or squamous cell carcinomas (SCC) of the head and neck, oesophagus, lung or ovary.

* * * * *